(12) United States Patent
Bonazzi et al.

(10) Patent No.: US 11,566,022 B2
(45) Date of Patent: Jan. 31, 2023

(54) 3-(5-METHOXY-1-OXOISOINDOLIN-2-YL) PIPERIDINE-2,6-DIONE DERIVATIVES AND USES THEREOF

(71) Applicant: NOVARTIS AG, Basel (CH)

(72) Inventors: Simone Bonazzi, Cambridge, MA (US); Artiom Cernijenko, Cambridge, MA (US); Jennifer Stroka Cobb, Stow, MA (US); Natalie Dales, Arlington, MA (US); John Ryan Kerrigan, Wakefield, MA (US); Philip Lam, Somerville, MA (US); Hasnain Ahmed Malik, Boston, MA (US); Gary O'Brien, Maynard, MA (US); Andrew W. Patterson, Somerville, MA (US); Noel Marie-France Thomsen, Chelmsford, MA (US); Pamela Ting, Cambridge, MA (US)

(73) Assignee: NOVARTIS AG, Basel (CH)

( * ) Notice: Subject to any disclaimer, the term of this patent is extended or adjusted under 35 U.S.C. 154(b) by 126 days.

(21) Appl. No.: 17/124,127

(22) Filed: Dec. 16, 2020

(65) Prior Publication Data

US 2022/0402904 A1    Dec. 22, 2022

Related U.S. Application Data

(60) Provisional application No. 62/950,048, filed on Dec. 18, 2019.

(51) Int. Cl.

| *C07D 413/14* | (2006.01) |
| *C07D 401/14* | (2006.01) |
| *A61K 45/06*  | (2006.01) |
| *C07D 417/14* | (2006.01) |
| *C07D 471/04* | (2006.01) |

(52) U.S. Cl.
CPC ............ *C07D 413/14* (2013.01); *A61K 45/06* (2013.01); *C07D 401/14* (2013.01); *C07D 417/14* (2013.01); *C07D 471/04* (2013.01)

(58) Field of Classification Search
CPC .... A61K 45/06; C07D 401/14; C07D 413/14; C07D 471/04; C07D 417/14
USPC ...................................................... 514/235.2
See application file for complete search history.

(56) References Cited

U.S. PATENT DOCUMENTS

| 9,133,161 B2    | 9/2015 | Traverse et al. |
| 2014/0031552 A1 | 1/2014 | Traverse et al. |
| 2017/0038387 A1 | 2/2017 | Gandhi et al. |
| 2018/0099940 A1 | 4/2018 | Crew et al. |
| 2018/0125821 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0237418 A1 | 8/2018 | Crew et al. |
| 2018/0256586 A1 | 9/2018 | Crew et al. |
| 2019/0092768 A1 | 3/2019 | Gray et al. |
| 2019/0151295 A1 | 5/2019 | Crew et al. |
| 2019/0192668 A1 | 6/2019 | Mainolfi et al. |
| 2019/0276459 A1 | 9/2019 | Crew et al. |
| 2019/0315732 A1 | 10/2019 | Crew et al. |
| 2021/0009559 A1 | 1/2021 | Henderson et al. |

FOREIGN PATENT DOCUMENTS

| EP | 2877462 B1    | 1/2014 |
| EP | 3202461 B1    | 12/2018 |
| WO | 2017024019 A1 | 2/2017 |
| WO | 2014018866 A1 | 10/2017 |
| WO | 2018071606 A1 | 4/2018 |
| WO | 2018102067 A2 | 6/2018 |
| WO | 2018102725 A1 | 6/2018 |
| WO | 2018118598 A1 | 6/2018 |
| WO | 2018119357 A1 | 6/2018 |

(Continued)

OTHER PUBLICATIONS

Olson et al., "Pharmacological perturbation of CDK9 using selective CDK9 inhibition or degradation", Nature Chemical Biology, 2018, 14(2):163-170 Suppl. Notes.

(Continued)

*Primary Examiner* — Kahsay Habte
(74) *Attorney, Agent, or Firm* — Asimina T. Georges Evangelinos

(57) ABSTRACT

The present disclosure relates to compounds of formula (I') and pharmaceutical compositions and their use in reducing Widely Interspaced Zinc Finger Motifs (WIZ) expression levels, or inducing fetal hemoglobin (HbF) expression, and in the treatment of inherited blood disorders, including hemoglobinopathies, sickle cell disease and beta-thalassemia.

20 Claims, 1 Drawing Sheet
Specification includes a Sequence Listing.

(56) References Cited

FOREIGN PATENT DOCUMENTS

| WO | 2018119441 A1 | 6/2018 |
| WO | 2018119448 A1 | 6/2018 |
| WO | 2018140809 A1 | 8/2018 |
| WO | 2019079569 A1 | 4/2019 |
| WO | 2019079701 A1 | 4/2019 |
| WO | 2019099926 A1 | 5/2019 |
| WO | 2019133531 A1 | 7/2019 |
| WO | 2019177902 A1 | 9/2019 |
| WO | 2020006265 A1 | 9/2019 |
| WO | 2019195609 A2 | 10/2019 |
| WO | 2020006233 A1 | 1/2020 |
| WO | 2020006262 A1 | 1/2020 |
| WO | 2020006264 A1 | 1/2020 |
| WO | 2020117759 A1 | 6/2020 |

OTHER PUBLICATIONS

Luo et al., "Syntheses of aromatic substituted 6'-thiothalidomides", Synthesis, 2008, 21:3415-3422.

SEQUENCE LISTING

```
<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Val Ser Gly Trp Arg Leu Phe Lys Lys Ile Ser
1               5                   10

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 2
agcccacaat gccacggaaa t                                              21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gcaacatcta caccctcaaa t                                              21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tgaccgagtg gtacgtcaat g                                              21

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
agcggcagaa catcaacaaa t                                              21

<210> SEQ ID NO 6
<211> LENGTH: 67
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
agcauagcaa guuaaaauaa ggcuaguccg uuaucaacuu gaaaaagugg caccgagucg    60
gugcuuu                                                              67

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
acggaggcta agcgtcgcaa                                                20

<210> SEQ ID NO 8
<211> LENGTH: 20
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aacatctttc gggccgtagg                                              20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gacatccgct gcgagttctg                                              20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tgcagcgtcc cgggcagagc                                              20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
caagccgtgc ctcatcaaga                                              20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cgggcacacc tgcggcagtt                                              20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
```

```
agtgggtgcg gcacttacag                                              20

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ctacatttta catgatagg                                               19
```

3-(5-METHOXY-1-OXOISOINDOLIN-2-YL) PIPERIDINE-2,6-DIONE DERIVATIVES AND USES THEREOF

CLAIM OF PRIORITY

This application claims the benefit of priority to U.S. Provisional Application No. 62/950,048 filed Dec. 18, 2019, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on May 20, 2021, is named PAT058748-US-NP_SL.txt and is 4,096 bytes in size.

FIELD OF THE DISCLOSURE

The present disclosure relates to 3-(5-methoxy-1-oxoisoindolin-2-yl)piperidine-2,6-dione compounds and pharmaceutical compositions and their use in reducing Widely Interspaced Zinc Finger Motifs (WIZ) protein expression levels and/or inducing fetal hemoglobin (HbF) protein expression levels, and in the treatment of inherited blood disorders (hemoglobinopathies, e.g., beta-hemoglobinopathies), such as sickle cell disease and beta-thalassemia.

BACKGROUND OF THE DISCLOSURE

Sickle cell disease (SCD) is a group of severe inherited blood disorders that cause red blood cells to contort into a sickle shape. These cells can cause blockages in blood flow, leading to intense pain, organ damage and premature death. Beta thalassemias are a group of inherited blood disorders that are caused by reduced or absent synthesis of beta globin, causing anemia.

Fetal hemoglobin (HbF) induction is known to ameliorate symptoms in SCD and beta-thalassemia patients, with both genetic (single nucleotide polymorphisms in the globin control locus & BCL11A) and pharmacologic (hydroxyurea) validation in the clinic (Vinjamur, D. S., et al. (2018), *The British Journal of Haematology,* 180(5), 630-643). Hydroxyurea is the current standard of care for SCD and is thought to provide benefit via induction of HbF, but is genotoxic, causes dose-limiting neutropenia and has a response rate of less than 40%. Other mechanisms being targeted clinically and preclinically include inhibition of HDAC1/2 (Shearstone et al., 2016, *PLoS One,* 11(4), e0153767), LSD1 (Rivers et al., 2018, *Experimental Hematology,* 67, 60-64), DNMT1, PDE9a (McArthur et al., 2019, *Haematologica.* doi:10.3324/haematol.2018.213462), HRI kinase (Grevet et al., 2018, *Science,* 361(6399), 285-290) and G9a/GLP (Krivega et al., 2015, *Blood,* 126(5), 665-672; Renneville et al., 2015, *Blood,* 126(16), 1930-1939). Additionally, the immunomodulators pomalidomide and lenalidomide induce HbF ex vivo in human primary erythroid cells (Moutouh-de Parseval, L. A. et al. (2008), *The Journal of Clinical Investigation,* 118(1), 248-258) and in vivo (Meiler, S. E. et al. (2011), Blood, 118(4), 1109-1112). WIZ is ubiquitously expressed and plays a role in targeting the G9a/GLP histone methyltransferases to genomic loci to regulate chromatin structure and transcription (Bian, Chen, et al. (2015), *eLife* 2015; 4:e05606.

SUMMARY OF THE DISCLOSURE

The disclosure relates to a therapeutic agent, which is effective in reducing WIZ protein expression levels and/or inducing fetal hemoglobin (HbF) expression. In an embodiment, the therapeutic agent is a small molecule, siRNAs, shRNAs, ASOs, miRNAs, AMOs. The disclosure further relates to 3-(5-methoxy-1-oxoisoindolin-2-yl)piperidine-2,6-dione compounds, which are effective in reducing WIZ protein expression levels and/or inducing fetal hemoglobin (HbF) expression, pharmaceutically acceptable salts thereof, compositions thereof, and their use in therapies for the conditions and purposes detailed above.

The disclosure provides a compound of formula (I') or a pharmaceutically acceptable salt, hydrate, solvate, prodrug, stereoisomer, or tautomer thereof,

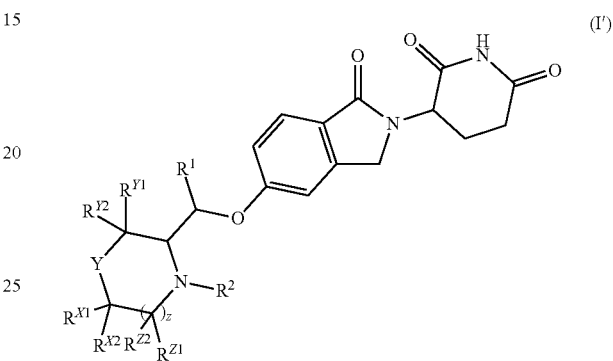

(I')

wherein:

Y is selected from O, $CH_2$, $CF_2$, and CHF;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^{Z1}$ and $R^{Z2}$ are both hydrogen or 1 of $R^{Z1}$ and $R^{Z2}$ and 1 of $R^{Y1}$ and $R^{Y2}$ together form a $C_1$-$C_2$ alkylene bridging group and the other of $R^{Z1}$ and $R^{Z2}$ and $R^{Y1}$ and $R^{Y2}$ are both hydrogen;

$R^1$ is selected from hydrogen and $C_1$-$C_6$alkyl;

$R^2$ is selected from hydrogen, —C(=O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, $C_3$-$C_8$cycloalkyl, and —O—($R^{2a}$), wherein the aryl, heteroaryl, heterocyclyl, and cycloalkyl are each independently substituted with 0-5 $R^4$;

$R^{2a}$ is $C_1$-$C_6$alkyl wherein the alkyl is substituted with 0-1 substituent independently selected from $C_6$-$C_{10}$aryl;

$R^3$ is selected from —CH=$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3a}$ and $R^{3b}$ together with the carbon atom to which they are attached form a $C_3$-$C_8$cycloalkyl ring;

each $R^{3c}$ is at each occurrence independently selected from —C(=O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-3 substituents each independently selected from —CN, $C_1$-$C_6$alkyl, $C_1$-$C_6$alkoxyl, hydroxyl and $C_1$-$C_6$haloalkyl;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, $C_1$-$C_6$alkyl, 4- to 6-membered heterocyclyl comprising 1-2 heteroatoms independently selected from N, O, and S and $C_3$-$C_6$cycloalkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, halogen, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen; $R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

In an embodiment, z is 1; and 1 of $R^{Z1}$ and $R^{Z2}$ and 1 of $R^{Y1}$ and $R^{Y2}$ together form a $C_1$-$C_2$ alkylene bridging group and the other of $R^{Z1}$ and $R^{Z2}$ and $R^{Y1}$ and $R^{Y2}$ are both hydrogen.

In an embodiment, z is 1; and 1 of $R^{Z1}$ and $R^{Z2}$ and 1 of $R^{Y1}$ and $R^{Y2}$ together form a $C_1$ alkylene bridging group and the other of $R^{Z1}$ and $R^{Z2}$ and $R^{Y1}$ and $R^{Y2}$ are both hydrogen.

In an embodiment, z is 1; and 1 of $R^{Z1}$ and $R^{Z2}$ and 1 of $R^{Y1}$ and $R^{Y2}$ together form a $C_2$ alkylene bridging group and the other of $R^{Z1}$ and $R^{Z2}$ and $R^{Y1}$ and $R^{Y2}$ are both hydrogen.

The disclosure provides, in a first aspect, a compound of formula (I) or a pharmaceutically acceptable salt hydrate, solvate, prodrug, stereoisomer, or tautomer thereof, wherein:

Y is selected from O, $CH_2$, and $CF_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^1$ is selected from hydrogen and $C_1$-$C_6$alkyl;

$R^2$ is selected from hydrogen, —C(=O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the aryl, heteroaryl, heterocyclyl, and cycloalkyl are each independently substituted with 0-5 $R^4$;

$R^3$ is selected from —CH=$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3a}$ and $R^{3b}$ together with the carbon atom to which they are attached form a $C_3$-$C_8$cycloalkyl ring;

each $R^{3c}$ is at each occurrence independently selected from —C(=O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-3 substituents each independently selected from —CN, $C_1$-$C_6$alkyl, $C_1$-$C_6$alkoxyl, and hydroxyl;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl; $R^{4b}$ is at each occurrence independently selected from —CN, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

In a second aspect, the disclosure provides a pharmaceutical composition comprising a therapeutically effective amount of a compound, or a pharmaceutically acceptable salt, hydrate, solvate, prodrug, stereoisomer, or tautomer thereof, and a pharmaceutically acceptable carrier or excipient.

In a third aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use as a medicament.

In a fourth aspect, the disclosure provides a method of treating or preventing a disease or disorder in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a fifth aspect, the disclosure provides a method of treating or preventing a disorder that is affected by the reduction of WIZ protein levels, in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a sixth aspect, the disclosure provides a method of inhibiting WIZ protein expression in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a seventh aspect, the disclosure provides a method of degrading WIZ protein in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f, (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In an eighth aspect, the disclosure provides a method of inhibiting, reducing, or eliminating the activity of WIZ protein or WIZ protein expression, the method comprising administering to the subject a compound of formula (I'), (I), (I-i), (I-i-a), (I-i-b), (I-i-c), (I-i-d), (I-i-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a ninth aspect, the disclosure provides a method of inducing or promoting fetal hemoglobin in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a tenth aspect, the disclosure provides a method of reactivating fetal hemoglobin production or expression in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-i), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In an eleventh aspect, the disclosure provides a method of increasing fetal hemoglobin expression in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a twelfth aspect, the disclosure provides a method of treating a hemoglobinopathy, e.g., a beta-hemoglobinopathy, in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a thirteenth aspect, the disclosure provides a method of treating a sickle cell disease in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a fourteenth aspect, the disclosure provides a method of treating beta-thalassemia in a subject in need thereof, the method comprising administering to the subject a therapeutically effective amount of a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof.

In a fifteenth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder.

In a sixteenth aspect, the disclosure provides a compound of (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-i), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder selected from sickle cell disease and beta-thalassemia.

In a seventeenth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment or prevention of a disease or disorder that is affected by the reduction of WIZ protein levels.

In an eighteenth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in reducing WIZ protein levels.

In a nineteenth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment or prevention of a disease or disorder that is affected by the inhibition of WIZ protein expression.

In a twentieth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment or prevention of a disease or disorder that is affected by the degradation of WIZ protein.

In a twenty-first aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in inhibiting, reducing, or eliminating the activity of WIZ protein or WIZ protein expression.

In a twenty-second aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in inducing or promoting fetal hemoglobin.

In a twenty-third aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in reactivating fetal hemoglobin production or expression.

In a twenty fourth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in increasing fetal hemoglobin expression.

In a twenty fifth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a hemoglobinopathy.

In a twenty sixth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f, (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a sickle cell disease In a twenty seventh aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of beta-thalassemia.

In a twenty eighth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder affected by an increase in fetal hemoglobin expression.

In a twenty ninth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder affected by the inhibition, reduction, or elimination of the activity of WIZ protein or WIZ protein expression.

In a thirtieth aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder affected by the induction or promotion of fetal hemoglobin.

In a thirty-first aspect, the disclosure provides a compound of formula (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i), or (Ih-ii), or a pharmaceutically acceptable salt, hydrate, solvate, prodrug, stereoisomer, or tautomer thereof, for use in the treatment of a disease or disorder affected by the reactivation of fetal hemoglobin production or expression.

Various aspects of the disclosure are described herein and in the claims.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise. Although methods and materials similar or equivalent to those described herein can be used in the practice or testing of the disclosure, suitable methods and materials are described below. All publications, patent applications, patents, and other references mentioned herein are incorporated by reference in their entireties for all purposes. The references cited herein are not admitted to be prior art to the claimed disclosure. In the case of conflict, the present specification, including definitions, will control. In addition, the materials, methods, and examples are illustrative only and are not intended to be limiting.

Other features and advantages of compounds, compositions, and methods disclosed herein will be apparent from the following detailed description and claims.

DETAILED DESCRIPTION OF THE DISCLOSURE

Figure 1A:
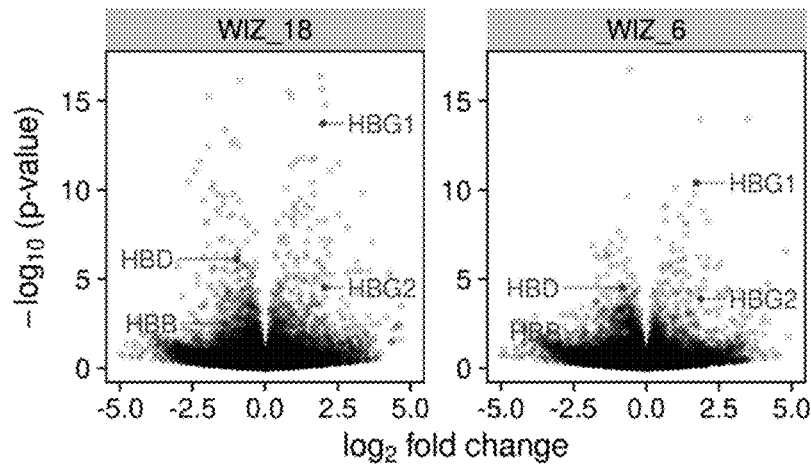
FIG. 1A depicts a volcano plot of differentially expressed genes from WIZ KO cells as compared to a scrambled gRNA control. Each dot represents a gene. HBG1/2 genes are differentially upregulated with WIZ_6 and WIZ_18 gRNA targeting WIZ KO.

The compounds disclosed herein are effective in reducing WIZ protein expression levels, or inducing fetal hemoglobin (HbF) expression. Without wishing to be bound by any theory, it is believed that the disclosed compounds may treat blood disorders, such as inherited blood disorders, e.g., sickle cell disease, and beta-thalassemia by inducing fetal hemoglobin HbF expression.

Definitions

Unless specified otherwise, the terms "compounds of the present disclosure," "compounds of the disclosure," or "compound of the disclosure" refer to compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), exemplified compounds, salts thereof, particularly pharmaceutically acceptable salts thereof, hydrates, solvates, prodrugs, as well as all stereoisomers (including diastereoisomers and enantiomers), rotamers, tautomers, and isotopically labeled compounds (including deuterium substitutions), as well as inherently formed moieties.

In the groups, radicals, or moieties defined below, the number of carbon atoms is often specified preceding the group, for example, $C_1$-$C_{10}$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Thus, the term $C_6$-$C_{10}$aryl$C_1$-$C_6$alkyl means a monovalent radical of the formula $C_6$-$C_{10}$aryl$C_1$-$C_6$alkyl-such that the group is attached to the base molecule via the $C_1$-$C_6$alkyl moiety.

In embodiments whereby $R^{3c}$ or $R^4$ are arylalkyl-O—, this means a monovalent O radical of the formula aryl-alkyl-O— or —O-alkyl-aryl.

Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

In embodiments whereby the bond to any R group, for example, to $R^4$, is not connected to any specified atom, for example, in the heteroaryl group as shown below,

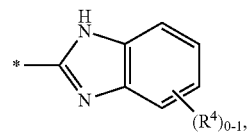

this means the $R^4$ group may be bonded via any atom on the ring.

As used herein the term "$C_1$-$C_{10}$alkyl" refers to a straight or branched hydrocarbon chain radical consisting solely of carbon and hydrogen atoms, containing no unsaturation, having from one to ten carbon atoms, and which is attached to the rest of the molecule by a single bond. The terms "$C_1$-$C_3$alkyl", "$C_1$-$C_4$alkyl", "$C_1$-$C_6$alkyl", "$C_1$-$C_5$alkyl" are to be construed accordingly. Examples of $C_1$-$C_{10}$alkyl include, but are not limited to, methyl, ethyl, n-propyl, 1-methylethyl (isopropyl), n-butyl, 1-methylpropyl (sec-butyl), 2-methylpropyl (iso-butyl), 1,1-dimethylethyl (t-butyl), n-pentyl, n-hexyl, n-heptyl, 4-heptyl, n-octyl, 2-isopropyl-3-methylbutyl, n-nonyl and n-decyl.

As used herein, the term "$C_1$-$C_6$alkoxyl" refers to a radical of the formula —$OR_a$ where $R_a$ is a $C_1$-$C_6$alkyl radical as generally defined above. Examples of $C_1$-$C_6$alkoxyl include, but are not limited to, methoxy, ethoxy, propoxy, iso-propoxy, butoxy, iso-butoxy, tert-butoxy, sec-butoxy, pentoxy, and hexoxy.

"Alkynyl" means a straight or branched chain unsaturated hydrocarbon containing 2-12 carbon atoms. The "alkynyl" group contains at least one triple bond in the chain. The term "$C_2$-$C_4$alkynyl" is to be construed accordingly. Examples of alkynyl groups include ethynyl, propargyl, n-butynyl, isobutynyl, pentynyl, or hexynyl. An alkynyl group can be unsubstituted or substituted.

Preferred examples of "$C_2$-$C_4$alkynyl" include, without limitations, ethynyl, prop-1-ynyl, prop-2-ynyl and but-2-ynyl.

As used herein, the term "$C_1$-$C_6$haloalkyl" refers to $C_1$-$C_6$alkyl radical, as defined above, substituted by one or more halo radicals, as defined herein. Examples of $C_1$-$C_6$haloalkyl include, but are not limited to, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl, 1,3-dibromopropan-2-yl, 3-bromo-2-fluoropropyl and 1,4,4-trifluorobutan-2-yl.

As used herein, the term "$C_1$-$C_6$haloalkoxyl" means a $C_1$-$C_6$alkoxyl group as defined herein substituted with one or more halo radicals. Examples of $C_1$-$C_6$haloalkoxyl groups include, but are not limited to, trifluoromethoxy, difluoromethoxy, fluoromethoxy, trichloromethoxy, 1,1-difluoroethoxy, 2,2-difluoroethoxy, 2,2,2-trifluoroethoxy, 1-fluoromethyl-2-fluoroethoxy, pentafluoroethoxy, 2-fluoropropoxy, 3,3-difluoropropoxy and 3-dibromopropoxy. Preferably, the one or more halo radicals of $C_1$-$C_6$haloalkoxyl is fluoro. Preferably, $C_1$-$C_6$haloalkoxyl is selected from trifluoromethoxy, difluoromethoxy, fluoromethoxy, 1,1-difluoroethoxy, 2,2-difluoroethoxy, 2,2,2-trifluoroethoxy, 1-fluoromethyl-2-fluoroethoxy, and pentafluoroethoxy.

The term "halogen" or "halo" means fluorine, chlorine, bromine or iodine.

As used herein, the term "cycloalkyl" means a monocyclic or polycyclic saturated or partially unsaturated carbon ring containing 3-18 carbon atoms wherein there are no delocalized pi electrons (aromaticity) shared among the ring carbon. The terms "$C_3$-$C_8$cycloalkyl" and "$C_3$-$C_6$cycloalkyl" are to be construed accordingly. The term polycyclic encompasses bridged (e.g., norbomane), fused (e.g., decalin) and spirocyclic cycloalkyl. Preferably, cycloalkyl, e.g., $C_3$-$C_8$cycloalkyl, is a monocyclic or bridged hydrocarbon group of 3 to 8 carbon atoms.

Examples of cycloalkyl groups include, without limitations, cyclopropenyl, cyclopropyl cyclobutyl, cyclobutenyl, cyclopentyl, cyclohexyl, cycloheptanyl, cyclooctanyl, norboranyl, norborenyl, bicyclo[2.2.2]octanyl, bicyclo[2.2.2]octenyl, bicyclo[1.1.1]pentanyl and derivatives thereof.

Preferred examples of $C_3$-$C_8$cycloalkyl include, but are not limited to, cyclopropyl, cyclobutyl, cyclopentyl, cyclohexyl, bicyclo[1.1.1]pentyl, bicyclo[2.1.1]hexyl, bicyclo[2.1.1]heptyl, bicyclo[2.2.2]octyl and bicyclo[1.1.1]pentanyl.

"Heterocyclyl" means a saturated or partially saturated monocyclic or polycyclic ring containing carbon and at least one heteroatom selected from oxygen, nitrogen, and sulfur (O, N, and S) and wherein there are no delocalized pi electrons (aromaticity) shared among the ring carbon or heteroatoms. The terms "4- to 6-membered heterocyclyl" and "4- to 11-membered heterocyclyl" are to be construed accordingly. The heterocyclyl ring structure may be substituted by one or more substituents. The substituents can themselves be optionally substituted. The heterocyclyl may be bonded via a carbon atom or heteroatom. The term polycyclic encompasses bridged, fused and spirocyclic heterocyclyl.

Examples of heterocyclyl rings include, but are not limited to, oxetanyl, azetidinyl, tetrahydrofuranyl, tetrahydropyranyl, pyrrolidinyl, oxazolinyl, isoxazolinyl, oxazolidinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, dihydroisoxazolinyl, pyrrolinyl, pyrazolinyl, oxazepinyl, dithiolanyl, homotropanyl, dihydropyranyl (e.g., 3,6-dihydro-2H-pyranyl), oxaspiroheptanyl (e.g., 2-oxaspiro[3.3]heptan-6-yl) and the like.

Preferred examples of heterocyclyl include, without limitations, azetidinyl, pyrrolidinyl, tetrahydrofuranyl, tetrahydrothienyl, piperidinyl, piperazinyl, dihydroisoxazolinyl, tetrahydropyranyl, morpholinyl, dihydropyranyl (e.g., 3,6-dihydro-2H-pyranyl) and oxaspiroheptanyl (e.g., 2-oxaspiro[3.3]heptan-6-yl).

As used herein, the term "aryl" as used herein means monocyclic, bicyclic or polycyclic carbocyclic aromatic rings. Examples of aryl include, but are not limited to, phenyl, naphthyl (e.g., naphth-1-yl, naphth-2-yl), anthryl (e.g., anthr-1-yl, anthr-9-yl), phenanthryl (e.g., phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl, biphenyl-4-yl), phenylnaphthyl (e.g., 1-phenylnaphth-2-yl, 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl, inden-5-yl), 1,2,3,4-tetrahydronaphthyl (e.g., 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g., 1,2-dihydronaphth-1-yl, 1,2-dihydronaphth-4-yl, 1,2-dihydronaphth-6-yl), fluorenyl (e.g., fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl, benzonorborn-6-yl), 1,4-ethano-1,2,3,4-tetrahydronapthyl (e.g., 1,4-ethano-1,2,3,4-tetrahydronapth-2-yl, 1,4-ethano-1,2,3,4-tetrahydronapth-10-yl), and the like. The term "$C_6$-$C_{10}$aryl" is to be construed accordingly.

Preferred examples of aryl include, but are not limited to, indenyl, (e.g., inden-1-yl, inden-5-yl) phenyl ($C_6H_5$), naphthyl ($C_{10}H_7$) (e.g., naphth-1-yl, naphth-2-yl), indanyl (e.g., indan-1-yl, indan-5-yl), and tetrahydronaphthalenyl (e.g., 1,2,3,4-tetrahydronaphthalenyl).

Preferably, $C_6$-$C_{10}$aryl refers to a monocyclic or bicyclic carbocyclic aromatic ring.

Preferred examples of $C_6$-$C_{10}$aryl include, but are not limited to, phenyl and naphthyl. In an embodiment, $C_6$-$C_{10}$aryl is phenyl.

As used herein, the term "heteroaryl" as used herein is intended to include monocyclic heterocyclic aromatic rings containing one or more heteroatoms selected from oxygen, nitrogen, and sulfur (O, N, and S). Representative examples are pyrrolyl, furanyl, thienyl, oxazolyl, thiazolyl, imidazolyl, pyrazolyl, isothiazolyl, isooxazolyl, triazolyl, (e.g., 1,2,4-triazolyl), oxadiazolyl, (e.g., 1,2,3-oxadiazolyl, 1,2,4-oxadiazolyl, 1,2,5-oxadiazolyl, 1,3,4-oxadiazolyl), thiadiazolyl (e.g., 1,2,3-thiadiazolyl, 1,2,4-thiadiazolyl, 1,2,5-thiadiazolyl, 1,3,4-thiadiazolyl), tetrazolyl, pyranyl, pyridinyl, pyridazinyl, pyrimidinyl, pyrazinyl, 1,2,3-triazinyl, 1,2,4-triazinyl, 1,3,5-triazinyl, thiadiazinyl, azepinyl, azecinyl, and the like.

Heteroaryl is also intended to include bicyclic heterocyclic aromatic rings containing one or more heteroatoms selected from oxygen, nitrogen, and sulfur (O, N, and S). Representative examples are indolyl, isoindolyl, benzofuranyl, benzothiophenyl, indazolyl, benzopyranyl, benzimidazolyl, benzothiazolyl, benzisothiazolyl, benzoxazolyl, benzisoxazolyl, benzoxazinyl, benzotriazolyl, naphthyridinyl, phthalazinyl, pteridinyl, purinyl, quinazolinyl, cinnolinyl, quinolinyl, isoquinolinyl, quinoxalinyl, oxazolopyridinyl, isooxazolopyridinyl, pyrrolopyridinyl, furopyridinyl, thienopyridinyl, imidazopyridinyl, imidazopyrimidinyl, pyrazolopyridinyl, pyrazolopyrimidinyl, pyrazolotriazinyl, thiazolopyridinyl, thiazolopyrimidinyl, imdazothiazolyl, triazolopyridinyl, triazolopyrimidinyl, and the like.

Heteroaryl is also intended to include polycyclic heterocyclic aromatic rings containing one or more heteroatoms selected from oxygen, nitrogen, and sulfur (O, N, and S).

Representative examples are carbazolyl, phenoxazinyl, phenazinyl, acridinyl, phenothiazinyl, carbolinyl, phenanthrolinyl, and the like.

Heteroaryl is also intended to include partially saturated monocyclic, bicyclic or polycyclic heterocylyls containing one or more heteroatoms selected oxygen, nitrogen, and sulfur (O, N, and S). Representative examples are imidazolinyl, indolinyl, dihydrobenzofuranyl, dihydrobenzothienyl, dihydrobenzopyranyl, dihydropyridooxazinyl, dihydrobenzodioxinyl (e.g., 2,3-dihydrobenzo[b][1,4]dioxinyl), benzodioxolyl (e.g., benzo[d][1,3]dioxole), dihydrobenzooxazinyl (e.g., 3,4-dihydro-2H-benzo[b][1,4]oxazine), tetrahydroindazolyl, tetrahydrobenzimidazolyl, tetrahydroimidazo[4,5-c]pyridyl, tetrahydroquinolinyl, tetrahydroisoquinolinyl, tetrahydroquinoxalinyl, and the like.

The heteroaryl ring structure may be substituted by one or more substituents. The substituents can themselves be optionally substituted. The heteroaryl ring may be bonded via a carbon atom or heteroatom.

The term "5-10 membered heteroaryl" is to be construed accordingly.

Examples of 5-10 membered heteroaryl include, but are not limited to, indolyl, imidazopyridyl, isoquinolinyl, benzooxazolonyl, pyridinyl, pyrimidinyl, pyridinonyl, benzotriazolyl, pyridazinyl, pyrazolotriazinyl, indazolyl, benzimidazolyl, quinolinyl, triazolyl, (e.g., 1,2,4-triazolyl), pyrazolyl, thiazolyl, oxazolyl, isooxazolyl, pyrrolyl, oxadiazolyl, (e.g., 1,2,3-oxadiazolyl, 1,2,4-oxadiazolyl, 1,2,5-oxadiazolyl, 1,3,4-oxadiazolyl), imidazolyl, pyrrolopyridinyl, tetrahydroindazolyl, quinoxalinyl, thiadiazolyl (e.g., 1,2,3-thiadiazolyl, 1,2,4-thiadiazolyl, 1,2,5-thiadiazolyl, 1,3,4-thiadiazolyl), pyrazinyl, oxazolopyridinyl, pyrazolopyrimidinyl, benzoxazolyl, indolinyl, isooxazolopyridinyl, dihydropyridooxazinyl, tetrazolyl, dihydrobenzodioxinyl (e.g., 2,3-dihydrobenzo[b][1,4]dioxinyl), benzodioxolyl (e.g., benzo[d][1,3]dioxole) and dihydrobenzooxazinyl (e.g., 3,4-dihydro-2H-benzo[b][1,4]oxazine).

As used herein, the term "$C_6$-$C_{10}$aryl$C_1$-$C_6$alkyl" refers to a monovalent radical of the formula —$R_a$—$C_6$-$C_{10}$aryl where $R_a$ is a $C_1$-$C_6$alkyl radical as generally defined above. Examples of $C_6$-$C_{10}$aryl$C_1$-$C_6$alkyl include, but are not limited to, C1alkyl-$C_6H_5$(benzyl), C1alkyl-$C_{10}H_7$, —CH($CH_3$)—$C_6H_5$, —C($CH_3$)$_2$—$C_6H_5$, and —($CH_2$)$_{2-6}$—$C_6H_5$.

As used herein, the term "oxo" refers to the radical =O.

As used herein, the term "di($C_1$-$C_6$alkyl)amino$C_1$-$C_6$alkyl" refers to a radical of the formula —$R_{a1}$—N($R_{a2}$)—$R_{a2}$ where $R_{a1}$ is a $C_1$-$C_6$alkyl radical as defined above and each $R_{a2}$ is a $C_1$-$C_6$alkyl radical, which may be the same or different, as defined above. The nitrogen atom may be bonded to any carbon atom in any alkyl radical. Examples include, but are not limited to, (C1alkyl-$NR^{6a}R^{6b}$), (C1alkyl-$CH_2$—$NR^{6a}R^{6b}$), (—($CH_2$)$_3$—$NR^{6a}R^{6b}$), (—($CH_2$)$_4$—$NR^{6a}R^{6b}$), (—($CH_2$)$_5$—$NR^{6a}R^{6b}$), and (—($CH_2$)$_6$—$NR^{6a}R^{6b}$), wherein $R^{6a}$ and $R^{6b}$ are as defined herein.

As used herein, the term "di($C_1$-$C_6$alkyl)amino" refers to an amino radical of formula —N($R_{a1}$)—$R_{a1}$, where each $R_{a1}$ is a $C_1$-$C_6$alkyl radical, which may be the same or different, as defined above.

"Cyano" or "—CN" means a substituent having a carbon atom joined to a nitrogen atom by a triple bond, e.g., C≡N.

As used herein, the term "$C_1$-$C_2$alkylene" refers to a straight or branched hydrocarbon chain bivalent radical consisting solely of carbon and hydrogen atoms, containing no unsaturation, having from one to two carbon atoms. The term "$C_1$-$C_2$alkylene" is to be construed accordingly.

In relation to embodiments whereby 1 of $R^{Z1}$ and $R^{Z2}$ and 1 of $R^{Y1}$ and $R^{Y2}$ form a bridging group, this is to be understood as a ring formed at two non-adjacent carbon atoms of the N-containing heterocycloalkyl, linked to form a $C_1$-$C_2$ alkylene linker, e.g., $C_1$ or $C_2$ alkylene group. An example of a bridging group comprised within compounds of formula (I') includes, but is not limited to,

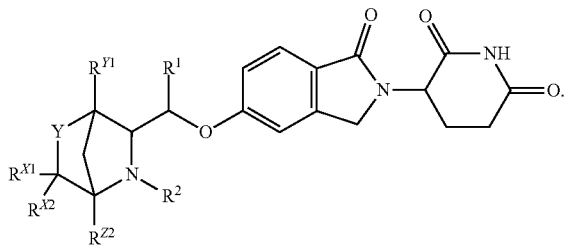

As used herein, the term "optionally substituted" includes unsubstituted or substituted.

As used herein, "⁎" denotes the point of attachment to the other part of the molecule.

As used herein, the term nitrogen protecting group (PG) in a compound of formula (X) or any intermediates in any of the general schemes 1 to 4 and subformulae thereof refers to a group that should protect the functional groups concerned against unwanted secondary reactions, such as acylations, etherifications, esterifications, oxidations, solvolysis and similar reactions. It may be removed under deprotection conditions. Depending on the protecting group employed, the skilled person would know how to remove the protecting group to obtain the free amine $NH_2$ group by reference to known procedures. These include reference to organic chemistry textbooks and literature procedures such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$alkyl (e.g., tert-butyl), preferably $C_1$-$C_4$alkyl, more preferably $C_1$-$C_2$alkyl, most preferably $C_1$alkyl which is mono-, di- or tri-substituted by trialkylsilyl-$C_1$-$C_7$alkoxy (e.g., trimethylsilylethoxy), aryl, preferably phenyl, or a heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g., two or three, residues, e.g., selected from the group consisting of $C_1$-$C_7$alkyl, hydroxy, $C_1$-$C_7$alkoxy (e.g., para-methoxy benzyl (PMB)), $C_2$-$C_8$-alkanoyl-oxy, halogen, nitro, cyano, and $CF_3$, aryl-$C_1$-$C_2$-alkoxycarbonyl (preferably phenyl-$C_1$-$C_2$-alkoxycarbonyl (e.g., benzyloxycarbonyl (Cbz), benzyloxymethyl (BOM), pivaloyloxymethyl (POM)), $C_1$-$C_{10}$-alkenyloxycarbonyl, $C_1$-$C_6$alkylcarbonyl (e.g., acetyl or pivaloyl), $C_6$-$C_{10}$-arylcarbonyl; $C_1$-$C_6$-alkoxycarbonyl (e.g., tertbutoxycarbonyl (Boc), methylcarbonyl, trichloroethoxycarbonyl (Troc), pivaloyl (Piv), allyloxycarbonyl), $C_6$-$C_{10}$-aryl$C_1$-$C_6$-alkoxycarbonyl (e.g., 9-fluorenylmethyloxycarbonyl (Fmoc)), allyl or cinnamyl, sulfonyl or sulfenyl, succinimidyl group, silyl groups (e.g., triarylsilyl, trialkylsilyl, triethylsilyl (TES), trimethylsilylethoxymethyl (SEM), trimethylsilyl (TMS), triisopropylsilyl or tertbutyldimethylsilyl).

According to the disclosure, the preferred protecting group (PG) can be selected from the group comprising tert-butyloxycarbonyl (Boc), benzyloxycarbonyl (Cbz), para-methoxy benzyl (PMB), methyloxycarbonyl, trimethylsilylethoxymethyl (SEM) and benzyl. The protecting group (PG) is preferably tert-butyloxycarbonyl (Boc).

In some embodiments, the compounds of the disclosure are selective over other proteins.

As used herein, the term "therapeutic agent" in connection with methods of reducing WIZ protein expression levels and/or inducing fetal hemoglobin (HbF) expression, refers to a substance that results in a detectably lower expression of WIZ gene or WIZ protein or lower activity level of WIZ proteins as compared to those levels without such substance. In some embodiments, the substance is a small molecule compound that can target WIZ for degradation (e.g., through E3 ubiquitin pathway, also known as "WIZ degrader", e.g., a compound as described herein). In some embodiments, the substance is an anti-WIZ shRNA. In some embodiments, the substance is an anti-WIZ siRNA. In some embodiments, the substance is an anti-WIZ ASO. In some embodiments, the substance is an anti-WIZ AMO (anti-miRNA oligonucleotide). In some embodiments, the substance is an anti-WIZ antisense nucleic acid. In some embodiments, the substance is a composition or a cell or a population of cells (that comprises gRNA molecules described herein) described herein.

As used herein, the term "small molecule" refers to an agent with a molecular weight <900 daltons. The small molecule according to the present disclosure can target WIZ protein for degradation, e.g., through E3 ubiquitin pathway and/or induce fetal hemoglobin (HbF) expression. In an embodiment the small molecule refers to a compound as disclosed herein, e.g. a compound of formula (I').

As used herein, an "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

As used herein, antisense oligonucleotides (ASOs) are single strands of DNA or RNA that are complementary to a chosen sequence. In the case of antisense RNA they prevent protein translation of certain messenger RNA strands by binding to them, in a process called hybridization. Antisense oligonucleotides can be used to target a specific, complementary (coding or non-coding) RNA. If binding takes place this hybrid can be degraded by the enzyme RNase H.

As used herein "modulator" or "degrader", means, for example, a compound of the disclosure, that effectively modulates, decreases, or reduces the levels of a specific protein (e.g., WIZ) or degrades a specific protein (e.g., WIZ). The amount of a specific protein (e.g., WIZ) degraded can be measured by comparing the amount of the specific protein (e.g., WIZ) remaining after treatment with a compound of the disclosure as compared to the initial amount or level of the specific protein (e.g., WIZ) present as measured prior to treatment with a compound of the disclosure.

As used herein "selective modulator", "selective degrader", or "selective compound" means, for example, a compound of the disclosure, that effectively modulates, decreases, or reduces the levels of a specific protein (e.g., WIZ) or degrades a specific protein (e.g., WIZ) to a greater extent than any other protein. A "selective modulator", "selective degrader", or "selective compound" can be identified, for example, by comparing the ability of a compound to modulate, decrease, or reduce the levels of or to degrade a specific protein (e.g., WIZ) to its ability to modulate, decrease, or reduce the levels of or to degrade other proteins. In some embodiments, the selectivity can be identified by measuring the $EC_{50}$ or $IC_{50}$ of the compounds. Degradation may be achieved through mediation of an E3 ligase, e.g., E3-ligase complexes comprising the protein Cereblon.

In one embodiment, the specific protein degraded is WIZ protein. In an embodiment, at least about 30% of WIZ is degraded compared to initial levels. In an embodiment, at least about 40% of WIZ is degraded compared to initial levels. In an embodiment, at least about 50% of WIZ is degraded compared to initial levels. In an embodiment, at least about 60% of WIZ is degraded compared to initial levels. In an embodiment, at least about 70% of WIZ is degraded compared to initial levels. In an embodiment, at least about 75% of WIZ is degraded compared to initial levels. In an embodiment, at least about 80% of WIZ is degraded compared to initial levels. In an embodiment, at least about 85% of WIZ is degraded compared to initial levels. In an embodiment, at least about 90% of WIZ is degraded compared to initial levels. In an embodiment, at least about 95% of WIZ is degraded compared to initial levels. In an embodiment, over 95% of WIZ is degraded compared to initial levels. In an embodiment, at least about 99% of WIZ is degraded compared to initial levels.

In an embodiment, the WIZ is degraded in an amount of from about 30% to about 99% compared to initial levels. In an embodiment, the WIZ is degraded in an amount of from about 40% to about 99% compared to initial levels. In an embodiment, the WIZ is degraded in an amount of from about 50% to about 99% compared to initial levels. In an embodiment, the WIZ is degraded in an amount of from about 60% to about 99% compared to initial levels. In an embodiment, the WIZ is degraded in an amount of from about 70% to about 99% compared to initial levels. In an embodiment, the WIZ is degraded in an amount of from about 80% to about 99% compared to initial levels. In an embodiment, the WIZ is degraded in an amount of from about 90% to about 99% compared to initial levels. In an embodiment, the WIZ is degraded in an amount of from about 95% to about 99% compared to initial levels. In an embodiment, the WIZ is degraded in an amount of from about 90% to about 95% compared to initial levels.

As used herein, the terms "inducing fetal hemoglobin", "fetal hemoglobin induction", or "increasing fetal hemoglobin expression" refer to increasing the percentage of HbF in the blood of a subject. In an embodiment, the amount of total HbF in the blood of the subject increases. In an embodiment, the amount of total hemoglobin in the blood of the subject increases. In an embodiment, the amount of HbF is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

In an embodiment, the total hemoglobin in the blood, e.g., the blood in a subject, is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the disclosure that, when administered to a subject, is effective to (1) at least partially alleviate, prevent and/or ameliorate a condition, or a disorder or a disease (i) mediated by WIZ, or (ii) associated with WIZ activity, or (iii) characterized by activity (normal or abnormal) of WIZ: (2) reduce or inhibit the activity of WIZ; or (3) reduce or inhibit the expression of WIZ. In another embodiment, the term "a therapeutically effective amount" refers to the amount of the compound of the disclosure that, when administered to a cell, or a tissue, or a non-cellular biological material, or a medium, is effective to at least partially reducing or inhibiting the activity of WIZ; or at least partially reducing or inhibiting the expression of WIZ.

"HBF-dependent disease or disorder" means any disease or disorder which is directly or indirectly affected by the modulation of HbF protein levels.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the disclosure (especially in the context of the claims) are to be construed to cover both the singular and plural unless otherwise indicated herein or clearly contradicted by the context.

Various enumerated embodiments of the disclosure are described herein. It will be recognized that features specified in each embodiment may be combined with other specified features to provide further embodiments of the disclosure.

ENUMERATED EMBODIMENTS

Embodiment 1. A compound of formula (I') or a pharmaceutically acceptable salt, hydrate, solvate, prodrug, stereoisomer, or tautomer thereof,

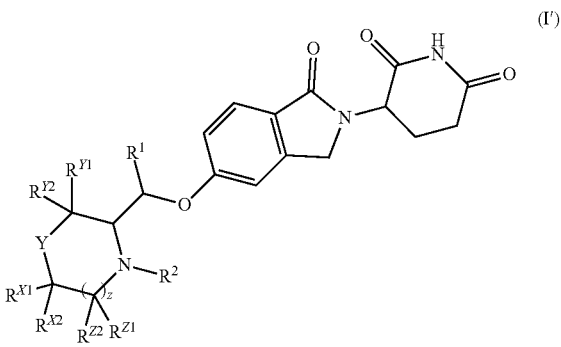

wherein:
Y is selected from O, $CH_2$, $CF_2$, and CHF;
z is an integer from 0 to 2;
$R^{X1}$ and $R^{X2}$ are each independently selected from hydrogen and $C_1$-$C_6$alkyl;
$R^{Y1}$ and $R^{Y2}$ are each independently selected from hydrogen and $C_1$-$C_6$alkyl;
$R^{Z1}$ and $R^{Z2}$ are both hydrogen or
1 of $R^{Z1}$ and $R^{Z2}$ and 1 of $R^{Y1}$ and $R^{Y2}$ together form a $C_1$-$C_2$ alkylene bridging group and the other of $R^{Z1}$ and $R^{Z2}$ and $R^{Y1}$ and $R_{Y2}$ are both hydrogen;
$R^1$ is selected from hydrogen and $C_1$-$C_6$alkyl;
$R^2$ is selected from hydrogen, —C(=O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, $C_3$-$C_8$cycloalkyl and —O—($R^{2a}$),
wherein the aryl, heteroaryl, heterocyclyl, and cycloalkyl are each independently substituted with 0-5 $R^4$;
$R^{2a}$ is $C_1$-$C_6$alkyl wherein the alkyl is substituted with 0-1 substituent independently selected from $C_6$-$C_{10}$aryl;
$R^3$ is selected from —CH=$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and
wherein the aryl, heteroaryl, heterocyclyl, and cycloalkyl are each independently substituted with 0-5 $R^4$;
$R^{3a}$ and $R^{3b}$ together with the carbon atom to which they are attached form a $C_3$-$C_8$cycloalkyl ring;

each $R^{3c}$ is at each occurrence independently selected from —C(=O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-3 substituents each independently selected from —CN, $C_1$-$C_6$alkyl, $C_1$-$C_6$alkoxyl, hydroxyl and $C_1$-$C_6$haloalkyl;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, $C_1$-$C_6$alkyl, 4- to 6-membered heterocyclyl comprising 1-2 heteroatoms independently selected from N, O, and S and $C_3$-$C_6$cycloalkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, halogen, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

Embodiment 2. A compound of formula (I') according to claim 1 or a pharmaceutically acceptable salt, hydrate, solvate, prodrug, stereoisomer, or tautomer thereof, wherein: z is 1; and 1 of $R^{Z1}$ and $R^{Z2}$ and 1 of $R^{Y1}$ and $R^{Y2}$ together form a $C_1$-$C_2$ alkylene bridging group and the other of $R^{Z1}$ and $R^{Z2}$ and $R^{Y1}$ and $R^{Y2}$ are both hydrogen.

Embodiment 3. A compound of formula (I') according to claim 1 or 2 or a pharmaceutically acceptable salt, hydrate, solvate, prodrug, stereoisomer, or tautomer thereof, wherein: z is 1; and 1 of $R^{Z1}$ and $R^{Z2}$ and 1 of $R^{Y1}$ and $R^{Y2}$ together form a $C_1$ alkylene bridging group and the other of $R^{Z1}$ and $R^{Z2}$ and $R^{Y1}$ and $R^{Y2}$ are both hydrogen.

Embodiment 4. A compound according to Embodiment 1 or a pharmaceutically acceptable salt, hydrate, solvate, prodrug, stereoisomer, or tautomer thereof, of formula (I)

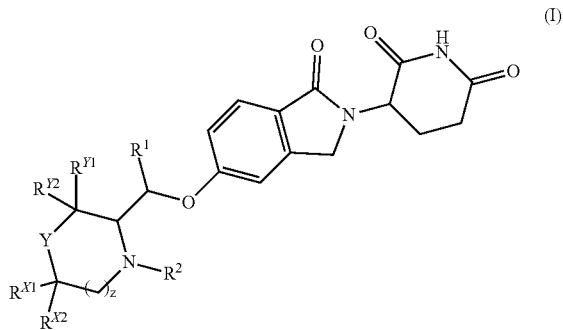

(I)

wherein:

Y is selected from O, $CH_2$, and $CF_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^1$ is selected from hydrogen and $C_1$-$C_6$alkyl;

$R^2$ is selected from hydrogen, —C(=O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the aryl, heteroaryl, heterocyclyl, and cycloalkyl are each independently substituted with 0-5 $R^4$;

$R^3$ is selected from —CH=$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3a}$ and $R^{3b}$ together with the carbon atom to which they are attached form a $C_3$-$C_6$cycloalkyl ring;

each $R^{3c}$ is at each occurrence independently selected from —C(=O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-3 substituents each independently selected from —CN, $C_1$-$C_6$alkyl, $C_1$-$C_6$alkoxyl, and hydroxyl;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

Embodiment 5. The compound of Embodiment 1 or 4, or a pharmaceutically acceptable salt thereof, of formula (I-i)

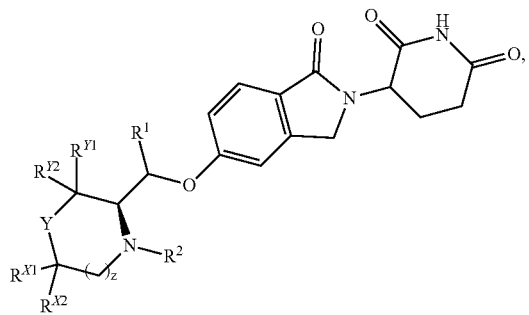

wherein $R^{X1}$, $R^{X2}$, $R^{Y1}$, $R^{Y2}$, $R^1$, $R^2$ and z are defined according to any of the preceding Embodiments.

Embodiment 6. The compound of Embodiment 1, 4 or 5, or a pharmaceutically acceptable salt thereof, of formula (I-i-a) or (I-i-b)

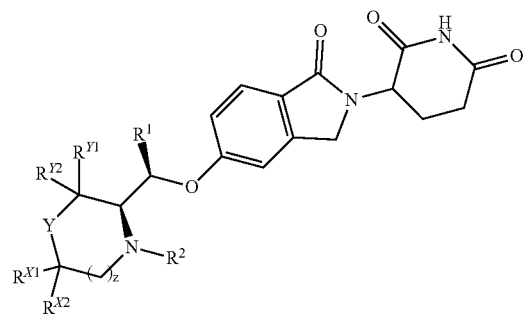

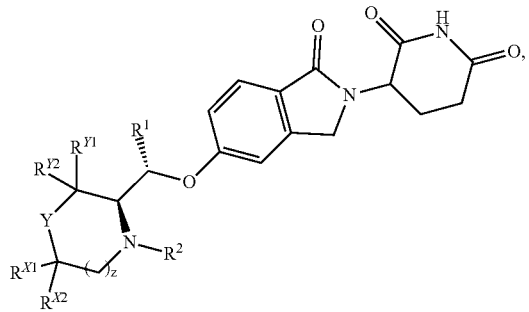

wherein $R^{X1}$, $R^{X2}$, $R^{Y1}$, $R^{Y2}$, $R^1$, $R^2$ and z are defined according to any of the preceding Embodiments.

Embodiment 7. The compound of Embodiment 1, 4 to 6, or a pharmaceutically acceptable salt, hydrate, solvate, prodrug, stereoisomer, or tautomer thereof, of formula (I-i-c) or (I-i-d)

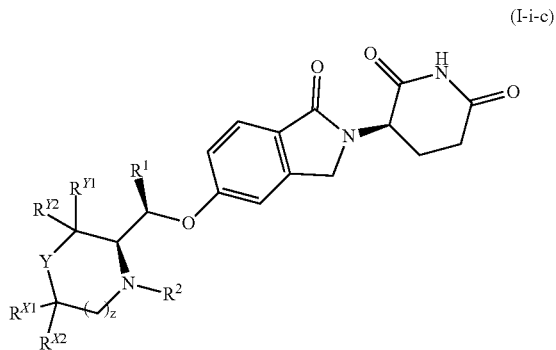

(I-i-c)

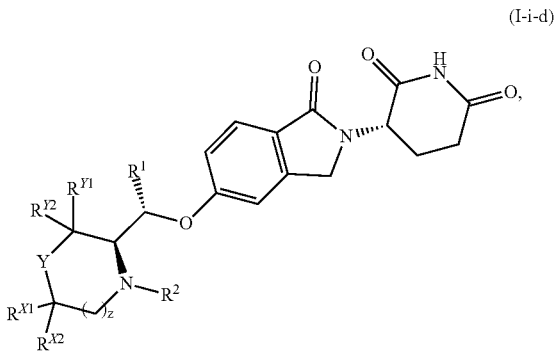

(I-i-d)

wherein $R^{X1}$, $R^{X2}$, $R^{Y1}$, $R^{Y2}$, $R^1$, $R^2$ and z are defined according to any of the preceding Embodiments.

Embodiment 8. The compound of Embodiment 1, 4 to 6, or a pharmaceutically acceptable salt, hydrate, solvate, prodrug, stereoisomer, or tautomer thereof, of formula (I-i-e) or (I-i-f)

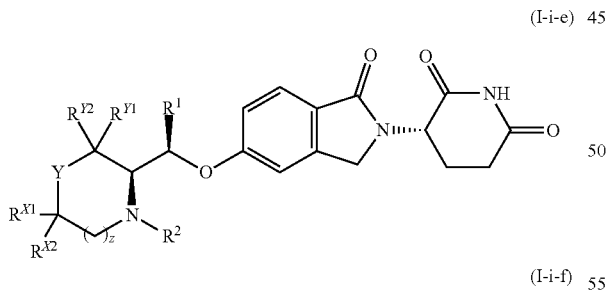

(I-i-e)

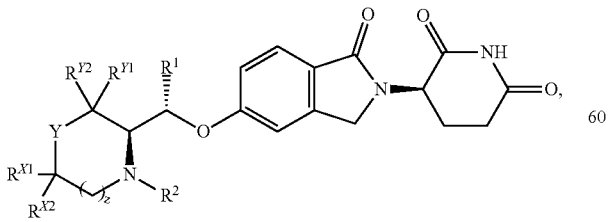

(I-i-f)

wherein $R^{X1}$, $R^{X2}$, $R^{Y1}$, $R^{Y2}$, $R^1$, $R^2$ and z are defined according to any of the preceding Embodiments.

Embodiment 9. The compound of Embodiment 1 or 4, or a pharmaceutically acceptable salt, hydrate, solvate, prodrug, stereoisomer, or tautomer thereof, of formula (I-ii)

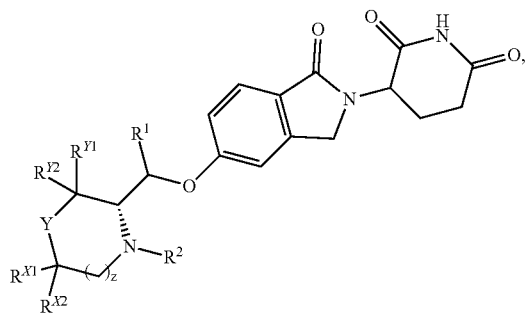

(I-i), wherein $R^{X1}$, $R^{X2}$, $R^{Y1}$, $R^{Y2}$, $R^1$, $R^2$ and z are defined according to any of the preceding Embodiments.

Embodiment 10. The compound of Embodiment 1, 4, 9, or a pharmaceutically acceptable salt, hydrate, solvate, prodrug, stereoisomer, or tautomer thereof, of formula (I-ii-a) or (I-ii-b)

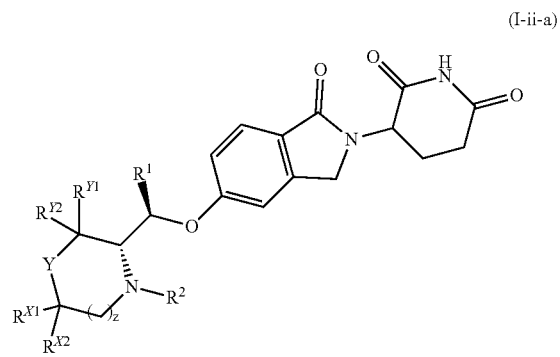

(I-ii-a)

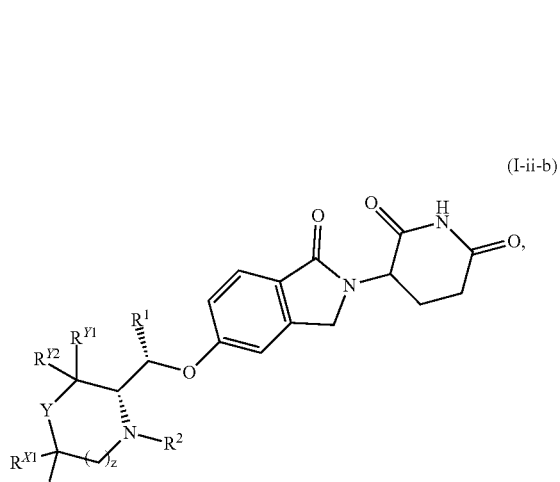

(I-ii-b)

wherein $R^{X1}$, $R^{X2}$, $R^{Y1}$, $R^{Y2}$, $R^1$, $R^2$ and z are defined according to any of the preceding Embodiments.

Embodiment 11. The compound of Embodiment 1, 4, 9, 10, or a pharmaceutically acceptable salt, hydrate, solvate, prodrug, stereoisomer, or tautomer thereof, of formula (I-ii-c) or (I-ii-d)

(I-ii-c)

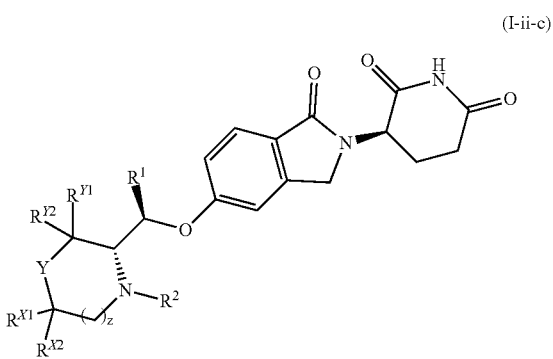

(I-ii-d)

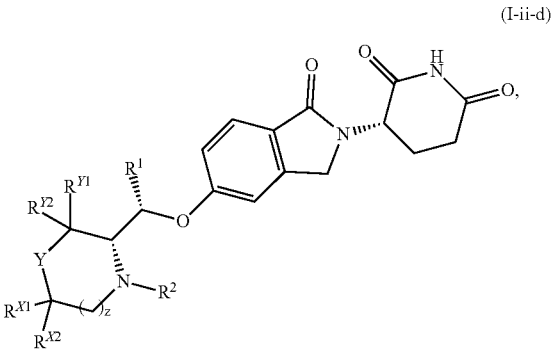

wherein $R^{X1}$, $R^{X2}$, $R^{Y1}$, $R^{Y2}$, $R^1$, $R^2$ and z are defined according to any of the preceding Embodiments.

Embodiment 12. The compound of Embodiment 1, 4, 9, 10, or a pharmaceutically acceptable salt, hydrate, solvate, prodrug, stereoisomer, or tautomer thereof, of formula (I-ii-e) or (I-ii-f)

(I-ii-e)

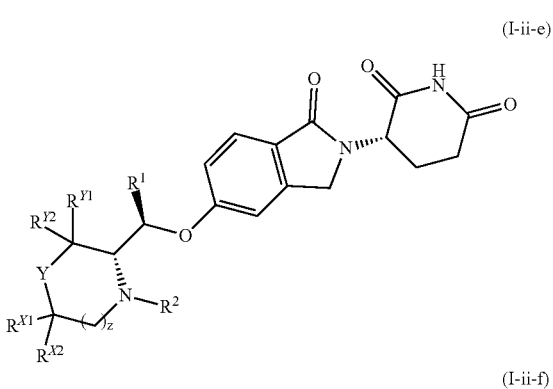

(I-ii-f)

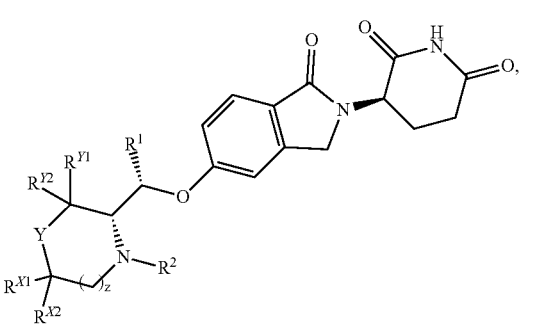

wherein $R^{X1}$, $R^{X2}$, $R^{Y1}$, $R^{Y2}$, $R^1$, $R^2$ and z are defined according to any of the preceding Embodiments.

Embodiment 13. The compound of any of the preceding Embodiments, or a pharmaceutically acceptable salt, hydrate, solvate, prodrug, stereoisomer, or tautomer thereof, wherein:

Y is selected from O, $CH_2$, and $CF_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^1$ is selected from hydrogen and $C_1$-$C_6$alkyl;

$R^2$ is selected from hydrogen, —C(=O)—$R^3$, $C_3$-$C_8$cycloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, and wherein the aryl, heteroaryl, heterocyclyl, and cycloalkyl are each independently substituted with 0-5 $R^4$;

$R^3$ is selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3c}$ is at each occurrence independently selected from $NR^{3e}R^{3f}$, $C_1$-$C_6$alkoxyl, —O—$R^{3d}$ hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

$R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-2 substituents each independently selected from —CN, $C_1$-$C_6$alkyl, and $C_1$-$C_6$alkoxyl;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

Embodiment 14. The compound of any of the preceding Embodiments, or a pharmaceutically acceptable salt, hydrate, solvate, prodrug, stereoisomer, or tautomer thereof, wherein:

Y is selected from 0, and $CH_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^1$ is selected from hydrogen and $C_1$-$C_6$alkyl;

$R^2$ is selected from hydrogen, —C(=O)—$R^3$, $C_3$-$C_8$cycloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, and wherein the aryl, heteroaryl, heterocyclyl, and cycloalkyl are each independently substituted with 0-5 $R^4$;

$R^3$ is selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3c}$ is at each occurrence independently selected from di($C_1$-$C_6$alkyl)amino, $C_1$-$C_6$alkoxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^4$ is at each occurrence independently selected from $C_6$-$C_{10}$aryl, —O—$C_6$-$C_{10}$aryl $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-2 substituents each independently selected from —CN $C_1$-$C_6$alkyl, methoxy, and ethoxy;

$R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl; $R^{4b}$ is at each occurrence independently selected from —CN, —C(=O)$NR^{6a}R^{6b}$, $NR^{6a}R^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, $NH_2$, and halogen; $R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

Embodiment 15. The compound of any of the preceding Embodiments, or a pharmaceutically acceptable salt, hydrate, solvate, prodrug, stereoisomer, or tautomer thereof, wherein:

Y is selected from O, and $CH_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

wherein when $R^{X1}$ and $R^{X2}$ are both $C_1$-$C_6$alkyl, then $R^{Y1}$ and $R^{Y2}$ are both hydrogen, and wherein when $R^{X1}$ and $R^{X2}$ are both hydrogen, then $R^{Y1}$ and $R^{Y2}$ are both $C_1$-$C_6$alkyl;

$R^1$ is selected from hydrogen and $C_1$-$C_6$alkyl;

$R^2$ is selected from hydrogen, —C(=O)—$R^3$, $C_3$-$C_8$cycloalkyl, and $C_1$-$C_6$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, and wherein the aryl, heteroaryl, heterocyclyl, and cycloalkyl are each independently substituted with 0-5 $R^4$;

$R^3$ is selected from $C_6$-$C_{10}$aryl, 5- to 10-membered heteroaryl comprising 1-4 heteroatoms independently selected from N, O, and S, and $C_3$-$C_8$cycloalkyl, and $C_1$-$C_3$alkyl, wherein the alkyl is substituted with 0-2 $R^{3c}$, and wherein the aryl, heteroaryl, and cycloalkyl are each independently substituted with 0-5 $R^4$;

$R^{3c}$ is at each occurrence independently selected from $C_6$-$C_{10}$aryl, 5- to 10-membered heteroaryl comprising 1-4 heteroatoms independently selected from N, O, and S, and $C_3$-$C_8$cycloalkyl, wherein the aryl, heteroaryl, and cycloalkyl are each independently substituted with 0-5 $R^4$;

$R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_{10}$alkyl, $C_1$-$C_6$alkoxyl, $C_1$-$C_6$haloalkyl, —$SO_2R^{4c}$, halogen, hydroxyl, —CN, oxo, $C_1$-$C_6$haloalkoxyl, —C(=O)—O—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-1 substituent independently selected from —CN; $R^{4a}$ is at each occurrence independently selected from —CN, $C_1$-$C_6$alkoxyl, $C_1$-$C_6$haloalkyl, halogen, hydroxyl, —C(=O)—O—($R^5$), 5- to 10-membered heteroaryl comprising 1-4 heteroatoms independently selected from N, O, and S, di($C_1$-$C_6$alkyl)amino$C_1$-$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, —C(=O)$NR^{6a}R^{6b}$, 5- to 10-membered heteroaryl comprising 1-4 heteroatoms independently selected from N, O, and S, —C(=O)—OH, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, $NH_2$, and halogen;

$R^5$ is selected from $C_1$-$C_6$alkyl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N and O, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from 4- to 6-membered heterocyclyl comprising 1-2 heteroatoms independently selected from N, O, and S.

Embodiment 16. The compound of any of the preceding Embodiments, or a pharmaceutically acceptable salt, hydrate, solvate, prodrug, stereoisomer, or tautomer thereof, wherein:

Y is selected from O, and $CH_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

wherein when $R^{X1}$ and $R^{X2}$ are both $C_1$-$C_6$alkyl, then $R^{Y1}$ and $R^{Y2}$ are both hydrogen, and wherein when $R^{X1}$ and $R^{X2}$ are both hydrogen, then $R^{Y1}$ and $R^{Y2}$ are both $C_1$-$C_6$alkyl;

$R^1$ is selected from hydrogen and $C_1$-$C_6$alkyl;

$R^2$ is selected from $C_3$-$C_8$cycloalkyl, $C_1$-$C_6$alkyl, —$(CH_2)_{1-2}$-$C_6$-$C_{10}$aryl, —$(CH_2)_{1-2}$-5- to 10-membered heteroaryl comprising 1-4 heteroatoms independently selected from N, O, and S, —$(CH_2)_{1-2}$-4- to 6-membered heterocyclyl comprising 1-2 heteroatoms independently selected from N and O, and —$(CH_2)_{1-2}$—$C_3$-$C_8$cycloalkyl, and wherein the aryl, heteroaryl, heterocyclyl, and cycloalkyl are each independently substituted with 0-4 $R^4$;

$R^4$ is at each occurrence independently selected from $C_6$-$C_{10}$aryl, —O—$C_6$-$C_{10}$aryl, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_{10}$alkyl, $C_1$-$C_6$alkoxyl, $C_1$-$C_6$haloalkyl, —$SO_2R^{4c}$, halogen, hydroxyl, —CN, oxo, $C_1$-$C_6$haloalkoxyl, —C(=O)—O—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-1 substituent independently selected from —CN;

$R^{4a}$ is at each occurrence independently selected from —CN, $C_1$-$C_6$alkoxyl, $C_1$-$C_6$haloalkyl, halogen, —C(=O)—O—($R^5$), 5- to 10-membered heteroaryl comprising 1-4 heteroatoms independently selected from N, O, and S, and $C_1$-$C_6$alkyl, wherein the alkyl is substituted with 0-1 $R^{4b}$, and wherein the heteroaryl is substituted with 0-2 $R^{4a-1}$;

$R^{4a-1}$ is at each occurrence independently selected from $C_1$-$C_6$alkyl, and di($C_1$-$C_6$alkyl)amino$C_1$-$C_6$alkyl;

$R^{4b}$ is at each occurrence independently selected from —C(=O)N$R^{6a}R^{6b}$, 5- to 10-membered heteroaryl comprising 1-4 heteroatoms independently selected from N and O, —C(=O)—OH, 4- to 6-membered heterocyclyl comprising 1 or 2 heteroatoms independently selected from N, O, and S, and $C_6$-$C_{10}$aryl, wherein the aryl is substituted with 0-1 substituent each independently selected from —CN, and $C_1$-$C_6$haloalkyl;

$R^{4c}$ is selected from $C_6$-$C_{10}$aryl, and $NH_2$;

$R^5$ is selected from $C_1$-$C_6$alkyl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N and O, wherein the heterocyclyl is substituted with 0-1 $R^{6c}$;

$R^{6c}$ is at each occurrence independently selected from $C_6$-$C_{10}$aryl$C_1$-$C_6$alkyl, —C(=O)—O—($C_1$-$C_6$alkyl), oxo, and $C_1$-$C_6$alkyl, wherein the alkyl is substituted with 0-1 substituent independently selected from 4- to 6-membered heterocyclyl comprising 1-2 heteroatoms independently selected from N, O, and S.

Embodiment 17. The compound of any of the preceding Embodiments, or a pharmaceutically acceptable salt, hydrate, solvate, prodrug, stereoisomer, or tautomer thereof, wherein:

Y is selected from O, and $CH_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

wherein when $R^{X1}$ and $R^{X2}$ are both $C_1$-$C_6$alkyl, then $R^{Y1}$ and $R^{Y2}$ are both hydrogen, and wherein $R^{X1}$ and $R^{X2}$ are both hydrogen, then $R^{Y1}$ and $R^{Y2}$ are both $C_1$-$C_6$alkyl;

$R^1$ is selected from hydrogen and $C_1$-$C_6$alkyl;

$R^2$ is selected from $C_1$-$C_6$alkyl, —($CH_2$)-phenyl, —($CH_2$)-5- to 10-membered heteroaryl comprising 1-4 heteroatoms independently selected from N, O, and S, —($CH_2$)-6-membered heterocyclyl comprising 1 heteroatom independently selected from N and O, and —($CH_2$)—$C_3$-$C_8$cycloalkyl, and wherein the phenyl, heteroaryl, heterocyclyl, and cycloalkyl are each independently substituted with 0-3 $R^4$;

$R^4$ is at each occurrence independently selected from phenyl, —O-phenyl, —O-(5- to 10-membered heteroaryl comprising 1-4 heteroatoms independently selected from N, O, and S), 5- to 10-membered heteroaryl comprising 1-4 heteroatoms independently selected from N, O, and S, 6-membered heterocyclyl comprising 1-2 heteroatoms independently selected from N and O, $C_1$-$C_{10}$alkyl, $C_1$-$C_6$alkoxyl, $C_1$-$C_6$fluoroalkyl, —$SO_2R^{4c}$, halogen, hydroxyl, —CN, oxo, $C_1$-$C_6$fluoroalkoxyl, —C(=O)—O—($R^5$), —C(=O)—N$R^{6a}R^{6b}$, N$R^{6a}R^{6b}$, —NH—C(=O)—O—($C_1$-$C_6$alkyl), and $C_3$-$C_8$cycloalkyl, wherein the phenyl, —O-phenyl, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-1 substituent independently selected from —CN;

$R^{4a}$ is at each occurrence independently selected from $C_1$-$C_6$fluoroalkyl, fluoro, —C(=O)—O—($R^5$), 5- to 10-membered heteroaryl comprising 1-4 heteroatoms independently selected from N, O, and S, and $C_1$-$C_6$alkyl, wherein the alkyl is substituted with 0-1 $R^{4b}$, and wherein the heteroaryl is substituted with 0-2 $R^{4a-1}$;

$R^{4a-1}$ is at each occurrence independently selected from $C_1$-$C_6$alkyl, and di($C_1$-$C_6$alkyl)amino$C_1$-$C_6$alkyl;

$R^{4b}$ is at each occurrence independently selected from —C(=O)N$R^{6a}R^{6b}$, 5- to 10-membered heteroaryl comprising 1-4 heteroatoms independently selected from N, O, and S, —C(=O)—OH, 4- to 6-membered heterocyclyl comprising 1 or 2 heteroatoms independently selected from N and O, and phenyl, wherein the phenyl is substituted with 0-1 substituent each independently selected from —CN;

$R^{4c}$ is selected from phenyl, and $NH_2$;

$R^5$ is selected from $C_1$-$C_6$alkyl, and benzyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N and O, wherein the heterocyclyl is substituted with 0-1 $R^{6c}$;

$R^{6c}$ is at each occurrence independently selected from benzyl, —C(=O)—O—($C_1$-$C_6$alkyl), oxo, and $C_1$-$C_6$alkyl, wherein the alkyl is substituted with 0-1 substituent independently selected from 4-membered heterocyclyl comprising 1 O heteroatom.

Embodiment 18. The compound of any of the preceding Embodiments, or a pharmaceutically acceptable salt, hydrate, solvate, prodrug, stereoisomer, or tautomer thereof, wherein $R^3$ is selected from phenyl, 5- to 10-membered heteroaryl comprising 1-4 heteroatoms independently selected from N, O, and S, 4- to 6-membered heterocyclyl comprising 1-2 heteroatoms independently selected from N and O, $C_3$-$C_6$cycloalkyl, and $C_1$-$C_6$alkyl, wherein the alkyl is substituted with 0-3 $R^{3c}$, and wherein the phenyl, heteroaryl, heterocyclyl, and cycloalkyl are each independently substituted with 0-4 $R^4$.

Embodiment 19. The compound of any of the preceding Embodiments, or a pharmaceutically acceptable salt, hydrate, solvate, prodrug, stereoisomer, or tautomer thereof, wherein $R^3$ is selected from phenyl, 5- to 10-membered heteroaryl comprising 1-4 heteroatoms independently selected from N, O, and S, 4- to 6-membered heterocyclyl comprising 1-2 heteroatoms independently selected from N and O, $C_3$-$C_6$cycloalkyl, and $C_1$-$C_6$alkyl, wherein the alkyl is substituted with 0-1 $R^{3c}$, wherein the phenyl, heteroaryl, heterocyclyl, and cycloalkyl are each independently substituted with 0-4 $R^4$, and wherein $R^{3c}$ at each occurrence is independently selected from phenyl, 5- to 10-membered heteroaryl comprising 1-4 heteroatoms independently selected from N, O, and S, 4- to 6-membered heterocyclyl comprising 1-2 heteroatoms independently selected from N and O, and $C_3$-$C_6$cycloalkyl.

Embodiment 20. The compound of any of the preceding Embodiments, or a pharmaceutically acceptable salt, hydrate, solvate, prodrug, stereoisomer, or tautomer thereof, wherein $R^3$ is selected from phenyl, 5-10 membered heteroaryl comprising 1-4 heteroatoms independently selected from N, O, and S, 4-, 5-, or 6-membered heterocyclyl comprising 1-2 heteroatoms independently selected from N, O, and S, $C_3$-$C_8$cycloalkyl, —($CH_2$)$_{1-2}$-phenyl, —($CH_2$)$_{1-2}$-5-10 membered heteroaryl comprising 1-4 heteroatoms independently selected from N, O, and S, —($CH_2$)$_{1-2}$-4- to 6-membered heterocyclyl comprising 1-2 heteroatoms independently selected from N, O, and S, and —($CH_2$)$_{1-2}$—$C_3$-$C_8$cycloalkyl.

Embodiment 21. The compound of any of the preceding Embodiments, or a pharmaceutically acceptable salt, hydrate, solvate, prodrug, stereoisomer, or tautomer thereof, wherein each $R^4$ is, at each occurrence, independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, heteroaryl, and heterocyclyl are each independently substituted with 0-2 $R^{4a}$, wherein the —O-aryl, arylalkyl-O—, and —O-heteroaryl, are each independently substituted with 0-3 $R^{4a}$, wherein the alkyl and alkoxyl are each independently substituted with 0-1 $R^{4b}$, and wherein the cycloalkyl is substituted with 0-2 substituents each independently selected from —CN, $C_1$-$C_6$alkyl, methoxy and ethoxy.

Embodiment 22. The compound of any of the preceding Embodiments, or a pharmaceutically acceptable salt, hydrate, solvate, prodrug, stereoisomer, or tautomer thereof, wherein each $R^4$ is at each occurrence independently selected from phenyl, —O-phenyl, benzyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_5$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the alkyl and alkoxyl are each independently substituted with 0-1 $R^{4b}$, wherein the cycloalkyl is substituted with 0-2 substituents each independently selected from —CN, $C_1$-$C_6$alkyl, methoxy and ethoxy, wherein the phenyl, and heteroaryl, are each independently substituted with 0-2 substituents each independently selected from —CN, $C_1$-$C_6$alkyl, $C_1$-$C_6$alkoxyl, $C_1$-$C_6$haloalkyl, and halogen, wherein the heterocyclyl is independently substituted with 0-2 substituents each independently selected from —C(=O)—O—($R^5$), and $C_1$-$C_6$alkyl, wherein the alkyl is independently substituted with 0-1 substituent independently selected from $C_6$-$C_{10}$aryl, and 4- to 6-membered heterocyclyl comprising 1-2 heteroatoms independently selected from N and O, and wherein the —O-phenyl, benzyl-O—, and —O-heteroaryl are each independently substituted with 0-3 substituents each independently selected from hydroxyl, —C(=O)—O—($R^5$), halogen, $C_1$-$C_6$alkyl, wherein the alkyl is independently substituted with 0-1 substituent independently selected from —C(=O)—$NR^{6a}R^{6b}$, and $NR^{6a}R^{6b}$, and 5-10 membered heteroaryl comprising 1-4 heteroatoms independently selected from N, O, and S, which heteroaryl is substituted with 0-2 substituents each independently selected from $C_1$-$C_6$alkyl, and di($C_1$-$C_6$alkyl)amino$C_1$-$C_6$alkyl.

Embodiment 23. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(=O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from indolyl, imidazopyridyl, isoquinolinyl, benzooxazolonyl, pyridinyl, pyrimidinyl, pyridinonyl, benzotriazolyl, pyridazinyl, pyrazolotriazinyl, indazolyl, benzimidazolyl, quinolinyl, triazolyl, pyrazolyl, thiazolyl, oxazolyl, isooxazolyl, pyrrolyl, oxadiazolyl, imidazolyl, pyrrolopyridinyl, tetrahydroindazolyl, quinoxalinyl, thiadiazolyl, pyrazinyl, oxazolopyridinyl, pyrazolopyrimidinyl, benzoxazolyl, indolinyl, isooxazolopyridinyl, dihydropyridooxazinyl, and tetrazolyl, and wherein said heteroaryl is, at each occurrence, independently substituted with 0-4 $R^4$, wherein $R^4$ is as defined according to any of the preceding Embodiments.

Embodiment 24. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(=O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from:

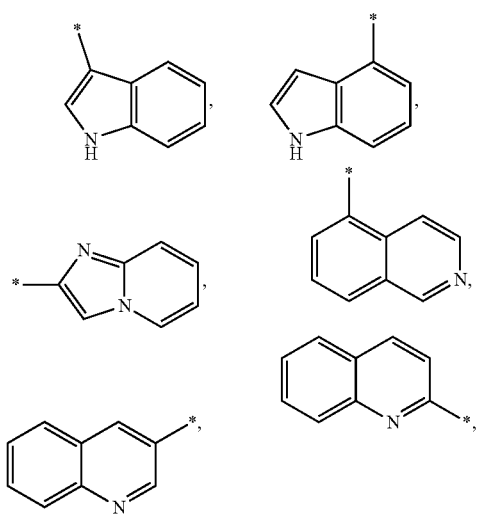

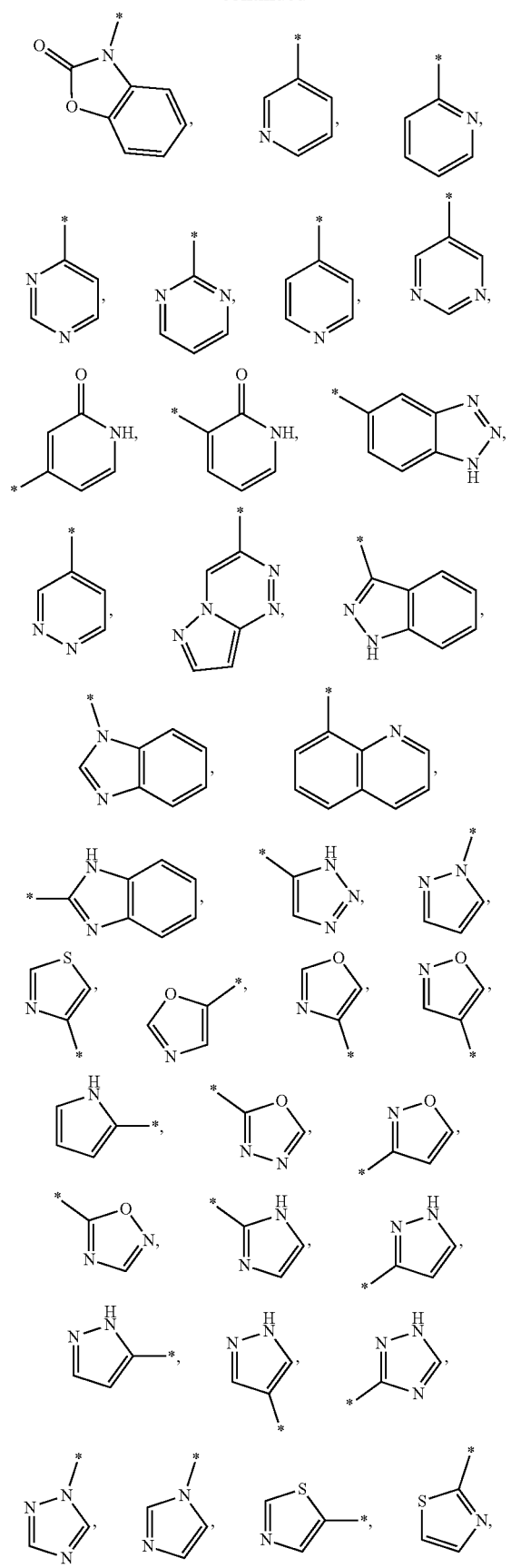
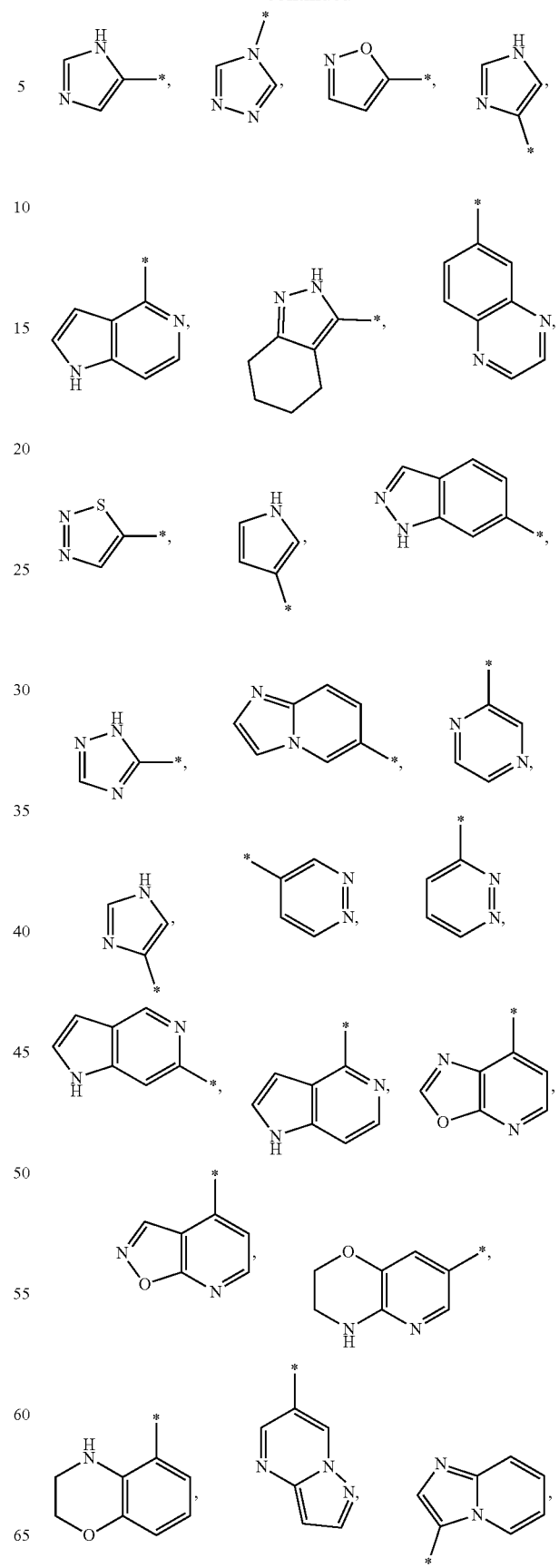

-continued

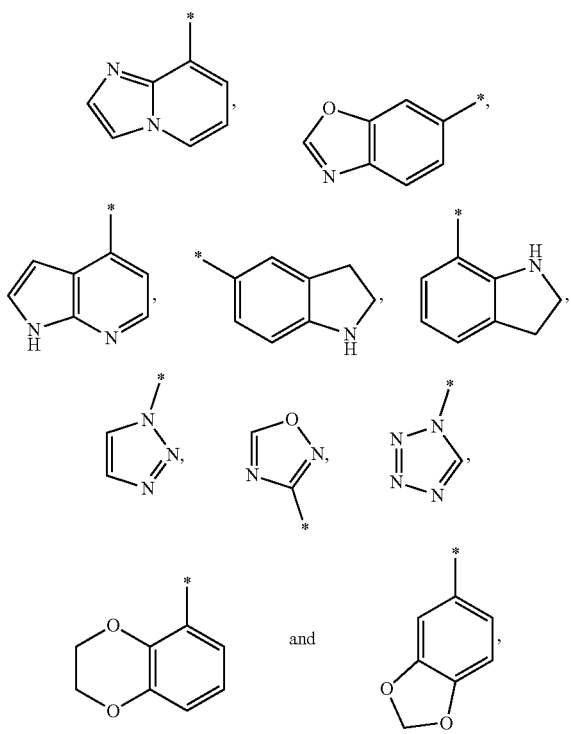

and wherein said heteroaryl is, at each occurrence, independently substituted with 0-4 $R^4$, wherein $R^4$ is as defined according to any of the preceding Embodiments.

Embodiment 25. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(=O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from:

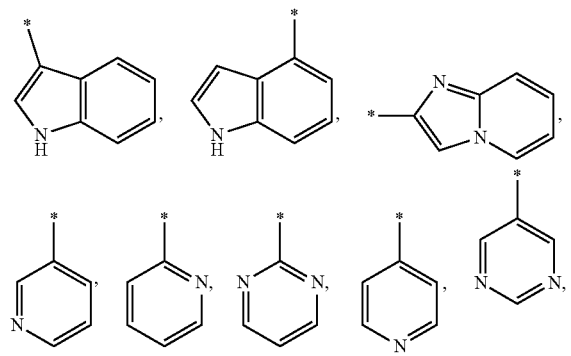

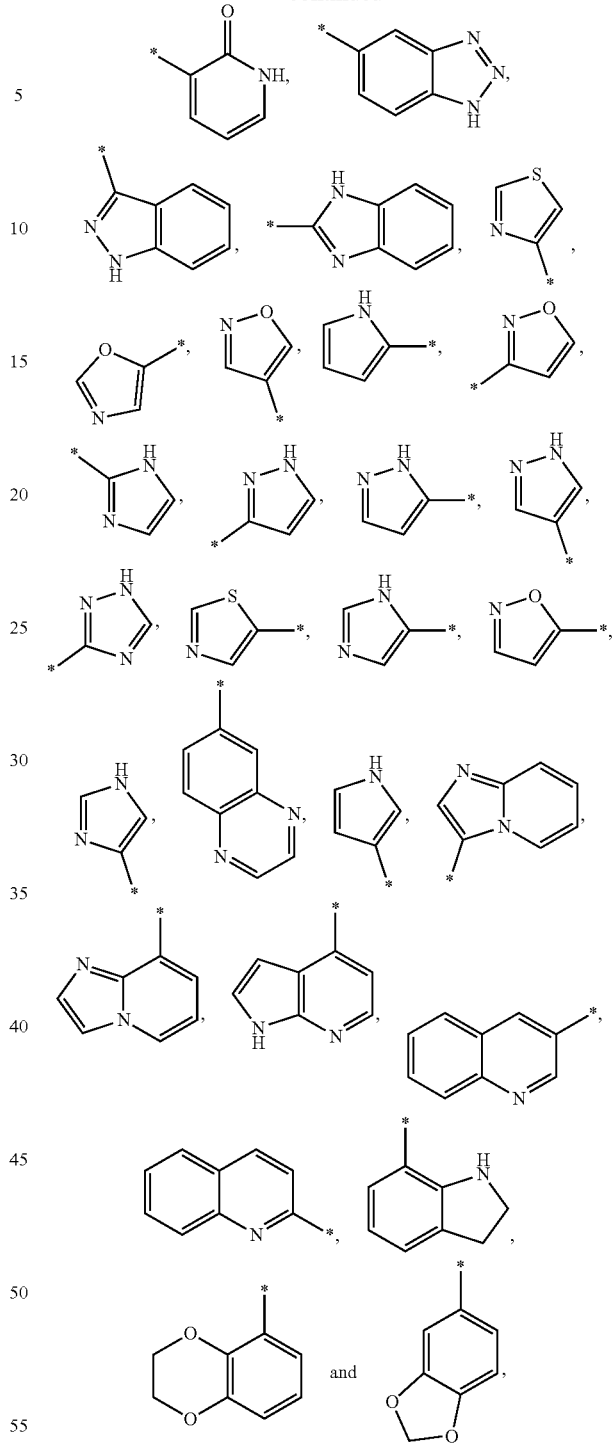

and wherein said heteroaryl is, at each occurrence, independently substituted with 0-3 $R^4$, wherein $R^4$ is as defined according to any of the preceding Embodiments.

Embodiment 26. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(=O)—R$^3$, wherein R$^3$ is 5- to 10-membered heteroaryl comprising 1-4 heteroatoms independently selected from N, O, and S, or C$_1$-C$_6$alkyl substituted with 5- to 10-membered heteroaryl comprising 1-4 heteroatoms independently selected from N, O, and S, wherein the heteroaryl is, at each occurrence, independently selected from:

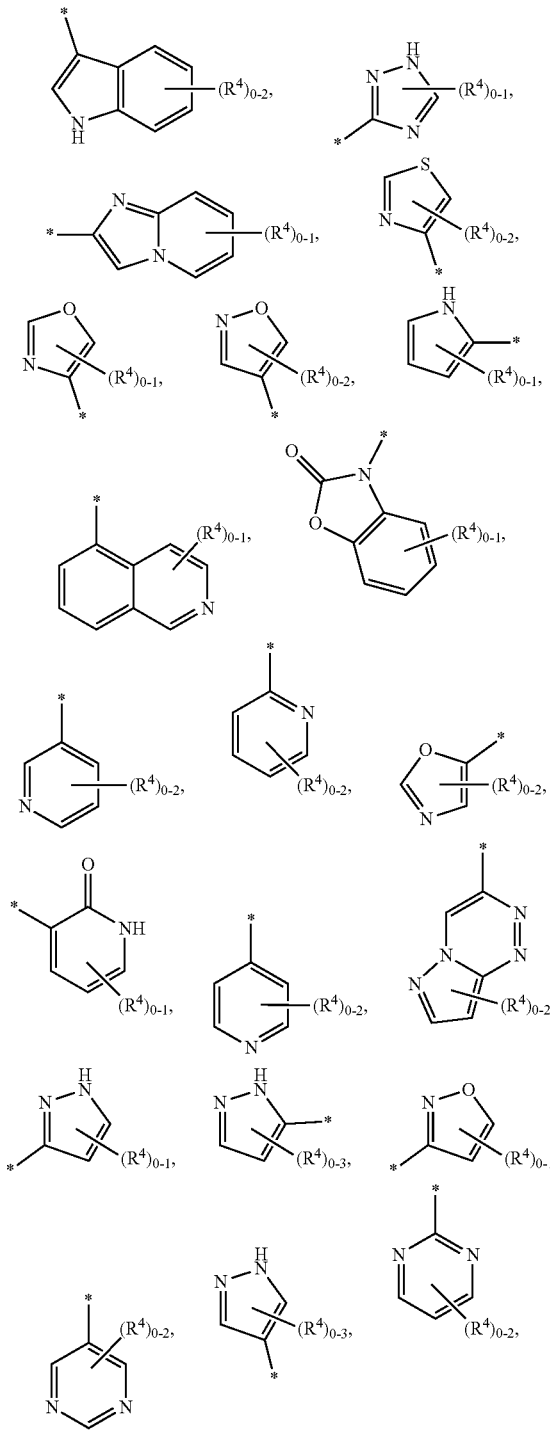
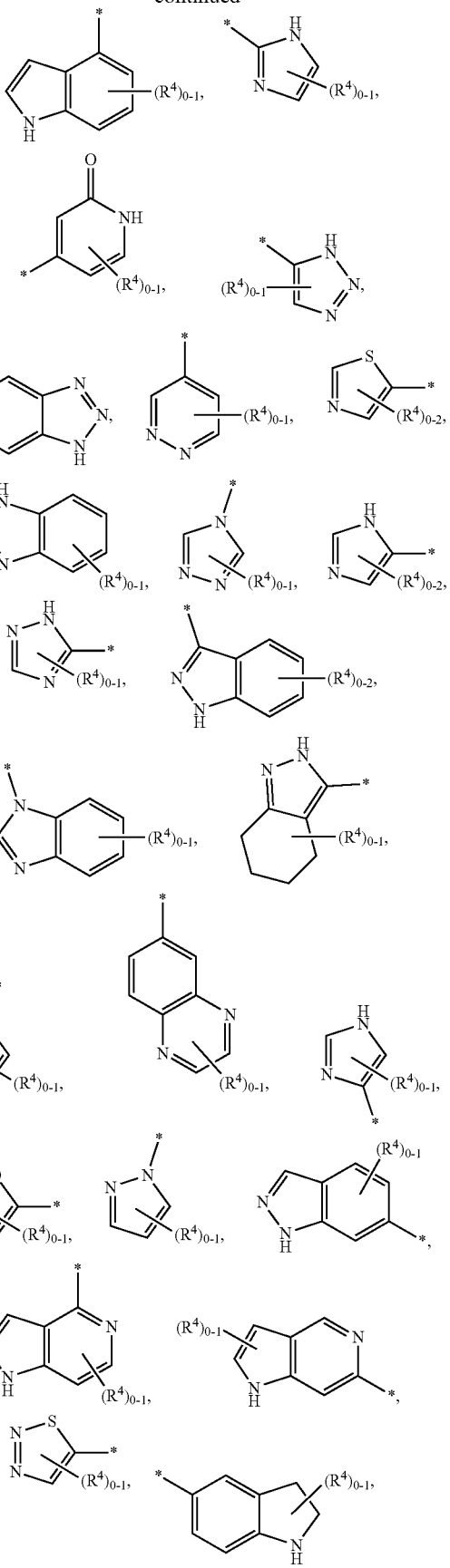

-continued

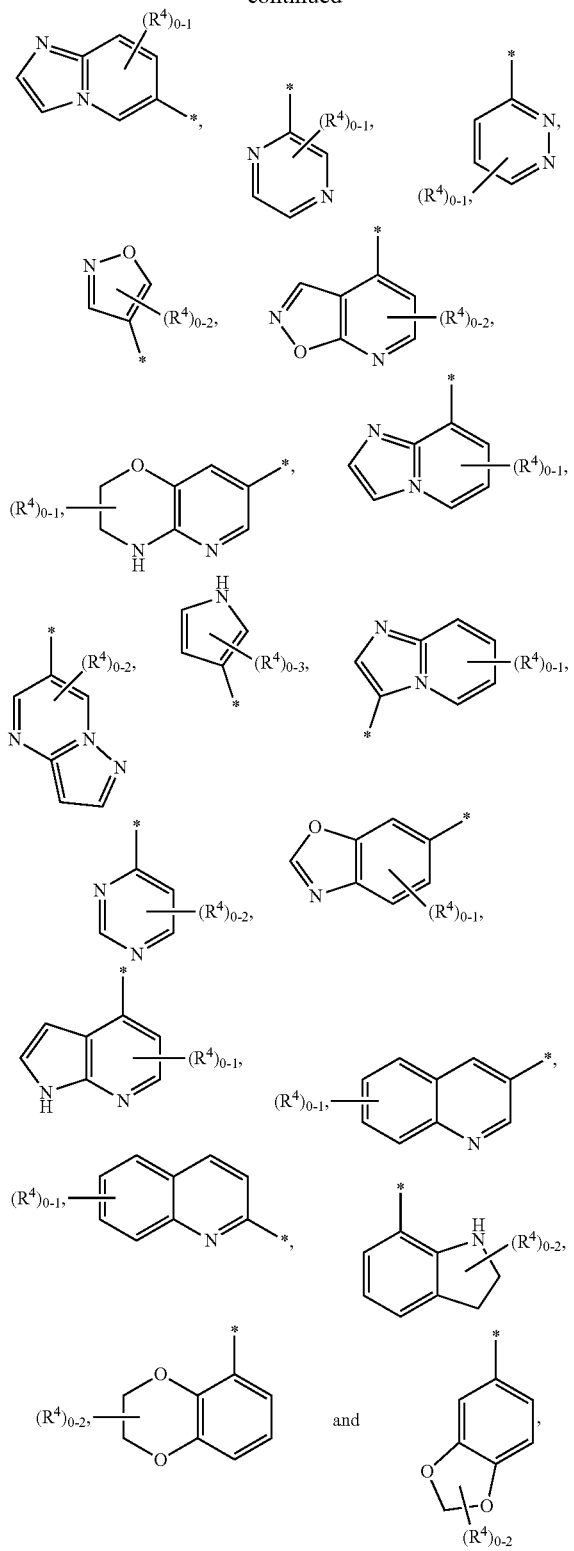

wherein R⁴ is as defined according to any of the preceding Embodiments.

Embodiment 27. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(═O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from:

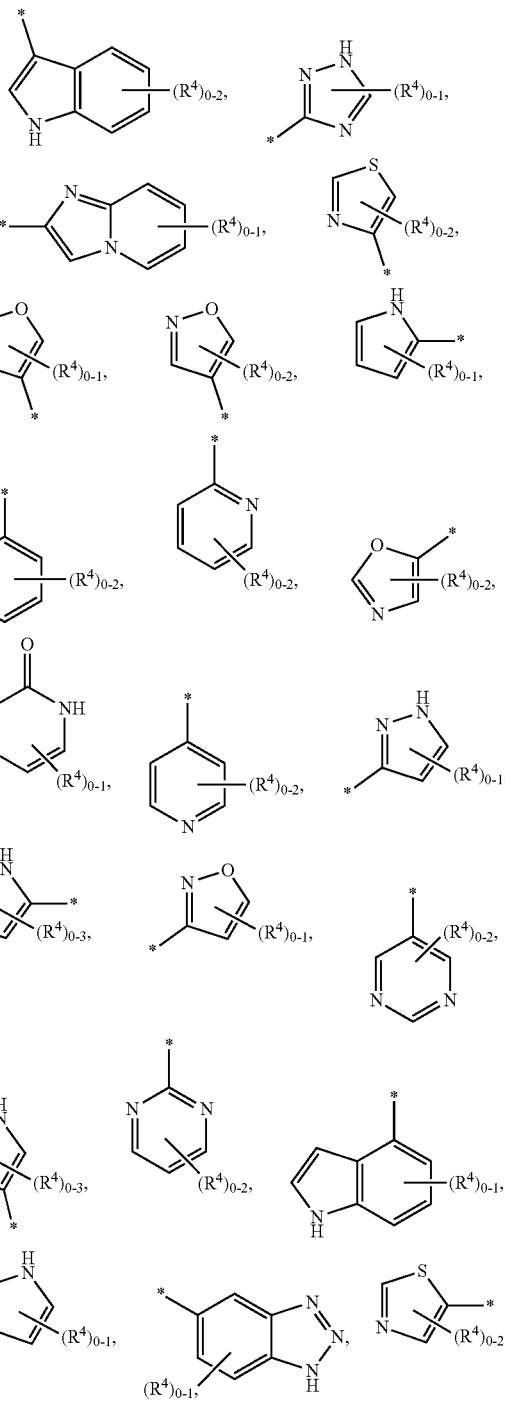

-continued

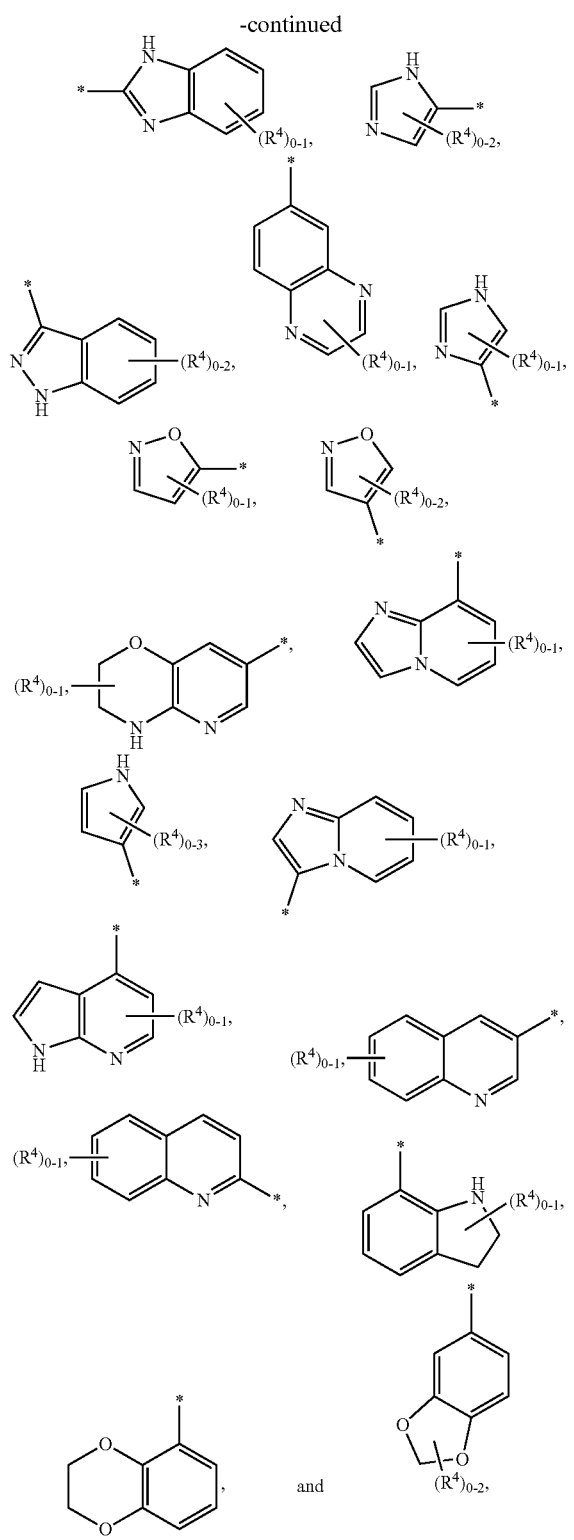

wherein $R^4$ is as defined according to any of the preceding Embodiments.

Embodiment 28. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 5- to 10-membered heteroaryl comprising 1-4 heteroatoms independently selected from N, O, and S, or —C(=O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from:

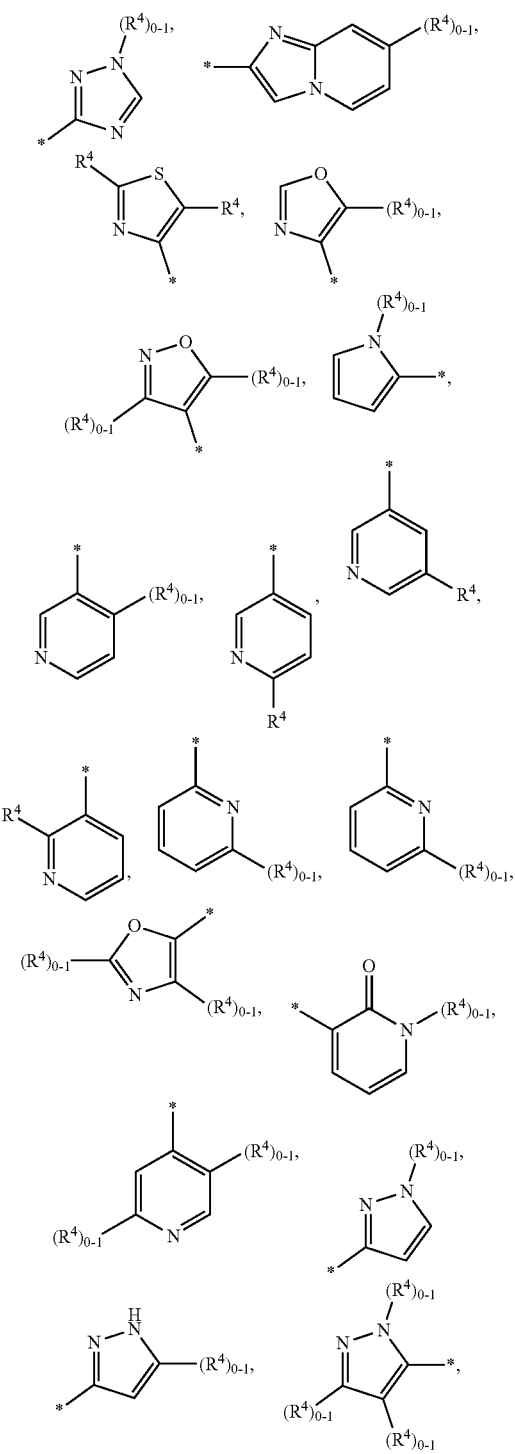

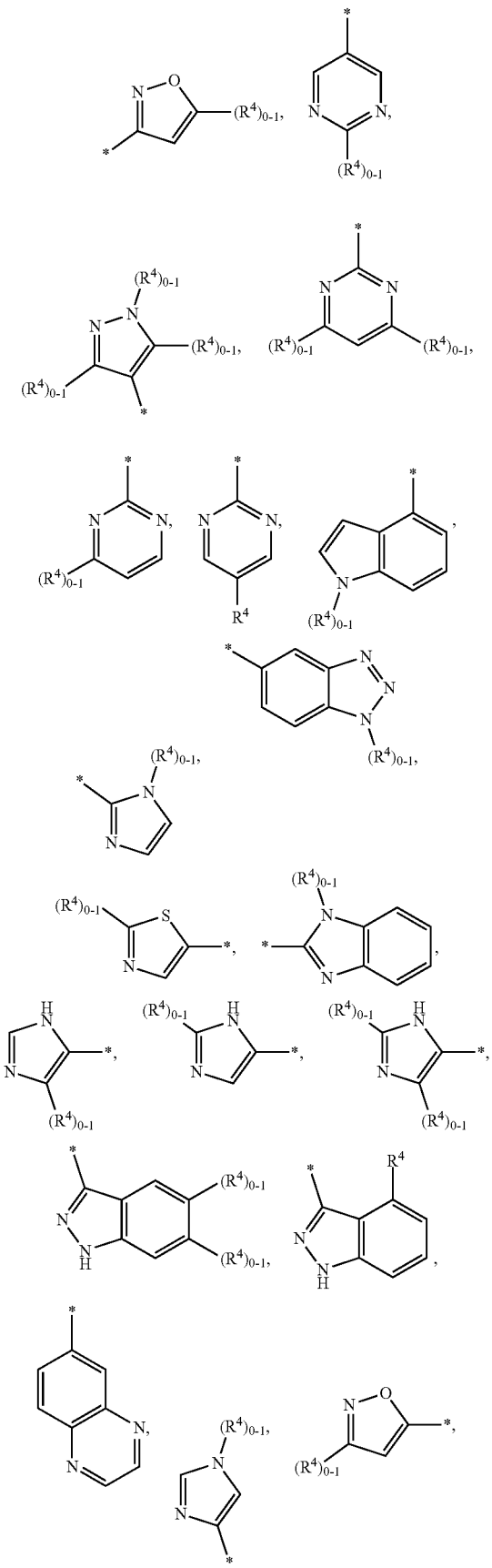
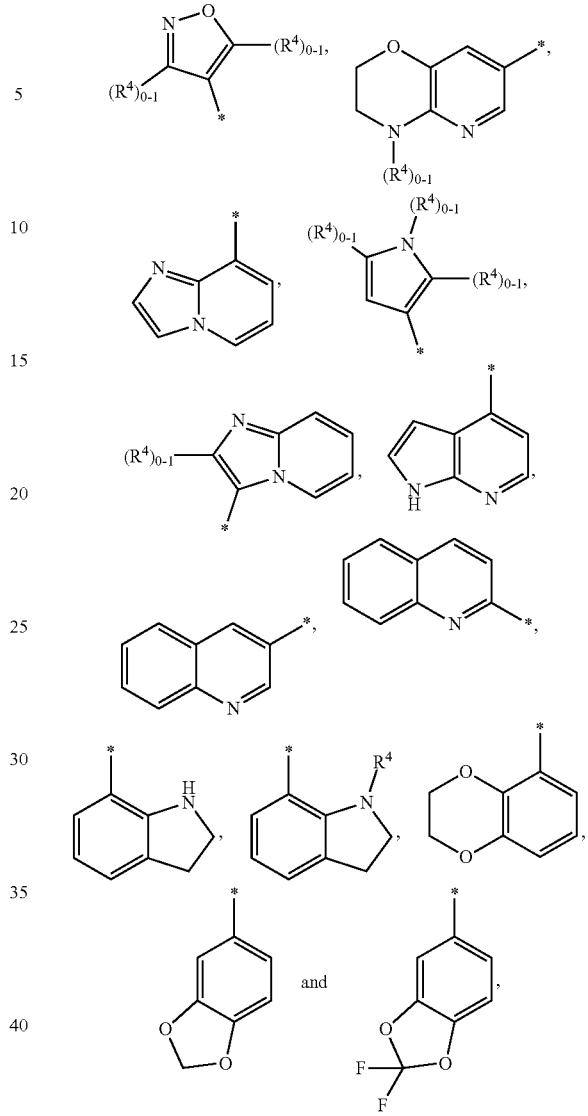

wherein R⁴ is as defined according to any of the preceding Embodiments.

Embodiment 29. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from piperidinyl, piperazinyl, morpholinyl, tetrahydrofuran, dihydroisoxazolyl, tetrahydropyran, pyrrolidinyl and 2-oxaspiro[3.3]heptanyl, and wherein said heterocyclyl is, at each occurrence, independently substituted with 0-4 $R^4$, wherein $R^4$ is as defined according to any of the preceding Embodiments.

Embodiment 30. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from:

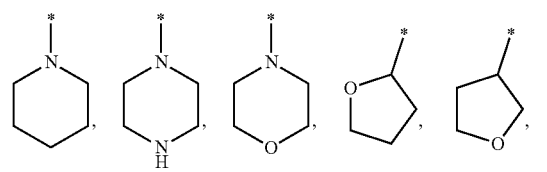

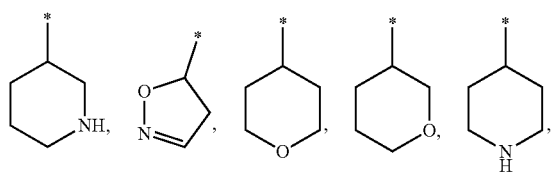

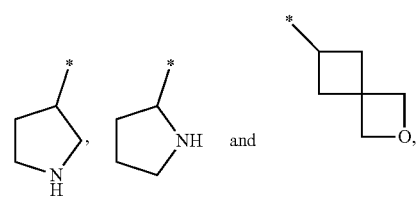

and wherein said heterocyclyl is, at each occurrence, independently substituted with 0-3 $R^4$, wherein $R^4$ is as defined according to any of the preceding Embodiments.

Embodiment 31. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$alkyl, e.g., $C_1$alkyl) substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from

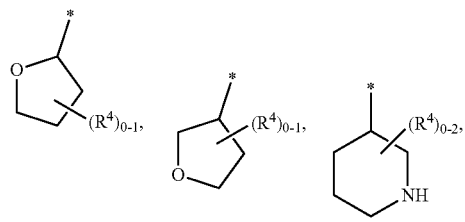

-continued

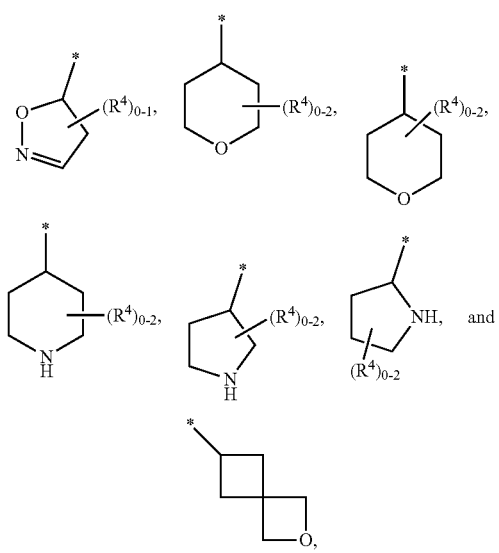

wherein $R^4$ is as defined according to any of the preceding Embodiments.

Embodiment 32. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$alkyl, e.g., $C_1$alkyl) substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from:

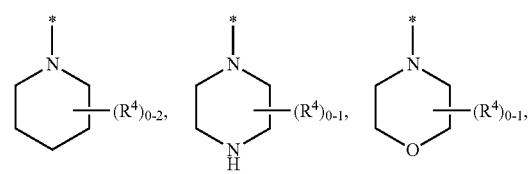

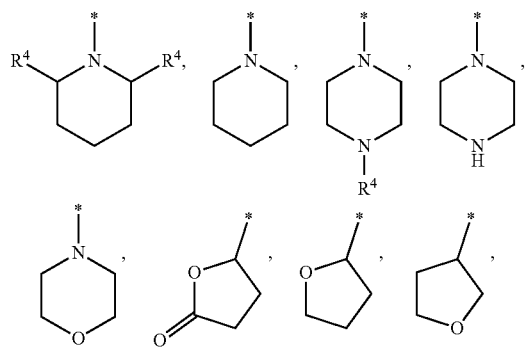

-continued

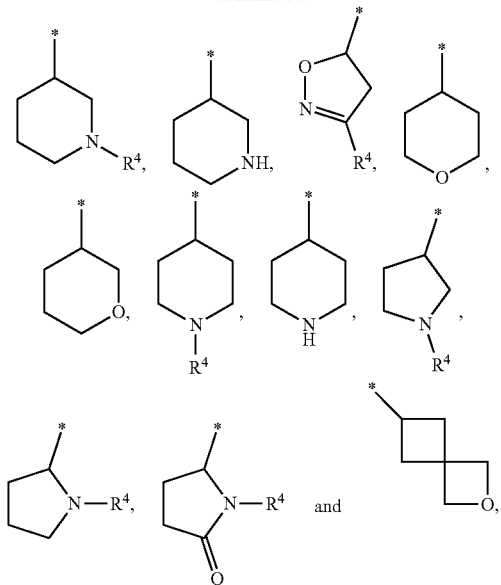

wherein $R^4$ is as defined according to any of the preceding Embodiments.

Embodiment 33. The compound of any of the preceding Embodiments, or a pharmaceutically acceptable salt, hydrate, solvate, prodrug, stereoisomer, or tautomer thereof, wherein each $R^4$ is, at each occurrence, independently selected from phenyl, —O-phenyl, benzyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_5$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—$NR^{6a}R^{6b}$, $NR^{6a}R^{6b}$, —NH—C(=O)—O—($C_1$-$C_6$alkyl), and $C_3$-$C_6$cycloalkyl, wherein the phenyl, —O-phenyl, benzyl-O—, —O-heteroaryl, heteroaryl, and heterocyclyl are each independently substituted with 0-3 $R^4$,
wherein the alkyl and alkoxyl are each independently substituted with 0-1 $R^{4b}$, and
wherein the cycloalkyl is substituted with 0-3 substituents each independently selected from —CN, $C_1$-$C_6$alkyl, $C_1$-$C_6$alkoxyl, and hydroxyl.

Embodiment 34. The compound of any of the preceding Embodiments, or a pharmaceutically acceptable salt, hydrate, solvate, prodrug, stereoisomer, or tautomer thereof, wherein each $R^4$ is, at each occurrence, independently selected from phenyl, —O-phenyl, benzyl-O—, —O-(5- to 10-membered heteroaryl comprising 1-4 heteroatoms independently selected from N, O, and S), 5- to 10-membered heteroaryl comprising 1-4 heteroatoms independently selected from N and O, 4- to 6-membered heterocyclyl comprising 1-2 heteroatoms independently selected from N, O, and S, $C_1$-$C_5$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_6$cycloalkyl, wherein the phenyl, —O-phenyl, benzyl-O—, —O— heteroaryl, heteroaryl, and heterocyclyl are each independently substituted with 0-3 $R^4$,
wherein the alkyl and alkoxyl are each independently substituted with 0-1 $R^{4b}$, and
wherein the cycloalkyl is substituted with 0-3 substituents each independently selected from —CN, $C_1$-$C_5$alkyl, $C_1$-$C_6$alkoxyl, and hydroxyl.

Embodiment 35. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_6$-$C_{10}$aryl, or —C(=O)—$R^3$,
wherein $R^3$ is $C_6$-$C_{10}$aryl, or $C_1$-$C_6$alkyl substituted with $C_6$-$C_{10}$aryl,
wherein the aryl is, at each occurrence, independently substituted with 0-3 $R^4$,
wherein each $R^4$ is, at each occurrence, independently selected from phenyl, —O-phenyl, benzyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_5$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, $C_1$-$C_6$haloalkoxyl, —C(=O)—O—($R^5$), —C(=O)—$NR^{6a}R^{6b}$, $NR^{6a}R^{6b}$, —NH—C(=O)—O—($C_1$-$C_6$alkyl), and $C_3$-$C_6$cycloalkyl, wherein the phenyl, —O-phenyl, benzyl-O—, —O-heteroaryl, heteroaryl, and heterocyclyl are each independently substituted with 0-3 $R^{4a}$,
wherein the alkyl and alkoxyl are each independently substituted with 0-1 $R^{4b}$, and
wherein the cycloalkyl is substituted with 0-1 substituent independently selected from —CN.

Embodiment 36. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_6$-$C_{10}$aryl, or —C(=O)—$R^3$,
wherein $R^3$ is $C_6$-$C_{10}$aryl, or $C_1$-$C_6$alkyl substituted with $C_6$-$C_{10}$aryl,
wherein the aryl is, at each occurrence, independently substituted with 0-3 $R^4$,
wherein each $R^4$ is, at each occurrence, independently selected from —O-phenyl, benzyl-O—, —O-(5- to 10-membered heteroaryl comprising 1-4 heteroatoms independently selected from N, O, and S), 5- to 6-membered heteroaryl comprising 1-4 heteroatoms independently selected from N, O, and S, 4- to 6-membered heterocyclyl comprising 1 heteroatom independently selected from N and O, $C_1$-$C_5$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, $C_1$-$C_6$haloalkoxyl, —C(=O)—$NR^{6a}R^{61}$, and $NR^{6a}R^{6b}$,
wherein the alkyl and alkoxyl are each independently substituted with 0-1 $R^{4b}$,
wherein the —O-phenyl, benzyl-O—, and —O-heteroaryl, are each independently substituted with 0-2 substituents each independently selected from hydroxyl, —C(=O)—O—(R⁵), halogen, and C₁-C₆alkyl,
wherein the heterocyclyl is independently substituted with 0-1 substituent independently selected from C₁-C₆alkyl, and
wherein the heteroaryl is independently substituted with 0-1 substituent independently selected from —CN, C₁-C₆alkyl, C₁-C₆alkoxyl, and C₁-C₆haloalkyl.

Embodiment 37. The compound of any of the preceding Embodiments, or a pharmaceutically acceptable salt, hydrate, solvate, prodrug, stereoisomer, or tautomer thereof, wherein R² is unsubstituted C₁-C₆ alkyl or C₁-C₁₀ alkyl (e.g., C₁-C₆ alkyl, e.g., C₁alkyl) substituted with C₆-C₁₀aryl, or —C(=O)—R³,
wherein R³ is C₆-C₁₀aryl, or C₁-C₆alkyl substituted with C₆-C₁₀aryl,
wherein the aryl is, at each occurrence, independently substituted with 0-3 R⁴,
wherein each R⁴ is, at each occurrence, independently selected from oxadiazolyl, pyrazolyl, tetrazolyl, 4-membered heterocyclyl comprising 1 O heteroatom, C₁-C₅alkyl, C₁-C₆alkoxyl, C₁-C₆haloalkyl, fluoro, chloro, iodo, hydroxyl, —CN, —O-4- to 6-membered heterocyclyl comprising 1-2 heteroatoms independently selected from N, O, and S, —C(=O)—NR⁶ᵃR⁶ᵇ, and NR⁶ᵃR⁶ᵇ,
wherein the alkyl is independently substituted with 0-1 substituent independently selected from 5-6 membered heteroaryl comprising 1-4 heteroatoms independently selected from N, O, and S, C₁-C₆alkoxyl, and phenyl,
wherein the alkoxyl is independently substituted with 0-1 substituent independently selected from —C(=O)—N(CH₂)₄₋₅, and morpholinyl, wherein the point of attachment to said morpholinyl is via the N atom,
wherein the heterocyclyl is independently substituted with 0-1 substituent independently selected from C₁-C₆alkyl, and
wherein the oxadiazolyl, pyrazolyl, and tetrazolyl are each independently substituted with 0-1 substituent independently selected from —CN, C₁-C₆alkyl, C₁-C₆alkoxyl, and C₁-C₆haloalkyl.

Embodiment 38. The compound of any of the preceding Embodiments, or a pharmaceutically acceptable salt, hydrate, solvate, prodrug, stereoisomer, or tautomer thereof, wherein R² is selected from C₁-C₆ alkyl,

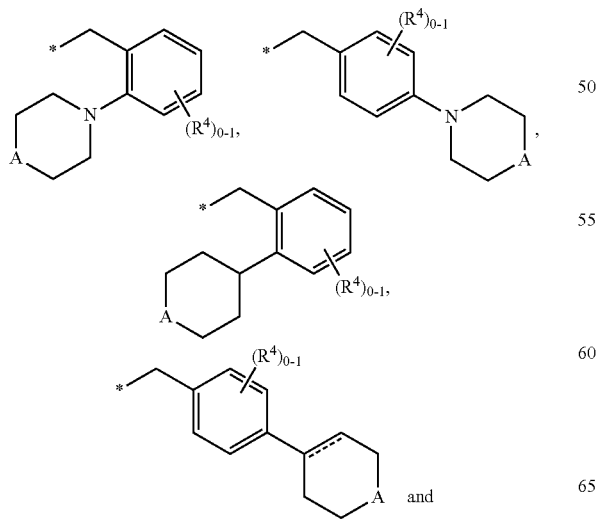

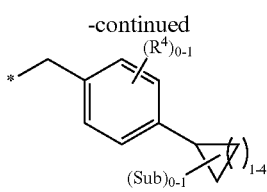

wherein
---- represent's an optional C=C double bond, which when present, A is O;
A is selected from N—R⁴ᵈ, O and CH₂;
R⁴ is selected from C₁-C₆alkyl, C₁-C₆alkoxyl, C₁-C₆haloalkyl, fluoro, chloro, iodo, hydroxyl and —CN;
R⁴ᵈ is selected from hydrogen, —C(=O)—O—(C₁-C₆alkyl), 4- to 6-membered heterocyclyl comprising 1 heteroatom selected from N and O, C₃-C₆cycloalkyl, C₁-C₆haloalkyl and C₁-C₆alkyl, wherein the alkyl is substituted with 0-1 substituent selected from C₃-C₆cycloalkyl, 4- to 6-membered heterocyclyl comprising 1-2 heteroatoms independently selected from N and O;
Sub is selected from C₁-C₆alkyl, halogen and C₁-C₆haloalkyl.

Embodiment 39. The compound of any of the preceding claims, or a pharmaceutically acceptable salt, hydrate, solvate, prodrug, stereoisomer, or tautomer thereof, wherein R² is selected from C₁-C₆ alkyl,

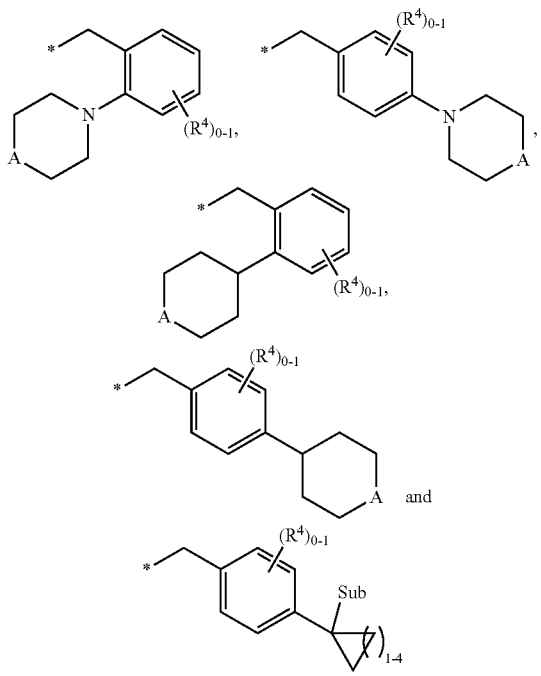

wherein
A is selected from N—R⁴ᵈ, O and CH₂;
R⁴ is C₁-C₆alkyl;
R⁴ᵈ is selected from hydrogen, —C(=O)—O—(C₁-C₆alkyl), 4- to 6-membered heterocyclyl comprising 1 heteroatom selected from N and O, C₃-C₆cycloalkyl, C₁-C₆haloalkyl and C₁-C₆alkyl, wherein the alkyl is substituted with 0-1 substituent selected from C₃-C₆cycloalkyl, 4- to 6-membered heterocyclyl comprising 1 O heteroatom;
Sub is C₁-C₆haloalkyl, e.g., CF₃.

Embodiment 40. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_3$-$C_8$cycloalkyl, or —C(=O)—$R^3$, wherein $R^3$ is $C_3$-$C_8$cycloalkyl, or $C_1$-$C_6$alkyl substituted with $C_3$-$C_8$cycloalkyl, wherein the cycloalkyl is, at each occurrence, independently selected from cyclopropyl, cyclobutyl, cyclopentyl, cyclohexyl, cycloheptyl, and bridged $C_5$-$C_8$cycloalkyl, and wherein said cycloalkyl is, at each occurrence, independently substituted with 0-3 $R^4$, wherein $R^4$ is as defined according to any of the preceding Embodiments.

Embodiment 41. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_3$-$C_8$cycloalkyl, or —C(=O)—$R_3$, wherein $R^3$ is $C_3$-$C_8$cycloalkyl, or $C_1$-$C_6$alkyl substituted with $C_3$-$C_8$cycloalkyl, wherein the cycloalkyl is, at each occurrence, independently selected from cyclopropyl, cyclobutyl, cyclopentyl, cyclohexyl, bicyclo[1.1.1]pentyl, bicyclo[2.1.1]hexyl, bicyclo[2.1.1]heptyl, bicyclo[2.2.2]octyl and bicyclo[1.1.1]pentanyl, and wherein said cycloalkyl is, at each occurrence, independently substituted with 0-3 $R^4$, wherein $R^4$ is as defined according to any of the preceding Embodiments.

Embodiment 42. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_3$-$C_8$cycloalkyl, or —C(=O)—$R^3$, wherein $R^3$ is $C_3$-$C_8$cycloalkyl, or $C_1$-$C_6$alkyl substituted with $C_3$-$C_8$cycloalkyl, wherein the cycloalkyl is, at each occurrence, independently selected from cyclopropyl, cyclobutyl, cyclopentyl, cyclohexyl and

, and wherein said cycloalkyl is, at each occurrence, independently substituted with 0-3 $R^4$, wherein $R^4$ is as defined according to any of the preceding Embodiments.

Embodiment 43. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_{10}$ alkyl (e.g., $C_1$-$C_6$ alkyl, e.g., $C_1$alkyl) substituted with $C_3$-$C_8$cycloalkyl, or —C(=O)—$R^3$, wherein $R^3$ is $C_3$-$C_8$cycloalkyl, or $C_1$-$C_6$alkyl substituted with $C_3$-$C_8$cycloalkyl, wherein the cycloalkyl is, at each occurrence, independently selected from cyclobutyl, cyclopentyl, cyclohexyl and

wherein said cycloalkyl is substituted on 0-2 occurrences with $R^4$, wherein $R^4$ is as defined according to any of the preceding Embodiments.

Embodiment 44. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_6$ alkyl (e.g., $C_1$alkyl) substituted with one $C_3$-$C_8$cycloalkyl selected from:

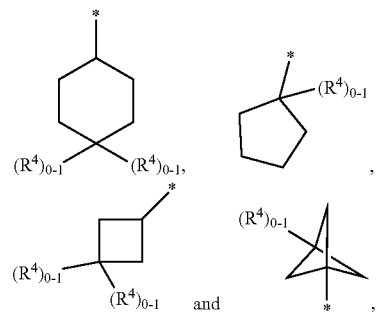

wherein $R^4$ is as defined according to any of the preceding Embodiments.

Embodiment 45. The compound of any of the preceding Embodiments, or a pharmaceutically acceptable salt, hydrate, solvate, prodrug, stereoisomer, or tautomer thereof, wherein $R^2$ is unsubstituted $C_1$-$C_6$ alkyl or $C_1$-$C_6$ alkyl (e.g., $C_1$alkyl) substituted with one $C_3$-$C_8$cycloalkyl selected from

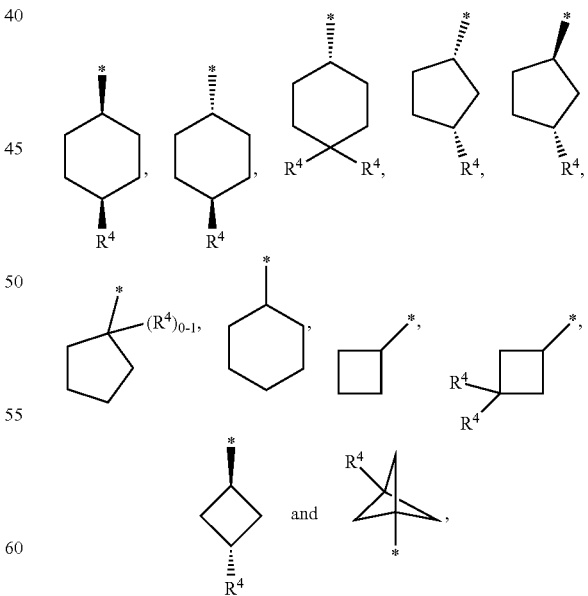

wherein $R^4$ is as defined according to any of the preceding Embodiments.

Embodiment 46. The compound of any of the preceding Embodiments, or a pharmaceutically acceptable salt, hydrate, solvate, prodrug, stereoisomer, or tautomer thereof, wherein each R⁴ is, at each occurrence, independently selected from $C_1$-$C_6$alkoxyl, —NH—C(=O)—, O—($C_1$-$C_6$alkyl), —C(=O)—O—($C_1$-$C_6$alkyl), halogen, and —CN.

Embodiment 47. The compound of any of the preceding Embodiments, or a pharmaceutically acceptable salt, hydrate, solvate, prodrug, stereoisomer, or tautomer thereof, wherein each R⁴ is, at each occurrence, independently selected from $C_1$-$C_6$alkoxyl, —NH—C(=O)—, O—($C_1$-$C_6$alkyl), —C(=O)—O—($C_1$-$C_3$alkyl), fluoro, and —CN.

Embodiment 48. The compound of any of Embodiments 1, 4 to 47, or a pharmaceutically acceptable salt, hydrate, solvate, prodrug, stereoisomer, or tautomer thereof, of formula (Ia)

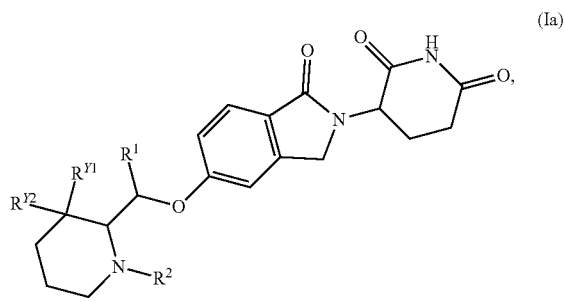

(Ia)

wherein $R^{Y1}$, $R^{Y2}$, $R^1$ and $R^2$ are defined according to any of the preceding Embodiments.

Embodiment 49. The compound of any of Embodiments 1, 4 to 47, or a pharmaceutically acceptable salt, hydrate, solvate, prodrug, stereoisomer, or tautomer thereof, of formula (Ib)

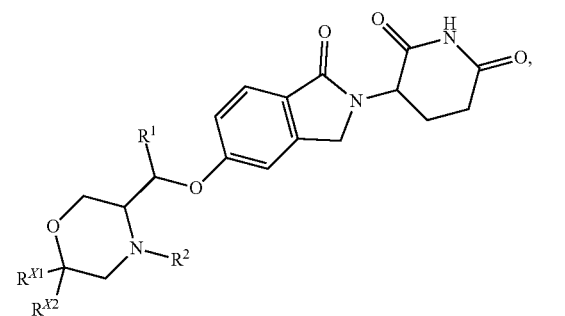

(Ib)

wherein $R^{X1}$, $R^{X2}$, $R^1$ and $R^2$ are defined according to any of the preceding Embodiments.

Embodiment 50. The compound of any of Embodiments 1, 4 to 47, or a pharmaceutically acceptable salt, hydrate, solvate, prodrug, stereoisomer, or tautomer thereof, of formula (Ic)

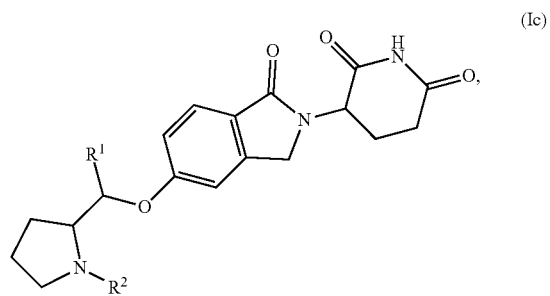

(Ic)

wherein $R^1$ and $R^2$ are defined according to any of the preceding Embodiments.

Embodiment 51. The compound of any of Embodiments 1, 4 to 47, or a pharmaceutically acceptable salt, hydrate, solvate, prodrug, stereoisomer, or tautomer thereof, of formula (Id)

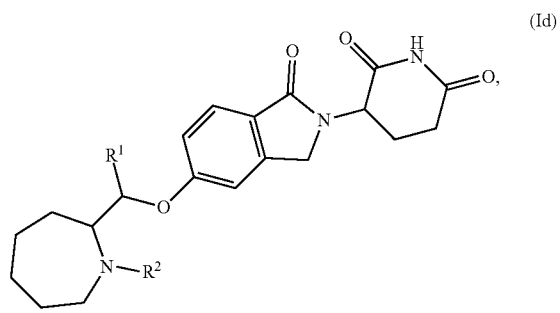

(Id)

wherein $R^1$ and $R^2$ are defined according to any of the preceding Embodiments.

Embodiment 52. The compound of any of Embodiments 1, 4 to 48, or a pharmaceutically acceptable salt, hydrate, solvate, prodrug, stereoisomer, or tautomer thereof, of formula (Ia-i)

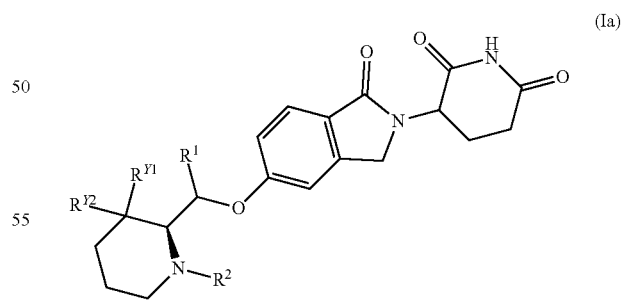

(Ia)

wherein $R^{Y1}$, $R^{Y2}$, $R^1$ and $R^2$ are as defined in any of the preceding Embodiments.

Embodiment 53. The compound of any of Embodiments 1, 4 to 48, or a pharmaceutically acceptable salt, hydrate, solvate, prodrug, stereoisomer, or tautomer thereof, of formula (Ia-ii)

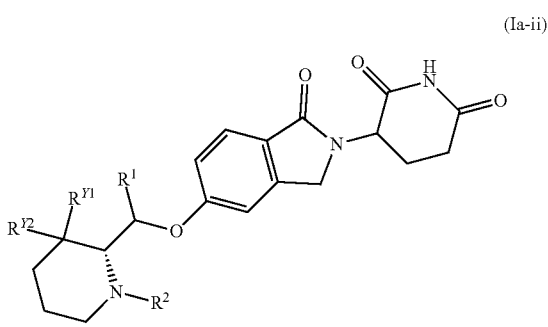
(Ia-ii)

wherein $R^{Y1}$, $R^{Y2}$, $R^1$ and $R^2$ are as defined in any of the preceding Embodiments.

Embodiment 54. The compound of any of Embodiments 1, 4 to 48, 53, or a pharmaceutically acceptable salt, hydrate, solvate, prodrug, stereoisomer, or tautomer thereof, of formula (Ia-iii)

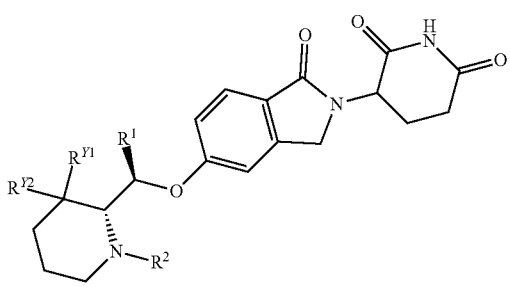
(Ia-iii)

wherein $R^{Y1}$, $R^{Y2}$, $R^1$ and $R^2$ are as defined in any of the preceding Embodiments.

Embodiment 55. The compound of any of Embodiments 1, 4 to 48, 53, or a pharmaceutically acceptable salt, hydrate, solvate, prodrug, stereoisomer, or tautomer thereof, of formula (Ia-iv)

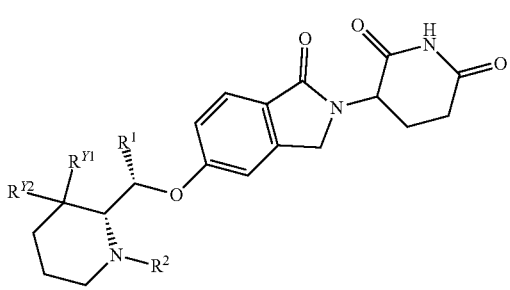
(Ia-iv)

wherein $R^{Y1}$, $R^{Y2}$, $R^1$ and $R^2$ are as defined in any of the preceding Embodiments.

Embodiment 56. The compound of any of Embodiments 1, 4 to 48, 52, or a pharmaceutically acceptable salt, hydrate, solvate, prodrug, stereoisomer, or tautomer thereof, of formula (Ia-v) or (Ia-vi)

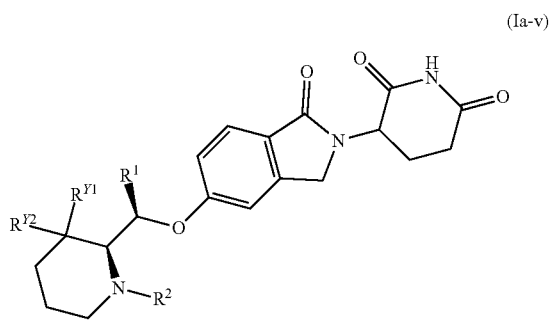
(Ia-v)

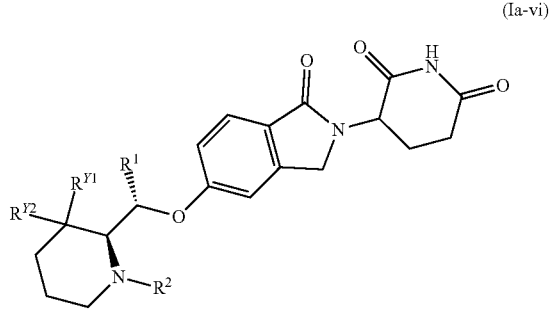
(Ia-vi)

wherein $R^{Y1}$, $R^{Y2}$, $R^1$ and $R^2$ are as defined in any of the preceding Embodiments.

Embodiment 57. The compound of any of Embodiments 1, 4 to 48, 52, 56, or a pharmaceutically acceptable salt, hydrate, solvate, prodrug, stereoisomer, or tautomer thereof, of formula (Ia-vii) or (Ia-viii)

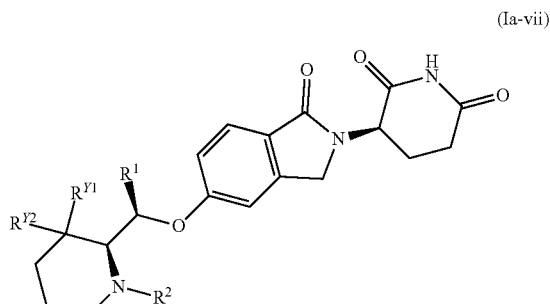
(Ia-vii)

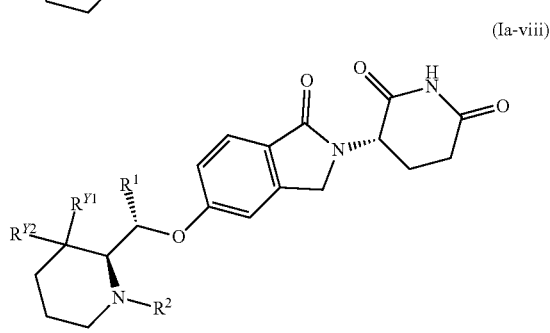
(Ia-viii)

wherein $R^{Y1}$, $R^{Y2}$, $R^1$ and $R^2$ are as defined in any of the preceding Embodiments.

Embodiment 58. The compound of any of Embodiments 1, 4 to 48, 52, 56, or a pharmaceutically acceptable salt, hydrate, solvate, prodrug, stereoisomer, or tautomer thereof, of formula (Ia-ix) or (Ia-x)

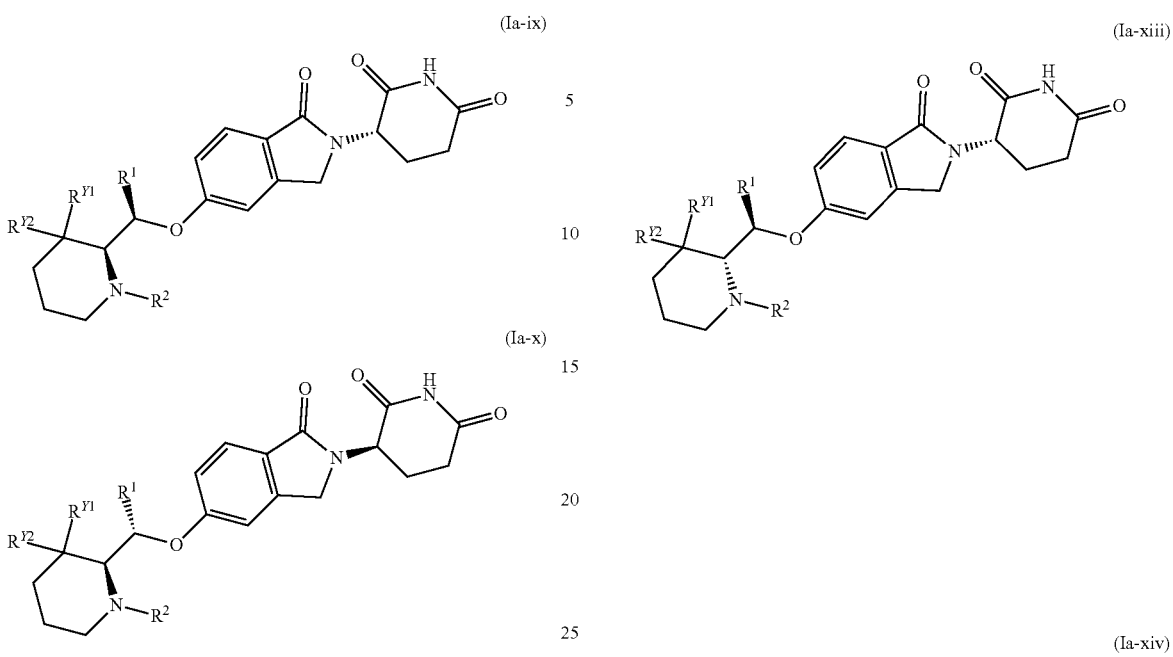

wherein $R^{Y1}$, $R^{Y2}$, $R^1$ and $R^2$ are as defined in any of the preceding Embodiments.

Embodiment 59. The compound of any of Embodiments 1, 4 to 48, 53 to 55, or a pharmaceutically acceptable salt, hydrate, solvate, prodrug, stereoisomer, or tautomer thereof, of formula (Ia-xi) or (Ia-xii)

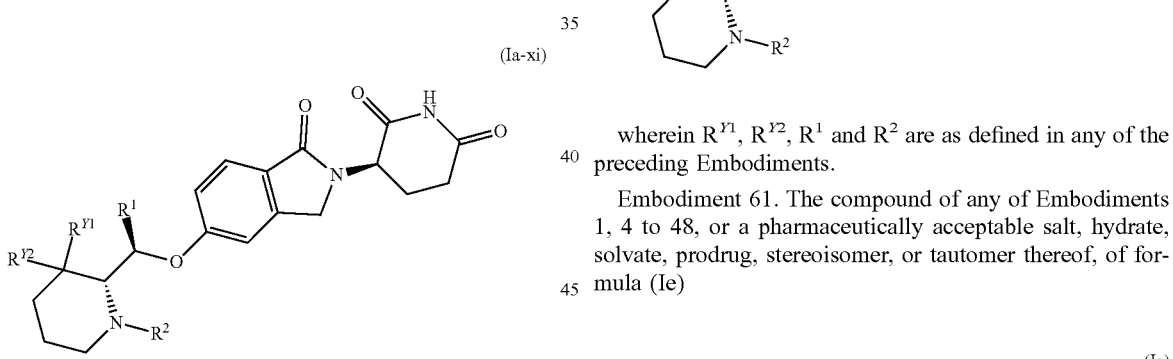

wherein $R^{Y1}$, $R^{Y2}$, $R^1$ and $R^2$ are as defined in any of the preceding Embodiments.

Embodiment 60. The compound of any of Embodiments 1, 4 to 48, 53 to 55, or a pharmaceutically acceptable salt, hydrate, solvate, prodrug, stereoisomer, or tautomer thereof, of formula (Ia-xiii) or (Ia-xiv)

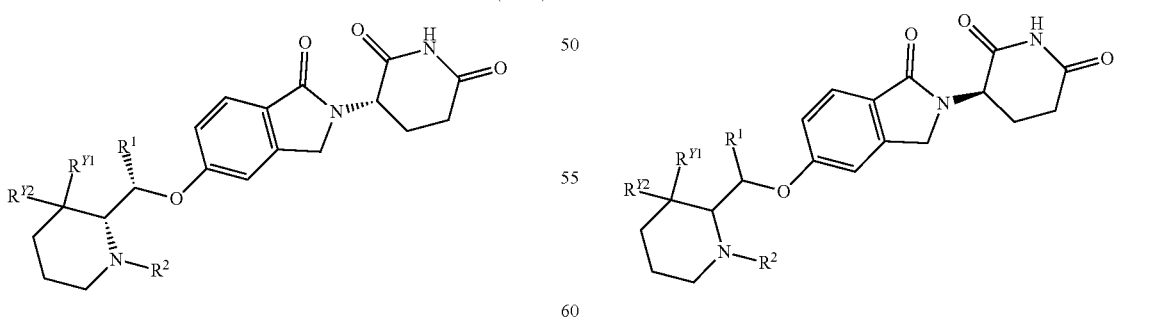

wherein $R^{Y1}$, $R^{Y2}$, $R^1$ and $R^2$ are as defined in any of the preceding Embodiments.

Embodiment 61. The compound of any of Embodiments 1, 4 to 48, or a pharmaceutically acceptable salt, hydrate, solvate, prodrug, stereoisomer, or tautomer thereof, of formula (Ie)

Embodiment 62. The compound of any of Embodiments 1, 4 to 48, or a pharmaceutically acceptable salt, hydrate, solvate, prodrug, stereoisomer, or tautomer thereof, of formula (If)

(If)

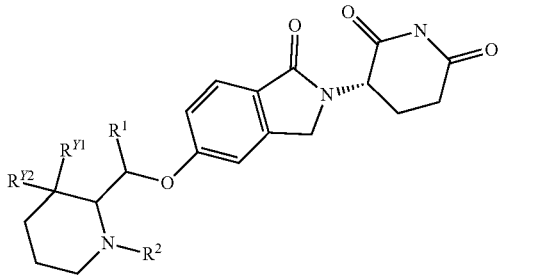

wherein $R^{Y1}$, $R^{Y2}$, $R^1$ and $R^2$ are as defined in any of the preceding Embodiments.

Embodiment 63. The compound of any of the preceding Embodiments, or a pharmaceutically acceptable salt, hydrate, solvate, prodrug, stereoisomer, or tautomer thereof, wherein:

$R^{Y1}$ and $R^{Y2}$ are each independently selected from hydrogen and $C_1$-$C_6$alkyl;

$R^1$ is selected from hydrogen and $C_1$-$C_6$alkyl;

$R^2$ is selected from hydrogen, $C_1$-$C_6$alkyl, —C(=O)—CH$_2$—(CH$_2$)-1-$R^{3c}$, $C_3$-$C_8$cycloalkyl, —(CH$_2$)$_{1-2}$-phenyl, —(CH$_2$)$_{1-2}$-5-10 membered heteroaryl comprising 1-4 heteroatoms independently selected from N, O, and S, —(CH$_2$)$_{1-2}$-4- to 6-membered heterocyclyl comprising 1-2 heteroatoms independently selected from N, O, and S, and —(CH$_2$)$_{1-2}$—$C_3$-$C_8$cycloalkyl, and wherein the phenyl, heteroaryl, heterocyclyl, and cycloalkyl are each independently substituted with 0-5 $R^4$.

Embodiment 64. The compound of any of the preceding Embodiments, or a pharmaceutically acceptable salt, hydrate, solvate, prodrug, stereoisomer, or tautomer thereof, wherein:

$R^{Y1}$ and $R^{Y2}$ are each independently selected from hydrogen and methyl;

$R^1$ is selected from hydrogen and $C_1$-$C_6$alkyl;

$R^2$ is selected from $C_1$-$C_6$alkyl, $C_3$-$C_8$cycloalkyl, —(CH$_2$)$_{1-2}$-phenyl, —(CH$_2$)$_{1-2}$-5-10 membered heteroaryl comprising 1-4 heteroatoms independently selected from N, O, and S, —(CH$_2$)$_{1-2}$-4- to 6-membered heterocyclyl comprising 1-2 heteroatoms independently selected from N, O, and S, and —(CH$_2$)$_{1-2}$—$C_3$-$C_8$cycloalkyl, and wherein the phenyl, heteroaryl, heterocyclyl, and cycloalkyl are each independently substituted with 0-5 $R^4$.

Embodiment 65. The compound of any of the preceding Embodiments, or a pharmaceutically acceptable salt, hydrate, solvate, prodrug, stereoisomer, or tautomer thereof, wherein $R^{Y1}$ and $R^{Y2}$ are the same and are selected from hydrogen and $C_1$-$C_6$alkyl.

Embodiment 66. The compound of any of the preceding Embodiments, or a pharmaceutically acceptable salt, hydrate, solvate, prodrug, stereoisomer, or tautomer thereof, wherein $R^{X1}$ and $R^{X2}$ are the same and are selected from hydrogen and $C_1$-$C_6$alkyl.

Embodiment 67. The compound of any of the preceding Embodiments, or a pharmaceutically acceptable salt, hydrate, solvate, prodrug, stereoisomer, or tautomer thereof, wherein $R^1$ is selected from hydrogen, and $C_1$-$C_4$alkyl.

Embodiment 68. The compound of any of the preceding Embodiments, or a pharmaceutically acceptable salt, hydrate, solvate, prodrug, stereoisomer, or tautomer thereof, wherein $R^1$ is hydrogen.

Embodiment 69. The compound of any of the preceding Embodiments, or a pharmaceutically acceptable salt, hydrate, solvate, prodrug, stereoisomer, or tautomer thereof, wherein $R^1$ is methyl.

Embodiment 70. The compound of any of the preceding Embodiments, or a pharmaceutically acceptable salt, hydrate, solvate, prodrug, stereoisomer, or tautomer thereof, wherein $R^2$ is selected from hydrogen, $C_1$-$C_6$alkyl, —C(=O)—$R^3$, $C_3$-$C_8$cycloalkyl, —(CH$_2$)$_{1-2}$-phenyl, —(CH$_2$)$_{1-2}$-5-10 membered heteroaryl comprising 1-4 heteroatoms independently selected from N, O, and S, —(CH$_2$)$_{1-2}$-4- to 6-membered heterocyclyl comprising 1-2 heteroatoms independently selected from N, O, and S, and —(CH$_2$)$_{1-2}$—$C_3$-$C_8$cycloalkyl, wherein the phenyl, heteroaryl, and heterocyclyl are each independently substituted with 0-4 $R^4$, and wherein the cycloalkyl is independently substituted with 0-3 $R^4$.

Embodiment 71. The compound of any of the preceding Embodiments, or a pharmaceutically acceptable salt, hydrate, solvate, prodrug, stereoisomer, or tautomer thereof, wherein $R^2$ is selected from $C_1$-$C_6$alkyl, and —(CH$_2$)-phenyl, wherein the phenyl is substituted on 0-4 occurrences with $R^4$.

Embodiment 72. The compound of any of the preceding Embodiments, or a pharmaceutically acceptable salt, hydrate, solvate, prodrug, stereoisomer, or tautomer thereof, wherein $R^2$ is $C_1$-$C_6$alkyl.

Embodiment 73. The compound of any of the preceding Embodiments, or a pharmaceutically acceptable salt, hydrate, solvate, prodrug, stereoisomer, or tautomer thereof, wherein $R^2$ is —(CH$_2$)-phenyl, wherein the phenyl is substituted on 0-3 occurrences with $R^4$.

Embodiment 74. The compound of any of Embodiments 1, 4 to 48, or a pharmaceutically acceptable salt, hydrate, solvate, prodrug, stereoisomer, or tautomer thereof, of formula (Ig)

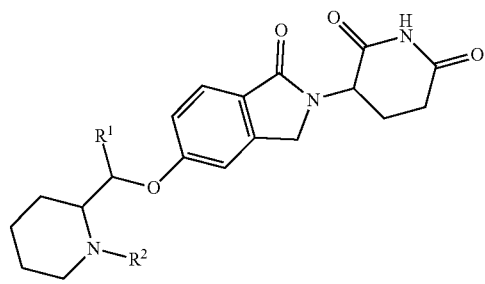

wherein $R^1$ and $R^2$ are as defined in any of the preceding Embodiments, e.g., $R^1$ is selected from hydrogen and $C_1$-$C_6$alkyl and $R^2$ is selected from $C_1$-$C_6$alkyl, e.g., unsubstituted $C_1$-$C_6$alkyl,

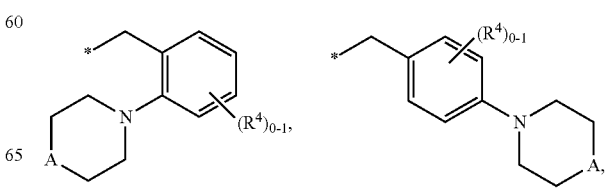

-continued

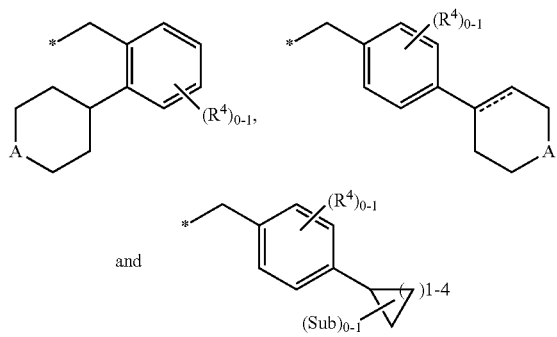

and

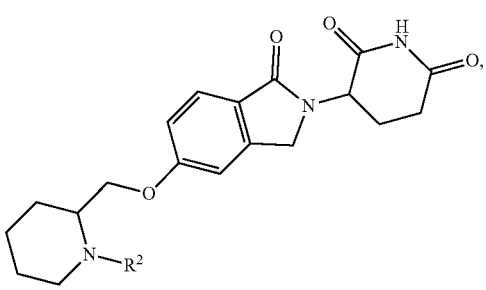

wherein

╌╌╌ represents an optional C═C double bond, which when present, A is O;

A is selected from N—$R^{4d}$, O and $CH_2$;

$R^4$ is selected from $C_1$-$C_6$alkyl, $C_1$-$C_6$alkoxyl, $C_1$-$C_6$haloalkyl, fluoro, chloro, iodo, hydroxyl and —CN;

$R^{4d}$ is selected from hydrogen, —C(═O)—O—($C_1$-$C_6$alkyl), 4- to 6-membered heterocyclyl comprising 1 heteroatom selected from N and O, $C_3$-$C_6$cycloalkyl, $C_1$-$C_6$haloalkyl and $C_1$-$C_6$alkyl, wherein the alkyl is substituted with 0-1 substituent selected from $C_3$-$C_6$cycloalkyl, 4- to 6-membered heterocyclyl comprising 1-2 heteroatoms independently selected from N and O;

Sub is selected from $C_1$-$C_6$alkyl, halogen and $C_1$-$C_6$haloalkyl.

Embodiment 75. The compound of any of Embodiments 1, 4 to 48, 63 to 74, or a pharmaceutically acceptable salt, hydrate, solvate, prodrug, stereoisomer, or tautomer thereof, of formula (Ih)

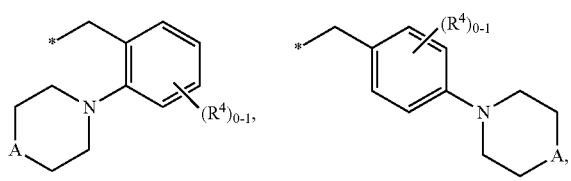

(Ih)

wherein $R^2$ is as defined in any of the preceding Embodiments, e.g., $R^2$ is selected from $C_1$-$C_6$alkyl, e.g., unsubstituted $C_1$-$C_6$alkyl,

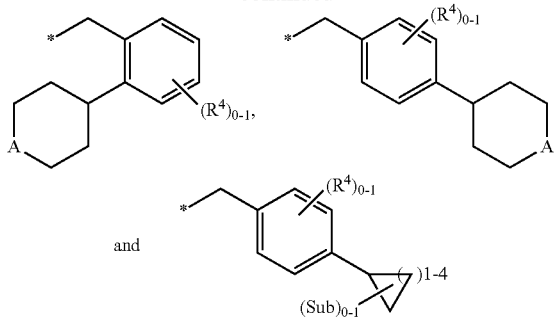

and

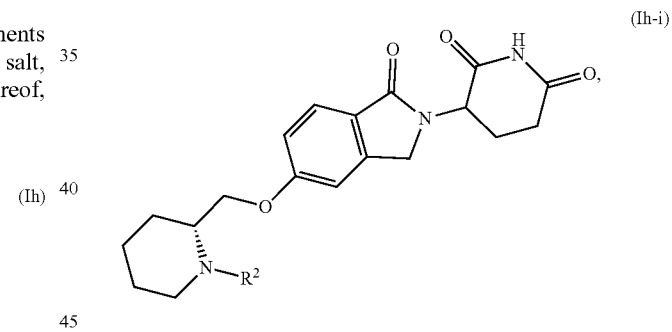

wherein

A is selected from N—$R^{4d}$, O and $CH_2$;

$R^4$ is selected from $C_1$-$C_6$alkyl, $C_1$-$C_6$alkoxyl, $C_1$-$C_6$haloalkyl, fluoro, chloro, iodo, hydroxyl and —CN;

$R^{4d}$ is selected from hydrogen, —C(═O)—O—($C_1$-$C_6$alkyl), 4- to 6-membered heterocyclyl comprising 1 heteroatom selected from N and O, $C_3$-$C_6$cycloalkyl, $C_1$-$C_6$haloalkyl and $C_1$-$C_6$alkyl, wherein the alkyl is substituted with 0-1 substituent selected from $C_3$-$C_6$cycloalkyl, 4- to 6-membered heterocyclyl comprising 1-2 heteroatoms independently selected from N and O; Sub is selected from $C_1$-$C_6$alkyl, halogen and $C_1$-$C_6$haloalkyl.

Embodiment 76. The compound of any of Embodiments 1, 4 to 48, 63 to 75, or a pharmaceutically acceptable salt, hydrate, solvate, prodrug, stereoisomer, or tautomer thereof, of formula (Ih-i)

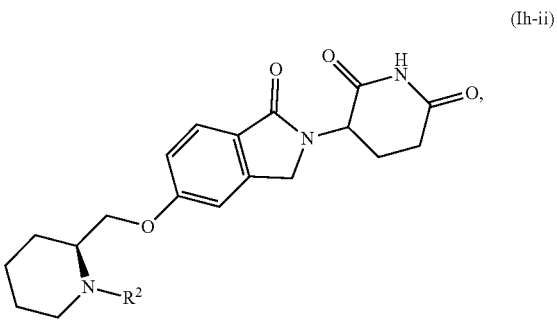

(Ih-i)

wherein $R^2$ is as defined in any of the preceding Embodiments, e.g., $R^2$ is as defined in Embodiment 75.

Embodiment 77. The compound of any of Embodiments 1, 4 to 48, 63 to 75, or a pharmaceutically acceptable salt, hydrate, solvate, prodrug, stereoisomer, or tautomer thereof, of formula (Ih-ii)

(Ih-ii)

wherein R² is as defined in any of the preceding Embodiments, e.g., R² is as defined in Embodiment 75.

Embodiment 78. A compound according to any of the preceding claims, wherein the glutarimide moiety of the molecule is

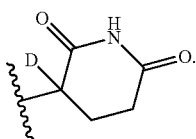 [SMILES: *C1([2H])CCC(=O)NC1=O]

Embodiment 79. A compound according to any of the preceding claims, wherein the glutarimide moiety of the molecule is

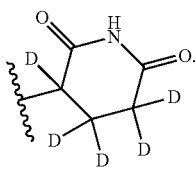 [SMILES: *C1([2H])C(=O)NC(=O)C([2H])([2H])C1([2H])[2H]]

Embodiment 80. A compound, or a pharmaceutically acceptable salt, hydrate, solvate, prodrug, stereoisomer, or tautomer thereof, selected from:

3-(5-(((R)-1-((1-cyclohexyl-1H-pyrazol-4-yl)methyl)piperidin-2-yl)methoxy)-1-oxoisoindolin-2-yl)piperidine-2,6-dione;

3-(5-(((R)-1-((1-methyl-5-phenyl-1H-pyrazol-3-yl)methyl)piperidin-2-yl)methoxy)-1-oxoisoindolin-2-yl)piperidine-2,6-dione;

methyl 4-(4-(((2R)-2-(((2-(2,6-dioxopiperidin-3-yl)-1-oxoisoindolin-5-yl)oxy)methyl) piperidin-1-yl)methyl)phenoxy)benzoate;

3-(5-(((R)-1-((1-benzyl-1H-pyrazol-4-yl)methyl)piperidin-2-yl)methoxy)-1-oxoisoindolin-2-yl)piperidine-2,6-dione;

3-(1-oxo-5-(((R)-1-(3-(pyrrolidin-1-yl)benzyl)piperidin-2-yl)methoxy)isoindolin-2-yl)piperidine-2,6-dione;

3-(5-(((R)-1-(3-((1H-pyrazol-1-yl)methyl)benzyl)piperidin-2-yl)methoxy)-1-oxoisoindolin-2-yl)piperidine-2,6-dione;

3-(1-oxo-5-(((R)-1-((3-(m-tolyl)-1H-pyrazol-4-yl)methyl)piperidin-2-yl)methoxy)isoindolin-2-yl)piperidine-2,6-dione;

3-(5-(((R)-1-(4-(2H-1,2,3-triazol-2-yl)benzyl) piperidin-2-yl)methoxy)-1-oxoisoindolin-2-yl)piperidine-2,6-dione;

3-(1-oxo-5-(((R)-1-((6-(pyrrolidin-1-yl)pyridin-3-yl)methyl)piperidin-2-yl)methoxy)isoindolin-2-yl)piperidine-2,6-dione;

3-(5-(((R)-1-(3-methoxy-4-methylbenzyl)piperidin-2-yl)methoxy)-1-oxoisoindolin-2-yl)piperidine-2,6-dione;

3-(5-(((R)-1-(4-(2-methyl-1H-imidazol-1-yl)benzyl)piperidin-2-yl)methoxy)-1-oxoisoindolin-2-yl)piperidine-2,6-dione;

3-(5-(((R)-1-(4-((1H-imidazol-1-yl)methyl)benzyl)piperidin-2-yl)methoxy)-1-oxoisoindolin-2-yl)piperidine-2,6-dione;

3-(5-(((R)-1-((1-isobutyl-1H-pyrazol-4-yl)methyl) piperidin-2-yl)methoxy)-1-oxoisoindolin-2-yl)piperidine-2,6-dione;

3-(5-(((2S)-1-((1-(cyclohex-3-en-1-ylmethyl)piperidin-4-yl)methyl)piperidin-2-yl)methoxy)-1-oxoisoindolin-2-yl)piperidine-2,6-dione;

3-(5-(((R)-1-((6-(diethylamino)pyridin-3-yl)methyl)piperidin-2-yl)methoxy)-1-oxoisoindolin-2-yl)piperidine-2,6-dione;

3-(5-(((S)-1-(2-chloro-6-fluorobenzyl)piperidin-2-yl)methoxy)-1-oxoisoindolin-2-yl)piperidine-2,6-dione;

3-(5-(((R)-1-((5-(benzyloxy)-6-methoxy-1H-indazol-3-yl)methyl)piperidin-2-yl)methoxy)-1-oxoisoindolin-2-yl)piperidine-2,6-dione;

3-(5-(((R)-1-((1-benzylpiperidin-4-yl)methyl)piperidin-2-yl)methoxy)-1-oxoisoindolin-2-yl)piperidine-2,6-dione;

3-(5-(((R)-1-(4-morpholinobenzyl)piperidin-2-yl)methoxy)-1-oxoisoindolin-2-yl)piperidine-2,6-dione;

3-(5-((R)-1-((R)-1-ethylpiperidin-2-yl)ethoxy)-1-oxoisoindolin-2-yl)piperidine-2,6-dione;

tert-butyl 4-(4-(((2R)-2-(((2-(2,6-dioxopiperidin-3-yl)-1-oxoisoindolin-5-yl)oxy)methyl)piperidin-1-yl)methyl)phenyl)piperazine-1-carboxylate;

3-(5-(((R)-1-(3-((1H-imidazol-1-yl)methyl)benzyl)piperidin-2-yl)methoxy)-1-oxoisoindolin-2-yl)piperidine-2,6-dione;

3-(5-(((S)-1-((3,5-dimethylisoxazol-4-yl)methyl)piperidin-2-yl)methoxy)-1-oxoisoindolin-2-yl)piperidine-2,6-dione;

3-(5-(((R)-1-((1-methyl-1H-indol-4-yl)methyl)piperidin-2-yl)methoxy)-1-oxoisoindolin-2-yl)piperidine-2,6-dione;

3-(5-(((R)-1-(2-(4-methylpiperazin-1-yl)benzyl)piperidin-2-yl)methoxy)-1-oxoisoindolin-2-yl)piperidine-2,6-dione;

3-(1-oxo-5-(((S)-1-(3-(pyrrolidin-1-yl)benzyl)piperidin-2-yl)methoxy)isoindolin-2-yl)piperidine-2,6-dione;

3-(1-oxo-5-(((R)-1-(4-(pyrrolidine-1-carbonyl)benzyl)piperidin-2-yl)methoxy)isoindolin-2-yl)piperidine-2,6-dione;

3-(5-(((R)-1-(4-(4-benzylpiperazin-1-yl)benzyl)piperidin-2-yl)methoxy)-1-oxoisoindolin-2-yl)piperidine-2,6-dione;

3-(5-(((R)-1-((1-ethyl-1H-pyrazol-4-yl)methyl)piperidin-2-yl)methoxy)-1-oxoisoindolin-2-yl)piperidine-2,6-dione;

3-(5-(((S)-1-((5-(cyclohexa-1,5-dien-1-yl)-1-methyl-1H-pyrazol-3-yl)methyl)piperidin-2-yl)methoxy)-1-oxoisoindolin-2-yl)piperidine-2,6-dione;

3-(5-(((S)-1-((1-cyclohexyl-1H-pyrazol-4-yl)methyl)piperidin-2-yl)methoxy)-1-oxoisoindolin-2-yl)piperidine-2,6-dione;

3-(5-(((R)-1-(4-(2-morpholinoethoxy)benzyl)piperidin-2-yl)methoxy)-1-oxoisoindolin-2-yl)piperidine-2,6-dione;

3-(5-(((S)-1-((1H-pyrrolo[2,3-b]pyridin-4-yl)methyl)piperidin-2-yl)methoxy)-1-oxoisoindolin-2-yl)piperidine-2,6-dione;

3-(5-(((R)-1-((1-benzyl-1H-imidazol-2-yl)methyl)piperidin-2-yl)methoxy)-1-oxoisoindolin-2-yl)piperidine-2,6-dione;

3-(5-(((S)-1-ethylpiperidin-2-yl)methoxy)-1-oxoisoindolin-2-yl)piperidine-2,6-dione;

3-(5-(((R)-1-(4-(4-methylpiperazin-1-yl)benzyl)piperidin-2-yl)methoxy)-1-oxoisoindolin-2-yl)piperidine-2,6-dione;

3-(5-(((S)-1-((4-methyl-1H-imidazol-5-yl)methyl)piperidin-2-yl)methoxy)-1-oxoisoindolin-2-yl)piperidine-2,6-dione;

3-(5-(((R)-1-(2-(2-morpholinoethoxy)benzyl)piperidin-2-yl)methoxy)-1-oxoisoindolin-2-yl)piperidine-2,6-dione;

3-(5-(((R)-1-ethylpiperidin-2-yl)methoxy)-1-oxoisoindolin-2-yl)piperidine-2,6-dione;

(R)-3-(5-(((R)-1-ethylpiperidin-2-yl)methoxy)-1-oxoisoindolin-2-yl)piperidine-2,6-dione;
(S)-3-(5-(((R)-1-ethylpiperidin-2-yl)methoxy)-1-oxoisoindolin-2-yl)piperidine-2,6-dione;
ethyl 3-(((2R)-2-(((2-(2,6-dioxopiperidin-3-yl)-1-oxoisoindolin-5-yl)oxy)methyl)piperidin-1-yl)methyl)-1H-indazole-4-carboxylate;
3-(5-(((S)-1-((2-ethyl-4-methyl-1H-imidazol-5-yl)methyl)piperidin-2-yl)methoxy)-1-oxoisoindolin-2-yl)piperidine-2,6-dione;
methyl 4-(4-(((2S)-2-(((2-(2,6-dioxopiperidin-3-yl)-1-oxo-2,3,3a,7a-tetrahydro-1H-isoindol-5-yl)oxy)methyl)piperidin-1-yl)methyl)phenoxy)benzoate;
3-(5-(((R)-1-((5-methylisoxazol-3-yl)methyl)piperidin-2-yl)methoxy)-1-oxoisoindolin-2-yl)piperidine-2,6-dione;
3-(5-(((R)-1-((1H-pyrrolo[2,3-b]pyridin-4-yl)methyl)piperidin-2-yl)methoxy)-1-oxoisoindolin-2-yl)piperidine-2,6-dione;
3-(5-(((R)-1-((2-morpholinopyridin-4-yl)methyl)piperidin-2-yl)methoxy)-1-oxoisoindolin-2-yl)piperidine-2,6-dione;
3-(5-(((R)-1-((1-methyl-1H-benzo[d][1,2,3]triazol-5-yl)methyl) piperidin-2-yl)methoxy)-1-oxoisoindolin-2-yl) piperidine-2,6-dione;
3-(5-(((S)-1-((1-methyl-1H-indol-4-yl)methyl)piperidin-2-yl)methoxy)-1-oxoisoindolin-2-yl)piperidine-2,6-dione;
4-(((2R)-2-(((2-(2,6-dioxopiperidin-3-yl)-1-oxoisoindolin-5-yl)oxy)methyl)piperidin-1-yl)methyl)benzenesulfonamide;
3-(5-(((S)-1-(3-((1H-pyrazol-1-yl)methyl)benzyl)piperidin-2-yl)methoxy)-1-oxoisoindolin-2-yl)piperidine-2,6-dione;
3-(5-(((S)-1-((6-(diethylamino)pyridin-3-yl)methyl)piperidin-2-yl)methoxy)-1-oxoisoindolin-2-yl)piperidine-2,6-dione;
3-(5-(((S)-1-(3-methoxy-4-methylbenzyl)piperidin-2-yl)methoxy)-1-oxoisoindolin-2-yl)piperidine-2,6-dione;
3-(5-(((S)-1-((1-isobutyl-1H-pyrazol-4-yl)methyl)piperidin-2-yl)methoxy)-1-oxoisoindolin-2-yl)piperidine-2,6-dione;
3-(5-(((S)-1-((1-benzyl-1H-pyrazol-4-yl)methyl)piperidin-2-yl)methoxy)-1-oxoisoindolin-2-yl)piperidine-2,6-dione;
3-(5-(((S)-1-(3-chloro-4-hydroxybenzyl)piperidin-2-yl)methoxy)-1-oxoisoindolin-2-yl)piperidine-2,6-dione;
3-(1-oxo-5-(((S)-1-((1-(phenylsulfonyl)-1H-pyrrol-2-yl)methyl) piperidin-2-yl)methoxy)isoindolin-2-yl)piperidine-2,6-dione;
3-(5-(((S)-1-(2-(4-methylpiperazin-1-yl)benzyl)piperidin-2-yl)methoxy)-1-oxoisoindolin-2-yl)piperidine-2,6-dione;
3-(5-(((R)-1-((1H-pyrazol-4-yl)methyl)piperidin-2-yl)methoxy)-1-oxoisoindolin-2-yl)piperidine-2,6-dione;
3-(1-oxo-5-(((S)-1-((6-(pyrrolidin-1-yl)pyridin-3-yl)methyl)piperidin-2-yl)methoxy)isoindolin-2-yl)piperidine-2,6-dione;
3-(5-(((R)-1-((1-isopropylpiperidin-4-yl)methyl)piperidin-2-yl)methoxy)-1-oxoisoindolin-2-yl)piperidine-2,6-dione;
3-(1-oxo-5-(((R)-1-((1-(pyrazin-2-yl)-1H-pyrazol-4-yl)methyl)piperidin-2-yl)methoxy)isoindolin-2-yl)piperidine-2,6-dione;
3-(5-(((S)-1-(3-isopropyl-1-methyl-1H-pyrazole-5-carbonyl)piperidin-2-yl)methoxy)-1-oxoisoindolin-2-yl)piperidine-2,6-dione;
3-(5-(((R)-1-isopropylpiperidin-2-yl)methoxy)-1-oxoisoindolin-2-yl)piperidine-2,6-dione;
3-(5-(((S)-1-((5-chloro-3-(4-(2-((dimethylamino)methyl)-1-methyl-1H-imidazol-5-yl)phenoxy)pyridin-2-yl)methyl)piperidin-2-yl)methoxy)-1-oxoisoindolin-2-yl)piperidine-2,6-dione;
3-(5-(((R)-1-((5-chloro-3-(4-(2-((dimethylamino)methyl)-1-methyl-1H-imidazol-5-yl)phenoxy)pyridin-2-yl)methyl)piperidin-2-yl)methoxy)-1-oxoisoindolin-2-yl)piperidine-2,6-dione;
3-(5-(((S)-1-(5-(4-bromophenyl)isoxazole-3-carbonyl)piperidin-2-yl)methoxy)-1-oxoisoindolin-2-yl)piperidine-2,6-dione;
3-(5-(((R)-1-(3-(5-methyl-1,2,4-oxadiazol-3-yl)benzyl)piperidin-2-yl)methoxy)-1-oxoisoindolin-2-yl)piperidine-2,6-dione;
3-(5-(((S)-1-(2-methoxybenzyl)piperidin-2-yl)methoxy)-1-oxoisoindolin-2-yl)piperidine-2,6-dione;
3-(5-(((R)-1-((2-(dimethylamino)pyrimidin-5-yl)methyl)piperidin-2-yl)methoxy)-1-oxoisoindolin-2-yl)piperidine-2,6-dione;
3-(5-(((S)-1-(3,5-diethylisoxazole-4-carbonyl)piperidin-2-yl)methoxy)-1-oxoisoindolin-2-yl)piperidine-2,6-dione;
3-(5-(((S)-1-(4-(2H-1,2,3-triazol-2-yl)benzyl)piperidin-2-yl)methoxy)-1-oxoisoindolin-2-yl)piperidine-2,6-dione;
3-(5-(((S)-1-(3',5-dimethyl-[3,5'-biisoxazole]-4'-carbonyl)piperidin-2-yl)methoxy)-1-oxoisoindolin-2-yl)piperidine-2,6-dione;
benzyl 4-(((2R)-2-(((2-(2,6-dioxopiperidin-3-yl)-1-oxoisoindolin-5-yl)oxy)methyl)piperidin-1-yl)methyl)piperidine-1-carboxylate;
3-(5-(((R)-1-(imidazo[1,2-a]pyridin-8-ylmethyl)piperidin-2-yl)methoxy)-1-oxoisoindolin-2-yl)piperidine-2,6-dione;
3-(5-(((S)-1-((2-morpholinopyridin-4-yl)methyl)piperidin-2-yl)methoxy)-1-oxoisoindolin-2-yl)piperidine-2,6-dione;
3-(5-(((S)-1-(3,4-dimethoxybenzyl)piperidin-2-yl)methoxy)-1-oxoisoindolin-2-yl)piperidine-2,6-dione;
3-(5-(((S)-1-(4-(4-methylpiperazin-1-yl)benzyl)piperidin-2-yl)methoxy)-1-oxoisoindolin-2-yl)piperidine-2,6-dione;
3-(5-(((S)-1-((1-isopropylpiperidin-4-yl)methyl)piperidin-2-yl)methoxy)-1-oxoisoindolin-2-yl)piperidine-2,6-dione;
3-(5-(((S)-1-(3,5-difluoro-4-methoxybenzoyl)piperidin-2-yl)methoxy)-1-oxoisoindolin-2-yl)piperidine-2,6-dione;
methyl (1R,3S)-3-(((2R)-2-(((2-(2,6-dioxopiperidin-3-yl)-1-oxoisoindolin-5-yl)oxy)methyl)piperidin-1-yl)methyl)cyclopentane-1-carboxylate;
3-(5-(((R)-1-(((1r,4R)-4-methoxycyclohexyl)methyl)piperidin-2-yl)methoxy)-1-oxoisoindolin-2-yl)piperidine-2,6-dione;
3-(5-(((R)-1-((2-(methylamino)pyridin-3-yl)methyl)piperidin-2-yl)methoxy)-1-oxoisoindolin-2-yl)piperidine-2,6-dione;
3-(5-(((S)-1-(4-(3-methyl-1,2,4-oxadiazol-5-yl)benzoyl)piperidin-2-yl)methoxy)-1-oxoisoindolin-2-yl)piperidine-2,6-dione;
3-(5-(((S)-1-(2,5-dimethyl-1-(5-methylisoxazol-3-yl)-1H-pyrrole-3-carbonyl)piperidin-2-yl)methoxy)-1-oxoisoindolin-2-yl)piperidine-2,6-dione;
3-(5-(((S)-1-((1H-pyrazol-4-yl)methyl)piperidin-2-yl)methoxy)-1-oxoisoindolin-2-yl)piperidine-2,6-dione;
3-(5-(((S)-1-(3-(benzyloxy)-4-methoxybenzoyl)piperidin-2-yl)methoxy)-1-oxoisoindolin-2-yl)piperidine-2,6-dione;
3-(1-oxo-5-(((R)-1-(2-(2-oxo-2-(piperidin-1-yl)ethoxy)benzyl)piperidin-2-yl)methoxy)isoindolin-2-yl)piperidine-2,6-dione;

3-(5-(((R)-1-(((1s,4S)-4-methoxycyclohexyl)methyl)piperidin-2-yl)methoxy)-1-oxoisoindolin-2-yl)piperidine-2,6-dione;
3-(5-(((R)-1-((4-methyl-1H-imidazol-5-yl)methyl)piperidin-2-yl)methoxy)-1-oxoisoindolin-2-yl)piperidine-2,6-dione;
3-(5-(((R)-1-((1H-imidazol-4-yl)methyl)piperidin-2-yl)methoxy)-1-oxoisoindolin-2-yl)piperidine-2,6-dione;
3-(1-oxo-5-(((S)-1-(2-(piperidin-1-yl)thiazole-5-carbonyl)piperidin-2-yl)methoxy)isoindolin-2-yl)piperidine-2,6-dione;
3-(5-(((S)-1-(4-(2-methyl-1H-imidazol-1-yl)benzyl)piperidin-2-yl)methoxy)-1-oxoisoindolin-2-yl)piperidine-2,6-dione;
3-(1-oxo-5-(((S)-1-(4-pentylbenzoyl)piperidin-2-yl)methoxy)isoindolin-2-yl)piperidine-2,6-dione;
3-(5-(((R)-1-((2-methylimidazo[1,2-a]pyridin-3-yl)methyl)piperidin-2-yl)methoxy)-1-oxoisoindolin-2-yl)piperidine-2,6-dione;
3-(5-(((R)-1-((3,3-difluorocyclobutyl)methyl)piperidin-2-yl)methoxy)-1-oxoisoindolin-2-yl)piperidine-2,6-dione;
3-(5-(((S)-1-(4-methyl-3,4-dihydro-2H-pyrido[3,2-b][1,4]oxazine-7-carbonyl)piperidin-2-yl)methoxy)-1-oxoisoindolin-2-yl)piperidine-2,6-dione;
3-(5-(((S)-4-ethyl-6,6-dimethylmorpholin-3-yl)methoxy)-1-oxoisoindolin-2-yl)piperidine-2,6-dione;
4-(((2R)-2-(((2-(2,6-dioxopiperidin-3-yl)-1-oxoisoindolin-5-yl)oxy)methyl)piperidin-1-yl)methyl)-3-methoxybenzonitrile;
2-(((2R)-2-(((2-(2,6-dioxopiperidin-3-yl)-1-oxoisoindolin-5-yl)oxy)methyl)piperidin-1-yl)methyl)imidazo[1,2-a]pyridine-7-carbonitrile;
3-(5-(((R)-1-((2-ethyl-4-methyl-1H-imidazol-5-yl)methyl)piperidin-2-yl)methoxy)-1-oxoisoindolin-2-yl)piperidine-2,6-dione;
3-(5-(((R)-1-(cyclohexylmethyl)piperidin-2-yl)methoxy)-1-oxoisoindolin-2-yl)piperidine-2,6-dione;
3-(5-(((R)-1-((2-methyl-1H-imidazol-5-yl)methyl)piperidin-2-yl)methoxy)-1-oxoisoindolin-2-yl)piperidine-2,6-dione;
3-(1-oxo-5-(((R)-1-((2-oxo-1,2-dihydropyridin-3-yl)methyl)piperidin-2-yl)methoxy)isoindolin-2-yl)piperidine-2,6-dione;
3-(1-oxo-5-(((S)-1-(4-(pyrrolidine-1-carbonyl)benzyl)piperidin-2-yl)methoxy)isoindolin-2-yl)piperidine-2,6-dione;
3-((3-(((2R)-2-(((2-(2,6-dioxopiperidin-3-yl)-1-oxoisoindolin-5-yl)oxy)methyl)piperidin-1-yl)methyl)-2-oxopyridin-1(2H)-yl)methyl)benzonitrile;
2-(4-(((2R)-2-(((2-(2,6-dioxopiperidin-3-yl)-1-oxoisoindolin-5-yl)oxy)methyl)piperidin-1-yl)methyl)-1H-imidazol-1-yl)acetic acid;
3-(5-(((R)-1-(4-(5-methyl-1,3,4-oxadiazol-2-yl)benzyl)piperidin-2-yl)methoxy)-1-oxoisoindolin-2-yl)piperidine-2,6-dione;
3-(5-(((S)-1-(5-(4-fluorophenyl)picolinoyl)piperidin-2-yl)methoxy)-1-oxoisoindolin-2-yl)piperidine-2,6-dione;
3-(5-(((S)-1-((1-methyl-1H-imidazol-5-yl)methyl)piperidin-2-yl)methoxy)-1-oxoisoindolin-2-yl)piperidine-2,6-dione;
2-(((2R)-2-(((2-(2,6-dioxopiperidin-3-yl)-1-oxoisoindolin-5-yl)oxy)methyl)piperidin-1-yl)methyl)benzonitrile;
3-(5-(((S)-1-(5-butyl-4-methoxypyrimidine-2-carbonyl)piperidin-2-yl)methoxy)-1-oxoisoindolin-2-yl)piperidine-2,6-dione;
2-(((2S)-2-(((2-(2,6-dioxopiperidin-3-yl)-1-oxoisoindolin-5-yl)oxy)methyl)piperidin-1-yl)methyl)benzonitrile;
ethyl 4-(((2R)-2-(((2-(2,6-dioxopiperidin-3-yl)-1-oxoisoindolin-5-yl)oxy)methyl)piperidin-1-yl)methyl)-1H-pyrazole-3-carboxylate;
4-(((2S)-2-(((2-(2,6-dioxopiperidin-3-yl)-1-oxoisoindolin-5-yl)oxy)methyl)piperidin-1-yl)methyl)benzenesulfonamide;
3-(1-oxo-5-(((S)-1-(4-(2-oxopyrrolidin-1-yl)benzyl)piperidin-2-yl)methoxy)isoindolin-2-yl)piperidine-2,6-dione;
3-(5-(((S)-1-(4-(3-methyloxetan-3-yl)benzoyl)piperidin-2-yl)methoxy)-1-oxoisoindolin-2-yl)piperidine-2,6-dione;
3-(5-(((S)-1-(3,5-dimethyl-1-phenyl-1H-pyrazole-4-carbonyl)piperidin-2-yl)methoxy)-1-oxoisoindolin-2-yl)piperidine-2,6-dione;
3-(5-(((S)-1-((6-morpholinopyridin-2-yl)methyl)piperidin-2-yl)methoxy)-1-oxoisoindolin-2-yl)piperidine-2,6-dione;
3-(1-oxo-5-(((S)-1-((5-(pyridin-3-yloxy)-1H-indazol-3-yl)methyl)piperidin-2-yl)methoxy)isoindolin-2-yl)piperidine-2,6-dione;
3-(5-(((S)-1-(3-(5-methyl-1,2,4-oxadiazol-3-yl)benzyl)piperidin-2-yl)methoxy)-1-oxoisoindolin-2-yl)piperidine-2,6-dione;
3-(5-(((S)-1-(2,3-dihydroxybenzyl)piperidin-2-yl)methoxy)-1-oxoisoindolin-2-yl)piperidine-2,6-dione;
3-(5-(((R)-1-((1-methyl-1H-imidazol-5-yl)methyl)piperidin-2-yl)methoxy)-1-oxoisoindolin-2-yl)piperidine-2,6-dione;
3-(1-oxo-5-(((S)-1-(4-(pent-3-yn-1-yloxy)benzoyl)piperidin-2-yl)methoxy)isoindolin-2-yl)piperidine-2,6-dione;
3-(5-(((S)-1-((1H-imidazol-4-yl)methyl)piperidin-2-yl)methoxy)-1-oxoisoindolin-2-yl)piperidine-2,6-dione;
3-(5-(((S)-1-(4-morpholinobenzoyl)piperidin-2-yl)methoxy)-1-oxoisoindolin-2-yl)piperidine-2,6-dione;
3-(5-(((S)-1-((5-(benzyloxy)-6-methoxy-1H-indazol-3-yl)methyl)piperidin-2-yl)methoxy)-1-oxoisoindolin-2-yl)piperidine-2,6-dione;
benzyl 4-(((2S)-2-(((2-(2,6-dioxopiperidin-3-yl)-1-oxoisoindolin-5-yl)oxy)methyl)piperidin-1-yl)methyl)piperidine-1-carboxylate;
3-(5-(((S)-1-(4-chloro-3-iodobenzoyl)piperidin-2-yl)methoxy)-1-oxoisoindolin-2-yl)piperidine-2,6-dione;
3-(5-(((S)-1-(3-fluoro-4-methoxybenzyl)piperidin-2-yl)methoxy)-1-oxoisoindolin-2-yl)piperidine-2,6-dione;
3-(5-(((S)-1-(4-methyl-3-phenyl-1H-pyrazole-5-carbonyl)piperidin-2-yl)methoxy)-1-oxoisoindolin-2-yl)piperidine-2,6-dione;
3-(1-oxo-5-(((R)-1-((tetrahydro-2H-pyran-4-yl)methyl)piperidin-2-yl)methoxy)isoindolin-2-yl)piperidine-2,6-dione;
3-(5-(((S)-1-((6-methoxypyridin-3-yl)methyl)piperidin-2-yl)methoxy)-1-oxoisoindolin-2-yl)piperidine-2,6-dione;
3-(5-(((S)-1-(2-(2-morpholinoethoxy)benzyl)piperidin-2-yl)methoxy)-1-oxoisoindolin-2-yl)piperidine-2,6-dione;
methyl (1R,3S)-3-(((2S)-2-(((2-(2,6-dioxopiperidin-3-yl)-1-oxoisoindolin-5-yl)oxy)methyl)piperidin-1-yl)methyl)cyclopentane-1-carboxylate;
3-(5-(((R)-1-((1H-imidazol-2-yl)methyl)piperidin-2-yl)methoxy)-1-oxoisoindolin-2-yl)piperidine-2,6-dione;
3-(1-oxo-5-(((S)-1-(1-phenyl-1H-1,2,4-triazole-3-carbonyl)piperidin-2-yl)methoxy)isoindolin-2-yl)piperidine-2,6-dione;
3-(5-(((S)-1-(5-neopentylisoxazole-3-carbonyl)piperidin-2-yl)methoxy)-1-oxoisoindolin-2-yl)piperidine-2,6-dione;
3-(5-(1-((S)-1-ethylpyrrolidin-2-yl)ethoxy)-1-oxoisoindolin-2-yl)piperidine-2,6-dione;
3-(5-((R)-1-((S)-1-ethylpyrrolidin-2-yl)ethoxy)-1-oxoisoindolin-2-yl)piperidine-2,6-dione;

3-(5-(((S)-1-((2-(dimethylamino)pyrimidin-5-yl)methyl)piperidin-2-yl)methoxy)-1-oxoisoindolin-2-yl)piperidine-2,6-dione;

3-(5-(((S)-1-((1-methyl-1H-benzo[d][1,2,3]triazol-5-yl)methyl)piperidin-2-yl)methoxy)-1-oxoisoindolin-2-yl)piperidine-2,6-dione;

3-(5-(((S)-1-(4-(5-methyl-1,3,4-oxadiazol-2-yl)benzoyl)piperidin-2-yl)methoxy)-1-oxoisoindolin-2-yl)piperidine-2,6-dione;

3-(5-(((R)-1-isobutylpiperidin-2-yl)methoxy)-1-oxoisoindolin-2-yl)piperidine-2,6-dione;

3-(1-oxo-5-(((R)-1-(pyrimidin-5-ylmethyl)piperidin-2-yl)methoxy)isoindolin-2-yl)piperidine-2,6-dione;

3-(5-(((S)-1-((2-hydroxypyridin-4-yl)methyl)piperidin-2-yl)methoxy)-1-oxoisoindolin-2-yl)piperidine-2,6-dione;

3-(5-(((S)-1-((2-aminopyrimidin-5-yl)methyl)piperidin-2-yl)methoxy)-1-oxoisoindolin-2-yl)piperidine-2,6-dione;

3-(5-(((S)-1-(3-(4-methoxyphenyl)-1H-pyrazole-5-carbonyl)piperidin-2-yl)methoxy)-1-oxoisoindolin-2-yl)piperidine-2,6-dione;

2-chloro-5-(((2S)-2-(((2-(2,6-dioxopiperidin-3-yl)-1-oxoisoindolin-5-yl)oxy)methyl)piperidin-1-yl)methyl)benzenesulfonamide;

3-(5-(((S)-1-(oxazol-4-ylmethyl)piperidin-2-yl)methoxy)-1-oxoisoindolin-2-yl)piperidine-2,6-dione;

3-(1-oxo-5-(((S)-1-(2-(2-oxo-2-(piperidin-1-yl)ethoxy)benzyl)piperidin-2-yl)methoxy)isoindolin-2-yl)piperidine-2,6-dione;

3-(1-oxo-5-(((S)-1-(5-propylisoxazole-3-carbonyl)piperidin-2-yl)methoxy)isoindolin-2-yl)piperidine-2,6-dione;

methyl 4-(((2R)-2-(((2-(2,6-dioxopiperidin-3-yl)-1-oxoisoindolin-5-yl)oxy)methyl)piperidin-1-yl)methyl)-1-(3-(trifluoromethyl)phenyl)-1H-pyrazole-3-carboxylate;

3-(5-(((R)-1-(2-((1H-1,2,4-triazol-1-yl)methyl)benzyl)piperidin-2-yl)methoxy)-1-oxoisoindolin-2-yl)piperidine-2,6-dione;

3-(5-(((R)-1-((1-methyl-1H-benzo[d]imidazol-2-yl)methyl)piperidin-2-yl)methoxy)-1-oxoisoindolin-2-yl)piperidine-2,6-dione;

2-(((2S)-2-(((2-(2,6-dioxopiperidin-3-yl)-1-oxoisoindolin-5-yl)oxy)methyl)piperidin-1-yl)methyl)imidazo[1,2-a]pyridine-7-carbonitrile;

tert-butyl (1-(((2R)-2-(((2-(2,6-dioxopiperidin-3-yl)-1-oxoisoindolin-5-yl)oxy)methyl)piperidin-1-yl)methyl)cyclopentyl)carbamate;

3-(((2S)-2-(((2-(2,6-dioxopiperidin-3-yl)-1-oxoisoindolin-5-yl)oxy)methyl)piperidin-1-yl)methyl)benzonitrile;

3-(5-(((S)-1-(1-methyl-5-phenyl-1H-pyrazole-3-carbonyl)piperidin-2-yl)methoxy)-1-oxoisoindolin-2-yl)piperidine-2,6-dione;

3-(5-(((S)-1-(5-isopropylisoxazole-3-carbonyl)piperidin-2-yl)methoxy)-1-oxoisoindolin-2-yl)piperidine-2,6-dione;

3-(1-oxo-5-(((S)-1-((2-oxo-1,2-dihydropyridin-3-yl)methyl)piperidin-2-yl)methoxy)isoindolin-2-yl)piperidine-2,6-dione;

3-(5-((1-ethyl-3,3-dimethylpiperidin-2-yl)methoxy)-1-oxoisoindolin-2-yl)piperidine-2,6-dione;

3-(5-(((S)-1-ethyl-3,3-dimethylpiperidin-2-yl)methoxy)-1-oxoisoindolin-2-yl)piperidine-2,6-dione;

4-(((2S)-2-(((2-(2,6-dioxopiperidin-3-yl)-1-oxoisoindolin-5-yl)oxy)methyl)piperidin-1-yl)methyl)-3-methoxybenzonitrile;

3-(5-(((S)-1-(2-ethylthiazole-5-carbonyl)piperidin-2-yl)methoxy)-1-oxoisoindolin-2-yl)piperidine-2,6-dione;

3-(5-(((S)-1-((2-(methylamino)pyrimidin-5-yl)methyl)piperidin-2-yl)methoxy)-1-oxoisoindolin-2-yl)piperidine-2,6-dione;

3-(5-(((R)-1-(2-hydroxy-5-(5-(trifluoromethyl)-1H-tetrazol-1-yl)benzyl)piperidin-2-yl)methoxy)-1-oxo-1,3,3a,4,7,7a-hexahydro-2H-isoindol-2-yl)piperidine-2,6-dione;

3-(5-(((S)-1-(7-methoxy-1H-indole-3-carbonyl)piperidin-2-yl)methoxy)-1-oxoisoindolin-2-yl)piperidine-2,6-dione;

3-(5-(((S)-1-(3-isopropylisoxazole-5-carbonyl)piperidin-2-yl)methoxy)-1-oxoisoindolin-2-yl)piperidine-2,6-dione;

3-(5-(((R)-1-((3,5-dimethylisoxazol-4-yl)methyl)piperidin-2-yl)methoxy)-1-oxoisoindolin-2-yl)piperidine-2,6-dione;

3-(5-(((S)-1-((1-methyl-1H-benzo[d]imidazol-2-yl)methyl)piperidin-2-yl)methoxy)-1-oxoisoindolin-2-yl)piperidine-2,6-dione;

3-(5-(1-((S)-1-ethylpyrrolidin-2-yl)ethoxy)-1-oxoisoindolin-2-yl)piperidine-2,6-dione;

3-(5-((S)-1-((S)-1-ethylpyrrolidin-2-yl)ethoxy)-1-oxoisoindolin-2-yl)piperidine-2,6-dione;

3-(5-((4-ethyl-6,6-dimethylmorpholin-3-yl)methoxy)-1-oxoisoindolin-2-yl)piperidine-2,6-dione;

3-(5-(((R)-4-ethyl-6,6-dimethylmorpholin-3-yl)methoxy)-1-oxoisoindolin-2-yl)piperidine-2,6-dione;

3-(5-(((R)-1-((4-methyltetrahydro-2H-pyran-4-yl)methyl)piperidin-2-yl)methoxy)-1-oxoisoindolin-2-yl)piperidine-2,6-dione;

3-(5-(((S)-4-ethylmorpholin-3-yl)methoxy)-1-oxoisoindolin-2-yl)piperidine-2,6-dione;

3-(1-oxo-5-(((S)-1-(pyrimidin-5-ylmethyl)piperidin-2-yl)methoxy)isoindolin-2-yl)piperidine-2,6-dione;

3-(5-(((S)-1-((5-methylisoxazol-3-yl)methyl)piperidin-2-yl)methoxy)-1-oxoisoindolin-2-yl)piperidine-2,6-dione;

4-(((2S)-2-(((2-(2,6-dioxopiperidin-3-yl)-1-oxoisoindolin-5-yl)oxy)methyl)piperidin-1-yl)methyl)picolinonitrile;

3-(1-oxo-5-(((S)-1-(quinoxaline-6-carbonyl)piperidin-2-yl)methoxy)isoindolin-2-yl)piperidine-2,6-dione;

3-(5-(((S)-1-(3-(difluoromethoxy)benzoyl)piperidin-2-yl)methoxy)-1-oxoisoindolin-2-yl)piperidine-2,6-dione;

3-(5-(((S)-1-(3-(1-methyl-1H-pyrazol-3-yl)benzoyl)piperidin-2-yl)methoxy)-1-oxoisoindolin-2-yl)piperidine-2,6-dione;

3-(5-(((S)-1-(2-morpholinothiazole-4-carbonyl)piperidin-2-yl)methoxy)-1-oxoisoindolin-2-yl)piperidine-2,6-dione;

3-(5-(((S)-1-(3-fluorobicyclo[1.1.1]pentane-1-carbonyl)piperidin-2-yl)methoxy)-1-oxoisoindolin-2-yl)piperidine-2,6-dione;

3-(5-((1-ethyl-3,3-dimethylpiperidin-2-yl)methoxy)-1-oxoisoindolin-2-yl)piperidine-2,6-dione;

3-(5-(((R)-1-ethyl-3,3-dimethylpiperidin-2-yl)methoxy)-1-oxoisoindolin-2-yl)piperidine-2,6-dione;

3-(5-(((R)-1-((6-fluoropyridin-3-yl)methyl)piperidin-2-yl)methoxy)-1-oxoisoindolin-2-yl)piperidine-2,6-dione;

3-(5-(((R)-1-(4,4-difluorocyclohexyl)piperidin-2-yl)methoxy)-1-oxoisoindolin-2-yl)piperidine-2,6-dione;

3-(5-(((R)-1-(4-(4-ethylpiperazin-1-yl)benzyl)piperidin-2-yl)methoxy)-1-oxoisoindolin-2-yl)piperidine-2,6-dione;

3-(1-oxo-5-(((R)-1-(4-(trifluoromethoxy)benzyl)piperidin-2-yl)methoxy)isoindolin-2-yl)piperidine-2,6-dione;

3-(5-((S)-1-((R)-1-ethylpiperidin-2-yl)ethoxy)-1-oxoisoindolin-2-yl)piperidine-2,6-dione;

3-(5-((S)-1-((S)-1-ethylpiperidin-2-yl)ethoxy)-1-oxoisoindolin-2-yl)piperidine-2,6-dione;

3-(5-(((R)-1-isobutyrylpiperidin-2-yl)methoxy)-1-oxoisoindolin-2-yl)piperidine-2,6-dione;

3-(5-(((R)-1-(2,4-difluorobenzyl)piperidin-2-yl)methoxy)-1-oxoisoindolin-2-yl)piperidine-2,6-dione;

3-(((2R)-2-(((2-(2,6-dioxopiperidin-3-yl)-1-oxoisoindolin-5-yl)oxy)methyl)piperidin-1-yl)methyl)bicyclo[1.1.1]pentane-1-carbonitrile;

3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione;
3-(5-(((R)-1-(3,4-difluorobenzyl)piperidin-2-yl)methoxy)-1-oxoisoindolin-2-yl)piperidine-2,6-dione;
3-(5-((R)-1-((S)-1-ethylpiperidin-2-yl)ethoxy)-1-oxoisoindolin-2-yl)piperidine-2,6-dione;
3-(5-(((R)-1-(4-(4-isobutylpiperazin-1-yl)benzyl)piperidin-2-yl)methoxy)-1-oxoisoindolin-2-yl)piperidine-2,6-dione;
3-(5-(((R)-1-benzoylpiperidin-2-yl)methoxy)-1-oxoisoindolin-2-yl)piperidine-2,6-dione;
3-(5-((1-ethylazepan-2-yl)methoxy)-1-oxoisoindolin-2-yl)piperidine-2,6-dione;
3-(5-(((R)-1-(oxazole-5-carbonyl)piperidin-2-yl)methoxy)-1-oxoisoindolin-2-yl)piperidine-2,6-dione;
3-(5-(((R)-1-(((1r,3R)-3-methoxycyclobutyl)methyl)piperidin-2-yl)methoxy)-1-oxoisoindolin-2-yl)piperidine-2,6-dione;
3-(5-(((R)-1-((3-fluorobicyclo[1.1.1]pentan-1-yl)methyl)piperidin-2-yl)methoxy)-1-oxoisoindolin-2-yl)piperidine-2,6-dione;
3-(5-(((R)-1-(2-morpholinobenzyl)piperidin-2-yl)methoxy)-1-oxoisoindolin-2-yl)piperidine-2,6-dione;
3-(5-(((R)-1-(4-(4-(cyclopropylmethyl)piperazin-1-yl)benzyl)piperidin-2-yl)methoxy)-1-oxoisoindolin-2-yl)piperidine-2,6-dione;
3-(5-(((R)-1-((2-oxaspiro[3.3]heptan-6-yl)methyl)piperidin-2-yl)methoxy)-1-oxoisoindolin-2-yl)piperidine-2,6-dione;
Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperazine-1-carboxylate;
3-(1-oxo-5-(((R)-1-(2-(piperazin-1-yl)benzyl)piperidin-2-yl)methoxy)isoindolin-2-yl)piperidine-2,6-dione;
3-(5-(((R)-1-(2-(4-isobutylpiperazin-1-yl)benzyl)piperidin-2-yl)methoxy)-1-oxoisoindolin-2-yl)piperidine-2,6-dione;
3-(1-oxo-5-(((R)-1-(2-(4-((tetrahydro-2H-pyran-4-yl)methyl)piperazin-1-yl)benzyl)piperidin-2-yl)methoxy)isoindolin-2-yl)piperidine-2,6-dione;
3-(1-oxo-5-(((R)-1-(4-(4-(tetrahydro-2H-pyran-4-yl) piperazin-1-yl)benzyl) piperidin-2-yl)methoxy)isoindolin-2-yl)piperidine-2,6-dione;
Tert-butyl 7-(((2R)-2-(((2-(2,6-dioxopiperidin-3-yl)-1-oxoisoindolin-5-yl)oxy)methyl)piperidin-1-yl)methyl)indoline-1-carboxylate;
3-(5-(((R)-1-(indolin-7-ylmethyl)piperidin-2-yl)methoxy)-1-oxoisoindolin-2-yl)piperidine-2,6-dione;
3-(5-(((R)-1-((1-ethylindolin-7-yl)methyl)piperidin-2-yl)methoxy)-1-oxoisoindolin-2-yl)piperidine-2,6-dione;
3-(5-(((R)-1-(4-fluorobenzyl)piperidin-2-yl)methoxy)-1-oxoisoindolin-2-yl)piperidine-2,6-dione;
3-(5-(((R)-1-(2-chloro-4-fluorobenzyl)piperidin-2-yl)methoxy)-1-oxoisoindolin-2-yl)piperidine-2,6-dione;
3-(5-(((R)-1-((5-fluoropyridin-2-yl)methyl)piperidin-2-yl)methoxy)-1-oxoisoindolin-2-yl)piperidine-2,6-dione;
3-(5-(((R)-1-(((1s,3S)-3-methoxycyclobutyl)methyl)piperidin-2-yl)methoxy)-1-oxoisoindolin-2-yl)piperidine-2,6-dione;
3-(1-oxo-5-(((R)-1-(2-(piperidin-1-yl)benzyl)piperidin-2-yl)methoxy)isoindolin-2-yl)piperidine-2,6-dione;
Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperidine-1-carboxylate;
3-(5-(((R)-1-(2-(1-ethylpiperidin-4-yl)benzyl)piperidin-2-yl)methoxy)-1-oxoisoindolin-2-yl)piperidine-2,6-dione;
Tert-butyl 4-(4-(((2R)-2-(((2-(2,6-dioxopiperidin-3-yl)-1-oxoisoindolin-5-yl)oxy)methyl)piperidin-1-yl)methyl)phenyl)piperidine-1-carboxylate;
3-(5-(((R)-1-(4-(1-ethylpiperidin-4-yl)benzyl)piperidin-2-yl)methoxy)-1-oxoisoindolin-2-yl)piperidine-2,6-dione;
3-(5-(((R)-1-(2,4-dimethoxybenzyl)piperidin-2-yl)methoxy)-1-oxoisoindolin-2-yl)piperidine-2,6-dione;
3-(5-(((R)-1-(2-methoxybenzyl)piperidin-2-yl)methoxy)-1-oxoisoindolin-2-yl)piperidine-2,6-dione;
3-(5-(((R)-1-((2,3-dihydrobenzo[b][1,4]dioxin-5-yl)methyl)piperidin-2-yl)methoxy)-1-oxoisoindolin-2-yl)piperidine-2,6-dione;
3-(5-(((R)-1-(benzo[d][1,3]dioxol-5-ylmethyl)piperidin-2-yl)methoxy)-1-oxoisoindolin-2-yl)piperidine-2,6-dione;
3-(5-(((R)-1-(((1r,3R)-3-hydroxycyclobutyl)methyl)piperidin-2-yl)methoxy)-1-oxoisoindolin-2-yl)piperidine-2,6-dione;
3-(5-(((R)-1-(((1s,3S)-3-hydroxycyclobutyl)methyl)piperidin-2-yl)methoxy)-1-oxoisoindolin-2-yl)piperidine-2,6-dione;
3-(5-(((R)-1-(3-fluoro-4-methoxybenzyl)piperidin-2-yl)methoxy)-1-oxoisoindolin-2-yl)piperidine-2,6-dione;
3-(5-(((R)-1-(3-fluoro-2-hydroxybenzyl)piperidin-2-yl)methoxy)-1-oxoisoindolin-2-yl)piperidine-2,6-dione;
3-(1-oxo-5-(((R)-1-(3,4,5-trifluorobenzyl)piperidin-2-yl)methoxy)isoindolin-2-yl)piperidine-2,6-dione;
(5-(((R)-1-((2,4-dimethylthiazol-5-yl)methyl)piperidin-2-yl)methoxy)-1-oxoisoindolin-2-yl)piperidine-2,6-dione;
3-(5-(((R)-1-((2,4-dimethylthiazol-5-yl)methyl)piperidin-2-yl)methoxy)-1-oxoisoindolin-2-yl)piperidine-2,6-dione;
3-(1-oxo-5-(((R)-1-(pyridin-4-ylmethyl)piperidin-2-yl)methoxy)isoindolin-2-yl)piperidine-2,6-dione;
3-(5-(((R)-1-(2,6-difluorobenzyl)piperidin-2-yl)methoxy)-1-oxoisoindolin-2-yl)piperidine-2,6-dione;
3-(5-(((R)-1-(4-hydroxybenzyl)piperidin-2-yl)methoxy)-1-oxoisoindolin-2-yl)piperidine-2,6-dione;
3-(5-(((R)-1-((2-fluoropyridin-3-yl)methyl)piperidin-2-yl)methoxy)-1-oxoisoindolin-2-yl)piperidine-2,6-dione;
3-(1-oxo-5-(((R)-1-(quinolin-3-ylmethyl)piperidin-2-yl)methoxy)isoindolin-2-yl)piperidine-2,6-dione;
3-(5-(((R)-1-((4-methylthiazol-2-yl)methyl)piperidin-2-yl)methoxy)-1-oxoisoindolin-2-yl)piperidine-2,6-dione;
3-(1-oxo-5-(((R)-1-(quinolin-2-ylmethyl)piperidin-2-yl)methoxy)isoindolin-2-yl)piperidine-2,6-dione;
Tert-butyl 4-(4-(((2R)-2-(((2-(2,6-dioxopiperidin-3-yl)-1-oxoisoindolin-5-yl)oxy)methyl)piperidin-1-yl)methyl)-2-ethylphenyl)piperidine-1-carboxylate;
3-(5-(((R)-1-(3-ethyl-4-(piperidin-4-yl)benzyl)piperidin-2-yl)methoxy)-1-oxoisoindolin-2-yl)piperidine-2,6-dione;
3-(5-(((R)-1-(3-ethyl-4-(1-ethylpiperidin-4-yl)benzyl) piperidin-2-yl)methoxy)-1-oxoisoindolin-2, 6-dione;
3-(5-(((R)-1-(4-(tert-butyl)benzyl)piperidin-2-yl)methoxy)-1-oxoisoindolin-2-yl)piperidine-2,6-dione;
3-(1-oxo-5-(((R)-1-(4-(piperidin-1-yl)benzyl)piperidin-2-yl)methoxy)isoindolin-2-yl)piperidine-2,6-dione;
3-(5-(((R)-1-((3-methoxybicyclo[1.1.1]pentan-1-yl)methyl) piperidin-2-yl)methoxy)-1-oxoisoindolin-2-yl)piperidine-2,6-dione;
Tert-butyl 4-(2-(((2R)-2-(((2-(2,6-dioxopiperidin-3-yl)-1-oxoisoindolin-5-yl)oxy)methyl)piperidin-1-yl)methyl)-4-fluorophenyl)piperazine-1-carboxylate;
3-(5-(((R)-1-(5-fluoro-2-(piperazin-1-yl)benzyl)piperidin-2-yl)methoxy)-1-oxoisoindolin-2-yl)piperidine-2,6-dione;

3-(5-(((R)-1-(2-(4-ethylpiperazin-1-yl)-5-fluorobenzyl)piperidin-2-yl)methoxy)-1-oxoisoindolin-2-yl)piperidine-2,6-dione;

3-(1-oxo-5-(((R)-1-(4-(1-(trifluoromethyl)cyclopropyl)benzyl)piperidin-2-yl)methoxy)isoindolin-2-yl)piperidine-2,6-dione;

3-(5-(((R)-1-((3,4-dihydro-2H-benzo[b][1,4]oxazin-5-yl)methyl)piperidin-2-yl)methoxy)-1-oxoisoindolin-2-yl)piperidine-2,6-dione;

3-(5-(((R)-1-((4-ethyl-3,4-dihydro-2H-benzo[b][1,4]oxazin-5-yl)methyl)piperidin-2-yl)methoxy)-1-oxoisoindolin-2-yl)piperidine-2,6-dione;

3-(1-oxo-5-(((R)-1-((3-oxo-3,4-dihydro-2H-benzo[b][1,4]oxazin-5-yl)methyl) piperidin-2-yl)methoxy)isoindolin-2-yl)piperidine-2,6-dione;

3-(5-(((R)-1-(2-(benzyloxy)ethyl)piperidin-2-yl)methoxy)-1-oxoisoindolin-2-yl)piperidine-2,6-dione;

3-(5-(((R)-1-((2,2-difluorobenzo[d][1,3]dioxol-5-yl)methyl)piperidin-2-yl)methoxy)-1-oxoisoindolin-2-yl)piperidine-2,6-dione;

3-(5-(((R)-1-((6-morpholinopyridin-3-yl)methyl)piperidin-2-yl)methoxy)-1-oxoisoindolin-2-yl)piperidine-2,6-dione;

3-(5-(((R)-1-(4-(3,6-dihydro-2H-pyran-4-yl)benzyl)piperidin-2-yl)methoxy)-1-oxoisoindolin-2-yl)piperidine-2,6-dione;

Tert-butyl 4-(5-(((2R)-2-(((2-(2,6-dioxopiperidin-3-yl)-1-oxoisoindolin-5-yl)oxy)methyl)piperidin-1-yl)methyl)pyridin-2-yl)piperazine-1-carboxylate;

3-(5-(((R)-1-((6-(4-ethylpiperazin-1-yl)pyridin-3-yl)methyl) piperidin-2-yl)methoxy)-1-oxoisoindolin-2-yl)piperidine-2,6-dione;

4-(((2R)-2-(((2-(2,6-dioxopiperidin-3-yl)-1-oxoisoindolin-5-yl)oxy)methyl)piperidin-1-yl)methyl)-2-methoxybenzonitrile;

3-(5-(((R)-1-((1H-benzo[d]imidazol-5-yl)methyl)piperidin-2-yl)methoxy)-1-oxoisoindolin-2-yl)piperidine-2,6-dione;

5-(((2R)-2-(((2-(2,6-dioxopiperidin-3-yl)-1-oxoisoindolin-5-yl)oxy)methyl)piperidin-1-yl)methyl)-2-methoxybenzonitrile;

3-(1-oxo-5-(((R)-1-(4-(1-((tetrahydro-2H-pyran-4-yl)methyl)piperidin-4-yl)benzyl)piperidin-2-yl)methoxy) isoindolin-2-yl)piperidine-2,6-dione;

3-(5-(((R)-1-(4-(1-(2-fluoroethyl)piperidin-4-yl)benzyl)piperidin-2-yl)methoxy)-1-oxoisoindolin-2-yl)piperidine-2,6-dione;

3-(5-(((R)-1-(benzo[d]oxazol-5-ylmethyl)piperidin-2-yl)methoxy)-1-oxoisoindolin-2-yl)piperidine-2,6-dione;

3-(5-(((R)-1-(oxetan-3-ylmethyl)piperidin-2-yl)methoxy)-1-oxoisoindolin-2-yl)piperidine-2,6-dione;

3-(5-(((R)-1-(4-(1-(oxetan-3-ylmethyl) piperidin-4-yl)benzyl)piperidin-2-yl)methoxy)-1-oxoisoindolin-2-yl)piperidine-2,6-dione;

3-(1-oxo-5-(((R)-1-(((R)-tetrahydrofuran-3-yl)methyl)piperidin-2-yl)methoxy)isoindolin-2-yl)piperidine-2,6-dione;

3-(1-oxo-5-(((R)-1-(((S)-tetrahydrofuran-3-yl)methyl)piperidin-2-yl)methoxy)isoindolin-2-yl)piperidine-2,6-dione;

3-(5-(((R)-1-(cyclopropylmethyl)piperidin-2-yl)methoxy)-1-oxoisoindolin-2-yl)piperidine-2,6-dione;

3-(5-(((1S)-1-(1-(((1r,4S)-4-methoxycyclohexyl)methyl)piperidin-2-yl)ethoxy)-1-oxoisoindolin-2-yl)piperidine-2,6-dione;

3-(5-(((1R)-1-(1-(((1r,4R)-4-methoxycyclohexyl)methyl)piperidin-2-yl)ethoxy)-1-oxoisoindolin-2-yl)piperidine-2,6-dione;

3-(5-(((1R,3S,4S)-2-ethyl-2-azabicyclo[2.2.1]heptan-3-yl)methoxy)-1-oxoisoindolin-2-yl)piperidine-2,6-dione;

3-(5-(((R)-1-(4-(4-isopropylpiperazin-1-yl)benzyl)piperidin-2-yl)methoxy)-1-oxoisoindolin-2-yl)piperidine-2,6-dione;

3-(5-(((R)-1-(4-(4-(tert-butyl)piperazin-1-yl)benzyl)piperidin-2-yl)methoxy)-1-oxoisoindolin-2-yl)piperidine-2,6-dione;

3-(5-(((R)-1-(4-(4-cyclopropylpiperazin-1-yl)benzyl)piperidin-2-yl)methoxy)-1-oxoisoindolin-2-yl)piperidine-2,6-dione;

3-(5-((1-ethyl-4-fluoropiperidin-2-yl)methoxy)-1-oxoisoindolin-2-yl)piperidine-2,6-dione;

3-(5-((4,4-difluoropiperidin-2-yl)methoxy)-1-oxoisoindolin-2-yl)piperidine-2,6-dione;

(S)-3-(5-(((S)-1-ethyl-4,4-difluoropiperidin-2-yl)methoxy)-1-oxoisoindolin-2-yl)piperidine-2,6-dione;

(R)-3-(5-(((S)-1-ethyl-4,4-difluoropiperidin-2-yl)methoxy)-1-oxoisoindolin-2-yl)piperidine-2,6-dione;

(R)-3-(5-(((R)-1-ethyl-4,4-difluoropiperidin-2-yl)methoxy)-1-oxoisoindolin-2-yl)piperidine-2,6-dione;

(S)-3-(5-(((R)-1-ethyl-4,4-difluoropiperidin-2-yl)methoxy)-1-oxoisoindolin-2-yl)piperidine-2,6-dione;

(R)-3-(5-(((1 S,3S,4R)-2-ethyl-2-azabicyclo[2.2.1]heptan-3-yl)methoxy)-1-oxoisoindolin-2-yl)piperidine-2,6-dione;

(S)-3-(5-(((1S,3S,4R)-2-ethyl-2-azabicyclo[2.2.1]heptan-3-yl)methoxy)-1-oxoisoindolin-2-yl)piperidine-2,6-dione;

(R)-3-(5-(((1R,3R,4S)-2-ethyl-2-azabicyclo[2.2.1]heptan-3-yl)methoxy)-1-oxoisoindolin-2-yl)piperidine-2,6-dione and (S)-3-(5-(((1R,3R,4S)-2-ethyl-2-azabicyclo[2.2.1]heptan-3-yl)methoxy)-1-oxoisoindolin-2-yl)piperidine-2,6-dione.

Embodiment 81. A compound, or a pharmaceutically acceptable salt, hydrate, solvate, prodrug, stereoisomer, or tautomer thereof, selected from:

3-(5-((R)-1-((R)-1-ethylpiperidin-2-yl)ethoxy)-1-oxoisoindolin-2-yl)piperidine-2,6-dione-3-d;

3-(5-((R)-1-((R)-1-ethylpiperidin-2-yl)ethoxy)-1-oxoisoindolin-2-yl)piperidine-2,6-dione-3,4,4,5,5-$d_5$;

3-(5-(((R)-1-(2-(4-methylpiperazin-1-yl)benzyl)piperidin-2-yl)methoxy)-1-oxoisoindolin-2-yl)piperidine-2,6-dione-3-d;

3-(5-(((R)-1-(2-(4-methylpiperazin-1-yl)benzyl)piperidin-2-yl)methoxy)-1-oxoisoindolin-2-yl)piperidine-2,6-dione-3,4,4,5,5-$d_5$;

3-(5-(((R)-1-(4-(4-methylpiperazin-1-yl)benzyl)piperidin-2-yl)methoxy)-1-oxoisoindolin-2-yl)piperidine-2,6-dione-3-d;

3-(5-(((R)-1-(4-(4-methylpiperazin-1-yl)benzyl)piperidin-2-yl)methoxy)-1-oxoisoindolin-2-yl)piperidine-2,6-dione-3,4,4,5,5-$d_5$;

3-(5-(((R)-1-ethylpiperidin-2-yl)methoxy)-1-oxoisoindolin-2-yl)piperidine-2,6-dione-3-d;

3-(5-(((R)-1-ethylpiperidin-2-yl)methoxy)-1-oxoisoindolin-2-yl)piperidine-2,6-dione-3,4,4,5,5-$d_5$;

3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione-3-d;

3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione-3,4,4,5,5-$d_5$;

3-(5-(((R)-1-(((1r,3R)-3-methoxycyclobutyl)methyl)piperidin-2-yl)methoxy)-1-oxoisoindolin-2-yl)piperidine-2,6-dione-3-d; and 3-(5-(((R)-1-(((1r,3R)-3-methoxycyclobutyl)methyl)piperidin-2-yl)methoxy)-1-oxoisoindolin-2-yl)piperidine-2,6-dione-3,4,4,5,5-$d_5$.

Embodiment 82. The compound of any of the preceding Embodiments, or a pharmaceutically acceptable salt, hydrate, solvate, prodrug, stereoisomer, or tautomer thereof, wherein the pharmaceutically acceptable salt is an acid addition salt.

Embodiment 83. A pharmaceutical composition comprising a therapeutically effective amount of a compound of any one of Embodiments 1 to 82, or a pharmaceutically acceptable salt thereof, and a pharmaceutically acceptable carrier or excipient.

Embodiment 84. A method of treating or preventing a disease or disorder in a subject in need thereof, the method comprising administering to the subject a therapeutically effective amount of a compound of any one of claims 1 to 82, or a pharmaceutically acceptable salt, hydrate, solvate, prodrug, stereoisomer, or tautomer thereof.

Embodiment 85. A method of degrading WIZ protein in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 86. A method of inhibiting WIZ protein expression in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 87. A method of inhibiting, reducing, or eliminating the activity of WIZ protein or WIZ protein expression, the method comprising administering to the subject a compound of of any one of Embodiments 1 to 82, or a pharmaceutically acceptable salt, hydrate, solvate, prodrug, stereoisomer, or tautomer thereof.

Embodiment 88. A method of inducing or promoting fetal hemoglobin in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 89. A method of reactivating fetal hemoglobin production or expression in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 90. A method of increasing fetal hemoglobin expression in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 91. A method of treating a hemoglobinopathy, e.g., a beta-hemoglobinopathy, in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 92. A method of treating a sickle cell disease in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 93. A method of treating beta-thalassemia in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 94. A method of treating a disease or disorder that is affected by the modulation of WIZ protein levels comprising administering to the patient in need thereof a compound of any one of Embodiments 1 to 82, or a pharmaceutically acceptable salt, hydrate, solvate, prodrug, stereoisomer, or tautomer thereof.

Embodiment 95. A method of treating or preventing a disorder that is affected by the reduction of WIZ protein levels, in a subject in need thereof, the method comprising administering to the subject a therapeutically effective amount of a compound of any one of Embodiments 1 to 82, or a pharmaceutically acceptable salt, hydrate, solvate, prodrug, stereoisomer, or tautomer thereof.

Embodiment 96. A method for reducing WIZ protein levels in a subject comprising the step of administering to a subject in need thereof a therapeutically effective amount of a compound of any one of the Embodiments 1 to 82, or a pharmaceutically acceptable salt, hydrate, solvate, prodrug, stereoisomer, or tautomer thereof.

Embodiment 97. A compound according to any one of Embodiments 1 to 82, or a pharmaceutically acceptable salt, hydrate, solvate, prodrug, stereoisomer, or tautomer thereof, for use as a medicament.

Embodiment 98. A compound of any one of Embodiments 1 to 82, or a pharmaceutically acceptable salt, hydrate, solvate, prodrug, stereoisomer, or tautomer thereof, for use in the treatment of a disease or disorder selected from sickle cell disease and beta-thalassemia.

Embodiment 99. A compound of any one of Embodiments 1 to 82, or a pharmaceutically acceptable salt, hydrate, solvate, prodrug, stereoisomer, or tautomer thereof, for use in treating or preventing a disease or disorder in a subject in need thereof.

Embodiment 100. A compound of any one of Embodiments 1 to 82, or a pharmaceutically acceptable salt, hydrate, solvate, prodrug, stereoisomer, or tautomer thereof, for use in treating or preventing a disorder that is affected by the reduction of WIZ protein levels, in a subject in need thereof.

Embodiment 101. A compound of any one of Embodiments 1 to 82, or a pharmaceutically acceptable salt, hydrate, solvate, prodrug, stereoisomer, or tautomer thereof, for use in inhibiting WIZ protein expression in a subject in need thereof.

Embodiment 102. A compound of any one of Embodiments 1 to 82, or a pharmaceutically acceptable salt, hydrate, solvate, prodrug, stereoisomer, or tautomer thereof, for use in degrading WIZ protein in a subject in need thereof.

Embodiment 103. A compound of any one of Embodiments 1 to 82, or a pharmaceutically acceptable salt, hydrate, solvate, prodrug, stereoisomer, or tautomer thereof, for use in inhibiting, reducing, or eliminating the activity of WIZ protein or WIZ protein expression in a subject in need thereof.

Embodiment 104. A compound of any one of Embodiments 1 to 82, or a pharmaceutically acceptable salt, hydrate, solvate, prodrug, stereoisomer, or tautomer thereof, for use in inducing or promoting fetal hemoglobin in a subject in need thereof.

Embodiment 105. A compound of any one of Embodiments 1 to 82 or a pharmaceutically acceptable salt, hydrate, solvate, prodrug, stereoisomer, or tautomer thereof, for use in reactivating fetal hemoglobin production or expression in a subject in need thereof.

Embodiment 106. A compound of any one of Embodiments 1 to 82, or a pharmaceutically acceptable salt, hydrate, solvate, prodrug, stereoisomer, or tautomer thereof, for use in increasing fetal hemoglobin expression in a subject in need thereof.

Embodiment 107. A compound of any one of Embodiments 1 to 82, or a pharmaceutically acceptable salt, hydrate, solvate, prodrug, stereoisomer, or tautomer thereof, for use in treating a hemoglobinopathy in a subject in need thereof.

Embodiment 108. A compound of any one of Embodiments 1 to 82, or a pharmaceutically acceptable salt, hydrate, solvate, prodrug, stereoisomer, or tautomer thereof, for use in treating a sickle cell disease in a subject in need thereof.

Embodiment 109. A compound of any one of Embodiments 1 to 82, or a pharmaceutically acceptable salt, hydrate, solvate, prodrug, stereoisomer, or tautomer thereof, for use in treating beta-thalassemia in a subject in need thereof.

Embodiment 110. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

Embodiment 111. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by inducing or promoting fetal hemoglobin.

Embodiment 112. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

Embodiment 113. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by increasing fetal hemoglobin expression.

Embodiment 114. The use of a compound of any of Embodiments 110 to 113, wherein the disease or disorder is selected from sickle cell disease and beta-thalassemia.

Embodiment 115. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

Embodiment 116. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by inducing fetal hemoglobin.

Embodiment 117. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

Embodiment 118. Use of a compound of any one of Embodiments 1 to 82, or a pharmaceutically acceptable salt, hydrate, solvate, prodrug, stereoisomer, or tautomer thereof, in the manufacture of a medicament for treating a disease or disorder that is affected by increasing fetal hemoglobin expression.

Embodiment 119. The use of a compound of any of Embodiments 115 to 118, wherein the disease or disorder is selected from sickle cell disease and beta-thalassemia.

Embodiment 120. Use of a compound of any one of Embodiments 1 to 82, or a pharmaceutically acceptable salt, hydrate, solvate, prodrug, stereoisomer, or tautomer thereof, in the treatment of a disease or disorder that is affected by the reduction of WIZ protein levels, inhibition of WIZ protein expression or degradation of WIZ protein.

Embodiment 121. Use of a compound of any one of Embodiments 1 to 82, or a pharmaceutically acceptable salt, hydrate, solvate, prodrug, stereoisomer, or tautomer thereof, in the treatment of a disease or disorder that is affected by inducing fetal hemoglobin, reactivating fetal hemoglobin production or expression, or increasing fetal hemoglobin expression.

Embodiment 122. The use of Embodiment 120 or 121, wherein the disease or disorder is selected from sickle cell disease and beta-thalassemia.

Embodiment 123. A pharmaceutical combination comprising a compound of any of Embodiments 1 to 82, or a pharmaceutically acceptable salt, hydrate, solvate, prodrug, stereoisomer, or tautomer thereof, and one or more additional therapeutic agent(s).

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centres. The disclosure is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The disclosure includes cis and trans configurations of substituted cycloalkyl groups as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

Pharmaceutically Acceptable Salts

As used herein, the terms "salt" or "salts" refers to an acid addition or base addition salt of a compound of the disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. The compounds of the disclosure may be capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, formic acid, trifluoroacetic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the disclosure provides compounds in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Preferably, pharmaceutically acceptable salts of compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) are acid addition salts.

Isotopically Labelled Compounds

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, sulfur, fluorine, chlorine and iodine, such as $^{2}H$, $^{3}H$, $^{11}C$, $^{13}C$, $^{14}C$, $^{18}O$, $^{15}N$, $^{18}F$, $^{17}O$, $^{18}O$, $^{35}S$, $^{36}Cl$, $^{123}I$, $^{124}I$, $^{125}I$ respectively. The disclosure includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ compound may be particularly desirable for PET or SPECT studies. Isotopically-labeled compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) can generally be prepared by conventional techniques known to those skilled in the art or by processes analogous to those described in the accompanying Examples and General Schemes (e.g., General Schemes 5a and 5b) using an appropriate isotopically-labeled reagent in place of the non-labeled reagent previously employed.

In one embodiment of any aspect of the present disclosure, the hydrogens in the compound of Formula (I') or Formula (I) are present in their normal isotopic abundances. In a another embodiment, the hydrogens are isotopically enriched in deuterium (D), and in a particular embodiment of the invention the hydrogen(s) at the glutarimide portion in compounds of Formula (I') or Formula (I) are enriched in D, for example,

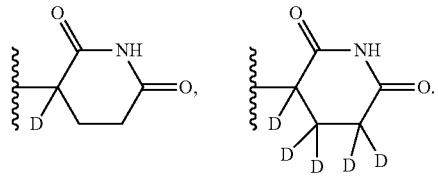 [SMILES: *C1([2H])CCC(=O)NC1=O ; *C1([2H])C(=O)NC(=O)C([2H])([2H])C1([2H])[2H]]

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the disclosure include those wherein the solvent of crystallization may be isotopically substituted, e.g., $D_2O$, $d_6$-acetone, $d_6$-DMSO.

Compounds of the disclosure, i.e. compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) that contain groups capable of acting as donors and/or acceptors for hydrogen bonds may be capable of forming co-crystals with suitable co-crystal formers. These co-crystals may be prepared from compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) by known co-crystal forming procedures. Such procedures include grinding, heating, co-subliming, co-melting, or contacting in solution compounds of (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) with the co-crystal former under crystallization conditions and isolating co-crystals thereby formed. Suitable co-crystal formers include those described in WO 2004/078163.

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

Any asymmetric center (e.g., carbon or the like) of the compound(s) of the disclosure can be present in racemic or enantiomerically enriched, for example the (R)-, (S)- or (R,S)-configuration. In certain embodiments, for example, as a mixture of enantiomers, each asymmetric center is present in at least 10% enantiomeric excess, at least 20% enantiomeric excess, at least 30% enantiomeric excess, at least 40% enantiomeric excess, at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric center is present in at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. Thus, compounds of the disclosure can be present in a racemic mixture or in enantiomerically enriched form or in an enantiopure form or as a mixture of diastereoisomers.

In one embodiment, the compound of formula (I') comprises a compound of formulae (I-i-a), (I-i-b), (I-ii-a), or (I-ii-b):

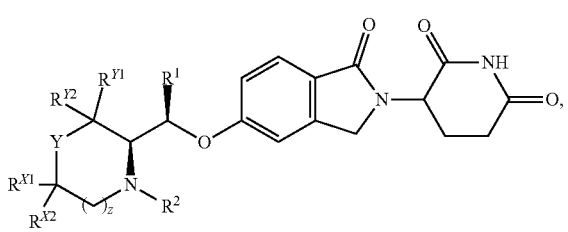

(I-i-a)

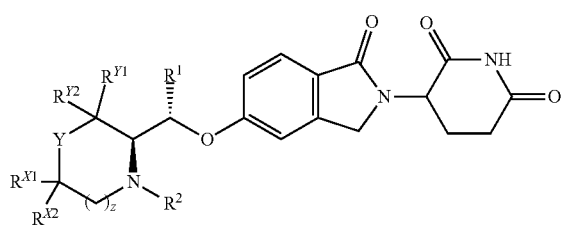

(I-i-b)

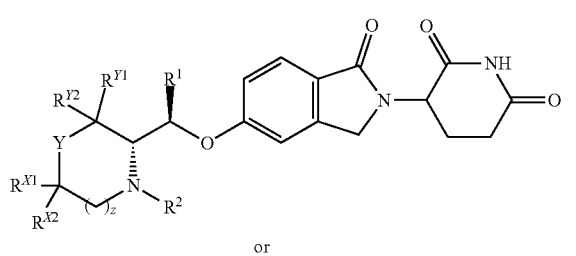

(I-ii-a)

or

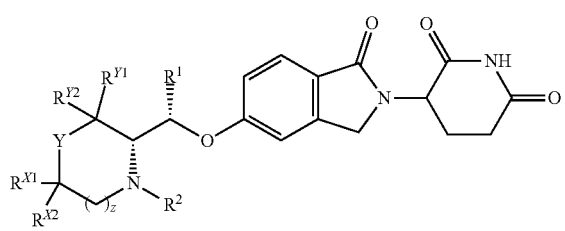

(I-ii-b)

or a pharmaceutically acceptable salt, hydrate, solvate, prodrug, stereoisomer, or tautomer thereof.

In one embodiment, the compound of formula (I-i-a) comprises a compound of formulae (I-i-ai) or (I-i-aii):

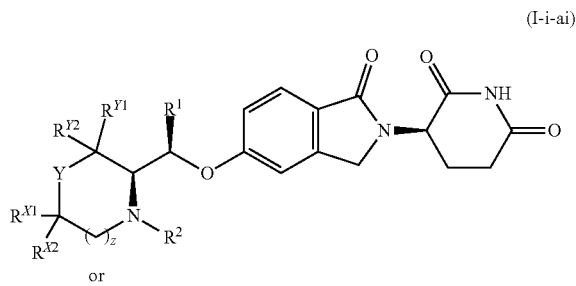

(I-i-ai)

or

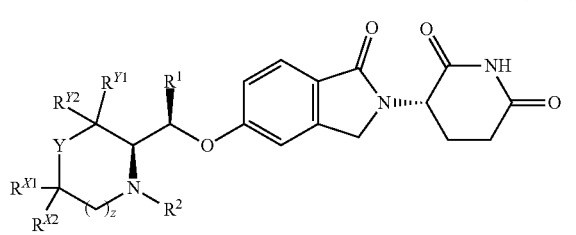

(I-i-aii)

or a pharmaceutically acceptable salt, hydrate, solvate, prodrug, stereoisomer, or tautomer thereof.

In one embodiment, the compound of formula (I-i-b) comprises a compound of formulae (I-i-bi) or (I-i-bii):

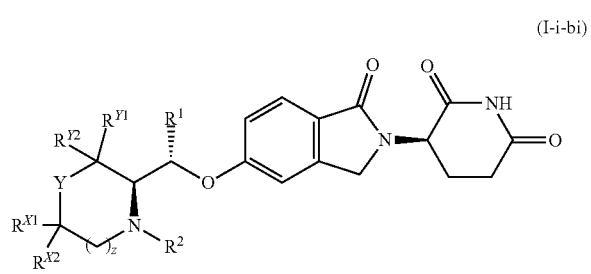
(I-i-bi)

or

(I-i-bii)

or a pharmaceutically acceptable salt, hydrate, solvate, prodrug, stereoisomer, or tautomer thereof.

In one embodiment, the compound of formula (I-ii-a) comprises a compound of formulae (I-ii-ai) or (I-ii-aii):

(I-ii-ai)

or (I-ii-aii)

or a pharmaceutically acceptable salt, hydrate, solvate, prodrug, stereoisomer, or tautomer thereof.

In one embodiment, the compound of formula (I-ii-b) comprises a compound of formulae (I-ii-bi) or (I-ii-bii):

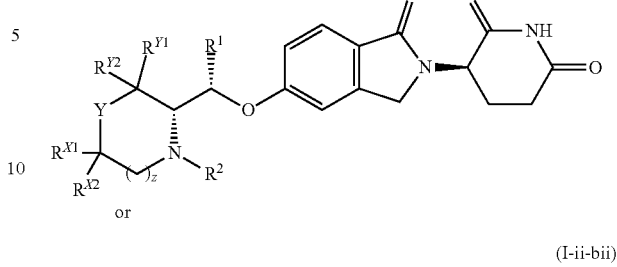
(I-ii-bi)

or (I-ii-bii)

or a pharmaceutically acceptable salt, hydrate, solvate, prodrug, stereoisomer, or tautomer thereof.

In another embodiment, the compound of formula (I') comprises a compound of formulae (I-i) or (I-ii):

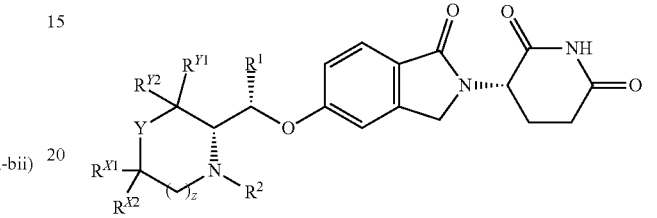
(I-i)

or (I-ii)

or a pharmaceutically acceptable salt, hydrate, solvate, prodrug, stereoisomer, or tautomer thereof.

In the formulae of the present application the term "⫽" on a C-sp³ indicates the absolute stereochemistry, either (R) or (S). In the formulae of the present application the term "⫽" on a C-sp³ indicates the absolute stereochemistry, either (R) or (S). In the formulae of the present application the term "⫽" on a C-sp³ represents a covalent bond wherein the stereochemistry of the bond is not defined. This means that the term "⫽" on a C-sp³ comprises an (S) configuration or an (R) configuration of the respective chiral centre. Furthermore, mixtures may also be present. Therefore, mixtures of stereoisomers, e.g., mixtures of enantiomers, such as racemates, and/or mixtures of diastereoisomers are encompassed by the present disclosure.

For the avoidance of doubt, where compound structures are drawn with undefined stereochemistry with respect to any R group, for example, to $R^1$ in formula (I-i) or (I-ii), as represented by a bond ( ), this means the asymmetric center has either a (R)- or (S)-configuration, or exists as a mixture thereof and stated as such.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers, racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical isomers (enantiomers) by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Furthermore, the compounds of the disclosure, including their salts, can also be obtained in the form of their hydrates, or include other solvents used for their crystallization. The compounds of the disclosure may inherently or by design form solvates with pharmaceutically acceptable solvents (including water); therefore, it is intended that the disclosure embrace both solvated and unsolvated forms. The term "solvate" refers to a molecular complex of a compound of the disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The presence of solvates can be identified by a person of skill in the art with tools such as NMR.

The compounds of the disclosure, including salts, hydrates and solvates thereof, may inherently or by design form polymorphs.

In compounds of the present disclosure, the stereocenter at C-3 of the glutarimide moiety (marked with a *) may be prone to epimerization under basic conditions.

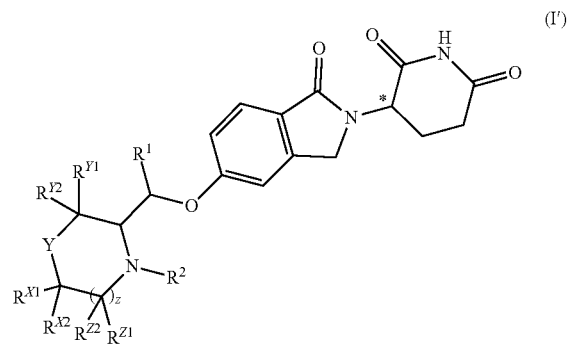

Separation of the diastereoisomers (or enantiomers as the case may be) at this position can be achieved according to known chiral separation techniques in the art. Particularly, separation may be carried out according to Example 26.

In one embodiment of the compounds of the present disclosure, the absolute configuration at the glutarimide stereocentre (marked with a * above) is S.

In another embodiment of the compounds of the present disclosure, the absolute configuration at the glutarimide stereocentre (marked with a * above) is R.

In one embodiment, there is provided a compound as described in any one of the Examples or according to any of Embodiments 1 to 82, wherein the absolute configuration at the glutarimide stereocentre (marked with a * above) is S.

In another embodiment, there is provided a compound as described in any one of the Examples or according to any of Embodiments 1 to 82, wherein the absolute configuration at the glutarimide stereocentre (marked with a * above) is R.

Methods of Making

The compounds of the disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art.

Generally, the compounds of formula (I') and formula (I) can be prepared according to the Schemes provided infra.

General scheme 1

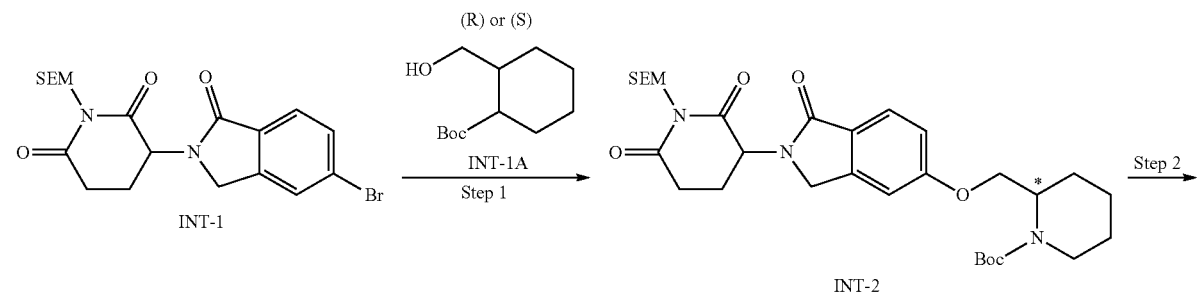

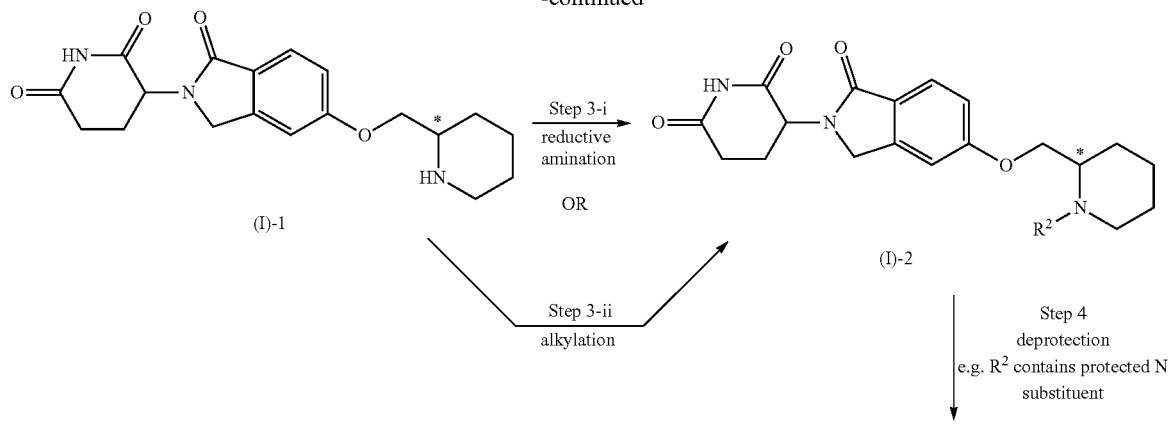

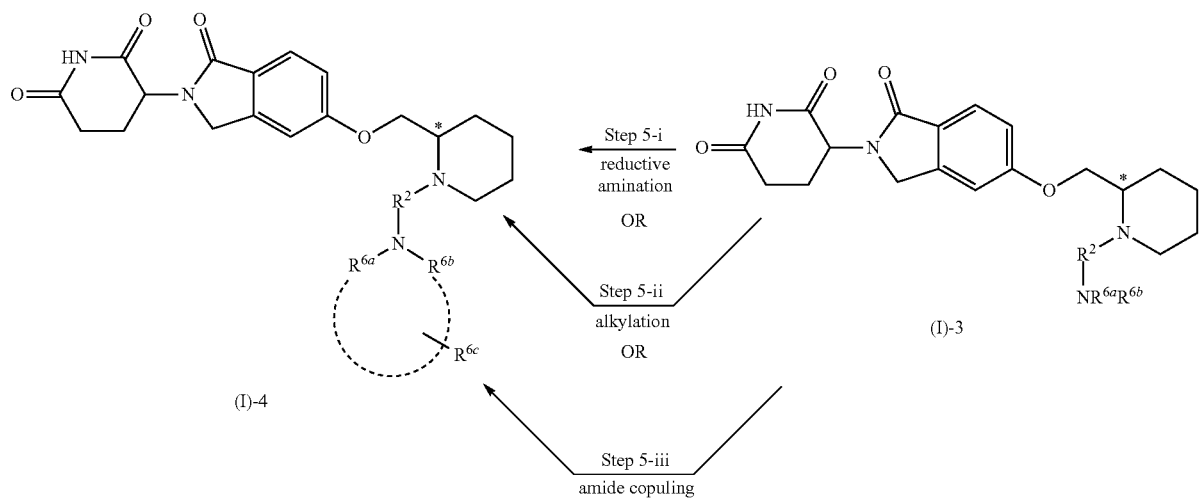

The starting materials for the above reaction scheme are commercially available or can be prepared according to methods known to one skilled in the art or by methods disclosed herein. In general, the compounds of the disclosure are prepared in the above reaction Scheme 1 as follows:

A metallaphotoredox reaction, such as an iridium (Ir)-catalysed photoredox coupling of INT-1 with an alcohol partner of formula INT-1A in the presence of a polar solvent, such as acetonitrile (ACN) can provide the cross-coupled ether product INT-2 in Step 1. Removal of the protecting group (e.g., Boc) under acidic conditions can provide the free amine (I)-1 (Step 2), which can then be converted to (I)-2 via a reductive amination (Step 3-i) with an appropriate aldehyde in the presence of a borohydride reagent, such as sodium borohydride acetate, or an alkylation reaction (Step 3-ii) with an appropriate alkyl mesylate in the presence of an amine base and polar solvent, such as diisopropylethylamine (DIPEA) and dimethylformamide (DMF). Where compounds of formula (I)-2 contain a N-protected moiety, e.g., N-protected piperazine group, these can further be converted to (I)-3 in Step 4 by deprotection (e.g., Boc) under acidic conditions, and subsequent reductive amination with an appropriate aldehyde and sodium borohydride reagent, or alkylation reaction with an appropriate alkylating reagent, or amide coupling with an appropriate activating agent and a base to provide a compound of formula (I)-4. For Scheme 1, $R^2$, $R^{6a}$, $R^{6b}$ and $R^{6c}$ are as defined herein, in particular according to any of enumerated Embodiments 1 to 80.

General scheme 2

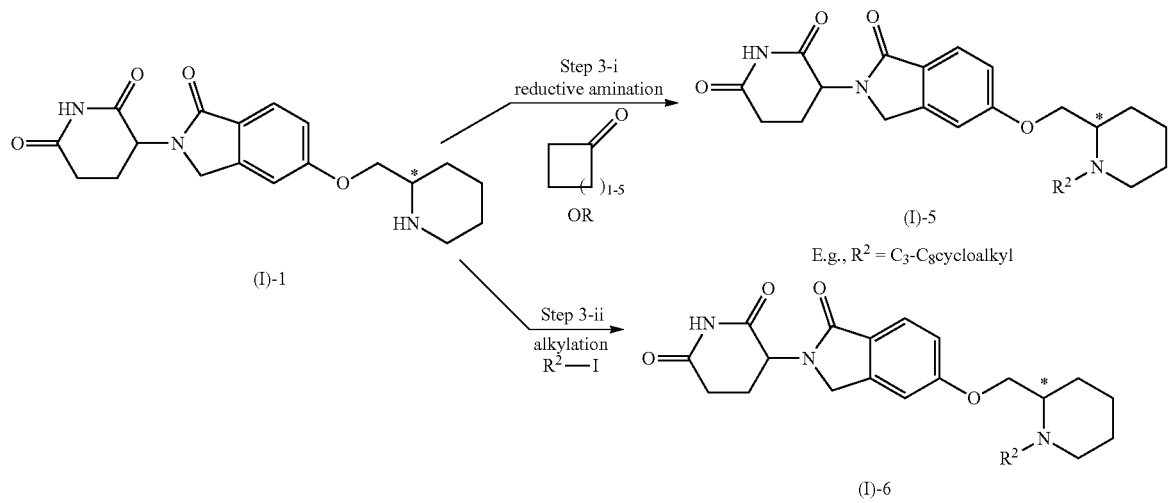

The starting materials for the above reaction scheme are commercially available or can be prepared according to methods known to one skilled in the art or by methods disclosed herein. In general, the compounds of the disclosure are prepared in the above reaction Scheme 2 as follows: The compound of formula (I)-1 can be converted into (I)-5 via a reductive amination (Step 3-i) with an appropriate ketone in the presence of a borohydride reagent, such as sodium borohydride acetate or (I)-6 via an alkylation reaction with an appropriate alkyl iodide in the presence of a base, such as $K_2CO_3$, and a polar solvent, such as dimethylacetamide (DMA). For Scheme 2 $R^2$ is as defined herein, in particular according to any of enumerated Embodiments 1 to 80.

General scheme 3

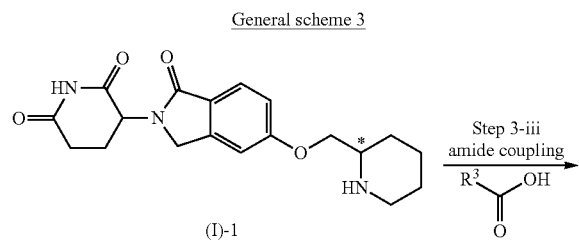

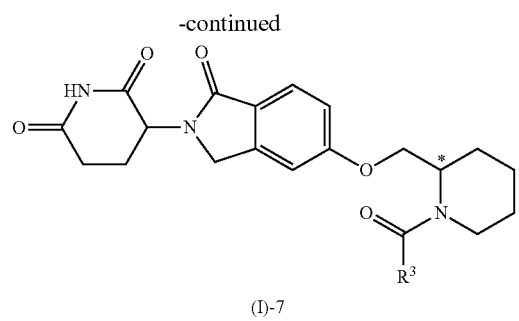

The starting materials for the above reaction scheme are commercially available or can be prepared according to methods known to one skilled in the art or by methods disclosed herein. In general, the compounds of the disclosure are prepared in the above reaction Scheme 3 as follows: An amide coupling reaction of the compound (I)-1 with an appropriate carboxylic acid, an activating agent, such as HATU, and a base such as DIPEA or NMM, affords the amide product (I)-7. For Scheme 3 $R^3$ is as defined herein, in particular according to any of enumerated Embodiments 1 to 80.

General scheme 4

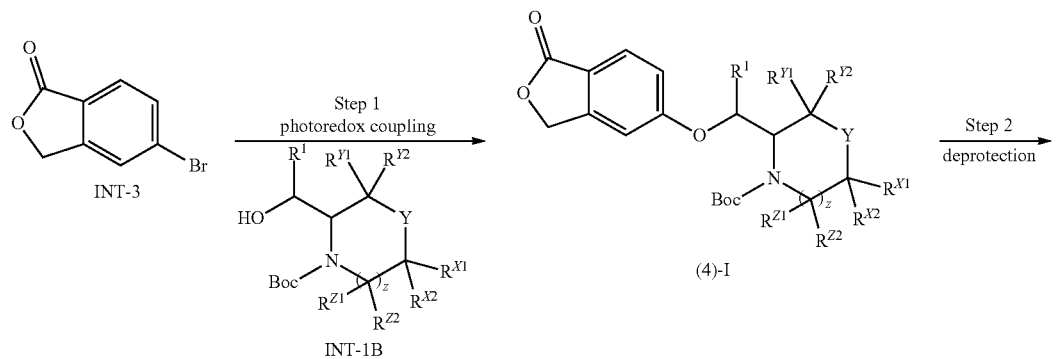

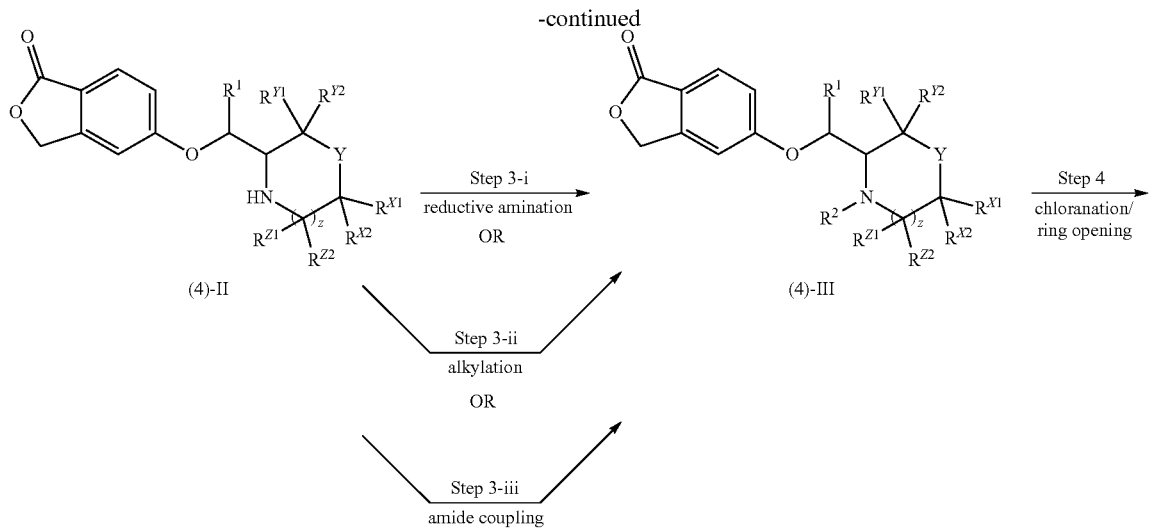

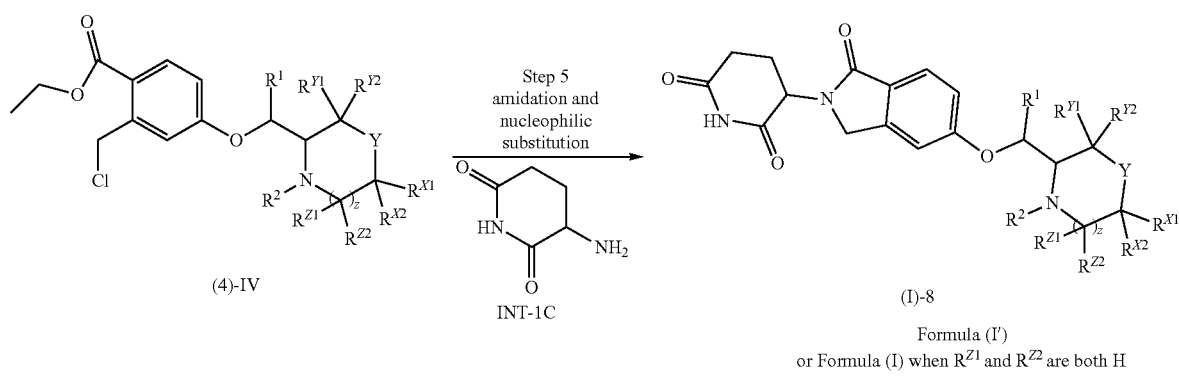

Formula (I')
or Formula (I) when $R^{Z1}$ and $R^{Z2}$ are both H

The starting materials for the above reaction scheme are commercially available or can be prepared according to methods known to one skilled in the art or by methods disclosed herein.

In general, the compounds of the disclosure are prepared in the above reaction Scheme 4 as follows:

A metallaphotoredox reaction, such as an iridium (Ir)-catalysed photoredox coupling, of (INT-3) with an alcohol partner of formula (INT-1B) in the presence of a polar solvent, such as acetonitrile (ACN) can provide the cross-coupled ether product (4)-I in Step 1. Removal of the protecting group (e.g., Boc) under acidic conditions, can provide the free amine (4)-II (Step 2), which can then be converted to (4)-III via reductive amination (Step 3-i) with an appropriate aldehyde in the presence of a borohydride reagent, such as sodium borohydride acetate.

Alternatively, (4)-II may be converted into 4-(III) via an alkylation reaction (Step 3-ii) with an appropriate alkyl mesylate or alkyl halide in the presence of an amine base and polar solvent, such as diisopropylethylamine (DIPEA) and dimethylformamide (DMF) as described in general schemes 1 and 2. Alternatively, (4)-II may be converted into 4-(III) via an amide coupling reaction (Step 3-iii) with an appropriate carboxylic acid, an activating agent, such as HATU, and a base, such as DIPEA or NMM in a polar solvent, such as DMF, as described in general schemes 1 and 3. Chlori-nation with a suitable agent, such as $SOCl_2$ and ring opening of lactone (4)-III affords (4)-IV. Subsequent ring closing by amidation and nucleophilic substitution using INT-IC under acidic conditions yields final product of Formula (I') or Formula (I). For Scheme 4, Y, z, $R^{X1}$, $R^{X2}$, $R^{Y1}$, $R^{Y2}$, $R^{Z1}$, $R^{Z2}$, $R^1$ and $R^2$ are as defined herein, in particular according to any of enumerated Embodiments 1 to 80.

General Schemes 5a and 5b: Deuterated Compounds of the Disclosure

Scheme 5a

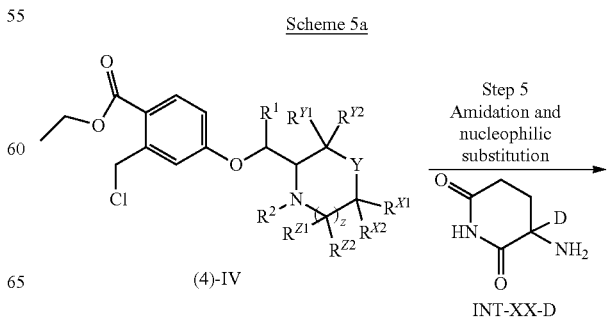

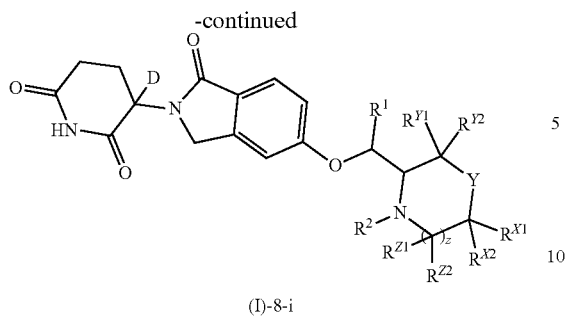

(I)-8-i

Deuterated Formula (I′)
or Formula (I) when $R^{Z1}$ and $R^{Z2}$ are both H

Scheme 5b

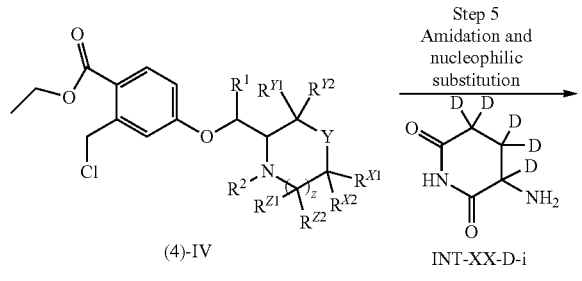

Step 5
Amidation and
nucleophilic
substitution

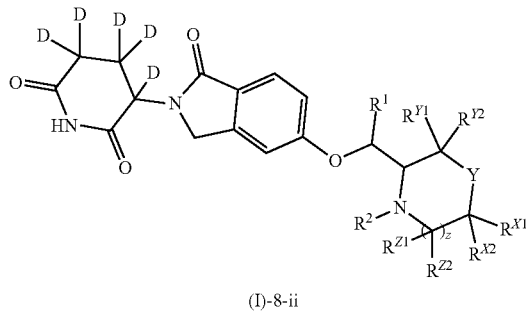

(I)-8-ii

Deuterated Formula (I′)
or Formula (I) when $R^{Z1}$ and $R^{Z2}$ are both H

Compound (4)-IV can be prepared according to General Scheme 4. Subsequent ring closing by amidation and nucleophilic substitution using deuterated INT-XX-D (prepared according to WO 2012/068512) or deuterated INT-XX-D-i (prepared according to WO 2012/079022) under acidic conditions yields the final deuterated compounds of Formula (I′), wherein Y, z, $R^1$, $R^2$, $R^{X1}$, $R^{X2}$, $R^{Y1}$, $R^{Y2}$, $R^{Z1}$, $R^{Z2}$ are as defined according to any of Embodiments 1 to 80.

In an embodiment there is provided a compound of formula INT-2 or a salt thereof. In another embodiment, there is provided a compound of formula (I)-1 or a salt thereof.

In a further embodiment, there is provided a compound of formula (X) or a salt thereof,

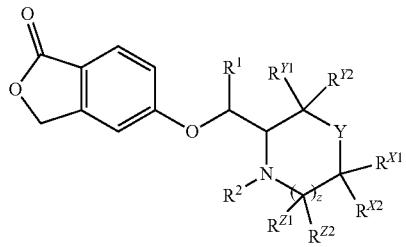

(X)

wherein:
Y is selected from O, and $CH_2$, $CF_2$ and CHF;
z is an integer from 0 to 2;
$R^{X1}$ and $R^{X2}$ are each independently selected from hydrogen, and $C_1$-$C_6$alkyl;
$R^{Y1}$ and $R^{Y2}$ are each independently selected from hydrogen, and $C_1$-$C_6$alkyl;
$R^{Z1}$ and $R^{Z2}$ are both hydrogen
or
1 of $R^{Z1}$ and $R^{Z2}$ and 1 of $R^{Y1}$ and $R^{Y2}$ together form a $C_1$-$C_2$ alkylene bridging group and the other of $R^{Z1}$ and $R^{Z2}$ and $R^{Y1}$ and $R^{Y2}$ are both hydrogen;
$R^1$ is selected from hydrogen, and $C_1$-$C_6$alkyl;
$R^2$ is selected from hydrogen, a nitrogen protecting group (PG) (suitably, tert-butyl carbamate (Boc)), —C(═O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, $C_3$-$C_8$cycloalkyl and —O—($R^{2a}$),
and wherein the aryl, heterocyclyl, and cycloalkyl are each independently substituted with 0-5 $R^4$;
$R^{2a}$ is $C_1$-$C_6$alkyl wherein the alkyl is substituted with 0-1 substituent independently selected from $C_6$-$C_{10}$aryl;
$R^3$ is selected from —CH═$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and
wherein the aryl, heteroaryl, heterocyclyl, and cycloalkyl are each independently substituted with 0-5 $R^4$;
$R^{3a}$ and $R^{3b}$ together with the carbon atom to which they are attached form a $C_3$-$C_8$cycloalkyl ring;
each $R^{3c}$ is at each occurrence independently selected from —C(═O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl,
wherein the —O-aryl, arylalkyl-O—, and —O-heteroaryl are each independently substituted with 0-3 $R^{4a}$, and
wherein the aryl, heteroaryl, heterocyclyl, and cycloalkyl are each independently substituted with 0-5 $R^4$;
$R^{3d}$ is a 4- to 6-membered heterocyclyl comprising 1-2 heteroatoms independently selected from N, O, and S;
$R^{3e}$ and $R^{3f}$are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —SO$_2$R$^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—(R$^5$), —C(=O)—(R$^5$), —C(=O)—NR$^{6a}$R$^{6b}$, NR$^{6a}$R$^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 R$^{4a}$, wherein the alkyl and alkoxyl are each independently substituted with 0-1 R$^{4b}$, and wherein the cycloalkyl is substituted with 0-3 substituents each independently selected from —CN, $C_1$-$C_6$alkyl, $C_1$-$C_6$alkoxyl, hydroxyl and $C_1$-$C_6$haloalkyl;

each $R^{4a}$ is at each occurrence independently selected from —CN, $C_1$-$C_6$alkoxyl, $C_1$-$C_6$haloalkyl, halogen, hydroxyl, —C(=O)—O—(R$^5$), 5- to 10-membered heteroaryl comprising 1-4 heteroatoms independently selected from N, O, and S, di($C_1$-$C_6$alkyl)amino$C_1$-$C_6$alkyl, $C_1$-$C_6$alkyl, 4- to 6-membered heterocyclyl comprising 1-2 heteroatoms independently selected from N, O, and S and $C_3$-$C_6$cycloalkyl, wherein the alkyl is substituted with 0-1 R$^{4b}$, and wherein the heteroaryl is substituted with 0-3 R$^{4a-1}$;

each $R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

each $R^{4b}$ is at each occurrence independently selected from —CN, halogen, —C(=O)NR$^{6a}$R$^{6b}$, NR$^{6a}$R$^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, NH$_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 R$^{6c}$;

each $R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

In an embodiment, z is 1; and 1 of R$^{Z1}$ and R$^{Z2}$ and 1 of R$^{Y1}$ and R$^{Y2}$ together form a $C_1$-$C_2$ alkylene bridging group and the other of R$^{Z1}$ and R$^{Z2}$ and R$^{Y1}$ and R$^{Y2}$ are both hydrogen.

In an embodiment, z is 1; and 1 of R$^{Z1}$ and R$^{Z2}$ and 1 of R$^{Y1}$ and R$^{Y2}$ together form a $C_1$ alkylene bridging group and the other of R$^{Z1}$ and R$^{Z2}$ and R$^{Y1}$ and R$^{Y2}$ are both hydrogen.

In an embodiment, R$^{Z1}$ and R$^{Z2}$ are both hydrogen.

In an embodiment, R$^1$ is hydrogen.

In an embodiment, R$^{Z1}$ and R$^{Z2}$ are both hydrogen and R$^1$ is hydrogen.

In an embodiment, R$^{Z1}$ and R$^{Z2}$ are both hydrogen and R$^1$ is hydrogen and R$^2$ is hydrogen.

In a further embodiment, R$^1$, R$^2$, R$^{Y1}$, R$^{Y2}$, R$^{X1}$, R$^{X2}$, R$^{Z1}$, R$^{Z2}$, Y and z are as defined in any of enumerated embodiments 1 to 80. Additionally, R$^2$ can be a nitrogen protecting group (PG) (e.g., tert-butyl carbamate (Boc)).

In a further embodiment, the compound of Formula (X) is of Formula (X)-i

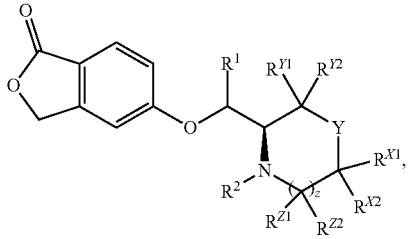

(X)-i wherein R$^1$, R$^2$, R$^{X1}$, R$^{X2}$, R$^{Y1}$, R$^{Y2}$, R$^{Z1}$, R$^{Z2}$, Y and z are defined according to Formula (X) above.

In a further embodiment, the compound of Formula (X) is of Formula (X)-ii

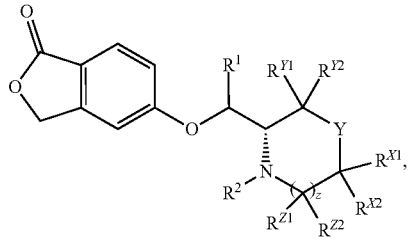

(X)-ii wherein R$^1$, R$^2$, R$^{X1}$, R$^{X2}$, R$^{Y1}$, R$^{Y2}$, R$^{Z1}$, R$^{Z2}$, Y and z are defined according to Formula (X) above.

In a further embodiment of Formula (X) (or Formula (X)-i or Formula (X)-ii), there is provided a compound selected from:

(R)-5-((1-ethylpiperidin-2-yl)methoxy)isobenzofuran-1 (3H)-one;

(S)-5-((1-ethylpiperidin-2-yl)methoxy)isobenzofuran-1 (3H)-one;

5-((R)-1-((S)-1-ethylpiperidin-2-yl)ethoxy)isobenzofuran-1 (3H)-one;

5-((S)-1-((S)-1-ethylpiperidin-2-yl)ethoxy)isobenzofuran-1 (3H)-one;

5-((S)-1-((R)-1-ethylpiperidin-2-yl)ethoxy)isobenzofuran-1 (3H)-one; and 5-((R)-1-((R)-1-ethylpiperidin-2-yl)ethoxy)isobenzofuran-1 (3H)-one.

In a further embodiment, there is provided a compound of Formula (Y)

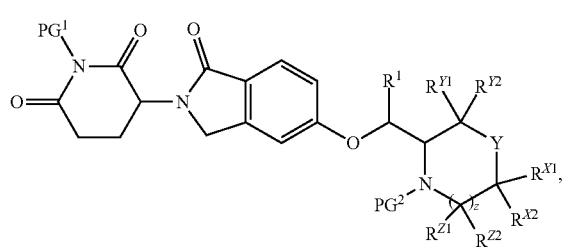

(Y)

wherein $R^1$, $R^{X1}$, $R^{X2}$, $R^{Y1}$, $R^{Y2}$, $R^{Z1}$, $R^{Z2}$, Y and z are defined according to Formula (X) above, and $PG^1$ and $PG^2$ are both a nitrogen protecting group, as defined herein.

In an embodiment, $PG^1$ is a base labile protecting group and $PG^2$ is an acid labile protecting group.

In an embodiment, $PG^1$ is the SEM protecting group (trimethylsilylethoxymethyl) and $PG^2$ is the BOC protecting group (tert-butyloxycarbonyl).

In a further embodiment, the compound of Formula (Y) is of Formula (Y)-i

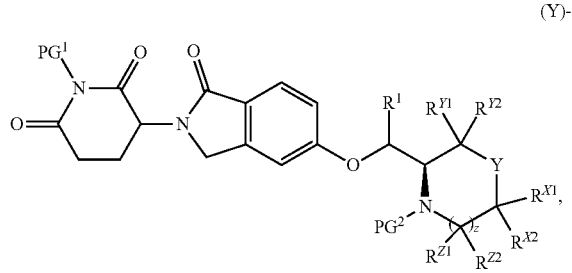

(Y)-i wherein $R^1$, $R^{X1}$, $R^{X2}$, $R^{Y1}$, $R^{Y2}$, $R^{Z1}$, $R^{Z2}$, Y, z, $PG^1$ and $PG^2$ are defined according to Formula (Y) above.

In a further embodiment, the compound of Formula (Y) is of Formula (Y)-ii

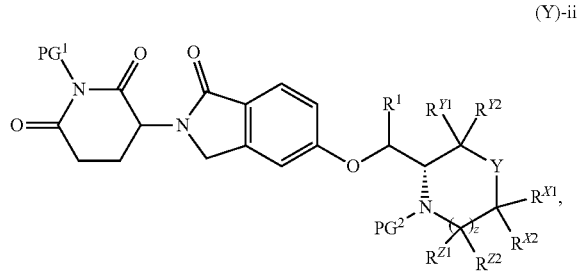

(Y)-ii wherein $R^1$, $R^{X1}$, $R^{X2}$, $R^{Y1}$, $R^{Y2}$, $R^{Z1}$, $R^{Z2}$, Y, z, $PG^1$ and $PG^2$ are defined according to Formula (Y) above.

In a further embodiment of Formula (X) (or Formula (X)-i or Formula (X)-ii), there is provided a compound selected from:
tert-butyl (2R)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate; and
tert-butyl (2S)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate.

In a further aspect, the disclosure provides to a process for the preparation of a compound of formula (I') or formula (I), in free form or in pharmaceutically acceptable salt form, comprising the step of:
1) coupling an aryl bromide of formula (INT-1) or formula (INT-3) with an alcohol of formula (INT-1A) or (INT-1B) under photo redox coupling conditions, to give a compound of formula (INT-2) or formula (4)-I as defined herein.

In a further aspect, the disclosure provides a process for the preparation of a compound of formula (I') or formula (I), in free form or in pharmaceutically acceptable salt form, comprising the steps of:
1) coupling an aryl bromide of formula (INT-3) with an alcohol of formula (INT-1B) under photo redox coupling conditions, to give a compound of formula (4)-I as defined herein;
2) deprotecting a compound of formula (4)-I to give a compound of formula (4)-II as defined herein;
3) reacting a compound of formula (4)-II under reductive amination conditions to give a compound of formula (4)-III as defined herein;
4) chlorinating a compound of formula (4)-III with a nucleophilic chlorinating reagent, such as $SOCl_2$, to give a compound of formula (4)-IV as defined herein;
5) reacting a compound of formula (4)-IV with a compound of formula (INT-1C) to give a compound of formula (I') or formula (I) (or formula (I)-8 as depicted in General scheme 4) as defined herein; and
6) optionally purifying the compound of formula (I') or formula (I) (or formula (I)-8 as depicted in General scheme 4) as defined herein.

In a further aspect, the disclosure provides a process for the preparation of a compound of formula (I') or formula (I), in free form or in pharmaceutically acceptable salt form, comprising the steps of:
1) coupling an aryl bromide of formula (INT-1) with an alcohol of formula (INT-1A) under photo redox coupling conditions, to give a compound of formula (INT-2) as defined herein;
2) deprotecting a compound of formula (INT-2) to give a compound of formula (I)-1 (or formula (I') or formula (I)) as defined herein;
3-i) optionally reacting a compound of formula (I)-1 under reductive amination conditions to give a compound of formula (I)-2 (or formula (I') or formula (I)) as defined herein; or
3-ii) optionally reacting a compound of formula (I)-1 under alkylation conditions to give a compound of formula (I)-2 (or formula (I') or formula (I)) as defined herein; or
3-iii) optionally reacting a compound of formula (I)-1 under amide coupling conditions to give a compound of formula (I)-7 (or formula (I') or formula (I)) as defined herein;
4) optionally deprotecting the compound of formula (I)-2 to give a compound of formula (I)-3 (or formula (I') or formula (I)) as defined herein; and
5) optionally reacting a compound of formula (I)-3 under reductive amination conditions to give a compound of formula (I)-4 (or formula (I') or formula (I)) as defined herein.

Photo redox coupling reaction conditions for any of the aforementioned process steps or hereinafter involve the use of an Ir(III) catalyst, such as [Ir{dF(CF$_3$)ppy}$_2${dtbbpy}]PF$_6$, a Ni(II) complex, such as [NiCl$_2$.dtbbpy], base, such as TMP, a suitable solvent, such as acetonitrile, a light source, such as 34 W blue LED, the reaction conducted at room temperature (r.t.) for a suitable amount of time, for example 12 hours.

Reductive amination conditions for any of the aforementioned process steps or hereinafter involve the use of a corresponding aldehyde, a suitable hydride reagent, such as NaBH(OAc)$_3$, a suitable solvent, such as DMF, the reaction conducted at room temperature (r.t.).

Alkylation reaction conditions for any of the aforementioned process steps or hereinafter involve the use of a corresponding sulfonate ester, such as a corresponding mesylate, a suitable base, such as DIPEA, a suitable solvent, such as DMF, the reaction conducted at a suitable temperature, such as 100° C., under microwave.

Amide coupling reaction conditions for any of the aforementioned process steps or hereinafter involve the use of a corresponding carboxylic acid, an activating agent, such as HATU, a suitable base, such as DIPEA or NMM, a suitable solvent, such as DMF, the reaction conducted at a suitable temperature, such as r.t., for a suitable amount of time, for example 12 hours.

In a further embodiment there is provided a process for the preparation of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) in free form or in pharmaceutically acceptable salt form according to any of General Schemes 1 to 4.

Compounds of formula (INT-1), (I)-I and (X) as defined herein are useful in the preparation of compounds of the disclosure, e.g., compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii). Thus, in an aspect, the disclosure relates to a compound of formula (INT-1) or (I)-I or (X) or salts thereof. In another aspect, the disclosure relates to the use of a compound of formula (INT-1) or (I)-I or (X) or salts thereof in the manufacture of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii). The disclosure further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Pharmaceutical Compositions

In another aspect, the disclosure provides a pharmaceutical composition comprising one or more compounds of described herein or a pharmaceutically acceptable salt, hydrate, solvate, prodrug, stereoisomer, or tautomer thereof, and one or more pharmaceutically acceptable carriers. As used herein, the term "pharmaceutical composition" refers to a compound of the disclosure, or a pharmaceutically acceptable salt thereof, together with at least one pharmaceutically acceptable carrier, in a form suitable for oral or parenteral administration. As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

In an aspect of the present disclosure, there is provided a pharmaceutical composition comprising an agent which is effective in reducing WIZ protein expression levels and/or inducing fetal hemoglobin (HbF) expression. Such compositions include, but are not limited to, small molecule compounds (e.g., small molecule compounds that can target WIZ protein for degradation, e.g., through E3 ubiquitin pathway, e.g. a compound as described herein), siRNAs, shRNA, ASOs, miRNAs, AMOs.

In another aspect, the disclosure provides a pharmaceutical composition comprising a compound of the disclosure, or a pharmaceutically acceptable salt thereof, and a pharmaceutically acceptable carrier. In a further embodiment, the composition comprises at least two pharmaceutically acceptable carriers, such as those described herein. For purposes of the disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol;

c) binders, e.g., magnesium aluminum silicate, starch paste, gelatin, tragacanth, methylcellulose, sodium carboxymethylcellulose and/or polyvinylpyrrolidone;

d) disintegrants, e.g., starches, agar, alginic acid or its sodium salt, or effervescent mixtures; and e) absorbents, colorants, flavors and sweeteners.

In an embodiment, the pharmaceutical compositions are capsules comprising the active ingredient only.

Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers.

In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) in free form or in pharmaceutically acceptable salt form, exhibit valuable pharmacological properties, e.g., WIZ modulating properties or WIZ degrading properties or Hbf inducing properties e.g., as indicated in the in vitro tests as provided in the examples, and are therefore indicated for therapy or for use as research chemicals, e.g., as tool compounds.

Additional properties of the disclosed compounds include having good potency in the biological assays described herein, favorable safety profile, and possess favorable pharmacokinetic properties.

Diseases and Disorders

In an embodiment of the present disclosure, there is provided a therapeutic agent which is effective in reducing WIZ protein expression levels and/or inducing fetal hemoglobin (HbF) expression. In a further embodiment, the agent is a small molecule (e.g., small molecule compounds that can target WIZ protein for degradation, e.g., through E3 ubiquitin pathway, e.g., a compound as described herein), siRNAs, shRNA, ASOs, miRNAs, AMOs. In an embodiment, the method of reducing WIZ protein expression levels and/or inducing fetal hemoglobin (HbF) expression is for the treatment of a hemoglobinopathy, e.g., beta hemoglobinopathy, including sickle cell disease (SCD) and beta-thalassemia.

The compounds of the disclosure can be used to treat one or more of the diseases or disorders described herein below. In one embodiment, the disease or disorder is affected by the reduction of WIZ protein expression levels and/or induction of fetal hemoglobin protein expression levels. In another embodiment, the disease or disorder is a hemoglobinopathy, e.g., beta hemoglobinopathy, including sickle cell disease (SCD) and beta-thalassemia.

Methods of Use

In an aspect of the present disclosure, there is provided a method of reducing WIZ protein expression levels and/or inducing fetal hemoglobin (HbF) expression comprising administering to a subject a therapeutically effective amount of an agent, e.g., a small molecule (e.g., a small molecule compound that can target WIZ protein for degradation, e.g., through E3 ubiquitin pathway, e.g. a compound as described herein), siRNAs, shRNA, ASOs, miRNAs, AMOs. In an embodiment, the method of reducing WIZ protein expression levels and/or inducing fetal hemoglobin (HbF) expression is for the treatment of a hemoglobinopathy, e.g., beta hemoglobinopathy, including sickle cell disease (SCD) and beta-thalassemia.

All the aforementioned embodiments and embodiments hereinafter relating to the methods of reducing WIZ protein expression levels and/or inducing fetal hemoglobin (HbF) expression are equally applicable to:

A therapeutic agent, e.g., a small molecule (e.g., small molecule compounds that can target WIZ protein for degradation, e.g., through E3 ubiquitin pathway, e.g., a compound as described herein), siRNAs, shRNA, ASOs, miRNAs, AMOs, for use in a method of reducing WIZ protein expression levels and/or inducing fetal hemoglobin (HbF) expression;

A therapeutic agent, e.g., a small molecule (e.g., small molecule compounds that can target WIZ protein for degradation, e.g., through E3 ubiquitin pathway, e.g., a compound as described herein), siRNAs, shRNA, ASOs, miRNAs, AMOs, for use in the of the aforementioned diseases or disorders according to the present disclosure;

Use of an agent, e.g., a small molecule (e.g. a compound as described herein), siRNAs, shRNA, ASOs, miRNAs, AMOs, in the treatment of the aforementioned diseases or disorders according to the present disclosure; and A pharmaceutical composition comprising an agent, e.g., a small molecule (e.g., small molecule compounds that can target WIZ protein for degradation, e.g., through E3 ubiquitin pathway, e.g., a compound as described herein), siRNAs, shRNA, ASOs, miRNAs, AMOs, for use in the treatment of the aforementioned diseases or disorders according to the present disclosure.

Having regard to their activity as WIZ modulators or degraders, compounds of formulae (Ia-xii), (Ia-xiii), (Ia-xiv), (Ie), (If), (Ig), (Ih), (Ih-i) and (Ih-ii) in free or pharmaceutically acceptable salt form, are useful in the treatment of conditions which may be treated by modulation of WIZ protein expression levels, reduction of WIZ protein expression levels, or induction of fetal hemoglobin (HbF), such as in a blood disorder, for example an inherited blood disorder, e.g., sickle cell disease, or beta-thalassemia. In one aspect, the disclosure provides a method of treating or preventing a disease or disorder in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of treating or preventing a disorder that is affected by the reduction of WIZ protein levels, in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of inhibiting WIZ protein expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of degrading WIZ protein in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of inhibiting, reducing, or eliminating the activity of WIZ protein or WIZ protein expression, the method comprising administering to the subject a compound of formulae (I'), (I), (I-i), (I-i-a), (I-i-b), (I-i-c), (I-i-d), (I-i-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of inducing or promoting fetal hemoglobin in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of reactivating fetal hemoglobin production or expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of increasing fetal hemoglobin expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of treating a hemoglobinopathy, e.g., a beta-hemoglobinopathy, in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of treating a sickle cell disease in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a method of treating beta-thalassemia in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-iia), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In an embodiment, the beta-thalassemia major or *intermedia* is the result of homozygous null or compound heterozygous mutations resulting with beta-globin deficiency and the phenotypic complications of beta-thalassemia, whether transfusion-dependent or not.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of treating or preventing a disease or disorder in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (b), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of treating or preventing a disorder that is affected by the reduction of WIZ protein levels, in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of inhibiting WIZ protein expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of degrading WIZ protein in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f, (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of inhibiting, reducing, or eliminating the activity of WIZ protein or WIZ protein expression, the method comprising administering to the subject a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of inducing or promoting fetal hemoglobin in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of reactivating fetal hemoglobin production or expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of increasing fetal hemoglobin expression in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of treating a hemoglobinopathy, e.g., a beta-hemoglobinopathy, in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of treating a sickle cell disease in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In another aspect, the disclosure provides a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof for use in a method of treating beta-thalassemia in a subject in need thereof, the method comprising administering to the subject a therapeutically effective amount of a compound of formulae (I'), (I), (I-i), (I-i-a), (I-i-b), (I-i-c), (I-i-d), (I-i-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof.

In an embodiment, the beta-thalassemia major or *intermedia* is the result of homozygous null or compound heterozygous mutations resulting with beta-globin deficiency and the phenotypic complications of beta-thalassemia, whether transfusion-dependent or not.

Dosage

The pharmaceutical composition or combination of the disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The activity of a compound according to the disclosure can be assessed by the in vitro methods described in the Examples.

Combination Therapy

In another aspect, the disclosure provides a pharmaceutical combination comprising a compound of formulae (I'), (I), (I-i), (I-i-a), (I-i-b), (I-i-c), (I-i-d), (I-i-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii), or a pharmaceutically acceptable salt, hydrate, solvate, prodrug, stereoisomer, or tautomer thereof, and one or more additional therapeutic agent(s) for simultaneous, separate or sequential use in therapy. In an embodiment, the additional therapeutic agent is a myelosuppressive agent, such as hydroxyurea.

Combination therapy includes the administration of the subject compounds in further combination with other biologically active ingredients (such as, but not limited to, a second and different antineoplastic agent or a therapeutic agent that targets Hbf or another cancer target) and non-drug therapies (such as, but not limited to, surgery or radiation treatment). For instance, the compounds of the application can be used in combination with other pharmaceutically active compounds, preferably compounds that are able to enhance the effect of the compounds of the application.

The compound of the disclosure may be administered either simultaneously with, or before or after, one or more other therapeutic agent. The compound of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the disclosure. Thus, in one embodiment, the disclosure provides a combination comprising a therapeutically effective amount of a compound of formulae (I'), (I), (I-i), (I-i-a), (I-i-b), (I-i-c), (I-i-d), (I-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) or a pharmaceutically acceptable salt thereof and one or more additional therapeutically active agents.

In one embodiment, the disclosure provides a product comprising a compound of formulae (I'), (I), (I-i), (I-i-a), (I-i-b), (I-i-c), (I-i-d), (I-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) and at least one other therapeutic agent as a combined preparation for simultaneous, separate or sequential use in therapy. In one embodiment, the therapy is the treatment of a disease or condition modulated by WIZ. Products provided as a combined preparation include a composition comprising the compound of formulae (I'), (I), (I-i), (I-i-a), (I-i-b), (I-i-c), (I-i-d), (I-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) and the other therapeutic agent(s) together in the same pharmaceutical composition, or the compound of formulae (I'), (I), (I-i), (I-i-a), (I-i-b), (I-i-c), (I-i-d), (I-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) and the other therapeutic agent(s) in separate form, e.g., in the form of a kit.

In one embodiment, the disclosure provides a pharmaceutical composition comprising a compound of formulae (I'), (I), (I-i), (I-i-a), (I-i-b), (I-i-c), (I-i-d), (I-e), (I-i-f), (I-i), (I-ii-a), (I-ii-b), (I-ii-c), (I-ii-d), (I-ii-e), (I-ii-f), (Ia), (Ib), (Ic), (Id), (Ia-i), Ia-ii), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii) and another therapeutic agent(s). Optionally, the pharmaceutical composition may comprise a pharmaceutically acceptable carrier, as described above.

In one embodiment, the disclosure provides a kit comprising two or more separate pharmaceutical compositions, at least one of which contains a compound of formulae (I'), (I), (I-i), (I-i-a), (I-i-b), (I-i-c), (I-i-d), (I-e), (I-i-f), (I-ii), (I-ii-a), (I-ii-b), (I-ii-c), (I-ii-d), (I-ii-e), (I-ii-f), (Ia), (Ib), (Ic), (Id), (Ia-i), la-i), (Ia-iii), (Ia-iv), (Ia-v), (Ia-vi), (Ia-vii), (Ia-viii), (Ia-ix), (Ia-x), (Ia-xi), (Ia-xii), (Ia-xiii), (Ia-xiv), (Ie), (If), (Ig), (Ih), (Ih-i) and (Ih-ii). In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of the disclosure and the other therapeutic agent may be manufactured and/or formulated by the same or different manufacturers. Moreover, the compound of the disclosure and the other therapeutic may be brought together into a combination therapy: (i) prior to release of the combination product to physicians (e.g., in the case of a kit comprising the compound of the disclosure and the other therapeutic agent); (ii) by the physician themselves (or under the guidance of the physician) shortly before administration; (iii) in the patient themselves, e.g., during sequential administration of the compound of the disclosure and the other therapeutic agent.

Preparation of Compounds

It is understood that in the following description, combinations of substituents and/or variables of the depicted formulae are permissible only if such combinations result in stable compounds.

It will also be appreciated by those skilled in the art that in the processes described below, the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

The protecting group may also be a polymer resin, such as a Wang resin or a 2-chlorotrityl-chloride resin.

The following reaction schemes illustrate methods to make compounds of this disclosure.

It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this disclosure.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in a suitable solvent such as MeCN, DMSO, or MeOH and was injected directly into the column using an automated sample handler. The analysis is performed on Waters Acquity UPLC system (Column: Waters Acquity UPLC BEH C18 1.7 µm, 2.1×30 mm; Flow rate: 1 mL/min; 55° C. (column temperature); Solvent A: 0.05% formic acid in water, Solvent B: 0.04% formic acid in MeOH; gradient 95% Solvent A from 0 to 0.10 min; 95% Solvent A to 20% Solvent A from 0.10 to 0.50 min; 20% Solvent A to 5% Solvent A from 0.50 to 0.60 min; hold at 5% Solvent A from 0.6 min to 0.8 min; 5% Solvent A to 95% Solvent A from 0.80 to 0.90 min; and hold 95% Solvent A from 0.90 to 1.15 min.

| Abbreviations: | |
|---|---|
| ACN | acetonitrile |
| AcOH | acetic acid |
| AIBN | azobisisobutyronitrile |
| aq. | aqueous |
| $B_2pin_2$ | bis(pinacolato)diboron |
| $Boc_2O$ | di-tert-butyl dicarbonate |
| Bn | benzyl |
| BnBr | benzyl bromide |
| br | broad |
| d | doublet |
| dd | doublet of doublets |
| ddd | doublet of doublet of doublets |
| ddq | doublet of doublet of quartets |
| ddt | doublet of doublet of triplets |
| dq | doublet of quartets |
| dt | doublet of triplets |
| dtbbpy | 4,4'-di-tert-butyl-2,2'-dipyridyl |
| dtd | doublet of triplet of doublets |
| $Cs_2CO_3$ | cesium carbonate |
| DCE | 1,2-dichloroethane |
| DCM | dichloromethane |
| DHP | dihydropyran |
| DIBAL-H | diisobutylaluminium hydride |
| DIPEA (DIEA) | diisopropylethylamine |
| DIPEA | N,N-diisopropylethylamine |
| DMA | N,N-dimethylacetamide |
| DMAP | 4-dimethylaminopyridine |
| DME | 1,2-dimethoxyethane |
| DMF | N,N-dimethylformamide |
| DMP | Dess-Martin periodinane or 1,1,1-Tris(acetyloxy)-1,1-dihydro-1,2-benziodoxol-3-(1H)-one |
| DMSO | dimethylsulfoxide |
| $EC_{50}$ | half maximal effective concentration |
| ELSD | evaporative light scattering detector |
| EtOH | ethanol |
| $Et_2O$ | diethyl ether |
| $Et_3N$ | triethylamine |
| EtOAc | ethyl acetate |
| HATU | 1-[bis(dimethylamino)methylene]-1H-1,2,3-triazolo[4,5-b]pyridinium 3-oxid hexafluorophosphate |
| HCl | hydrogen chloride |
| hept | heptet |
| HPLC | high performance liquid chromatography |
| h or hr | hour |
| HRMS | high resolution mass spectrometry |
| g | gram |
| g/min | gram per minute |
| $IC_{50}$ | half maximal inhibitory concentration |
| IPA (iPrOH) | isopropyl alcohol |
| $Ir[(dF(CF_3)ppy)_2$ dtbbpy]$PF_6$ | [4,4'-Bis(1,1-dimethylethyl)-2,2'-bipyridine-N1,N1']bis[3,5-difluoro-2-[5-(trifluoromethyl)-2-pyridinyl-N] phenyl-C]Iridium(III) hexafluorophosphate |
| $K_2CO_3$ | potassium carbonate |
| KI | potassium iodide |
| KOAc | potassium Acetate |
| $K_3PO_4$ | tripotassium phosphate |
| LCMS | liquid chromatography mass spectrometry |
| LDA | lithium diisopropylamide |
| m | multiplet |
| MeCN | acetonitrile |
| MeOH | methanol |
| mg | milligram |
| MHz | megahertz |
| min | minutes |
| mL | milliliter |
| mmol | millimole |
| M | molar |
| MS | mass spectrometry |
| NaH | sodium hydride |
| $NaHCO_3$ | sodium bicarbonate |
| $NaBH(OAc)_3$ | sodium triacetoxyborohydride |
| $Na_2SO_4$ | sodium sulfate |
| NBS | N-bromosuccinimide |
| NMM | N-methylmorpholine |
| NMP | N-methyl-2-pyrrolidone |
| NMR | nuclear magnetic resonance |
| on | overnight |
| Pd/C | palladium on carbon |
| $PdCl_2(dppf)$- | [1,1'-bis(diphenylphosphino)ferrocene]dichloropalladium(II) complex with dichloromethane |
| DCM | |
| $Pd(PPh_3)_4$ | tetrakis(triphenylphosphine)palladium(0) |
| PMB | para-methoxybenzyl |
| q | quartet |
| qd | quartet of doublets |
| quint | quintet |
| quintd | quintet of doublets |
| rbf | round bottom flask |
| RockPhos G3 Pd | [(2-di-tert-butylphosphino-3-methoxy-6-methyl-2',4',6'-triisopropyl-1,1'-biphenyl)-2-(2-aminobiphenyl)] palladium(II) methanesulfonate |
| rt or r.t. | room temperature |
| Rt | retention time |
| s | singlet |
| SEM | 2-(trimethylsilyl)ethontmethyl |
| $SnBu_3$ | tributyltin |
| t | triplet |
| td | triplet of doublets |
| tdd | triplet of doublet of doublets |
| TBAI | tetrabutylammonium iodide |
| TEA ($NEt_3$) | triethylamine |
| TFA | trifluoroacetic acid |
| TfOH | triflic Acid |
| THF | tetrahydrofuran |
| THP | tetrahydropyran |
| TMP | 2,2,6,6-tetramethylpiperidine |
| Ts | tosyl |
| tt | triplet of triplets |
| ttd | triplet of triplet of doublets |
| TLC | thin-layer chromatography |
| UPLC | ultra-Performance liquid Chromatography |
| XPhos Pd G2 | chloro(2-dicyclohentlphosphino-2',4',6'-triisopropyl-1,1'-biphenyl)[2-(2'-amino-1,1'-biphenyl)]palladium(II) |
| µW or uW | microwave |

General Method I—Representative Procedure for Photoredox Catalysis with Lactone

A 40 mL vial was charged with 5-bromoisobenzofuran-1(3H)-one (5-I) (1 equiv), an alcohol building block (1 equiv), NiCl$_2$(glyme) (0.05 equiv), dtbbpy (0.05 equiv), and Ir[(dF(CF$_3$)ppy)$_2$dtbbpy]PF$_6$ (0.01 equiv). ACN (0.186 M) was then added, followed by 2,2,6,6-tetramethylpiperidine (1 equiv). The reaction flask was evacuated and backfilled with nitrogen three times. The resulting mixture was placed in MacMillian Blue LED light photoreactor for 18 hrs. The reaction mixture was then filtered and the solid was washed with dichloromethane. The filtrate was concentrated and purified by reverse phase HPLC or silica gel chromatography.

General Method II—Representative Procedure for Boc Deprotection

Amino-ether lactone ex. (4)-I (1 equiv) was suspended in dioxane (0.2 M). 4M HCl in dioxane (6 equiv) was then added and the resulting mixture was stirred at 40° C. for 2 hrs. The reaction mixture was concentrated under reduced pressure to afford free amino-ether lactone ex. (4)-II. The obtained product was carried on to the next step without purification.

General Method III—Representative Procedure for Reduction Amination

Free amino-ether lactone ex. (4)-II (1 equiv) was suspended in DMF (0.2 M). Aldehyde (3 equiv) was added. The reaction stirred for 5 minutes at r.t. then NaBH(OAc)$_3$ (3 equiv) was added. The reaction stirred at r.t. for 18 hrs. The reaction was quenched with saturated aqueous sodium bicarbonate and extracted three times with dichloromethane. The organic phases were combined, passed through a phase separator and concentrated. The crude material was purified by silica gel chromatography.

General Method IV—Representative Procedure for SOCl$_2$ Lactone Opening

To a solution of lactone (1 equiv) in dichloroethane (0.2 M) and EtOH (0.2 M) stirred at 70° C. was added thionyl chloride (12 equiv) dropwise and the resulting mixture was stirred at 70° C. overnight. The reaction mixture was cooled to r.t., diluted with water and quenched with saturated aqueous sodium bicarbonate. The reaction mixture was extracted with EtOAc three times and the combined organic phases were passed through a phase separator and concentrated onto CELITE®. The crude material was purified by silica gel chromatography.

General Method V—Representative Procedure for Lactam Ring Closing 3-aminopiperidine-2,6-dione hydrochloride (2 equiv) was dissolved in DMF (0.2 M) in a 2 mL microwave vial. DIPEA (5 equiv) was then added and the resulting mixture was stirred at r.t. for 15 minutes. α-chloro-ester (1 equiv) was dissolved in DMF (0.2 M) and added and stirring was continued at 85° C. for 18 hrs and then at 150° C. for 2 hrs under microwave radiation. The reaction mixture was concentrated onto CELITE® and purified by silica gel chromatography.

General Method VI—Representative Procedure for Photoredox Catalysis with 3-(5-bromo-1-oxoisoindolin-2-yl)-1-((2-(trimethylsilyl)ethoxy)methyl)piperidine-2,6-dione To an 8 mL red capped vial, 3-(5-bromo-1-oxoisoindolin-2-yl)-1-((2-(trimethylsilyl)ethoxy)methyl)piperidine-2,6-dione INT-XXX (1 equiv), alcohol building block (1.2 equiv), dtbbpy (0.05 equiv), NiCl$_2$(glyme) (0.05 equiv), and Ir[(dF(CF$_3$)ppy)$_2$dtbbpy]PF$_6$ (0.01 equiv) were added. ACN (0.3 M) was then added followed by 2,2,6,6-tetramethylpiperidine (1.05 equiv). The reaction flask was evacuated and backfilled with nitrogen three times. The reaction mixture was placed in a photoreactor plate under blue LED light for 18 hrs, and then filtered and concentrated.

General Method VII—Representative Procedure for Global Deprotection

To a solution of SEM protected glutarimide, Boc protected amine and isoindoline derivative (ex. INT-2) (1 equiv) in ACN (0.11 M) was added methanesulfonic acid (11.2 equiv). The resulting mixture was stirred at r.t. for 72 hrs and then cooled to 0° C. Triethylamine (13.04 equiv) was then added, followed by N1,N2-dimethylethane-1,2-diamine (1.5 equiv). The reaction mixture was then stirred at r.t. for 4 hrs, concentrated, and purified by reverse phase HPLC.

Method of Preparation of INT-XXX:

3-(5-bromo-1-oxoisoindolin-2-yl)piperidine-2,6-dione (INT-XX)

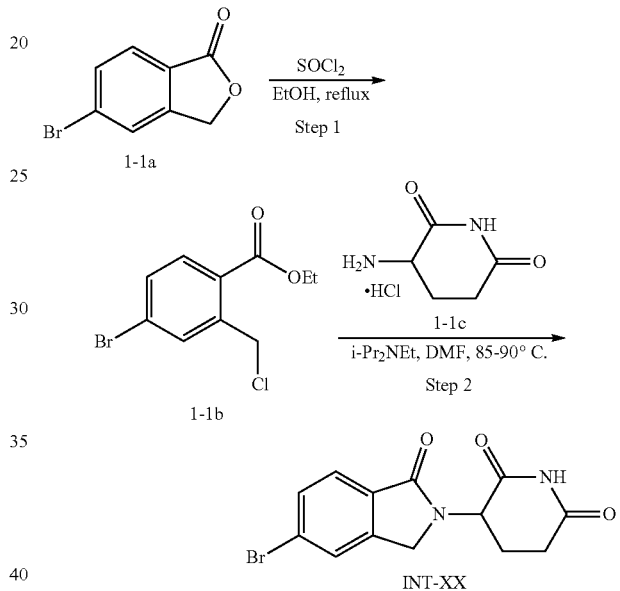

Step 1. Ethyl 4-bromo-2-(chloromethyl)benzoate (1-1b)

A stirred suspension of 5-bromophthalide 1-1a (1200 g, 5.633 mol) in EtOH (12 L) was heated to 68-72° C. SOCl$_2$ (2.40 L, 33.0 mol) was then added dropwise over a period of 7 h. The reaction mixture was concentrated under reduced pressure to about 4 L, and then water (5 L) and MTBE (5 L) were added. The resulting mixture was stirred for 40 min. The phases were separated and the aqueous phase was extracted with MTBE (1×5 L). The combined organic layers were washed with 5% aq. NaHCO$_3$ (5 L), dried over Na$_2$SO$_4$, filtered, and concentrated to dryness to afford 1-1b (1450 g, 5.25 mol, 93% yield) as a pale brown solid. MS [M+Na]$^+$=298.9. $^1$H NMR (400 MHz, Chloroform-d) δ 7.85 (d, J=8.4 Hz, 1H), 7.72 (d, J=2.0 Hz, 1H), 7.52 (dd, J=8.3, 2.0 Hz, 1H), 5.00 (s, 2H), 4.38 (q, J=7.1 Hz, 2H), 1.40 (t, J=7.1 Hz, 3H).

Step 2. 3-(5-bromo-1-oxoisoindolin-2-yl)piperidine-2,6-dione (INT-XX)

To a stirred suspension of 3-aminopiperidine-2,6-dione hydrochloride 1-1c (596.3 g, 3.623 mol) and i-Pr$_2$NEt (2.50 L, 14.3 mol) in DMF (5.0 L) was added 1-1b (1000 g, 3.623 mmol) and the resulting reaction mixture was stirred at 85-90° C. for 24 h. The reaction mixture was then allowed to cool to room temperature, water (20 L) was added, and the resulting mixture was stirred for 12 h. The formed precipitate was filtered and washed with water (5 L) and MeOH (2 L). The crude solid was slurried in MeOH (5 L) for 1 h, filtered, and washed with MeOH (2 L). The resulting solid was then taken in EtOAc (10 L) and stirred for 1 h. The obtained suspension was then filtered, washed with EtOAc (5 L), and dried under reduced pressure at 45-50° C. to afford INT-XX (740 g, 2.29 mol, 63% yield) as an off-white solid. MS [M+1]$^+$=323.2. $^1$H NMR (400 MHz, DMSO-d$_6$) δ 10.99 (s, 1H), 7.91-7.88 (m, 1H), 7.72 (dd, J=8.1, 1.6 Hz, 1H), 7.67 (d, J=8.0 Hz, 1H), 5.11 (dd, J=13.3, 5.1 Hz, 1H), 4.47 (d, J=17.7 Hz, 1H), 4.34 (d, J=17.7 Hz, 1H), 2.98-2.83 (m, 1H), 2.65-2.55 (m, 1H), 2.45-2.29 (m, 1H), 2.01 (dtd, J=12.7, 5.3, 2.3 Hz, 1H).

3-(5-bromo-1-oxoisoindolin-2-yl)-1-((2-(trimethylsilyl)ethoxy)methyl)piperidine-2,6-dione (INT-XXX)

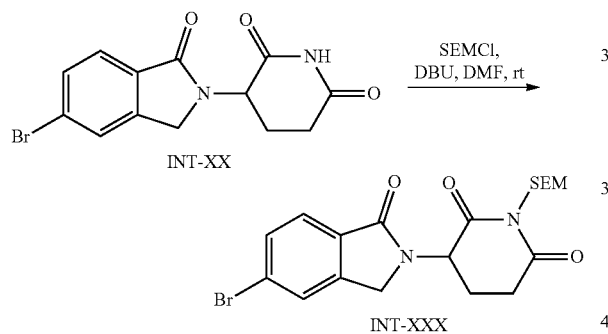

To a stirred solution of INT-XX (10.0 g, 30.9 mmol) and DBU (6.9 mL, 46 mmol) in DMF (95 mL) was added SEMCl (6.6 mL, 37 mmol) at 0° C. and the resulting reaction mixture was allowed to warm to room temperature and then stirred for 5 h. An additional portion of DBU (3.5 mL, 23 mmol) and SEMCl (3.3 mL, 19 mmol) was added and stirring was continued for an additional 2 h.

The reaction mixture was then quenched with sat. aq. NH$_4$Cl (250 mL) and extracted with EtOAc (×3). The combined organic phases were dried over Na$_2$SO$_4$, filtered, and concentrated to dryness. The crude material was dissolved in minimal amount of EtOAc (~50 mL) and Et$_2$O: heptane (v/v=1:2, 400 mL) was added. The resulting cloudy solution was left standing at −5° C. overnight. The formed precipitate was filtered, washed with heptane (×3), and dried under vacuum to afford INT-XXX (11.53 g, 25.4 mmol, 82% yield) as an off-white solid. MS [M+H]$^+$=453.4. $^1$H NMR (400 MHz, Chloroform-d) δ 7.75 (d, J=8.6 Hz, 1H), 7.66-7.61 (m, 2H), 5.37-5.09 (m, 3H), 4.48 (d, J=16.2 Hz, 1H), 4.32 (d, J=16.2 Hz, 1H), 3.74-3.50 (m, 2H), 3.11-2.98 (m, 1H), 2.94-2.83 (m, 1H), 2.33 (qd, J=13.2, 4.7 Hz, 1H), 2.24-2.15 (m, 1H), 0.97-0.90 (m, 2H), 0.00 (s, 9H).

Example 1: Diastereomeric Mixture of Tert-butyl 2-(1-hydroxyethyl)piperidine-1-carboxylate (INT-1)

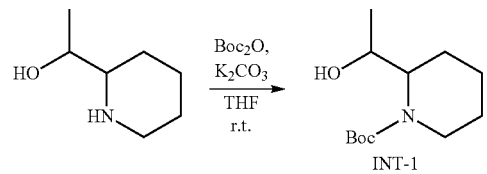

A 20 mL vial was charged with 1-(piperidin-2-yl)ethanol (0.5 g, 3.87 mmol), di-tert-butyl dicarbonate (0.98 mL, 4.26 mmol), K$_2$CO$_3$ (0.59 g, 4.26 mmol) and THF (20 mL) and the resulting mixture was stirred vigorously at r.t. for 48 hours. The reaction mixture was diluted with brine and extracted with EtOAc three times. The organic phases were combined, passed through a phase separator, and concentrated onto CELITE®. The CELITE® residue was purified by silica gel chromatography (eluting with 0-100% ethyl acetate in heptane using ELSD detection) to afford a diastereomeric mixture of tert-butyl 2-(1-hydroxyethyl)piperidine-1-carboxylate INT-1 (680 mg, 2.97 mmol, 77% yield) as a clear oil. $^1$H NMR (400 MHz, Chloroform-d) δ 4.17-3.90 (m, 3H), 2.99-2.68 (m, 1H), 2.05-1.98 (m, 1H), 1.85-1.54 (m, 5H), 1.49 (s, 9H), 1.23 (dd, J=9.3, 6.1 Hz, 3H).

Example 2: Diastereomers of 5-(1-(1-ethylpiperidin-2-yl)ethoxy)isobenzofuran-1(3H)-one (INT-3)

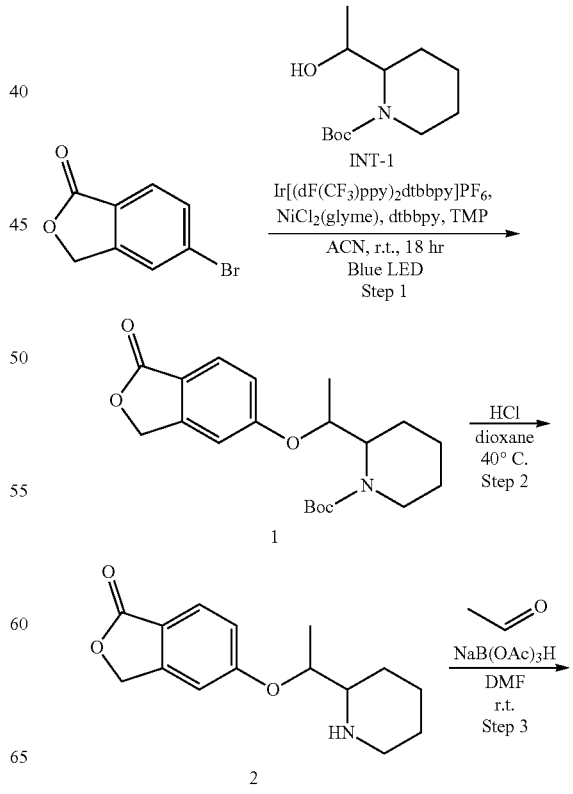

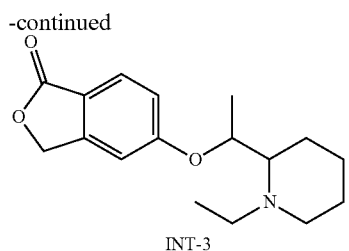

INT-3

Step 1: Diastereomeric Mixture of Tert-butyl 2-(1-((1-oxo-1,3-dihydroisobenzofuran-5-yl)oxy)ethyl)piperidine-1-carboxylate (1)

5-((R)-1-((S)-1-ethylpiperidin-2-yl)ethoxy)isobenzofuran-1(3H)-one, 5-((S)-1-((S)-1-ethylpiperidin-2-yl)ethoxy)isobenzofuran-1(3H)-one 5-((S)-1-((R)-1-ethylpiperidin-2-yl)ethoxy)isobenzofuran-1(3H)-one, 5-((R)-1-((R)-1-ethylpiperidin-2-yl)ethoxy)isobenzofuran-1(3H)-one The product was made according to General Method I starting from 5-bromoisobenzofuran-1(3H)-one and a diastereomeric mixture of tert-butyl 2-(1-hydroxyethyl)piperidine-1-carboxylate INT-1 (0.67 g, 2.93 mmol). The reaction mixture was filtered and the solid was washed with dichloromethane. The filtrate was concentrated and the crude material was dissolved in minimal methanol and purified by reverse phase ELSD/uV triggered silica gel chromatography (eluting with 5-50% 95:5 ACN:H$_2$O to 95:5 H$_2$O:ACN both with 5 mM NH$_4$OAc as modifier) to afford a diastereomeric mixture of tert-butyl 2-(1-((1-oxo-1,3-dihydroisobenzofuran-5-yl)oxy)ethyl)piperidine-1-carboxylate 1 (533 mg, 1.46 mmol, 50.3% yield) as an orange solid. Alternatively, the crude material can be purified by silica gel chromatography (eluting with 0-100% 3:1 EtOAc:EtOH with 1% TEA in heptane) to afford the desired product. LCMS [M+H–tButyl]$^+$: 306.1. $^1$H NMR (400 MHz, Chloroform-d) δ 7.69 (d, J=8.5 Hz, 1H), 6.91 (dd, J=8.5, 2.1 Hz, 1H), 6.79 (dd, J=6.9, 2.0 Hz, 1H), 5.12 (d, J=6.0 Hz, 2H), 4.64 (ddd, J=14.1, 8.3, 6.2 Hz, 1H), 4.32-4.14 (m, 1H), 2.69-2.48 (m, 1H), 1.90-1.81 (m, 1H), 1.69-1.58 (m, 1H), 1.54-1.40 (m, 4H), 1.34 (s, 10H), 1.19 (d, J=6.1 Hz, 3H).

Step 2: Diastereomeric mixture of 5-(1-(piperidin-2-yl)ethoxy)isobenzofuran-1(3H)-one (2)

The product was made according to General Method II starting from a diastereomeric mixture of tert-butyl 2-(1-((1-oxo-1,3-dihydroisobenzofuran-5-yl)oxy)ethyl)piperidine-1-carboxylate 1 (0.53 g, 1.46 mmol). The reaction mixture was concentrated to afford a diastereomeric mixture of 5-(1-(piperidin-2-yl)ethoxy)isobenzofuran-1(3H)-one 2 as a crude orange solid. The crude product was carried on to the next step without purification. LCMS [M+H]$^+$: 262.1.

Step 3: Diastereomers 5-(1-(1-ethylpiperidin-2-yl)ethoxy)isobenzofuran-1(3H)-one (INT-3)

The product was made according to General Method III starting from a diastereomeric mixture of 5-(1-(piperidin-2-yl)ethoxy)isobenzofuran-1(3H)-one 2 (0.39 g, 1.48 mmol) and acetaldehyde (0.25 mL, 4.42 mmol). The reaction mixture was quenched with saturated aqueous sodium bicarbonate and extracted three times with dichloromethane. The organic phases were combined, passed through a phase separator and concentrated. The crude material was purified by silica gel chromatography (eluting with 0-20% methanol in dichloromethane) to afford a diastereomeric mixture of 5-(1-(1-ethylpiperidin-2-yl)ethoxy)isobenzofuran-1 (3H)-one INT-3 (372 mg, 1.29 mmol, 87% yield) as brown oil. LCMS [M+H]$^+$: 290.2. $^1$H NMR (400 MHz, Chloroform-d) δ 7.81 (dd, J=8.5, 1.9 Hz, 1H), 7.03 (dd, J=8.5, 2.1 Hz, 1H), 6.92 (s, 1H), 5.24 (s, 2H), 4.93-4.62 (m, 1H), 3.06-2.81 (m, 2H), 2.60-2.43 (m, 2H), 2.32-2.17 (m, 1H), 1.77 (dd, J=27.1, 14.7 Hz, 2H), 1.66-1.48 (m, 3H), 1.35 (dd, J=11.4, 6.3 Hz, 4H), 1.11-0.97 (m, 3H). The diastereomeric mixture of isomers was separated via chiral SFC [Column 21×250 mm Chiralpak IC; CO$_2$ Co-solvent 30% IPA with 10 mM NH$_3$; at 80 g/min at 125 bar at 25° C.] to afford a mixture of two diastereomers and two clean single diastereomers: Peak 3: Diastereomer 3 of 5-(1-(1-ethylpiperidin-2-yl)ethoxy)isobenzofuran-1(3H)-one (101 mg, 0.349 mmol, 23.7%) as an orange solid. Chiral SFC Rt 14 mins. Peak 4: Diastereomer 4 of 5-(1-(1-ethylpiperidin-2-yl)ethoxy)isobenzofuran-1(3H)-one (105 mg, 0.363 mmol, 24.6%) as an orange solid. Chiral SFC Rt 19 mins. The mixture of isomers was further separated via chiral SFC [Column 21×250 mm Chiralpak IG; CO$_2$ Co-solvent 25% 1:1 MeOH:IPA with 10 mM NH$_3$; at 80 g/min at 125 bar at 25° C.] to afford the other two diastereomers: Peak 1: Diastereomer 1 of 5-(1-(1-ethylpiperidin-2-yl)ethoxy)isobenzofuran-1(3H)-one (30.4 mg, 0.105 mmol, 7.1%) as an orange solid. Chiral SFC Rt 4.9 mins. Peak 2: Diastereomer 2 of 5-(1-(1-ethylpiperidin-2-yl)ethoxy)isobenzofuran-1(3H)-one (35 mg, 0.121 mmol, 8.2%) as an orange solid. Chiral SFC Rt 4.7 mins.

Example 3: Diastereomer of 3-(5-(1-(1-ethylpiperidin-2-yl)ethoxy)-1-oxoisoindolin-2-yl)piperidine-2,6-dione(I-5)

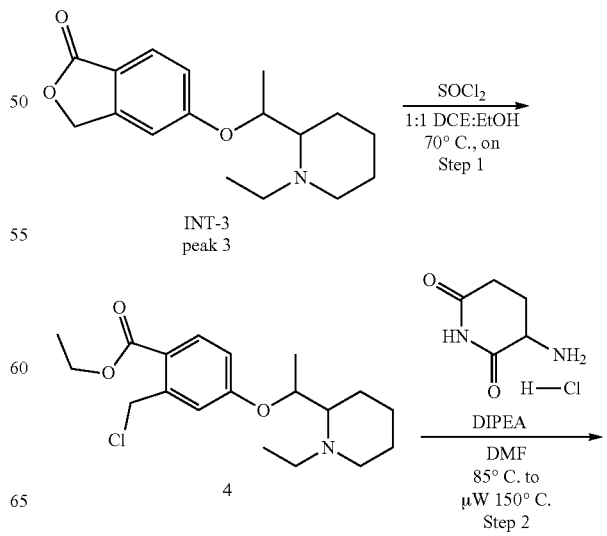

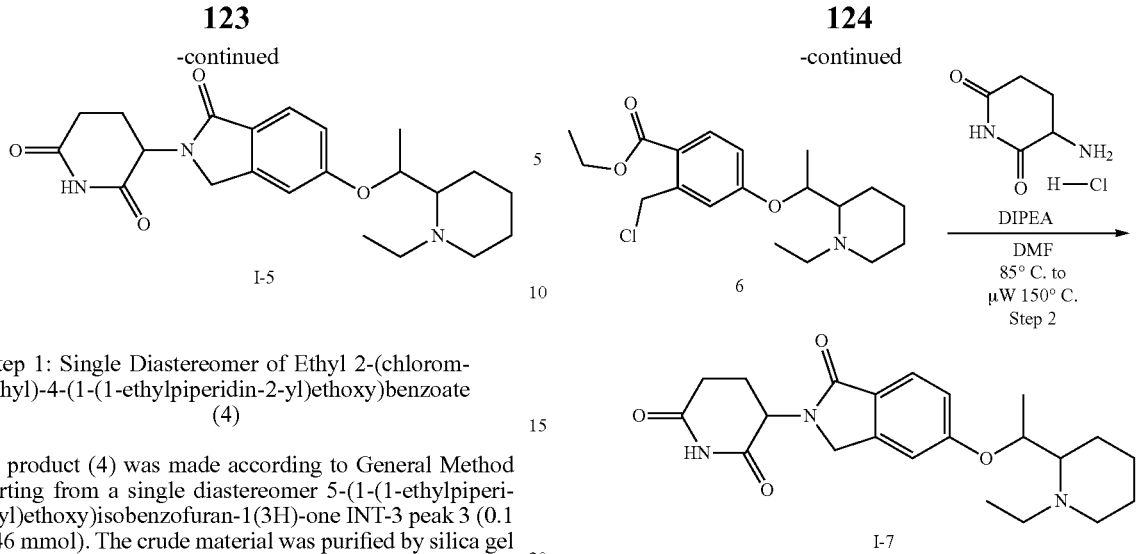

Step 1: Single Diastereomer of Ethyl 2-(chloromethyl)-4-(1-(1-ethylpiperidin-2-yl)ethoxy)benzoate (4)

The product (4) was made according to General Method IV starting from a single diastereomer 5-(1-(1-ethylpiperidin-2-yl)ethoxy)isobenzofuran-1(3H)-one INT-3 peak 3 (0.1 g, 0.346 mmol). The crude material was purified by silica gel chromatography (eluting with 0-100% ethyl acetate in heptane) to afford a single diastereomer ethyl 2-(chloromethyl)-4-(1-(1-ethylpiperidin-2-yl)ethoxy)benzoate 4 (102 mg, 0.288 mmol, 83% yield) as an orange oil. LCMS [M+H]$^+$: 354.6. $^1$H NMR (400 MHz, Chloroform-d) δ 7.98 (d, J=8.7 Hz, 1H), 7.07 (d, J=2.6 Hz, 1H), 6.85 (dd, J=8.8, 2.6 Hz, 1H), 5.05 (s, 2H), 4.65 (qd, J=6.4, 2.8 Hz, 1H), 4.35 (q, J=7.1 Hz, 2H), 3.02-2.89 (m, 2H), 2.58-2.49 (m, 1H), 2.45 (dt, J=10.2, 2.9 Hz, 1H), 2.23 (ddd, J=12.0, 10.8, 3.2 Hz, 1H), 1.83-1.68 (m, 2H), 1.63-1.45 (m, 3H), 1.39 (t, J=7.1 Hz, 3H), 1.36-1.21 (m, 4H), 1.02 (t, J=7.1 Hz, 3H).

Step 2: Diastereomer 3-(5-(1-(1-ethylpiperidin-2-yl)ethoxy)-1-oxoisoindolin-2-yl)piperidine-2,6-dione (I-5)

Compound I-5 was made according to General Method V starting from a single diastereomer ethyl 2-(chloromethyl)-4-(1-(1-ethylpiperidin-2-yl)ethoxy)benzoate 4 (102 mg, 0.288 mmol). The reaction mixture was purified by silica gel chromatography (eluting with 0-100% 3:1 EtOAc:EtOH with 1% TEA in EtOAc) to afford single diastereomer 3-(5-(1-(1-ethylpiperidin-2-yl)ethoxy)-1-oxoisoindolin-2-yl)piperidine-2,6-dione I-5 (28.4 mg, 0.069 mmol, 23.92% yield) as a white solid. LCMS [M+H]$^+$: 400.3. $^1$H NMR (400 MHz, DMSO-d$_6$) δ 10.97 (s, 1H), 7.61 (d, J=8.4 Hz, 1H), 7.18 (d, J=2.2 Hz, 1H), 7.03 (dd, J=8.4, 2.2 Hz, 1H), 5.07 (dd, J=13.3, 5.1 Hz, 1H), 4.77-4.68 (m, 1H), 4.39 (d, J=17.2 Hz, 1H), 4.26 (d, J=17.1 Hz, 1H), 2.96-2.83 (m, 3H), 2.64-2.54 (m, 1H), 2.45-2.30 (m, 2H), 2.26-2.13 (m, 1H), 2.01-1.92 (m, 1H), 1.70 (d, J=10.2 Hz, 2H), 1.55-1.22 (m, 8H), 0.94 (t, J=7.0 Hz, 3H).

Example 4: Diastereomer 3-(5-(1-(1-ethylpiperidin-2-yl)ethoxy)-1-oxoisoindolin-2-yl)piperidine-2,6-dione (I-7)

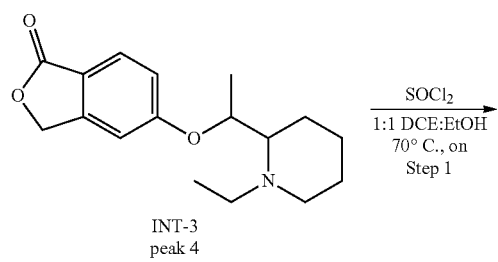

Step 1: Single Diastereomer Ethyl 2-(chloromethyl)-4-(1-(1-ethylpiperidin-2-yl)ethoxy)benzoate (6)

Intermediate 6 was made according to General Method IV starting from a single diastereomer 5-(1-(1-ethylpiperidin-2-yl)ethoxy)isobenzofuran-1(3H)-one INT-3 peak 4 (0.1 g, 0.346 mmol). The crude material was purified by reverse phase silica gel chromatography (eluting with 5-60% ACN in water with 0.1% TFA as modifier). Fractions containing product were combined and concentrated to minimal aqueous phase. The aqueous phase was extracted with dichloromethane three times. The organic phases were combined, passed through a phase separator and concentrated to afford a single diastereomer ethyl 2-(chloromethyl)-4-(1-(1-ethylpiperidin-2-yl)ethoxy)benzoate 6 (104 mg, 0.294 mmol, 85% yield) as an orange oil. LCMS [M+H]$^+$: 354.3.

Step 2: Diastereomer 3-(5-(1-(1-ethylpiperidin-2-yl)ethoxy)-1-oxoisoindolin-2-yl)piperidine-2,6-dione (I-7)

Compound I-7 was made according to General Method V starting from ethyl 2-(chloromethyl)-4-(1-(1-ethylpiperidin-2-yl)ethoxy)benzoate 6 (104 mg, 0.294 mmol). The crude material was purified by silica gel chromatography (eluting with 0-100% 3:1 EtOAc:EtOH with 1% triethylamine in EtOAc) to afford a single diastereomer 3-(5-(1-(1-ethylpiperidin-2-yl)ethoxy)-1-oxoisoindolin-2-yl)piperidine-2,6-dione I-7 (40.5 mg, 0.096 mmol, 32.8% yield) as a grey solid. LCMS [M+H]$^+$: 400.3. $^1$H NMR (400 MHz, DMSO-d$_6$) δ 10.99 (s, 1H), 7.65 (d, J=8.4 Hz, 1H), 7.19 (d, J=2.1 Hz, 1H), 7.06 (dd, J=8.5, 2.2 Hz, 1H), 5.04 (dd, J=13.3, 5.1 Hz, 1H), 4.75 (dd, J=6.3, 3.1 Hz, 1H), 4.41 (d, J=17.3 Hz, 1H), 4.28 (d, J=17.3 Hz, 1H), 2.96-2.82 (m, 3H), 2.67-2.59 (m, 1H), 2.50-2.32 (m, 2H), 2.24 (t, J=11.2 Hz, 1H), 2.05-1.96 (m, 1H), 1.77-1.67 (m, 2H), 1.58-1.19 (m, 8H), 0.95 (t, J=7.0 Hz, 3H).

Example 5: Diastereomer 3-(5-(1-(1-ethylpiperidin-2-yl)ethoxy)-1-oxoisoindolin-2-yl)piperidine-2,6-dione (I-9)

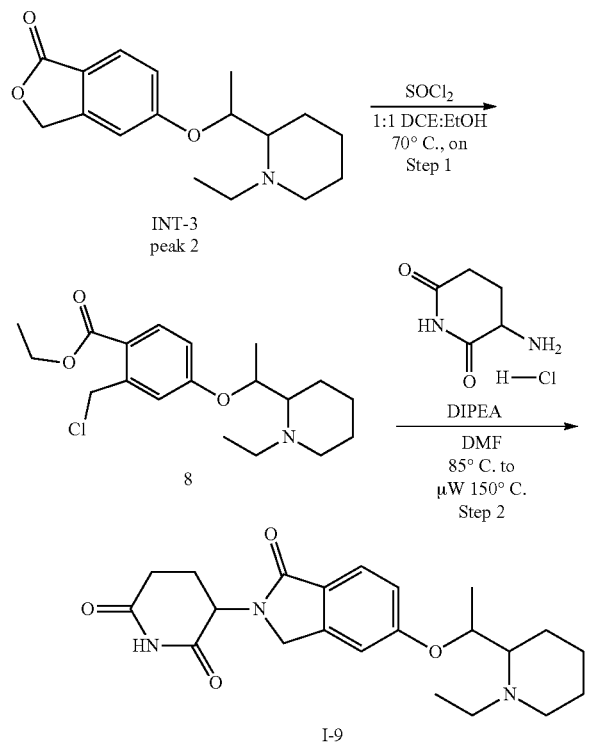

Step 1: Single Diastereomer Ethyl 2-(chloromethyl)-4-(1-(1-ethylpiperidin-2-yl)ethoxy)benzoate (8)

Intermediate 8 was made according to General Method IV starting from 5-(1-(piperidin-2-yl)ethoxy)isobenzofuran-1(3H)-one INT-3 peak 2 (43.1 mg, 0.149 mmol). The crude material was purified by reverse phase silica gel chromatography (5-50% ACN in water with 0.1% TFA as modifier). Fractions containing product were combined and concentrated into a minimal aqueous phase. The aqueous phase was extracted with dichloromethane three times. The organic phases were combined, passed through a phase separator, and concentrated to afford a single diastereomer ethyl 2-(chloromethyl)-4-(1-(1-ethylpiperidin-2-yl)ethoxy)benzoate 8 (52 mg, 0.147 mmol, 99% yield) as a yellow oil. LCMS [M+H]$^+$: 354.3.

Step 2: Diasteromer 3-(5-(1-(1-ethylpiperidin-2-yl)ethoxy)-1-oxoisoindolin-2-yl)piperidine-2,6-dione (I-9)

Compound I-9 was made according to General Method V starting from a single diastereomer ethyl 2-(chloromethyl)-4-(1-(1-ethylpiperidin-2-yl)ethoxy)benzoate 8 (0.052 g, 0.147 mmol). The reaction mixture was purified by silica gel (eluting with 0-100% 3:1 EtOAc:EtOH with 1% TEA in EtOAc) to afford a single diastereomer 3-(5-(1-(1-ethylpiperidin-2-yl)ethoxy)-1-oxoisoindolin-2-yl)piperidine-2,6-dione I-9 (16.6 mg, 37 μmol, 25.5% yield) as a cream solid. LCMS [M+H]$^+$: 400.1. $^1$H NMR (400 MHz, DMSO-d$_6$) δ 10.97 (s, 1H), 7.61 (d, J=8.4 Hz, 1H), 7.21 (d, J=2.1 Hz, 1H), 7.06 (dd, J=8.4, 2.2 Hz, 1H), 5.07 (dd, J=13.3, 5.1 Hz, 1H), 4.98 (p, J=6.1 Hz, 1H), 4.39 (d, J=17.1 Hz, 1H), 4.26 (d, J=17.1 Hz, 1H), 2.96-2.81 (m, 2H), 2.78-2.71 (m, 1H), 2.63-2.55 (m, 1H), 2.48-2.31 (m, 3H), 2.18-2.10 (m, 1H), 2.02-1.92 (m, 1H), 1.79-1.65 (m, 2H), 1.57-1.51 (m, 1H), 1.44-1.27 (m, 2H), 1.22 (dd, J=6.2, 1.3 Hz, 3H), 1.19-1.11 (m, 1H), 0.96 (t, J=7.1 Hz, 3H).

Example 6: Diastereomer 3-(5-(1-(1-ethylpiperidin-2-yl)ethoxy)-1-oxoisoindolin-2-yl)piperidine-2,6-dione (I-11)

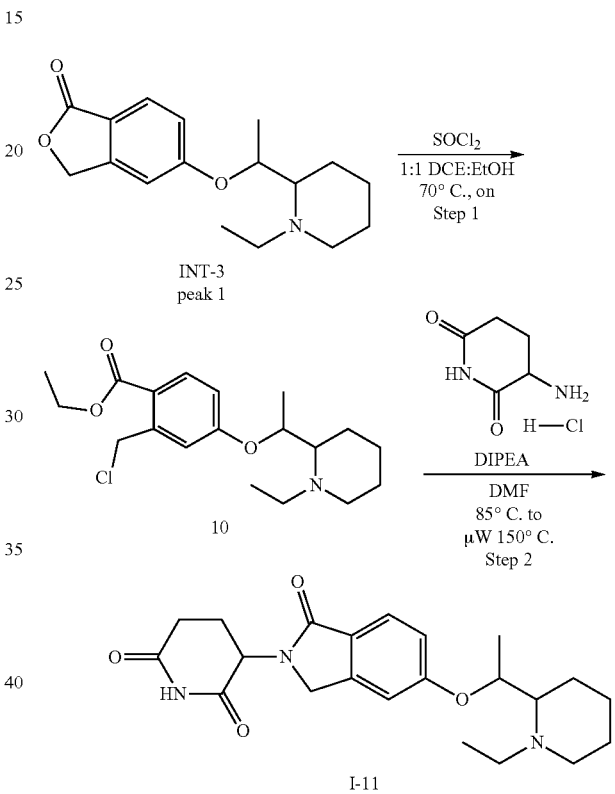

Step 1: Single Diastereomer Ethyl 2-(chloromethyl)-4-(1-(1-ethylpiperidin-2-yl)ethoxy)benzoate (10)

Intermediate 10 was made according to General Method IV starting from single diastereomer 5-(1-(piperidin-2-yl)ethoxy)isobenzofuran-1(3H)-one INT-3 Peak 1 (38 mg, 0.131 mmol). The crude material was purified by silica gel chromatography (eluting with 0-100% ethyl acetate in heptane) to afford a single diastereomer ethyl 2-(chloromethyl)-4-(1-(1-ethylpiperidin-2-yl)ethoxy)benzoate 10 (43 mg, 0.122 mmol, 93% yield) as a yellow oil. LCMS [M+H]$^+$: 354.1. $^1$H NMR (400 MHz, Chloroform-d) δ 7.99 (d, J=8.8 Hz, 1H), 7.10 (d, J=2.5 Hz, 1H), 6.87 (dd, J=8.7, 2.6 Hz, 1H), 5.06 (s, 2H), 4.92-4.83 (m, 1H), 4.37 (q, J=7.1 Hz, 2H), 2.94 (dtd, J=11.7, 3.8, 1.3 Hz, 1H), 2.86-2.75 (m, 1H), 2.59-2.50 (m, 2H), 2.24 (td, J=11.5, 3.2 Hz, 1H), 1.88-1.81 (m, 1H), 1.81-1.73 (m, 1H), 1.67-1.47 (m, 2H), 1.43-1.38 (m, 4H), 1.33 (d, J=6.3 Hz, 3H), 1.30-1.21 (m, 1H), 1.07 (t, J=7.1 Hz, 3H).

Step 2: Diastereomer 3-(5-(1-(1-ethylpiperidin-2-yl)ethoxy)-1-oxoisoindolin-2-yl)piperidine-2,6-dione (I-11)

Compound I-11 was made according to General Method V starting from a single diastereomer ethyl 2-(chloromethyl)-4-(1-(1-ethylpiperidin-2-yl)ethoxy)benzoate 10 (43 mg, 0.122 mmol). The reaction mixture was purified by silica gel (eluting with 0-100% 3:EtOAc:EtOH with 1% TEA in ethyl acetate) to afford 3-(5-(1-(1-ethylpiperidin-2-yl)ethoxy)-1-oxoisoindolin-2-yl)piperidine-2,6-dione I-11 (22.2 mg, 56 μmol, 45.7% yield) as a cream solid. LCMS [M+H]$^+$: 400.2. $^1$H NMR (400 MHz, DMSO-d$_6$) δ 10.97 (s, 1H), 7.61 (d, J=8.4 Hz, 1H), 7.21 (d, J=2.1 Hz, 1H), 7.06 (dd, J=8.4, 2.2 Hz, 1H), 5.07 (dd, J=13.3, 5.1 Hz, 1H), 4.98 (p, J=6.1 Hz, 1H), 4.39 (d, J=16.9 Hz, 1H), 4.26 (d, J=17.1 Hz, 1H), 2.98-2.81 (m, 2H), 2.80-2.69 (m, 1H), 2.65-2.55 (m, 1H), 2.41 (ddd, J=26.6, 13.6, 5.7 Hz, 3H), 2.20-2.08 (m, 1H), 1.98 (ddd, J=10.3, 5.2, 2.8 Hz, 1H), 1.81-1.65 (m, 2H), 1.59-1.50 (m, 1H), 1.45-1.27 (m, 2H), 1.22 (dd, J=6.2, 1.3 Hz, 3H), 1.19-1.11 (m, 1H), 0.96 (t, J=7.0 Hz, 3H).

Example 7: rac-Tert-butyl 2-(hydroxymethyl)-3,3-dimethylpiperidine-1-carboxylate (INT-12)

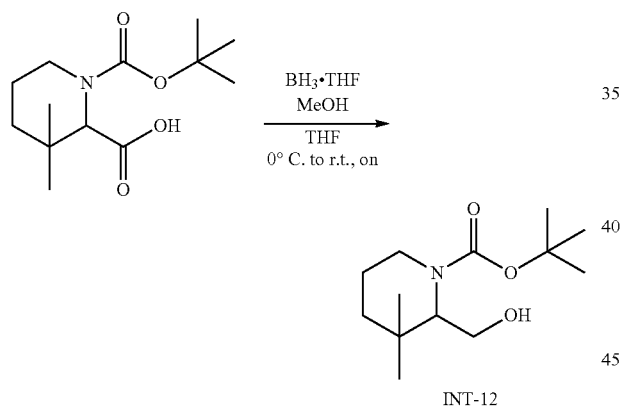

Racemic 1-(tert-butoxycarbonyl)-3,3-dimethylpiperidine-2-carboxylic acid (0.3 g, 1.17 mmol) was dissolved in THF (3.9 mL) and the resulting mixture was cooled to 0° C. 1M borane tetrahydrofuran complex in THF (3.50 mL, 3.50 mmol) was added dropwise and the reaction mixture was stirred at r.t. overnight, and then cooled to 0° C. and quenched with methanol (3 mL, 74.2 mmol) and stirred at r.t. for 2 hrs. The reaction mixture was concentrated to dryness and then dissolved in methanol (5 mL) and stirred at r.t. overnight. The reaction mixture was concentrated onto CELITE® and purified by silica gel chromatography (eluting with 0-100% ethyl acetate in heptane using ELSD detection) to afford rac-tert-butyl 2-(hydroxymethyl)-3,3-dimethylpiperidine-1-carboxylate INT-12 (210 mg, 0.863 mmol, 74.0% yield) as a clear oil. LCMS [M+H−tButyl]$^+$: 188.3. $^1$H NMR (400 MHz, Chloroform-d) δ 4.22-3.88 (m, 2H), 3.86-3.70 (m, 2H), 2.96-2.62 (m, 1H), 1.79-1.58 (m, 2H), 1.50-1.42 (m, 10H), 1.36-1.25 (m, 2H), 1.03 (s, 3H), 0.92 (s, 3H).

Example 8: Enantiomers 3-(5-((1-ethyl-3,3-dimethylpiperidin-2-yl)methoxy)-1-oxoisoindolin-2-yl)piperidine-2,6-dione (INT-15)

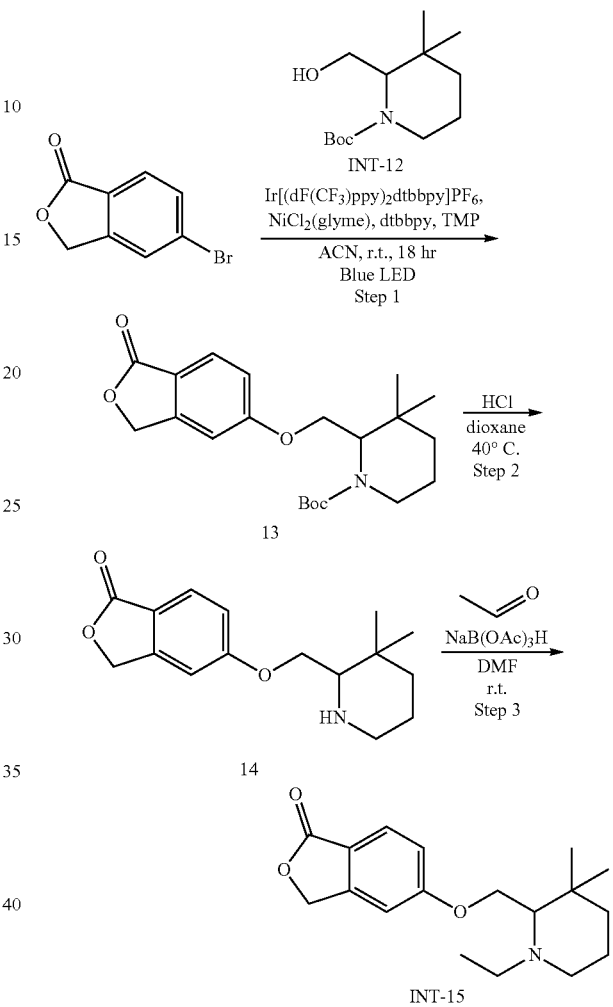

Step 1: rac-Tert-butyl 3,3-dimethyl-2-(((1-oxo-1,3-dihydroisobenzofuran-5-yl)oxy)methyl)piperidine-1-carboxylate (13)

Intermediate 13 was made according to General Method I starting from an enantiomeric mixture of tert-butyl 2-(hydroxymethyl)-3,3-dimethylpiperidine-1-carboxylate INT-12 (0.21 g, 0.863 mmol). The reaction mixture was purified by silica gel chromatography (eluting with 0-100% ethyl acetate in heptane) to afford rac-tert-butyl 3,3-dimethyl-2-(((1-oxo-1,3-dihydroisobenzofuran-5-yl)oxy)methyl)piperidine-1-carboxylate 13 (342 mg, 0.911 mmol, 108% yield) as a yellow oil. LCMS [M+H−tButyl]$^+$: 320.2. $^1$H NMR (400 MHz, Chloroform-d) δ 7.72-7.64 (m, 1H), 6.94 (dd, J=8.5, 2.1 Hz, 1H), 6.89-6.83 (m, 1H), 5.16 (s, 2H), 4.28-3.68 (m, 5H), 1.69-1.51 (m, 2H), 1.45-1.29 (m, 11H), 1.00 (s, 3H), 0.95 (s, 3H).

Step 2: rac-5-((3,3-dimethylpiperidin-2-yl)methoxy)isobenzofuran-1(3H)-one (14)

Intermediate 14 was made according to General Method II starting from an enantiomeric mixture of tert-butyl 3,3- dimethyl-2-(((1-oxo-1,3-dihydroisobenzofuran-5-yl)oxy) methyl)piperidine-1-carboxylate 13 (342 mg, 0.911 mmol) to afford rac-5-((3,3-dimethylpiperidin-2-yl)methoxy) isobenzofuran-1(3H)-one 14 as a white solid. The crude product was carried on to the next step without purification. LCMS [M+H]⁺: 276.2.

Step 3: Enantiomers 5-((1-ethyl-3,3-dimethylpiperidin-2-yl)methoxy)isobenzofuran-1(3H)-one (INT-15)

INT-15 was made according to General Method III starting from rac-5-((3,3-dimethylpiperidin-2-yl)methoxy) isobenzofuran-1(3H)-one 14 (251 mg, 0.911 mmol) and acetaldehyde (0.31 mL, 5.47 mmol). The crude material was purified by silica gel chromatography (eluting with 0-100% ethyl acetate in heptane) to afford rac-5-((1-ethyl-3,3-dimethylpiperidin-2-yl)methoxy)isobenzofuran-1(3H)-one INT-15 (143 mg, 0.471 mmol, 51.7% yield) as an orange oil. LCMS [M+H]⁺: 304.4. ¹H NMR (400 MHz, Chloroform-d) δ 7.84 (d, J=8.5 Hz, 1H), 7.06 (dd, J=8.5, 2.1 Hz, 1H), 6.99-6.90 (m, 1H), 5.27 (s, 2H), 4.20-4.04 (m, 2H), 2.98 (s, 3H), 2.91 (s, 3H), 2.78-2.64 (m, 2H), 2.62-2.52 (m, 2H), 2.46-2.35 (m, 1H), 1.68-1.59 (m, 2H), 1.50-1.39 (m, 1H), 1.35-1.25 (m, 1H), 1.06 (t, J=7.0 Hz, 3H). The enantiomeric mixture of isomers was separated via chiral SFC [Column 21×250 mm Chiralpak IG; CO₂ Co-solvent 25% MeOH with 10 mM NH₃; at 80 g/min at 125 bar at 25° C.] to afford enantiomers: Peak 1: Enantiomer 1 of 5-((1-ethyl-3,3-dimethylpiperidin-2-yl)methoxy)isobenzofuran-1(3H)-one (65.2 mg, 0.215 mmol, 23.59% yield) as a yellow oil. Chiral SFC Rt 3.8 mins. Peak 2: Enantiomer 2 of 5-((1-ethyl-3,3-dimethylpiperidin-2-yl)methoxy)isobenzofuran-1(3H)-one (71 mg, 0.234 mmol, 25.7% yield) as an orange oil. Chiral SFC Rt 5.9 mins.

Example 9: Diastereomer 3-(5-((1-ethyl-3,3-dimethylpiperidin-2-yl)methoxy)-1-oxoisoindolin-2-yl) piperidine-2,6-dione (I-17)

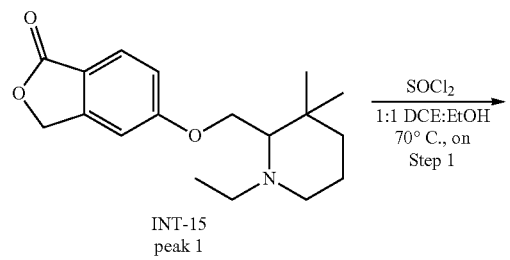

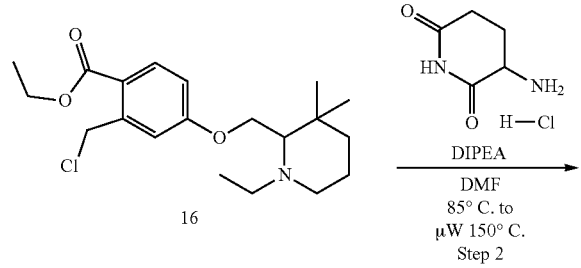

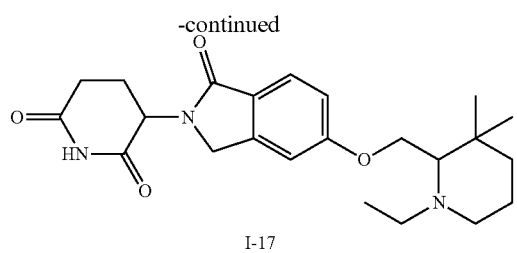

I-17

Step 1: Single Enantiomer Ethyl 2-(chloromethyl)-4-((1-ethyl-3,3-dimethylpiperidin-2-yl)methoxy) benzoate (16)

Intermediate 16 was made according to General Method IV starting from a single enantiomer of 5-((3,3-dimethylpiperidin-2-yl)methoxy)isobenzofuran-1(3H)-one INT-15 peak 1 (65.2 mg, 0.215 mmol) to afford a single enantiomer of ethyl 2-(chloromethyl)-4-((1-ethyl-3,3-dimethylpiperidin-2-yl)methoxy)benzoate 16 as a brown oil. The crude material was taken through to the next step without purification. LCMS [M+H]⁺: 368.3.

Step 2: Diastereomer 3-(5-((1-ethyl-3,3-dimethylpiperidin-2-yl)methoxy)-1-oxoisoindolin-2-yl)piperidine-2,6-dione (I-17)

Compound I-17 was made according to General Method V starting from a single enantiomer ethyl 2-(chloromethyl)-4-((1-ethyl-3,3-dimethylpiperidin-2-yl)methoxy)benzoate 16 (79 mg, 0.215 mmol). The reaction mixture was purified by silica gel chromatography (eluting with 0-100% 3:1 EtOAc:EtOH with 1% TEA as modifier in heptane). Fractions containing desired product were combined, concentrated, and lyophilized to afford a single diastereomer of 3-(5-((1-ethyl-3,3-dimethylpiperidin-2-yl)methoxy)-1-oxoisoindolin-2-yl)piperidine-2,6-dione I-17 (37.7 mg, 0.090 mmol, 42.0% yield) as a light purple solid. LCMS [M+H]⁺: 414.5. ¹H NMR (400 MHz, DMSO-d₆) δ 10.89 (s, 1H), 7.55 (d, J=8.3 Hz, 1H), 7.20-7.12 (m, 1H), 6.99 (dd, J=8.4, 2.2 Hz, 1H), 5.00 (dd, J=13.4, 5.1 Hz, 1H), 4.32 (d, J=17.3 Hz, 1H), 4.26-4.07 (m, 2H), 4.05-3.93 (m, 1H), 2.84 (ddd, J=17.2, 13.6, 5.4 Hz, 1H), 2.63-2.48 (m, 4H), 2.37-2.19 (m, 3H), 1.95-1.85 (m, 1H), 1.51-1.41 (m, 2H), 1.39-1.31 (m, 1H), 1.18-1.11 (m, 1H), 0.99 (s, 3H), 0.91 (t, J=7.0 Hz, 3H), 0.86 (s, 3H).

Example 10: Diastereomer 3-(5-((1-ethyl-3,3-dimethylpiperidin-2-yl)methoxy)-1-oxoisoindolin-2-yl) piperidine-2,6-dione (I-19)

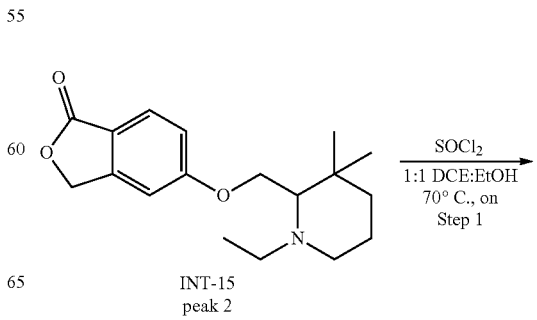

Step 1: Single Enantiomer Ethyl 2-(chloromethyl)-4-((1-ethyl-3,3-dimethylpiperidin-2-yl)methoxy)benzoate (18)

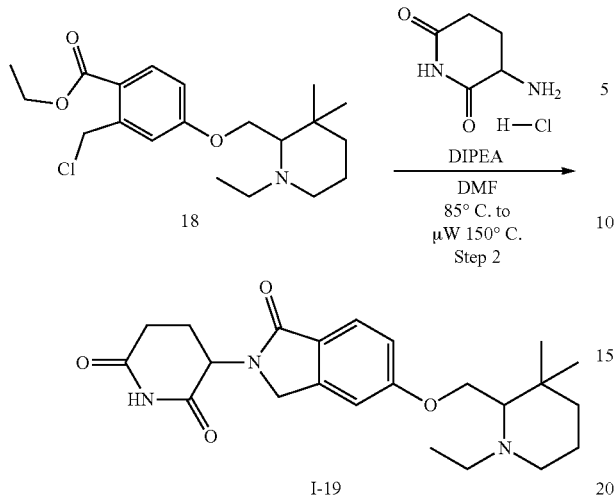

Intermediate 18 was made according to General Method IV starting from a single enantiomer of 5-((3,3-dimethylpiperidin-2-yl)methoxy)isobenzofuran-1(3H)-one INT-15 peak 2 (71 mg, 0.234 mmol) to afford a single enantiomer of ethyl 2-(chloromethyl)-4-((1-ethyl-3,3-dimethylpiperidin-2-yl)methoxy)benzoate 18 as a brown oil. The crude material was taken through to the next step without purification. LCMS [M+H]$^+$: 368.2.

Step 2: Diastereomer 3-(5-((1-ethyl-3,3-dimethylpiperidin-2-yl)methoxy)-1-oxoisoindolin-2-yl)piperidine-2,6-dione (I-19)

Compound I-19 was made according to General Method V starting from a single enantiomer ethyl 2-(chloromethyl)-4-((1-ethyl-3,3-dimethylpiperidin-2-yl)methoxy)benzoate 18 (86 mg, 0.234 mmol). The reaction mixture was purified by silica gel chromatography (eluting with 0-100% 3:1 EtOAc:EtOH with 1% TEA as modifier in heptane). Fractions containing desired product were combined, concentrated, and lyophilized to afford a mixture of diastereomers of 3-(5-((1-ethyl-3,3-dimethylpiperidin-2-yl)methoxy)-1-oxoisoindolin-2-yl)piperidine-2,6-dione I-19 (45.6 mg, 0.109 mmol, 46.7% yield) as a light purple solid. LCMS [M+H]$^+$: 414.3. $^1$H NMR (400 MHz, DMSO-$d_6$) δ 10.97 (s, 1H), 7.63 (d, J=8.3 Hz, 1H), 7.23 (d, J=2.2 Hz, 1H), 7.07 (dd, J=8.4, 2.3 Hz, 1H), 5.08 (dd, J=13.3, 5.1 Hz, 1H), 4.40 (d, J=17.1 Hz, 1H), 4.27 (d, J=17.3 Hz, 1H), 4.23-4.16 (m, 1H), 4.13-4.02 (m, 1H), 2.91 (ddd, J=17.1, 13.6, 5.4 Hz, 1H), 2.70-2.56 (m, 4H), 2.47-2.27 (m, 3H), 2.03-1.93 (m, 1H), 1.57-1.47 (m, 2H), 1.47-1.38 (m, 1H), 1.27-1.18 (m, 1H), 1.06 (s, 3H), 0.99 (t, J=7.0 Hz, 3H), 0.94 (s, 3H).

Example 11: Diastereomeric mixture Tert-butyl (2S)-2-(1-hydroxyethyl)pyrrolidine-1-carboxylate (INT-20)

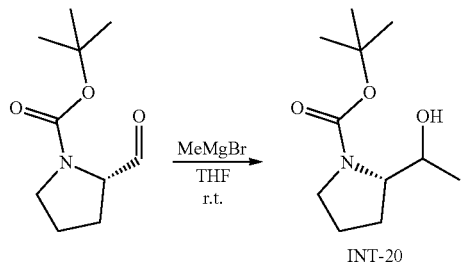

To a 100 mL rbf was added N-Boc-L-prolinal (0.5 mL, 2.67 mmol) was dissolved in THF (21.3 mL) and the resulting mixture was cooled to −78° C. 3M methylmagnesium bromide in diethylether (1.78 mL, 5.34 mmol) was added dropwise and the reaction mixture was stirred at r.t. for 2 hrs and then cooled to −78° C. Additional 3M methylmagnesium bromide in diethylether (1 mL, 3.00 mmol) was added stirring was continued at r.t. for 2 hrs. The reaction mixture was cooled to 0° C., quenched with saturated aqueous ammonium chloride, and extracted three times with ethyl acetate. The organic phases were combined, passed through a phase separator and concentrated onto CELITE®. The crude material was purified by silica gel chromatography (eluting with 0-100% ethyl acetate in heptane using ELSD detector) to afford a diastereomeric mixture of tert-butyl (2S)-2-(1-hydroxyethyl)pyrrolidine-1-carboxylate INT-20 (541 mg, 2.51 mmol, 84% yield) as a clear oil. LCMS [M+H−tButyl]$^+$: 160.1. $^1$H NMR (400 MHz, Chloroform-d) δ 4.01-3.90 (m, 1H), 3.78-3.64 (m, 1H), 3.62-3.47 (m, 1H), 3.34-3.22 (m, 1H), 2.07-1.93 (m, 1H), 1.91-1.59 (m, 3H), 1.49 (s, 9H), 1.14 (dd, J=25.7, 6.2 Hz, 3H).

Example 12: Diastereomers 5-((S)-1-((S)-1-ethylpyrrolidin-2-yl)ethoxy)isobenzofuran-1(3H)-one

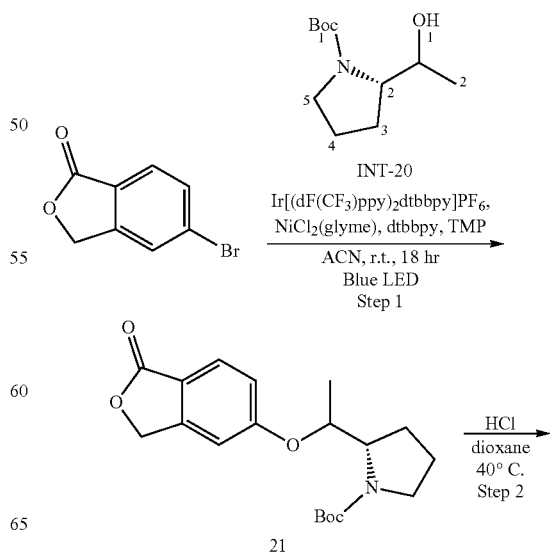

133
-continued

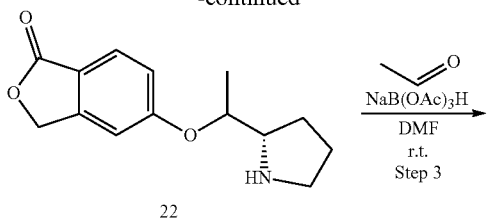

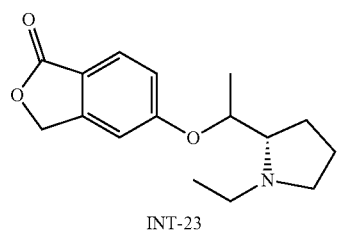

Step 1: Diastereomeric Mixture tert-butyl (2S)-2-(1-((1-oxo-1,3-dihydroisobenzofuran-5-yl)oxy)ethyl)pyrrolidine-1-carboxylate (21)

Intermediate 1 was made according to General Method I starting from a diastereomeric mixture of tert-butyl (2S)-2-(1-hydroxyethyl)pyrrolidine-1-carboxylate INT-20 (0.541 g, 2.51 mmol). The reaction mixture was purified by silica gel chromatography (eluting with 0-100% ethyl acetate in heptane) to afford an impure diastereomeric mixture of tert-butyl (2S)-2-(1-((1-oxo-1,3-dihydroisobenzofuran-5-yl)oxy)ethyl)pyrrolidine-1-carboxylate 21 (716 mg, 2.06 mmol, 82% yield) as a yellow oil. LCMS [M+H]$^+$: 348.2.

Step 2: Diastereomeric mixture 5-(1-((S)-pyrrolidin-2-yl)ethoxy)isobenzofuran-1(3H)-one (22)

Intermediate 22 was made according to General Method II starting from a diastereomeric mixture of tert-butyl (2S)-2-(1-((1-oxo-1,3-dihydroisobenzofuran-5-yl)oxy)ethyl)pyrrolidine-1-carboxylate 21 (716 mg, 2.06 mmol). The reaction mixture was concentrated to afford diastereomeric mixture 5-(1-((S)-pyrrolidin-2-yl)ethoxy)isobenzofuran-1(3H)-one 22 as an orange solid. The crude material was taken through to the next reaction without purification. LCMS [M+H]$^+$: 248.2.

Step 3: Diastereomer 5-(1-((S)-1-ethylpyrrolidin-2-yl)ethoxy)isobenzofuran-1(3H)-one (INT-23)

Intermediate 23 was made according to General Method III starting from 5-(1-((S)-pyrrolidin-2-yl)ethoxy)isobenzofuran-1(3H)-one 22 (510 mg, 2.06 mmol) and acetaldehyde (0.35 mL, 6.18 mmol). The crude material was purified by silica gel chromatography (eluting with 0-20% methanol in dichloromethane) to afford 5-(1-((S)-1-ethylpyrrolidin-2-yl)ethoxy)isobenzofuran-1(3H)-one INT-23 (330 mg, 1.198 mmol, 58.2% yield) as a light yellow oil. LCMS [M+H]$^+$: 276.1. The mixture of diastereomers was separated via chiral SFC [Column 21×250 mm Chiralpak IG; CO$_2$ Co-solvent 13% MeOH with 10 mM NH$_3$; at 80 g/min at 150 bar at 25° C.] to afford diastereomers: Peak 1: Diastereomer 1 of 5-(1-((S)-1-ethylpyrrolidin-2-yl)ethoxy)isobenzofuran-1(3H)-one (145.1 mg, 0.527 mmol, 25.6% yield) as an orange oil. Chiral SFC Rt 8.4 mins. $^1$H NMR (400 MHz, Chloroform-d) δ 7.72 (d, J=8.5 Hz, 1H), 6.98 (d, J=8.6 Hz, 1H), 6.90 (s, 1H), 5.19 (s, 2H), 4.53-4.39 (m, 1H), 3.10 (dt, J=8.8,

134
4.1 Hz, 1H), 2.87 (dq, J=14.6, 7.5 Hz, 1H), 2.62 (td, J=7.7, 7.2, 3.7 Hz, 1H), 2.32 (dq, J=13.7, 7.1 Hz, 1H), 2.18 (q, J=8.5 Hz, 1H), 1.88-1.63 (m, 4H), 1.28 (d, J=6.3 Hz, 3H), 1.03 (t, J=7.2 Hz, 3H). Peak 2: Diastereomer 2 of 5-(1-((S)-1-ethylpyrrolidin-2-yl)ethoxy)isobenzofuran-1(3H)-one (116.5 mg, 0.423 mmol, 20.53% yield) as orange oil. Chiral SFC Rt 11.6 mins. $^1$H NMR (400 MHz, Chloroform-d) δ 7.71 (d, J=8.5 Hz, 1H), 6.97 (dd, J=8.5, 2.1 Hz, 1H), 6.90 (d, J=2.0 Hz, 1H), 5.18 (s, 2H), 4.45 (p, J=6.2 Hz, 1H), 3.11 (dt, J=9.2, 4.6 Hz, 1H), 2.92 (dq, J=12.0, 7.4 Hz, 1H), 2.74 (dt, J=8.6, 5.5 Hz, 1H), 2.35 (dq, J=11.8, 7.0 Hz, 1H), 2.20 (q, J=8.3 Hz, 1H), 1.89-1.77 (m, 1H), 1.74-1.62 (m, 3H), 1.25 (d, J=6.2 Hz, 3H), 1.00 (t, J=7.2 Hz, 3H).

Example 13: Diastereomer 3-(5-(1-((S)-1-ethylpyrrolidin-2-yl)ethoxy)-1-oxoisoindolin-2-yl)piperidine-2,6-dione

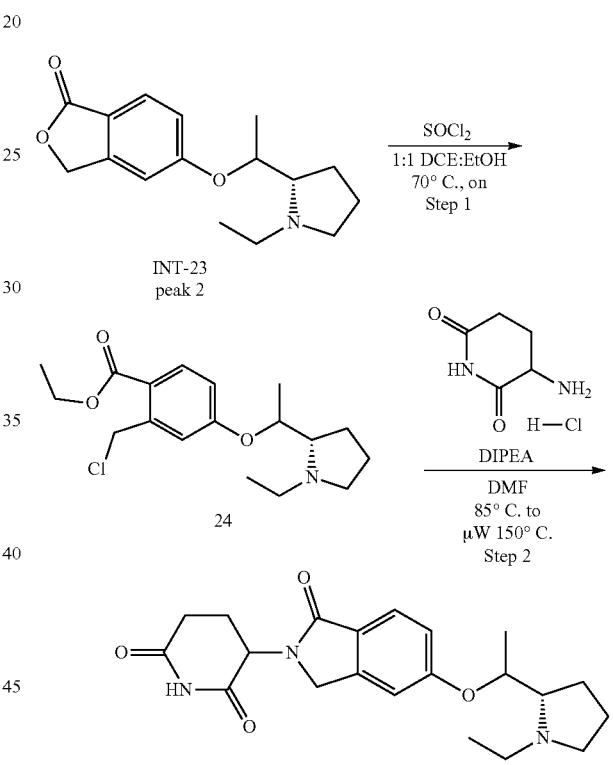

Step 1: Single Diastereomer ethyl 2-(chloromethyl)-4-(1-((S)-1-ethylpyrrolidin-2-yl)ethoxy)benzoate (24)

Intermediate 24 was made according to General Method IV starting from 5-(1-((S)-1-ethylpyrrolidin-2-yl)ethoxy)isobenzofuran-1(3H)-one INT-23 peak 2 (145.1 mg, 0.527 mmol). The crude material was purified by silica gel chromatography (eluting with 0-100% ethyl acetate in heptane) to afford ethyl 2-(chloromethyl)-4-(1-((S)-1-ethylpyrrolidin-2-yl)ethoxy)benzoate 24 (152 mg, 0.447 mmol, 85% yield) as a brown oil. LCMS [M+H]$^+$: 340.2. $^1$H NMR (400 MHz, Chloroform-d) δ 7.97 (d, J=8.7 Hz, 1H), 7.08 (d, J=2.6 Hz, 1H), 6.87 (dd, J=8.8, 2.6 Hz, 1H), 5.05 (s, 2H), 4.50 (p, J=6.1 Hz, 1H), 4.35 (q, J=7.1 Hz, 2H), 3.20-3.12 (m, 1H), 2.97 (dq, J=12.0, 7.4 Hz, 1H), 2.77 (dt, J=8.5, 5.6 Hz, 1H), 2.39 (dq, J=12.0, 7.0 Hz, 1H), 2.28-2.19 (m, 1H), 1.92-1.68 (m, 4H), 1.39 (t, J=7.1 Hz, 3H), 1.29 (d, J=6.2 Hz, 3H), 1.07 (t, J=7.2 Hz, 3H).

Step 2: Diastereomer 3-(5-(1-((S)-1-ethylpyrrolidin-2-yl)ethoxy)-1-oxoisoindolin-2-yl)piperidine-2,6-dione (I-25)

Compound I-25 was made according to General Method V starting from ethyl 2-(chloromethyl)-4-(1-((S)-1-ethylpyrrolidin-2-yl)ethoxy)benzoate 24 (152 mg, 0.447 mmol). The reaction mixture was purified by silica gel (eluting with 100% 3:1 EtOAc:EtOH with 1% TEA in ethyl acetate) to afford diastereomer 3-(5-(1-((S)-1-ethylpyrrolidin-2-yl)ethoxy)-1-oxoisoindolin-2-yl)piperidine-2,6-dione I-25 (95.9 mg, 0.246 mmol, 55.1% yield) as an off white solid. LCMS [M+H]$^+$: 386.2. $^1$H NMR (400 MHz, DMSO-d$_6$) δ 10.97 (s, 1H), 7.60 (d, J=8.4 Hz, 1H), 7.17 (d, J=2.1 Hz, 1H), 7.03 (dd, J=8.4, 2.2 Hz, 1H), 5.07 (dd, J=13.3, 5.1 Hz, 1H), 4.59 (p, J=6.1 Hz, 1H), 4.38 (dd, J=17.1, 4.9 Hz, 1H), 4.25 (dd, J=17.2, 4.2 Hz, 1H), 3.10-3.02 (m, 1H), 3.00-2.85 (m, 2H), 2.76-2.68 (m, 1H), 2.64-2.55 (m, 1H), 2.45-2.25 (m, 2H), 2.19-2.11 (m, 1H), 2.04-1.93 (m, 1H), 1.84-1.57 (m, 4H), 1.21 (dd, J=6.2, 1.1 Hz, 3H), 0.99 (t, J=7.2 Hz, 3H).

Example 14: Diastereomer 3-(5-(1-((S)-1-ethylpyrrolidin-2-yl)ethoxy)-1-oxoisoindolin-2-yl)piperidine-2,6-dione (I-27)

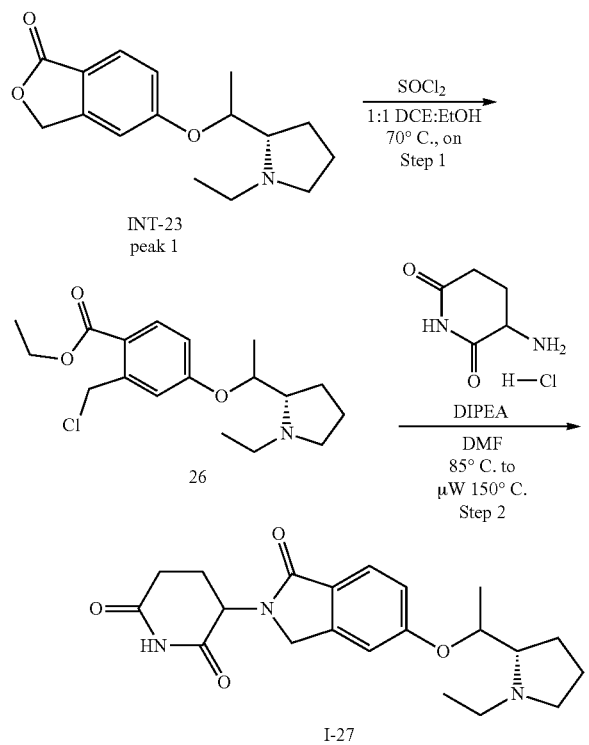

Step 1: Single Diastereomer ethyl 2-(chloromethyl)-4-(1-((S)-1-ethylpyrrolidin-2-yl)ethoxy)benzoate (26)

Intermediate 26 was made according to General Method IV starting from 5-(1-((S)-1-ethylpyrrolidin-2-yl)ethoxy) isobenzofuran-1(3H)-one INT-23 Peak 1 (116.5 mg, 0.423 mmol). The crude material was purified by silica gel chromatography (eluting with 0-100% ethyl acetate in heptane) to afford a single diastereomer ethyl 2-(chloromethyl)-4-(1-((S)-1-ethylpyrrolidin-2-yl)ethoxy)benzoate 26 (117 mg, 0.344 mmol, 81% yield) as a brown oil. LCMS [M+H]$^+$: 340.1. $^1$H NMR (400 MHz, Chloroform-d) δ 7.96 (d, J=8.8 Hz, 1H), 7.08 (d, J=2.6 Hz, 1H), 6.86 (dd, J=8.8, 2.6 Hz, 1H), 5.04 (s, 2H), 4.46 (qd, J=6.3, 3.9 Hz, 1H), 4.34 (q, J=7.1 Hz, 2H), 3.15 (ddd, J=9.0, 5.8, 2.9 Hz, 1H), 2.93 (dq, J=12.0, 7.4 Hz, 1H), 2.64 (ddd, J=7.7, 6.3, 3.8 Hz, 1H), 2.35 (dq, J=12.0, 7.0 Hz, 1H), 2.25-2.17 (m, 1H), 1.90-1.69 (m, 4H), 1.38 (t, J=7.1 Hz, 3H), 1.30 (d, J=6.2 Hz, 3H), 1.08 (t, J=7.2 Hz, 3H).

Step 2: Diastereomer 3-(5-(1-((S)-1-ethylpyrrolidin-2-yl)ethoxy)-1-oxoisoindolin-2-yl)piperidine-2,6-dione (I-27)

Compound I-27 was made according to General Method V starting from ethyl 2-(chloromethyl)-4-(1-((S)-1-ethylpyrrolidin-2-yl)ethoxy)benzoate 26 (117 mg, 0.344 mmol). The crude material was purified by silica gel (eluting with 0-100% 3:1 EtOAc:EtOH with 1% TEA in ethyl acetate) to afford 3-(5-(1-((S)-1-ethylpyrrolidin-2-yl)ethoxy)-1-oxoisoindolin-2-yl)piperidine-2,6-dione I-27 (68 mg, 0.162 mmol, 47.1% yield) as an off white solid. LCMS [M+H]$^+$: 386.1. $^1$H NMR (400 MHz, DMSO-d$_6$) δ 10.96 (s, 1H), 7.59 (d, J=8.4 Hz, 1H), 7.15 (d, J=2.2 Hz, 1H), 7.02 (dd, J=8.4, 2.2 Hz, 1H), 5.07 (dd, J=13.3, 5.1 Hz, 1H), 4.60-4.48 (m, 1H), 4.37 (dd, J=17.2, 5.9 Hz, 1H), 4.31-4.19 (m, 1H), 3.06-2.99 (m, 1H), 2.96-2.85 (m, 2H), 2.68-2.55 (m, 2H), 2.43-2.22 (m, 2H), 2.18-2.11 (m, 1H), 2.02-1.94 (m, 1H), 1.88-1.78 (m, 1H), 1.77-1.62 (m, 3H), 1.26-1.21 (m, 3H), 0.98 (t, J=7.2 Hz, 3H).

Example 15: Diastereomeric mixture tert-butyl (2S)-2-(1-hydroxypropyl)pyrrolidine-1-carboxylate (INT-28)

To a 100 mL rbf and and cooled to −78° C. was added N-Boc-L-prolinal (1 mL, 5.34 mmol) was dissolved in THF (42.7 mL). 1M ethylmagnesium bromide in THF (16.0 mL, 16.01 mmol) was then added dropwise the resulting mixture was stirred at r.t. for 3 hrs, cooled to 0° C., quenched with saturated aqueous ammonium chloride and extracted three times with ethyl acetate. The organic phases were combined, passed through a phase separator, and concentrated onto CELITE®. The crude material was purified by silica gel chromatography (eluting with 0-100% ethyl acetate in heptane using ELSD detector) to afford tert-butyl (2S)-2-(1-hydroxypropyl)pyrrolidine-1-carboxylate INT-28 (1.09 g, 4.75 mmol, 89% yield) as a clear oil. LCMS [M+H−tButyl]$^+$: 174.1. $^1$H NMR (400 MHz, Chloroform-d) δ 3.95-3.71 (m, 2H), 3.61-3.39 (m, 2H), 3.35-3.22 (m, 1H), 2.03-1.52 (m, 5H), 1.49 (s, 9H), 1.44-1.31 (m, 1H), 1.03 (td, J=7.4, 2.4 Hz, 3H).

Example 16: Diastereomers 5-(1-((S)-1-ethylpyrrolidin-2-yl)propoxy)isobenzofuran-1(3H)-one

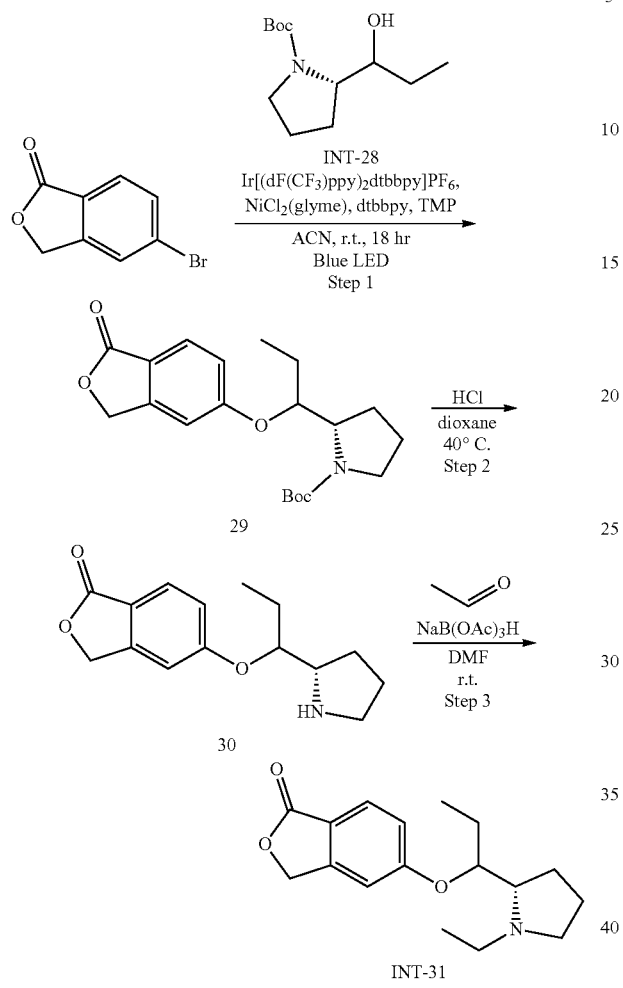

Step 1: Diastereomeric Mixture tert-butyl (2S)-2-(1-((1-oxo-1,3-dihydroisobenzofuran-5-yl)oxy)propyl)pyrrolidine-1-carboxylate (29)

Intermediate 29 was made according to General Method I starting from tert-butyl (2S)-2-(1-hydroxypropyl)pyrrolidine-1-carboxylate INT-28 (538 mg, 2.347 mmol). The reaction mixture was purified by silica gel chromatography (eluting with 0-100% ethyl acetate in heptane) to afford a diastereomeric mixture of tert-butyl (2S)-2-(1-((1-oxo-1,3-dihydroisobenzofuran-5-yl)oxy)propyl)pyrrolidine-1-carboxylate 29 (526 mg, 1.455 mmol, 62.0% yield) as a yellow oil. LCMS [M+H]$^+$: 362.2.

Step 2: Diastereomeric Mixture 5-(1-((S)-pyrrolidin-2-yl)propoxy)isobenzofuran-1(3H)-one (30)

Intermediate 30 was made according to General Method II starting from a diastereomeric mixture of tert-butyl (2S)-2-(1-((1-oxo-1,3-dihydroisobenzofuran-5-yl)oxy)propyl)pyrrolidine-1-carboxylate 29 (526 mg, 1.46 mmol) to afford diastereomeric mixture 5-(1-((S)-pyrrolidin-2-yl)propoxy)isobenzofuran-1(3H)-one 30 as an orange solid. The crude material was used directly in the next reaction without purification. LCMS [M+H]$^+$: 262.2.

Step 3: Diastereomers 5-(1-((S)-1-ethylpyrrolidin-2-yl)propoxy)isobenzofuran-1(3H)-one (INT-31)

INT-31 was made according to General Method III starting from a diastereomeric mixture 5-(1-((S)-pyrrolidin-2-yl)propoxy)isobenzofuran-1(3H)-one (380 mg, 1.46 mmol) and acetaldehyde (0.25 mL, 4.27 mmol). The crude material was purified by silica gel chromatography (eluting with 0-100% ethyl acetate in heptane) to afford a diastereomeric mixture of 5-(1-((S)-1-ethylpyrrolidin-2-yl)propoxy)isobenzofuran-1 (3H)-one INT-31 (221 mg, 0.764 mmol, 52.5% yield) as a yellow oil. LCMS [M+H]$^+$: 290.2. The mixture of isomers was separated via chiral SFC [Column 21×250 mm Chiralpak IG; $CO_2$ Co-solvent 18% MeOH with 10 mM $NH_3$; at 80 g/min at 150 bar at 25° C.] to afford diastereomers: Peak 1: Diastereomer 1 of 5-(1-((S)-1-ethylpyrrolidin-2-yl)propoxy)isobenzofuran-1(3H)-one (92.8 mg, 0.321 mmol, 22.04% yield) as an orange oil. Chiral SFC Rt 3.8 mins. $^1$H NMR (400 MHz, Chloroform-d) δ 7.74 (d, J=8.5 Hz, 1H), 7.04 (dd, J=8.5, 2.1 Hz, 1H), 6.97 (d, J=2.1 Hz, 1H), 5.20 (s, 2H), 4.32 (ddd, J=7.7, 5.1, 2.7 Hz, 1H), 3.06 (dt, J=9.1, 4.3 Hz, 1H), 2.86 (dq, J=11.9, 7.4 Hz, 1H), 2.66 (ddd, J=8.7, 5.7, 2.8 Hz, 1H), 2.27 (dq, J=11.9, 7.0 Hz, 1H), 2.12 (q, J=8.6 Hz, 1H), 1.93-1.57 (m, 6H), 1.01 (t, J=7.2 Hz, 3H), 0.95 (t, J=7.4 Hz, 3H). Peak 2: Diastereomer 2 of 5-(1-((S)-1-ethylpyrrolidin-2-yl)propoxy)isobenzofuran-1 (3H)-one (116.3 mg, 0.402 mmol, 27.6% yield) as an orange oil. Chiral SFC Rt 5.1 mins. $^1$H NMR (400 MHz, Chloroform-d) δ 7.73 (d, J=8.5 Hz, 1H), 7.04 (dd, J=8.5, 2.1 Hz, 1H), 6.97 (s, 1H), 5.20 (s, 2H), 4.34-4.18 (m, 1H), 3.11 (dt, J=9.1, 4.5 Hz, 1H), 2.94-2.82 (m, 1H), 2.78 (dt, J=8.4, 5.2 Hz, 1H), 2.32 (dq, J=13.6, 7.0 Hz, 1H), 2.18 (q, J=8.1 Hz, 1H), 1.89-1.75 (m, 2H), 1.75-1.52 (m, 4H), 1.01-0.88 (m, 6H).

Example 17: Diastereomer 3-(5-(1-((S)-1-ethylpyrrolidin-2-yl)propoxy)-1-oxoisoindolin-2-yl)piperidine-2,6-dione

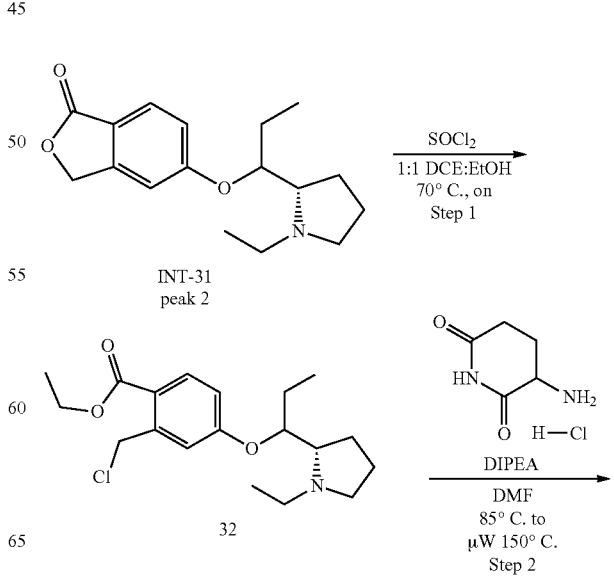

139

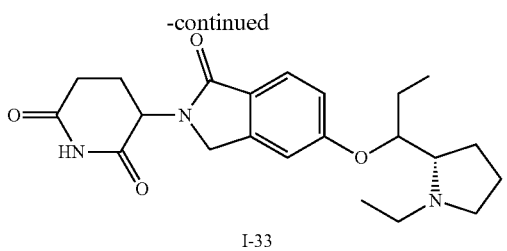

I-33

Step 1: Single Diastereomer ethyl 2-(chloromethyl)-4-(1-((S)-1-ethylpyrrolidin-2-yl)propoxy)benzoate (32)

Intermediate 32 was made according to General Method IV starting from 5-(1-((S)-1-ethylpyrrolidin-2-yl)propoxy)isobenzofuran-1(3H)-one INT-31 Peak 2 (116.3 mg, 0.402 mmol). The crude material was purified by silica gel chromatography (eluting with 0-100% ethyl acetate in heptane) to afford ethyl 2-(chloromethyl)-4-(1-((S)-1-ethylpyrrolidin-2-yl)propoxy)benzoate 32 (113 mg, 0.319 mmol, 79% yield) as a brown oil. LCMS [M+H]$^+$: 354.6. $^1$H NMR (400 MHz, Chloroform-d) δ 7.98 (d, J=8.8 Hz, 1H), 7.15 (d, J=2.6 Hz, 1H), 6.92 (dd, J=8.8, 2.6 Hz, 1H), 5.06 (s, 2H), 4.40-4.25 (m, 3H), 3.15 (ddd, J=9.4, 6.2, 3.6 Hz, 1H), 2.93 (dq, J=11.9, 7.4 Hz, 1H), 2.81 (dt, J=8.2, 5.4 Hz, 1H), 2.36 (dq, J=11.9, 7.0 Hz, 1H), 2.26-2.15 (m, 1H), 1.93-1.57 (m, 6H), 1.40 (t, J=7.1 Hz, 3H), 1.03 (t, J=7.2 Hz, 3H), 0.98 (t, J=7.4 Hz, 3H).

Step 2: Diastereomer 3-(5-(1-((S)-1-ethylpyrrolidin-2-yl)propoxy)-1-oxoisoindolin-2-yl)piperidine-2,6-dione (I-33)

Compound I-33 was made according to General Method V starting from ethyl 2-(chloromethyl)-4-(1-((S)-1-ethylpyrrolidin-2-yl)propoxy)benzoate 32 (113 mg, 0.319 mmol). The crude material was purified by silica gel (eluting with 0-100% 3:1 EtOAc:EtOH with 1% TEA in ethyl acetate) to afford impure product. The material was further purified by basic mass triggered reverse phase HPLC (25-50% ACN in water with 5 mM NH$_4$OH). Fraction tubes contained 3 drops of formic acid prior to collection. Fractions containing pure desired product were combined, concentrated, and lyophilized to afford diastereomer 3-(5-(1-((S)-1-ethylpyrrolidin-2-yl)propoxy)-1-oxoisoindolin-2-yl)piperidine-2,6-dione I-33 (37.9 mg, 73 μmol, 23% yield) as a white solid. LCMS [M+H]$^+$: 400.5. $^1$H NMR (400 MHz, DMSO-d$_6$) δ 8.32 (s, 1H), 7.61 (d, J=8.4 Hz, 1H), 7.20 (d, J=2.1 Hz, 1H), 7.08 (dd, J=8.4, 2.1 Hz, 1H), 5.07 (dd, J=13.3, 5.1 Hz, 1H), 4.48-4.34 (m, 2H), 4.26 (d, J=17.2 Hz, 1H), 3.13-3.06 (m, 1H), 3.00-2.78 (m, 3H), 2.60 (ddd, J=17.3, 4.4, 2.3 Hz, 1H), 2.44-2.28 (m, 2H), 2.24-2.16 (m, 1H), 2.02-1.94 (m, 1H), 1.86-1.62 (m, 5H), 1.55 (dt, J=14.6, 7.4 Hz, 1H), 0.94 (dt, J=16.2, 7.2 Hz, 6H).

140

Example 18: Diastereomer 3-(5-(1-((S)-1-ethylpyrrolidin-2-yl)propoxy)-1-oxoisoindolin-2-yl)piperidine-2,6-dione (I-35)

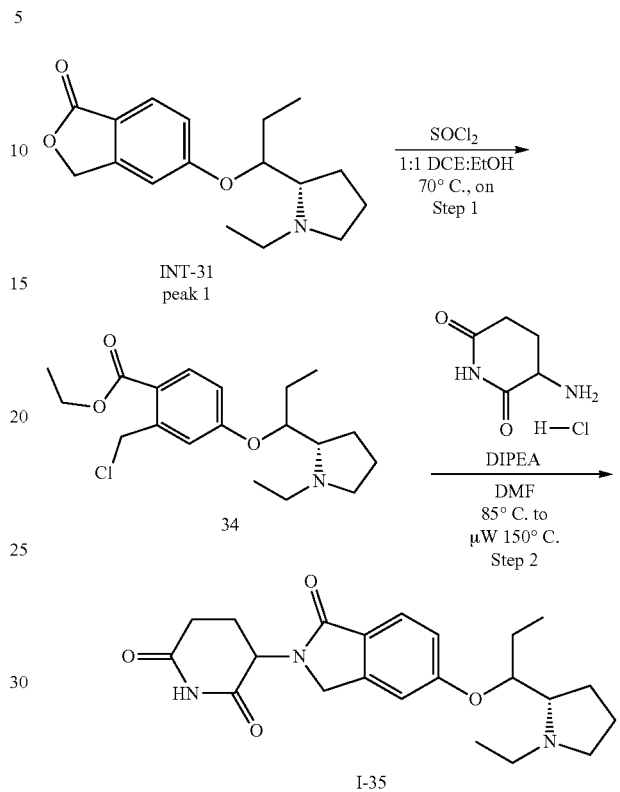

Step 1: Single Diasteromer ethyl 2-(chloromethyl)-4-(1-((S)-1-ethylpyrrolidin-2-yl)propoxy)benzoate (34)

Intermediate 34 was made according to General Method IV starting from 5-(1-((S)-1-ethylpyrrolidin-2-yl)propoxy)isobenzofuran-1(3H)-one INT-31 Peak 1 (92.8 mg, 0.321 mmol). The crude material was purified by silica gel chromatography (eluting with 0-100% ethyl acetate in heptane) to afford a single diastereomer of ethyl 2-(chloromethyl)-4-(1-((S)-1-ethylpyrrolidin-2-yl)propoxy)benzoate 34 (90 mg, 0.254 mmol, 79% yield) as a brown oil. LCMS [M+H]$^+$: 354.1. $^1$H NMR (400 MHz, Chloroform-d) δ 7.97 (d, J=8.7 Hz, 1H), 7.15 (d, J=2.6 Hz, 1H), 6.91 (dd, J=8.8, 2.6 Hz, 1H), 5.06 (s, 2H), 4.42-4.29 (m, 3H), 3.12 (ddd, J=9.0, 5.1, 3.2 Hz, 1H), 2.91 (dq, J=11.9, 7.4 Hz, 1H), 2.68 (ddd, J=8.8, 5.6, 3.0 Hz, 1H), 2.30 (dq, J=11.9, 7.0 Hz, 1H), 2.20-2.11 (m, 1H), 1.94-1.63 (m, 6H), 1.40 (t, J=7.1 Hz, 3H), 1.07 (t, J=7.2 Hz, 3H), 0.98 (t, J=7.4 Hz, 3H).

Step 2: Diastereomer 3-(5-(1-((S)-1-ethylpyrrolidin-2-yl)propoxy)-1-oxoisoindolin-2-yl)piperidine-2,6-dione (I-35)

Compound I-35 was made according to General Method V starting from a single diastereomer of ethyl 2-(chloromethyl)-4-(1-((S)-1-ethylpyrrolidin-2-yl)propoxy)benzoate 34 (90 mg, 0.254 mmol). The reaction mixture was purified by silica gel (eluting with 0-100% 3:1 EtOAc:EtOH with 1% TEA in ethyl acetate) to afford impure product. The product was further purified by basic mass triggered reverse phase HPLC (eluting with 25-50% ACN in water with 5 mM NH₄OH). Fraction tubes contained 3 drops of formic acid prior to collection. Fractions containing pure desired product were combined, concentrated, and lyophilized to afford diastereomer 3-(5-(1-((S)-1-ethylpyrrolidin-2-yl)propoxy)-1-oxoisoindolin-2-yl)piperidine-2,6-dione I-35 (19.6 mg, 0.040 mmol, 15.63% yield) as a white solid. LCMS [M+H]⁺: 400.3. ¹H NMR (400 MHz, DMSO-d₆) δ 8.30 (s, 1H), 7.58 (d, J=8.4 Hz, 1H), 7.19 (d, J=2.1 Hz, 1H), 7.06 (dt, J=8.5, 1.8 Hz, 1H), 5.06 (dd, J=13.3, 5.1 Hz, 1H), 4.49-4.31 (m, 2H), 4.24 (dd, J=17.1, 6.0 Hz, 1H), 3.02-2.84 (m, 3H), 2.67 (td, J=7.3, 2.6 Hz, 1H), 2.63-2.56 (m, 1H), 2.37 (qd, J=13.2, 4.4 Hz, 1H), 2.21 (dq, J=11.8, 6.9 Hz, 1H), 2.13-2.04 (m, 1H), 2.02-1.93 (m, 1H), 1.84-1.75 (m, 2H), 1.71-1.57 (m, 4H), 0.98-0.90 (m, 6H).

Example 19: Diastereomers (2S)-tert-butyl 2-(1-((1-oxo-1,3-dihydroisobenzofuran-5-yl)oxy)propyl)pyrrolidine-1-carboxylate (INT-36)

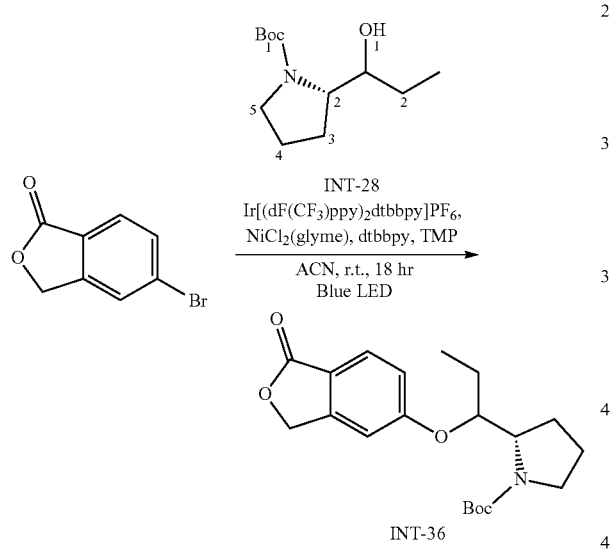

INT-36 was made according to General Method I starting from (S)-tert-butyl 2-((S)-1-hydroxypropyl)pyrrolidine-1-carboxylate INT-28 (541 mg, 2.361 mmol). The crude product was purified by silica gel chromatography (eluting with 0-100% ethyl acetate in heptane) to afford slightly impure mixture of diastereomers (2S)-tert-butyl 2-(1-((1-oxo-1,3-dihydroisobenzofuran-5-yl)oxy)propyl)pyrrolidine-1-carboxylate INT-36 (774 mg, 1.820 mmol, 77% yield) as a yellow oil. LCMS [M+H]⁺: 362.2. The mixture of isomers was separated via chiral SFC [Column 21×250 mm Phenomenx i-Cellulose-5; CO₂ Co-solvent 20% MeOH; at 80 g/min at 150 bar at 25° C.] to afford two diastereomers: Peak 1: Diastereomer 1 of (2S)-tert-butyl 2-(1-((1-oxo-1,3-dihydroisobenzofuran-5-yl)oxy)propyl)pyrrolidine-1-carboxylate(124.2 mg, 0.343 mmol, 14.6% yield) as a viscous yellow oil. Chiral SFC Rt 5.2 mins. Peak 2: Diastereomer 2 of (2S)-tert-butyl 2-(1-((1-oxo-1,3-dihydroisobenzofuran-5-yl)oxy)propyl)pyrrolidine-1-carboxylate (390.6 mg, 1.08 mmol, 45.8% yield) as a viscous yellow oil. Chiral SFC Rt 6.5 mins.

Example 20: Diastereomer 3-(5-(1-((S)-1-benzylpyrrolidin-2-yl)propoxy)-1-oxoisoindolin-2-yl)piperidine-2,6-dione (I-39)

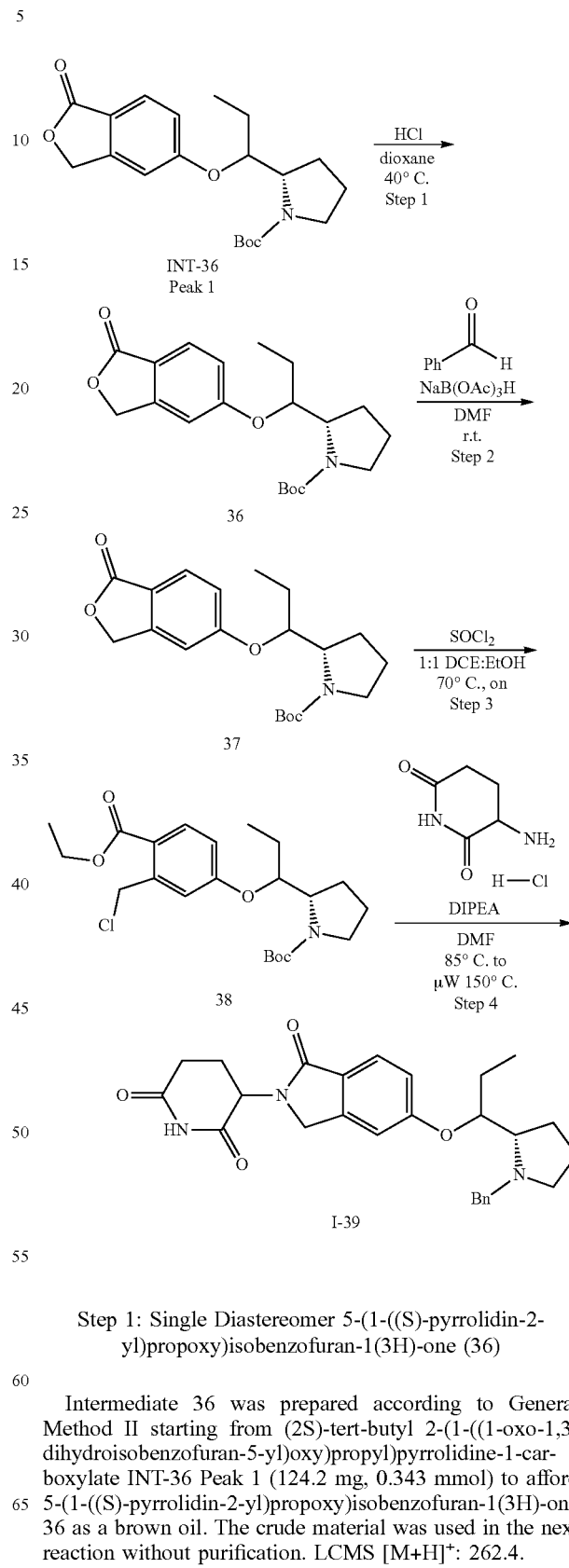

Step 1: Single Diastereomer 5-(1-((S)-pyrrolidin-2-yl)propoxy)isobenzofuran-1(3H)-one (36)

Intermediate 36 was prepared according to General Method II starting from (2S)-tert-butyl 2-(1-((1-oxo-1,3-dihydroisobenzofuran-5-yl)oxy)propyl)pyrrolidine-1-carboxylate INT-36 Peak 1 (124.2 mg, 0.343 mmol) to afford 5-(1-((S)-pyrrolidin-2-yl)propoxy)isobenzofuran-1(3H)-one 36 as a brown oil. The crude material was used in the next reaction without purification. LCMS [M+H]⁺: 262.4.

Step 2: Single Diastereomer 5-(1-((S)-1-benzylpyrrolidin-2-yl)propoxy)isobenzofuran-1(3H)-one (37)

Intermediate 37 was made according to General Method III starting from 5-(1-((S)-pyrrolidin-2-yl)propoxy)isobenzofuran-1(3H)-one 36 (90 mg, 0.343 mmol) and benzaldehyde (0.10 mL, 1.030 mmol). The crude material was purified by silica gel chromatography (eluting with 0-100% ethyl acetate in heptane) to afford 5-(1-((S)-1-benzylpyrrolidin-2-yl)propoxy)isobenzofuran-1(3H)-one 37 (150 mg, 0.427 mmol, quantitative yield) as a yellow oil. LCMS [M+H]$^+$: 352.1. $^1$H NMR (400 MHz, Chloroform-d) δ 7.79 (d, J=8.5 Hz, 1H), 7.37-7.36 (m, 1H), 7.24 (ddd, J=5.3, 4.2, 2.4 Hz, 2H), 7.16 (dd, J=7.4, 2.2 Hz, 2H), 7.07 (dd, J=8.5, 2.1 Hz, 1H), 6.94 (d, J=2.0 Hz, 1H), 5.19 (d, J=15.2 Hz, 1H), 5.12 (d, J=15.2 Hz, 1H), 4.36 (ddd, J=7.6, 4.9, 2.3 Hz, 1H), 4.06 (d, J=13.4 Hz, 1H), 3.42 (d, J=13.4 Hz, 1H), 2.94 (ddd, J=9.1, 5.5, 3.6 Hz, 1H), 2.88 (ddd, J=9.2, 5.5, 2.3 Hz, 1H), 2.20 (td, J=9.1, 7.7 Hz, 1H), 2.05-1.66 (m, 6H), 1.01 (t, J=7.5 Hz, 3H).

Step 3: Single Diastereomer ethyl 4-(1-((S)-1-benzylpyrrolidin-2-yl)propoxy)-2-(chloromethyl)benzoate (38)

Intermediate 38 was made according to General Method IV starting from 5-(1-((S)-1-benzylpyrrolidin-2-yl)propoxy)isobenzofuran-1(3H)-one 37 (150 mg, 0.427 mmol). The crude material was purified by silica gel chromatography (eluting with 0-100% ethyl acetate in heptane) to afford ethyl 2-(chloromethyl)-4-(1-((S)-1-ethylpyrrolidin-2-yl)propoxy)benzoate 38 (134 mg, 0.322 mmol, 75% yield) as an orange oil. LCMS [M+H]$^+$: 416.3. $^1$H NMR (400 MHz, Chloroform-d) δ 7.99 (d, J=8.7 Hz, 1H), 7.33-7.18 (m, 5H), 7.13 (d, J=2.6 Hz, 1H), 6.91 (dd, J=8.8, 2.6 Hz, 1H), 5.11-4.99 (m, 2H), 4.40 (q, J=7.1 Hz, 2H), 4.33 (td, J=4.9, 2.4 Hz, 1H), 4.08 (d, J=13.2 Hz, 1H), 3.40 (d, J=13.2 Hz, 1H), 2.97-2.84 (m, 2H), 2.20 (td, J=9.3, 7.0 Hz, 1H), 2.01-1.65 (m, 6H), 1.43 (t, J=7.1 Hz, 3H), 1.00 (t, J=7.4 Hz, 3H).

Step 4: Diastereomer 3-(5-(1-((S)-1-benzylpyrrolidin-2-yl)propoxy)-1-oxoisoindolin-2-yl)piperidine-2,6-dione (I-39)

Compound I-39 was made according to General Method V starting from ethyl 2-(chloromethyl)-4-(1-((S)-1-ethylpyrrolidin-2-yl)propoxy)benzoate 38 (134 mg, 0.322 mmol). The crude material was purified by silica gel (eluting with 0-100% 3:1 EtOAc:EtOH with 1% TEA in ethyl acetate) to afford 3-(5-(1-((S)-1-benzylpyrrolidin-2-yl)propoxy)-1-oxoisoindolin-2-yl)piperidine-2,6-dione I-39 (7.4 mg, 0.016 mmol, 4.83% yield) as a white solid. LCMS [M+H]$^+$: 462.4. $^1$H NMR (400 MHz, DMSO-d$_6$) δ 10.97 (s, 1H), 7.58 (d, J=8.4 Hz, 1H), 7.26-7.13 (m, 4H), 7.13-7.00 (m, 3H), 5.08 (dd, J=13.4, 5.1 Hz, 1H), 4.60-4.51 (m, 1H), 4.42-4.32 (m, 1H), 4.24 (d, J=6.9 Hz, 1H), 4.10 (dd, J=13.4, 3.6 Hz, 1H), 3.28-3.19 (m, 1H), 2.91 (ddd, J=18.3, 13.6, 5.4 Hz, 1H), 2.85-2.77 (m, 1H), 2.72-2.64 (m, 1H), 2.64-2.54 (m, 1H), 2.42-2.31 (m, 1H), 2.12-1.94 (m, 2H), 1.90-1.80 (m, 2H), 1.75-1.58 (m, 4H), 0.96 (td, J=7.4, 3.4 Hz, 3H).

Example 21: Diastereomer 3-(5-(1-((S)-1-benzylpyrrolidin-2-yl)propoxy)-1-oxoisoindolin-2-yl)piperidine-2,6-dione (I-43)

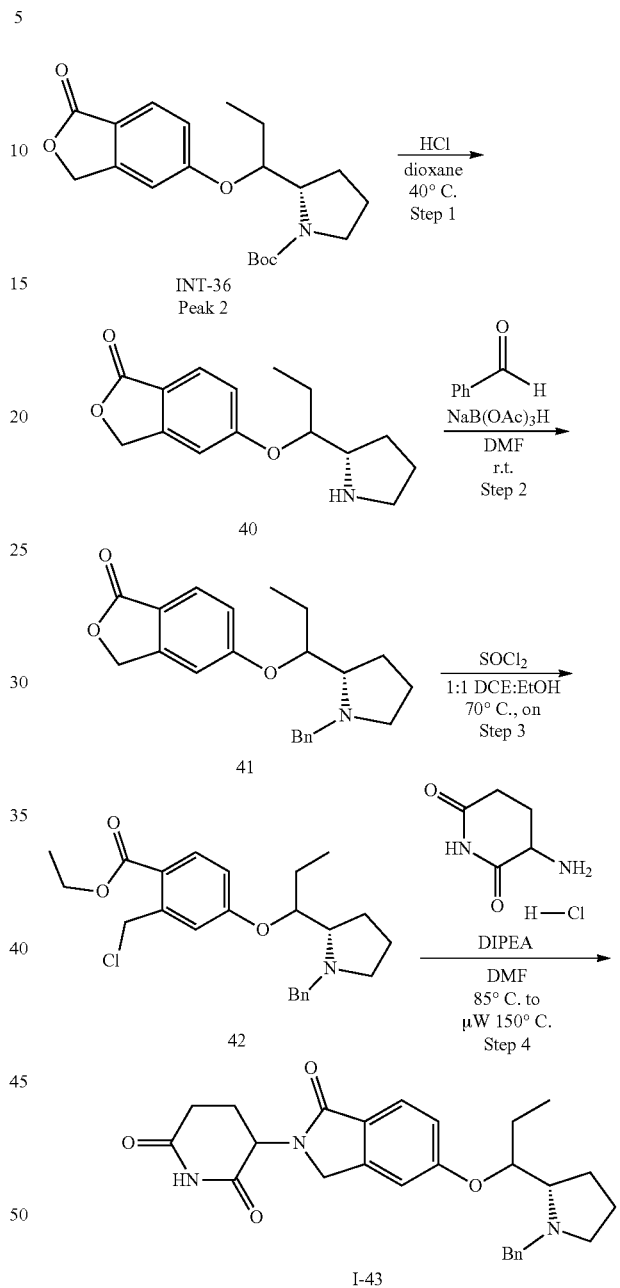

Step 1: Single Diastereomer 5-(1-((S)-pyrrolidin-2-yl)propoxy)isobenzofuran-1(3H)-one (40)

Intermediate 40 was prepared according to General Method II starting from (2S)-tert-butyl 2-(1-((1-oxo-1,3-dihydroisobenzofuran-5-yl)oxy)propyl)pyrrolidine-1-carboxylate INT-36 Peak 2 (290.6 mg, 0.804 mmol). The reaction mixture was concentrated to afford 5-(1-((S)-pyrrolidin-2-yl)propoxy)isobenzofuran-1(3H)-one 40 as a brown oil. The crude material was used in the next reaction without purification. LCMS [M+H]$^+$: 262.2.

Step 2: Single Diastereomer 5-(1-((S)-1-benzylpyrrolidin-2-yl)propoxy)isobenzofuran-1(3H)-one (41)

Intermediate 41 was prepared according to General Method III starting from 5-(1-((S)-pyrrolidin-2-yl)propoxy)isobenzofuran-1(3H)-one 40 (210 mg, 0.804 mmol) and benzaldehyde (0.24 mL, 2.41 mmol). The crude material was purified by silica gel chromatography (eluting with 0-100% ethyl acetate in heptane) to afford impure product. The material was further purified by silica gel chromatography (eluting with 0-100% ethyl acetate in heptane) to afford 5-(1-((S)-1-benzylpyrrolidin-2-yl)propoxy)isobenzofuran-1(3H)-one 41 (155 mg, 0.441 mmol, 54.9% yield) as a yellow oil. LCMS [M+H]$^+$: 352.2. $^1$H NMR (400 MHz, Chloroform-d) δ 7.74 (d, J=8.5 Hz, 1H), 7.35-7.20 (m, 5H), 6.92 (dd, J=8.5, 2.2 Hz, 1H), 6.70 (d, J=2.0 Hz, 1H), 5.24-5.11 (m, 2H), 4.17 (ddd, J=8.7, 5.8, 2.7 Hz, 1H), 3.96 (d, J=13.1 Hz, 1H), 3.64 (d, J=13.1 Hz, 1H), 3.08-2.92 (m, 2H), 2.40-2.31 (m, 1H), 2.01-1.55 (m, 6H), 0.96 (t, J=7.4 Hz, 3H).

Step 3: Single Diastereomer ethyl 4-(1-((S)-1-benzylpyrrolidin-2-yl)propoxy)-2-(chloromethyl)benzoate (42)

Intermediate 42 was made according to General Method IV starting from 5-(1-((S)-1-benzylpyrrolidin-2-yl)propoxy)isobenzofuran-1(3H)-one 41 (155 mg, 0.441 mmol). The crude material was purified by silica gel chromatography (eluting with 0-100% ethyl acetate in heptane to afford ethyl 4-(1-((S)-1-benzylpyrrolidin-2-yl)propoxy)-2-(chloromethyl)benzoate 42 (133 mg, 0.320 mmol, 72.5% yield) as an orange oil. LCMS [M+H]$^+$: 416.7. $^1$H NMR (400 MHz, Chloroform-d) δ 7.96 (d, J=8.7 Hz, 1H), 7.36-7.23 (m, 5H), 7.04 (d, J=2.6 Hz, 1H), 6.79 (dd, J=8.8, 2.6 Hz, 1H), 5.14-4.97 (m, 2H), 4.39 (q, J=7.1 Hz, 2H), 4.19 (ddd, J=8.6, 5.6, 2.7 Hz, 1H), 4.02 (d, J=13.1 Hz, 1H), 3.61 (d, J=13.1 Hz, 1H), 3.07-2.93 (m, 2H), 2.33 (dt, J=9.1, 8.3 Hz, 1H), 2.04-1.59 (m, 6H), 1.43 (t, J=7.1 Hz, 3H), 0.97 (t, J=7.4 Hz, 3H).

Step 4: Diastereomer 3-(5-(1-((S)-1-benzylpyrrolidin-2-yl)propoxy)-1-oxoisoindolin-2-yl)piperidine-2,6-dione (I-43)

Compound I-43 was made according to General Method V starting from ethyl 4-(1-((S)-1-benzylpyrrolidin-2-yl)propoxy)-2-(chloromethyl)benzoate 42 (133 mg, 0.320 mmol). The crude material was purified by silica gel chromatography (eluting with 0-50% 3:1 EtOAc:EtOH with 1% TEA in heptane) to afford 3-(5-(1-((S)-1-benzylpyrrolidin-2-yl)propoxy)-1-oxoisoindolin-2-yl)piperidine-2,6-dione I-43 (10 mg, 0.021 mmol, 6.71% yield) as a white solid. LCMS [M+H]$^+$: 462.3. $^1$H NMR (400 MHz, DMSO-d$_6$) δ 11.02-10.90 (m, 1H), 7.57 (d, J=8.3 Hz, 1H), 7.35-7.15 (m, 5H), 7.09-6.90 (m, 2H), 5.07 (ddd, J=13.3, 5.1, 3.2 Hz, 1H), 4.44-4.15 (m, 3H), 4.02 (d, J=13.1 Hz, 1H), 3.49 (d, J=13.1 Hz, 1H), 2.97-2.81 (m, 3H), 2.67-2.53 (m, 1H), 2.46-2.30 (m, 1H), 2.26-2.18 (m, 1H), 2.03-1.84 (m, 2H), 1.82-1.72 (m, 2H), 1.68-1.50 (m, 3H), 0.94-0.85 (m, 3H).

Example 22: Diastereomer 3-(1-oxo-5-(1-((S)-pyrrolidin-2-yl)propoxy)isoindolin-2-yl)piperidine-2,6-dione 3-(5-(1-((S)-1-benzylpyrrolidin-2-yl)propoxy)-1-oxoisoindolin-2-yl)piperidine-2,6-dione I-39 (76.8 mg, 0.166 mmol) was dissolved in DMF (2 mL) and the resulting mixture was purged with nitrogen for 5 minutes. Pd-C (1.8 mg, 0.017 mmol) was added and the reaction mixture was purged with hydrogen for 5 minutes. A hydrogen balloon was placed on top of the reaction mixture and the reaction mixture was stirred at room temperature for 18 hours. The reaction mixture was purged with nitrogen for 5 minutes, filtered through a syringe filter with acetonitrile, and concentrated. The crude material was purified by basic mass triggered reverse phase HPLC (eluting with 15-40% ACN in water with 5 mM NH$_4$OH). Fraction tubes contained 3 drops of formic acid prior to collection. Fractions containing pure desired product were combined, concentrated, and lyophilized to afford diastereomer 3-(1-oxo-5-(1-((S)-pyrrolidin-2-yl)propoxy)isoindolin-2-yl)piperidine-2,6-dione I-44 (19.7 mg, 0.045 mmol, 27.2% yield) as a white solid. LCMS [M+H]$^+$: 372.1. $^1$H NMR (400 MHz, DMSO-d$_6$) δ 10.97 (s, 1H), 8.19, (s, 1H), 7.61 (d, J=8.4 Hz, 1H), 7.21 (s, 1H), 7.08 (d, J=8.6 Hz, 1H), 5.07 (dd, J=13.3, 5.1 Hz, 1H), 4.38 (dd, J=17.0, 4.5 Hz, 2H), 4.25 (dd, J=17.1, 4.0 Hz, 1H), 3.41-3.37 (m, 1H), 2.97-2.85 (m, 3H), 2.64-2.54 (m, 2H), 2.43-2.31 (m, 1H), 2.02-1.94 (m, 1H), 1.92-1.82 (m, 1H), 1.77-1.58 (m, 5H), 0.90 (t, J=7.4 Hz, 3H).

Example 23: Diastereomer 3-(1-oxo-5-(1-((S)-pyrrolidin-2-yl)propoxy)isoindolin-2-yl)piperidine-2,6-dione (I-45)

3-(5-(1-((S)-1-benzylpyrrolidin-2-yl)propoxy)-1-oxoisoindolin-2-yl)piperidine-2,6-dione I-43 (73.6 mg, 0.159 mmol) was dissolved in DMF (2 mL) and the resulting mixture was purged with nitrogen for 5 minutes. Pd-C (1.7 mg, 0.016 mmol) was added and the reaction mixture was purged with hydrogen for 5 minutes. A hydrogen balloon was placed on top of the reaction and the reaction mixture was stirred at room temperature for 18 hours. The reaction mixture was purged with nitrogen for 5 minutes, filtered through a syringe filter with acetonitrile, and concentrated. The crude material was purified by basic mass triggered reverse phase HPLC (eluting with 15-40% ACN in water with 5 mM NH$_4$OH). Fraction tubes contained 3 drops of formic acid prior to collection. Fractions containing pure desired product were combined, concentrated, and lyophilized to afford a mixture of diastereomers of 3-(1-oxo-5-(1-((S)-pyrrolidin-2-yl)propoxy)isoindolin-2-yl)piperidine-2,6-dione I-45 (27.7 mg, 0.061 mmol, 38.4% yield) as a white solid. LCMS [M+H]$^+$: 372.1. $^1$H NMR (400 MHz, DMSO-d$_6$) δ 10.97 (s, 1H), 8.24 (s, 1H) 7.62 (d, J=8.4 Hz, 1H), 7.23 (s, 1H), 7.10 (d, J=8.5 Hz, 1H), 5.07 (dd, J=13.3, 5.1 Hz, 1H), 4.51-4.34 (m, 2H), 4.26 (dd, J=17.2, 5.7 Hz, 1H), 3.48-3.43 (m, 1H), 3.02-2.85 (m, 4H), 2.63-2.55 (m, 1H), 2.38 (dd, J=13.1, 4.5 Hz, 1H), 2.02-1.94 (m, 1H), 1.89 (s, 1H), 1.78 (dq, J=13.9, 7.1 Hz, 3H), 1.61 (dt, J=14.2, 6.9 Hz, 1H), 1.51 (q, J=10.2, 9.6 Hz, 1H), 0.90 (t, J=7.4 Hz, 3H).

Example 24: Diastereomer 3-(1-oxo-5-(((R)-piperidin-2-yl)methoxy)isoindolin-2-yl)piperidine-2,6-dione (I-47)

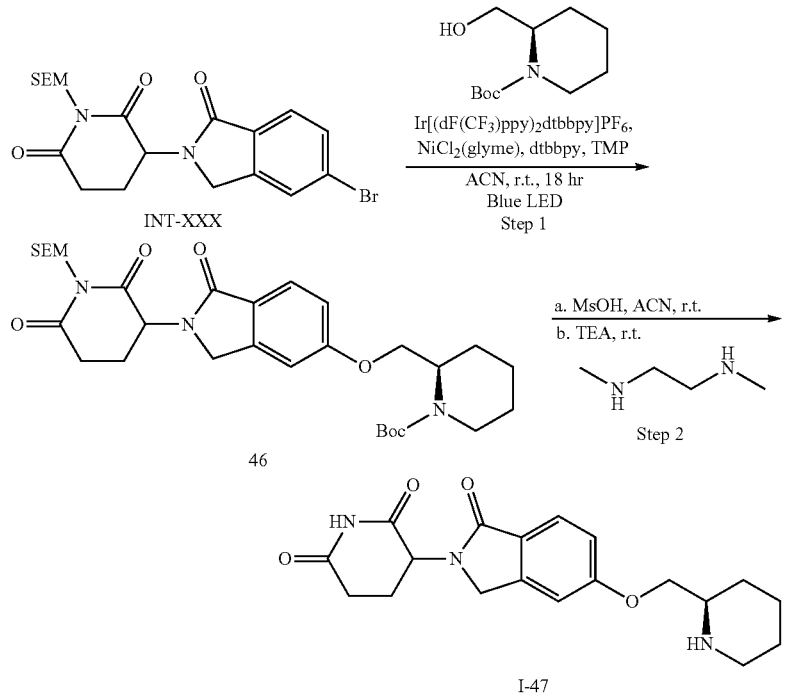

Step 1: Diastereomer Tert-butyl (2R)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate (46)

Intermediate 46 was prepared according to General Method VI starting from (R)-1-N-Boc-2-hydroxymethylpiperidine (28 mg, 0.132 mmol) and 3-(5-bromo-1-oxoisoindolin-2-yl)-1-((2-(trimethylsilyl)ethoxy)methyl)piperidine-2,6-dione INT-XXX. The reaction mixture was filtered and concentrated to afford diastereomer tert-butyl (2R)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate 46 as a brown solid. The crude material was taken through to the next step without purification. LCMS [M+H–156.3 (TMSCH2CH2,tButyl)]+: 432.26.

Step 2: Diastereomer 3-(1-oxo-5-(((R)-piperidin-2-yl)methoxy)isoindolin-2-yl)piperidine-2,6-dione (I-47)

Compound I-47 was prepared according to General Method VII starting from tert-butyl (2R)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate 46 (64.7 mg, 0.11 mmol). The reaction mixture was concentrated, dissolved in DMSO, and purified by basic mass triggered reverse phase HPLC (eluting with 10-30% ACN in water with 5 mM NH4OH as modifier). Each test-tube contained 3 drops of formic acid prior to collection. Pure fractions were combined, concentrated, and lyophilized to afford diastereomer 3-(1-oxo-5-(((R)-piperidin-2-yl)methoxy)isoindolin-2-yl)piperidine-2,6-dione I-47 (4.55 mg, 9.62 µmol, 8.74% yield) as a cream solid. LCMS [M+H]+: 358.3. $^1$H NMR (400 MHz, DMSO-$d_6$) δ 10.95 (s, 1H), 8.29 (s, 1H), 7.62 (d, J=8.4 Hz, 1H), 7.18 (d, J=2.3 Hz, 1H), 7.06 (dd, J=8.5, 2.2 Hz, 1H), 5.07 (dd, J=13.3, 5.0 Hz, 1H), 4.39 (d, J=17.1 Hz, 1H), 4.26 (d, J=17.3 Hz, 1H), 3.98 (dd, J=9.5, 4.6 Hz, 1H), 3.88 (ddd, J=9.2, 7.2, 1.6 Hz, 1H), 3.03-2.83 (m, 3H), 2.68-2.55 (m, 2H), 2.44-2.29 (m, 1H), 2.03-1.92 (m, 1H), 1.80-1.61 (m, 2H), 1.59-1.52 (m, 1H), 1.49-1.43 (m, 1H), 1.38-1.29 (m, 2H), 1.21-1.10 (m, 1H).

Example 25: Diastereomer 1-(hydroxymethyl)-3-(1-oxo-5-(((S)-piperidin-2-yl)methoxy)isoindolin-2-yl)piperidine-2,6-dione (I-49)

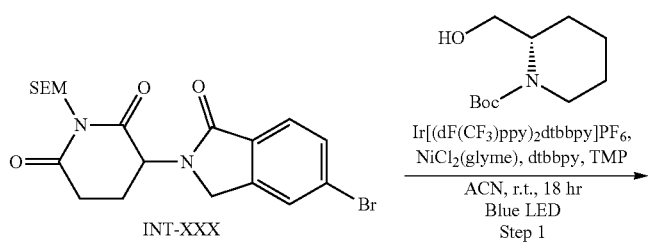

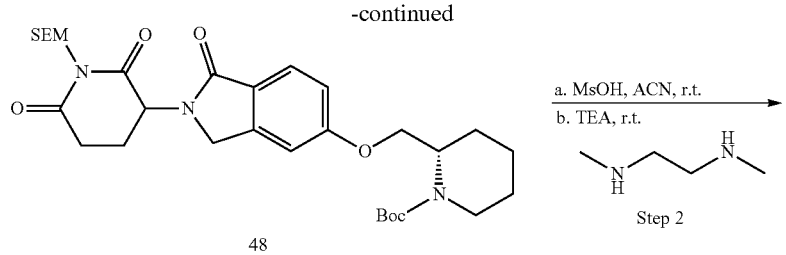

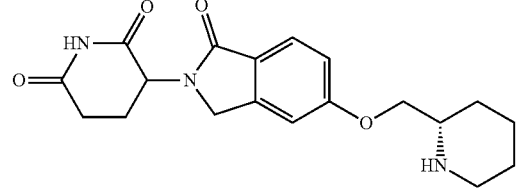

Step 1: Diastereomer tert-butyl (2S)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate (48)

Intermediate 48 was prepared according to General Method VI starting from (S)—N-Boc-piperidine-2-methanol (28 mg, 0.132 mmol) and 3-(5-bromo-1-oxoisoindolin-2-yl)-1-((2-(trimethylsilyl)ethoxy)methyl)piperidine-2,6-dione INT-XXX. The reaction mixture was filtered and concentrated to afford tert-butyl (2S)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate 48 as a brown oil. The crude material was carried through the next reaction without purification. LCMS [M+H−156.3 (TMSCH2CH2,tButyl)]$^+$: 432.2.

Step 2: Diastereomer 3-(1-oxo-5-(((S)-piperidin-2-yl)methoxy)isoindolin-2-yl)piperidine-2,6-dione (I-49)

Compound I-49 was prepared according to General Method VII starting from tert-butyl (2S)-2-(((2-(2,6-dioxo-1-((2-(trimethylsilyl)ethoxy)methyl)piperidin-3-yl)-1-oxoisoindolin-5-yl)oxy)methyl)piperidine-1-carboxylate 48 (64.7 mg, 0.11 mmol). The reaction mixture was concentrated and a third of the material was purified by basic mass triggered reverse phase HPLC (eluting with 10-30% ACN in water with 5 mM NH4OH as modifier). Each test-tube contained 3 drops of formic acid prior to collection. Pure fractions were combined, concentrated, and lyophilized to afford diastereomer 3-(1-oxo-5-(((S)-piperidin-2-yl)methoxy)isoindolin-2-yl)piperidine-2,6-dione I-49 (3.94 mg, 8.33 μmol, 4.48% yield) as a cream solid. The rest of the material was carried through to the next reaction without purification. LCMS [M+H]$^+$: 358.2. $^1$H NMR (400 MHz, DMSO-$d_6$) δ 10.92 (s, 1H), 7.62 (d, J=8.4 Hz, 1H), 7.21-7.15 (m, 1H), 7.06 (dd, J=8.4, 2.3 Hz, 1H), 5.07 (dd, J=13.3, 5.0 Hz, 1H), 4.39 (d, J=17.3 Hz, 1H), 4.26 (d, J=17.3 Hz, 1H), 4.05-3.96 (m, 1H), 3.96-3.83 (m, 1H), 3.02-2.87 (m, 3H), 2.63-2.54 (m, 2H), 2.45-2.33 (m, 1H), 2.03-1.91 (m, 1H), 1.80-1.59 (m, 2H), 1.59-1.50 (m, 1H), 1.49-1.43 (m, 2H), 1.38-1.31 (m, 1H), 1.21-1.09 (m, 1H).

Example 26: 3-(5-(((R)-1-ethylpiperidin-2-yl)methoxy)-1-oxoisoindolin-2-yl)piperidine-2,6-dione

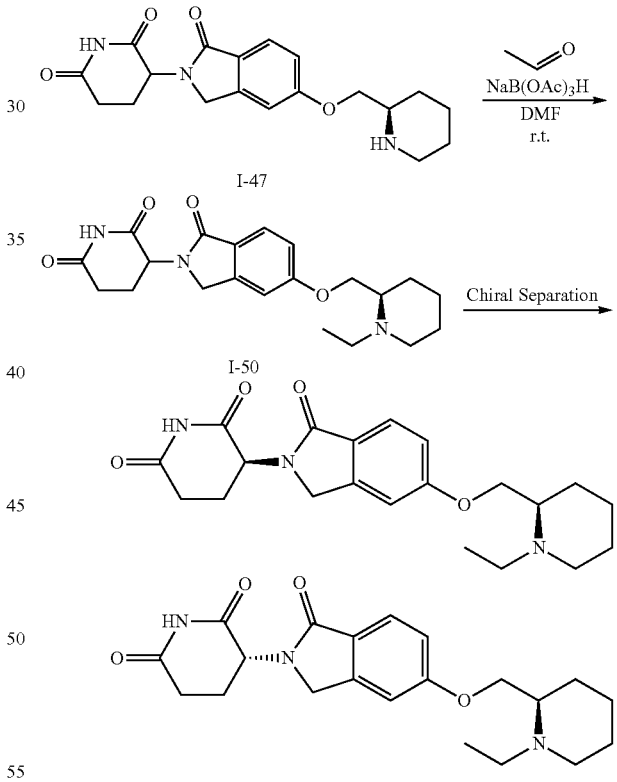

Compound I-50 was prepared according to General Method III starting from 1-(hydroxymethyl)-3-(1-oxo-5-(((R)-piperidin-2-yl)methoxy)isoindolin-2-yl)piperidine-2,6-dione I-47 (26 mg, 0.073 mmol) and acetaldehyde (0.5 mL, 8.85 mmol). The reaction mixture was quenched with saturated aqueous sodium bicarbonate and extracted 4 times with 4:1 dichloromethane:isopropanol. The organic phases were combined, passed through a phase separator and concentrated. The crude material was purified by basic mass triggered reverse phase HPLC (eluting with 15-40% ACN in water with 5 mM NH4OH as modifier). Each test-tube contained 3 drops of formic acid prior to sample collection. Pure fractions were combined, concentrated, and lyophilized to afford 3-(5-(((R)-1-ethylpiperidin-2-yl)methoxy)-1-oxoisoindolin-2-yl)piperidine-2,6-dione I-50 (4.59 mg, 9.90 µmol, 13.56% yield) as an orange solid. LCMS [M+H]+: 386.3. ¹H NMR (400 MHz, DMSO-d₆) δ 10.96 (s, 1H), 8.23 (s, 1H), 7.62 (d, J=8.4 Hz, 1H), 7.23-7.14 (m, 1H), 7.05 (dd, J=8.4, 2.2 Hz, 1H), 5.07 (dd, J=13.3, 5.1 Hz, 1H), 4.39 (d, J=17.2 Hz, 1H), 4.26 (d, J=17.2 Hz, 1H), 4.21-4.11 (m, 1H), 4.07-3.95 (m, 1H), 2.91 (ddd, J=18.0, 13.6, 5.5 Hz, 1H), 2.81-2.55 (m, 3H), 2.44-2.32 (m, 2H), 2.24 (td, J=11.6, 10.6, 3.2 Hz, 1H), 2.17-2.10 (m, 1H), 2.02-1.93 (m, 1H), 1.78-1.70 (m, 1H), 1.70-1.61 (m, 1H), 1.58-1.51 (m, 1H), 1.50-1.40 (m, 2H), 1.35-1.22 (m, 1H), 0.97 (t, J=7.1 Hz, 3H).

The diastereomeric mixture of I-50 was separated via chiral SFC [Column 21×250 mm Chiralpak IH; CO₂ Co-solvent 30% IPA with 10 mM NH₃; at 100 g/min at 125 bar at 25° C.] to afford the single diastereomers: Peak 1: Diastereomer 1 of 3-(5-(((R)-1-ethylpiperidin-2-yl)methoxy)-1-oxoisoindolin-2-yl)piperidine-2,6-dione (32.1 mg, 0.082 mmol, 31.80% yield) as a white solid. Chiral SFC Rt 3.6 mins. ¹H NMR (400 MHz, DMSO-d₆) δ 7.62 (d, J=8.4 Hz, 1H), 7.19 (d, J=2.2 Hz, 1H), 7.06 (dd, J=8.4, 2.2 Hz, 1H), 5.07 (dd, J=13.3, 5.1 Hz, 1H), 4.39 (d, J=17.2 Hz, 1H), 4.26 (d, J=17.2 Hz, 1H), 4.18 (dd, J=10.3, 4.7 Hz, 1H), 4.02 (dd, J=10.2, 5.0 Hz, 1H), 2.98-2.65 (m, 4H), 2.64-2.53 (m, 1H), 2.37 (td, J=12.9, 4.3 Hz, 2H), 2.31-2.22 (m, 1H), 2.03-1.94 (m, 1H), 1.80-1.36 (m, 6H), 0.97 (t, J=7.1 Hz, 3H).

Peak 2: Diastereomer 2 of 3-(5-(((R)-1-ethyl piperidin-2-yl) methoxy)-1-oxoisoindolin-2-yl)piperidine-2,6-dione (16.2 mg, 0.042 mmol, 16.04% yield) as a white solid. Chiral SFC Rt 6.5 mins. ¹H NMR (400 MHz, DMSO-d₆) δ 10.97 (s, 1H), 7.63 (d, J=8.4 Hz, 1H), 7.19 (d, J=2.2 Hz, 1H), 7.06 (dd, J=8.4, 2.2 Hz, 1H), 5.07 (dd, J=13.3, 5.1 Hz, 1H), 4.39 (d, J=17.2 Hz, 1H), 4.26 (d, J=17.2 Hz, 1H), 4.18 (dd, J=10.3, 4.7 Hz, 1H), 4.05 (dd, J=10.3, 4.9 Hz, 1H), 2.96-2.73 (m, 4H), 2.58 (dd, J=13.5, 6.8 Hz, 2H), 2.38 (dd, J=13.4, 4.6 Hz, 1H), 2.33 (s, 1H), 2.02-1.93 (m, 1H), 1.76 (d, J=12.7 Hz, 1H), 1.71-1.63 (m, 1H), 1.56 (s, 1H), 1.47 (d, J=11.1 Hz, 3H), 0.99 (t, J=7.1 Hz, 3H).

The following compounds were made according to Example 26, starting from the final product of either Example 24 (I-47) or Example 25 (I-49).

| Compound Number | Structure/NMR data | LCMS [M + H] | LCMS Rt |
|---|---|---|---|
| I-50a | | 496.3 | 0.41 |
| I-50b | | 498.27 | 0.4 |

-continued

| Compound Number | Structure/NMR data | LCMS [M + H] | LCMS Rt |
|---|---|---|---|
| I-50c | | 513.3 | 0.37 |
| I-50d | | 478.31 | 0.42 |
| I-50e | | 439.27 | 0.36 |
| I-50f | | 577.28 | 0.46 |

-continued

| Compound Number | Structure/NMR data | LCMS [M + H] | LCMS Rt |
|---|---|---|---|
| I-50g | | 598.32 | 0.5 |
| I-50h | | 473.31 | 0.41 |
| I-50i | | 530.33 | 0.39 |

| Compound Number | Structure/NMR data | LCMS [M + H] | LCMS Rt |
|---|---|---|---|
| I-50j | | 545.33 | 0.41 |
| I-50k | | 465.31 | 0.36 |
| I-50l | | 484.3 | 0.040 |
| I-50m | | 493.32 | 0.38 |

-continued
| Compound Number | Structure/NMR data | LCMS [M + H] | LCMS Rt |
|---|---|---|---|
| I-50n | 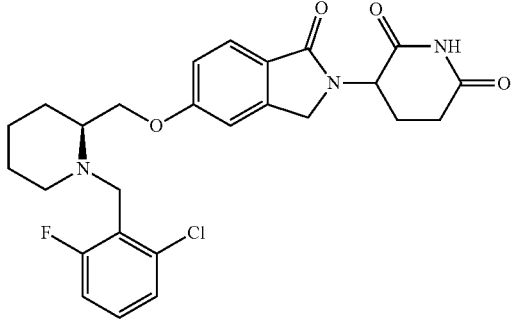 [SMILES: O=C1CCC(N2Cc3cc(OC[C@@H]4CCCCN4Cc4c(F)cccc4Cl)ccc3C2=O)C(=O)N1] | 500.24 | 0.43 |
| I-50o | 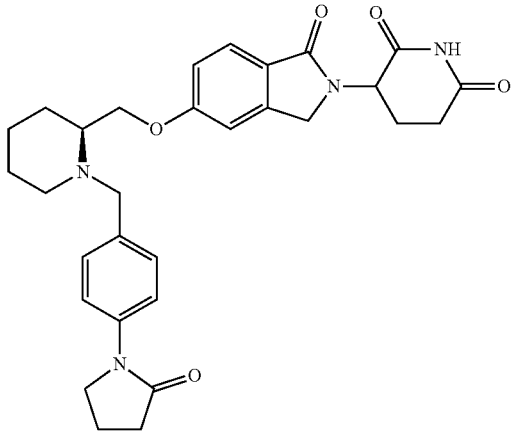 [SMILES: O=C1CCC(N2Cc3cc(OC[C@@H]4CCCCN4Cc4ccc(N5CCCC5=O)cc4)ccc3C2=O)C(=O)N1] | 531.34 | 0.4 |
| I-50p | 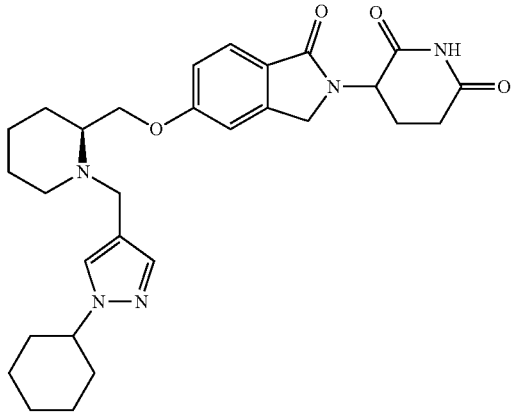 [SMILES: O=C1CCC(N2Cc3cc(OC[C@@H]4CCCCN4Cc4cnn(C5CCCCC5)c4)ccc3C2=O)C(=O)N1] | 520.37 | 0.45 |
| I-50q | 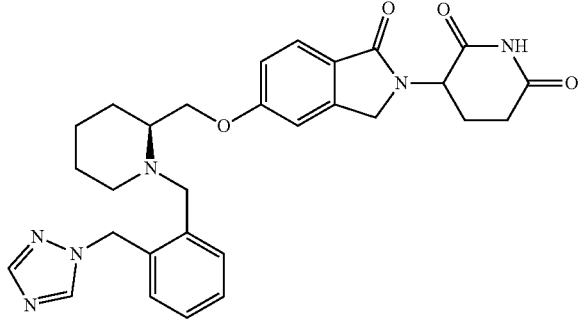 [SMILES: O=C1CCC(N2Cc3cc(OC[C@@H]4CCCCN4Cc4ccccc4Cn4cncn4)ccc3C2=O)C(=O)N1] | 529.32 | 0.39 |

| Compound Number | Structure/NMR data | LCMS [M + H] | LCMS Rt |
|---|---|---|---|
| I-50r | 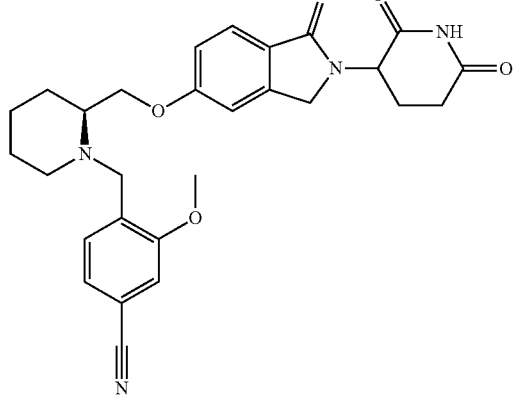 | 503.32 | 0.39 |
| I-50s | 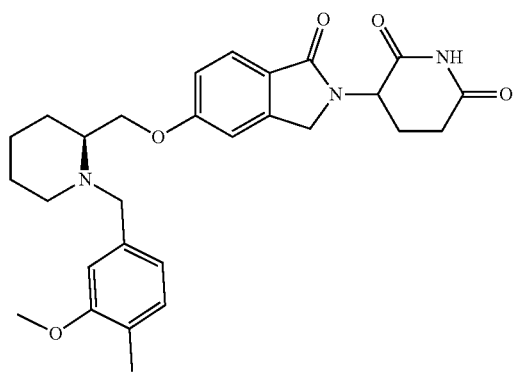 [SMILES: COc1cc(CN2CCCC[C@H]2COc2ccc3c(c2)CN(C2CCC(=O)NC2=O)C3=O)ccc1C] | 492.34 | 0.46 |
| I-50t | 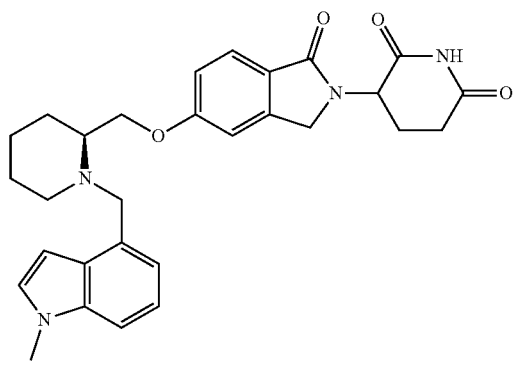 | 501.32 | 0.44 |

-continued
| Compound Number | Structure/NMR data | LCMS [M + H] | LCMS Rt |
|---|---|---|---|
| I-50u | 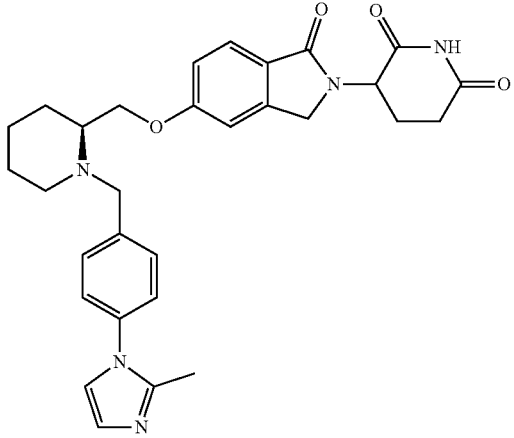 | 528.3 | 0.31 |
| I-50v | 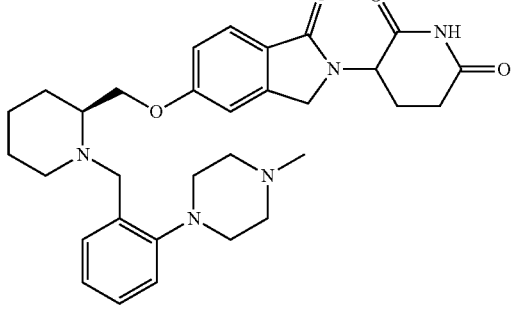 | 546.4 | 0.32 |
| I-50w | 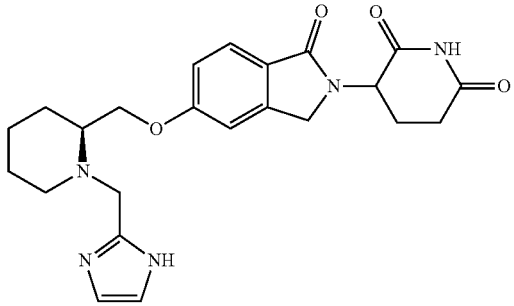 [SMILES: O=C1CCC(N2Cc3cc(OC[C@@H]4CCCCN4Cc4ncc[nH]4)ccc3C2=O)C(=O)N1] | 438.27 | 0.4 |
| I-50x | 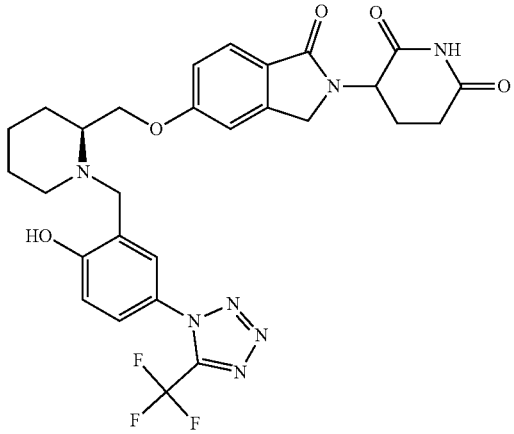 [SMILES: O=C1CCC(N2Cc3cc(OC[C@@H]4CCCCN4Cc4cc(-n5nnnc5C(F)(F)F)ccc4O)ccc3C2=O)C(=O)N1] | 600.26 | 0.44 |

-continued
| Compound Number | Structure/NMR data | LCMS [M + H] | LCMS Rt |
|---|---|---|---|
| I-50y | 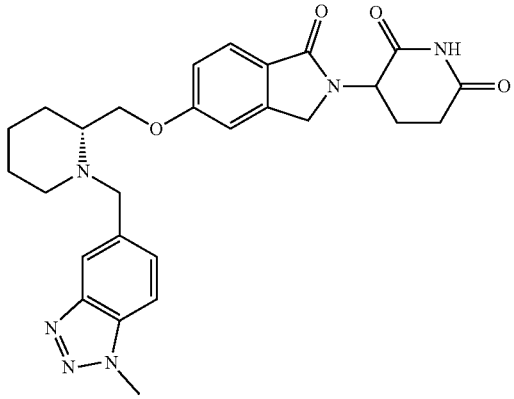 [SMILES: Cn1nnc2cc(CN3CCCC[C@@H]3COc3ccc4c(c3)CN(C3CCC(=O)NC3=O)C4=O)ccc21] | 503.32 | 0.37 |
| I-50z | 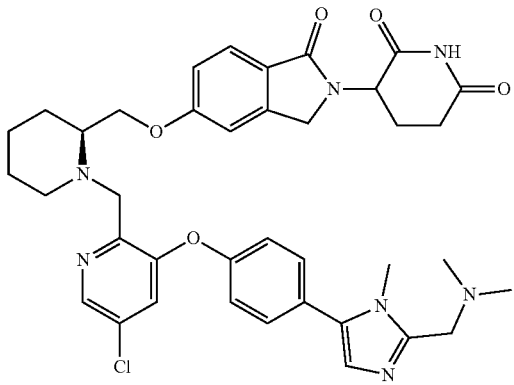 [SMILES: CN(C)Cc1ncc(-c2ccc(Oc3cc(Cl)cnc3CN3CCCC[C@H]3COc3ccc4c(c3)CN(C3CCC(=O)NC3=O)C4=O)cc2)n1C] | 712.42 | 0.4 |
| I-50aa | 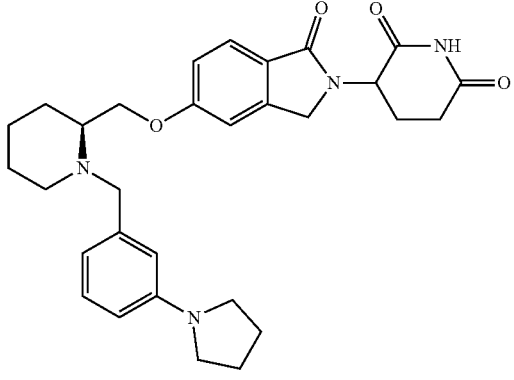 | 517.33 | 0.49 |
| I-50ab | 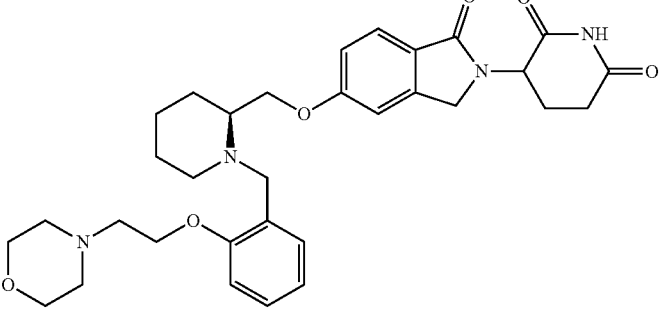 | 577.4 | 0.34 |

| Compound Number | Structure/NMR data | LCMS [M + H] | LCMS Rt |
|---|---|---|---|
| I-50ac | 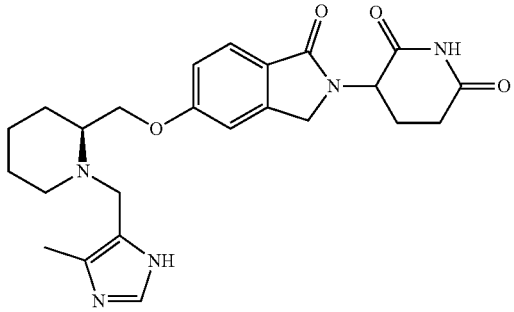 [SMILES: Cc1nc[nH]c1CN1CCCC[C@H]1COc1ccc2c(c1)CN(C1CCC(=O)NC1=O)C2=O] | 452.31 | 0.33 |
| I-50ad | 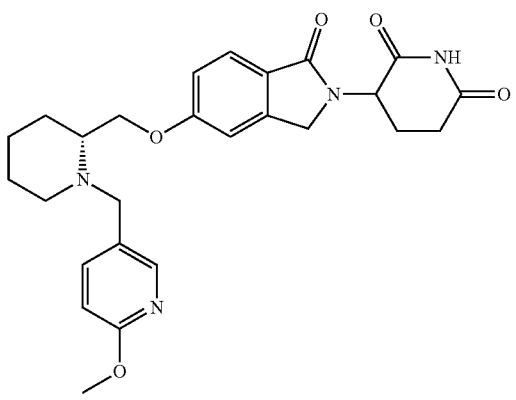 [SMILES: COc1ccc(CN2CCCC[C@@H]2COc2ccc3c(c2)CN(C2CCC(=O)NC2=O)C3=O)cn1] | 479.31 | 0.39 |
| I-50ae | 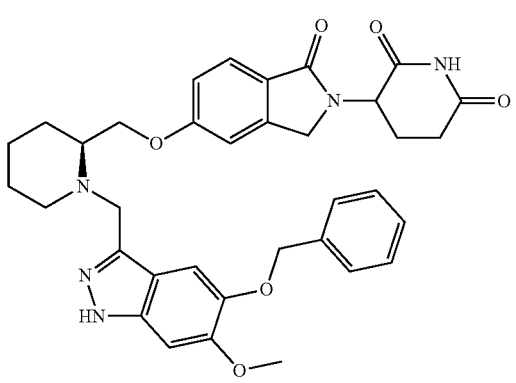 | 624.36 | 0.47 |
| I-50af | 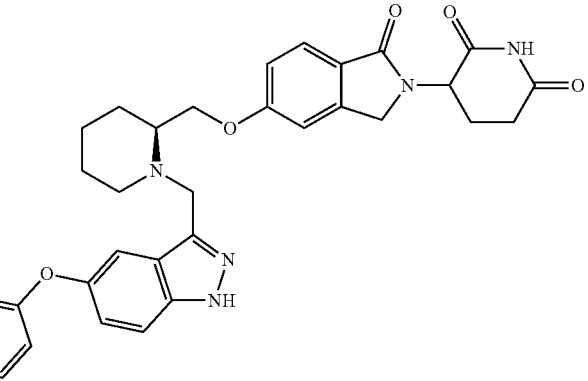 | 581.3 | 0.42 |

| Compound Number | Structure/NMR data | LCMS [M + H] | LCMS Rt |
|---|---|---|---|
| I-50ag | 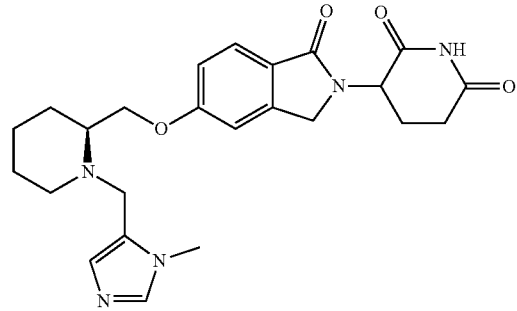 | 452.31 | 0.35 |
| I-50ah | 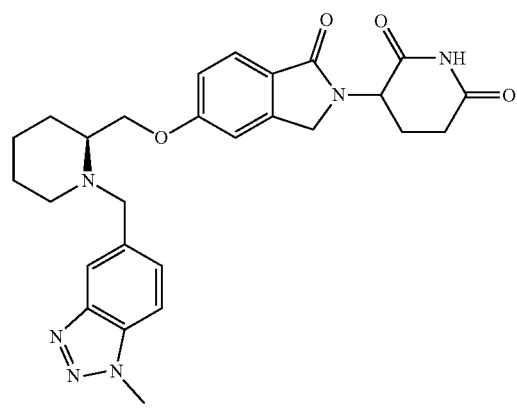 [SMILES: Cn1nnc2cc(CN3CCCC[C@H]3COc3ccc4c(c3)CN(C3CCC(=O)NC3=O)C4=O)ccc21] | 503.32 | 0.37 |
| I-50ai | 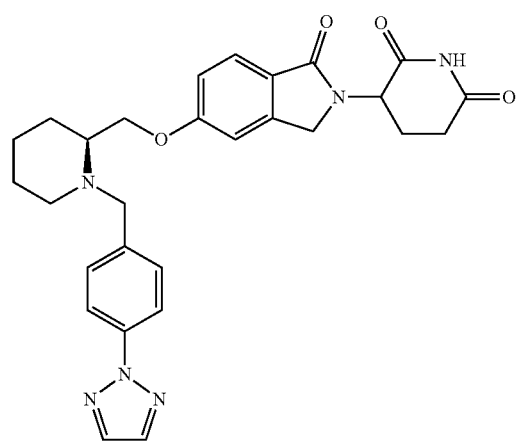 | 515.32 | 0.42 |

-continued
| Compound Number | Structure/NMR data | LCMS [M + H] | LCMS Rt |
|---|---|---|---|
| I-50aj | 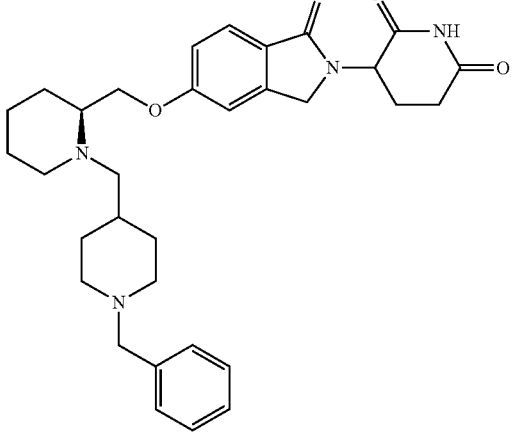 | 545.4 | 0.33 |
| I-50ak | 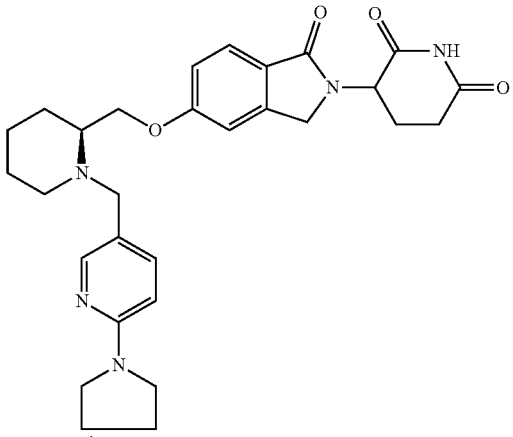<br>¹H NMR: (400 MHz, DMSO-d₆) δ 10.97 (s, 1H), 7.95 (d, J = 2.3 Hz, 1H), 7.62 (d, J = 8.4 Hz, 1H), 7.42 (dd, J = 8.7, 2.4 Hz, 1H), 7.20 (d, J = 2.5 Hz, 1H), 7.08 (dd, J = 8.4, 2.2 Hz, 1H), 6.38 (d, J = 8.5 Hz, 1H), 5.08 (dd, J = 13.3, 5.0 Hz, 1H), 4.42-4.23 (m, 3H), 4.14 (dd, J = 10.2, 5.3 Hz, 1H), 3.82 (d, J = 13.3 Hz, 1H), 3.35-3.31 (m, 5H), 2.92 (ddd, J = 17.3, 13.7, 5.4 Hz, 1H), 2.75-2.64 (m, 2H), 2.64-2.57 (m, 1H), 2.39 (dd, J = 13.2, 4.5 Hz, 1H), 2.14-2.07 (m, 1H), 2.02-1.89 (m, 5H), 1.82-1.73 (m, 1H), 1.70-1.59 (m, 1H), 1.57-1.46 (m, 2H), 1.41-1.31 (m, 2H). | 518.3 | 0.34 |
| I-50al | 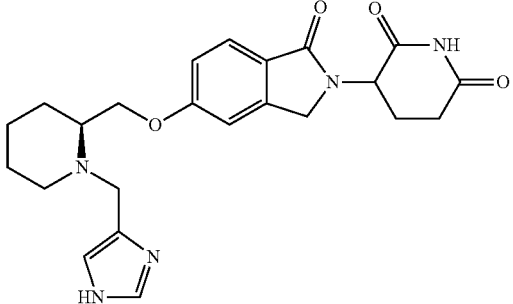 [SMILES: O=C1CCC(N2Cc3cc(OC[C@@H]4CCCCN4Cc4c[nH]cn4)ccc3C2=O)C(=O)N1] | 438.29 | 0.34 |

-continued

| Compound Number | Structure/NMR data | LCMS [M + H] | LCMS Rt |
|---|---|---|---|
| I-50am | | 589.36 | 0.48 |
| I-50an | | 438.26 | 0.35 |
| I-50ao | | 467.31 | 0.36 |

| Compound Number | Structure/NMR data | LCMS [M + H] | LCMS Rt |
|---|---|---|---|
| I-50ap | 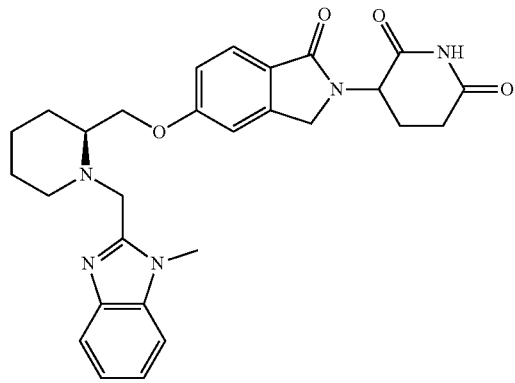 [SMILES: Cn1c(CN2CCCC[C@H]2COc2ccc3c(c2)CN(C2CCC(=O)NC2=O)C3=O)nc2ccccc21]<br>¹H NMR: (400 MHz, DMSO-d₆) δ 10.97 (s, 1H), 7.59 (d, J = 8.4 Hz, 1H), 7.54 (d, J = 7.8 Hz, 1H), 7.47 (dd, J = 8.0, 3.9 Hz, 1H), 7.22-7.10 (m, 3H), 7.06 (dd, J = 8.3, 2.2 Hz, 1H), 5.08 (dd, J = 13.2, 5.2 Hz, 1H), 4.38-4.18 (m, 5H), 3.86 (s, 3H), 3.79 (dd, J = 14.0, 3.3 Hz, 1H), 2.98-2.79 (m, 2H), 2.79-2.71 (m, 1H), 2.65-2.57 (m, 1H), 2.45-2.24 (m, 2H), 2.03-1.94 (m, 1H), 1.81-1.73 (m, 1H), 1.72-1.56 (m, 2H), 1.54-1.34 (m, 3H). | 502.32 | 0.45 |
| I-50aq | 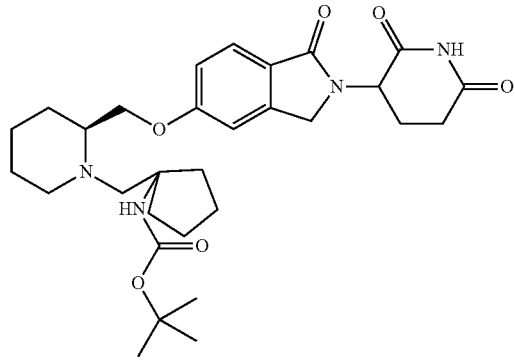 [SMILES: CC(C)(C)OC(=O)NC1(CN2CCCC[C@H]2COc2ccc3c(c2)CN(C2CCC(=O)NC2=O)C3=O)CCCC1] | 555.38 | 0.49 |

| Compound Number | Structure/NMR data | LCMS [M + H] | LCMS Rt |
|---|---|---|---|
| I-50ar | 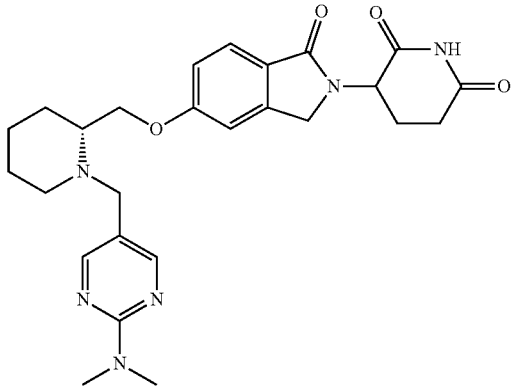 [SMILES: CN(C)c1ncc(CN2CCCC[C@@H]2COc2ccc3c(c2)CN(C2CCC(=O)NC2=O)C3=O)cn1]<br>¹H NMR: (400 MHz, DMSO-d₆) δ 10.97 (s, 1H), 7.63 (d, J = 8.3 Hz, 1H), 7.20 (t, J = 2.5 Hz, 1H), 7.08 (dd, J = 8.7, 2.4 Hz, 1H), 5.08 (dd, J = 13.3, 5.0 Hz, 1H), 4.45-4.22 (m, 3H), 4.19-4.11 (m, 1H), 3.78 (d, J = 13.7 Hz, 1H), 3.30 (s, 3H), 3.08 (s, 6H), 2.97-2.86 (m, 1H), 2.75-2.67 (m, 2H), 2.64-2.57 (m, 1H), 2.39 (qd, J = 13.5, 4.7 Hz, 1H), 2.16-2.09 (m, 1H), 2.03-1.94 (m, 1H), 1.80-1.74 (m, 1H), 1.70-1.61 (m, 1H), 1.58-1.47 (m, 2H), 1.43-1.30 (m, 2H). | 493.4 | 0.38 |
| I-50as | 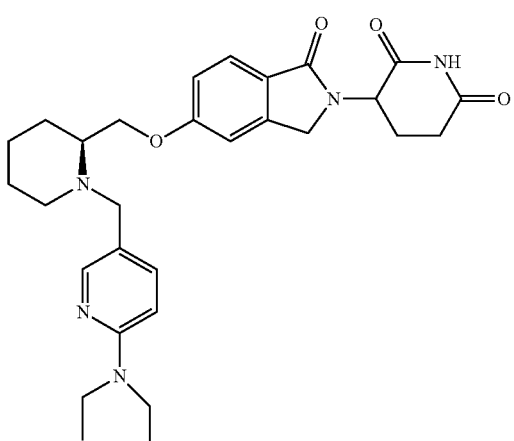<br>¹H NMR: (400 MHz, DMSO-d₆) δ 10.97 (s, 1H), 7.94 (d, J = 2.3 Hz, 1H), 7.62 (d, J = 8.4 Hz, 1H), 7.40 (dd, J = 8.7, 2.4 Hz, 1H), 7.26-7.16 (m, 1H), 7.08 (dd, J = 8.5, 2.2 Hz, 1H), 6.52 (d, J = 8.7 Hz, 1H), 5.08 (dd, J = 13.4, 5.1 Hz, 1H), 4.45-4.20 (m, 3H), 4.14 (dd, J = 10.2, 5.4 Hz, 1H), 3.81 (d, J =13.3 Hz, 1H), 3.45 (q, J = 7.0 Hz, 4H), 3.27 (d, J = 13.4 Hz, 1H), 2.97-2.85 (m, 1H), 2.75-2.66 (m, 2H), 2.64-2.56 (m, 1H), 2.39 (qd, J = 12.7, 12.2, 4.1 Hz, 1H), 2.14-2.06 (m, 1H), 2.02-1.94 (m, 1H), 1.82-1.74 (m, 1H), 1.69-1.61 (m, 1H), 1.56-1.46 (m, 2H), 1.43-1.29 (m, 2H), 1.07 (t, J = 6.9 Hz, 6H). | 520.4 | 0.36 |

| Compound Number | Structure/NMR data | LCMS [M + H] | LCMS Rt |
|---|---|---|---|
| I-50at | 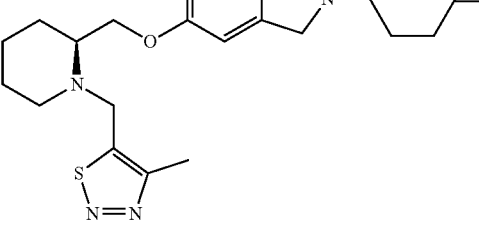 | 470.26 | 0.46 |
| I-50au | 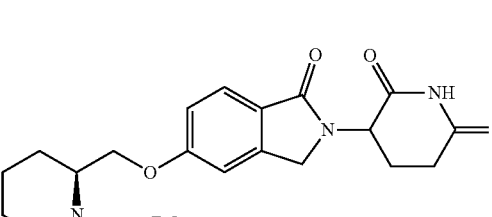 | 560.32 | 0.47 |
| I-50av |  | 546.4 | 0.36 |

| Compound Number | Structure/NMR data | LCMS [M + H] | LCMS Rt |
|---|---|---|---|
| I-50aw | | 580.33 | 0.43 |
| I-50ax | | 528.325 | 0.49 |
| I-50ay | | 640.31 | 0.49 |

-continued
| Compound Number | Structure/NMR data | LCMS [M + H] | LCMS Rt |
|---|---|---|---|
| I-50az | 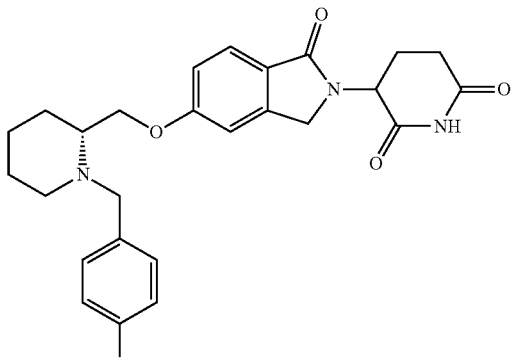 | 532.2 | 0.47 |
| I-50bb | 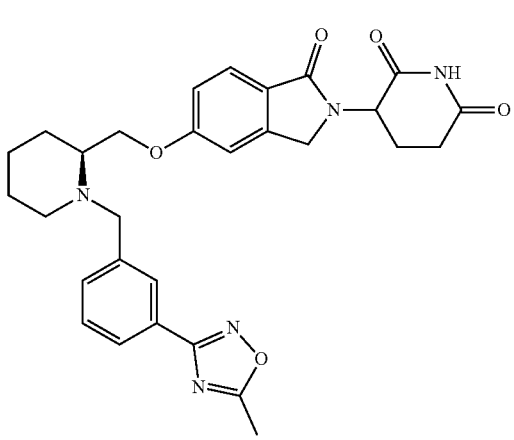 | 530.33 | 0.43 |
| I-50bc | 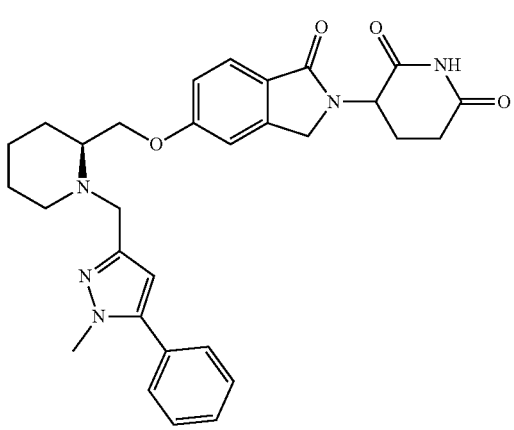 | 528.32 | 0.45 |

| Compound Number | Structure/NMR data | LCMS [M + H] | LCMS Rt |
|---|---|---|---|
| I-50bd | 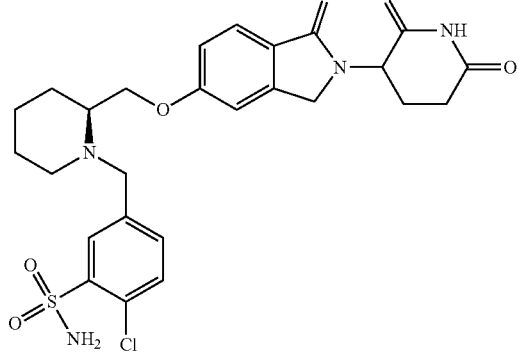 | 561.21 | 0.37 |
| I-50be | 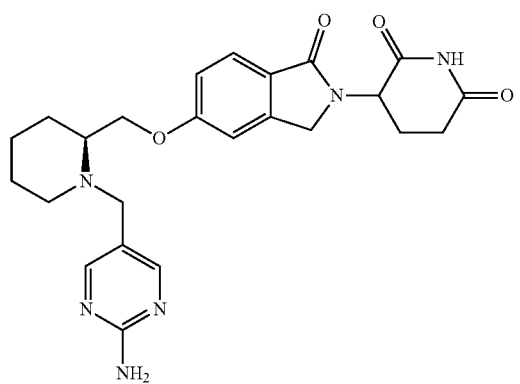 [SMILES: Nc1ncc(CN2CCCC[C@H]2COc2ccc3c(c2)CN(C2CCC(=O)NC2=O)C3=O)cn1] | 465.31 | 0.34 |
| I-50bf | 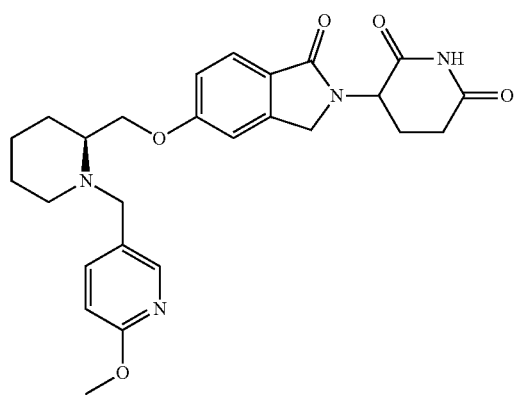 [SMILES: COc1ccc(CN2CCCC[C@H]2COc2ccc3c(c2)CN(C2CCC(=O)NC2=O)C3=O)cn1] | 479.3 | 0.39 |

-continued
| Compound Number | Structure/NMR data | LCMS [M + H] | LCMS Rt |
|---|---|---|---|
| I-50bg | 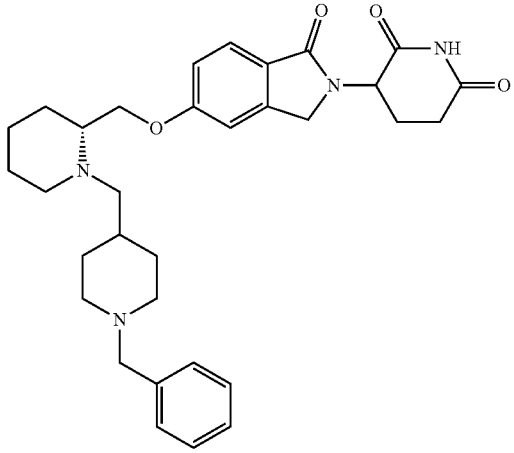 [SMILES: O=C1CCC(N2Cc3cc(OC[C@H]4CCCCN4CC4CCN(Cc5ccccc5)CC4)ccc3C2=O)C(=O)N1] | 545.4 | 0.32 |
| I-50bh | 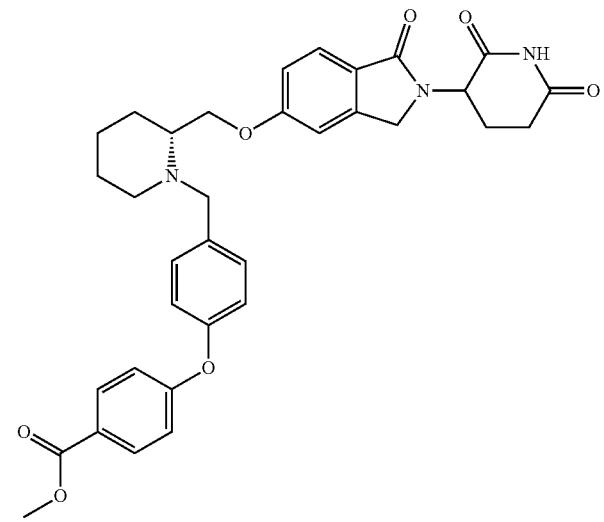 [SMILES: COC(=O)c1ccc(Oc2ccc(CN3CCCC[C@@H]3COc3ccc4c(c3)CN(C3CCC(=O)NC3=O)C4=O)cc2)cc1] | 598.31 | 0.5 |
| I-50bi | 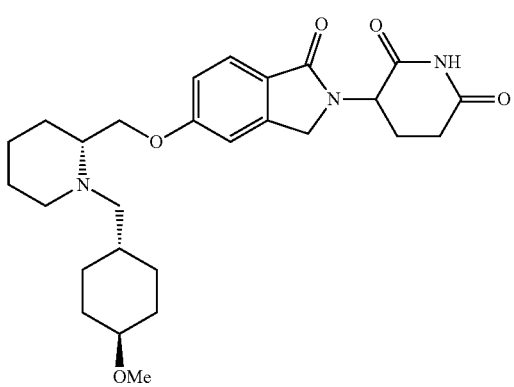 [SMILES: CO[C@H]1CC[C@H](CN2CCCC[C@@H]2COc2ccc3c(c2)CN(C2CCC(=O)NC2=O)C3=O)CC1] | 484.33 | 0.39 |

| Compound Number | Structure/NMR data | LCMS [M + H] | LCMS Rt |
|---|---|---|---|
| I-50bj | 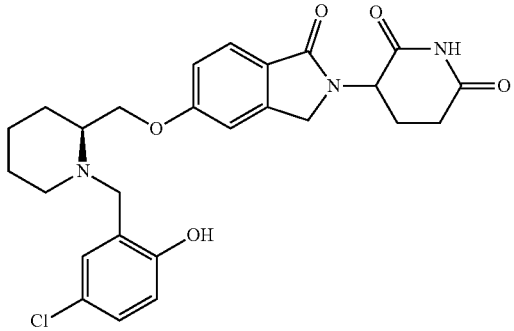 [SMILES: O=C1CCC(N2Cc3cc(OC[C@@H]4CCCCN4Cc4cc(Cl)ccc4O)ccc3C2=O)C(=O)N1] | 498.25 | 0.44 |
| I-50bk | 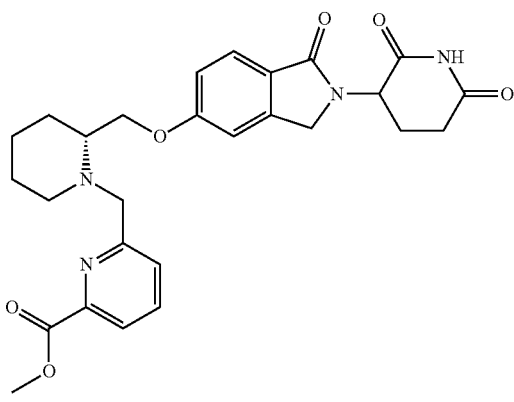 [SMILES: COC(=O)c1cccc(CN2CCCC[C@@H]2COc2ccc3c(c2)CN(C2CCC(=O)NC2=O)C3=O)n1] | 507.2 | 0.38 |
| I-50bl | 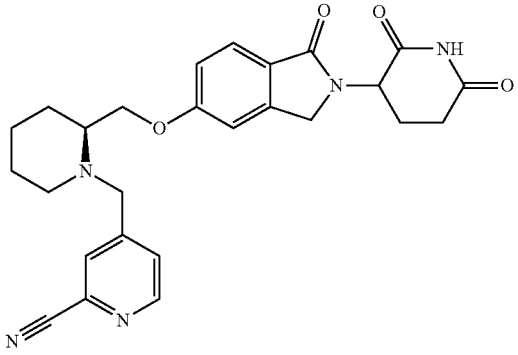 [SMILES: N#Cc1cc(CN2CCCC[C@H]2COc2ccc3c(c2)CN(C2CCC(=O)NC2=O)C3=O)ccn1] | 474.28 | 0.4 |
| I-50bm | 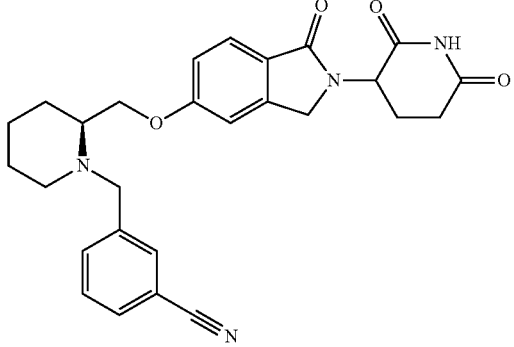 [SMILES: N#Cc1cccc(CN2CCCC[C@H]2COc2ccc3c(c2)CN(C2CCC(=O)NC2=O)C3=O)c1] | 473.31 | 0.39 |

| Compound Number | Structure/NMR data | LCMS [M + H] | LCMS Rt |
|---|---|---|---|
| I-50bn | 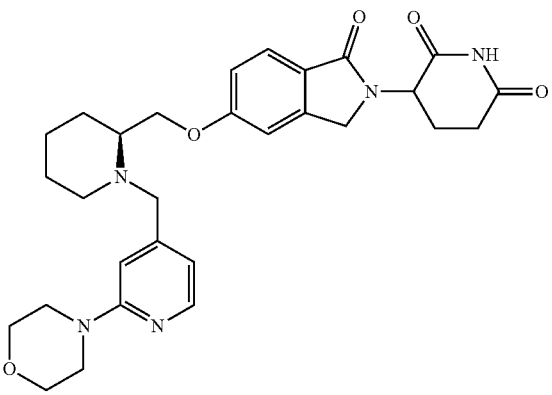 [SMILES: O=C1CCC(N2Cc3cc(OC[C@@H]4CCCCN4Cc4ccnc(N5CCOCC5)c4)ccc3C2=O)C(=O)N1]<br>¹H NMR: (400 MHz, DMSO-d₆) δ 10.97 (s, 1H), 8.03 (d, J = 5.0 Hz, 1H), 7.62 (d, J = 8.4 Hz, 1H), 7.16 (d, J = 2.2 Hz, 1H), 7.05 (dt, J = 8.7, 1.7 Hz, 1H), 6.74 (s, 1H), 6.70 (d, J = 5.1 Hz, 1H), 5.08 (dd, J = 13.2, 5.0 Hz, 1H), 4.37 (d, J = 17.1 Hz, 1H), 4.31-4.19 (m, 2H), 4.11 (dd, J = 10.3, 4.9 Hz, 1H), 3.93 (d, J = 14.6 Hz, 1H), 3.71-3.63 (m, 4H), 3.41-3.35 (m, 5H), 2.91 (ddd, J = 17.4, 13.6, 5.4 Hz, 1H), 2.82-2.65 (m, 2H), 2.64-2.56 (m, 1H), 2.39 (qd, J = 13.1, 4.3 Hz, 1H), 2.22-2.12 (m, 1H), 2.04-1.91 (m, 1H), 1.86-1.76 (m, 1H), 1.74-1.63 (m, 1H), 1.60-1.30 (m, 4H). | 534.35 | 0.38 |
| I-50bo | 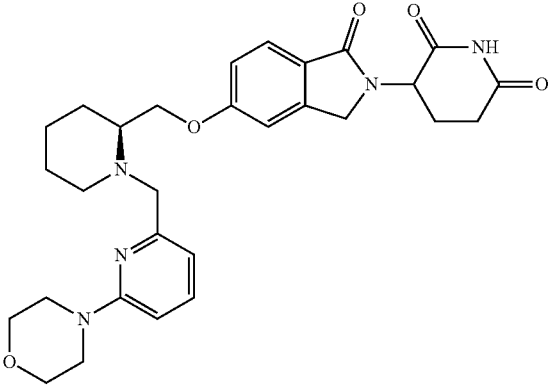 [SMILES: O=C1CCC(N2Cc3cc(OC[C@@H]4CCCCN4Cc4cccc(N5CCOCC5)n4)ccc3C2=O)C(=O)N1] | 534.33 | 0.42 |
| I-50bp | 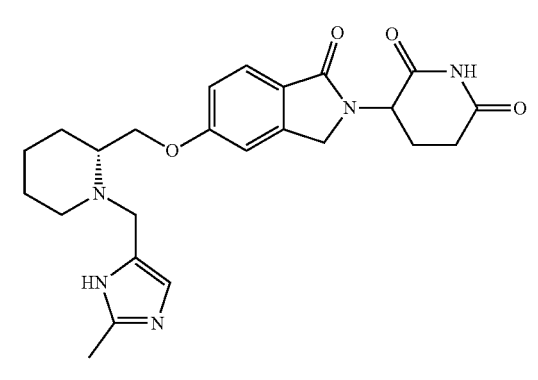 [SMILES: Cc1ncc(CN2CCCC[C@@H]2COc2ccc3c(c2)CN(C2CCC(=O)NC2=O)C3=O)[nH]1] | 452.31 | 0.33 |

-continued

| Compound Number | Structure/NMR data | LCMS [M + H] | LCMS Rt |
|---|---|---|---|
| I-50bq | | 498.37 | 0.4 |
| I-50br | | 622.4 | 0.37 |
| I-50bs | | 545.3134 | 0.4 |

| Compound Number | Structure/NMR data | LCMS [M + H] | LCMS Rt |
|---|---|---|---|
| I-50bt | 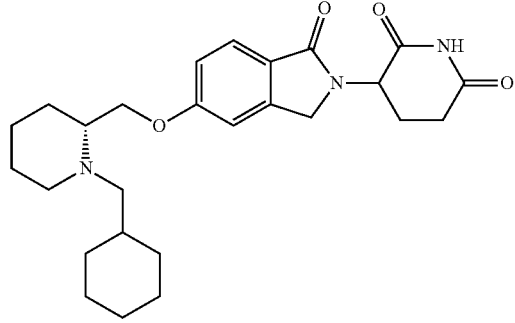 [SMILES: O=C1CCC(N2Cc3cc(OC[C@H]4CCCCN4CC4CCCCC4)ccc3C2=O)C(=O)N1] | 454.32 | 0.44 |
| I-50bu | 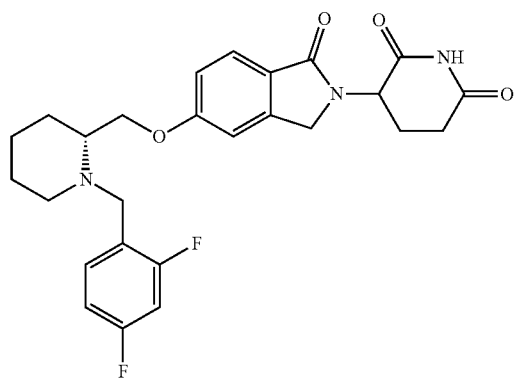 [SMILES: O=C1CCC(N2Cc3cc(OC[C@H]4CCCCN4Cc4ccc(F)cc4F)ccc3C2=O)C(=O)N1] | 484.2 | 0.41 |
| I-50bv | 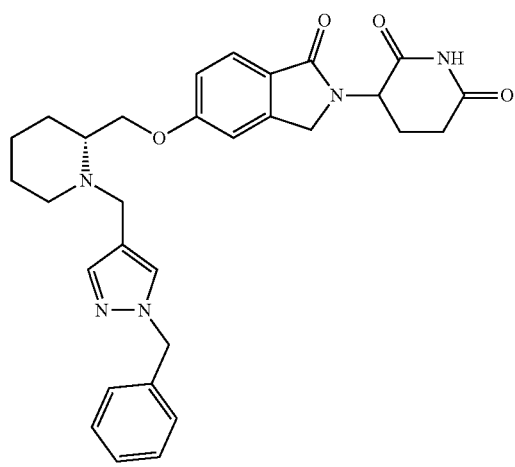 [SMILES: O=C1CCC(N2Cc3cc(OC[C@H]4CCCCN4Cc4cnn(Cc5ccccc5)c4)ccc3C2=O)C(=O)N1] | 528.31 | 0.43 |

| Compound Number | Structure/NMR data | LCMS [M + H] | LCMS Rt |
|---|---|---|---|
| I-50bw | 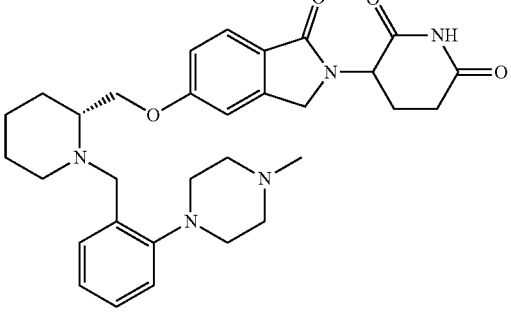 ¹H NMR: (400 MHz, DMSO-d₆) δ 11.03 (s, 1H), 7.68 (d, J = 8.4 Hz, 1H), 7.53 (d, J = 7.5 Hz, 1H), 7.31-7.18 (m, 2H), 7.18-7.05 (m, 3H), 5.13 (dd, J = 13.3, 5.1 Hz, 1H), 4.49-4.26 (m, 3H), 4.17 (dd, J = 10.2, 5.4 Hz, 1H), 3.99 (d, J = 13.8 Hz, 1H), 3.64 (d, J = 13.8 Hz, 1H), 3.03-2.85 (m, 6H), 2.81-2.71 (m, 2H), 2.69-2.62 (m, 3H), 2.50-2.27 (m, 6H), 2.07-2.00 (m, 1H), 1.88-1.80 (m, 1H), 1.74-1.42 (m, 5H). | 546.4 | 0.32 |
| I-50bx | 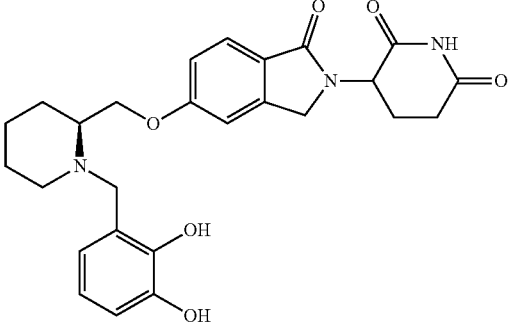 [SMILES: O=C1CCC(N2Cc3cc(OC[C@@H]4CCCCN4Cc4cccc(O)c4O)ccc3C2=O)C(=O)N1] | 480.31 | 0.39 |
| I-50by | 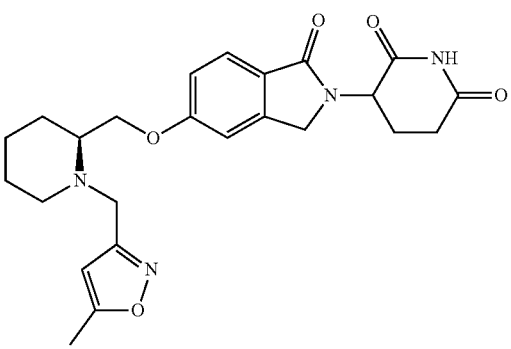 | 453.28 | 0.39 |

-continued
| Compound Number | Structure/NMR data | LCMS [M + H] | LCMS Rt |
|---|---|---|---|
| I-50bz | 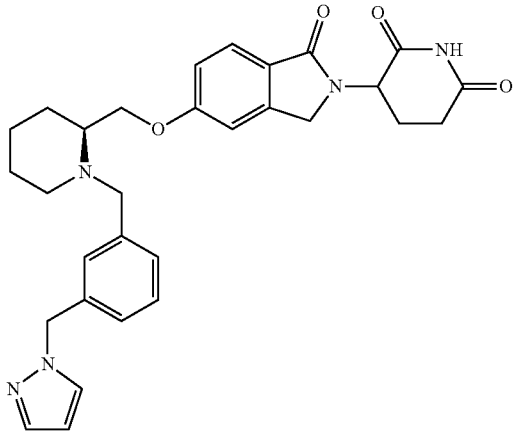 [SMILES: O=C1CCC(N2Cc3cc(OC[C@@H]4CCCCN4Cc4cccc(Cn5cccn5)c4)ccc3C2=O)C(=O)N1] | 528.32 | 0.42 |
| I-50ca | 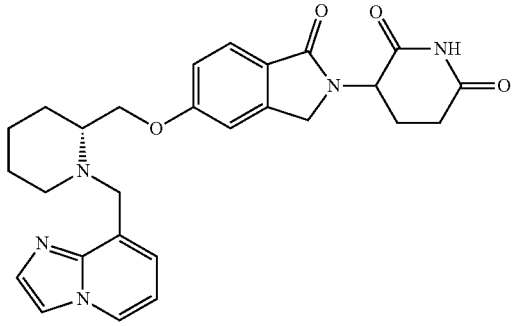 [SMILES: O=C1CCC(N2Cc3cc(OC[C@H]4CCCCN4Cc4cccn5ccnc45)ccc3C2=O)C(=O)N1] | 488.31 | 0.38 |
| I-50cb | 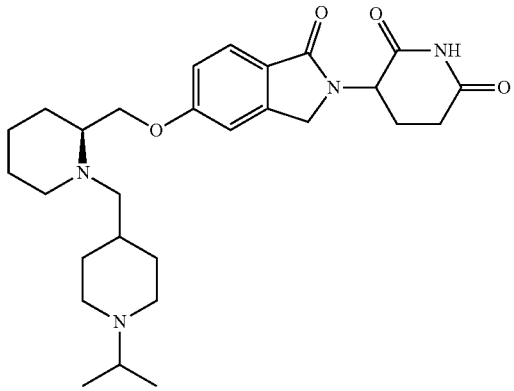 [SMILES: CC(C)N1CCC(CN2CCCC[C@H]2COc2ccc3c(c2)CN(C2CCC(=O)NC2=O)C3=O)CC1] | 497.4 | 0.3 |
| I-50cc | 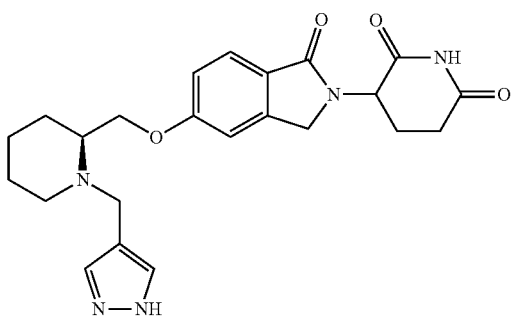 [SMILES: O=C1CCC(N2Cc3cc(OC[C@@H]4CCCCN4Cc4cn[nH]c4)ccc3C2=O)C(=O)N1] | 438.27 | 0.35 |

-continued
| Compound Number | Structure/NMR data | LCMS [M + H] | LCMS Rt |
|---|---|---|---|
| I-50cd | 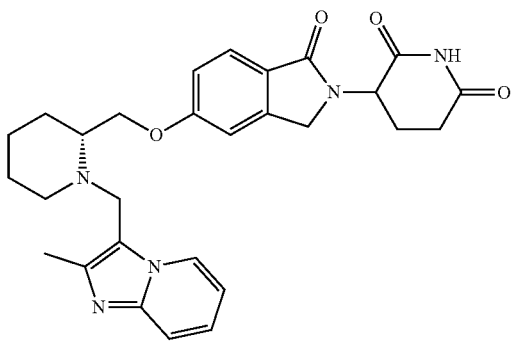 [SMILES: Cc1nc2ccccn2c1CN1CCCC[C@@H]1COc1ccc2c(c1)CN(C1CCC(=O)NC1=O)C2=O] | 502.3 | 0.4 |
| I-50ce | 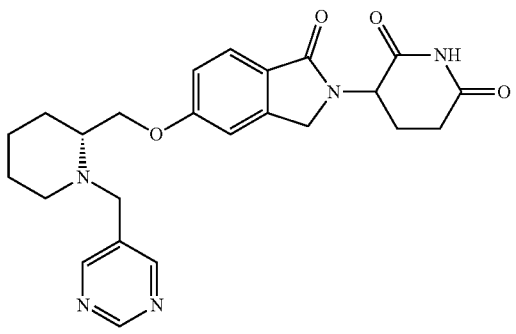 [SMILES: O=C1CCC(N2Cc3cc(OC[C@H]4CCCCN4Cc4cncnc4)ccc3C2=O)C(=O)N1] | 450.29 | 0.35 |
| I-50cf | 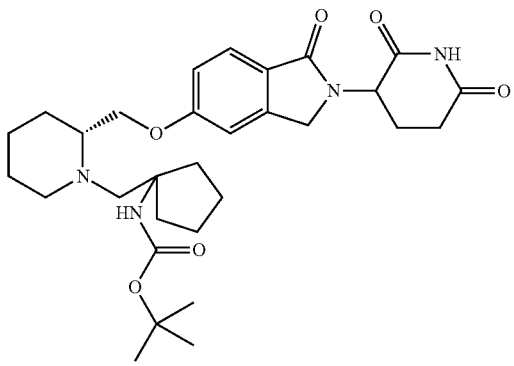 [SMILES: CC(C)(C)OC(=O)NC1(CN2CCCC[C@@H]2COc2ccc3c(c2)CN(C2CCC(=O)NC2=O)C3=O)CCCC1] | 555.38 | 0.49 |
| I-50cg | 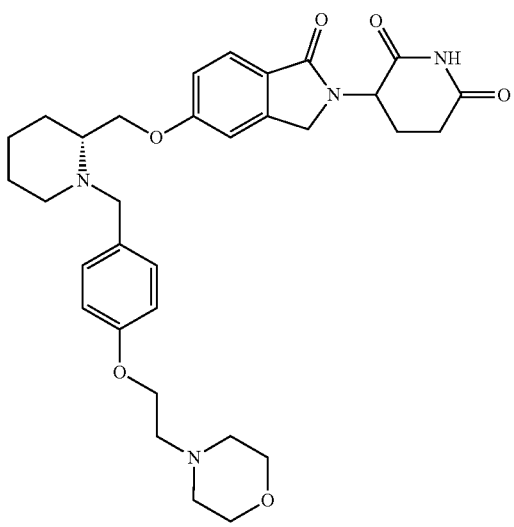 [SMILES: O=C1CCC(N2Cc3cc(OC[C@H]4CCCCN4Cc4ccc(OCCN5CCOCC5)cc4)ccc3C2=O)C(=O)N1] | 577.3 | 0.33 |

-continued

| Compound Number | Structure/NMR data | LCMS [M + H] | LCMS Rt |
|---|---|---|---|
| I-50ch | | 510.31 | 0.41 |
| I-50ci | | 494.36 | 0.42 |
| I-50cj | | 478.34 | 0.43 |
| I-50ck | | 528.32 | 0.43 |

| Compound Number | Structure/NMR data | LCMS [M + H] | LCMS Rt |
|---|---|---|---|
| I-50cl | 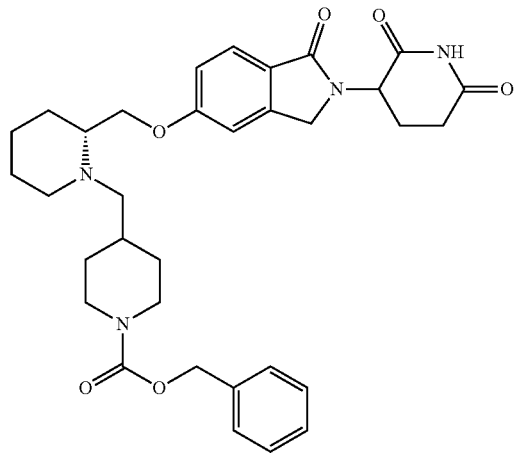 [SMILES: O=C1CCC(N2Cc3cc(OC[C@H]4CCCCN4CC4CCN(C(=O)OCc5ccccc5)CC4)ccc3C2=O)C(=O)N1] | 589.36 | 0.47 |
| I-50cm | 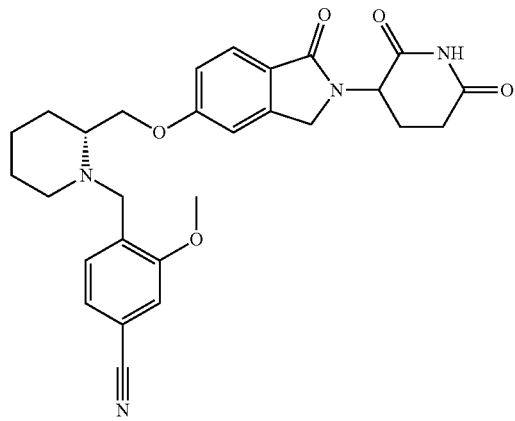 [SMILES: COc1cc(C#N)ccc1CN1CCCC[C@@H]1COc1ccc2c(c1)CN(C1CCC(=O)NC1=O)C2=O] | 503.31 | 0.4 |
| I-50cn | 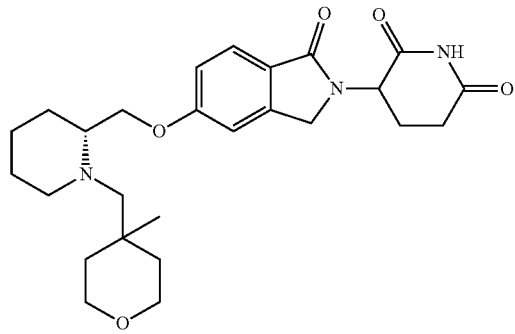 | 470.32 | 0.37 |

-continued
| Compound Number | Structure/NMR data | LCMS [M + H] | LCMS Rt |
|---|---|---|---|
| I-50co | 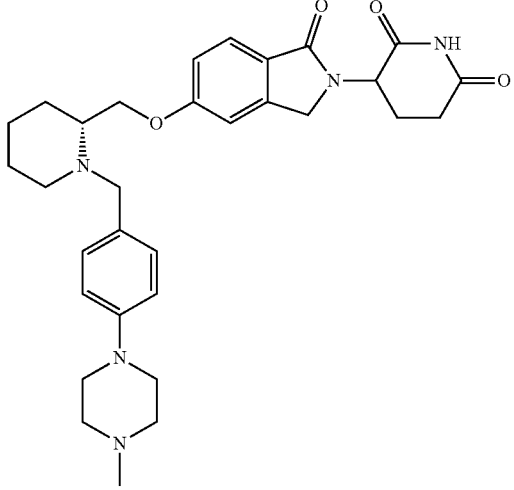 [SMILES: CN1CCN(c2ccc(CN3CCCC[C@@H]3COc3ccc4c(c3)CN(C3CCC(=O)NC3=O)C4=O)cc2)CC1] | 546.4 | 0.32 |
| I-50cp | 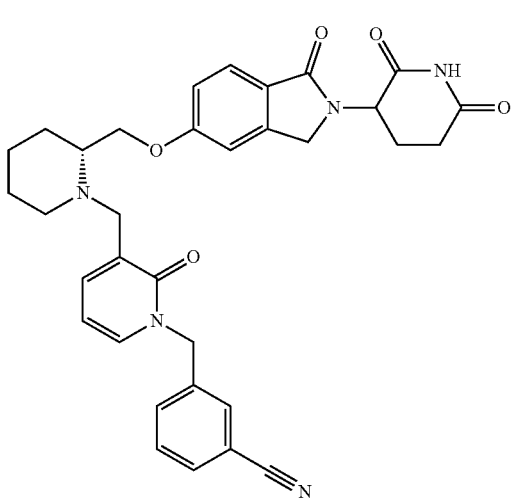 [SMILES: N#Cc1cccc(Cn2cccc(CN3CCCC[C@@H]3COc3ccc4c(c3)CN(C3CCC(=O)NC3=O)C4=O)c2=O)c1] | 580.29 | 0.43 |
| I-50cq | 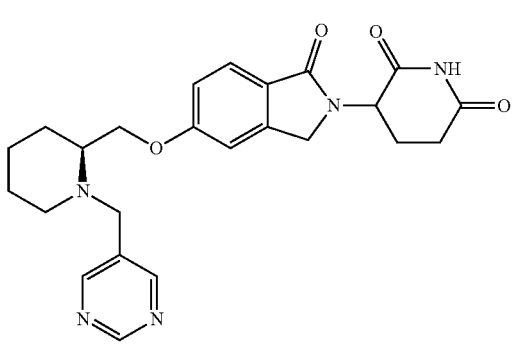 [SMILES: O=C1CCC(N2Cc3cc(OC[C@@H]4CCCCN4Cc4cncnc4)ccc3C2=O)C(=O)N1] | 450.25 | 0.35 |

-continued
| Compound Number | Structure/NMR data | LCMS [M + H] | LCMS Rt |
|---|---|---|---|
| I-50cr | 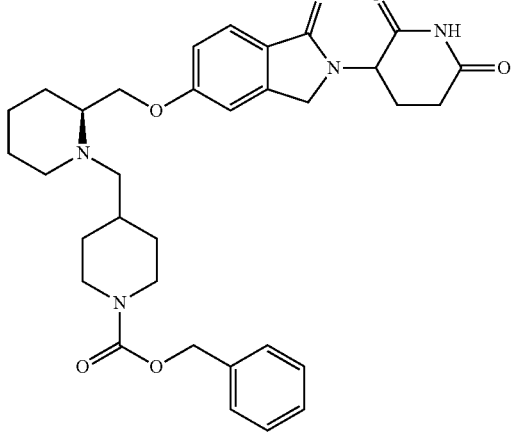 | 589.34 | 0.47 |
| I-50cs | 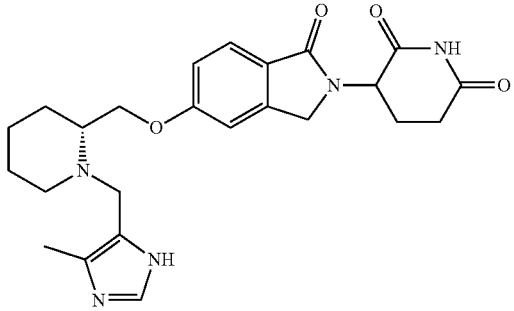 [SMILES: Cc1nc[nH]c1CN1CCCC[C@@H]1COc1ccc2c(c1)CN(C1CCC(=O)NC1=O)C2=O] | 452.31 | 0.34 |
| I-50ct | 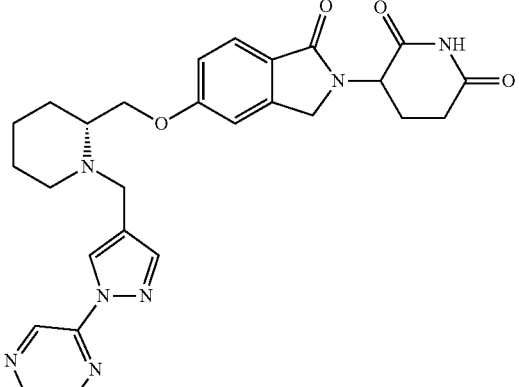 | 516.32 | 0.38 |
| I-50cu | 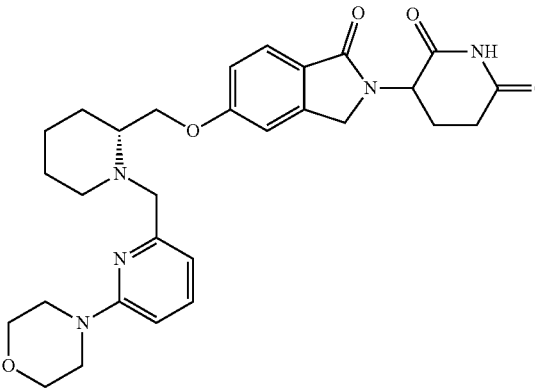 | 534.35 | 0.42 |

| Compound Number | Structure/NMR data | LCMS [M + H] | LCMS Rt |
|---|---|---|---|
| I-50cv | 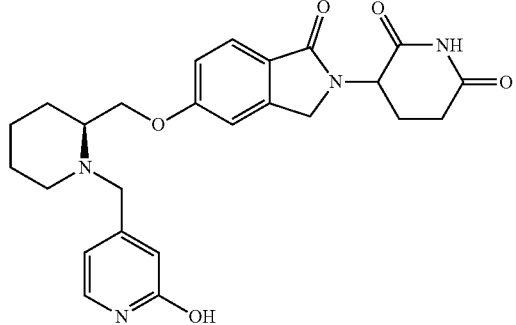 [SMILES: O=C1CCC(N2Cc3cc(OC[C@@H]4CCCCN4Cc4ccnc(O)c4)ccc3C2=O)C(=O)N1] | 465.31 | 0.35 |
| I-50cw | 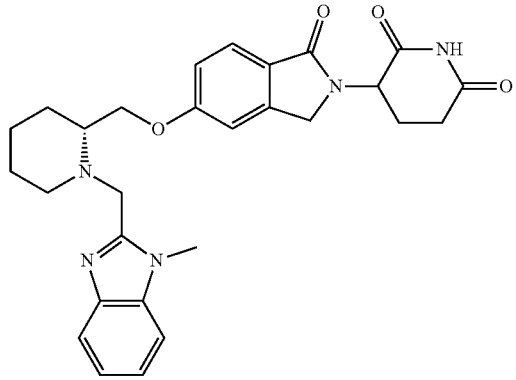 [SMILES: Cn1c(CN2CCCC[C@@H]2COc2ccc3c(c2)CN(C2CCC(=O)NC2=O)C3=O)nc2ccccc21]<br>$^1$H NMR: (400 MHz, DMSO-d$_6$) δ 10.97 (s, 1H), 7.59 (d, J = 8.3 Hz, 1H), 7.54 (d, J = 7.8 Hz, 1H), 7.47 (dd, J = 8.2, 3.9 Hz, 1H), 7.26-7.12 (m, 3H), 7.06 (dd, J = 8.4, 2.1 Hz, 1H), 5.08 (dd, J = 13.3, 5.1 Hz, 1H), 4.39-4.17 (m, 5H), 3.79 (dd, J = 14.1, 3.4 Hz, 1H), 3.33 (s, 3H), 2.98-2.81 (m, 2H), 2.79-2.70 (m, 1H), 2.64-2.57 (m, 1H), 2.44-2.26 (m, 2H), 2.03-1.94 (m, 1H), 1.80-1.73 (m, 1H), 1.71-1.58 (m, 2H), 1.55-1.35 (m, 3H). | 502.32 | 0.45 |
| I-50cx | 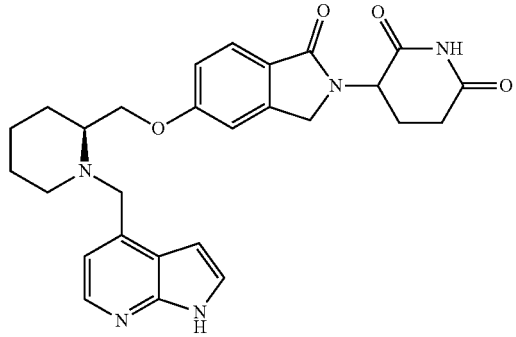 | 488.31 | 0.38 |

| Compound Number | Structure/NMR data | LCMS [M + H] | LCMS Rt |
|---|---|---|---|
| I-50cy | 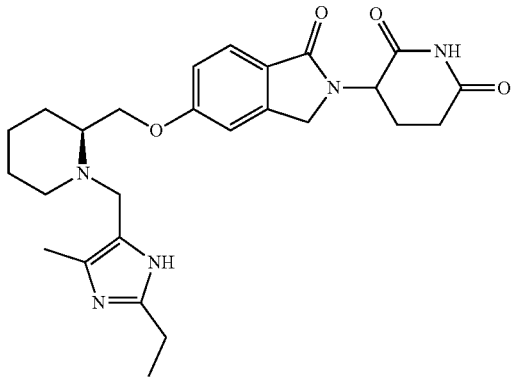 [SMILES: CCc1nc(C)c(CN2CCCC[C@H]2COc2ccc3c(c2)CN(C2CCC(=O)NC2=O)C3=O)[nH]1] | 480.34 | 0.34 |
| I-50cz | 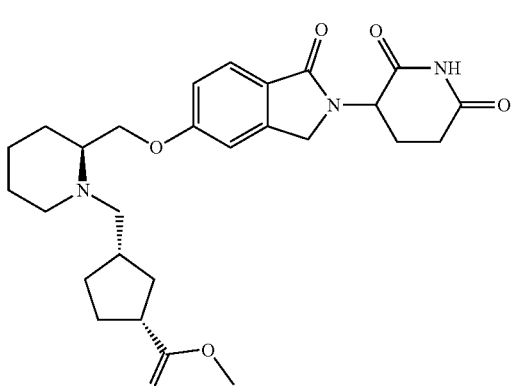 | 498.33 | 0.4 |
| I-50da | 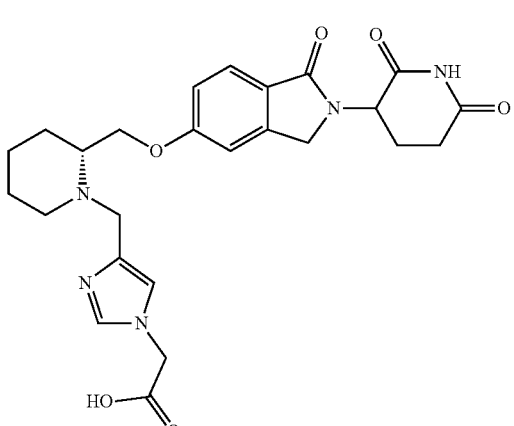 | 496.3 | 0.36 |
| I-50db | 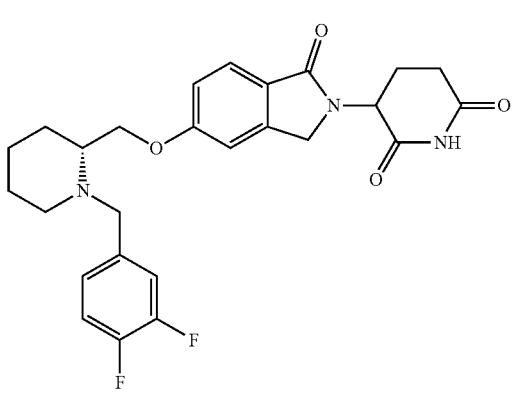 [SMILES: O=C1CCC(N2Cc3cc(OC[C@H]4CCCCN4Cc4ccc(F)c(F)c4)ccc3C2=O)C(=O)N1] | 484.2 | 0.42 |

-continued

| Compound Number | Structure/NMR data | LCMS [M + H] | LCMS Rt |
|---|---|---|---|
| I-50dc | | 640.31 | 0.48 |
| I-50dd | | 529.32 | 0.39 |
| I-50de | | 527.29 | 0.35 |

| Compound Number | Structure/NMR data | LCMS [M + H] | LCMS Rt |
|---|---|---|---|
| I-50df | 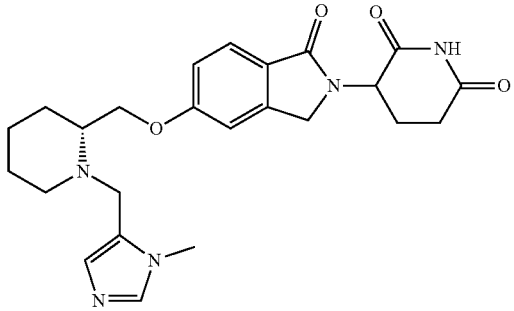 [SMILES: Cn1cncc1CN1CCCC[C@@H]1COc1ccc2c(c1)CN(C1CCC(=O)NC1=O)C2=O]<br>¹H NMR: (400 MHz, DMSO-d₆) δ 10.97 (s, 1H), 7.63 (d, J = 8.4 Hz, 1H), 7.51 (s, 1H), 7.21 (d, J = 2.2 Hz, 1H), 7.08 (dd, J =8.3, 2.3 Hz, 1H), 6.75 (s, 1H), 5.08 (dd, J = 13.2, 5.0 Hz, 1H), 4.44-4.28 (m, 3H), 4.23-4.14 (m, 1H), 3.96 (d, J = 14.1 Hz, 1H), 3.61 (s, 3H), 3.39 (dd, J = 13.8, 2.1 Hz, 1H), 2.97-2.85 (m, 1H), 2.78-2.64 (m, 2H), 2.64-2.57 (m, 1H), 2.39 (qd, J = 13.3, 4.6 Hz, 1H), 2.13-2.06 (m, 1H), 2.03-1.95 (m, 1H), 1.79-1.73 (m, 1H), 1.67-1.61 (m, 1H), 1.59-1.47 (m, 2H), 1.41-1.34 (m, 2H). | 452.29 | 0.35 |
| I-50dg | 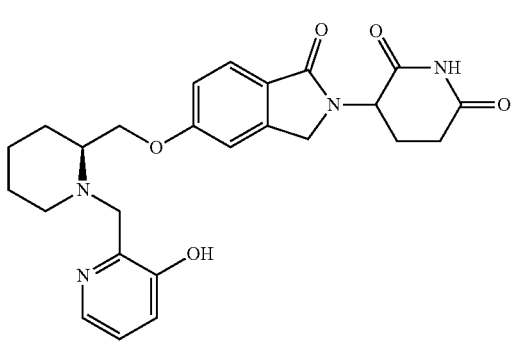 [SMILES: O=C1CCC(N2Cc3cc(OC[C@@H]4CCCCN4Cc4ncccc4O)ccc3C2=O)C(=O)N1] | 465.31 | 0.39 |
| I-50dh | 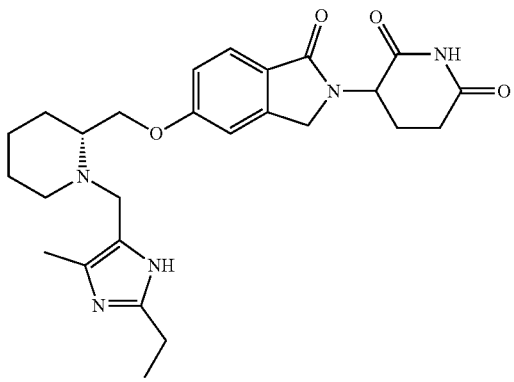 [SMILES: CCc1nc(C)c(CN2CCCC[C@@H]2COc2ccc3c(c2)CN(C2CCC(=O)NC2=O)C3=O)[nH]1] | 480.36 | 0.34 |

| Compound Number | Structure/NMR data | LCMS [M + H] | LCMS Rt |
|---|---|---|---|
| I-50di | | 712.35 | 0.4 |
| I-50dj | | 528.32 | 0.43 |
| I-50dk | | 488.29 | 0.37 |
| I-50dl | | 414.3 | 0.39 |

| Compound Number | Structure/NMR data | LCMS [M + H] | LCMS Rt |
|---|---|---|---|
| I-50dm | 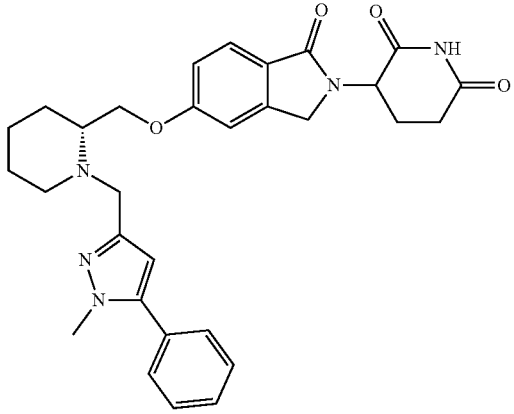 [SMILES: Cn1nc(CN2CCCC[C@@H]2COc2ccc3c(c2)CN(C2CCC(=O)NC2=O)C3=O)cc1-c1ccccc1] | 528.34 | 0.45 |
| I-50dn | 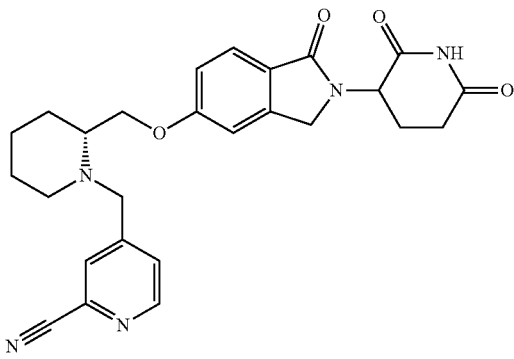 [SMILES: N#Cc1cc(CN2CCCC[C@@H]2COc2ccc3c(c2)CN(C2CCC(=O)NC2=O)C3=O)ccn1] | 474.31 | 0.4 |
| I-50do | 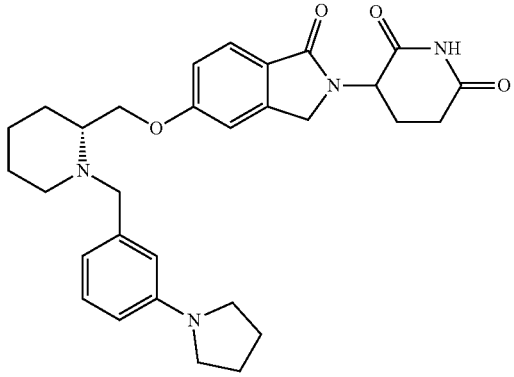 [SMILES: O=C1CCC(N2Cc3cc(OC[C@H]4CCCCN4Cc4cccc(N5CCCC5)c4)ccc3C2=O)C(=O)N1] | 517.35 | 0.48 |
| I-50dp | 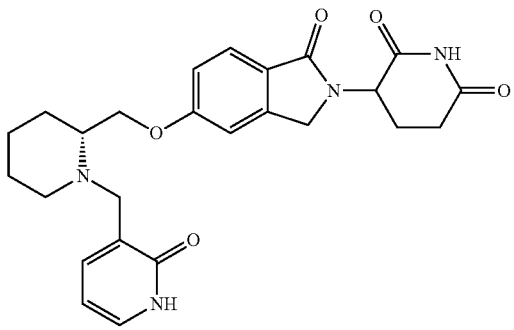 [SMILES: O=C1CCC(N2Cc3cc(OC[C@H]4CCCCN4Cc4ccc[nH]c4=O)ccc3C2=O)C(=O)N1] | 465.31 | 0.35 |

| Compound Number | Structure/NMR data | LCMS [M + H] | LCMS Rt |
|---|---|---|---|
| I-50dq | | 589.36 | 0.48 |
| I-50dr | | 534.33 | 0.37 |
| I-50ds | | 438.25 | 0.34 |
| I-50dt | | 513.29 | 0.37 |

-continued
| Compound Number | Structure/NMR data | LCMS [M + H] | LCMS Rt |
|---|---|---|---|
| I-50du | 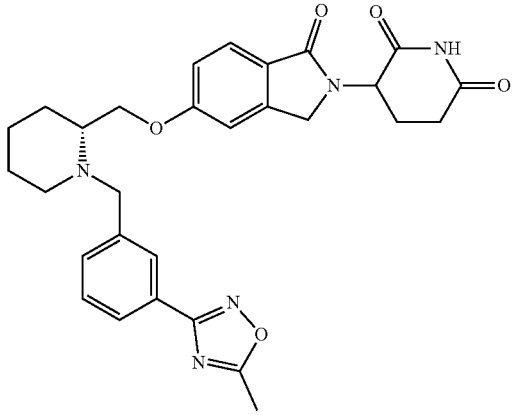 [SMILES: Cc1nc(-c2cccc(CN3CCCC[C@@H]3COc3ccc4c(c3)CN(C3CCC(=O)NC3=O)C4=O)c2)no1] | 530.33 | 0.43 |
| I-50dv | 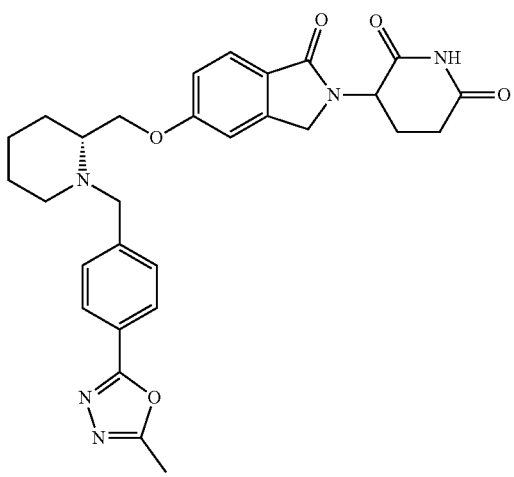 [SMILES: Cc1nnc(-c2ccc(CN3CCCC[C@@H]3COc3ccc4c(c3)CN(C3CCC(=O)NC3=O)C4=O)cc2)o1] | 530.32 | 0.39 |
| I-50dw | 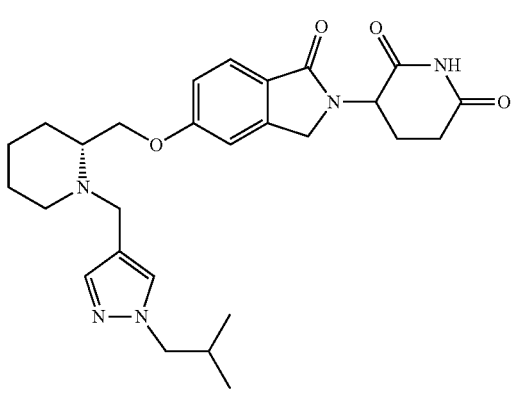 [SMILES: CC(C)Cn1cc(CN2CCCC[C@@H]2COc2ccc3c(c2)CN(C2CCC(=O)NC2=O)C3=O)cn1]<br>¹H NMR: (400 MHz, DMSO-d₆) δ 10.97 (s, 1H), 7.63 (d, J = 8.4 Hz, 1H), 7.56 (d, J = 3.4 Hz, 1H), 7.33 (s, 1H), 7.22 (d, J = 2.1 Hz, 1H), 7.09 (dd, J = 8.3, 2.2 Hz, 1H), 5.08 (dd, J = 13.3, 5.2 Hz, 1H), 4.44-4.21 (m, 3H), 4.18-4.07 (m, 1H), 3.85 (d, J = 7.0 Hz, 2H), 3.70 (d, J = 14.4 Hz, 1H), 3.55 (d, J = 14.2 Hz, 1H), 2.97-2.87 (m, 1H), 2.78-2.72 (m, 1H), 2.64-2.55 (m, 2H), 2.46-2.33 (m, 1H), 2.17-1.93 (m, 3H), 1.80-1.72 (m, 1H), 1.69-1.60 (m, 1H), 1.56-1.38 (m, 3H), 1.29-1.18 (m, 1H), 0.80 (d, J = 6.8 Hz, 6H). | 494.36 | 0.42 |

-continued

| Compound Number | Structure/NMR data | LCMS [M + H] | LCMS Rt |
|---|---|---|---|
| I-50dx | | 533.3 | 0.41 |
| I-50dy | | 501.3 | 0.44 |
| I-50dz | | 473.31 | 0.42 |
| I-50ea | | 497.4 | 0.3 |

| Compound Number | Structure/NMR data | LCMS [M + H] | LCMS Rt |
| --- | --- | --- | --- |
| I-50eb | 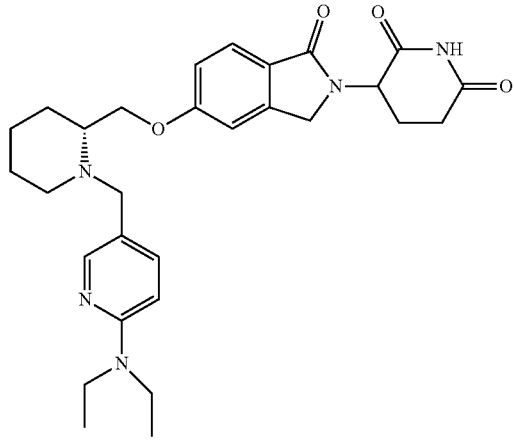 [SMILES: CCN(CC)c1ccc(CN2CCCC[C@@H]2COc2ccc3c(c2)CN(C2CCC(=O)NC2=O)C3=O)cn1]<br>¹H NMR: (400 MHz, DMSO-d₆) δ 10.97 (s, 1H), 7.94 (d, J = 2.3 Hz, 1H), 7.62 (d, J = 8.4 Hz, 1H), 7.40 (dd, J = 8.7, 2.4 Hz, 1H), 7.25-7.15 (m, 1H), 7.08 (dd, J = 8.3, 2.3 Hz, 1H), 6.52 (d, J = 8.8 Hz, 1H), 5.08 (dd, J = 13.3, 5.1 Hz, 1H), 4.45-4.20 (m, 3H), 4.14 (dd, J = 10.3, 5.4 Hz, 1H), 3.82 (d, J = 13.5 Hz, 1H), 3.45 (q, J = 7.0 Hz, 4H), 3.28 (d, J = 13.3 Hz, 1H), 2.97-2.83 (m, 1H), 2.77-2.67 (m, 2H), 2.64-2.57 (m, 1H), 2.39 (qd, J = 12.7, 12.3, 4.1 Hz, 1H), 2.15-2.09 (m, 1H), 2.04-1.94 (m, 1H), 1.82-1.74 (m, 1H), 1.70-1.62 (m, 1H), 1.57-1.47 (m, 2H), 1.43-1.30 (m, 2H), 1.07 (t, J = 7.0 Hz, 6H). | 520.3 | 0.36 |
| I-50ec | 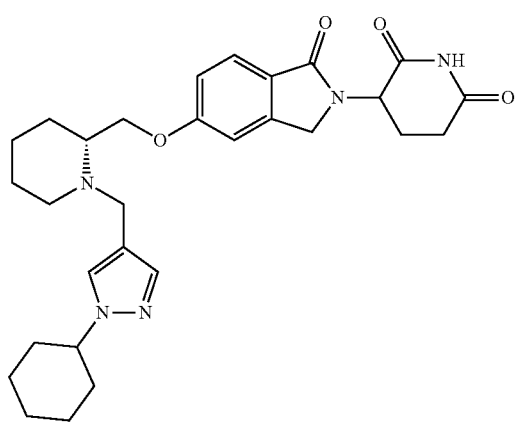 [SMILES: O=C1CCC(N2Cc3cc(OC[C@H]4CCCCN4Cc4cnn(C5CCCCC5)c4)ccc3C2=O)C(=O)N1]<br>¹H NMR: (400 MHz, DMSO-d₆) δ 10.98 (s, 1H), 7.68-7.54 (m, 2H), 7.32 (s, 1H), 7.21 (s, 1H), 7.09 (d, J = 8.7 Hz, 1H), 5.09 (dd, J = 13.3, 5.0 Hz, 1H), 4.40 (d, J = 17.4 Hz, 1H), 4.28 (d, J = 16.3 Hz, 2H), 4.17-3.98 (m, 2H), 3.71 (d, J = 14.2 Hz, 1H), 3.54 (d, J = 14.2 Hz, 1H), 2.92 (ddd, J = 18.1, 13.3, 5.3 Hz, 1H), 2.81-2.74 (m, 1H), 2.63-2.56 (m, 2H), 2.46-2.35 (m, 1H), 2.14 (t, J = 10.7 Hz, 1H), 2.04-1.89 (m, 3H), 1.83-1.73 (m, 3H), 1.70-1.13 (m, 11H). | 520.35 | 0.45 |

| Compound Number | Structure/NMR data | LCMS [M + H] | LCMS Rt |
|---|---|---|---|
| I-50ed | 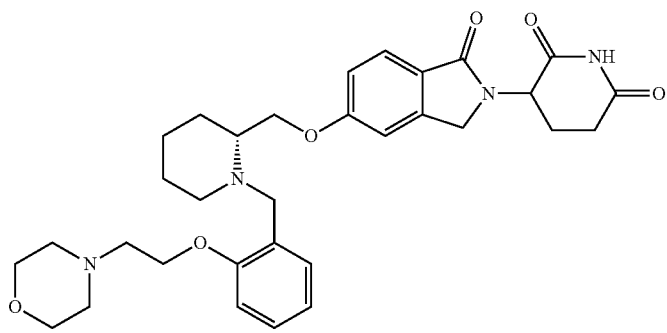 [SMILES: O=C1CCC(N2Cc3cc(OC[C@H]4CCCCN4Cc4ccccc4OCCN4CCOCC4)ccc3C2=O)C(=O)N1]<br>¹H NMR: (400 MHz, DMSO-d₆) δ 10.97 (s, 1H), 7.62 (d, J = 8.3 Hz, 1H), 7.34 (dd, J = 7.6, 1.8 Hz, 1H), 7.23-7.14 (m, 2H), 7.05 (dd, J = 8.6, 2.3 Hz, 1H), 7.00-6.86 (m, 2H), 5.08 (dd, J = 13.3, 5.0 Hz, 1H), 4.42-4.22 (m, 3H), 4.17-4.00 (m, 3H), 3.95 (d, J = 14.2 Hz, 1H), 3.54-3.50 (m, 4H), 3.43 (d, J = 14.2 Hz, 1H), 2.91 (ddd, J = 17.2, 13.6, 5.4 Hz, 1H), 2.81-2.73 (m, 2H), 2.69-2.56 (m, 3H), 2.44-2.35 (m, 5H), 2.21-2.13 (m, 1H), 2.03-1.93 (m, 1H), 1.85-1.76 (m, 1H), 1.72-1.60 (m, 1H), 1.56-1.30 (m, 4H). | 577.3 | 0.34 |
| I-50ee | 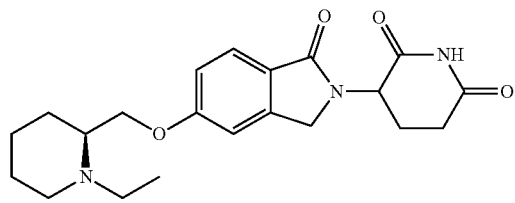 [SMILES: CCN1CCCC[C@H]1COc1ccc2c(c1)CN(C1CCC(=O)NC1=O)C2=O] | 386.2 | 0.36 |
| I-50ef | 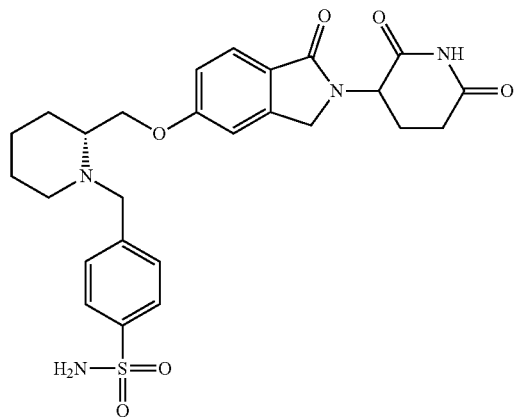 [SMILES: NS(=O)(=O)c1ccc(CN2CCCC[C@@H]2COc2ccc3c(c2)CN(C2CCC(=O)NC2=O)C3=O)cc1] | 527.26 | 0.35 |

| Compound Number | Structure/NMR data | LCMS [M + H] | LCMS Rt |
|---|---|---|---|
| I-50eg | 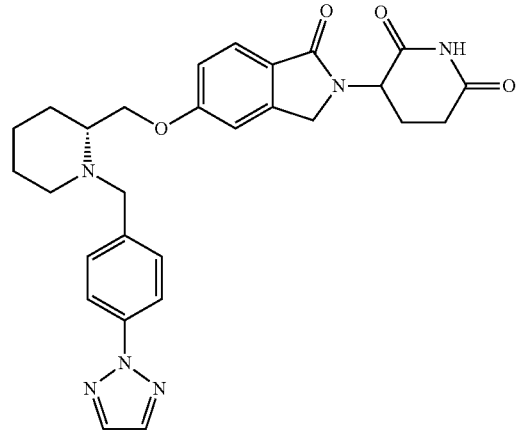 [SMILES: O=C1CCC(N2Cc3cc(OC[C@H]4CCCCN4Cc4ccc(-n5nccn5)cc4)ccc3C2=O)C(=O)N1] | 515.32 | 0.42 |
| I-50eh | 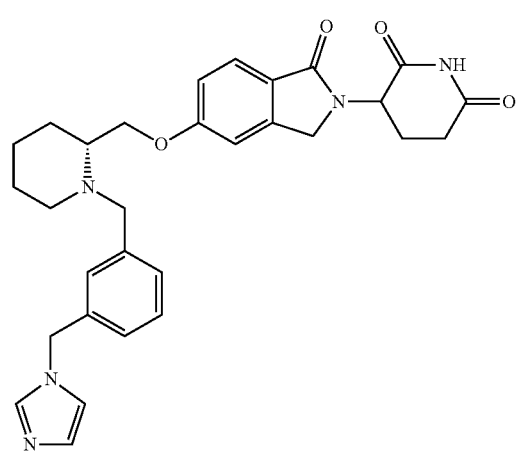 [SMILES: O=C1CCC(N2Cc3cc(OC[C@H]4CCCCN4Cc4cccc(Cn5ccnc5)c4)ccc3C2=O)C(=O)N1] | 528.3 | 0.32 |
| I-50ei | 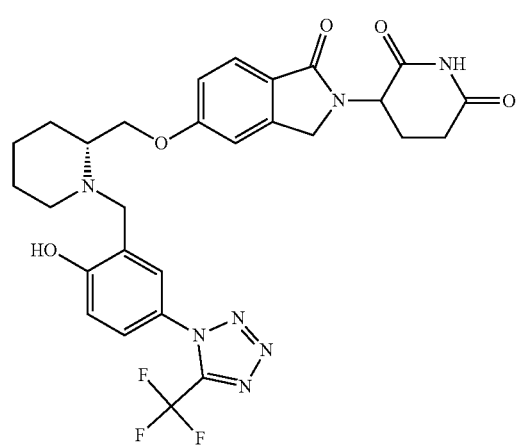 [SMILES: O=C1CCC(N2Cc3cc(OC[C@H]4CCCCN4Cc4cc(-n5nnnc5C(F)(F)F)ccc4O)ccc3C2=O)C(=O)N1] | 600.27 | 0.44 |

-continued
| Compound Number | Structure/NMR data | LCMS [M + H] | LCMS Rt |
|---|---|---|---|
| I-50ej | 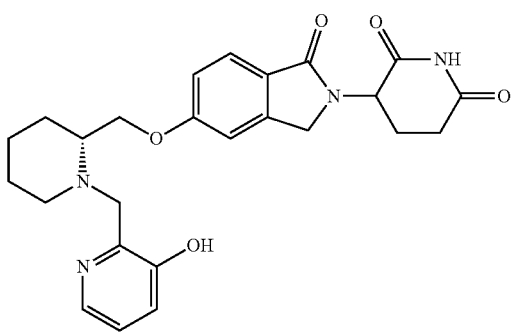 [SMILES: O=C1CCC(N2Cc3cc(OC[C@H]4CCCCN4Cc4ncccc4O)ccc3C2=O)C(=O)N1] | 465.31 | 0.39 |
| I-50ek | 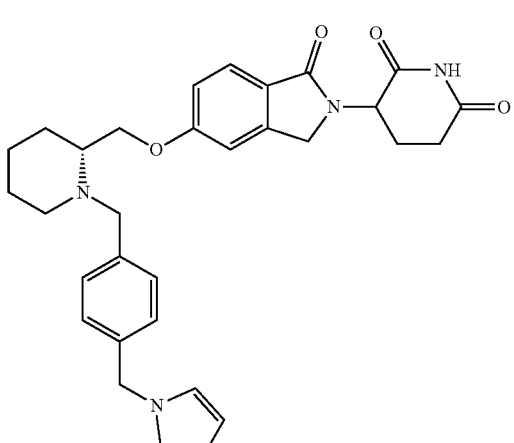 | 528.3 | 0.31 |
| I-50el | 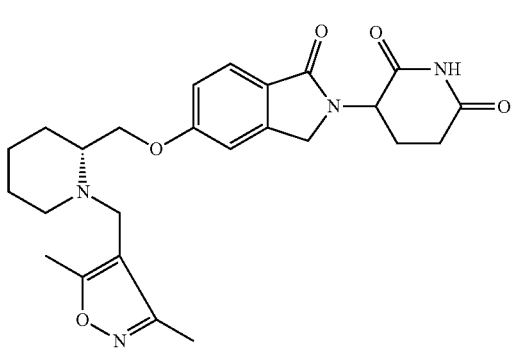 [SMILES: Cc1noc(C)c1CN1CCCC[C@@H]1COc1ccc2c(c1)CN(C1CCC(=O)NC1=O)C2=O] | 467.31 | 0.37 |
| I-50em | 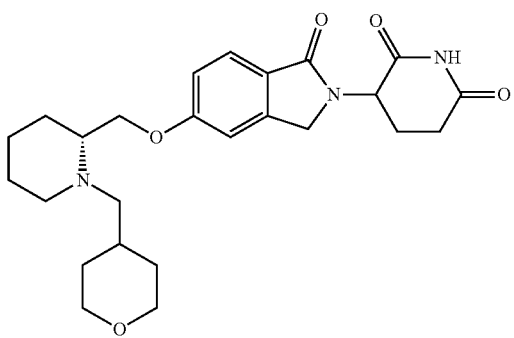 [SMILES: O=C1CCC(N2Cc3cc(OC[C@H]4CCCCN4CC4CCOCC4)ccc3C2=O)C(=O)N1] | 456.33 | 0.36 |

| Compound Number | Structure/NMR data | LCMS [M + H] | LCMS Rt |
|---|---|---|---|
| I-50en | | 528.3267 | 0.42 |
| I-50eo | | 466.31 | 0.37 |
| I-50ep | | 470.25 | 0.46 |
| I-50eq | | 453.2667 | 0.39 |

| Compound Number | Structure/NMR data | LCMS [M + H] | LCMS Rt |
|---|---|---|---|
| I-50er | | 560.32 | 0.47 |
| I-50es | | 518.3 | 0.33 |
| I-50et | | 438.28 | 0.4 |
| I-50eu | | 492.32 | 0.46 |

| Compound Number | Structure/NMR data | LCMS [M + H] | LCMS Rt |
|---|---|---|---|
| I-50ev | | 624.3333 | 0.47 |
| I-50ew | | 528.3 | 0.32 |

Example 27: (3,3-difluorocyclobutyl)methyl methanesulfonate (INT-51)

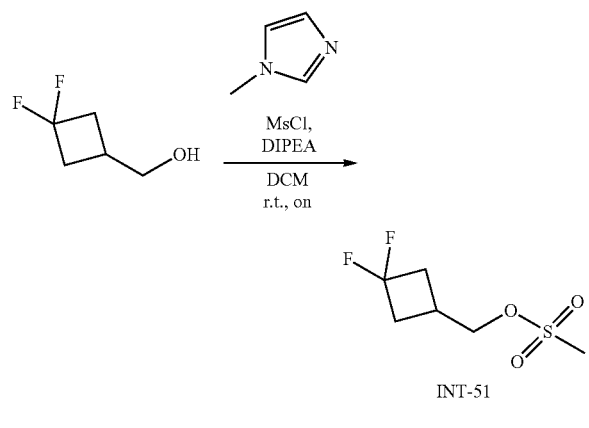

To a solution of (3,3-difluorocyclobutyl) methanol (0.16 g, 1.310 mmol) in DCM (1.4 mL) was added DIPEA (0.46 mL, 2.62 mmol), 1-methyl-1H-imidazole (0.21 mL, 2.62 mmol), and methanesulfonyl chloride (0.15 mL, 1.96 mmol) dropwise. The resulting mixture was stirred at r.t. for 18 hrs and then diluted with DCM (30 mL). The organic phase was washed with 1 M aqueous HCl three times and saturated aqueous sodium bicarbonate twice. The combined organic phases were passed through a phase separator and concentrated to afford (3,3-difluorocyclobutyl)methyl methanesulfonate INT-51 (227 mg, 1.134 mmol, 87% yield) as an orange oil. $^1$H NMR (400 MHz, Chloroform-d) δ 4.33-4.24 (m, 2H), 3.07 (s, 3H), 2.82-2.68 (m, 2H), 2.67-2.53 (m, 1H), 2.52-2.36 (m, 2H).

Example 28: Diastereomer 3-(5-(((R)-1-((3,3-difluorocyclobutyl)methyl)piperidin-2-yl)methoxy)-1-oxoisoindolin-2-yl)piperidine-2,6-dione

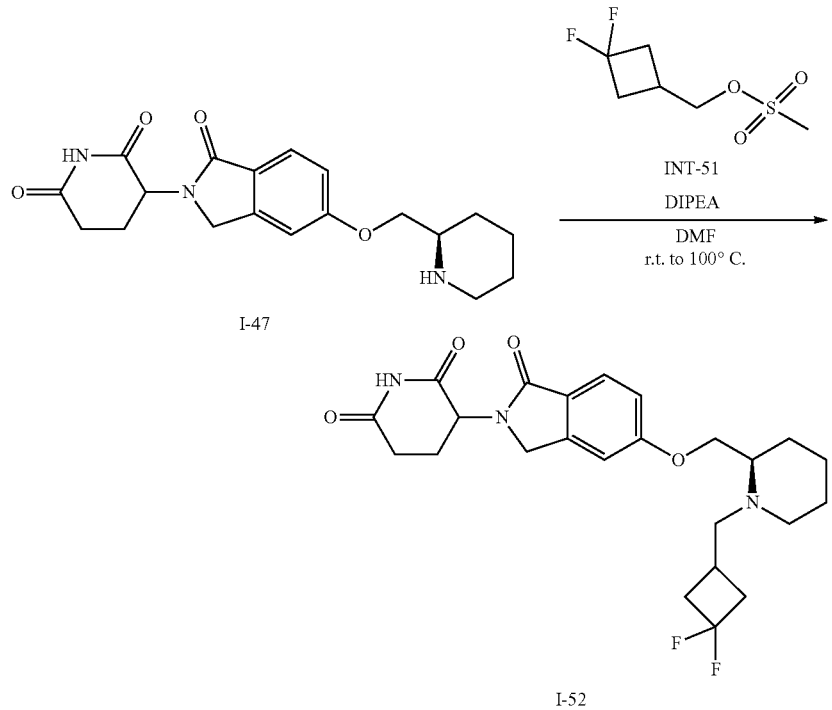

(3,3-difluorocyclobutyl)methyl methanesulfonate INT-51 (101 mg, 0.504 mmol) was added to a 40 mL vial and dissolved in DMF (2.1 mL). 1-(hydroxymethyl)-3-(1-oxo-5-(((R)-piperidin-2-yl)methoxy)isoindolin-2-yl)piperidine-2,6-dione I-47 (0.15 g, 0.420 mmol) was added followed by the addition of DIPEA (0.15 mL, 0.839 mmol). The resulting mixture was stirred at r.t. for 72 hrs, at 50° C. for 18 hrs, at 60° C. for 24 hrs, then at 100° C. for 24 hrs. The reaction mixture was quenched with saturated aqueous sodium bicarbonate and extracted with 4:1 DCM:iPrOH three times. The organic phases were combined, passed through a phase separator and concentrated onto CELITE® The crude material was purified by silica gel chromatography (eluting with 0-100% 3:1 EtOAc:EtOH with 1% TEA in heptane) to afford 3-(5-(((R)-1-((3,3-difluorocyclobutyl)methyl)piperidin-2-yl)methoxy)-1-oxoisoindolin-2-yl)piperidine-2,6-dione I-52 (38.9 mg, 0.081 mmol, 19.28% yield) as a white solid. LCMS [M+H]$^+$: 462.5. $^1$H NMR (400 MHz, DMSO-d$_6$) δ 10.97 (s, 1H), 7.64 (d, J=8.4 Hz, 1H), 7.20 (d, J=2.3 Hz, 1H), 7.07 (dd, J=8.4, 2.3 Hz, 1H), 5.08 (dd, J=13.3, 5.2 Hz, 1H), 4.40 (d, J=17.1 Hz, 1H), 4.28 (d, J=17.3 Hz, 1H), 4.23-4.13 (m, 1H), 4.13-4.01 (m, 1H), 2.98-2.77 (m, 3H), 2.74-2.57 (m, 4H), 2.45-2.13 (m, 6H), 2.04-1.93 (m, 1H), 1.77-1.60 (m, 2H), 1.58-1.27 (m, 4H).

Example 29: 3-(5-(((R)-1-isopropylpiperidin-2-yl)methoxy)-1-oxoisoindolin-2-yl)piperidine-2,6-dione (I-53)

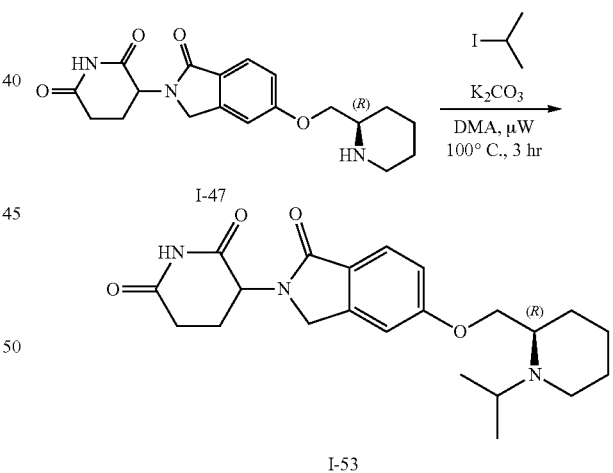

3-(1-oxo-5-(((R)-piperidin-2-yl)methoxy)isoindolin-2-yl)piperidine-2,6-dione I-47 (68 mg, 0.190 mmol) was suspended in DMA (1.90 mL). K$_2$CO$_3$ (39 mg, 0.285 mmol) was added and the resulting mixture was evacuated and backfilled with nitrogen 3 times. 2-iodopropane (0.10 mL, 0.95 mmol) was added and the reaction mixture was heated at 100° C. for 3 hrs under microwave radiation. The reaction mixture was quenched with 50% saturated aqueous sodium bicarbonate and extracted three times with 4:1 DCM:iPrOH. The organic phases were combined, passed through a phase separator, and concentrated onto CELITE®. The crude material was purified by silica gel chromatography (eluting with 0-100% 3:1 ethyl acetate:ethanol with 1% TEA in heptane). Pure fractions were combined, concentrated and lyophilized to afford 3-(5-(((R)-1-isopropylpiperidin-2-yl)methoxy)-1-oxoisoindolin-2-yl)piperidine-2,6-dione I-53 (52.96 mg, 0.130 mmol, 68.3% yield) as a white solid. LCMS [M+H]$^+$: 400.6. $^1$H NMR (400 MHz, DMSO-d$_6$) δ 10.96 (s, 1H), 7.62 (d, J=8.3 Hz, 1H), 7.19 (d, J=2.3 Hz, 1H), 7.05 (dd, J=8.7, 2.1 Hz, 1H), 5.07 (dd, J=13.3, 5.2 Hz, 1H), 4.39 (d, J=17.1 Hz, 1H), 4.26 (d, J=17.2 Hz, 1H), 4.20-3.92 (m, 2H), 3.25-3.09 (m, 1H), 2.97-2.70 (m, 3H), 2.59 (ddd, J=17.2, 4.7, 2.2 Hz, 1H), 2.45-2.31 (m, 1H), 2.15 (s, 1H), 2.02-1.91 (m, 1H), 1.82-1.64 (m, 2H), 1.62-1.52 (m, 1H), 1.44-1.22 (m, 3H), 1.12-0.98 (m, 3H), 0.96-0.86 (m, 3H).

Example 30: Enantiomers 5-((4-ethyl-6,6-dimethyl-morpholin-3-yl)methoxy)isobenzofuran-1(3H)-one (INT-56)

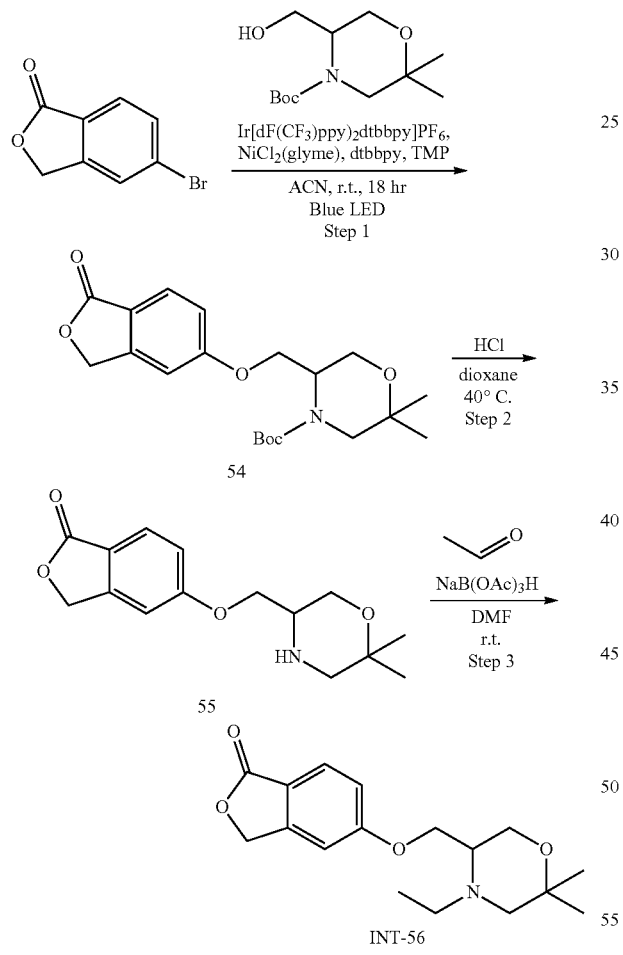

Step 1: rac-Tert-butyl 2,2-dimethyl-5-(((1-oxo-1,3-dihydroisobenzofuran-5-yl)oxy)methyl)morpholine-4-carboxylate (54)

Intermediate 54 was prepared according to General Method I starting from 4-boc-5-hydroxymethyl-2,2-dimethyl-morpholine (507 mg, 2.065 mmol). The crude material was purified by silica gel chromatography (eluting with 0-100% ethyl acetate in heptane) to afford rac-tert-butyl 2,2-dimethyl-5-(((1-oxo-1,3-dihydroisobenzofuran-5-yl)oxy)methyl)morpholine-4-carboxylate 54 (587 mg, 1.555 mmol, 83% yield) as a cream solid. LCMS [M+H]$^+$: 322.1 (mass without tert-butyl). $^1$H NMR (400 MHz, Chloroform-d) δ 7.73 (d, J=8.5 Hz, 1H), 7.00 (dd, J=8.5, 2.2 Hz, 1H), 6.93 (d, J=2.1 Hz, 1H), 5.19 (s, 2H), 4.29-4.06 (m, 2H), 3.94-3.54 (m, 5H), 1.41 (s, 9H), 1.20 (s, 3H), 1.16 (s, 3H).

Step 2: rac-5-((6,6-dimethylmorpholin-3-yl)methoxy)isobenzofuran-1(3H)-one (55)

Intermediate 55 was prepared according to General Method II starting from tert-butyl 2,2-dimethyl-5-(((1-oxo-1,3-dihydroisobenzofuran-5-yl)oxy)methyl)morpholine-4-carboxylate 54 (0.587 g, 1.555 mmol). The reaction mixture was concentrated to afford 5-((6,6-dimethylmorpholin-3-yl)methoxy)isobenzofuran-1(3H)-one 55 as a white solid. The crude material was used in the next reaction without purification. LCMS [M+H]$^+$: 278.3.

Step 3: Enantiomers 5-((4-ethyl-6,6-dimethylmorpholin-3-yl)methoxy)isobenzofuran-1(3H)-one (INT-56)

INT-56 was prepared according to General Method III starting from 5-((6,6-dimethylmorpholin-3-yl)methoxy)isobenzofuran-1(3H)-one 55 (1.11 g, 4.0 mmol) and acetaldehyde (0.5 mL, 9.33 mmol). The crude material was purified by silica gel chromatography (eluting with 0-100% 3:1 EtOAc:EtOH with 1% TEA in heptane) to afford 5-((4-ethyl-6,6-dimethylmorpholin-3-yl)methoxy)isobenzofuran-1(3H)-one INT-56 (275 mg, 0.901 mmol, 22.51% yield) as a pink solid. LCMS [M+H]$^+$: 306.5. $^1$H NMR (400 MHz, Chloroform-d) δ 7.79 (d, J=8.5 Hz, 1H), 7.03 (dd, J=8.5, 2.2 Hz, 1H), 6.95-6.89 (m, 1H), 5.23 (s, 2H), 4.20 (dd, J=9.5, 4.4 Hz, 1H), 4.07 (dd, J=9.5, 6.4 Hz, 1H), 3.85 (dd, J=11.6, 3.5 Hz, 1H), 3.70 (dd, J=11.6, 7.0 Hz, 1H), 2.92-2.79 (m, 1H), 2.79-2.66 (m, 1H), 2.62-2.47 (m, 2H), 2.23 (d, J=11.5 Hz, 1H), 1.28 (s, 3H), 1.25 (s, 3H), 1.05 (t, J=7.1 Hz, 3H). The mixture of isomers was separated via chiral SFC [Column 21×250 mm Chiralpak IF; CO$_2$ Co-solvent 25% MeOH; at 80 g/min at 125 bar at 25° C.] to afford two enantiomers: Peak 1: Enantiomer 1 of 5-((4-ethyl-6,6-dimethylmorpholin-3-yl)methoxy)isobenzofuran-1(3H)-one (99 mg, 0.324 mmol, 8.10% yield) as a light yellow solid. Chiral SFC Rt 2.5 mins. Peak 2: Enantiomer 2 of 5-((4-ethyl-6,6-dimethylmorpholin-3-yl)methoxy)isobenzofuran-1(3H)-one (111.5 mg, 0.365 mmol, 9.13% yield) as light red solid. Chiral SFC Rt 3.7 mins.

Example 31: Diastereomer 3-(5-((4-ethyl-6,6-dimethylmorpholin-3-yl)methoxy)-1-oxoisoindolin-2-yl)piperidine-2,6-dione (I-58)

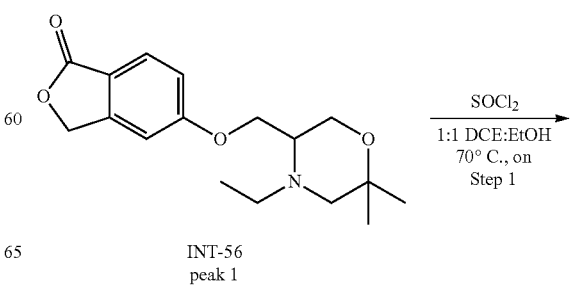

247

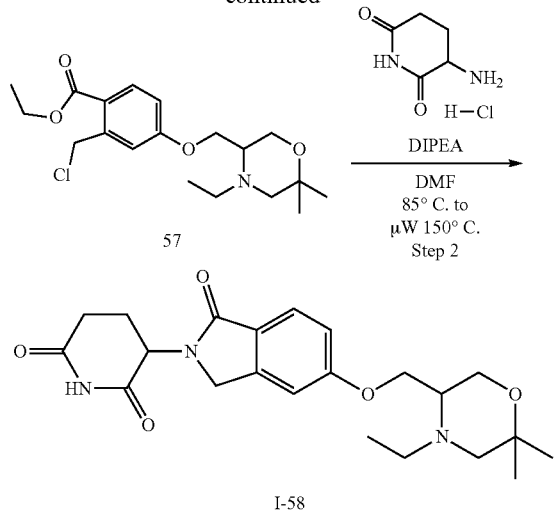

Step 1: Single Enantiomer Ethyl 2-(chloromethyl)-4-((4-ethyl-6,6-dimethylmorpholin-3-yl)methoxy)benzoate (57)

Intermediate 57 was made according to General Method IV starting from 5-((6,6-dimethylmorpholin-3-yl)methoxy) isobenzofuran-1(3H)-one INT-56 Peak 1 (99 mg, 0.324 mmol) to afford a single enantiomer ethyl 2-(chloromethyl)-4-((4-ethyl-6,6-dimethylmorpholin-3-yl)methoxy)benzoate 57 as a brown oil. The crude material was taken through to the next step without purification. LCMS [M+H]$^+$: 370.4.

Step 2: Diastereomer 3-(5-((4-ethyl-6,6-dimethyl-morpholin-3-yl)methoxy)-1-oxoisoindolin-2-yl)piperidine-2,6-dione (I-58)

Compound I-58 was made according to General Method V starting from ethyl 2-(chloromethyl)-4-((4-ethyl-6,6-dimethylmorpholin-3-yl)methoxy)benzoate 57 (120 mg, 0.324 mmol). The crude material was purified by silica gel chromatography (eluting with 0-100% 3:1 ethyl acetate:ethanol with 1% TEA as modifier in heptane). Fractions containing desired product were combined, concentrated, and lyophilized to afford 3-(5-((4-ethyl-6,6-dimethylmorpholin-3-yl)methoxy)-1-oxoisoindolin-2-yl)piperidine-2,6-dione I-58 (71 mg, 0.169 mmol, 52.2% yield) as a light purple solid. LCMS [M+H]$^+$: 416.6. $^1$H NMR (400 MHz, DMSO-d$_6$) δ 10.97 (s, 1H), 7.63 (d, J=8.3 Hz, 1H), 7.26-7.15 (m, 1H), 7.08 (dd, J=8.4, 2.3 Hz, 1H), 5.08 (dd, J=13.3, 5.2 Hz, 1H), 4.40 (dd, J=17.4, 1.8 Hz, 1H), 4.34-4.15 (m, 2H), 4.12-4.00 (m, 1H), 3.74 (dd, J=11.6, 3.4 Hz, 1H), 3.57 (dd, J=11.4, 7.4 Hz, 1H), 2.91 (ddd, J=17.3, 13.6, 5.4 Hz, 1H), 2.78-2.65 (m, 2H), 2.64-2.49 (m, 2H), 2.48-2.31 (m, 2H), 2.13 (d, J=11.4 Hz, 1H), 2.03-1.93 (m, 1H), 1.21 (s, 3H), 1.16 (s, 3H), 0.98 (t, J=7.1 Hz, 3H).

248

Example 32: Diastereomer 3-(5-((4-ethyl-6,6-dimethylmorpholin-3-yl)methoxy)-1-oxoisoindolin-2-yl)piperidine-2,6-dione (I-60)

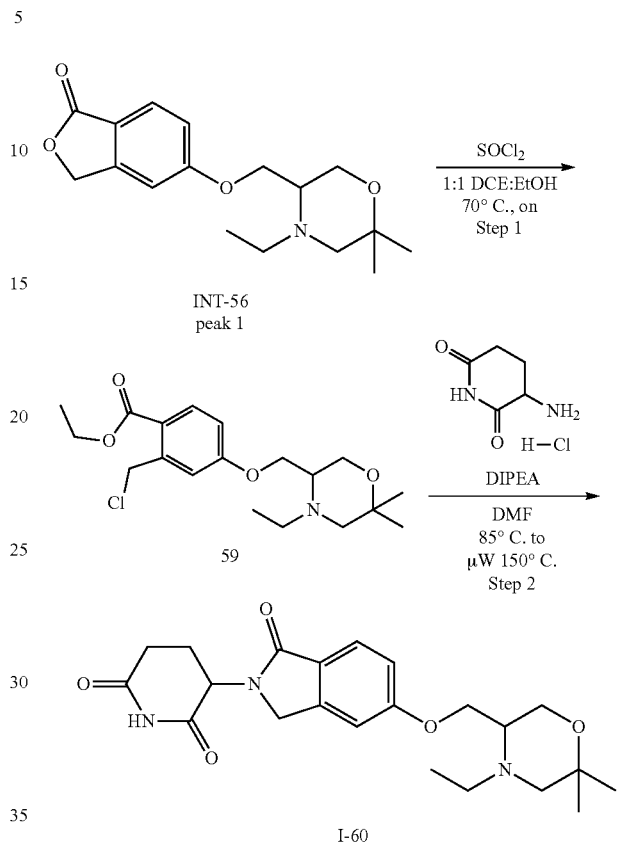

Step 1: Single Enantiomer Ethyl 2-(chloromethyl)-4-((4-ethyl-6,6-dimethylmorpholin-3-yl)methoxy)benzoate (59)

Intermediate 59 was made according to General Method IV starting from 5-((6,6-dimethylmorpholin-3-yl)methoxy) isobenzofuran-1(3H)-one INT-56 Peak 2 (111.5 mg, 0.365 mmol) to afford ethyl 2-(chloromethyl)-4-((4-ethyl-6,6-dimethylmorpholin-3-yl)methoxy)benzoate 59 as a brown oil. The crude material was taken through to the next step without purification. LCMS [M+H]$^+$:370.4.

Step 2: Diastereomer (5-((4-ethyl-6,6-dimethylmorpholin-3-yl)methoxy)-1-oxoisoindolin-2-yl)piperidine-2,6-dione (I-60)

Compound I-60 was made according to General Method V starting from ethyl 2-(chloromethyl)-4-((4-ethyl-6,6-dimethylmorpholin-3-yl)methoxy)benzoate 59 (135 mg, 0.365 mmol). The crude material was purified by silica gel chromatography (eluting with 0-100% 3:1 ethyl acetate:ethanol with 1% TEA as modifier in heptane). Fractions containing desired product were combined, concentrated, and lyophilized to afford (5-((4-ethyl-6,6-dimethylmorpholin-3-yl)methoxy)-1-oxoisoindolin-2-yl)piperidine-2,6-dione I-60 (68.1 mg, 0.161 mmol, 44.0% yield) as a light purple solid. LCMS [M+H]$^+$: 416.4. $^1$H NMR (400 MHz, DMSO-d$_6$) δ 10.97 (s, 1H), 7.63 (d, J=8.5 Hz, 1H), 7.25-7.17 (m, 1H), 7.08 (dd, J=8.5, 2.2 Hz, 1H), 5.08 (dd, J=13.3, 5.0 Hz, 1H), 4.40 (dd, J=17.6, 1.8 Hz, 1H), 4.34-4.16 (m, 2H), 4.12-4.01 (m, 1H), 3.74 (dd, J=11.3, 3.4 Hz, 1H), 3.57 (dd, J=11.6, 7.4 Hz, 1H), 2.91 (ddd, J=17.2, 13.6, 5.4 Hz, 1H), 2.78-2.64 (m, 2H), 2.63-2.54 (m, 2H), 2.48-2.31 (m, 2H), 2.17-2.10 (m, 1H), 2.03-1.92 (m, 1H), 1.21 (s, 3H), 1.16 (s, 3H), 0.98 (t, J=7.1 Hz, 3H).

Example 33: Tert-butyl (R)-3-(hydroxymethyl)morpholine-4-carboxylate (INT-61)

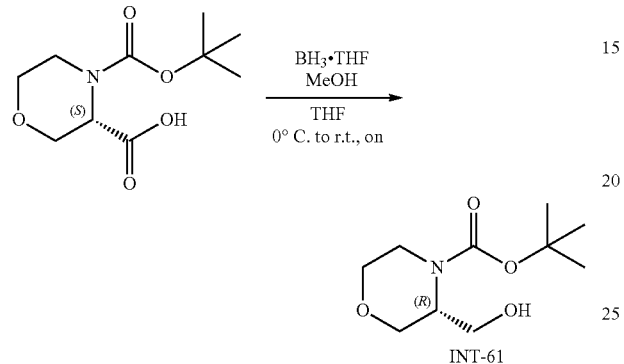

(S)-4-(tert-butoxycarbonyl)morpholine-3-carboxylic acid (0.2 g, 0.865 mmol) was dissolved in THF (2.9 mL) and cooled to 0° C. 1M borane tetrahydrofuran complex in THF (2.6 mL, 2.59 mmol) was added dropwise. The resulting mixture was stirred at r.t. overnight and then cooled to 0° C., quenched with methanol (2 mL, 49.4 mmol) and stirred at r.t. for 2 hrs. The reaction mixture was concentrated to dryness, dissolved in methanol (5 mL) and stirred at r.t. overnight. The reaction mixture was concentrated onto CELITE® and purified by silica gel chromatography (eluting with 0-100% ethyl acetate in heptane using ELSD detection) to afford tert-butyl (R)-3-(hydroxymethyl)morpholine-4-carboxylate INT-61 (85 mg, 0.391 mmol, 45.2% yield) as a white solid. $^1$H NMR (400 MHz, Chloroform-d) δ 4.04 (s, 1H), 3.94 (d, J=12.0 Hz, 1H), 3.91-3.81 (m, 3H), 3.77 (d, J=13.8 Hz, 1H), 3.60 (dd, J=11.9, 3.5 Hz, 1H), 3.49 (td, J=11.8, 3.1 Hz, 1H), 3.21 (t, J=12.6 Hz, 1H), 1.50 (s, 9H).

Example 34: Diastereomer 3-(5-(((S)-4-ethylmorpholin-3-yl)methoxy)-1-oxoisoindolin-2-yl)piperidine-2,6-dione (I-64)

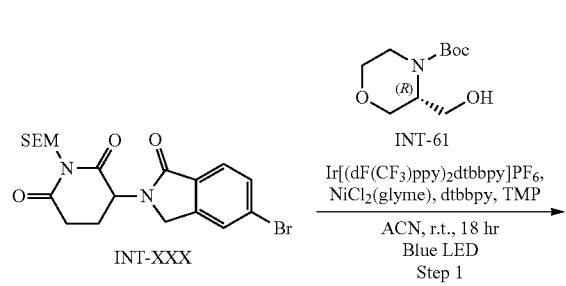

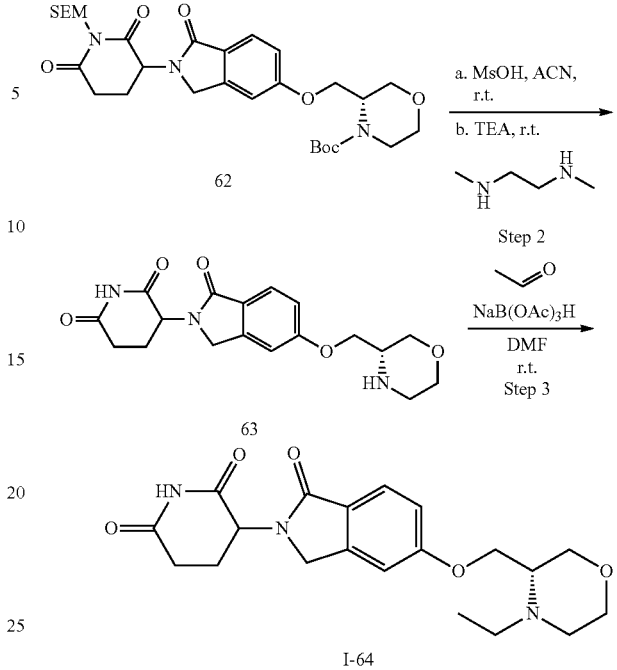

Step 1: Tert-butyl (3S)-3-(((2-(2,6-dioxo-1-((2-(trimethylsilyl)ethoxy)methyl)piperidin-3-yl)-1-oxoisoindolin-5-yl)oxy)methyl)morpholine-4-carboxylate (62)

Intermediate 62 was prepared according to General Method VI starting from tert-butyl (R)-3-(hydroxymethyl)morpholine-4-carboxylate INT-61 (58 mg, 0.265 mmol). The crude material was purified by silica gel chromatography (eluting with 0-100% ethyl acetate in heptane) to afford tert-butyl (3S)-3-(((2-(2,6-dioxo-1-((2-(trimethylsilyl)ethoxy)methyl)piperidin-3-yl)-1-oxoisoindolin-5-yl)oxy)methyl)morpholine-4-carboxylate 62 (119 mg, 0.202 mmol, 91% yield) as a white viscous solid. LCMS [M+H−156.3 (TMSCH$_2$CH$_2$,tButyl)]$^+$: 434.4. $^1$H NMR (400 MHz, Chloroform-d) δ 7.79 (d, J=8.4 Hz, 1H), 7.03 (dd, J=8.4, 2.2 Hz, 1H), 6.98 (s, 1H), 5.29-5.13 (m, 3H), 4.43 (d, J=15.9 Hz, 1H), 4.32-4.23 (m, 3H), 4.18-4.02 (m, 2H), 3.96-3.71 (m, 2H), 3.67-3.57 (m, 3H), 3.51 (td, J=11.9, 3.0 Hz, 1H), 3.13 (t, J=12.7 Hz, 1H), 3.02 (ddd, J=17.8, 4.7, 2.5 Hz, 1H), 2.89 (ddd, J=18.1, 13.3, 5.5 Hz, 1H), 2.32 (qd, J=13.2, 4.7 Hz, 1H), 2.18 (dtd, J=12.8, 5.3, 2.4 Hz, 1H), 1.49 (s, 9H), 0.94 (dd, J=9.2, 7.3 Hz, 2H), 0.00 (s, 9H).

Step 2: 3-(5-(((S)-morpholin-3-yl)methoxy)-1-oxoisoindolin-2-yl)piperidine-2,6-dione (63)

Intermediate 63 was prepared according to General Method VII starting from tert-butyl (3S)-3-(((2-(2,6-dioxo-1-((2-(trimethylsilyl)ethoxy)methyl)piperidin-3-yl)-1-oxoisoindolin-5-yl)oxy)methyl)morpholine-4-carboxylate 62 (119 mg, 0.202 mmol). The crude material was purified by silica gel chromatography (eluting with 0-100% ethanol with 1% TEA in dichloromethane) to afford 3-(5-(((S)-morpholin-3-yl)methoxy)-1-oxoisoindolin-2-yl)piperidine-2,6-dione 63 (54.5 mg, 0.152 mmol, 75% yield) as a white solid. LCMS [M+H]$^+$: 360.3. $^1$H NMR (400 MHz, Chloroform-d) δ 7.76 (d, J=8.4 Hz, 1H), 6.97 (dd, J=8.4, 2.2 Hz, 1H), 6.93-6.87 (m, 1H), 5.15 (ddd, J=13.2, 5.2, 1.2 Hz, 1H), 4.38 (d, J=15.9 Hz, 1H), 4.24 (d, J=15.9 Hz, 1H), 4.00-3.85 (m, 3H), 3.85-3.77 (m, 1H), 3.63-3.51 (m, 1H), 3.42 (ddd, J=11.0, 9.3, 3.1 Hz, 1H), 3.35-3.24 (m, 1H), 3.02-2.92 (m, 3H), 2.90-2.72 (m, 2H), 2.28 (qd, J=12.9, 5.2 Hz, 1H), 2.21-2.11 (m, 1H).

Step 3: 3-(5-(((S)-4-ethylmorpholin-3-yl)methoxy)-1-oxoisoindolin-2-yl)piperidine-2,6-dione (I-64)

Compound I-64 was prepared according to General Method III starting from a solution of 3-(5-(((S)-morpholin-3-yl)methoxy)-1-oxoisoindolin-2-yl)piperidine-2,6-dione 63 (54.5 mg, 0.152 mmol) and acetaldehyde (0.05 mL, 0.91 mmol). The crude material was purified by silica gel chromatography (eluting with 0-100% 3:1 ethylacetate:ethanol with 1% TEA in heptane). Pure fractions were combined, concentrated, and lyophilized to afford 3-(5-(((S)-4-ethyl-morpholin-3-yl)methoxy)-1-oxoisoindolin-2-yl)piperidine-2,6-dione I-64 (24.6 mg, 0.062 mmol, 40.6% yield) as an orange solid. LCMS [M+H]$^+$: 388.5. $^1$H NMR (400 MHz, DMSO-d$_6$) δ 10.89 (s, 1H), 7.55 (d, J=8.3 Hz, 1H), 7.18-7.06 (m, 1H), 7.00 (dd, J=8.4, 2.2 Hz, 1H), 5.00 (dd, J=13.3, 5.0 Hz, 1H), 4.32 (d, J=17.2 Hz, 1H), 4.24-4.09 (m, 2H), 3.98 (ddd, J=9.8, 6.2, 1.9 Hz, 1H), 3.72 (dd, J=11.1, 3.0 Hz, 1H), 3.65-3.55 (m, 1H), 3.55-3.45 (m, 1H), 3.41 (dd, J=11.0, 7.3 Hz, 1H), 2.91-2.76 (m, 1H), 2.75-2.56 (m, 3H), 2.57-2.48 (m, 1H), 2.38-2.21 (m, 3H), 1.95-1.87 (m, 1H), 0.93 (t, J=7.1 Hz, 3H).

Example 35: Tert-butyl 2-(hydroxymethyl)azepane-1-carboxylate, 2-(hydroxymethyl)azepane-1-carboxylic acid (INT-65)

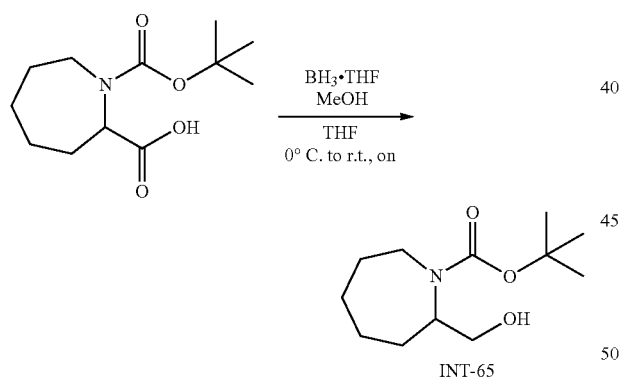

1-(tert-butoxycarbonyl)azepane-2-carboxylic acid (0.3 g, 1.233 mmol) was dissolved in THF (4.1 mL) and cooled to 0° C. 1M borane tetrahydrofuran complex in THF (3.70 mL, 3.70 mmol) was added dropwise. The resulting mixture was stirred at r.t. overnight, cooled to 0° C. and quenched with methanol (3 mL, 74.2 mmol) and stirred at r.t. for 2 hrs. The reaction mixture was concentrated to dryness and then redissolved in methanol (5 mL). stirred at r.t. overnight. The reaction mixture was concentrated onto CELITE® and purified by silica gel chromatography (eluting with 0-100% ethyl acetate in heptane using ELSD detector) to afford tert-butyl 2-(hydroxymethyl)azepane-1-carboxylate INT-65 (209 mg, 0.911 mmol, 73.9% yield) as a clear oil. LCMS [M+H−tButyl]$^+$: 174.2. $^1$H NMR (400 MHz, Chloroform-d) δ 4.10-3.97 (m, 1H), 3.95-3.65 (m, 1H), 3.62-3.52 (m, 1H), 3.51-3.33 (m, 2H), 3.21 (s, 1H), 2.76-2.63 (m, 1H), 1.99-1.86 (m, 1H), 1.78-1.66 (m, 2H), 1.63-1.55 (m, 1H), 1.42-1.33 (m, 9H), 1.25-1.10 (m, 2H).

Example 36: Enantiomers 5-((1-ethylazepan-2-yl)methoxy)isobenzofuran-1(3H)-one (INT-68)

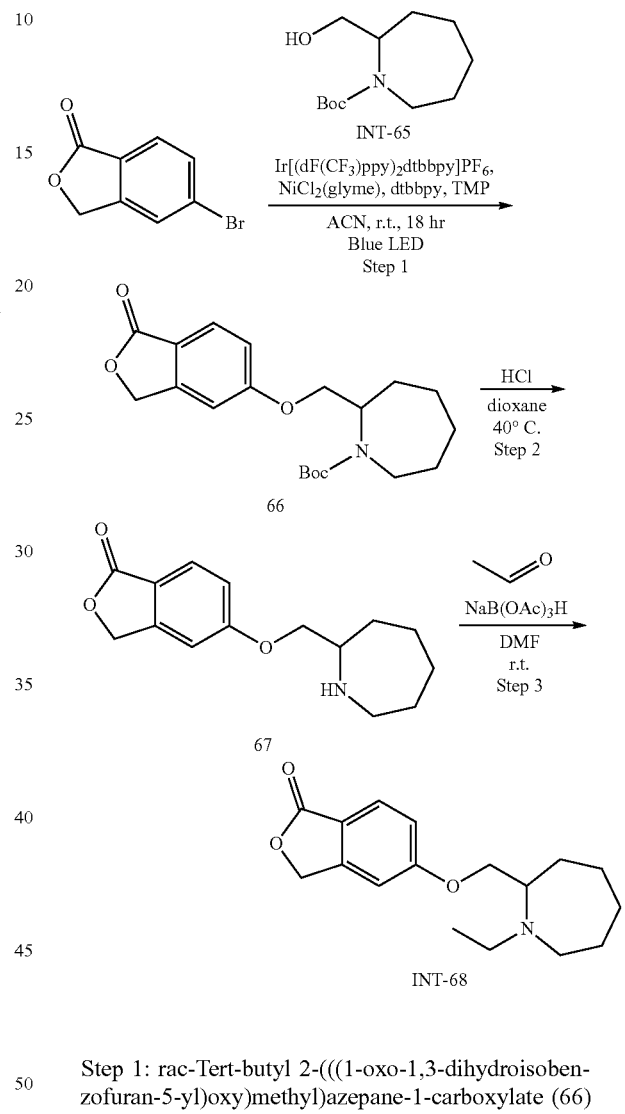

Step 1: rac-Tert-butyl 2-(((1-oxo-1,3-dihydroisobenzofuran-5-yl)oxy)methyl)azepane-1-carboxylate (66)

Intermediate 66 was prepared according to General Method I starting from tert-butyl 2-(hydroxymethyl)azepane-1-carboxylate INT-65 (209 mg, 0.912 mmol). The crude material was purified by silica gel chromatography (eluting with 0-100% ethyl acetate in heptane) to afford tert-butyl 2-(((1-oxo-1,3-dihydroisobenzofuran-5-yl)oxy)methyl)azepane-1-carboxylate 66 (245 mg, 0.678 mmol, 78% yield) as a viscous yellow solid. LCMS [M+H−6.3 (TMSCH$_2$CH$_2$,tButyl)]$^+$: 306.3. $^1$H NMR (400 MHz, Chloroform-d) δ 7.77-7.70 (m, 1H), 6.99 (dt, J=8.5, 2.4 Hz, 1H), 6.91 (dd, J=14.4, 2.1 Hz, 1H), 5.23-5.12 (m, 2H), 4.40-4.21 (m, 1H), 4.06-3.89 (m, 2H), 3.87-3.65 (m, 1H), 2.93-2.77 (m, 1H), 2.21-2.03 (m, 1H), 1.91-1.74 (m, 2H), 1.73-1.64 (m, 1H), 1.62-1.46 (m, 1H), 1.45-1.39 (m, 9H), 1.28-1.17 (m, 3H).

Step 2: rac-5-(azepan-2-ylmethoxy)isobenzofuran-1(3H)-one (67)

Intermediate 67 was prepared according to General Method II starting from tert-butyl 2-(((1-oxo-1,3-dihydroisobenzofuran-5-yl)oxy)methyl)azepane-1-carboxylate 66 (245 mg, 0.678 mmol) to afford 5-(azepan-2-ylmethoxy)isobenzofuran-1(3H)-one 67 as a white solid. The crude material was used in the next step without purification. LCMS [M+H]$^+$: 262.2.

Step 3: Enantiomers of 5-((1-ethylazepan-2-yl)methoxy)isobenzofuran-1(3H)-one (INT-68)

INT-68 was prepared according to General Method III starting from 5-(azepan-2-ylmethoxy)isobenzofuran-1(3H)-one 67 (0.18 g, 0.678 mmol) and acetaldehyde (0.23 mL, 4.07 mmol). The crude material was purified by silica gel chromatography (eluting with 0-100% ethyl acetate in heptane) to afford enantiomeric mixture 5-((1-ethylazepan-2-yl)methoxy)isobenzofuran-1(3H)-one INT-68 (101 mg, 0.349 mmol, 51.5% yield) as a cream solid. LCMS [M+H]$^+$: 290.4. $^1$H NMR (400 MHz, Chloroform-d) δ 7.81 (d, J=8.5 Hz, 1H), 7.05 (dd, J=8.5, 2.1 Hz, 1H), 6.94-6.88 (m, 1H), 5.25 (s, 2H), 3.99 (dd, J=9.1, 4.9 Hz, 1H), 3.82 (dd, J=9.1, 7.7 Hz, 1H), 3.09-3.00 (m, 1H), 2.93-2.87 (m, 2H), 2.84-2.69 (m, 2H), 2.07-1.97 (m, 1H), 1.85-1.75 (m, 1H), 1.74-1.34 (m, 6H), 1.09 (t, J=7.1 Hz, 3H). The mixture of isomers was separated via chiral SFC [Column 2.1×25.0 cm Chiralcel OD-H; CO$_2$ Co-solvent 15% IPA with 0.25% isopropylamine; at 100 g/min at 100 bar at 25° C.] to afford two enantiomers: Peak 1: Enantiomer 1 of 5-((1-ethylazepan-2-yl)methoxy)isobenzofuran-1(3H)-one (27.7 mg, 0.096 mmol, 14.12% yield) as a white solid. Chiral SFC Rt 1.84 mins. Peak 2: Enantiomer 2 of 5-((1-ethylazepan-2-yl)methoxy)isobenzofuran-1(3H)-one (30 mg, 0.104 mmol, 15.29% yield) as white solid. Chiral SFC Rt 2.05 mins.

Example 37: 3-(5-((1-ethylazepan-2-yl)methoxy)-1-oxoisoindolin-2-yl)piperidine-2,6-dione (I-70)

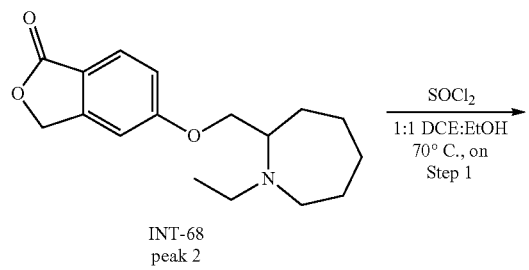

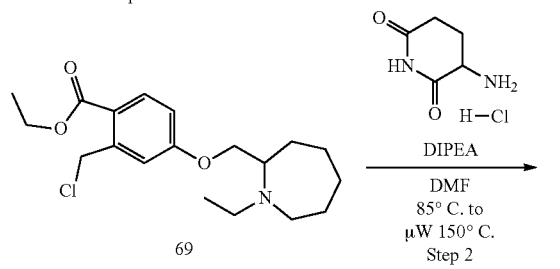

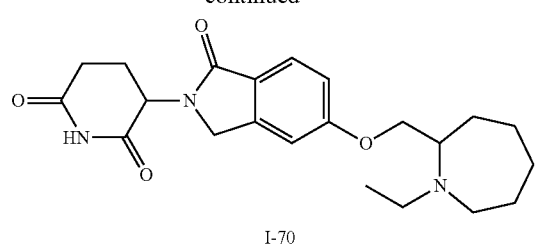

I-70

Step 1: Single Enantiomer Ethyl 2-(chloromethyl)-4-((1-ethylazepan-2-yl)methoxy)benzoate (69)

Intermediate 69 was made according to General Method IV starting from 5-(azepan-2-ylmethoxy)isobenzofuran-1(3H)-one INT 68 Peak 2 (30 mg, 0.104 mmol) to afford ethyl 2-(chloromethyl)-4-((1-ethylazepan-2-yl)methoxy)benzoate 69 as a brown oil. The crude material was taken through to the next step without purification. LCMS [M+H]$^+$: 354.1.

Step 2: Diastereomeric mixture 3-(5-((1-ethylazepan-2-yl)methoxy)-1-oxoisoindolin-2-yl)piperidine-2,6-dione (I-70)

Compound I-70 was made according to General Method V starting from ethyl 2-(chloromethyl)-4-((1-ethylazepan-2-yl)methoxy)benzoate 69 (36.8 mg, 0.104 mmol). The crude material was purified by silica gel chromatography (eluting with 0-100% 3:1 ethyl acetate:ethanol with 1% triethylamine as modifier in heptane). Fractions containing desired product were combined, concentrated, and lyophilized to afford impure product. The crude material was further purified by basic reverse phase HPLC (eluting with 35-60% ACN in water with 5 mM NH$_4$OH as modifier). Pure fractions were lyophilized to afford 3-(5-((1-ethylazepan-2-yl)methoxy)-1-oxoisoindolin-2-yl)piperidine-2,6-dione I-70 (3.95 mg, 9.00 μmol, 8.65% yield) as a white solid. LCMS [M+H]$^+$: 400.2. $^1$H NMR (400 MHz, DMSO-d$_6$) δ 10.89 (s, 1H), 7.54 (d, J=8.4 Hz, 1H), 7.12-7.04 (m, 1H), 6.97 (dd, J=8.4, 2.3 Hz, 1H), 5.00 (dd, J=13.3, 5.0 Hz, 1H), 4.31 (d, J=17.2 Hz, 1H), 4.19 (d, J=17.2 Hz, 1H), 3.96-3.65 (m, 2H), 2.98-2.60 (m, 5H), 2.57-2.49 (m, 1H), 2.37-2.26 (m, 1H), 1.95-1.83 (m, 2H), 1.68-1.19 (m, 8H), 0.93 (t, J=7.2 Hz, 3H).

Example 38: 3-(5-(((R)-1-benzoylpiperidin-2-yl)methoxy)-1-oxoisoindolin-2-yl)piperidine-2,6-dione (I-71)

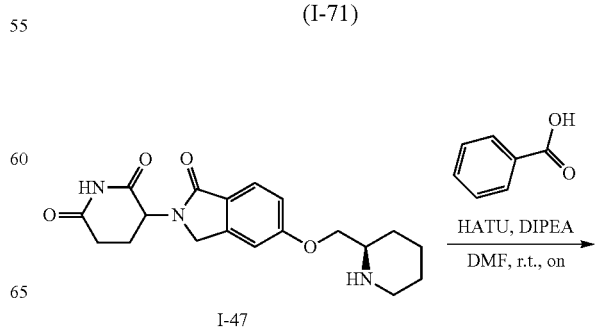

-continued

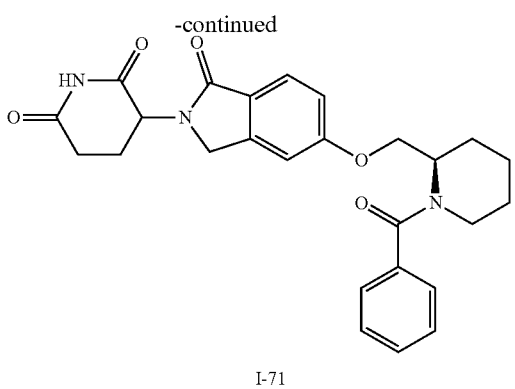

I-71

Benzoic acid (9.16 mg, 0.075 mmol) was dissolved in DMF (0.75 mL). HATU (34 mg, 0.090 mmol) and DIPEA (0.03 mL, 0.15 mmol) were added and the resulting mixture was stirred at r.t. for 15 minutes. A solution of 3-(1-oxo-5-(((R)-piperidin-2-yl)methoxy)isoindolin-2-yl)piperidine-2,6-dione I-47 (27 mg, 0.075 mmol) in DMF (0.75 mL) was the added and stirring was continued at r.t. overnight. The reaction mixture was concentrated and purified by acidic reverse phase HPLC (eluting with 15-40% ACN in water with 0.1% formic acid as modifier). Pure fractions were combined and lyophilized to afford 3-(5-(((R)-1-benzoylpiperidin-2-yl)methoxy)-1-oxoisoindolin-2-yl)piperidine-2,6-dione I-71 (21.3 mg, 0.046 mmol, 61.5% yield) as a white solid. LCMS [M+H]$^+$: 462.3. $^1$H NMR (400 MHz, DMSO-$d_6$) δ 10.97 (s, 1H), 7.61 (d, J=8.3 Hz, 1H), 7.48-6.86 (m, 7H), 5.08 (dd, J=13.2, 5.2 Hz, 1H), 4.60-3.94 (m, 5H), 3.31-3.25 (m, 2H), 2.91 (ddd, J=17.3, 13.6, 5.4 Hz, 1H), 2.59 (dt, J=16.6, 3.5 Hz, 1H), 2.45-2.35 (m, 1H), 2.03-1.94 (m, 1H), 1.86-1.55 (m, 5H), 1.50-1.33 (m, 1H).

The following compounds were made according to Example 38 starting from the final product of either Example 24 (I-47) or Example 25 (I-49).

| Compound Number | Structure | LCMS [M + H] | LCMS Rt |
|---|---|---|---|
| I-71a | 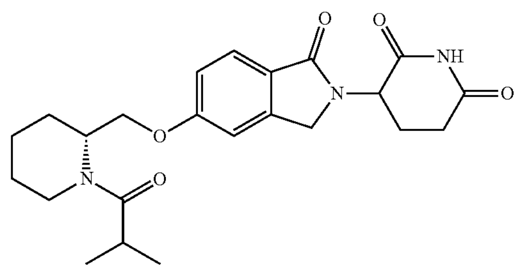 [SMILES: CC(C)C(=O)N1CCCC[C@@H]1COc1ccc2c(c1)CN(C1CCC(=O)NC1=O)C2=O] | 428.2 | 0.56 |
| I-71b | 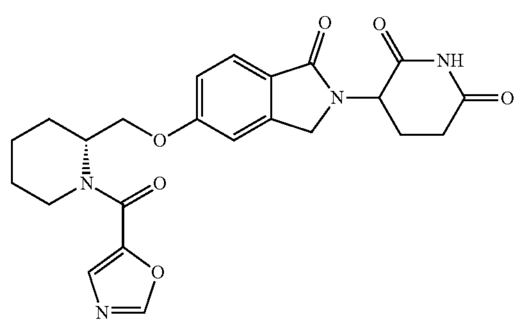 [SMILES: O=C1CCC(N2Cc3cc(OC[C@H]4CCCCN4C(=O)c4cnco4)ccc3C2=O)C(=O)N1] | 453.2 | 0.53 |

Example 39: 3-(5-(((S)-1-(2-(naphthalen-2-yloxy)acetyl)piperidin-2-yl)methoxy)-1-oxoisoindolin-2-yl)piperidine-2,6-dione (I-72)

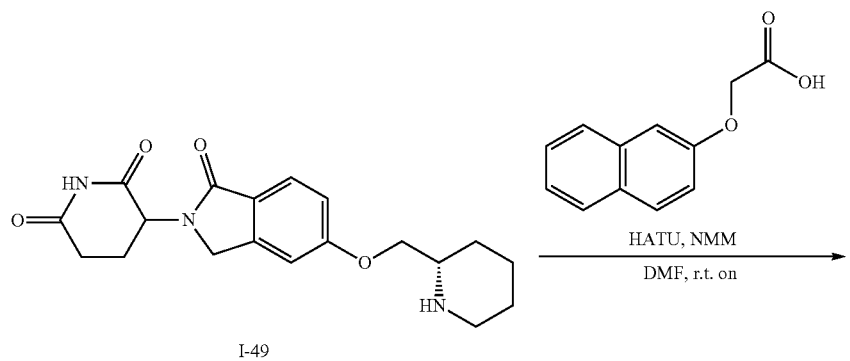

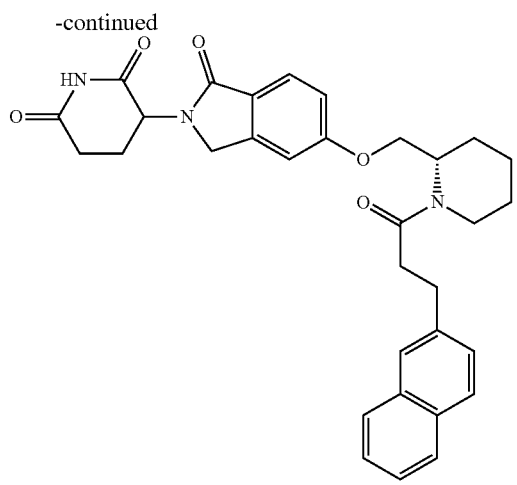

I-72

To a reaction vial containing 2-(naphthalen-2-yloxy)acetic acid (11.9 mg, 0.059 mmol) in DMF (200 µL) was added a solution of HATU (22.3 mg, 0.059 mmol) in DMF (200 µL) followed by mixture of 3-(1-oxo-5-(((S)-piperidin-2-yl)methoxy)isoindolin-2-yl)piperidine-2,6-dione I-49 (12 mg, 0.034 mmol) and NMM (0.02 mL, 0.168 mmol) in DMF (600 µL). The resulting mixture was stirred at r.t. overnight. The reaction mixture was concentrated and purified by acidic reverse phase HPLC (eluting with 10-90% ACN in water with 0.1% formic acid as modifier) to afford 3-(5-(((S)-1-(2-(naphthalen-2-yloxy)acetyl)piperidin-2-yl)methoxy)-1-oxoisoindolin-2-yl)piperidine-2,6-dione I-72 (10.9 mg, 0.019 mmol, 55.9% yield). LCMS [M+H]$^+$: 542.3, Rt 0.62 mins.

The following compounds were made according to Example 39, starting from the final product of either Example 24 (I-47) or Example 25 (I-49).

| Compound Number | Structure | LCMS [M + H] | LCMS Rt |
|---|---|---|---|
| I-72a | 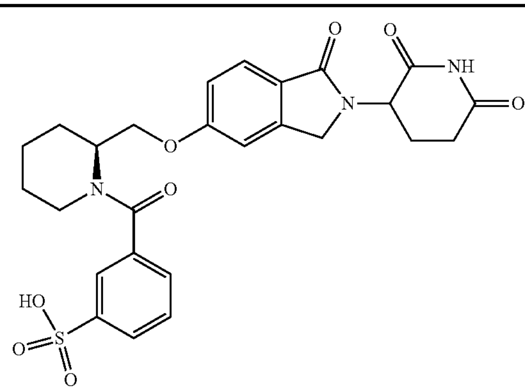 | 542.22 | 0.5 |
| I-72b | 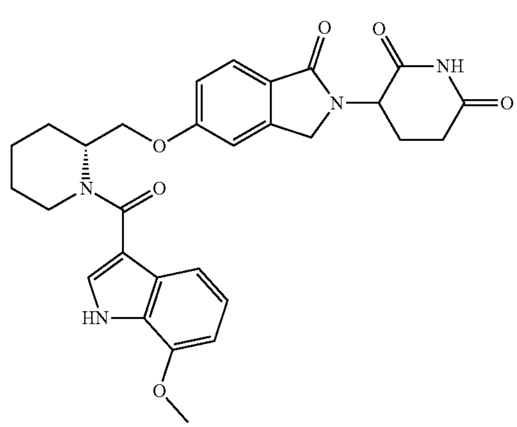 [SMILES: COc1cccc2c(C(=O)N3CCCC[C@@H]3COc3ccc4c(c3)CN(C3CCC(=O)NC3=O)C4=O)c[nH]c12] | 531.25 | 0.59 |

-continued
| Compound Number | Structure | LCMS [M + H] | LCMS Rt |
|---|---|---|---|
| I-72c | 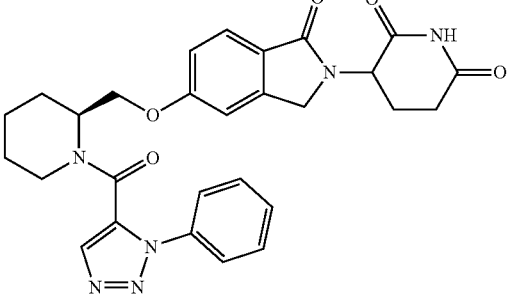 | 529.29 | 0.55 |
| I-72d | 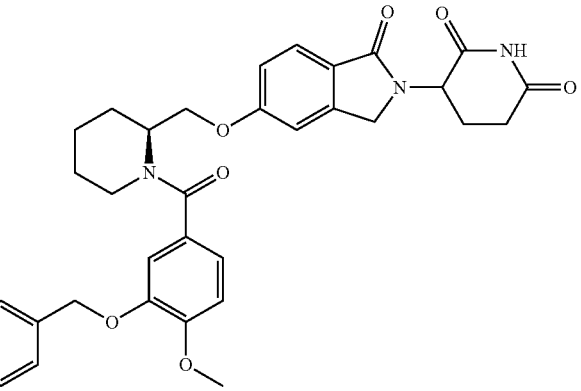 | 598.3 | 0.61 |
| I-72e | 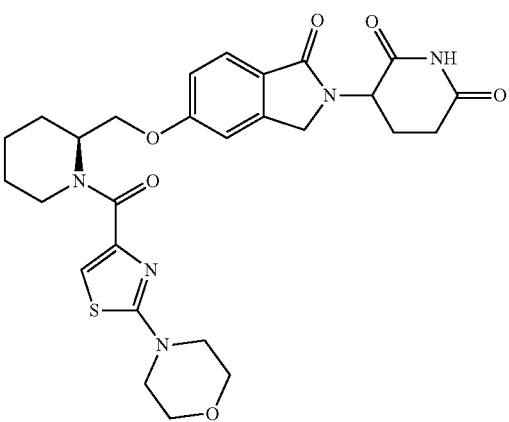 [SMILES: O=C1CCC(N2Cc3cc(OC[C@@H]4CCCCN4C(=O)c4csc(N5CCOCC5)n4)ccc3C2=O)C(=O)N1] | 554.25 | 0.56 |
| I-72f | 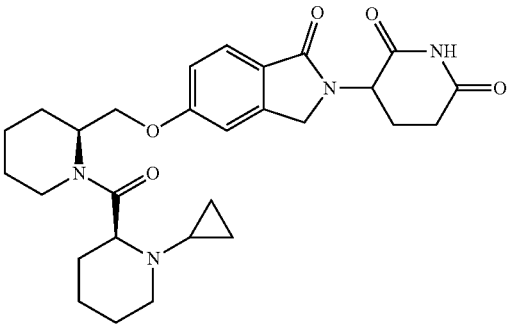 [SMILES: O=C1CCC(N2Cc3cc(OC[C@@H]4CCCCN4C(=O)[C@@H]4CCCCN4C4CC4)ccc3C2=O)C(=O)N1] | 509.32 | 0.42 |

-continued

| Compound Number | Structure | LCMS [M + H] | LCMS Rt |
| --- | --- | --- | --- |
| I-72g | 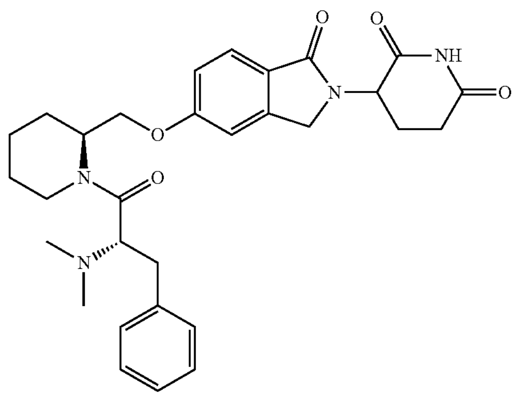 [SMILES: CN(C)[C@@H](Cc1ccccc1)C(=O)N1CCCC[C@H]1COc1ccc2c(c1)CN(C1CCC(=O)NC1=O)C2=O] | 533.33 | 0.48 |
| I-72h | 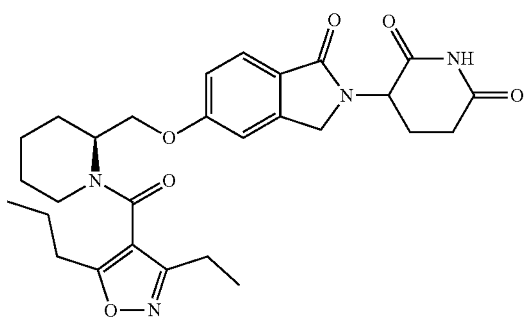 [SMILES: CCCc1onc(CC)c1C(=O)N1CCCC[C@H]1COc1ccc2c(c1)CN(C1CCC(=O)NC1=O)C2=O] | 523.2 | 0.59 |
| I-72i | 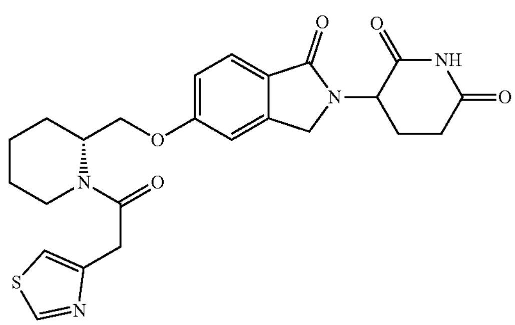 [SMILES: O=C1CCC(N2Cc3cc(OC[C@H]4CCCCN4C(=O)Cc4cscn4)ccc3C2=O)C(=O)N1] | 483.24 | 0.52 |
| I-72j | 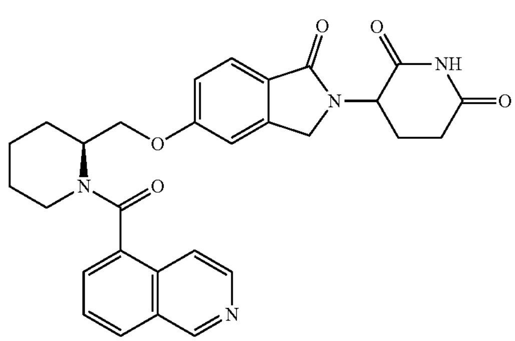 [SMILES: O=C1CCC(N2Cc3cc(OC[C@@H]4CCCCN4C(=O)c4cccc5cnccc45)ccc3C2=O)C(=O)N1] | 513.28 | 0.5 |

-continued

| Compound Number | Structure | LCMS [M + H] | LCMS Rt |
|---|---|---|---|
| I-72k | 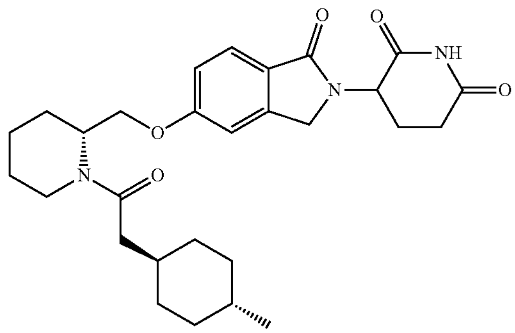 [SMILES: C[C@H]1CC[C@H](CC(=O)N2CCCC[C@@H]2COc2ccc3c(c2)CN(C2CCC(=O)NC2=O)C3=O)CC1] | 496.36 | 0.66 |
| I-72l | 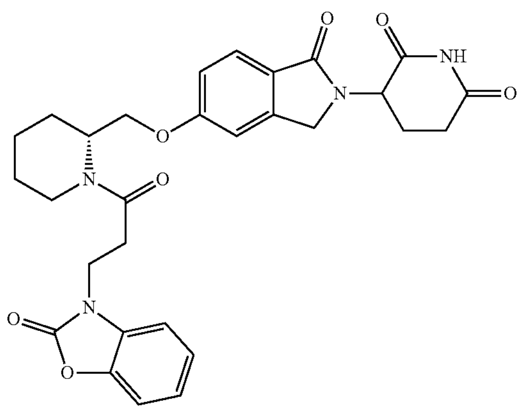 [SMILES: O=C1CCC(N2Cc3cc(OC[C@H]4CCCCN4C(=O)CCn4c(=O)oc5ccccc54)ccc3C2=O)C(=O)N1] | 547.28 | 0.57 |
| I-72m | 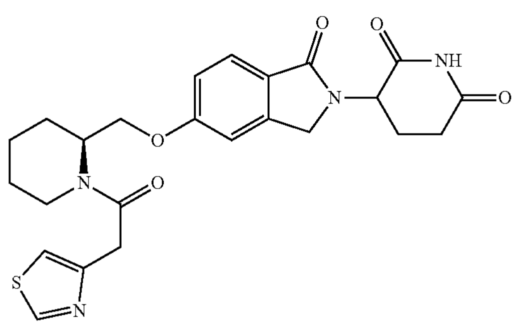 [SMILES: O=C1CCC(N2Cc3cc(OC[C@@H]4CCCCN4C(=O)Cc4cscn4)ccc3C2=O)C(=O)N1] | 483.26 | 0.52 |
| I-72n | 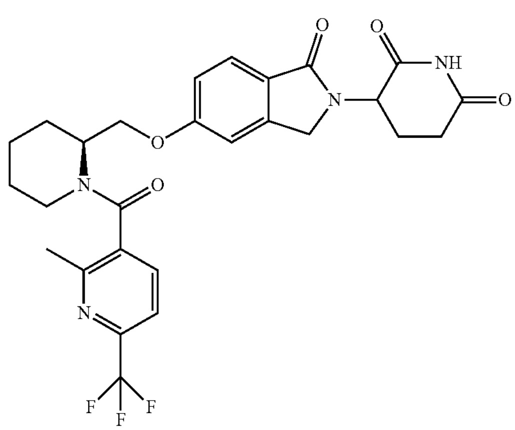 [SMILES: Cc1nc(C(F)(F)F)ccc1C(=O)N1CCCC[C@H]1COc1ccc2c(c1)CN(C1CCC(=O)NC1=O)C2=O] | 545.3 | 0.58 |

| Compound Number | Structure | LCMS [M + H] | LCMS Rt |
|---|---|---|---|
| I-72o | 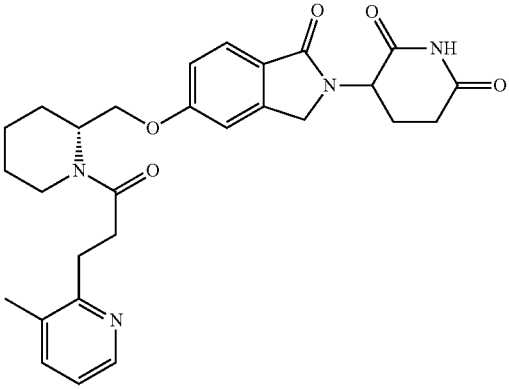 [SMILES: Cc1cccnc1CCC(=O)N1CCCC[C@@H]1COc1ccc2c(c1)CN(C1CCC(=O)NC1=O)C2=O] | 505.29 | 0.45 |
| I-72p | 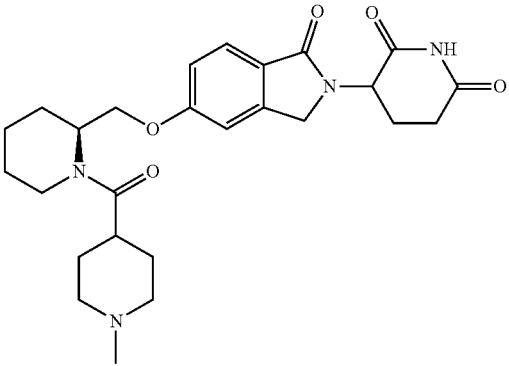 [SMILES: CN1CCC(C(=O)N2CCCC[C@H]2COc2ccc3c(c2)CN(C2CCC(=O)NC2=O)C3=O)CC1] | 483.34 | 0.42 |
| I-72q | 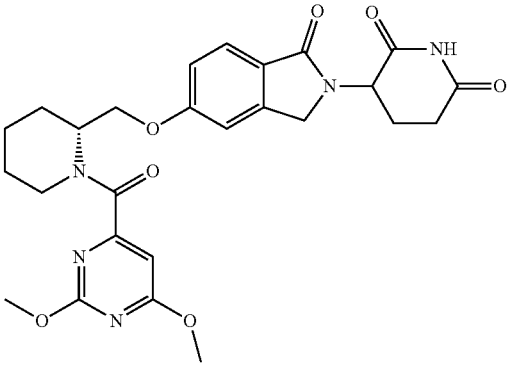 [SMILES: COc1cc(C(=O)N2CCCC[C@@H]2COc2ccc3c(c2)CN(C2CCC(=O)NC2=O)C3=O)nc(OC)n1] | 524.26 | 0.56 |
| I-72r | 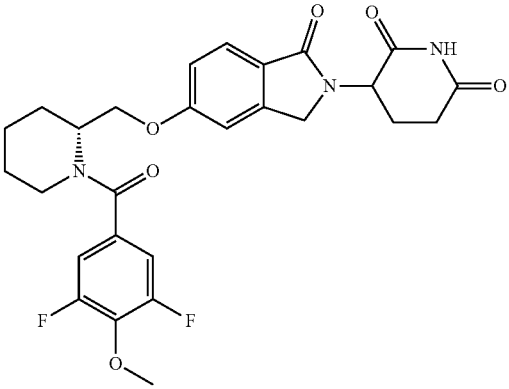 [SMILES: COc1c(F)cc(C(=O)N2CCCC[C@@H]2COc2ccc3c(c2)CN(C2CCC(=O)NC2=O)C3=O)cc1F] | 528.25 | 0.58 |

-continued
| Compound Number | Structure | LCMS [M + H] | LCMS Rt |
|---|---|---|---|
| I-72s | 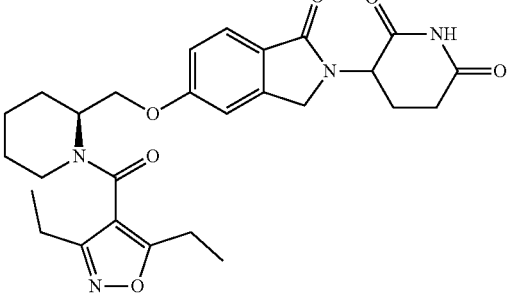 | 509.2 | 0.57 |
| I-72t | 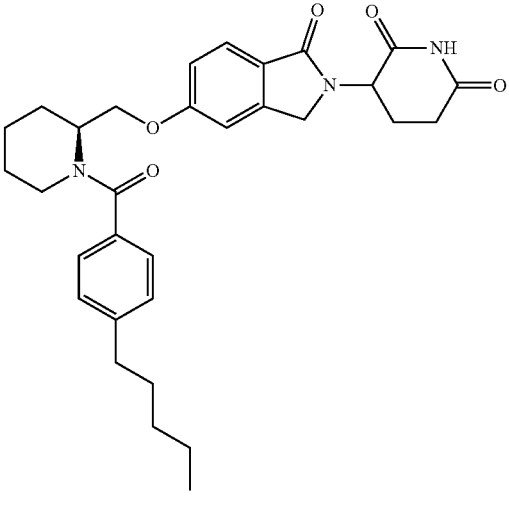 [SMILES: CCCCCc1ccc(C(=O)N2CCCC[C@H]2COc2ccc3c(c2)CN(C2CCC(=O)NC2=O)C3=O)cc1] | 532.33 | 0.68 |
| I-72u | 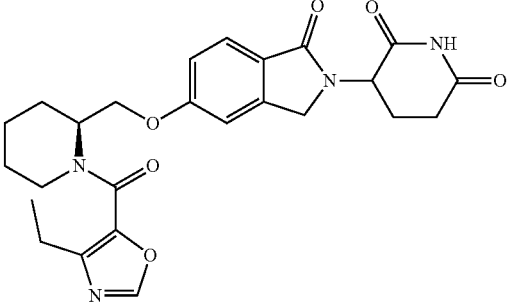 | 481.29 | 0.54 |
| I-72v | 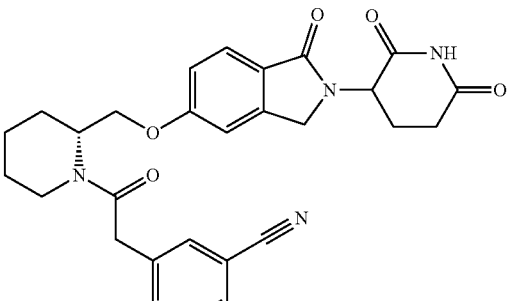 | 501.27 | 0.55 |

-continued

| Compound Number | Structure | LCMS [M + H] | LCMS Rt |
|---|---|---|---|
| I-72w | 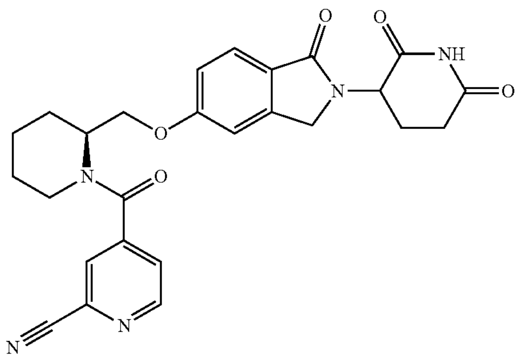 [SMILES: N#Cc1cc(C(=O)N2CCCC[C@H]2COc2ccc3c(c2)CN(C2CCC(=O)NC2=O)C3=O)ccn1] | 488.27 | 0.51 |
| I-72x | 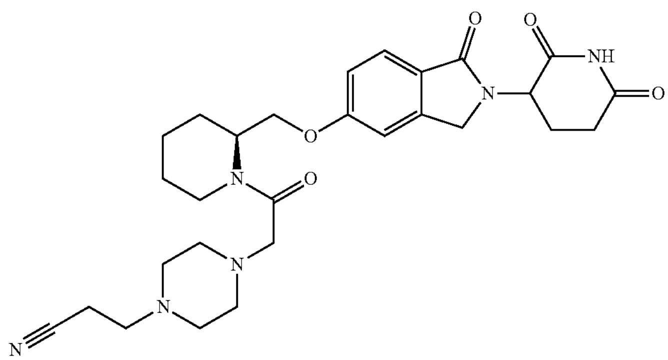 [SMILES: N#CCCN1CCN(CC(=O)N2CCCC[C@H]2COc2ccc3c(c2)CN(C2CCC(=O)NC2=O)C3=O)CC1] | 537.33 | 0.4 |
| I-72y | 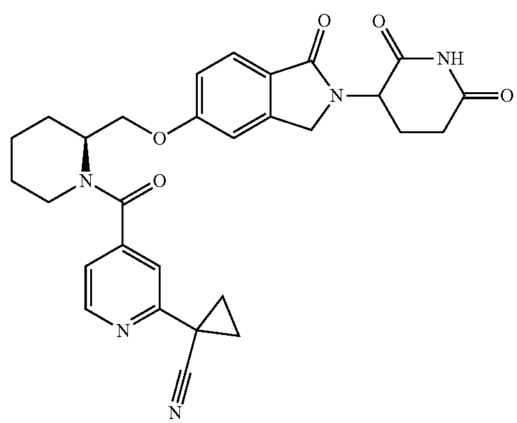 [SMILES: N#CC1(c2cc(C(=O)N3CCCC[C@H]3COc3ccc4c(c3)CN(C3CCC(=O)NC3=O)C4=O)ccn2)CC1] | 528.25 | 0.55 |
| I-72z | 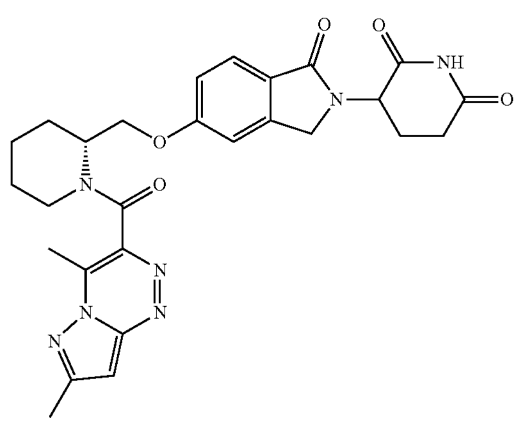 [SMILES: Cc1cc2nnc(C(=O)N3CCCC[C@@H]3COc3ccc4c(c3)CN(C3CCC(=O)NC3=O)C4=O)c(C)n2n1] | 532.3 | 0.54 |

-continued

| Compound Number | Structure | LCMS [M + H] | LCMS Rt |
|---|---|---|---|
| I-72aa | 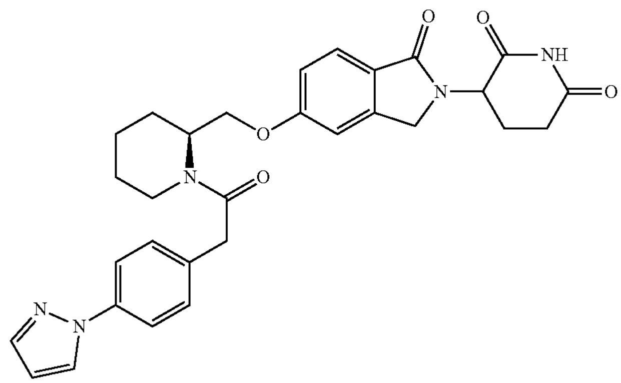 [SMILES: O=C1CCC(N2Cc3cc(OC[C@@H]4CCCCN4C(=O)Cc4ccc(-n5cccn5)cc4)ccc3C2=O)C(=O)N1] | 542.32 | 0.57 |
| I-72ab | 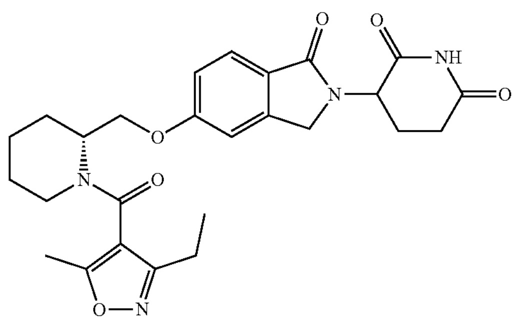 [SMILES: CCc1noc(C)c1C(=O)N1CCCC[C@@H]1COc1ccc2c(c1)CN(C1CCC(=O)NC1=O)C2=O] | 495.29 | 0.55 |
| I-72ac | 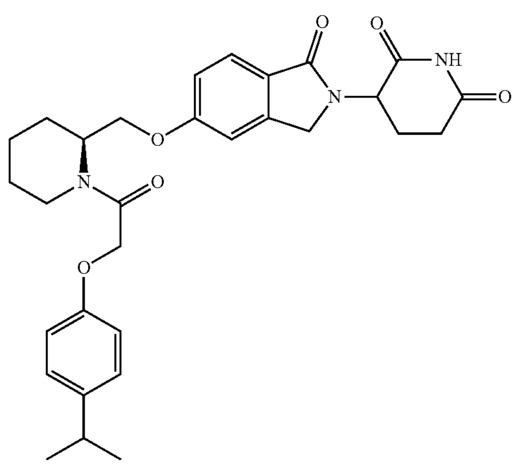 [SMILES: CC(C)c1ccc(OCC(=O)N2CCCC[C@H]2COc2ccc3c(c2)CN(C2CCC(=O)NC2=O)C3=O)cc1] | 534.29 | 0.64 |
| I-72ad | 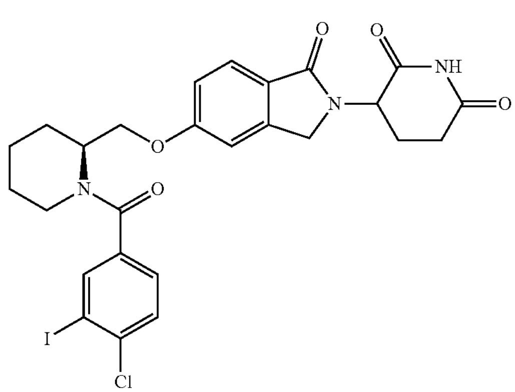 [SMILES: O=C1CCC(N2Cc3cc(OC[C@@H]4CCCCN4C(=O)c4ccc(Cl)c(I)c4)ccc3C2=O)C(=O)N1] | 622.08 | 0.62 |

-continued

| Compound Number | Structure | LCMS [M + H] | LCMS Rt |
|---|---|---|---|
| I-72ae | 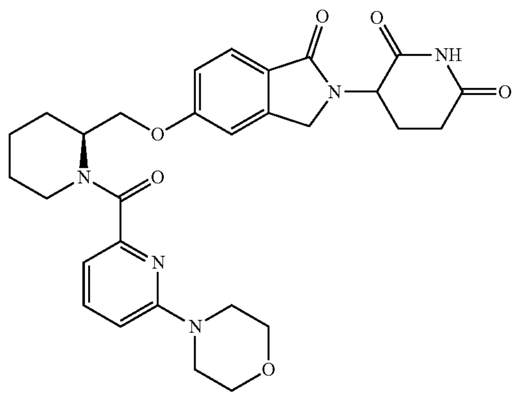 [SMILES: O=C1CCC(N2Cc3cc(OC[C@@H]4CCCCN4C(=O)c4cccc(N5CCOCC5)n4)ccc3C2=O)C(=O)N1] | 548.33 | 0.56 |
| I-72af | 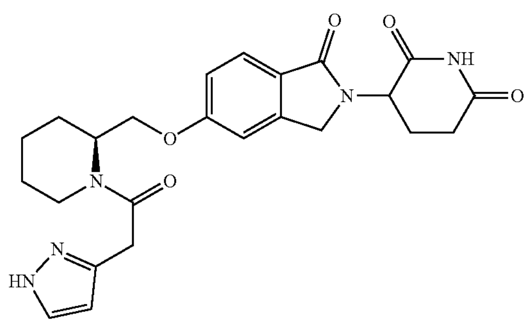 [SMILES: O=C1CCC(N2Cc3cc(OC[C@@H]4CCCCN4C(=O)Cc4cc[nH]n4)ccc3C2=O)C(=O)N1] | 466.29 | 0.51 |
| I-72ag | 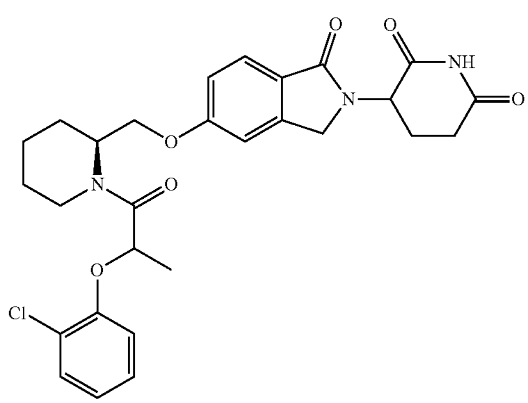 [SMILES: CC(Oc1ccccc1Cl)C(=O)N1CCCC[C@H]1COc1ccc2c(c1)CN(C1CCC(=O)NC1=O)C2=O] | 540.3 | 0.62 |
| I-72ah | 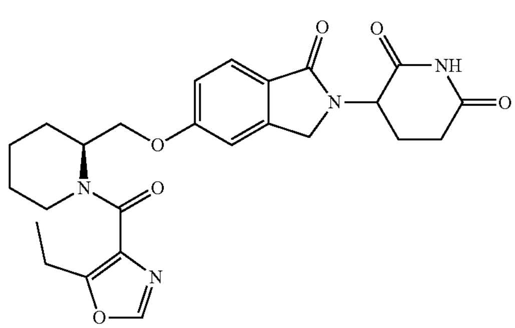 [SMILES: CCc1ocnc1C(=O)N1CCCC[C@H]1COc1ccc2c(c1)CN(C1CCC(=O)NC1=O)C2=O] | 481.26 | 0.56 |

| Compound Number | Structure | LCMS [M + H] | LCMS Rt |
|---|---|---|---|
| I-72ai | 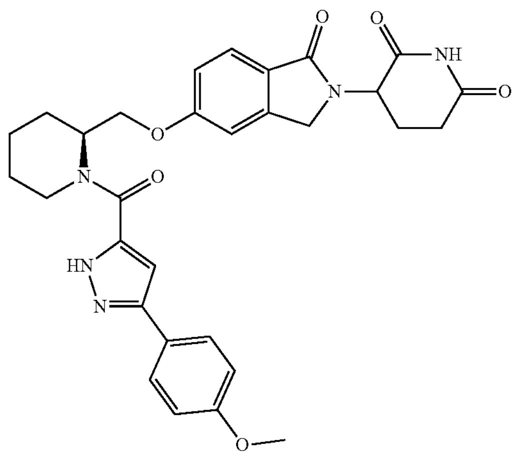 [SMILES: COc1ccc(-c2cc(C(=O)N3CCCC[C@H]3COc3ccc4c(c3)CN(C3CCC(=O)NC3=O)C4=O)[nH]n2)cc1] | 558.3 | 0.58 |
| I-72aj | 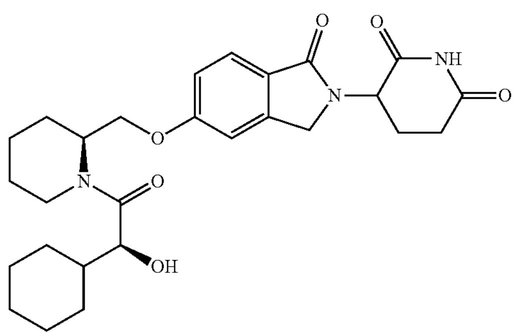 [SMILES: O=C1CCC(N2Cc3cc(OC[C@@H]4CCCCN4C(=O)[C@@H](O)C4CCCCC4)ccc3C2=O)C(=O)N1] | 498.34 | 0.6 |
| I-72ak | 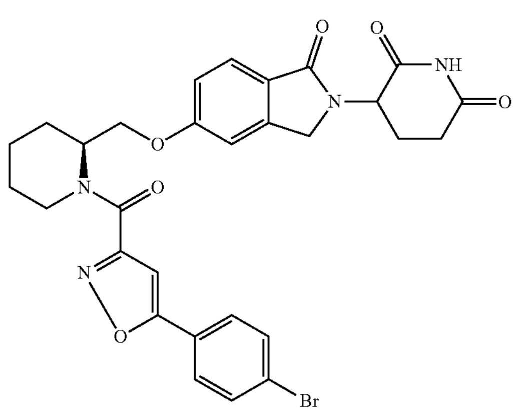 [SMILES: O=C1CCC(N2Cc3cc(OC[C@@H]4CCCCN4C(=O)c4cc(-c5ccc(Br)cc5)on4)ccc3C2=O)C(=O)N1] | 607.2 | 0.63 |

| Compound Number | Structure | LCMS [M + H] | LCMS Rt |
|---|---|---|---|
| I-72al | 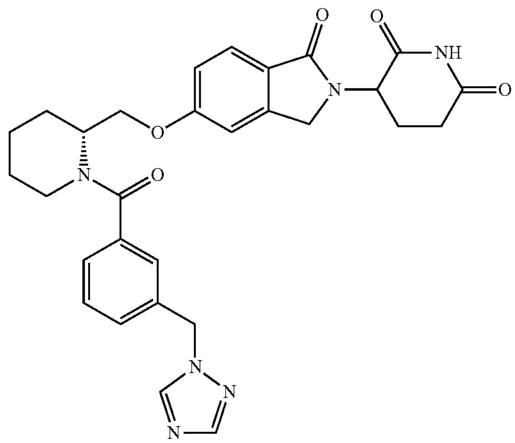 [SMILES: O=C1CCC(N2Cc3cc(OC[C@H]4CCCCN4C(=O)c4cccc(Cn5cncn5)c4)ccc3C2=O)C(=O)N1] | 543.28 | 0.52 |
| I-72am | 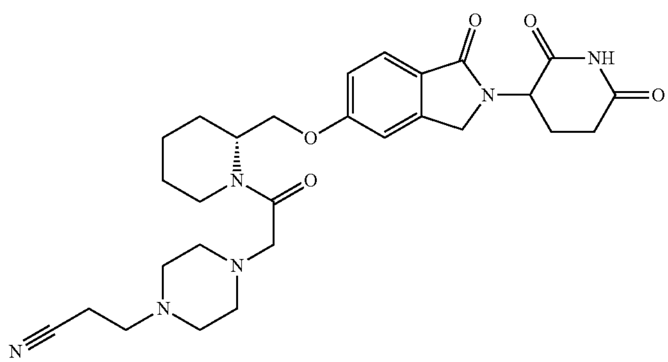 [SMILES: N#CCCN1CCN(CC(=O)N2CCCC[C@@H]2COc2ccc3c(c2)CN(C2CCC(=O)NC2=O)C3=O)CC1] | 537.36 | 0.4 |
| I-72an | 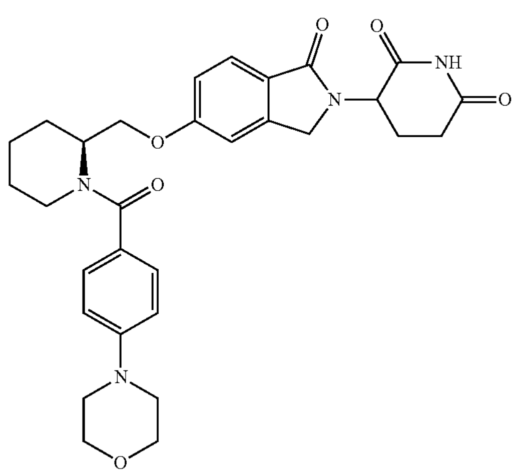 [SMILES: O=C1CCC(N2Cc3cc(OC[C@@H]4CCCCN4C(=O)c4ccc(N5CCOCC5)cc4)ccc3C2=O)C(=O)N1] | 547.32 | 0.56 |

| Compound Number | Structure | LCMS [M + H] | LCMS Rt |
|---|---|---|---|
| I-72ao | 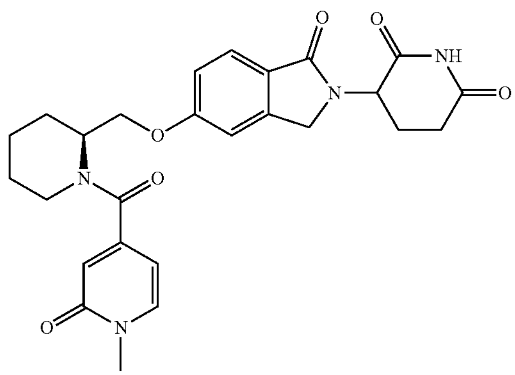 [SMILES: Cn1ccc(C(=O)N2CCCC[C@H]2COc2ccc3c(c2)CN(C2CCC(=O)NC2=O)C3=O)cc1=O] | 493.32 | 0.49 |
| I-72ap | 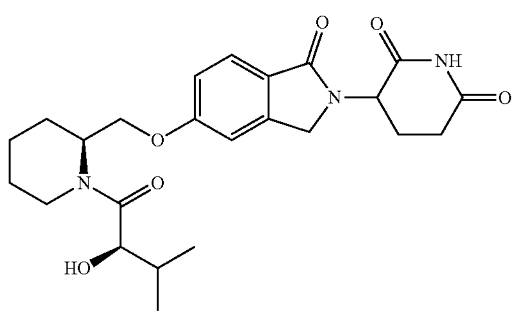 [SMILES: CC(C)[C@@H](O)C(=O)N1CCCC[C@H]1COc1ccc2c(c1)CN(C1CCC(=O)NC1=O)C2=O] | 458.27 | 0.56 |
| I-72aq | 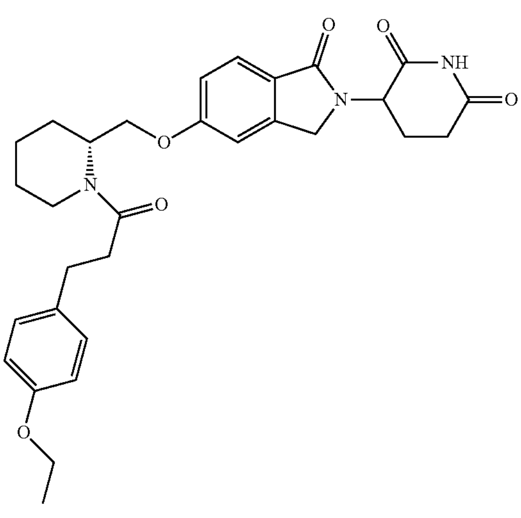 [SMILES: CCOc1ccc(CCC(=O)N2CCCC[C@@H]2COc2ccc3c(c2)CN(C2CCC(=O)NC2=O)C3=O)cc1] | 534.29 | 0.62 |

| Compound Number | Structure | LCMS [M + H] | LCMS Rt |
|---|---|---|---|
| I-72ar | 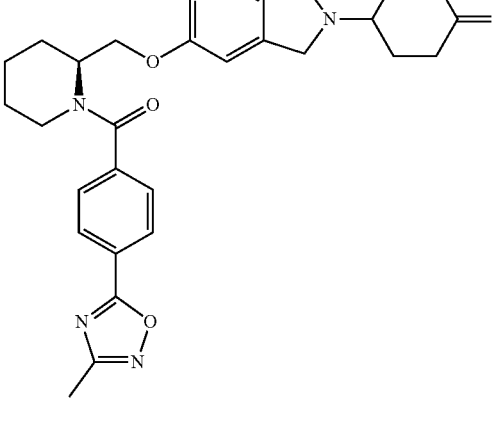 | 544.25 | 0.58 |
| I-72as | 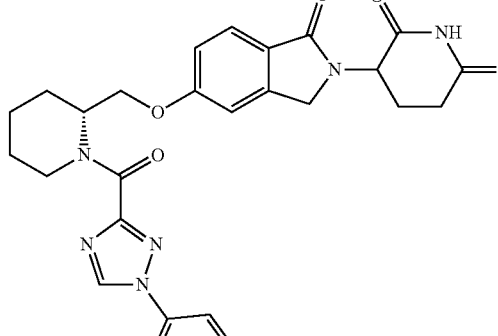 | 529.26 | 0.57 |
| I-72at | 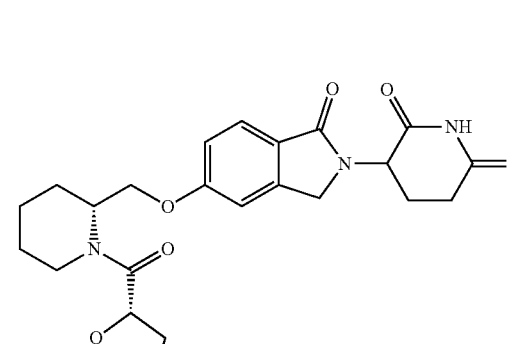 | 470.24 | 0.48 |

-continued

| Compound Number | Structure | LCMS [M + H] | LCMS Rt |
|---|---|---|---|
| I-72au | 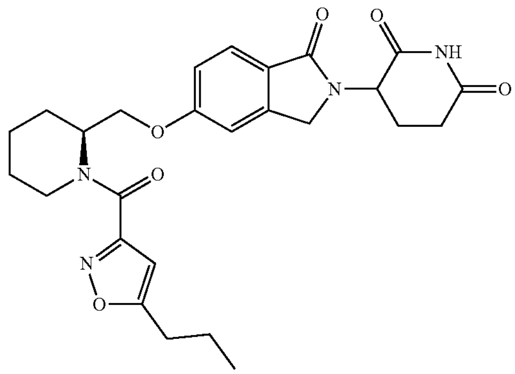 [SMILES: CCCc1cc(C(=O)N2CCCC[C@H]2COc2ccc3c(c2)CN(C2CCC(=O)NC2=O)C3=O)no1] | 495.28 | 0.59 |
| I-72av | 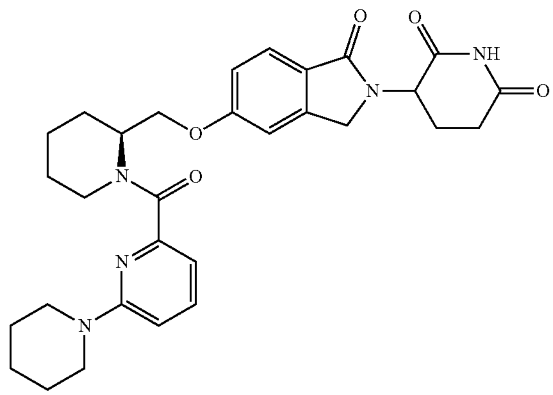 [SMILES: O=C1CCC(N2Cc3cc(OC[C@@H]4CCCCN4C(=O)c4cccc(N5CCCCC5)n4)ccc3C2=O)C(=O)N1] | 546.36 | 0.62 |
| I-72aw | 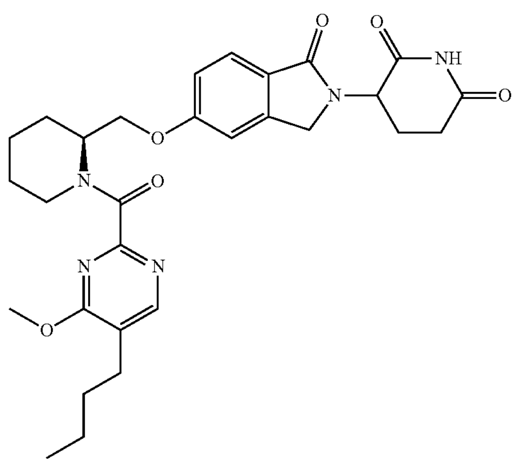 [SMILES: CCCCc1cnc(C(=O)N2CCCC[C@H]2COc2ccc3c(c2)CN(C2CCC(=O)NC2=O)C3=O)nc1OC] | 550.2 | 0.62 |
| I-72ax | 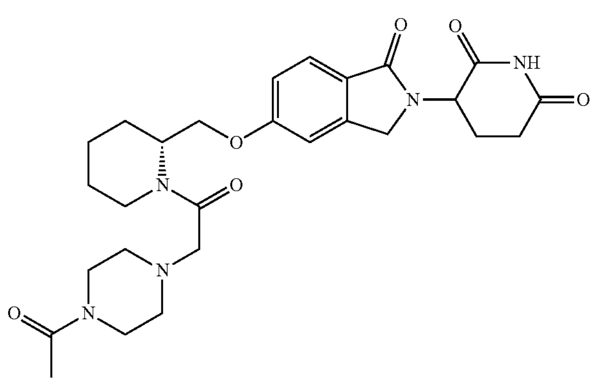 [SMILES: CC(=O)N1CCN(CC(=O)N2CCCC[C@@H]2COc2ccc3c(c2)CN(C2CCC(=O)NC2=O)C3=O)CC1] | 526.35 | 0.4 |

| Compound Number | Structure | LCMS [M + H] | LCMS Rt |
|---|---|---|---|
| I-72ay | 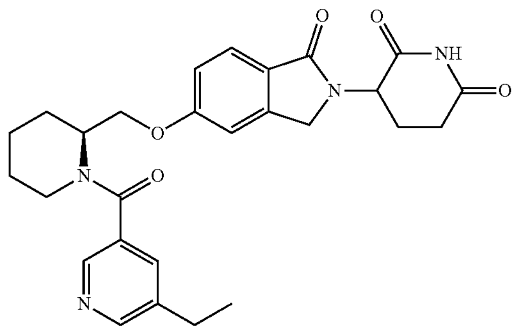 [SMILES: CCc1cncc(C(=O)N2CCCC[C@H]2COc2ccc3c(c2)CN(C2CCC(=O)NC2=O)C3=O)c1] | 491.31 | 0.54 |
| I-72az | 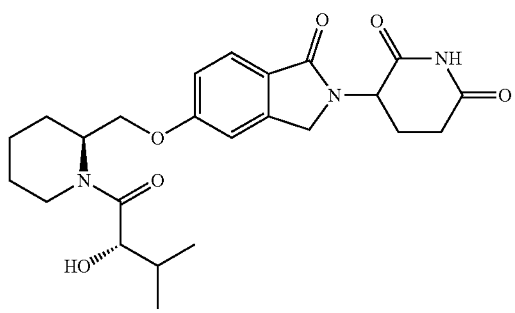 | 458.27 | 0.55 |
| I-72ba | 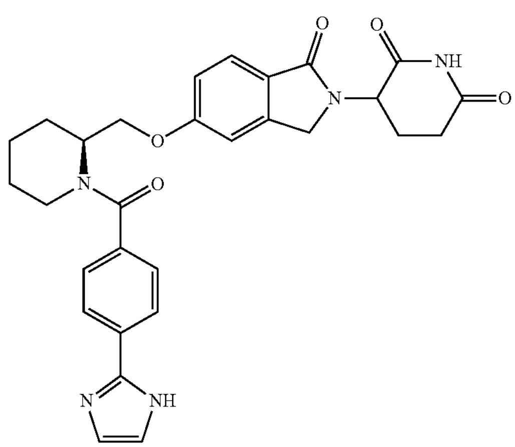 [SMILES: O=C1CCC(N2Cc3cc(OC[C@@H]4CCCCN4C(=O)c4ccc(-c5ncc[nH]5)cc4)ccc3C2=O)C(=O)N1] | 528.31 | 0.44 |
| I-72bb | 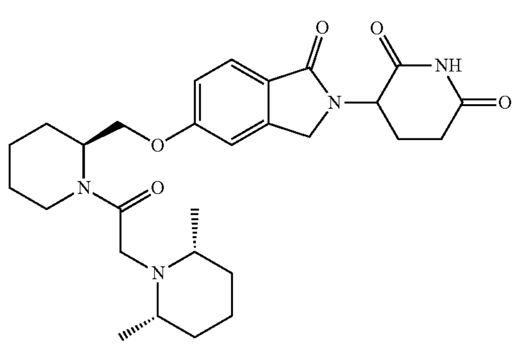 [SMILES: C[C@@H]1CCC[C@H](C)N1CC(=O)N1CCCC[C@H]1COc1ccc2c(c1)CN(C1CCC(=O)NC1=O)C2=O] | 511.34 | 0.43 |

| Compound Number | Structure | LCMS [M + H] | LCMS Rt |
|---|---|---|---|
| I-72bc | 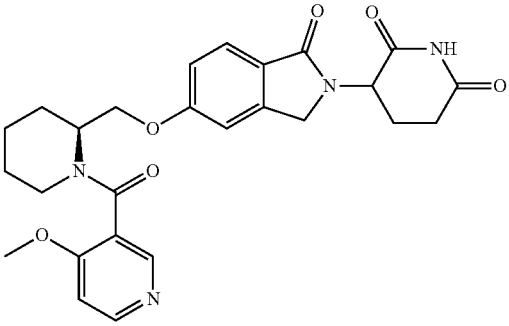 [SMILES: COc1ccncc1C(=O)N1CCCC[C@H]1COc1ccc2c(c1)CN(C1CCC(=O)NC1=O)C2=O] | 493.31 | 0.45 |
| I-72bd | 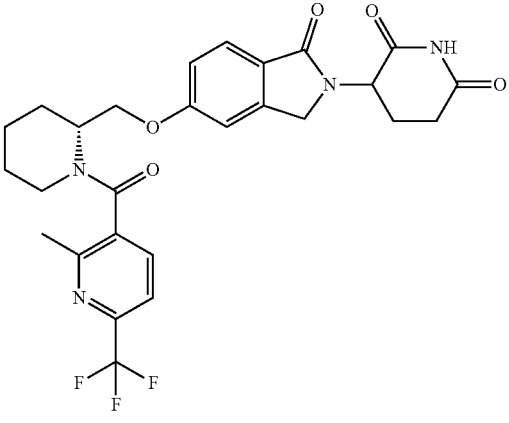 [SMILES: Cc1nc(C(F)(F)F)ccc1C(=O)N1CCCC[C@@H]1COc1ccc2c(c1)CN(C1CCC(=O)NC1=O)C2=O] | 545.22 | 0.58 |
| I-72be | 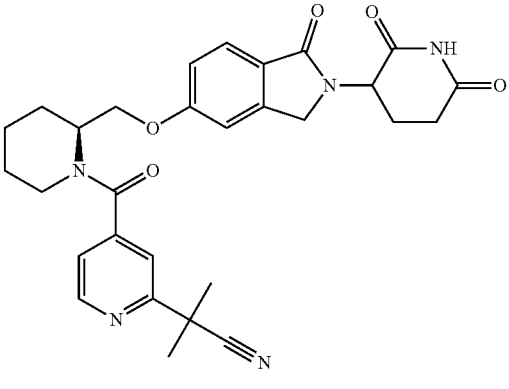 [SMILES: CC(C)(C#N)c1cc(C(=O)N2CCCC[C@H]2COc2ccc3c(c2)CN(C2CCC(=O)NC2=O)C3=O)ccn1] | 530.29 | 0.55 |
| I-72bf | 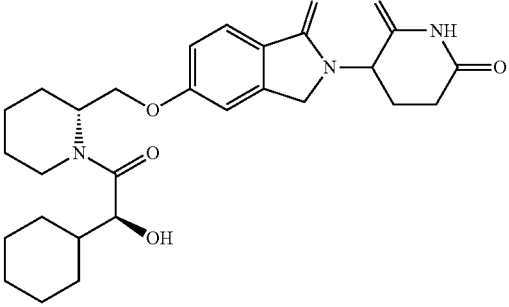 | 498.33 | 0.61 |

-continued

| Compound Number | Structure | LCMS [M + H] | LCMS Rt |
|---|---|---|---|
| I-72bg | 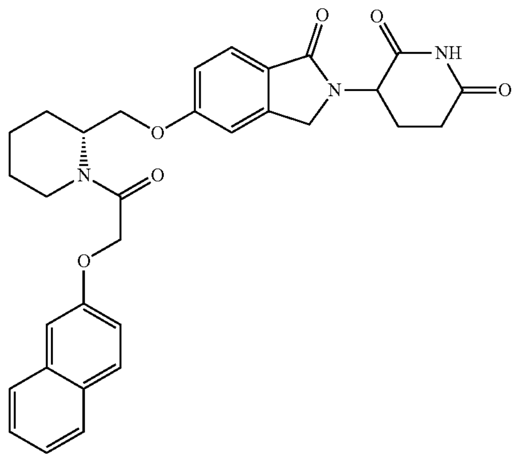 [SMILES: O=C1CCC(N2Cc3cc(OC[C@H]4CCCCN4C(=O)COc4ccc5ccccc5c4)ccc3C2=O)C(=O)N1] | 542.23 | 0.62 |
| I-72bh | 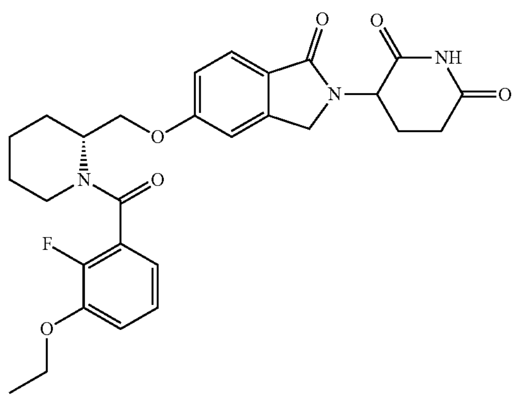 [SMILES: CCOc1cccc(C(=O)N2CCCC[C@@H]2COc2ccc3c(c2)CN(C2CCC(=O)NC2=O)C3=O)c1F] | 524.26 | 0.59 |
| I-72bi | 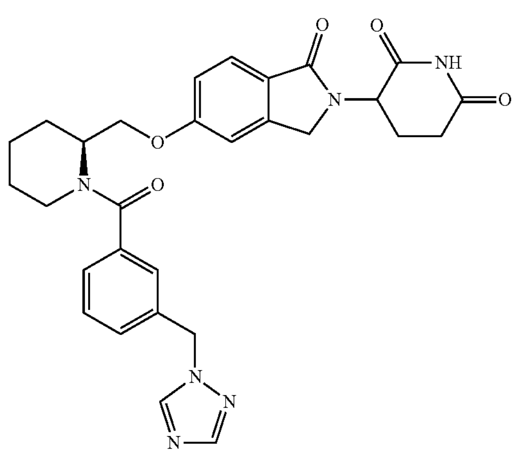 [SMILES: O=C1CCC(N2Cc3cc(OC[C@@H]4CCCCN4C(=O)c4cccc(Cn5cncn5)c4)ccc3C2=O)C(=O)N1] | 543.3 | 0.52 |

-continued
| Compound Number | Structure | LCMS [M + H] | LCMS Rt |
|---|---|---|---|
| I-72bj | 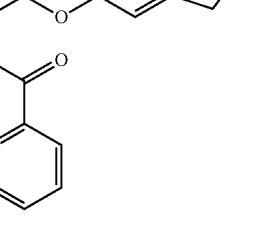 | 546.33 | 0.62 |
| I-72bk | 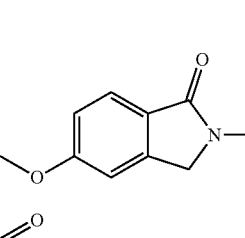 | 484.3 | 0.54 |
| I-72bl | 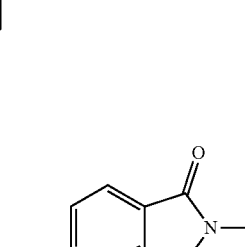 | 506.25 | 0.57 |
| I-72bm | 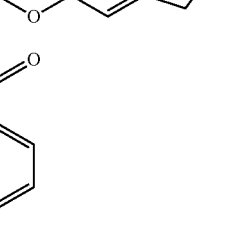 | 560.27 | 0.62 |

| Compound Number | Structure | LCMS [M + H] | LCMS Rt |
|---|---|---|---|
| I-72bn | 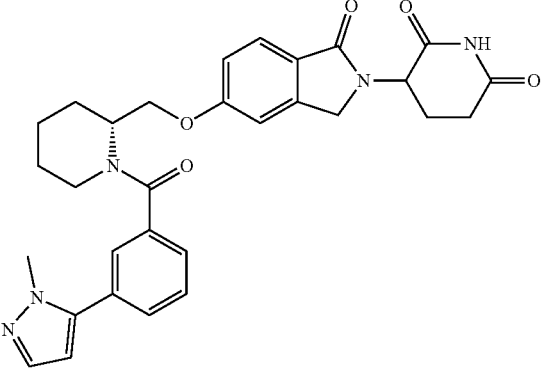 [SMILES: Cn1nccc1-c1cccc(C(=O)N2CCCC[C@@H]2COc2ccc3c(c2)CN(C2CCC(=O)NC2=O)C3=O)c1] | 542.31 | 0.57 |
| I-72bo | 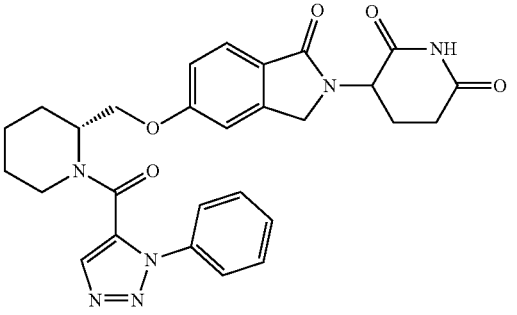 [SMILES: O=C1CCC(N2Cc3cc(OC[C@H]4CCCCN4C(=O)c4cnnn4-c4ccccc4)ccc3C2=O)C(=O)N1] | 529.3 | 0.55 |
| I-72bp | 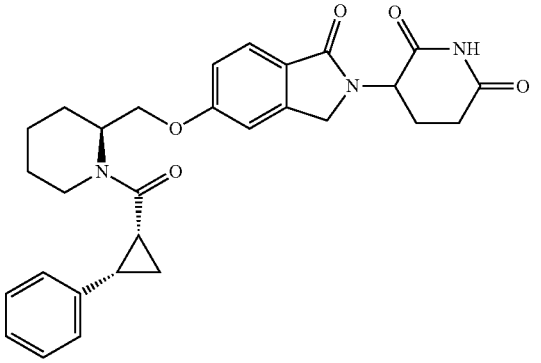 [SMILES: O=C1CCC(N2Cc3cc(OC[C@@H]4CCCCN4C(=O)[C@@H]4C[C@@H]4c4ccccc4)ccc3C2=O)C(=O)N1] | 502.3 | 0.61 |
| I-72bq | 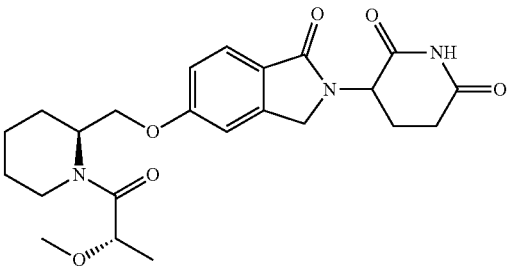 [SMILES: CO[C@@H](C)C(=O)N1CCCC[C@H]1COc1ccc2c(c1)CN(C1CCC(=O)NC1=O)C2=O] | 444.26 | 0.53 |

| Compound Number | Structure | LCMS [M + H] | LCMS Rt |
|---|---|---|---|
| I-72br | 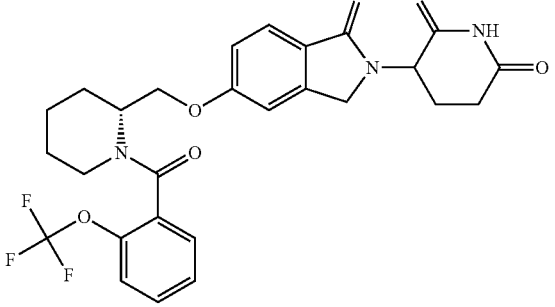 | 546.21 | 0.61 |
| I-72bs | 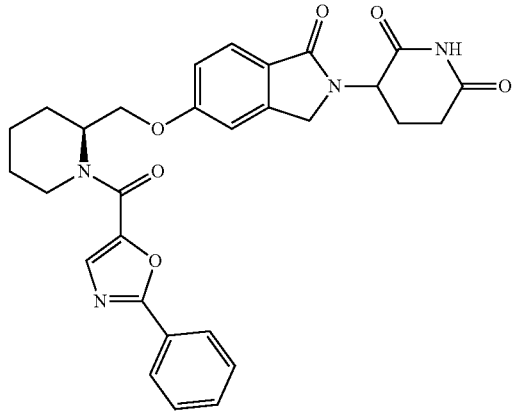 [SMILES: O=C1CCC(N2Cc3cc(OC[C@@H]4CCCCN4C(=O)c4cnc(-c5ccccc5)o4)ccc3C2=O)C(=O)N1] | 529.27 | 0.59 |
| I-72bt | 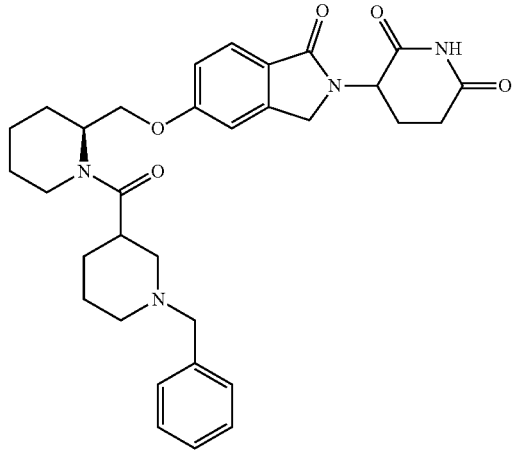 [SMILES: O=C1CCC(N2Cc3cc(OC[C@@H]4CCCCN4C(=O)C4CCCN(Cc5ccccc5)C4)ccc3C2=O)C(=O)N1] | 559.33 | 0.46 |
| I-72bu | 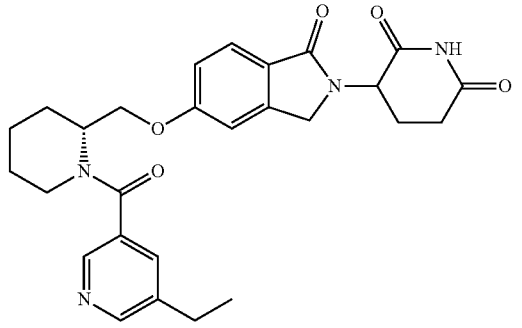 [SMILES: CCc1cncc(C(=O)N2CCCC[C@@H]2COc2ccc3c(c2)CN(C2CCC(=O)NC2=O)C3=O)c1] | 491.3 | 0.54 |

-continued
| Compound Number | Structure | LCMS [M + H] | LCMS Rt |
|---|---|---|---|
| I-72bv | 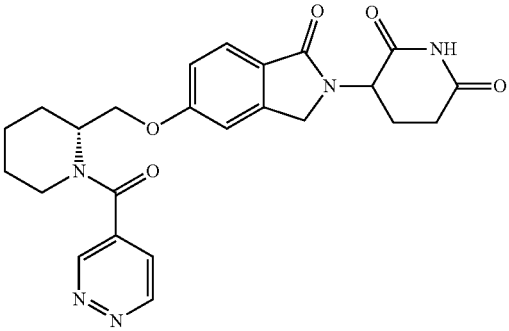 [SMILES: O=C1CCC(N2Cc3cc(OC[C@H]4CCCCN4C(=O)c4ccnnc4)ccc3C2=O)C(=O)N1] | 464.26 | 0.47 |
| I-72bw | 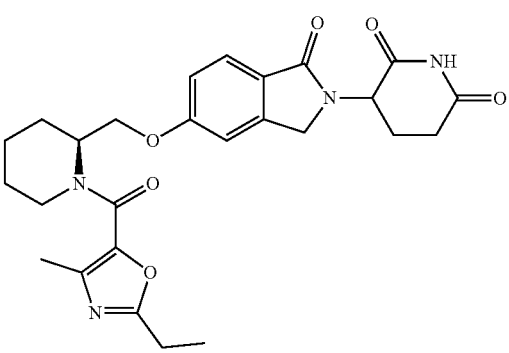 [SMILES: CCc1nc(C)c(C(=O)N2CCCC[C@H]2COc2ccc3c(c2)CN(C2CCC(=O)NC2=O)C3=O)o1] | 495.3 | 0.55 |
| I-72bx | 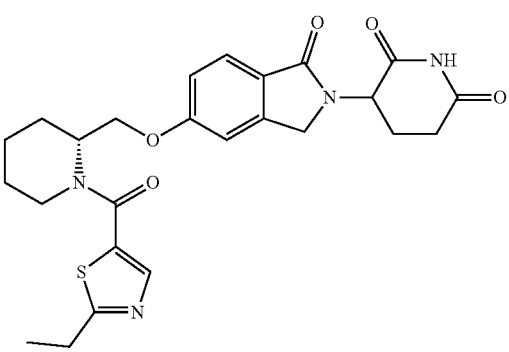 [SMILES: CCc1ncc(C(=O)N2CCCC[C@@H]2COc2ccc3c(c2)CN(C2CCC(=O)NC2=O)C3=O)s1] | 497.22 | 0.56 |
| I-72by | 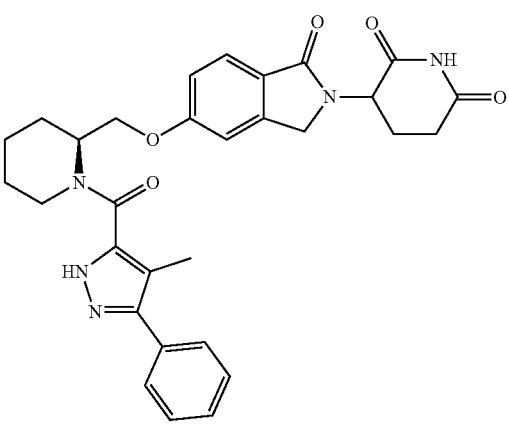 [SMILES: Cc1c(-c2ccccc2)n[nH]c1C(=O)N1CCCC[C@H]1COc1ccc2c(c1)CN(C1CCC(=O)NC1=O)C2=O] | 542.3 | 0.59 |

| Compound Number | Structure | LCMS [M + H] | LCMS Rt |
|---|---|---|---|
| I-72bz | 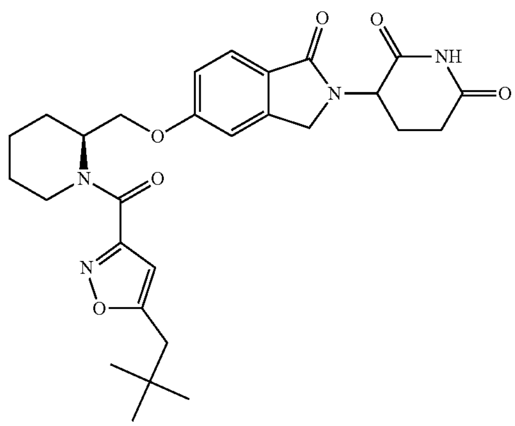 [SMILES: CC(C)(C)Cc1cc(C(=O)N2CCCC[C@H]2COc2ccc3c(c2)CN(C2CCC(=O)NC2=O)C3=O)no1] | 523.3 | 0.63 |
| I-72ca | 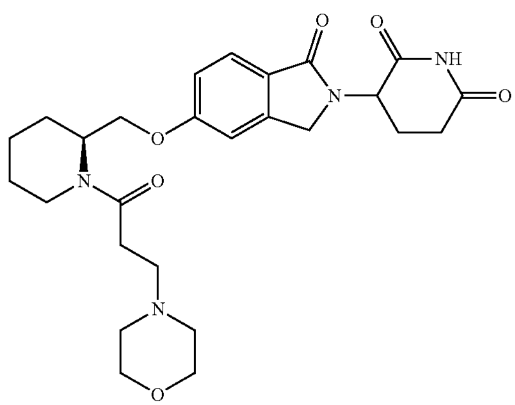 [SMILES: O=C1CCC(N2Cc3cc(OC[C@@H]4CCCCN4C(=O)CCN4CCOCC4)ccc3C2=O)C(=O)N1] | 499.34 | 0.41 |
| I-72cb | 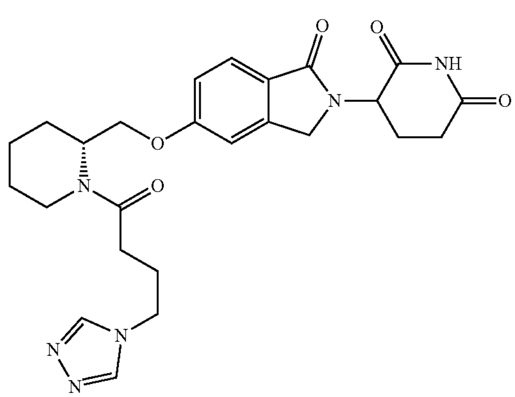 [SMILES: O=C1CCC(N2Cc3cc(OC[C@H]4CCCCN4C(=O)CCCn4cnnc4)ccc3C2=O)C(=O)N1] | 495.3 | 0.5 |
| I-72cc | 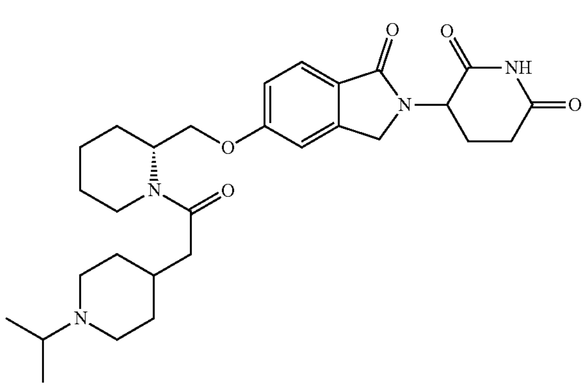 [SMILES: CC(C)N1CCC(CC(=O)N2CCCC[C@@H]2COc2ccc3c(c2)CN(C2CCC(=O)NC2=O)C3=O)CC1] | 525.37 | 0.44 |

-continued
| Compound Number | Structure | LCMS [M + H] | LCMS Rt |
|---|---|---|---|
| I-72cd | 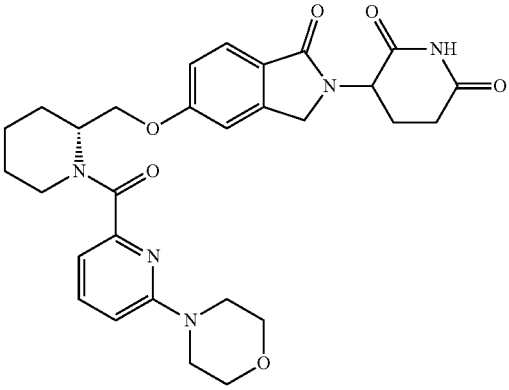 [SMILES: O=C1CCC(N2Cc3cc(OC[C@H]4CCCCN4C(=O)c4cccc(N5CCOCC5)n4)ccc3C2=O)C(=O)N1] | 548.33 | 0.56 |
| I-72ce | 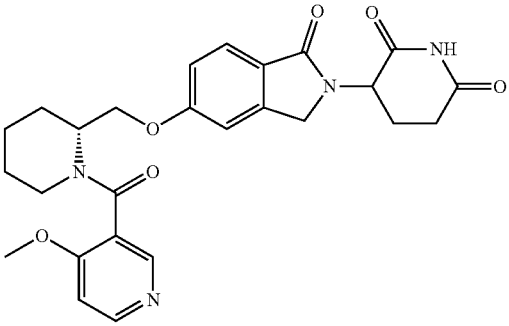 [SMILES: COc1ccncc1C(=O)N1CCCC[C@@H]1COc1ccc2c(c1)CN(C1CCC(=O)NC1=O)C2=O] | 493.28 | 0.45 |
| I-72cf | 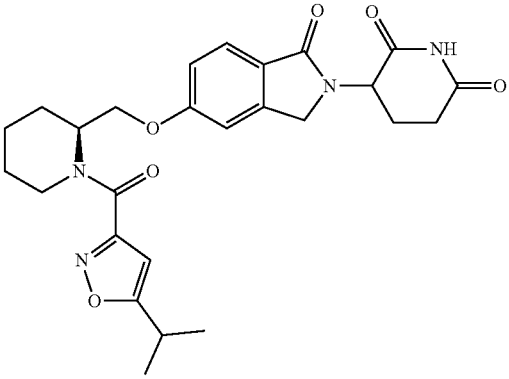 [SMILES: CC(C)c1cc(C(=O)N2CCCC[C@H]2COc2ccc3c(c2)CN(C2CCC(=O)NC2=O)C3=O)no1] | 495.32 | 0.59 |
| I-72cg | 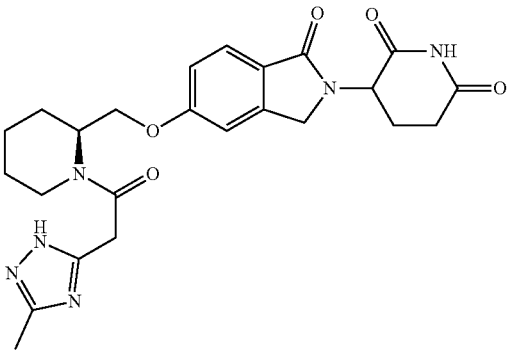 [SMILES: Cc1n[nH]c(CC(=O)N2CCCC[C@H]2COc2ccc3c(c2)CN(C2CCC(=O)NC2=O)C3=O)n1] | 481.31 | 0.48 |

-continued

| Compound Number | Structure | LCMS [M + H] | LCMS Rt |
|---|---|---|---|
| I-72ch | 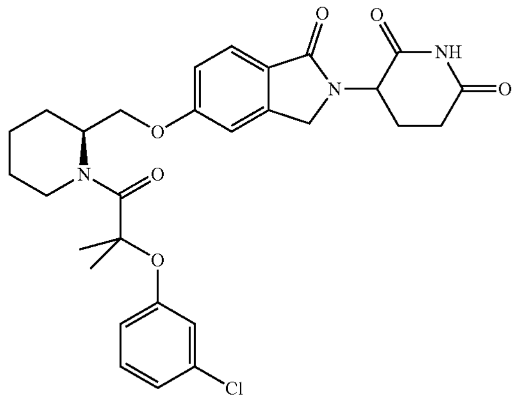 [SMILES: CC(C)(Oc1cccc(Cl)c1)C(=O)N1CCCC[C@H]1COc1ccc2c(c1)CN(C1CCC(=O)NC1=O)C2=O] | 554.22 | 0.67 |
| I-72ci | 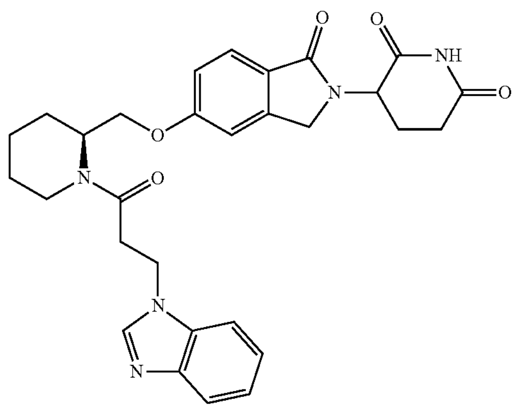 [SMILES: O=C1CCC(N2Cc3cc(OC[C@@H]4CCCCN4C(=O)CCn4cnc5ccccc54)ccc3C2=O)C(=O)N1] | 530.2 | 0.46 |
| I-72cj | 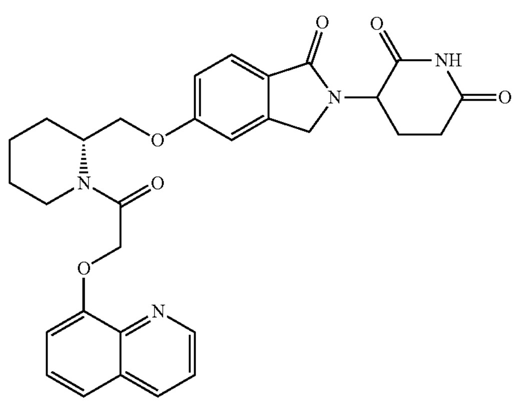 [SMILES: O=C1CCC(N2Cc3cc(OC[C@H]4CCCCN4C(=O)COc4cccc5cccnc45)ccc3C2=O)C(=O)N1] | 543.27 | 0.49 |
| I-72ck | 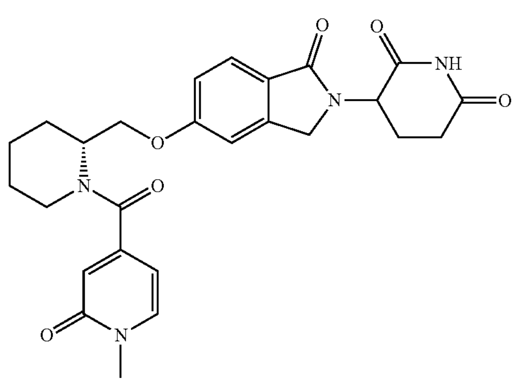 [SMILES: Cn1ccc(C(=O)N2CCCC[C@@H]2COc2ccc3c(c2)CN(C2CCC(=O)NC2=O)C3=O)cc1=O] | 493.26 | 0.48 |

-continued

| Compound Number | Structure | LCMS [M + H] | LCMS Rt |
|---|---|---|---|
| I-72cl | 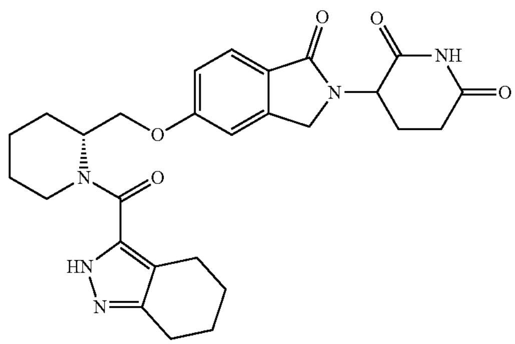 [SMILES: O=C1CCC(N2Cc3cc(OC[C@H]4CCCCN4C(=O)c4[nH]nc5c4CCCC5)ccc3C2=O)C(=O)N1] | 506.3 | 0.57 |
| I-72cm | 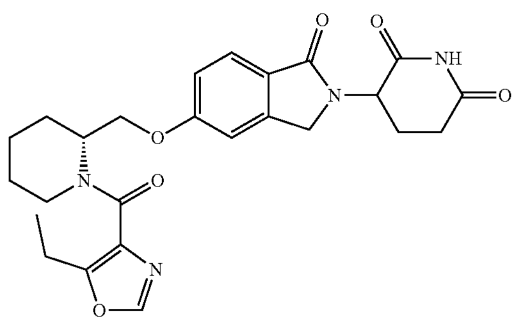 [SMILES: CCc1ocnc1C(=O)N1CCCC[C@@H]1COc1ccc2c(c1)CN(C1CCC(=O)NC1=O)C2=O] | 481.3 | 0.56 |
| I-72cn | 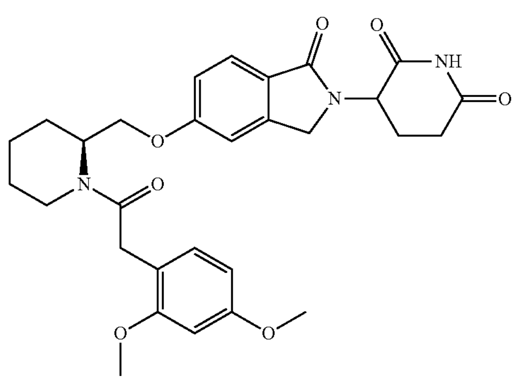 [SMILES: COc1ccc(CC(=O)N2CCCC[C@H]2COc2ccc3c(c2)CN(C2CCC(=O)NC2=O)C3=O)c(OC)c1] | 536.3 | 0.59 |
| I-72co | 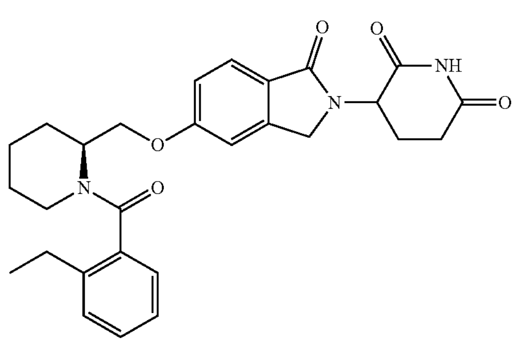 [SMILES: CCc1ccccc1C(=O)N1CCCC[C@H]1COc1ccc2c(c1)CN(C1CCC(=O)NC1=O)C2=O] | 490.3 | 0.61 |

-continued

| Compound Number | Structure | LCMS [M + H] | LCMS Rt |
|---|---|---|---|
| I-72cp | 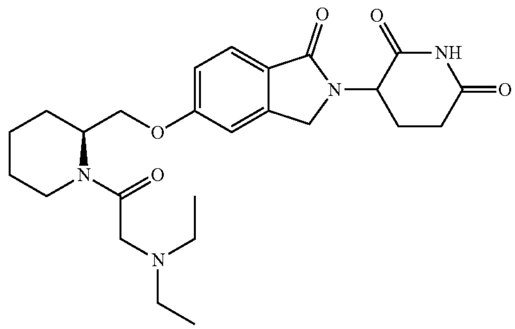 [SMILES: CCN(CC)CC(=O)N1CCCC[C@H]1COc1ccc2c(c1)CN(C1CCC(=O)NC1=O)C2=O] | 471.35 | 0.41 |
| I-72cq | 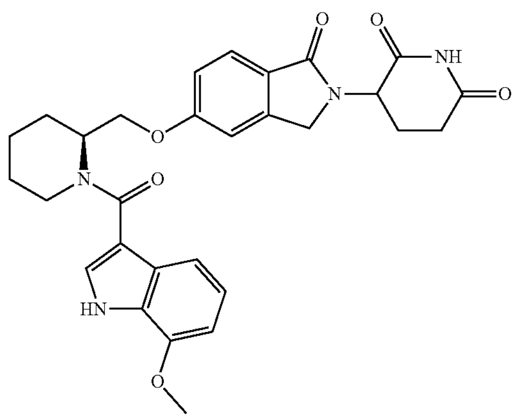 [SMILES: COc1cccc2c(C(=O)N3CCCC[C@H]3COc3ccc4c(c3)CN(C3CCC(=O)NC3=O)C4=O)c[nH]c12] | 531.25 | 0.59 |
| I-72cr | 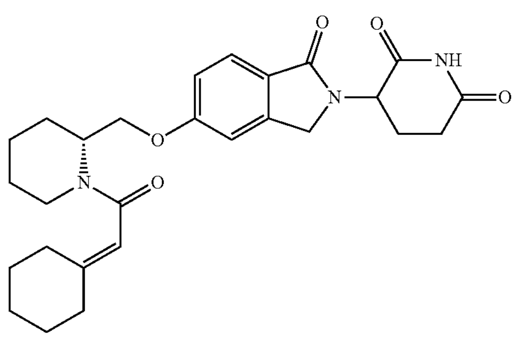 [SMILES: O=C1CCC(N2Cc3cc(OC[C@H]4CCCCN4C(=O)C=C4CCCCC4)ccc3C2=O)C(=O)N1] | 480.31 | 0.62 |
| I-72cs | 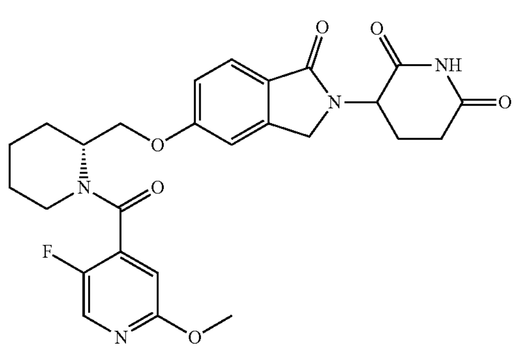 [SMILES: COc1cc(C(=O)N2CCCC[C@@H]2COc2ccc3c(c2)CN(C2CCC(=O)NC2=O)C3=O)c(F)cn1] | 511.23 | 0.57 |

-continued

| Compound Number | Structure | LCMS [M + H] | LCMS Rt |
|---|---|---|---|
| I-72ct | 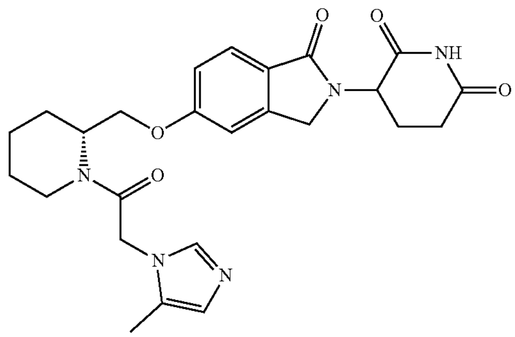 [SMILES: Cc1cncn1CC(=O)N1CCCC[C@@H]1COc1ccc2c(c1)CN(C1CCC(=O)NC1=O)C2=O] | 480.31 | 0.41 |
| I-72cu | 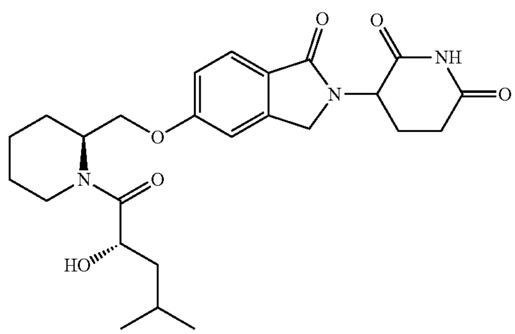 [SMILES: CC(C)C[C@H](O)C(=O)N1CCCC[C@H]1COc1ccc2c(c1)CN(C1CCC(=O)NC1=O)C2=O] | 472.28 | 0.58 |
| I-72cv | 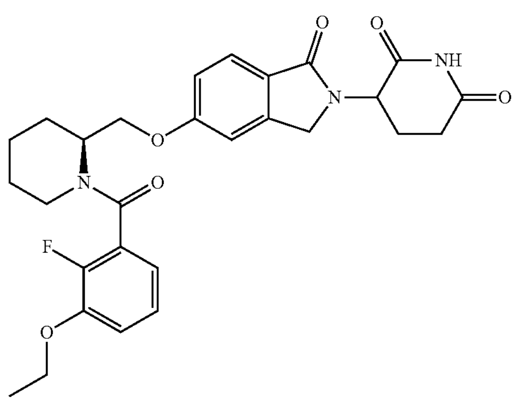 [SMILES: CCOc1cccc(C(=O)N2CCCC[C@H]2COc2ccc3c(c2)CN(C2CCC(=O)NC2=O)C3=O)c1F] | 524.27 | 0.59 |
| I-72cw | 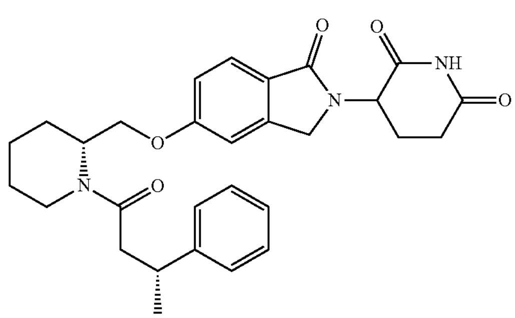 [SMILES: C[C@H](CC(=O)N1CCCC[C@@H]1COc1ccc2c(c1)CN(C1CCC(=O)NC1=O)C2=O)c1ccccc1] | 504.29 | 0.62 |

-continued

| Compound Number | Structure | LCMS [M + H] | LCMS Rt |
|---|---|---|---|
| I-72cx | 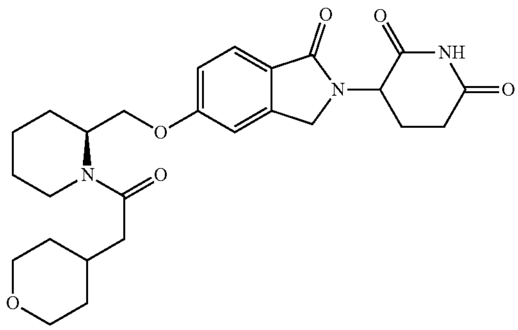 [SMILES: O=C1CCC(N2Cc3cc(OC[C@@H]4CCCCN4C(=O)CC4CCOCC4)ccc3C2=O)C(=O)N1] | 484.31 | 0.54 |
| I-72cy | 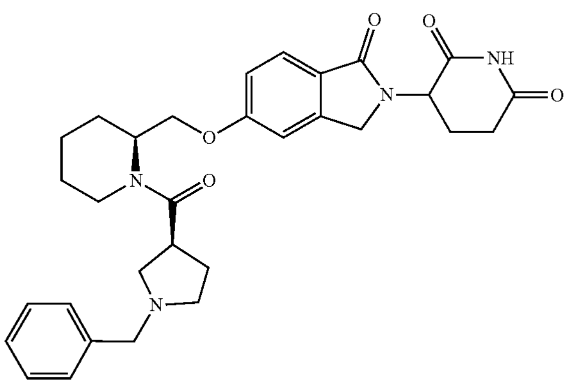 [SMILES: O=C1CCC(N2Cc3cc(OC[C@@H]4CCCCN4C(=O)[C@H]4CCN(Cc5ccccc5)C4)ccc3C2=O)C(=O)N1] | 545.33 | 0.46 |
| I-72cz | 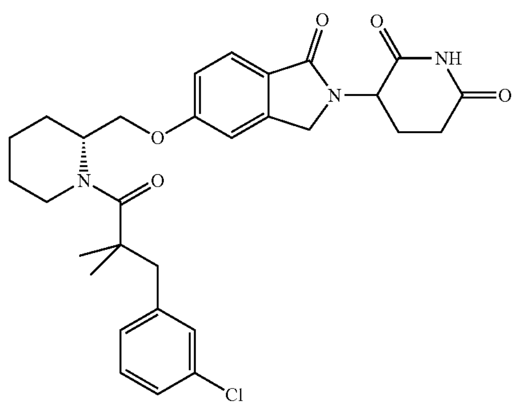 [SMILES: CC(C)(Cc1cccc(Cl)c1)C(=O)N1CCCC[C@@H]1COc1ccc2c(c1)CN(C1CCC(=O)NC1=O)C2=O] | 554.19 | 0.67 |
| I-72da | 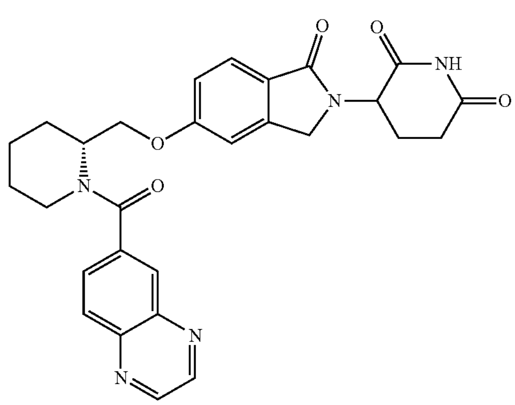 [SMILES: O=C1CCC(N2Cc3cc(OC[C@H]4CCCCN4C(=O)c4ccc5nccnc5c4)ccc3C2=O)C(=O)N1] | 514.27 | 0.53 |

-continued

| Compound Number | Structure | LCMS [M + H] | LCMS Rt |
|---|---|---|---|
| I-72db | 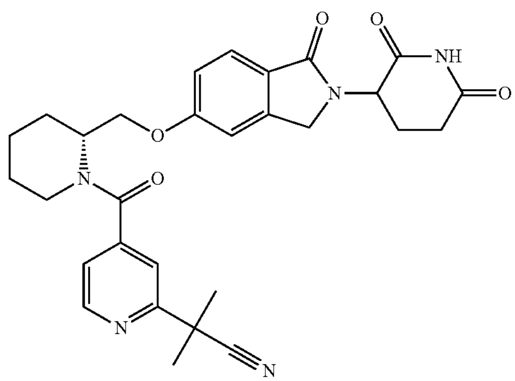 [SMILES: CC(C)(C#N)c1cc(C(=O)N2CCCC[C@@H]2COc2ccc3c(c2)CN(C2CCC(=O)NC2=O)C3=O)ccn1] | 530.3 | 0.55 |
| I-72dc | 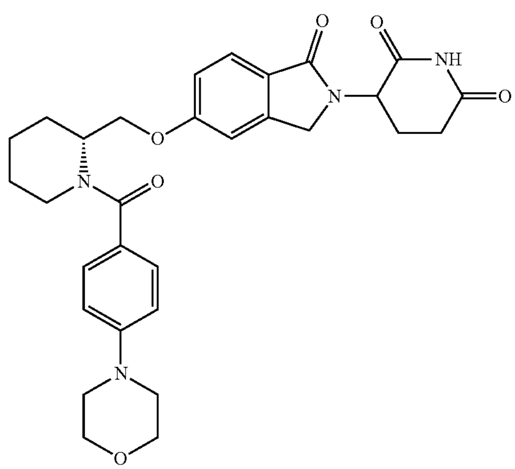 [SMILES: O=C1CCC(N2Cc3cc(OC[C@H]4CCCCN4C(=O)c4ccc(N5CCOCC5)cc4)ccc3C2=O)C(=O)N1] | 547.29 | 0.57 |
| I-72dd | 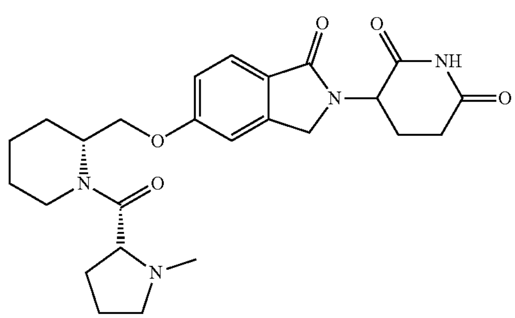 | 469.33 | 0.4 |
| I-72de | 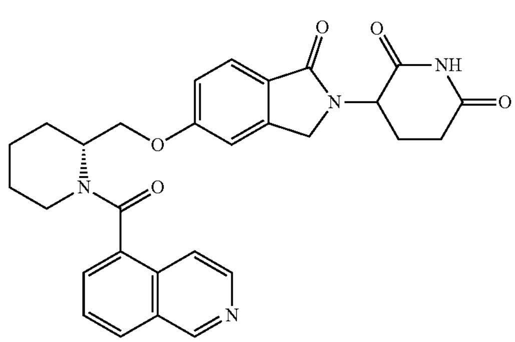 [SMILES: O=C1CCC(N2Cc3cc(OC[C@H]4CCCCN4C(=O)c4cccc5cnccc45)ccc3C2=O)C(=O)N1] | 513.27 | 0.5 |

-continued
| Compound Number | Structure | LCMS [M + H] | LCMS Rt |
|---|---|---|---|
| I-72df | 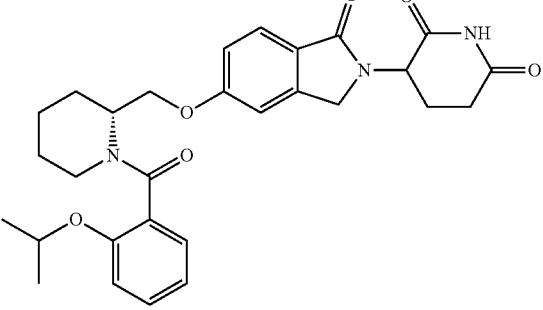 | 520.27 | 0.61 |
| I-72dg | 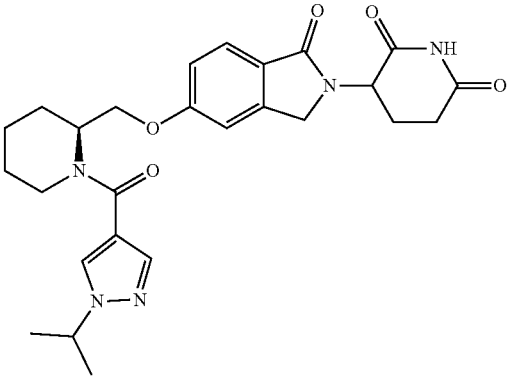 [SMILES: CC(C)n1cc(C(=O)N2CCCC[C@H]2COc2ccc3c(c2)CN(C2CCC(=O)NC2=O)C3=O)cn1] | 494.31 | 0.55 |
| I-72dh | 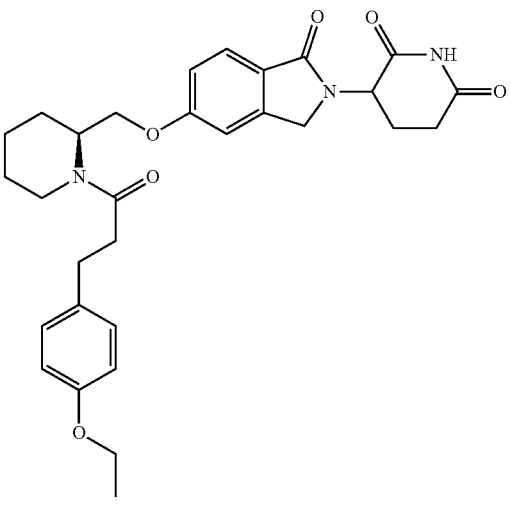 [SMILES: CCOc1ccc(CCC(=O)N2CCCC[C@H]2COc2ccc3c(c2)CN(C2CCC(=O)NC2=O)C3=O)cc1] | 534.34 | 0.62 |
| I-72di | 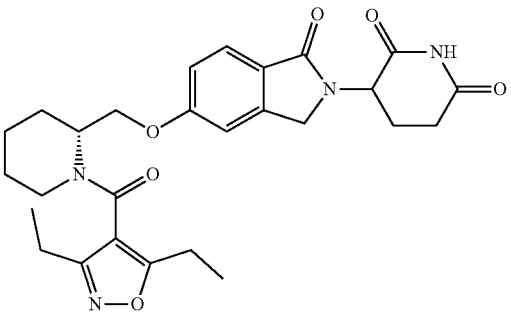 [SMILES: CCc1noc(CC)c1C(=O)N1CCCC[C@@H]1COc1ccc2c(c1)CN(C1CCC(=O)NC1=O)C2=O] | 509.2 | 0.57 |

-continued

| Compound Number | Structure | LCMS [M + H] | LCMS Rt |
|---|---|---|---|
| I-72dj | 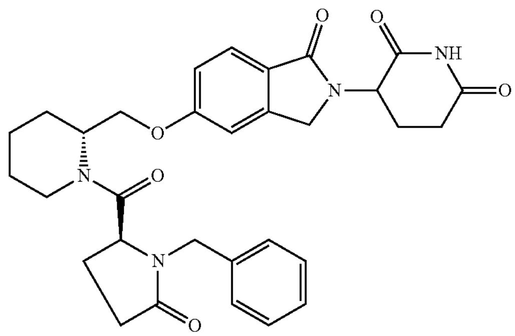 [SMILES: O=C1CCC(N2Cc3cc(OC[C@H]4CCCCN4C(=O)[C@@H]4CCC(=O)N4Cc4ccccc4)ccc3C2=O)C(=O)N1] | 559.28 | 0.56 |
| I-72dk | 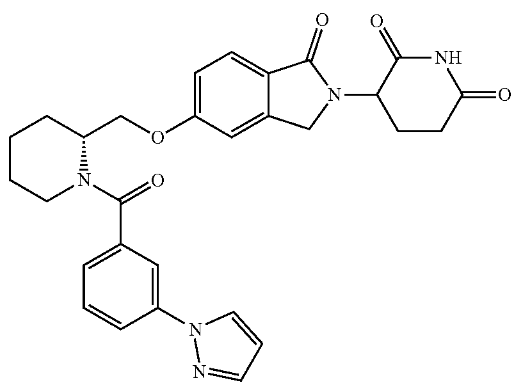 [SMILES: O=C1CCC(N2Cc3cc(OC[C@H]4CCCCN4C(=O)c4cccc(-n5cccn5)c4)ccc3C2=O)C(=O)N1] | 528.25 | 0.56 |
| I-72dl | 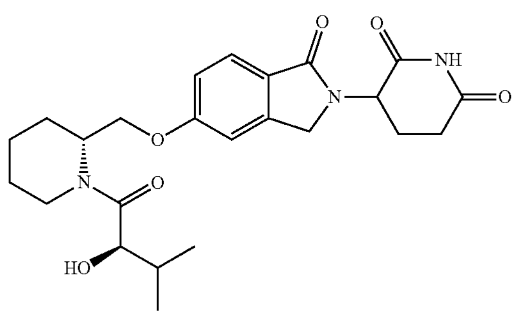 [SMILES: CC(C)[C@@H](O)C(=O)N1CCCC[C@@H]1COc1ccc2c(c1)CN(C1CCC(=O)NC1=O)C2=O] | 458.31 | 0.55 |
| I-72dm | 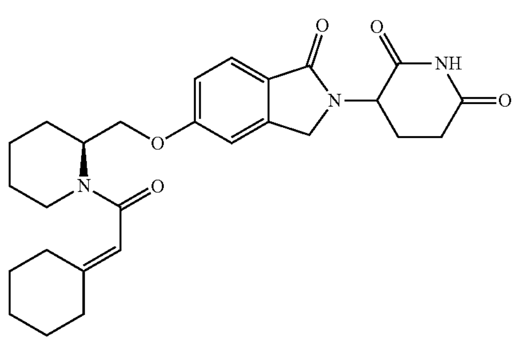 [SMILES: O=C1CCC(N2Cc3cc(OC[C@@H]4CCCCN4C(=O)C=C4CCCCC4)ccc3C2=O)C(=O)N1] | 480.3 | 0.61 |

-continued
| Compound Number | Structure | LCMS [M + H] | LCMS Rt |
|---|---|---|---|
| I-72dn | 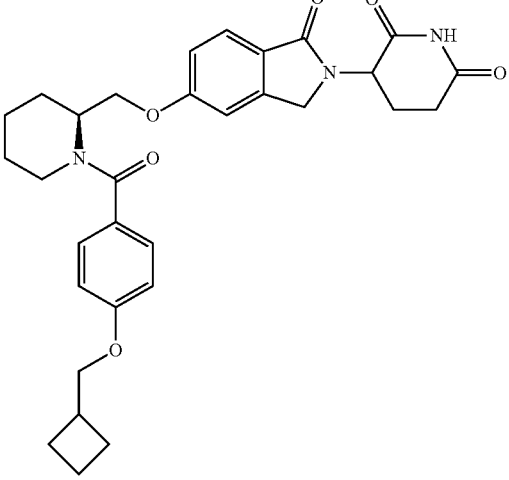 | 546.3 | 0.65 |
| I-72do | 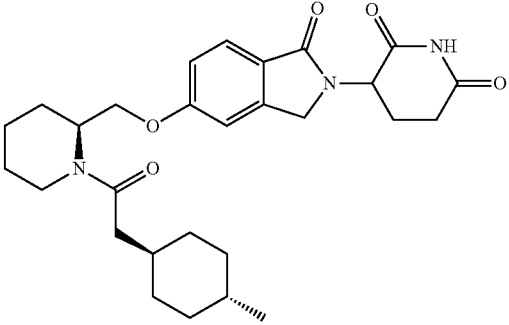 [SMILES: C[C@H]1CC[C@H](CC(=O)N2CCCC[C@H]2COc2ccc3c(c2)CN(C2CCC(=O)NC2=O)C3=O)CC1] | 496.36 | 0.66 |
| I-72dp | 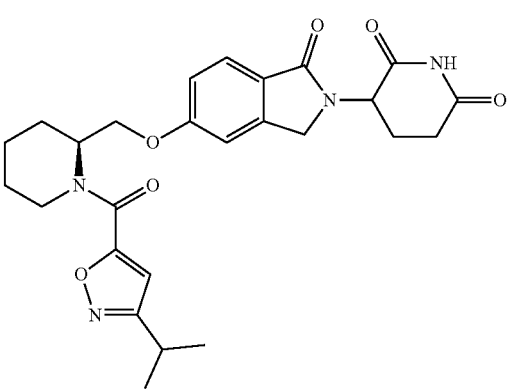 [SMILES: CC(C)c1cc(C(=O)N2CCCC[C@H]2COc2ccc3c(c2)CN(C2CCC(=O)NC2=O)C3=O)on1] | 495.32 | 0.58 |
| I-72dq | 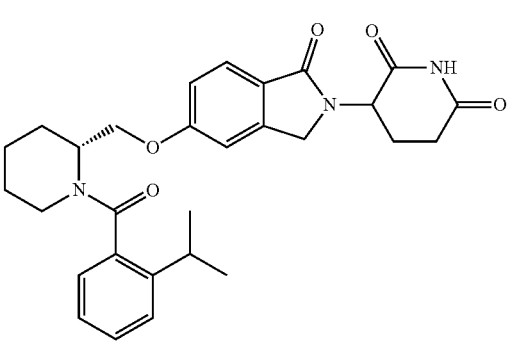 [SMILES: CC(C)c1ccccc1C(=O)N1CCCC[C@@H]1COc1ccc2c(c1)CN(C1CCC(=O)NC1=O)C2=O] | 504.33 | 0.62 |

-continued

| Compound Number | Structure | LCMS [M + H] | LCMS Rt |
|---|---|---|---|
| I-72dr | 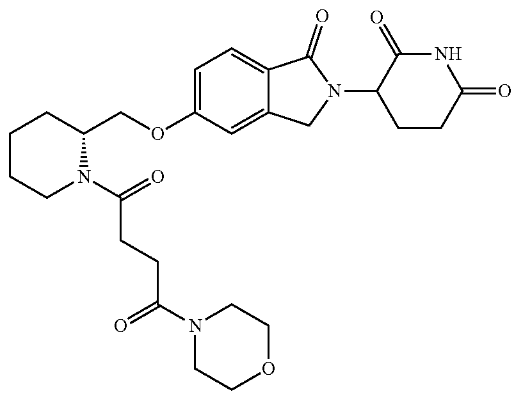 [SMILES: O=C1CCC(N2Cc3cc(OC[C@H]4CCCCN4C(=O)CCC(=O)N4CCOCC4)ccc3C2=O)C(=O)N1] | 527.29 | 0.51 |
| I-72ds | 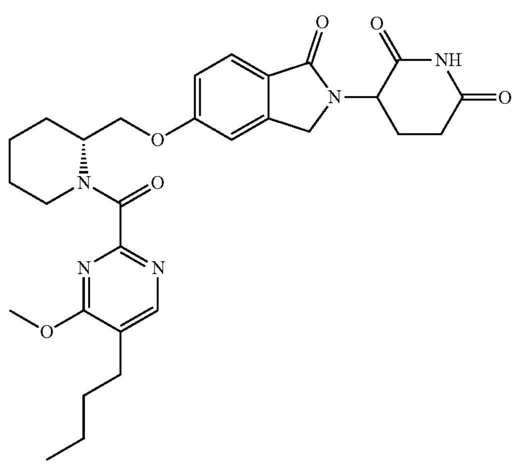 [SMILES: CCCCc1cnc(C(=O)N2CCCC[C@@H]2COc2ccc3c(c2)CN(C2CCC(=O)NC2=O)C3=O)nc1OC] | 550.33 | 0.62 |
| I-72dt | 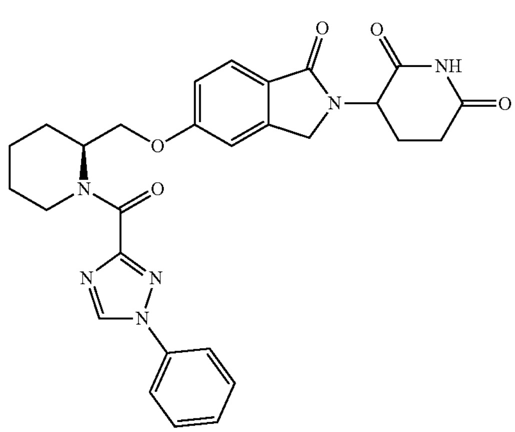 [SMILES: O=C1CCC(N2Cc3cc(OC[C@@H]4CCCCN4C(=O)c4ncn(-c5ccccc5)n4)ccc3C2=O)C(=O)N1] | 529.3 | 0.57 |

-continued
| Compound Number | Structure | LCMS [M + H] | LCMS Rt |
|---|---|---|---|
| I-72du | 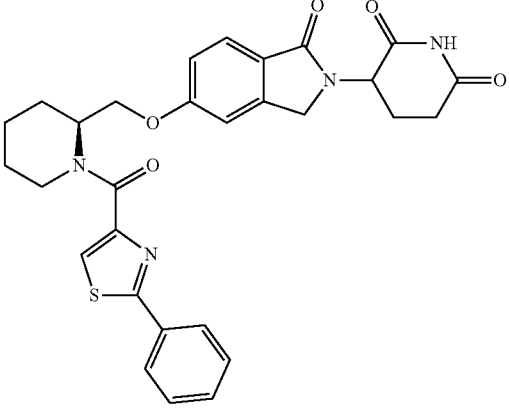 | 545.27 | 0.62 |
| I-72dv | 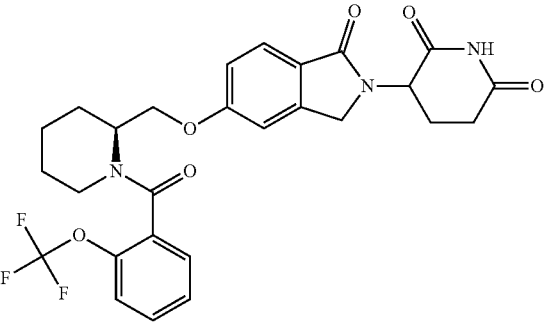 [SMILES: O=C1CCC(N2Cc3cc(OC[C@@H]4CCCCN4C(=O)c4ccccc4OC(F)(F)F)ccc3C2=O)C(=O)N1] | 546.2 | 0.61 |
| I-72dw | 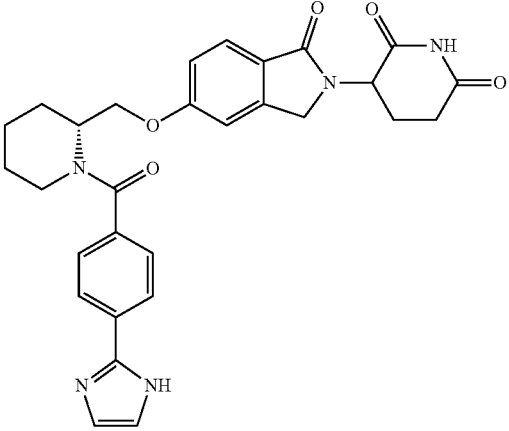 [SMILES: O=C1CCC(N2Cc3cc(OC[C@H]4CCCCN4C(=O)c4ccc(-c5ncc[nH]5)cc4)ccc3C2=O)C(=O)N1] | 528.27 | 0.45 |
| I-72dx | 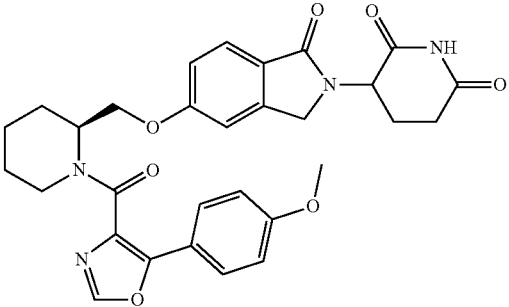 [SMILES: COc1ccc(-c2ocnc2C(=O)N2CCCC[C@H]2COc2ccc3c(c2)CN(C2CCC(=O)NC2=O)C3=O)cc1] | 559.23 | 0.58 |

| Compound Number | Structure | LCMS [M + H] | LCMS Rt |
|---|---|---|---|
| I-72dy | 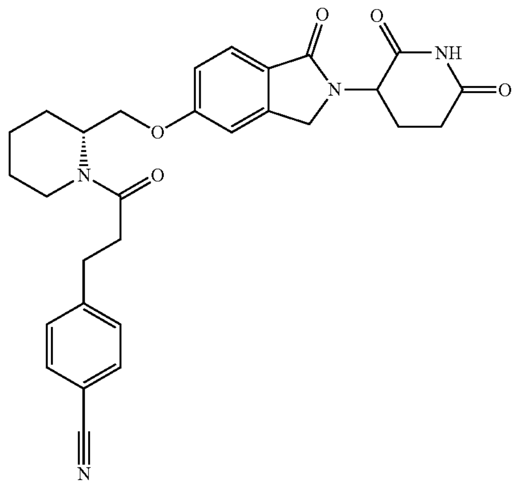 [SMILES: N#Cc1ccc(CCC(=O)N2CCCC[C@@H]2COc2ccc3c(c2)CN(C2CCC(=O)NC2=O)C3=O)cc1] | 515.31 | 0.57 |
| I-72dz | 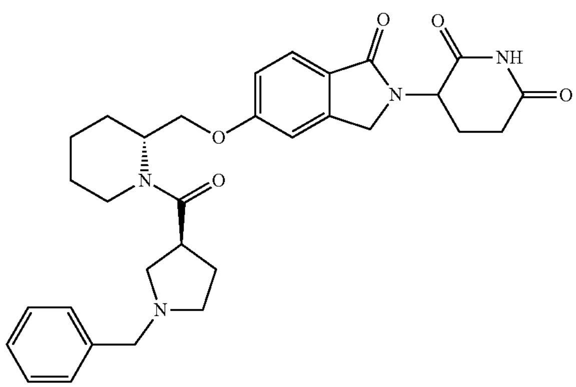 [SMILES: O=C1CCC(N2Cc3cc(OC[C@H]4CCCCN4C(=O)[C@H]4CCN(Cc5ccccc5)C4)ccc3C2=O)C(=O)N1] | 545.32 | 0.46 |
| I-72ea | 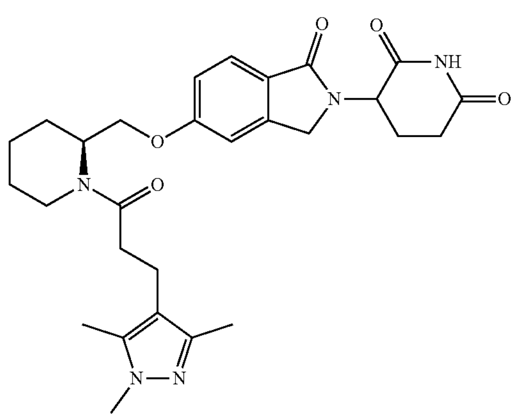 [SMILES: Cc1nn(C)c(C)c1CCC(=O)N1CCCC[C@H]1COc1ccc2c(c1)CN(C1CCC(=O)NC1=O)C2=O] | 522.36 | 0.54 |

-continued

| Compound Number | Structure | LCMS [M + H] | LCMS Rt |
|---|---|---|---|
| I-72eb | 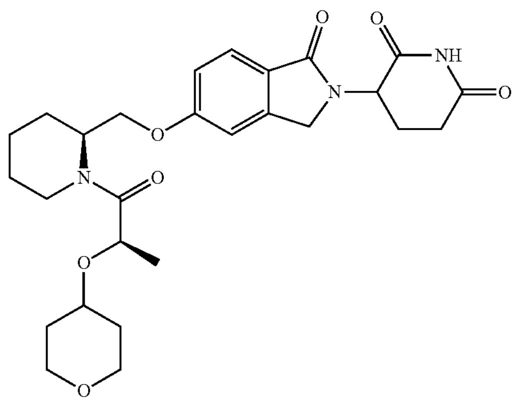 [SMILES: C[C@@H](OC1CCOCC1)C(=O)N1CCCC[C@H]1COc1ccc2c(c1)CN(C1CCC(=O)NC1=O)C2=O] | 514.34 | 0.54 |
| I-72ec | 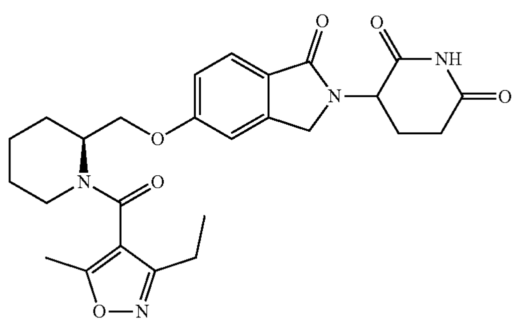 [SMILES: CCc1noc(C)c1C(=O)N1CCCC[C@H]1COc1ccc2c(c1)CN(C1CCC(=O)NC1=O)C2=O] | 495.3 | 0.55 |
| I-72ed | 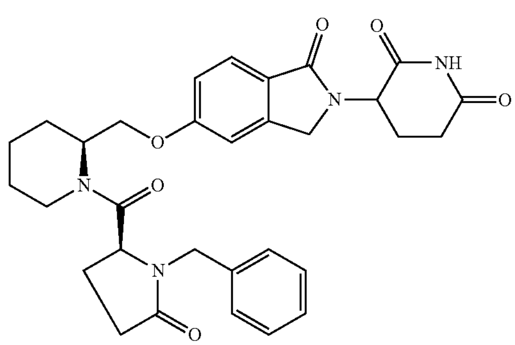 [SMILES: O=C1CCC(N2Cc3cc(OC[C@@H]4CCCCN4C(=O)[C@@H]4CCC(=O)N4Cc4ccccc4)ccc3C2=O)C(=O)N1] | 559.32 | 0.56 |
| I-72ee | 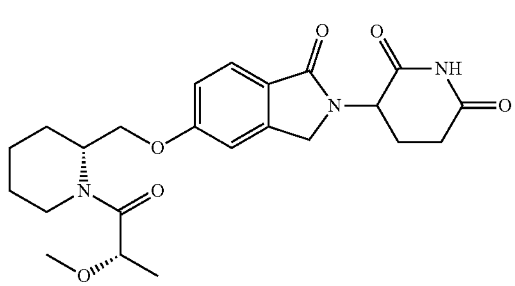 [SMILES: CO[C@@H](C)C(=O)N1CCCC[C@@H]1COc1ccc2c(c1)CN(C1CCC(=O)NC1=O)C2=O] | 444.27 | 0.52 |

| Compound Number | Structure | LCMS [M + H] | LCMS Rt |
|---|---|---|---|
| I-72ef | 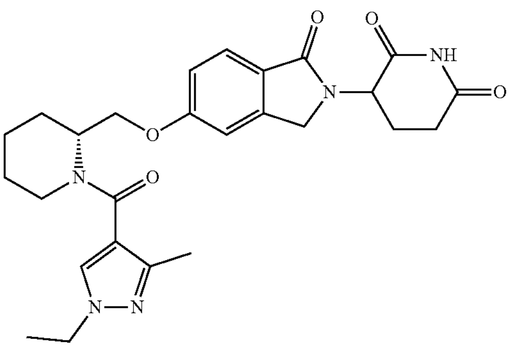 [SMILES: CCn1cc(C(=O)N2CCCC[C@@H]2COc2ccc3c(c2)CN(C2CCC(=O)NC2=O)C3=O)c(C)n1] | 494.3 | 0.53 |
| I-72eg | 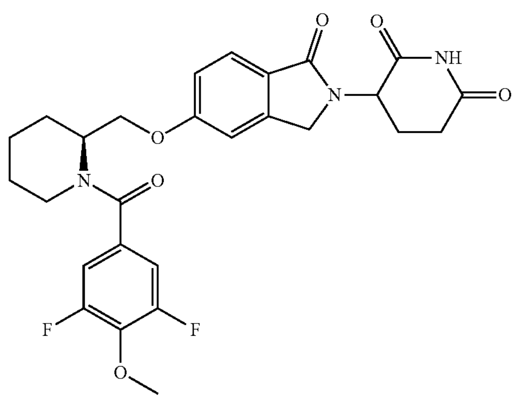 | 528.25 | 0.59 |
| I-72eh | 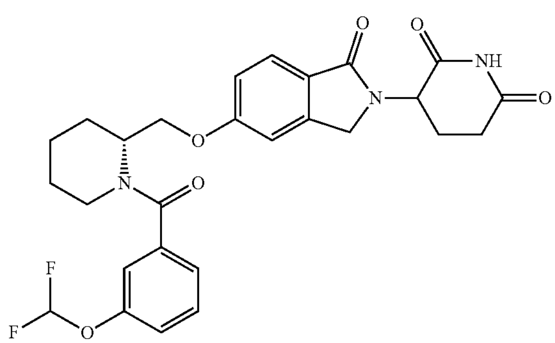 [SMILES: O=C1CCC(N2Cc3cc(OC[C@H]4CCCCN4C(=O)c4cccc(OC(F)F)c4)ccc3C2=O)C(=O)N1] | 528.24 | 0.58 |
| I-72ei | 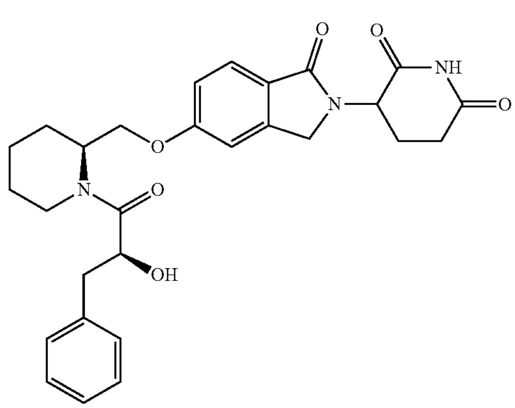 [SMILES: O=C1CCC(N2Cc3cc(OC[C@@H]4CCCCN4C(=O)[C@@H](O)Cc4ccccc4)ccc3C2=O)C(=O)N1] | 506.31 | 0.58 |

-continued

| Compound Number | Structure | LCMS [M + H] | LCMS Rt |
|---|---|---|---|
| I-72ej | 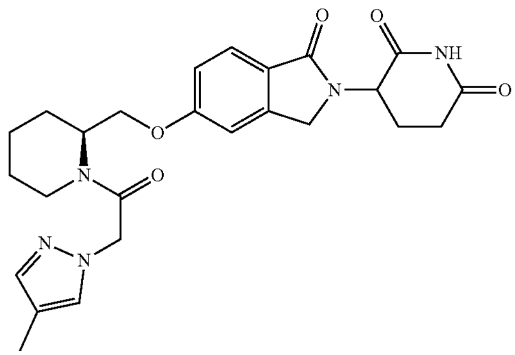 [SMILES: Cc1cnn(CC(=O)N2CCCC[C@H]2COc2ccc3c(c2)CN(C2CCC(=O)NC2=O)C3=O)c1] | 480.31 | 0.53 |
| I-72ek | 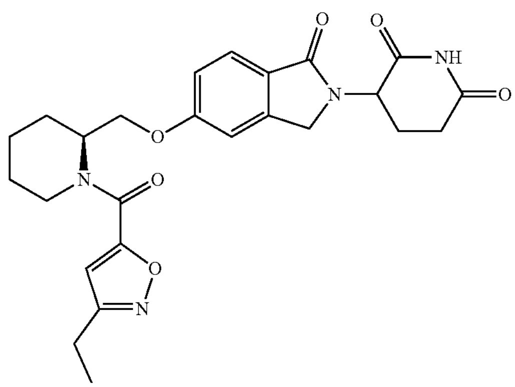 [SMILES: CCc1cc(C(=O)N2CCCC[C@H]2COc2ccc3c(c2)CN(C2CCC(=O)NC2=O)C3=O)on1] | 481.28 | 0.56 |
| I-72el | 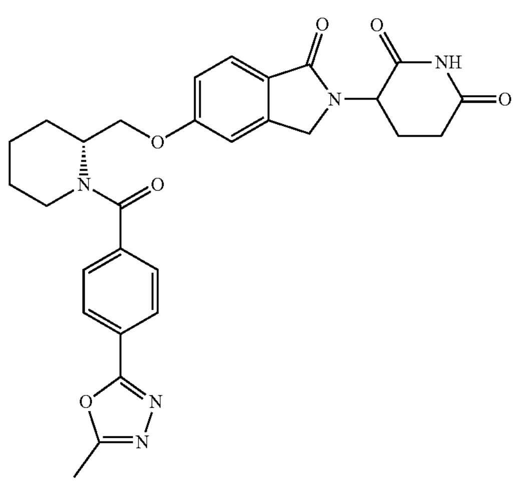 [SMILES: Cc1nnc(-c2ccc(C(=O)N3CCCC[C@@H]3COc3ccc4c(c3)CN(C3CCC(=O)NC3=O)C4=O)cc2)o1] | 544.28 | 0.54 |

-continued
| Compound Number | Structure | LCMS [M + H] | LCMS Rt |
|---|---|---|---|
| I-72em | 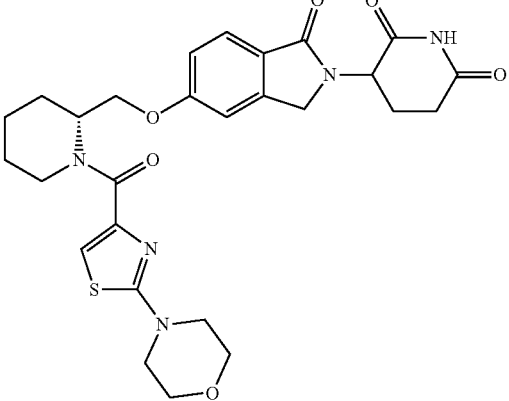 | 554.24 | 0.56 |
| I-72en | 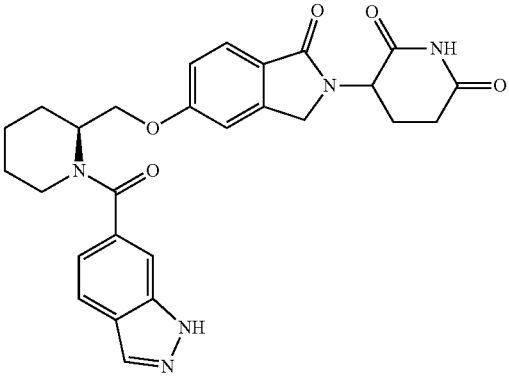 [SMILES: O=C1CCC(N2Cc3cc(OC[C@@H]4CCCCN4C(=O)c4ccc5cn[nH]c5c4)ccc3C2=O)C(=O)N1] | 502.27 | 0.54 |
| I-72eo | 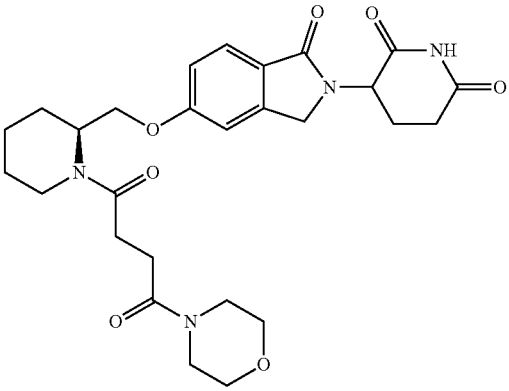 [SMILES: O=C1CCC(N2Cc3cc(OC[C@@H]4CCCCN4C(=O)CCC(=O)N4CCOCC4)ccc3C2=O)C(=O)N1] | 527.3 | 0.52 |
| I-72ep | 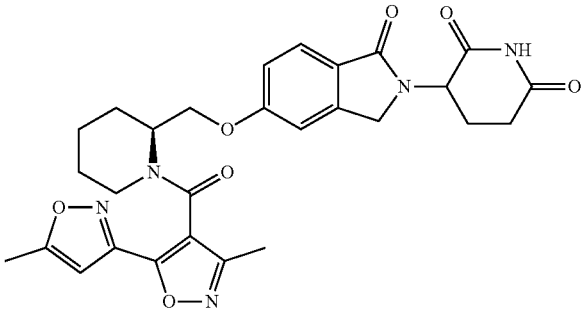 [SMILES: Cc1cc(-c2onc(C)c2C(=O)N2CCCC[C@H]2COc2ccc3c(c2)CN(C2CCC(=O)NC2=O)C3=O)no1] | 548.2 | 0.56 |

-continued

| Compound Number | Structure | LCMS [M + H] | LCMS Rt |
|---|---|---|---|
| I-72eq | 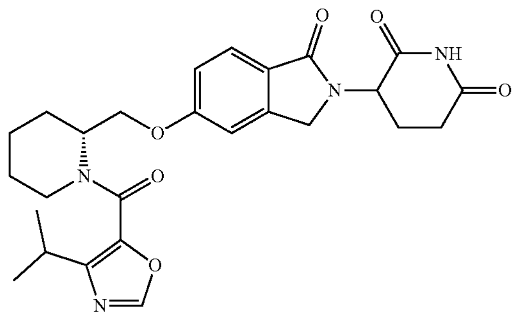 [SMILES: CC(C)c1ncoc1C(=O)N1CCCC[C@@H]1COc1ccc2c(c1)CN(C1CCC(=O)NC1=O)C2=O] | 481.25 | 0.54 |
| I-72er | 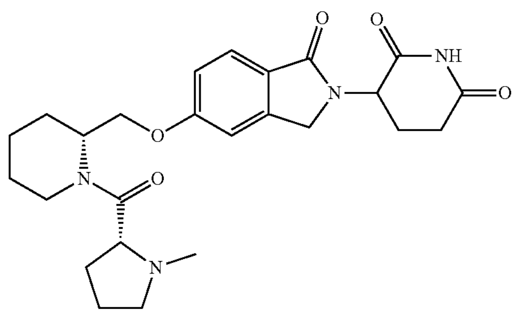 [SMILES: CN1CCC[C@@H]1C(=O)N1CCCC[C@@H]1COc1ccc2c(c1)CN(C1CCC(=O)NC1=O)C2=O] | 469.31 | 0.4 |
| I-72es | 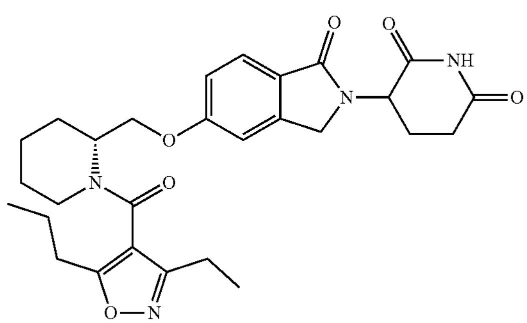 [SMILES: CCCc1onc(CC)c1C(=O)N1CCCC[C@@H]1COc1ccc2c(c1)CN(C1CCC(=O)NC1=O)C2=O] | 523.27 | 0.59 |
| I-72et | 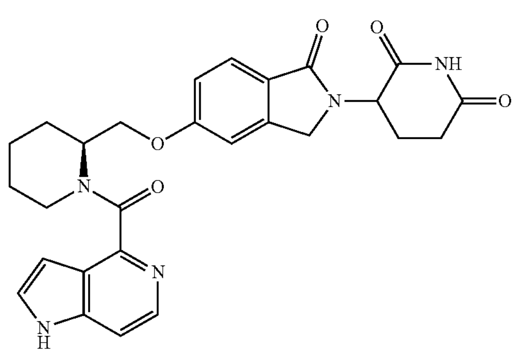 [SMILES: O=C1CCC(N2Cc3cc(OC[C@@H]4CCCCN4C(=O)c4nccc5[nH]ccc45)ccc3C2=O)C(=O)N1] | 502.27 | 0.44 |

-continued

| Compound Number | Structure | LCMS [M + H] | LCMS Rt |
|---|---|---|---|
| I-72eu | 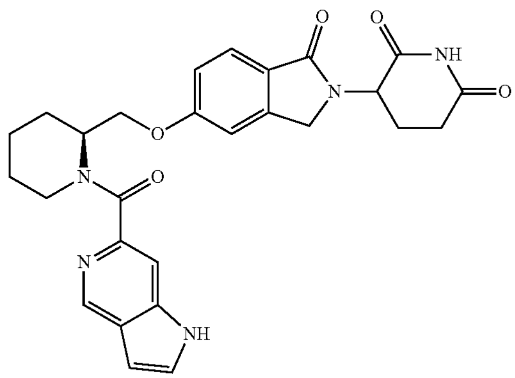 [SMILES: O=C1CCC(N2Cc3cc(OC[C@@H]4CCCCN4C(=O)c4cc5[nH]ccc5cn4)ccc3C2=O)C(=O)N1] | 502.27 | 0.43 |
| I-72ev | 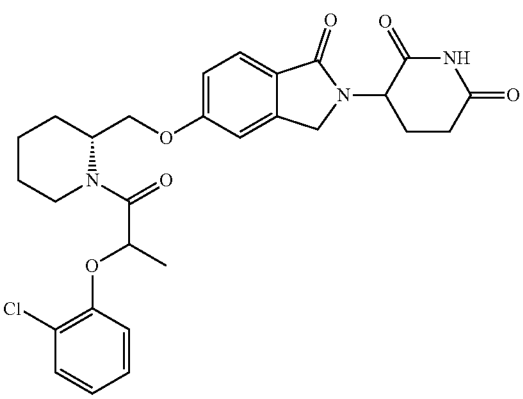 [SMILES: CC(Oc1ccccc1Cl)C(=O)N1CCCC[C@@H]1COc1ccc2c(c1)CN(C1CCC(=O)NC1=O)C2=O] | 540.21 | 0.62 |
| I-72ew | 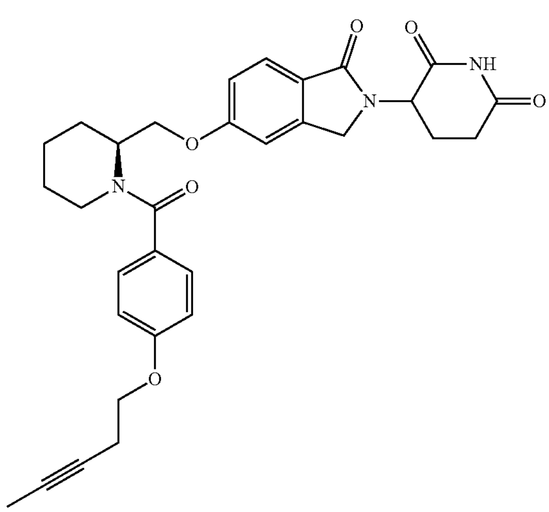 [SMILES: CC#CCCOc1ccc(C(=O)N2CCCC[C@H]2COc2ccc3c(c2)CN(C2CCC(=O)NC2=O)C3=O)cc1] | 544.29 | 0.62 |

| Compound Number | Structure | LCMS [M + H] | LCMS Rt |
|---|---|---|---|
| I-72ex | 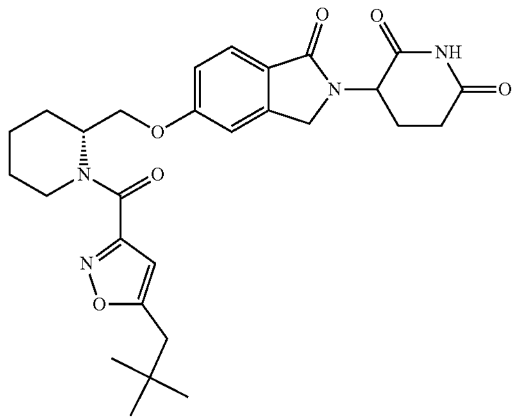 [SMILES: CC(C)(C)Cc1cc(C(=O)N2CCCC[C@@H]2COc2ccc3c(c2)CN(C2CCC(=O)NC2=O)C3=O)no1] | 523.3 | 0.63 |
| I-72ey | 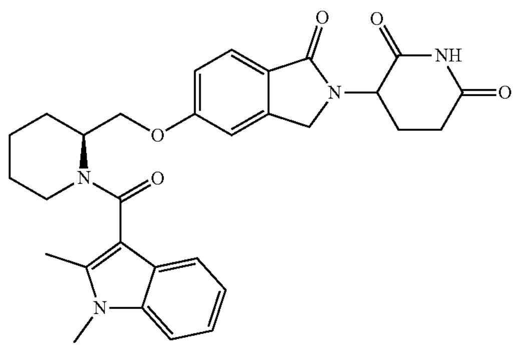 [SMILES: Cc1c(C(=O)N2CCCC[C@H]2COc2ccc3c(c2)CN(C2CCC(=O)NC2=O)C3=O)c2ccccc2n1C] | 529.3 | 0.6 |
| I-72ez | 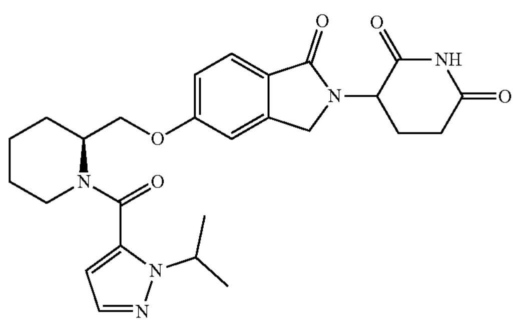 [SMILES: CC(C)n1nccc1C(=O)N1CCCC[C@H]1COc1ccc2c(c1)CN(C1CCC(=O)NC1=O)C2=O] | 494.32 | 0.56 |
| I-72fa | 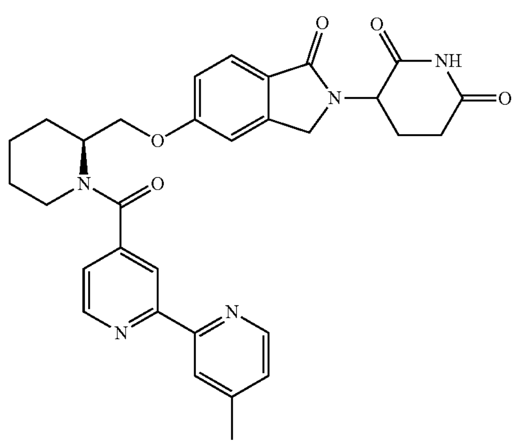 [SMILES: Cc1ccnc(-c2cc(C(=O)N3CCCC[C@H]3COc3ccc4c(c3)CN(C3CCC(=O)NC3=O)C4=O)ccn2)c1] | 554.33 | 0.54 |

-continued
| Compound Number | Structure | LCMS [M + H] | LCMS Rt |
|---|---|---|---|
| I-72fb | 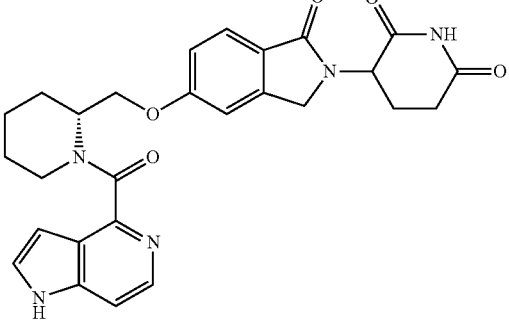 | 502.27 | 0.44 |
| I-72fc | 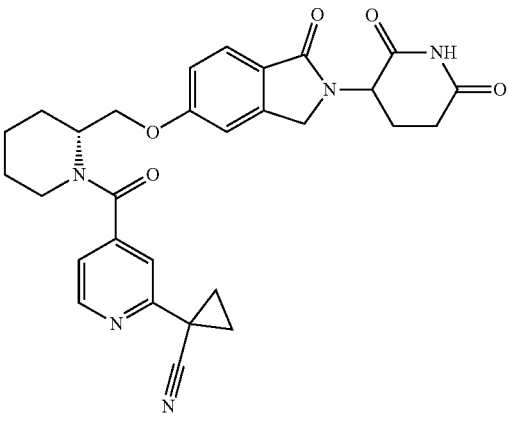 [SMILES: N#CC1(c2cc(C(=O)N3CCCC[C@@H]3COc3ccc4c(c3)CN(C3CCC(=O)NC3=O)C4=O)ccn2)CC1] | 528.27 | 0.55 |
| I-72fd | 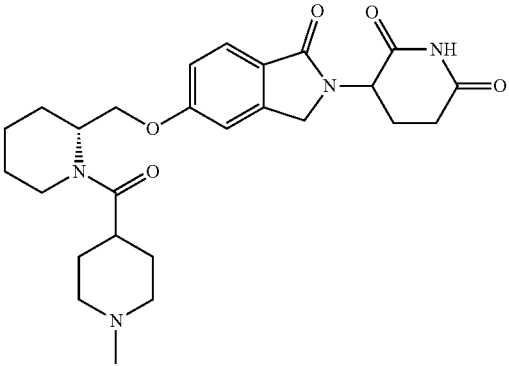 [SMILES: CN1CCC(C(=O)N2CCCC[C@@H]2COc2ccc3c(c2)CN(C2CCC(=O)NC2=O)C3=O)CC1] | 483.31 | 0.41 |
| I-72fe | 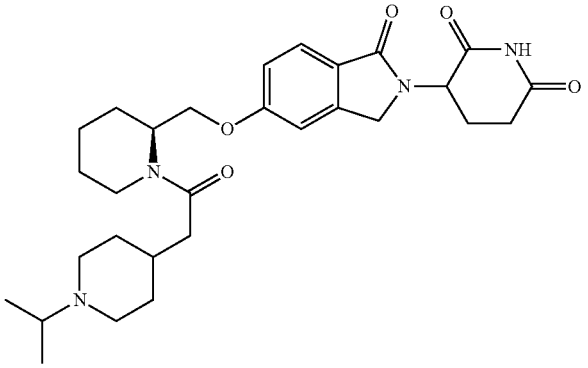 [SMILES: CC(C)N1CCC(CC(=O)N2CCCC[C@H]2COc2ccc3c(c2)CN(C2CCC(=O)NC2=O)C3=O)CC1] | 525.37 | 0.43 |

-continued

| Compound Number | Structure | LCMS [M + H] | LCMS Rt |
|---|---|---|---|
| I-72ff | 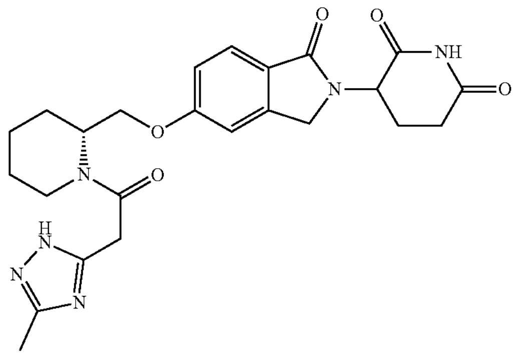 [SMILES: Cc1n[nH]c(CC(=O)N2CCCC[C@@H]2COc2ccc3c(c2)CN(C2CCC(=O)NC2=O)C3=O)n1] | 481.28 | 0.48 |
| I-72fg | 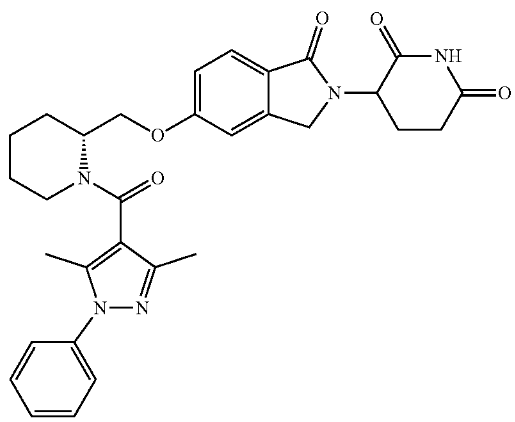 [SMILES: Cc1nn(-c2ccccc2)c(C)c1C(=O)N1CCCC[C@@H]1COc1ccc2c(c1)CN(C1CCC(=O)NC1=O)C2=O] | 556.28 | 0.58 |
| I-72fh | 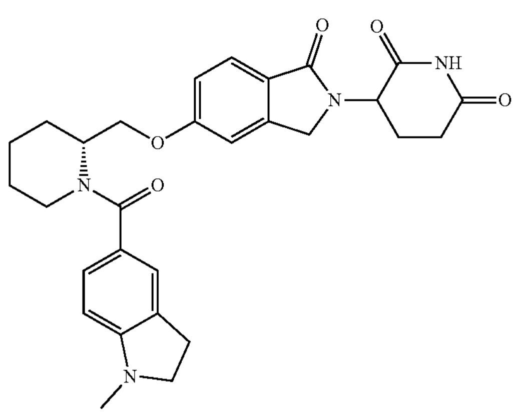 [SMILES: CN1CCc2cc(C(=O)N3CCCC[C@@H]3COc3ccc4c(c3)CN(C3CCC(=O)NC3=O)C4=O)ccc21] | 517.29 | 0.59 |

-continued

| Compound Number | Structure | LCMS [M + H] | LCMS Rt |
|---|---|---|---|
| I-72fi | 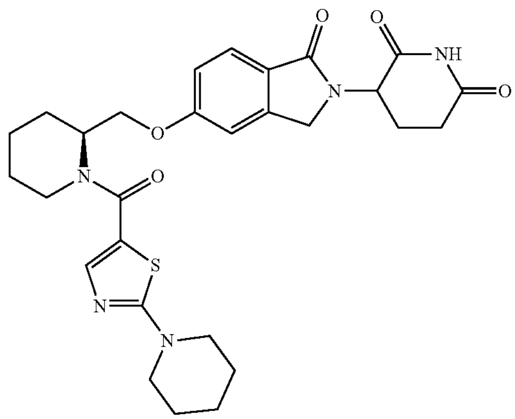 [SMILES: O=C1CCC(N2Cc3cc(OC[C@@H]4CCCCN4C(=O)c4cnc(N5CCCCC5)s4)ccc3C2=O)C(=O)N1] | 552.28 | 0.6 |
| I-72fj | 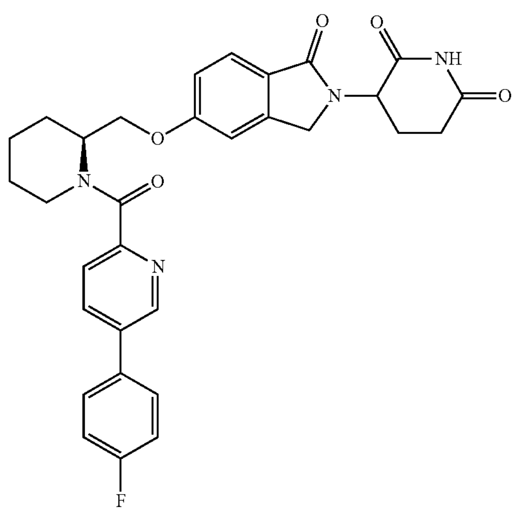 [SMILES: O=C1CCC(N2Cc3cc(OC[C@@H]4CCCCN4C(=O)c4ccc(-c5ccc(F)cc5)cn4)ccc3C2=O)C(=O)N1] | 557.3 | 0.6 |
| I-72fk | 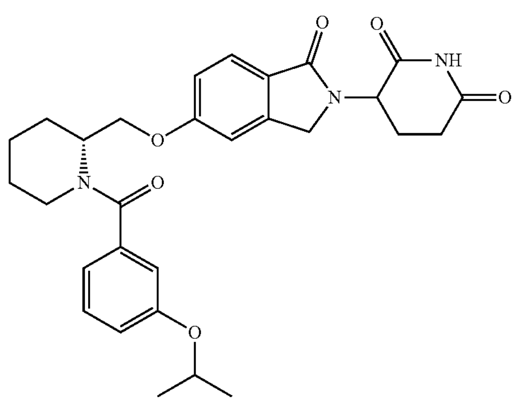 [SMILES: CC(C)Oc1cccc(C(=O)N2CCCC[C@@H]2COc2ccc3c(c2)CN(C2CCC(=O)NC2=O)C3=O)c1] | 520.33 | 0.61 |

-continued

| Compound Number | Structure | LCMS [M + H] | LCMS Rt |
|---|---|---|---|
| I-72fl | 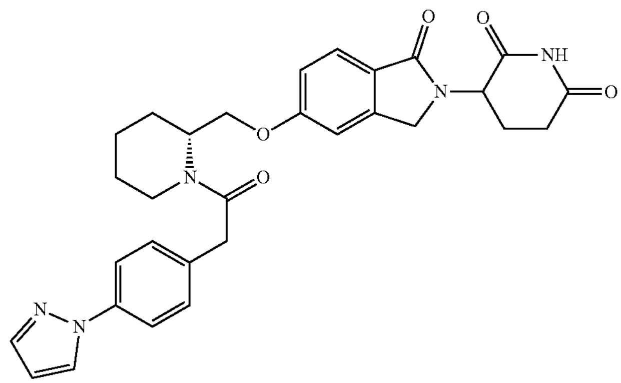 [SMILES: O=C1CCC(N2Cc3cc(OC[C@H]4CCCCN4C(=O)Cc4ccc(-n5cccn5)cc4)ccc3C2=O)C(=O)N1] | 542.29 | 0.57 |
| I-72fm | 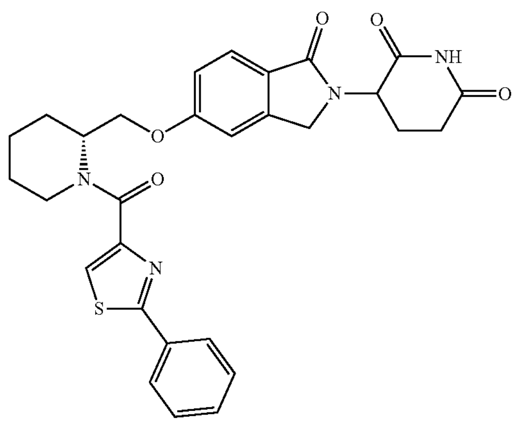 [SMILES: O=C1CCC(N2Cc3cc(OC[C@H]4CCCCN4C(=O)c4csc(-c5ccccc5)n4)ccc3C2=O)C(=O)N1] | 545.23 | 0.62 |
| I-72fn | 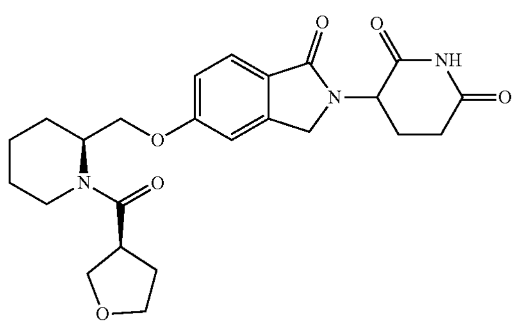 [SMILES: O=C1CCC(N2Cc3cc(OC[C@@H]4CCCCN4C(=O)[C@H]4CCOC4)ccc3C2=O)C(=O)N1] | 456.3 | 0.52 |
| I-72fo | 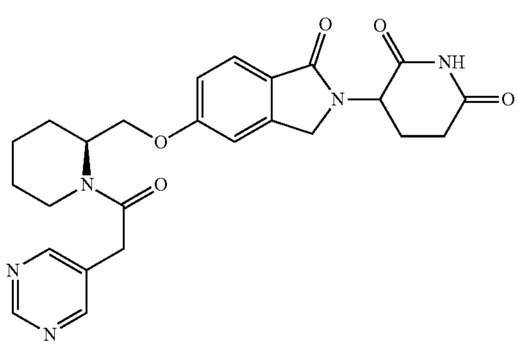 [SMILES: O=C1CCC(N2Cc3cc(OC[C@@H]4CCCCN4C(=O)Cc4cncnc4)ccc3C2=O)C(=O)N1] | 478.25 | 0.49 |

-continued

| Compound Number | Structure | LCMS [M + H] | LCMS Rt |
|---|---|---|---|
| I-72fp | 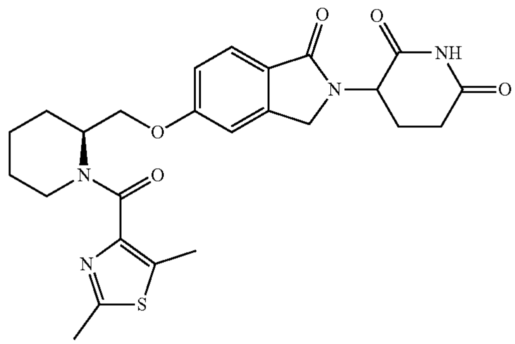 [SMILES: Cc1nc(C(=O)N2CCCC[C@H]2COc2ccc3c(c2)CN(C2CCC(=O)NC2=O)C3=O)c(C)s1] | 497.28 | 0.55 |
| I-72fq | 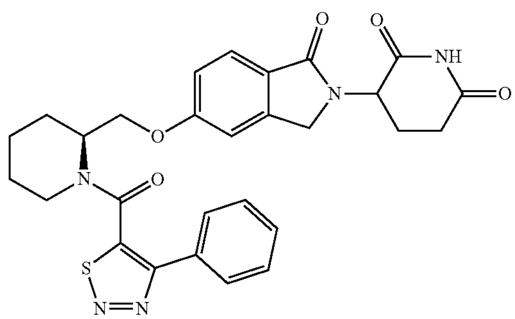 [SMILES: O=C1CCC(N2Cc3cc(OC[C@@H]4CCCCN4C(=O)c4snnc4-c4ccccc4)ccc3C2=O)C(=O)N1] | 546.19 | 0.59 |
| I-72fr | 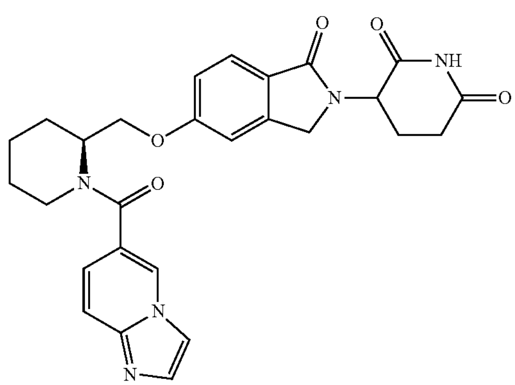 [SMILES: O=C1CCC(N2Cc3cc(OC[C@@H]4CCCCN4C(=O)c4ccc5nccn5c4)ccc3C2=O)C(=O)N1] | 502.27 | 0.42 |
| I-72fs | 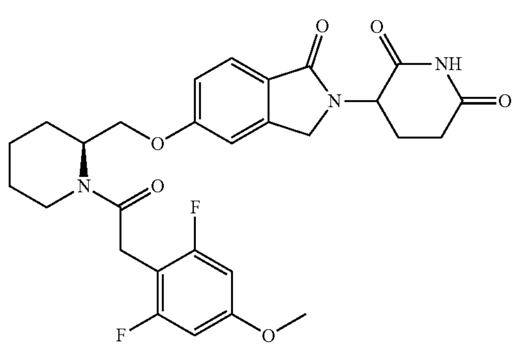 [SMILES: COc1cc(F)c(CC(=O)N2CCCC[C@H]2COc2ccc3c(c2)CN(C2CCC(=O)NC2=O)C3=O)c(F)c1] | 542.26 | 0.6 |

-continued
| Compound Number | Structure | LCMS [M + H] | LCMS Rt |
|---|---|---|---|
| I-72ft | 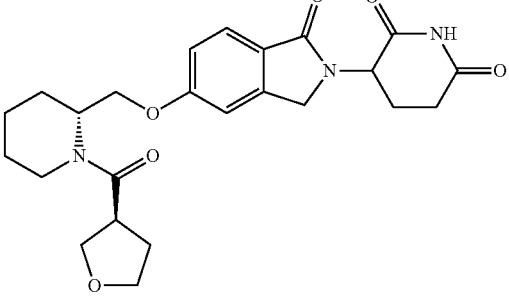 | 456.27 | 0.51 |
| I-72fu | 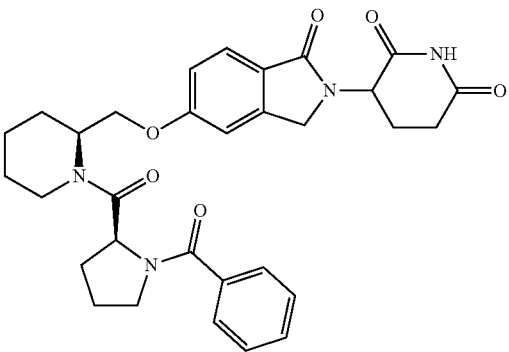 [SMILES: O=C1CCC(N2Cc3cc(OC[C@@H]4CCCCN4C(=O)[C@@H]4CCCN4C(=O)c4ccccc4)ccc3C2=O)C(=O)N1] | 559.28 | 0.56 |
| I-72fv | 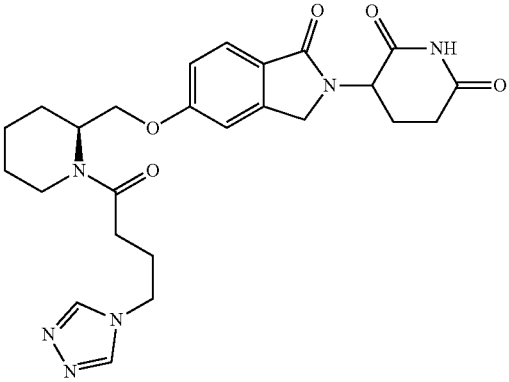 [SMILES: O=C1CCC(N2Cc3cc(OC[C@@H]4CCCCN4C(=O)CCCn4cnnc4)ccc3C2=O)C(=O)N1] | 495.32 | 0.5 |
| I-72fw | 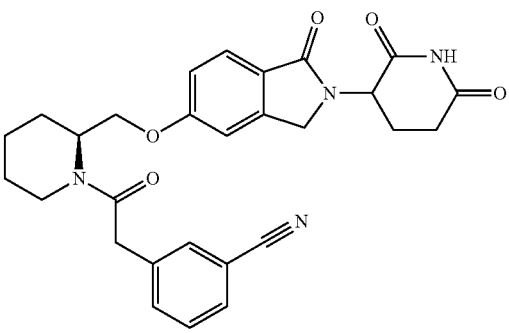 [SMILES: N#Cc1cccc(CC(=O)N2CCCC[C@H]2COc2ccc3c(c2)CN(C2CCC(=O)NC2=O)C3=O)c1] | 501.27 | 0.55 |

-continued

| Compound Number | Structure | LCMS [M + H] | LCMS Rt |
|---|---|---|---|
| I-72fx | 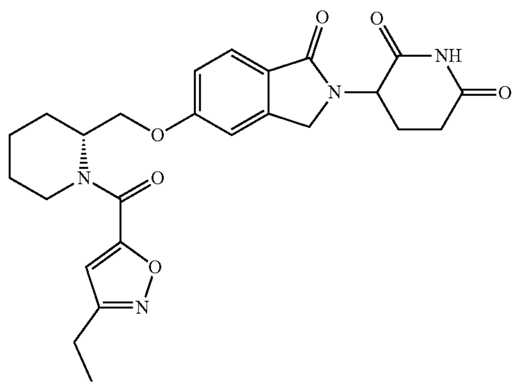 [SMILES: CCc1cc(C(=O)N2CCCC[C@@H]2COc2ccc3c(c2)CN(C2CCC(=O)NC2=O)C3=O)on1] | 481.26 | 0.56 |
| I-72fy | 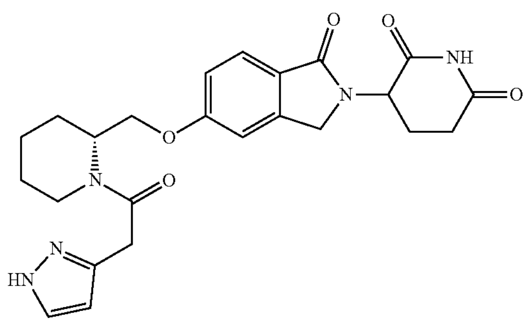 [SMILES: O=C1CCC(N2Cc3cc(OC[C@H]4CCCCN4C(=O)Cc4cc[nH]n4)ccc3C2=O)C(=O)N1] | 466.26 | 0.51 |
| I-72fz | 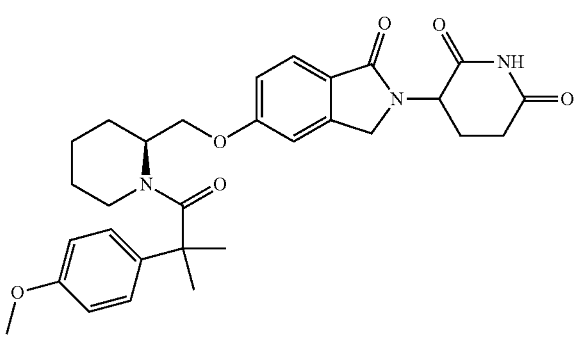 [SMILES: COc1ccc(C(C)(C)C(=O)N2CCCC[C@H]2COc2ccc3c(c2)CN(C2CCC(=O)NC2=O)C3=O)cc1] | 534.3 | 0.62 |
| I-72ga | 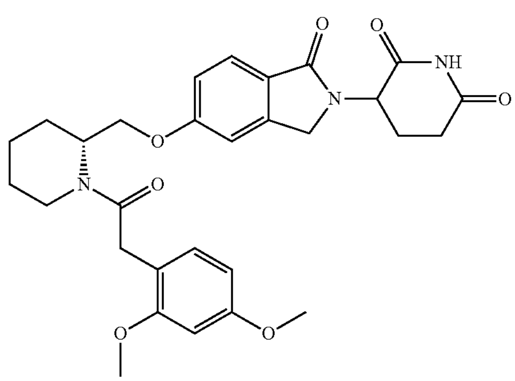 [SMILES: COc1ccc(CC(=O)N2CCCC[C@@H]2COc2ccc3c(c2)CN(C2CCC(=O)NC2=O)C3=O)c(OC)c1] | 536.29 | 0.59 |

-continued
| Compound Number | Structure | LCMS [M + H] | LCMS Rt |
|---|---|---|---|
| I-72gb | 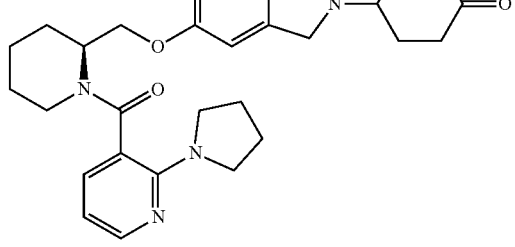 | 532.33 | 0.47 |
| I-72gc | 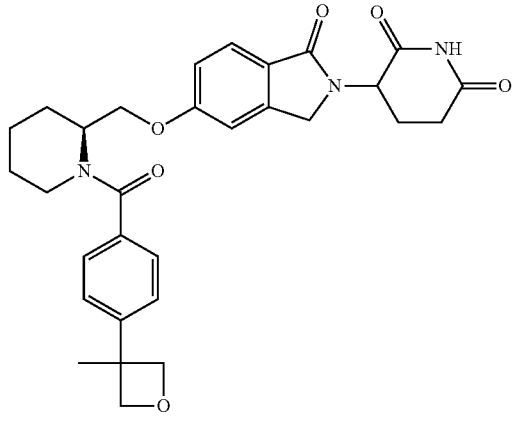 [SMILES: CC1(c2ccc(C(=O)N3CCCC[C@H]3COc3ccc4c(c3)CN(C3CCC(=O)NC3=O)C4=O)cc2)COC1] | 532.35 | 0.57 |
| I-72gd | 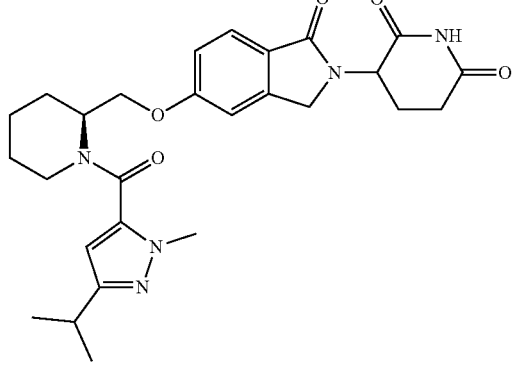 | 508.32 | 0.58 |
| I-72ge | 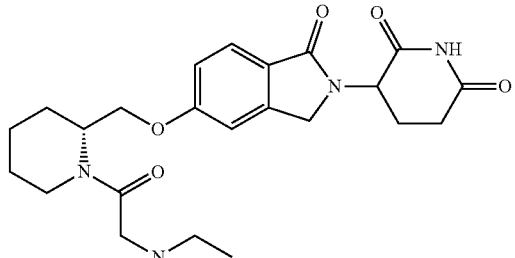 | 471.32 | 0.4 |

-continued

| Compound Number | Structure | LCMS [M + H] | LCMS Rt |
|---|---|---|---|
| I-72gf | 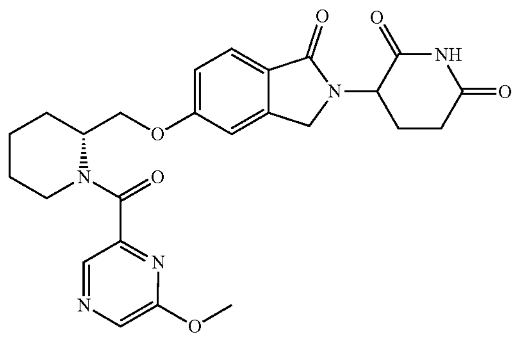 [SMILES: COc1cncc(C(=O)N2CCCC[C@@H]2COc2ccc3c(c2)CN(C2CCC(=O)NC2=O)C3=O)n1] | 494.25 | 0.55 |
| I-72gg | 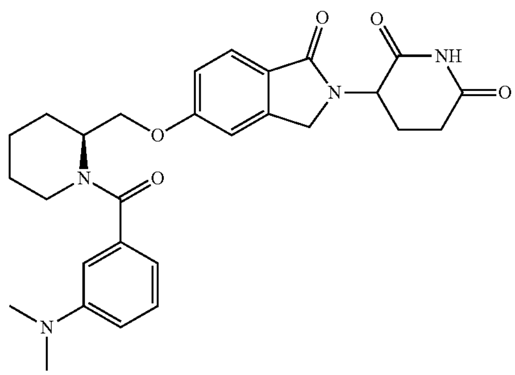 [SMILES: CN(C)c1cccc(C(=O)N2CCCC[C@H]2COc2ccc3c(c2)CN(C2CCC(=O)NC2=O)C3=O)c1] | 505.32 | 0.58 |
| I-72gh | 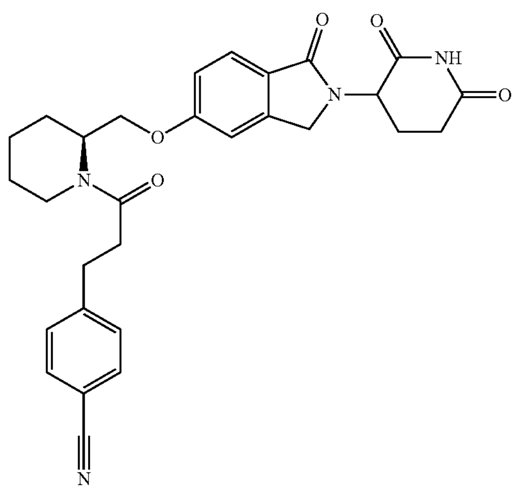 [SMILES: N#Cc1ccc(CCC(=O)N2CCCC[C@H]2COc2ccc3c(c2)CN(C2CCC(=O)NC2=O)C3=O)cc1] | 515.31 | 0.57 |
| I-72gi | 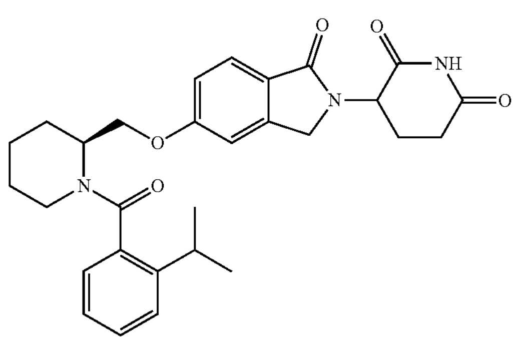 [SMILES: CC(C)c1ccccc1C(=O)N1CCCC[C@H]1COc1ccc2c(c1)CN(C1CCC(=O)NC1=O)C2=O] | 504.34 | 0.63 |

-continued

| Compound Number | Structure | LCMS [M + H] | LCMS Rt |
|---|---|---|---|
| I-72gj | 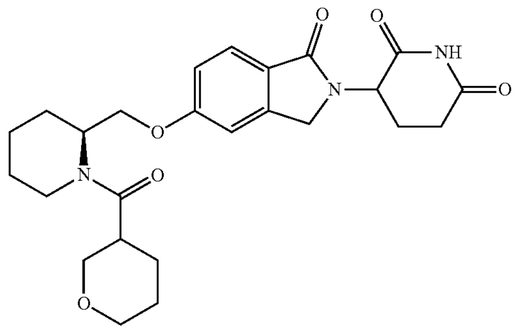 [SMILES: O=C1CCC(N2Cc3cc(OC[C@@H]4CCCCN4C(=O)C4CCCOC4)ccc3C2=O)C(=O)N1] | 470.29 | 0.54 |
| I-72gk | 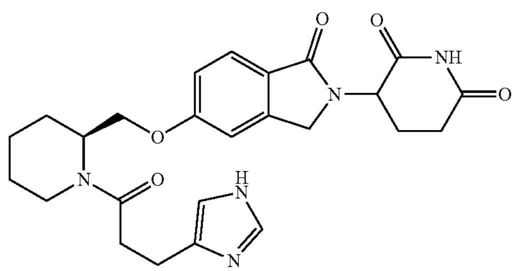 | 480.31 | 0.42 |
| I-72gl | 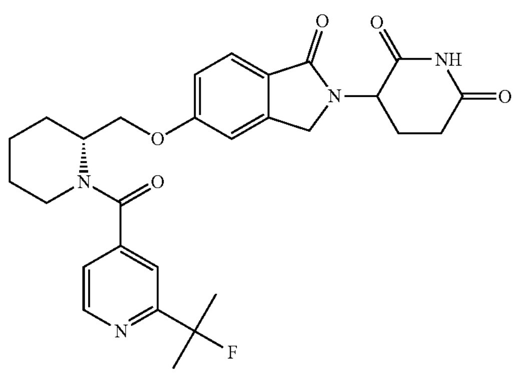 [SMILES: CC(C)(F)c1cc(C(=O)N2CCCC[C@@H]2COc2ccc3c(c2)CN(C2CCC(=O)NC2=O)C3=O)ccn1] | 523.32 | 0.57 |
| I-72gm | 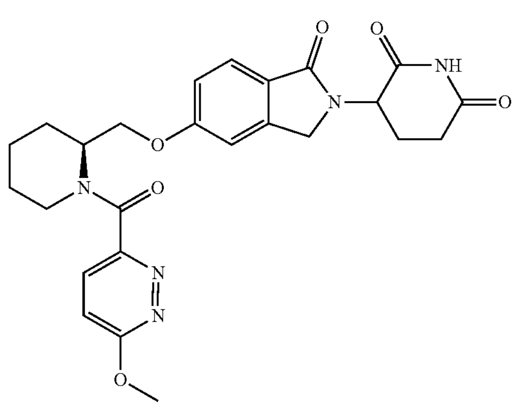 [SMILES: COc1ccc(C(=O)N2CCCC[C@H]2COc2ccc3c(c2)CN(C2CCC(=O)NC2=O)C3=O)nn1] | 494.3 | 0.53 |

-continued
| Compound Number | Structure | LCMS [M + H] | LCMS Rt |
|---|---|---|---|
| I-72gn | 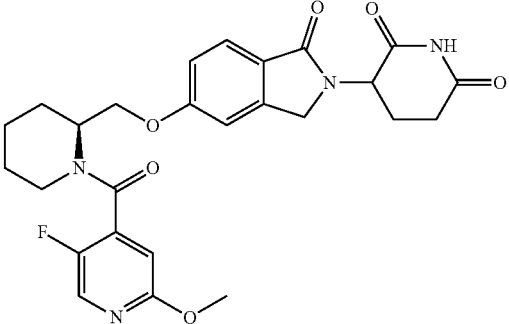 [SMILES: COc1cc(C(=O)N2CCCC[C@H]2COc2ccc3c(c2)CN(C2CCC(=O)NC2=O)C3=O)c(F)cn1] | 511.2 | 0.56 |
| I-72go | 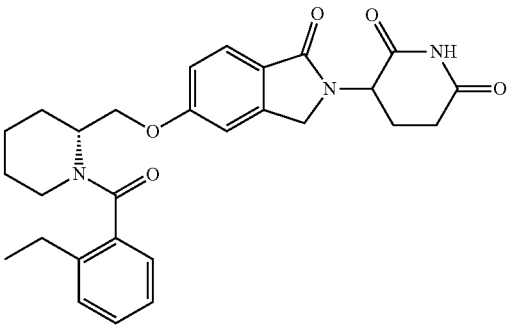 [SMILES: CCc1ccccc1C(=O)N1CCCC[C@@H]1COc1ccc2c(c1)CN(C1CCC(=O)NC1=O)C2=O] | 490.28 | 0.61 |
| I-72gp | 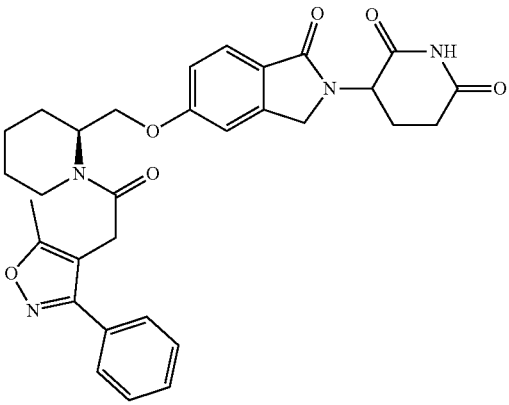 [SMILES: Cc1onc(-c2ccccc2)c1CC(=O)N1CCCC[C@H]1COc1ccc2c(c1)CN(C1CCC(=O)NC1=O)C2=O] | 557.3 | 0.58 |
| I-72gq | 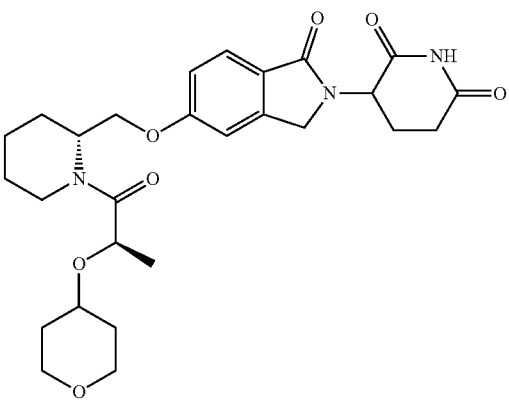 [SMILES: C[C@@H](OC1CCOCC1)C(=O)N1CCCC[C@@H]1COc1ccc2c(c1)CN(C1CCC(=O)NC1=O)C2=O] | 514.32 | 0.54 |

-continued

| Compound Number | Structure | LCMS [M + H] | LCMS Rt |
|---|---|---|---|
| I-72gr | 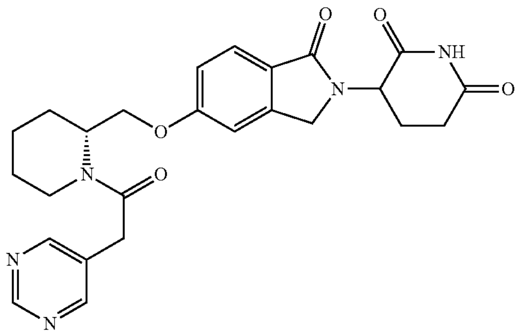 [SMILES: O=C1CCC(N2Cc3cc(OC[C@H]4CCCCN4C(=O)Cc4cncnc4)ccc3C2=O)C(=O)N1] | 478.25 | 0.49 |
| I-72gs | 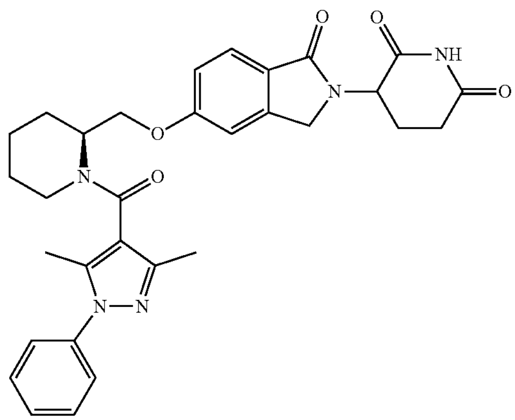 [SMILES: Cc1nn(-c2ccccc2)c(C)c1C(=O)N1CCCC[C@H]1COc1ccc2c(c1)CN(C1CCC(=O)NC1=O)C2=O] | 556.31 | 0.58 |
| I-72gt | 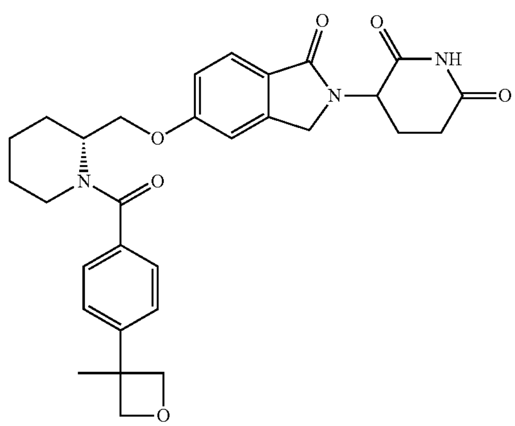 [SMILES: CC1(c2ccc(C(=O)N3CCCC[C@@H]3COc3ccc4c(c3)CN(C3CCC(=O)NC3=O)C4=O)cc2)COC1] | 532.29 | 0.57 |
| I-72gu | 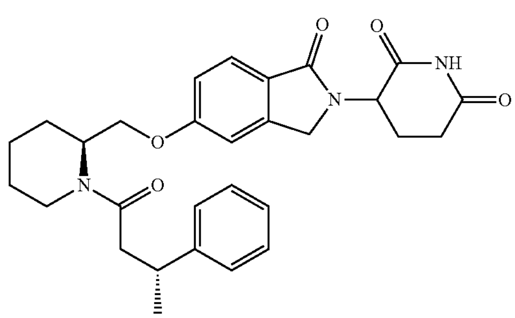 [SMILES: C[C@H](CC(=O)N1CCCC[C@H]1COc1ccc2c(c1)CN(C1CCC(=O)NC1=O)C2=O)c1ccccc1] | 504.32 | 0.62 |

| Compound Number | Structure | LCMS [M + H] | LCMS Rt |
|---|---|---|---|
| I-72gv | 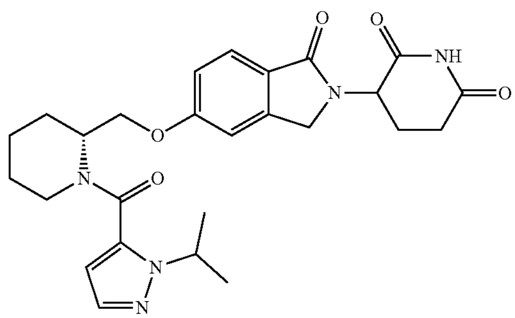 [SMILES: CC(C)n1nccc1C(=O)N1CCCC[C@@H]1COc1ccc2c(c1)CN(C1CCC(=O)NC1=O)C2=O] | 494.31 | 0.55 |
| I-72gw | 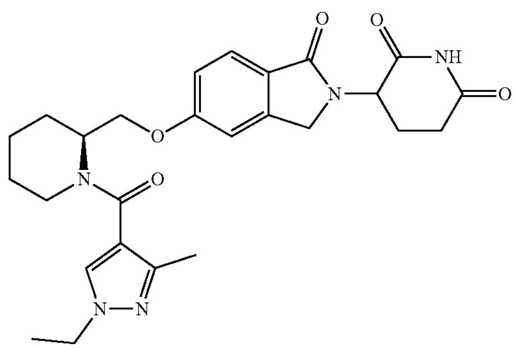 [SMILES: CCn1cc(C(=O)N2CCCC[C@H]2COc2ccc3c(c2)CN(C2CCC(=O)NC2=O)C3=O)c(C)n1] | 494.32 | 0.53 |
| I-72gx | 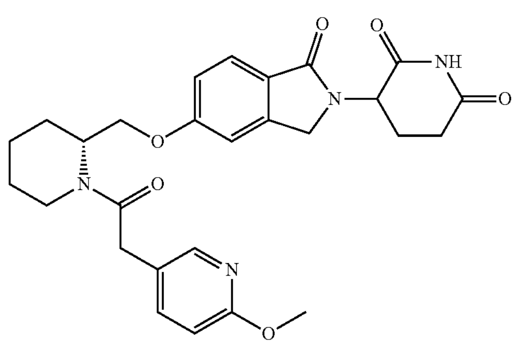 [SMILES: COc1ccc(CC(=O)N2CCCC[C@@H]2COc2ccc3c(c2)CN(C2CCC(=O)NC2=O)C3=O)cn1] | 507.27 | 0.56 |
| I-72gy | 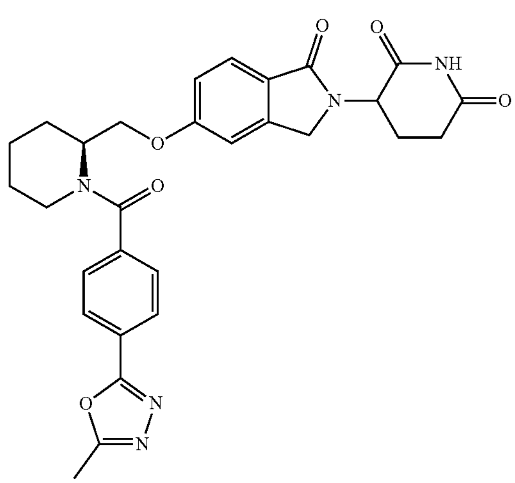 [SMILES: Cc1nnc(-c2ccc(C(=O)N3CCCC[C@H]3COc3ccc4c(c3)CN(C3CCC(=O)NC3=O)C4=O)cc2)o1] | 544.24 | 0.54 |

-continued
| Compound Number | Structure | LCMS [M + H] | LCMS Rt |
|---|---|---|---|
| I-72gz | 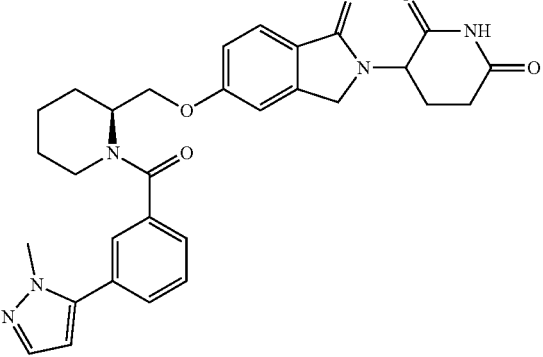 | 542.29 | 0.56 |
| I-72ha | 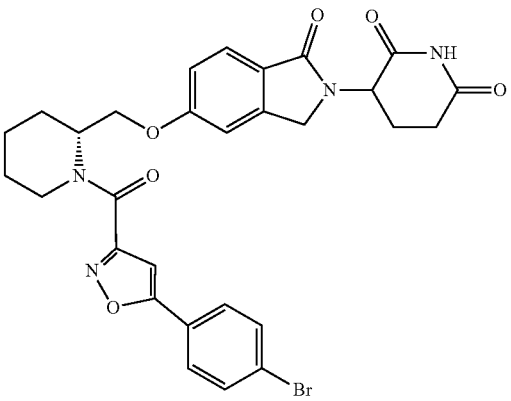 [SMILES: O=C1CCC(N2Cc3cc(OC[C@H]4CCCCN4C(=O)c4cc(-c5ccc(Br)cc5)on4)ccc3C2=O)C(=O)N1] | 607.13 | 0.65 |
| I-72hb | 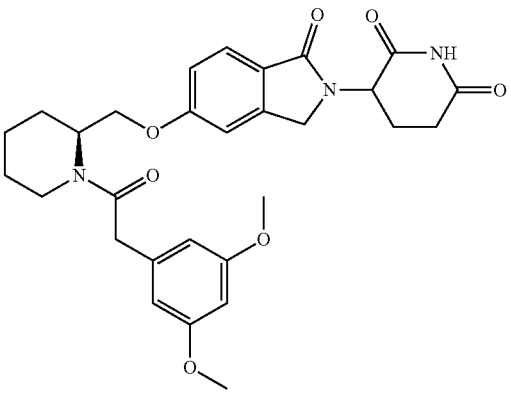 [SMILES: COc1cc(CC(=O)N2CCCC[C@H]2COc2ccc3c(c2)CN(C2CCC(=O)NC2=O)C3=O)cc(OC)c1] | 536.31 | 0.59 |
| I-72hc | 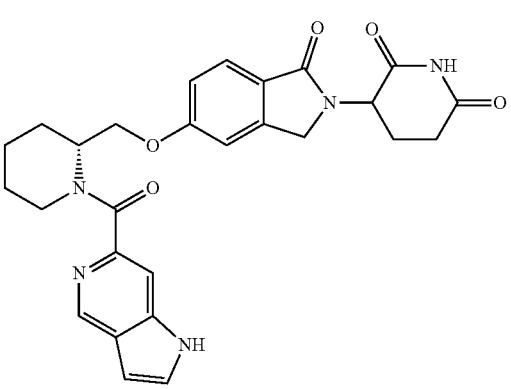 [SMILES: O=C1CCC(N2Cc3cc(OC[C@H]4CCCCN4C(=O)c4cc5[nH]ccc5cn4)ccc3C2=O)C(=O)N1] | 502.28 | 0.43 |

| Compound Number | Structure | LCMS [M + H] | LCMS Rt |
|---|---|---|---|
| I-72hd | 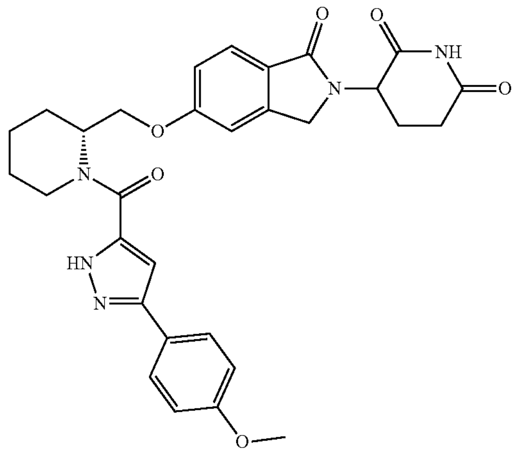 [SMILES: COc1ccc(-c2cc(C(=O)N3CCCC[C@@H]3COc3ccc4c(c3)CN(C3CCC(=O)NC3=O)C4=O)[nH]n2)cc1] | 558.25 | 0.58 |
| I-72he | 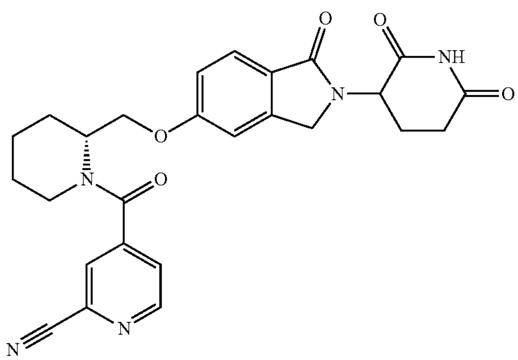 [SMILES: N#Cc1cc(C(=O)N2CCCC[C@@H]2COc2ccc3c(c2)CN(C2CCC(=O)NC2=O)C3=O)ccn1] | 488.24 | 0.51 |
| I-72hf | 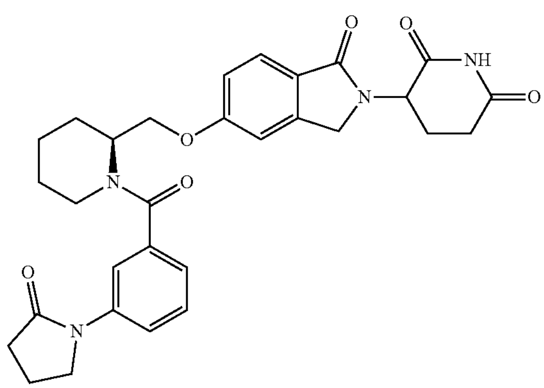 [SMILES: O=C1CCC(N2Cc3cc(OC[C@@H]4CCCCN4C(=O)c4cccc(N5CCCC5=O)c4)ccc3C2=O)C(=O)N1] | 545.31 | 0.55 |
| I-72hg | 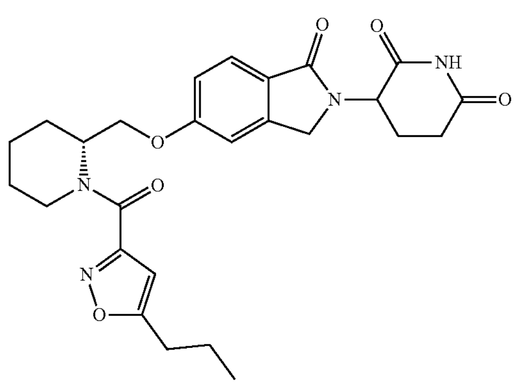 [SMILES: CCCc1cc(C(=O)N2CCCC[C@@H]2COc2ccc3c(c2)CN(C2CCC(=O)NC2=O)C3=O)no1] | 495.31 | 0.59 |

-continued

| Compound Number | Structure | LCMS [M + H] | LCMS Rt |
|---|---|---|---|
| I-72hh | 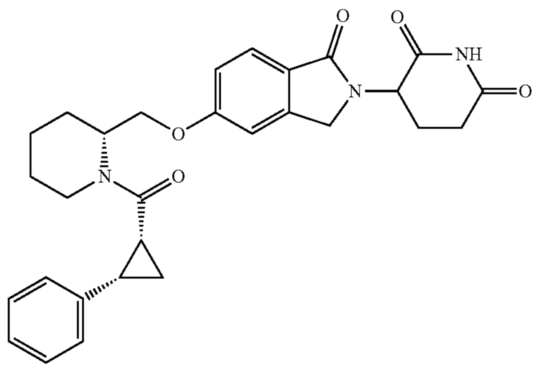 [SMILES: O=C1CCC(N2Cc3cc(OC[C@H]4CCCCN4C(=O)[C@@H]4C[C@@H]4c4ccccc4)ccc3C2=O)C(=O)N1] | 502.3 | 0.61 |
| I-72hi | 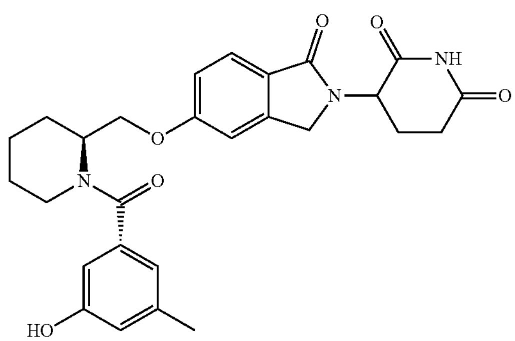 | 492.27 | 0.56 |
| I-72hj | 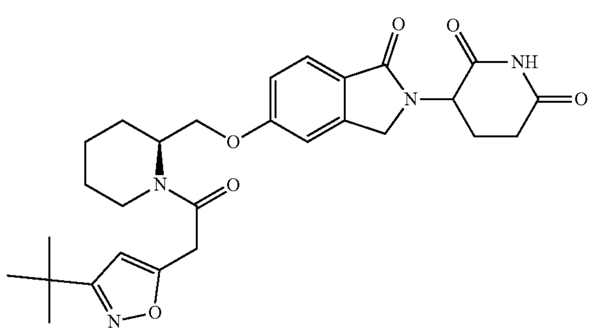 [SMILES: CC(C)(C)c1cc(CC(=O)N2CCCC[C@H]2COc2ccc3c(c2)CN(C2CCC(=O)NC2=O)C3=O)on1] | 523.33 | 0.59 |
| I-72hk | 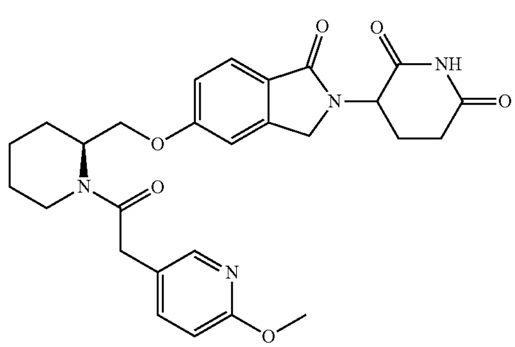 [SMILES: COc1ccc(CC(=O)N2CCCC[C@H]2COc2ccc3c(c2)CN(C2CCC(=O)NC2=O)C3=O)cn1] | 507.32 | 0.55 |

-continued

| Compound Number | Structure | LCMS [M + H] | LCMS Rt |
|---|---|---|---|
| I-72hl | 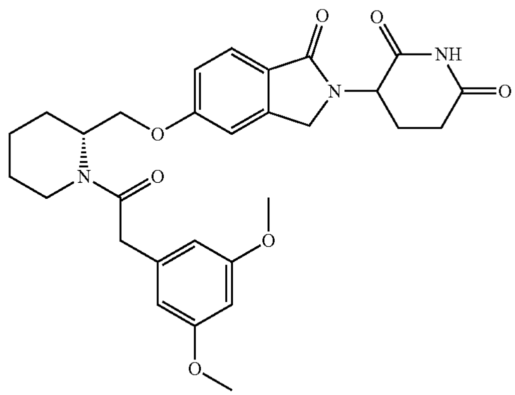 [SMILES: COc1cc(CC(=O)N2CCCC[C@@H]2COc2ccc3c(c2)CN(C2CCC(=O)NC2=O)C3=O)cc(OC)c1] | 536.29 | 0.58 |
| I-72hm | 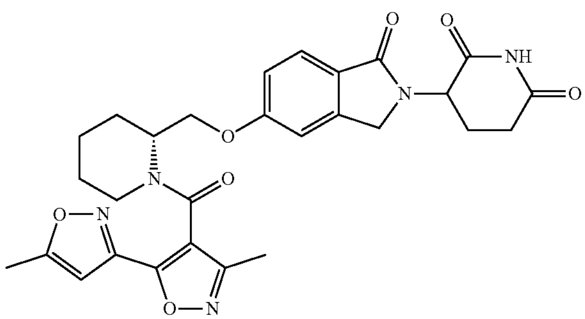 [SMILES: Cc1cc(-c2onc(C)c2C(=O)N2CCCC[C@@H]2COc2ccc3c(c2)CN(C2CCC(=O)NC2=O)C3=O)no1] | 548.25 | 0.56 |
| I-72hn | 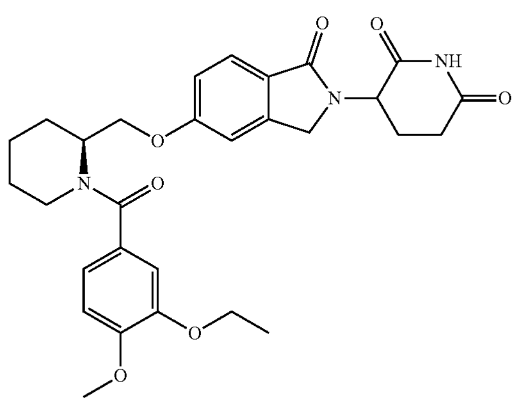 [SMILES: CCOc1cc(C(=O)N2CCCC[C@H]2COc2ccc3c(c2)CN(C2CCC(=O)NC2=O)C3=O)ccc1OC] | 536.3 | 0.57 |
| I-72ho | 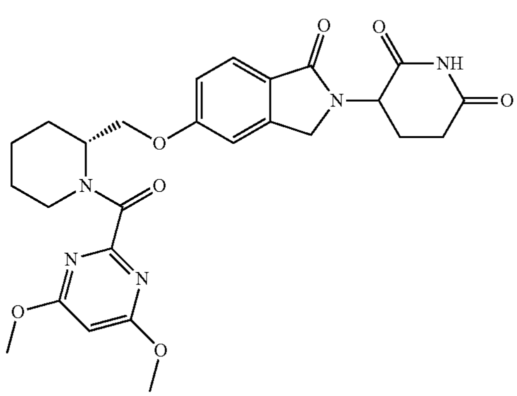 [SMILES: COc1cc(OC)nc(C(=O)N2CCCC[C@@H]2COc2ccc3c(c2)CN(C2CCC(=O)NC2=O)C3=O)n1] | 524.27 | 0.56 |

| Compound Number | Structure | LCMS [M + H] | LCMS Rt |
|---|---|---|---|
| I-72hp | 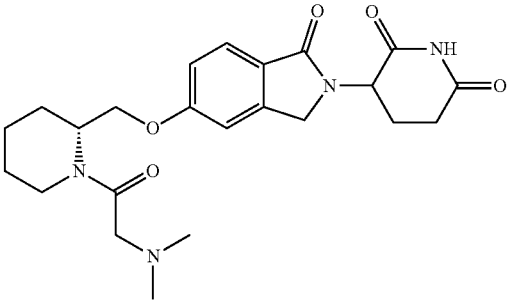 [SMILES: CN(C)CC(=O)N1CCCC[C@@H]1COc1ccc2c(c1)CN(C1CCC(=O)NC1=O)C2=O] | 443.29 | 0.39 |
| I-72hq | 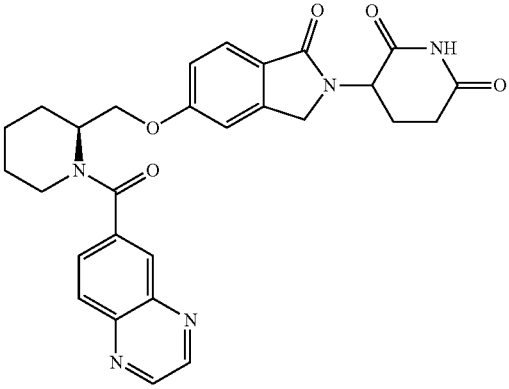 [SMILES: O=C1CCC(N2Cc3cc(OC[C@@H]4CCCCN4C(=O)c4ccc5nccnc5c4)ccc3C2=O)C(=O)N1] | 514.27 | 0.53 |
| I-72hr | 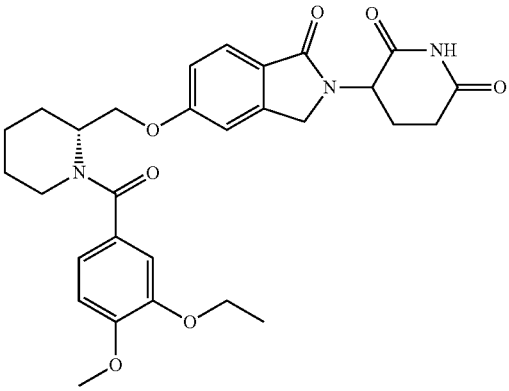 [SMILES: CCOc1cc(C(=O)N2CCCC[C@@H]2COc2ccc3c(c2)CN(C2CCC(=O)NC2=O)C3=O)ccc1OC] | 536.28 | 0.57 |
| I-72hs | 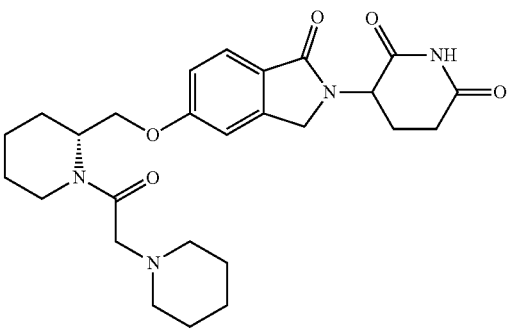 [SMILES: O=C1CCC(N2Cc3cc(OC[C@H]4CCCCN4C(=O)CN4CCCCC4)ccc3C2=O)C(=O)N1] | 483.33 | 0.41 |

| Compound Number | Structure | LCMS [M + H] | LCMS Rt |
|---|---|---|---|
| I-72ht | 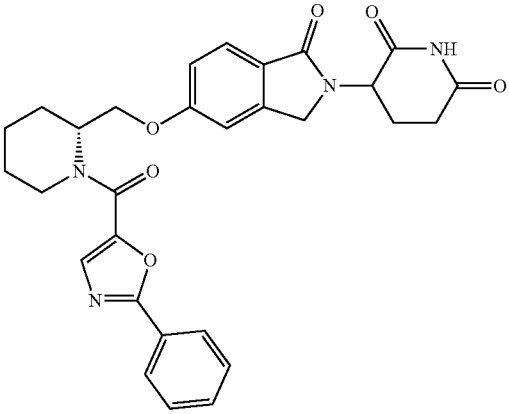 [SMILES: O=C1CCC(N2Cc3cc(OC[C@H]4CCCCN4C(=O)c4cnc(-c5ccccc5)o4)ccc3C2=O)C(=O)N1] | 529.26 | 0.59 |
| I-72hu | 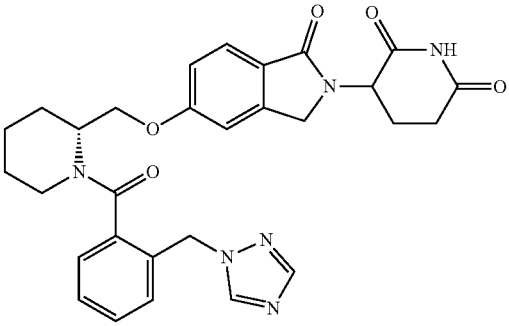 [SMILES: O=C1CCC(N2Cc3cc(OC[C@H]4CCCCN4C(=O)c4ccccc4Cn4cncn4)ccc3C2=O)C(=O)N1] | 543.29 | 0.54 |
| I-72hv | 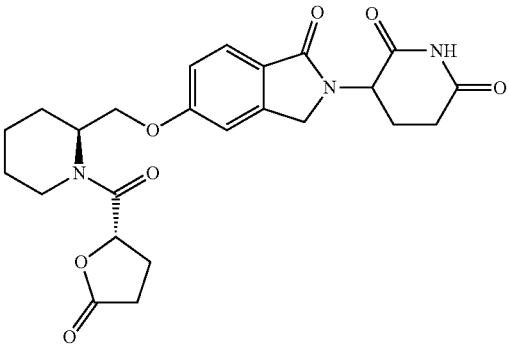 [SMILES: O=C1CCC(N2Cc3cc(OC[C@@H]4CCCCN4C(=O)[C@@H]4CCC(=O)O4)ccc3C2=O)C(=O)N1] | 470.24 | 0.48 |
| I-72hw | 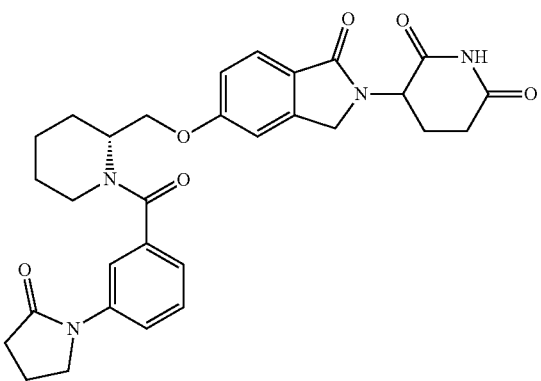 [SMILES: O=C1CCC(N2Cc3cc(OC[C@H]4CCCCN4C(=O)c4cccc(N5CCCC5=O)c4)ccc3C2=O)C(=O)N1] | 545.31 | 0.54 |

| Compound Number | Structure | LCMS [M + H] | LCMS Rt |
|---|---|---|---|
| I-72hx | 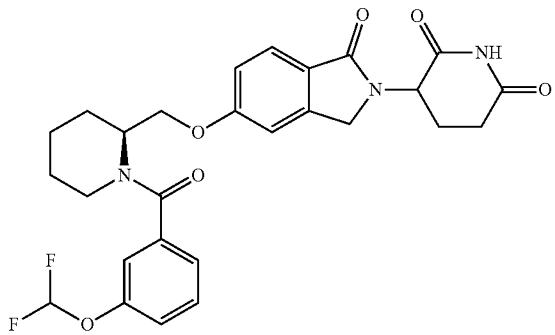 [SMILES: O=C1CCC(N2Cc3cc(OC[C@@H]4CCCCN4C(=O)c4cccc(OC(F)F)c4)ccc3C2=O)C(=O)N1] | 528.25 | 0.58 |
| I-72hy | 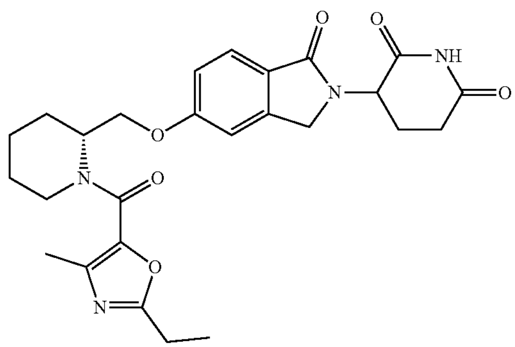 [SMILES: CCc1nc(C)c(C(=O)N2CCCC[C@@H]2COc2ccc3c(c2)CN(C2CCC(=O)NC2=O)C3=O)o1] | 495.28 | 0.56 |
| I-72hz | 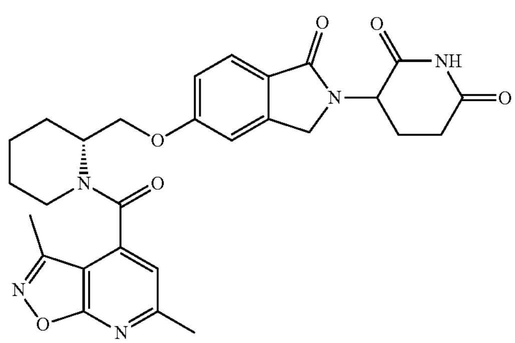 [SMILES: Cc1cc(C(=O)N2CCCC[C@@H]2COc2ccc3c(c2)CN(C2CCC(=O)NC2=O)C3=O)c2c(C)noc2n1] | 532.25 | 0.54 |
| I-72ia | 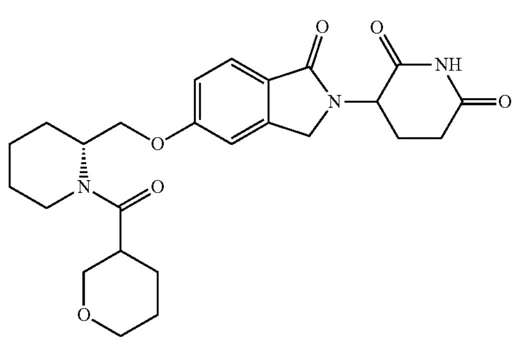 [SMILES: O=C1CCC(N2Cc3cc(OC[C@H]4CCCCN4C(=O)C4CCCOC4)ccc3C2=O)C(=O)N1] | 470.27 | 0.54 |

-continued

| Compound Number | Structure | LCMS [M + H] | LCMS Rt |
|---|---|---|---|
| I-72ib | 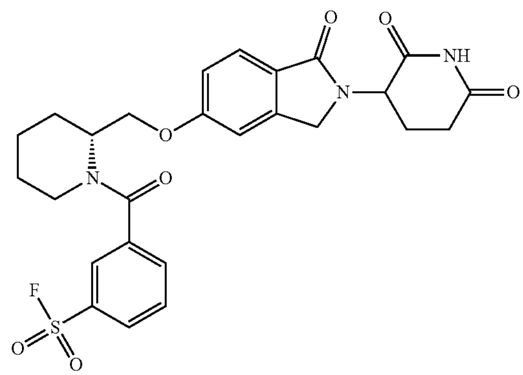 [SMILES: O=C1CCC(N2Cc3cc(OC[C@H]4CCCCN4C(=O)c4cccc(S(=O)(=O)F)c4)ccc3C2=O)C(=O)N1] | 544.21 | 0.57 |
| I-72ic | 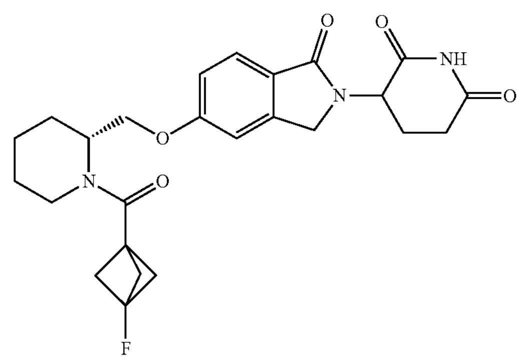 [SMILES: O=C1CCC(N2Cc3cc(OC[C@H]4CCCCN4C(=O)C45CC(F)(C4)C5)ccc3C2=O)C(=O)N1] | 470.27 | 0.56 |
| I-72id | 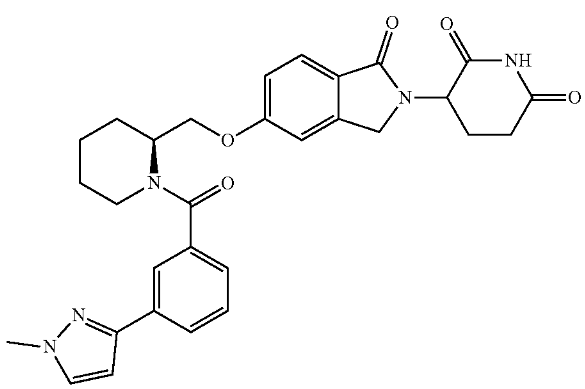 [SMILES: Cn1ccc(-c2cccc(C(=O)N3CCCC[C@H]3COc3ccc4c(c3)CN(C3CCC(=O)NC3=O)C4=O)c2)n1] | 542.28 | 0.57 |
| I-72ie | 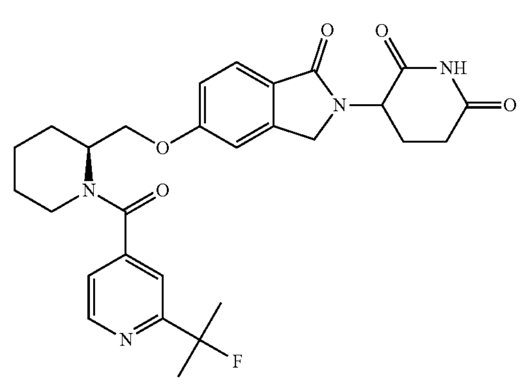 [SMILES: CC(C)(F)c1cc(C(=O)N2CCCC[C@H]2COc2ccc3c(c2)CN(C2CCC(=O)NC2=O)C3=O)ccn1] | 523.2 | 0.57 |

| Compound Number | Structure | LCMS [M + H] | LCMS Rt |
|---|---|---|---|
| I-72if | 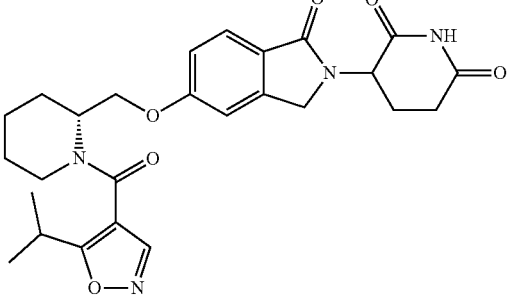 | 495.28 | 0.57 |
| I-72ig | 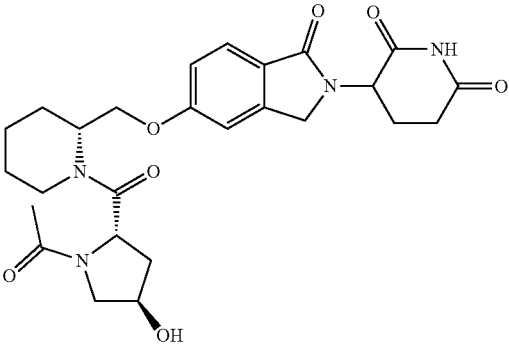 [SMILES: CC(=O)N1C[C@H](O)C[C@H]1C(=O)N1CCCC[C@@H]1COc1ccc2c(c1)CN(C1CCC(=O)NC1=O)C2=O] | 513.31 | 0.48 |
| I-72ih | 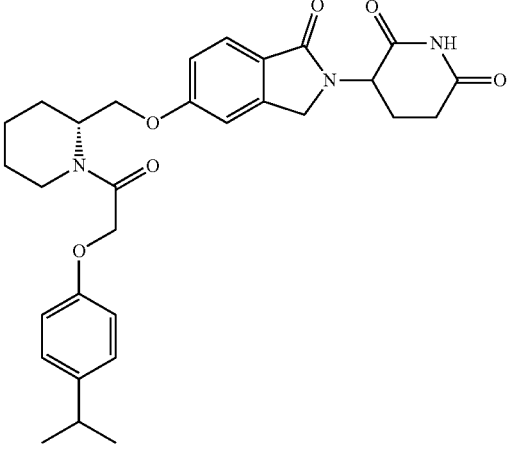 [SMILES: CC(C)c1ccc(OCC(=O)N2CCCC[C@@H]2COc2ccc3c(c2)CN(C2CCC(=O)NC2=O)C3=O)cc1] | 534.4 | 0.64 |
| I-72ii | 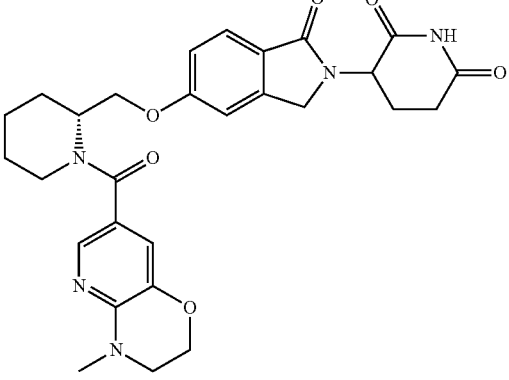 | 534.3 | 0.52 |

| Compound Number | Structure | LCMS [M + H] | LCMS Rt |
|---|---|---|---|
| I-72ij | 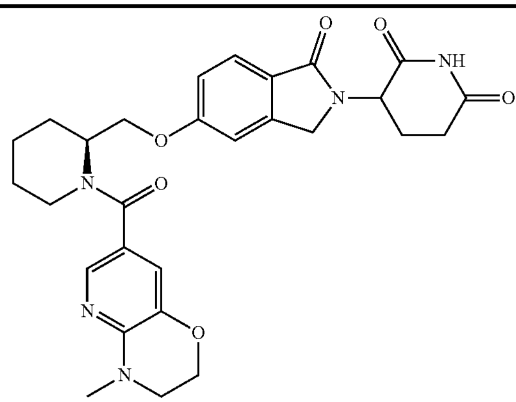 | 534.33 | 0.52 |
| I-72ik | 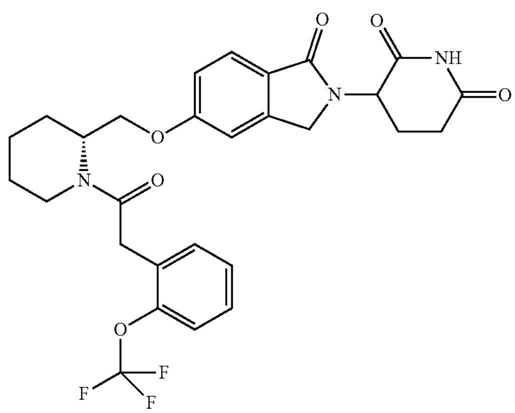 [SMILES: O=C1CCC(N2Cc3cc(OC[C@H]4CCCCN4C(=O)Cc4ccccc4OC(F)(F)F)ccc3C2=O)C(=O)N1] | 560.25 | 0.62 |
| I-72il | 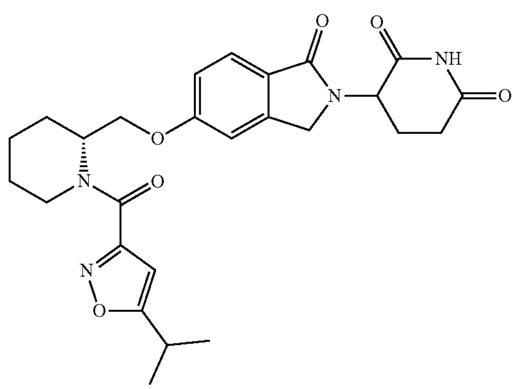 [SMILES: CC(C)c1cc(C(=O)N2CCCC[C@@H]2COc2ccc3c(c2)CN(C2CCC(=O)NC2=O)C3=O)no1] | 495.23 | 0.59 |
| I-72im | 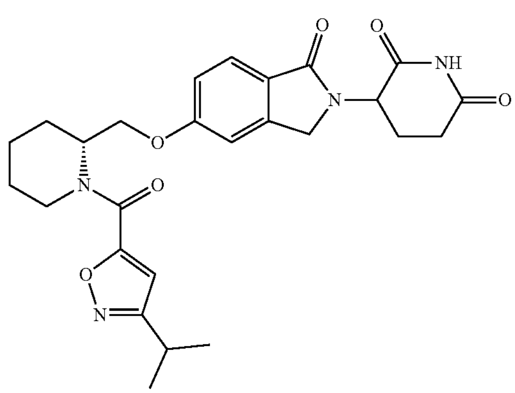 [SMILES: CC(C)c1cc(C(=O)N2CCCC[C@@H]2COc2ccc3c(c2)CN(C2CCC(=O)NC2=O)C3=O)on1] | 495.32 | 0.58 |

-continued
| Compound Number | Structure | LCMS [M + H] | LCMS Rt |
|---|---|---|---|
| I-72in | 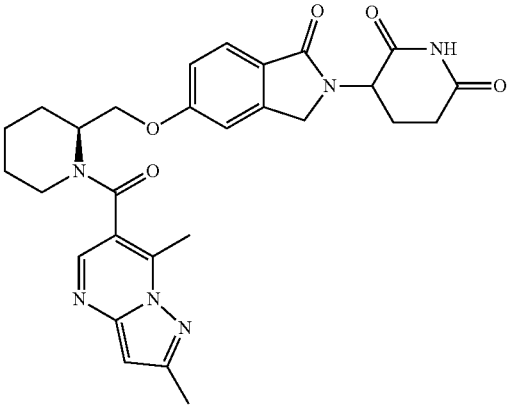 [SMILES: Cc1cc2ncc(C(=O)N3CCCC[C@H]3COc3ccc4c(c3)CN(C3CCC(=O)NC3=O)C4=O)c(C)n2n1] | 531.3 | 0.55 |
| I-72io | 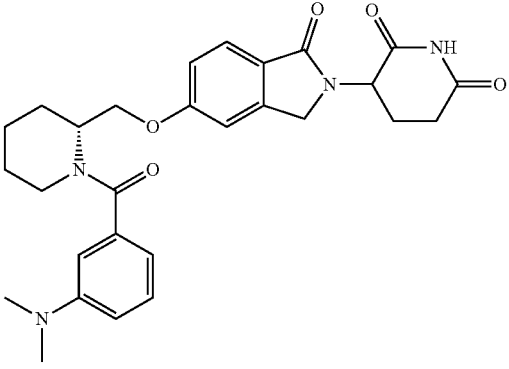 [SMILES: CN(C)c1cccc(C(=O)N2CCCC[C@@H]2COc2ccc3c(c2)CN(C2CCC(=O)NC2=O)C3=O)c1] | 505.31 | 0.58 |
| I-72ip | 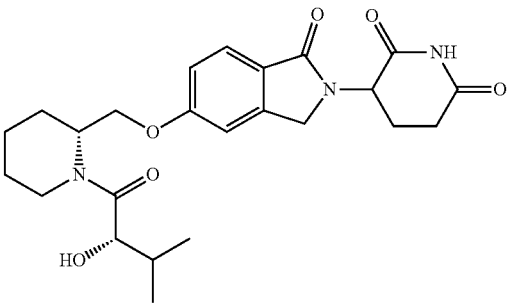 [SMILES: CC(C)[C@H](O)C(=O)N1CCCC[C@@H]1COc1ccc2c(c1)CN(C1CCC(=O)NC1=O)C2=O] | 458.24 | 0.56 |
| I-72iq | 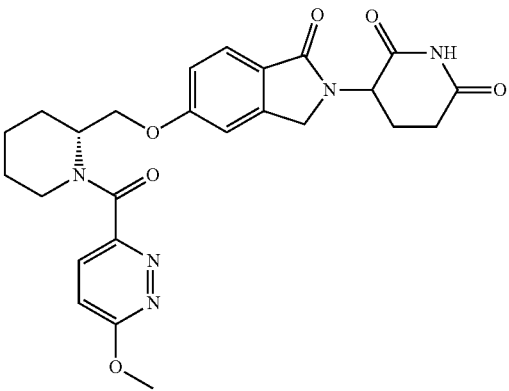 [SMILES: COc1ccc(C(=O)N2CCCC[C@@H]2COc2ccc3c(c2)CN(C2CCC(=O)NC2=O)C3=O)nn1] | 494.27 | 0.52 |

-continued
| Compound Number | Structure | LCMS [M + H] | LCMS Rt |
|---|---|---|---|
| I-72ir | 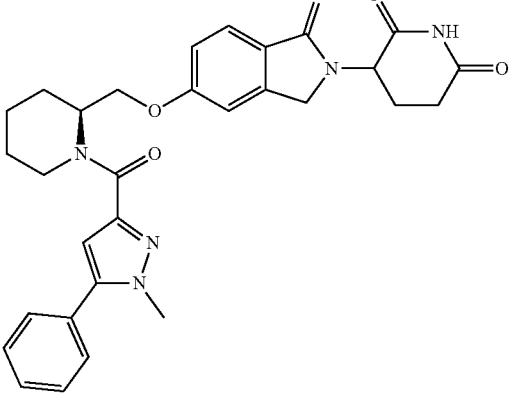 | 542.28 | 0.6 |
| I-72is | 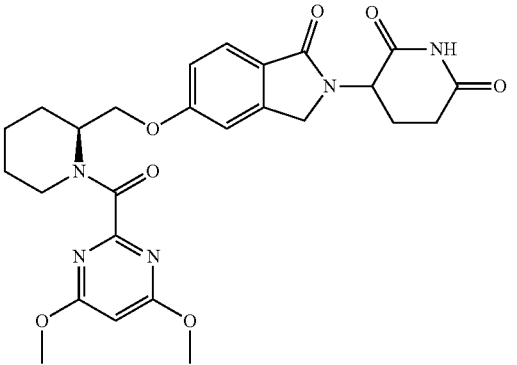 [SMILES: COc1cc(OC)nc(C(=O)N2CCCC[C@H]2COc2ccc3c(c2)CN(C2CCC(=O)NC2=O)C3=O)n1] | 524.27 | 0.57 |
| I-72it | 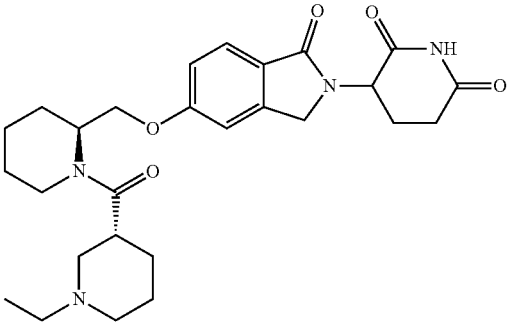 [SMILES: CCN1CCC[C@@H](C(=O)N2CCCC[C@H]2COc2ccc3c(c2)CN(C2CCC(=O)NC2=O)C3=O)C1] | 497.37 | 0.42 |
| I-72iu | 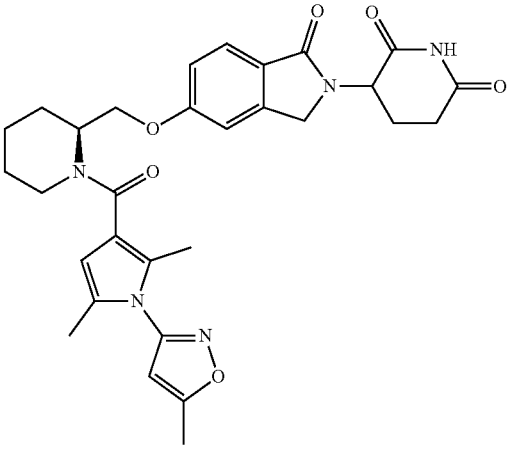 [SMILES: Cc1cc(-n2c(C)cc(C(=O)N3CCCC[C@H]3COc3ccc4c(c3)CN(C3CCC(=O)NC3=O)C4=O)c2C)no1] | 560.28 | 0.59 |

-continued

| Compound Number | Structure | LCMS [M + H] | LCMS Rt |
|---|---|---|---|
| I-72iv | 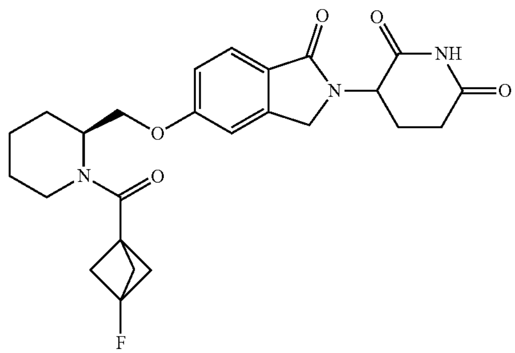 [SMILES: O=C1CCC(N2Cc3cc(OC[C@@H]4CCCCN4C(=O)C45CC(F)(C4)C5)ccc3C2=O)C(=O)N1] | 470.3 | 0.55 |
| I-72iw | 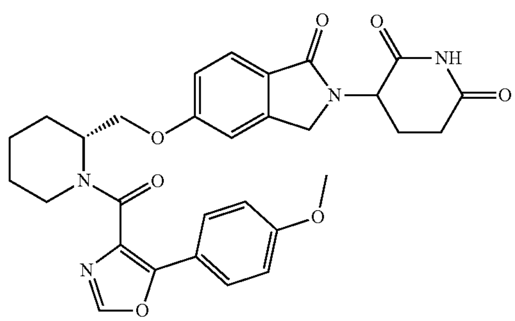 [SMILES: COc1ccc(-c2ocnc2C(=O)N2CCCC[C@@H]2COc2ccc3c(c2)CN(C2CCC(=O)NC2=O)C3=O)cc1] | 559.24 | 0.58 |
| I-72ix | 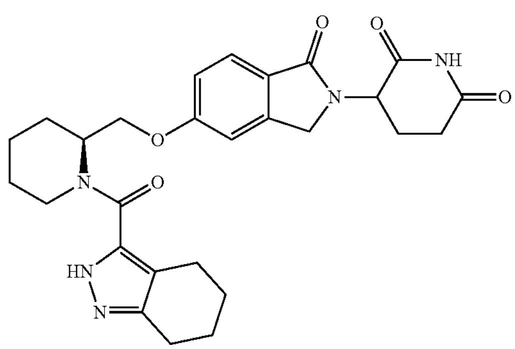 [SMILES: O=C1CCC(N2Cc3cc(OC[C@@H]4CCCCN4C(=O)c4[nH]nc5c4CCCC5)ccc3C2=O)C(=O)N1] | 506.32 | 0.57 |
| I-72iy | 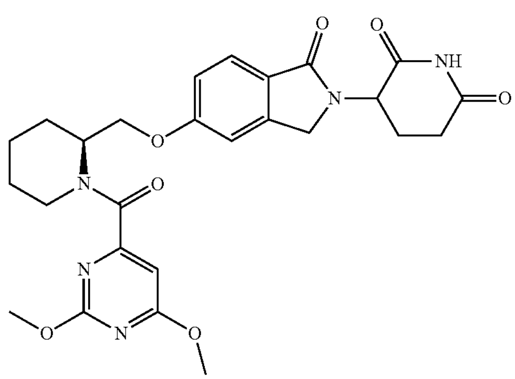 [SMILES: COc1cc(C(=O)N2CCCC[C@H]2COc2ccc3c(c2)CN(C2CCC(=O)NC2=O)C3=O)nc(OC)n1] | 524.3 | 0.55 |

-continued

| Compound Number | Structure | LCMS [M + H] | LCMS Rt |
|---|---|---|---|
| I-72iz | 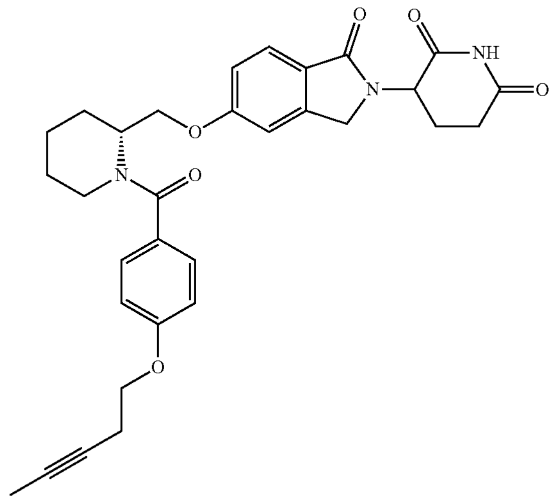 [SMILES: CC#CCCOc1ccc(C(=O)N2CCCC[C@@H]2COc2ccc3c(c2)CN(C2CCC(=O)NC2=O)C3=O)cc1] | 544.28 | 0.62 |
| I-72ja | 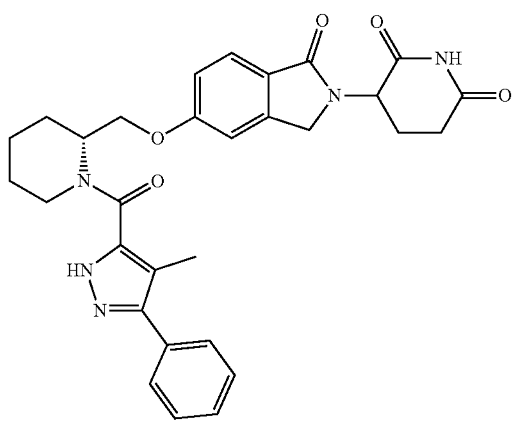 [SMILES: Cc1c(-c2ccccc2)n[nH]c1C(=O)N1CCCC[C@@H]1COc1ccc2c(c1)CN(C1CCC(=O)NC1=O)C2=O] | 542.3 | 0.59 |
| I-72jb | 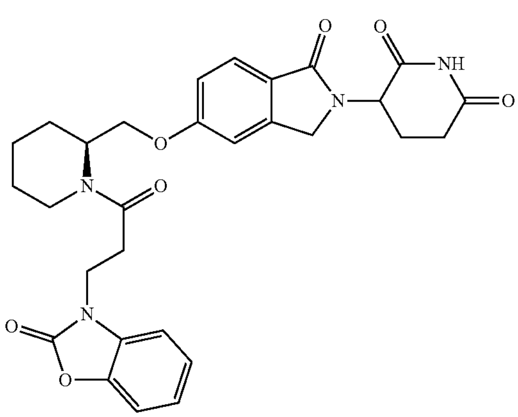 [SMILES: O=C1CCC(N2Cc3cc(OC[C@@H]4CCCCN4C(=O)CCn4c(=O)oc5ccccc54)ccc3C2=O)C(=O)N1] | 547.3 | 0.57 |

-continued

| Compound Number | Structure | LCMS [M + H] | LCMS Rt |
|---|---|---|---|
| I-72jc | 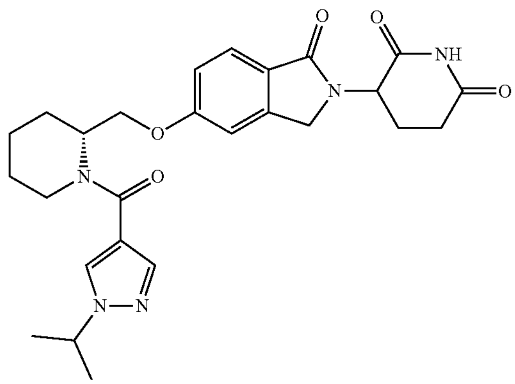 [SMILES: CC(C)n1cc(C(=O)N2CCCC[C@@H]2COc2ccc3c(c2)CN(C2CCC(=O)NC2=O)C3=O)cn1] | 494.3 | 0.54 |
| I-72jd | 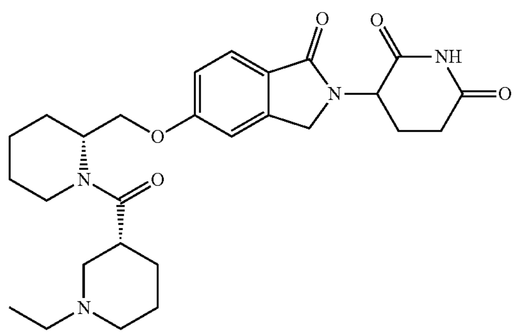 [SMILES: CCN1CCC[C@@H](C(=O)N2CCCC[C@@H]2COc2ccc3c(c2)CN(C2CCC(=O)NC2=O)C3=O)C1] | 497.35 | 0.42 |
| I-72je | 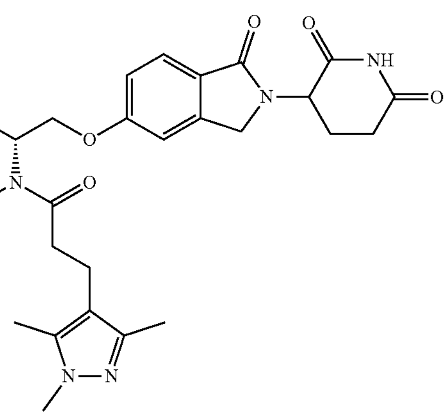 | 522.32 | 0.53 |
| I-72jf | 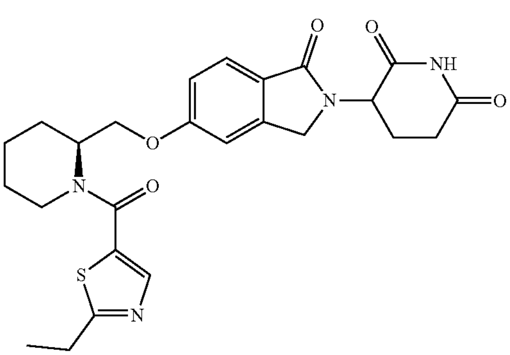 [SMILES: CCc1ncc(C(=O)N2CCCC[C@H]2COc2ccc3c(c2)CN(C2CCC(=O)NC2=O)C3=O)s1] | 497.26 | 0.56 |

| Compound Number | Structure | LCMS [M + H] | LCMS Rt |
|---|---|---|---|
| I-72jg | 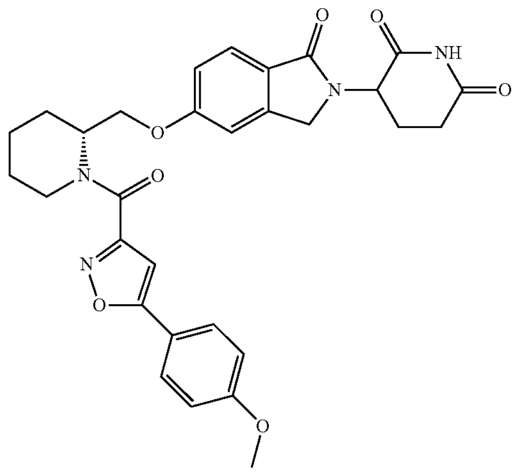 [SMILES: COc1ccc(-c2cc(C(=O)N3CCCC[C@@H]3COc3ccc4c(c3)CN(C3CCC(=O)NC3=O)C4=O)no2)cc1] | 559.24 | 0.61 |
| I-72jh | 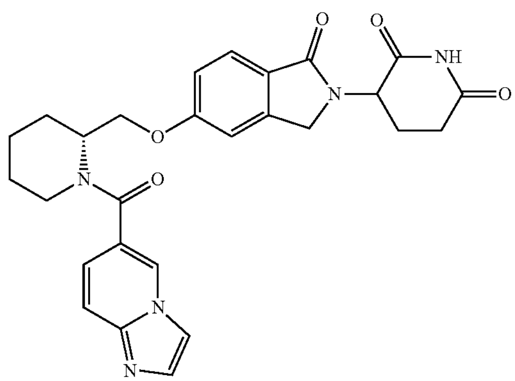 [SMILES: O=C1CCC(N2Cc3cc(OC[C@H]4CCCCN4C(=O)c4ccc5nccn5c4)ccc3C2=O)C(=O)N1] | 502.2 | 0.41 |
| I-72ji | 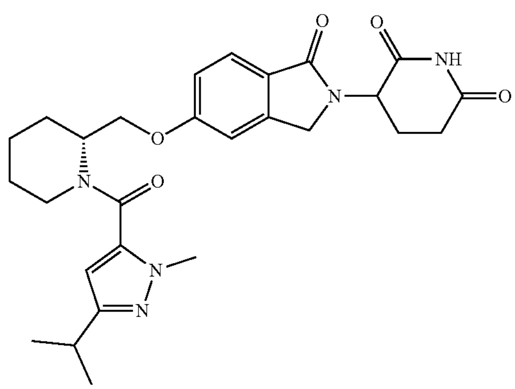 [SMILES: CC(C)c1cc(C(=O)N2CCCC[C@@H]2COc2ccc3c(c2)CN(C2CCC(=O)NC2=O)C3=O)n(C)n1] | 508.32 | 0.58 |
| I-72jj | 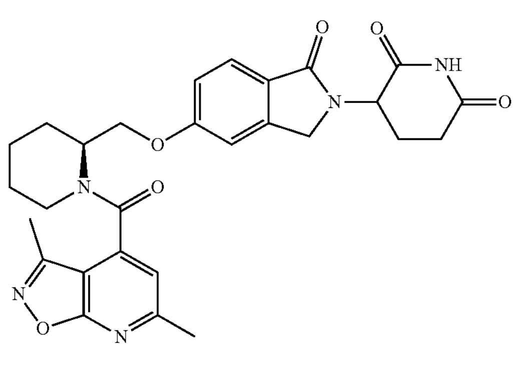 [SMILES: Cc1cc(C(=O)N2CCCC[C@H]2COc2ccc3c(c2)CN(C2CCC(=O)NC2=O)C3=O)c2c(C)noc2n1] | 532.31 | 0.54 |

-continued

| Compound Number | Structure | LCMS [M + H] | LCMS Rt |
|---|---|---|---|
| I-72jk | 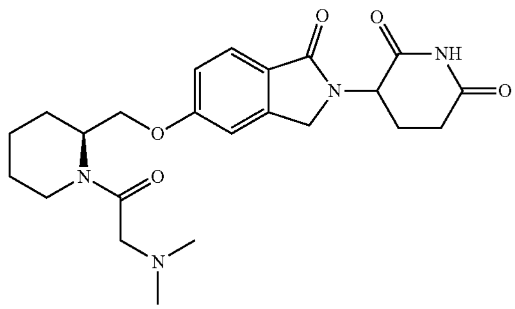 [SMILES: CN(C)CC(=O)N1CCCC[C@H]1COc1ccc2c(c1)CN(C1CCC(=O)NC1=O)C2=O] | 443.3 | 0.39 |
| I-72jl | 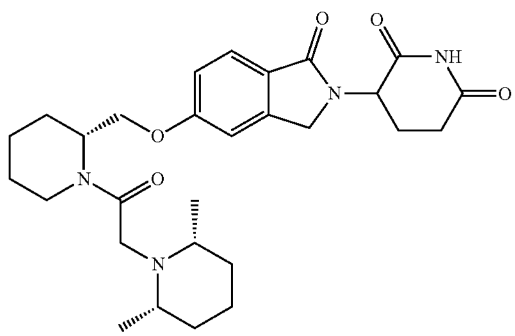 [SMILES: C[C@@H]1CCC[C@H](C)N1CC(=O)N1CCCC[C@@H]1COc1ccc2c(c1)CN(C1CCC(=O)NC1=O)C2=O] | 511.34 | 0.43 |
| I-72jm | 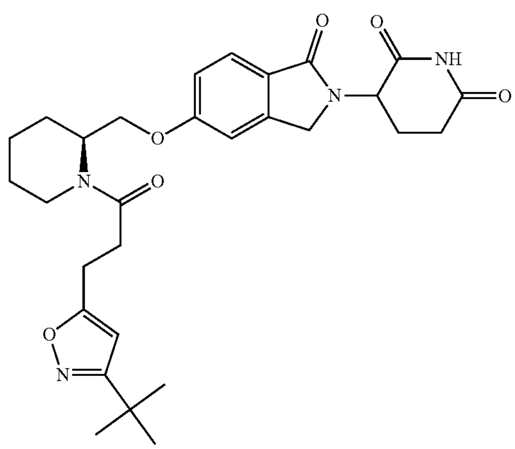 [SMILES: CC(C)(C)c1cc(CCC(=O)N2CCCC[C@H]2COc2ccc3c(c2)CN(C2CCC(=O)NC2=O)C3=O)on1] | 537.34 | 0.6 |
| I-72jn | 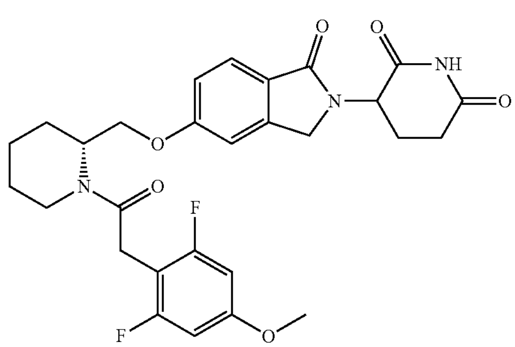 [SMILES: COc1cc(F)c(CC(=O)N2CCCC[C@@H]2COc2ccc3c(c2)CN(C2CCC(=O)NC2=O)C3=O)c(F)c1] | 542.21 | 0.6 |

-continued
| Compound Number | Structure | LCMS [M + H] | LCMS Rt |
|---|---|---|---|
| I-72jo | 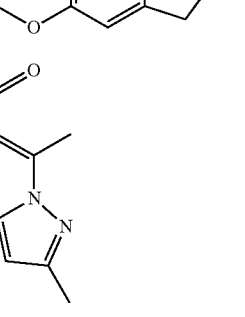 | 531.28 | 0.55 |
| I-72jp | 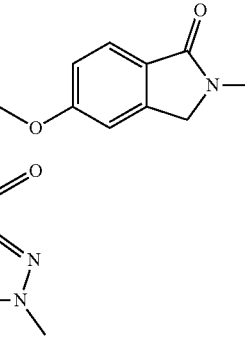 | 542.28 | 0.59 |
| I-72jq | 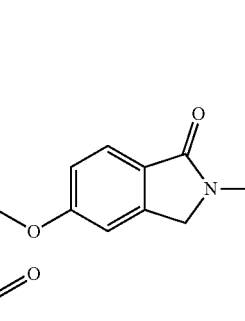 | 483.36 | 0.41 |
| I-72jr | 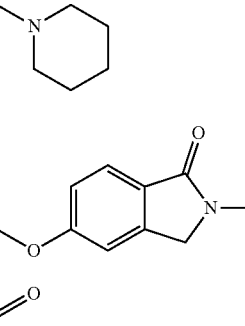 | 502.26 | 0.54 |

-continued
| Compound Number | Structure | LCMS [M + H] | LCMS Rt |
|---|---|---|---|
| I-72js | 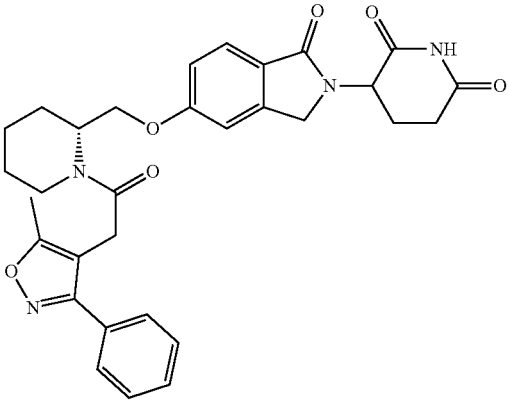 [SMILES: Cc1onc(-c2ccccc2)c1CC(=O)N1CCCC[C@@H]1COc1ccc2c(c1)CN(C1CCC(=O)NC1=O)C2=O] | 557.26 | 0.58 |
| I-72jt | 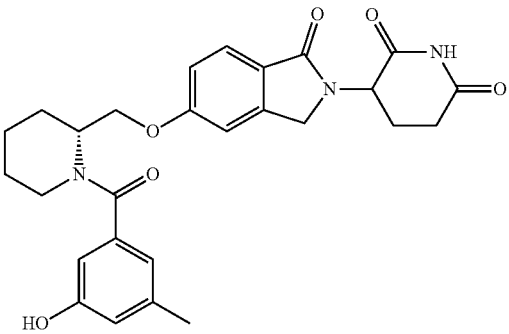 [SMILES: Cc1cc(O)cc(C(=O)N2CCCC[C@@H]2COc2ccc3c(c2)CN(C2CCC(=O)NC2=O)C3=O)c1] | 492.32 | 0.56 |
| I-72ju | 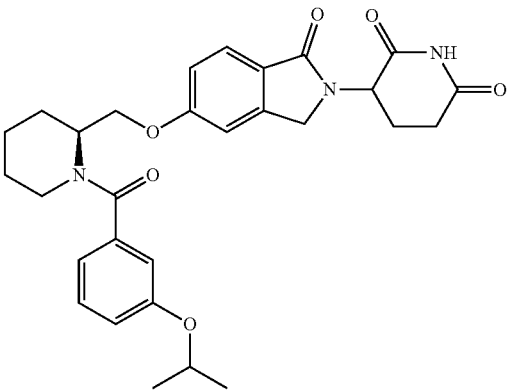 [SMILES: CC(C)Oc1cccc(C(=O)N2CCCC[C@H]2COc2ccc3c(c2)CN(C2CCC(=O)NC2=O)C3=O)c1] | 520.32 | 0.61 |
| I-72jv | 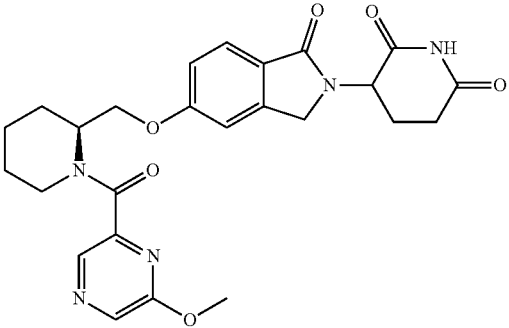 [SMILES: COc1cncc(C(=O)N2CCCC[C@H]2COc2ccc3c(c2)CN(C2CCC(=O)NC2=O)C3=O)n1] | 494.28 | 0.55 |

-continued

| Compound Number | Structure | LCMS [M + H] | LCMS Rt |
|---|---|---|---|
| I-72jw | 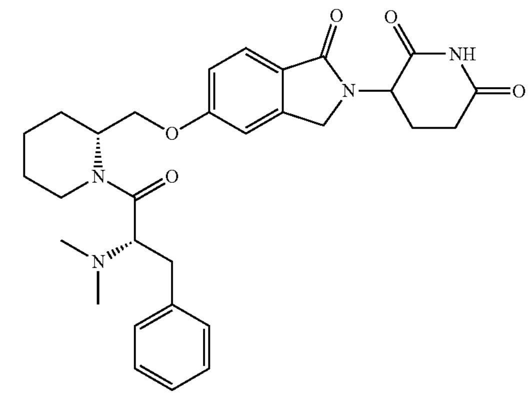 [SMILES: CN(C)[C@@H](Cc1ccccc1)C(=O)N1CCCC[C@@H]1COc1ccc2c(c1)CN(C1CCC(=O)NC1=O)C2=O] | 533.34 | 0.48 |
| I-72jx | 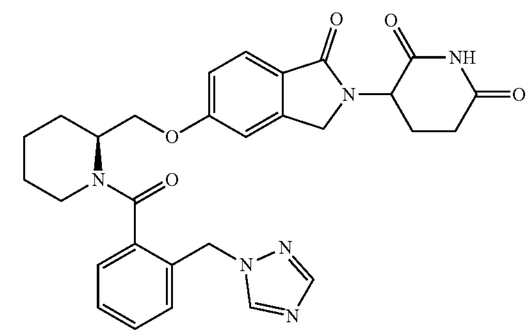 [SMILES: O=C1CCC(N2Cc3cc(OC[C@@H]4CCCCN4C(=O)c4ccccc4Cn4cncn4)ccc3C2=O)C(=O)N1] | 543.28 | 0.54 |
| I-72jy | 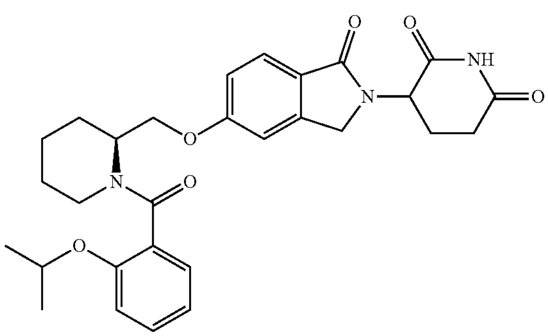 [SMILES: CC(C)Oc1ccccc1C(=O)N1CCCC[C@H]1COc1ccc2c(c1)CN(C1CCC(=O)NC1=O)C2=O] | 520.32 | 0.61 |
| I-72jz | 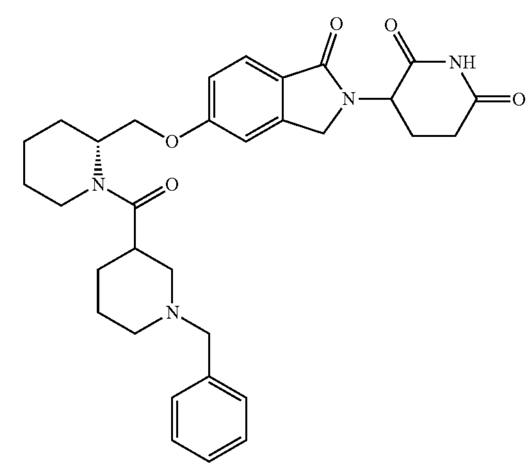 [SMILES: O=C1CCC(N2Cc3cc(OC[C@H]4CCCCN4C(=O)C4CCCN(Cc5ccccc5)C4)ccc3C2=O)C(=O)N1] | 559.35 | 0.47 |

-continued
| Compound Number | Structure | LCMS [M + H] | LCMS Rt |
|---|---|---|---|
| I-72ka | 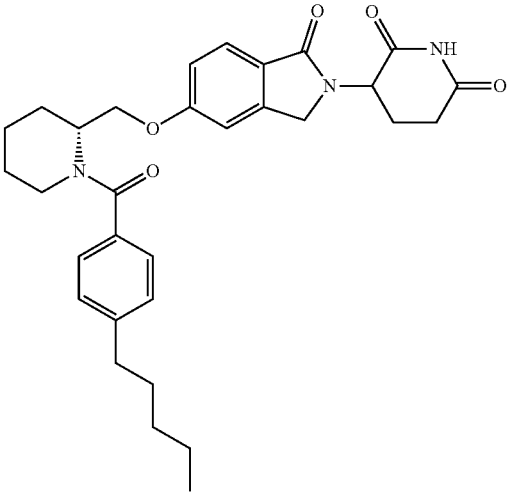 [SMILES: CCCCCc1ccc(C(=O)N2CCCC[C@@H]2COc2ccc3c(c2)CN(C2CCC(=O)NC2=O)C3=O)cc1] | 532.34 | 0.68 |
| I-72kb | 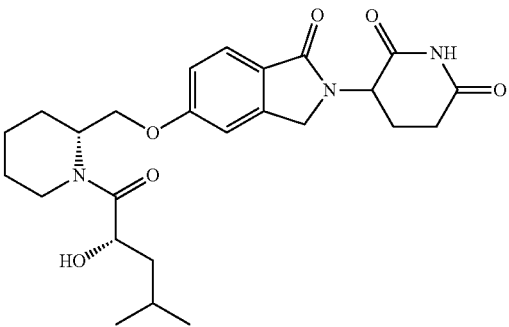 [SMILES: CC(C)C[C@H](O)C(=O)N1CCCC[C@@H]1COc1ccc2c(c1)CN(C1CCC(=O)NC1=O)C2=O] | 472.34 | 0.58 |
| I-72kc | 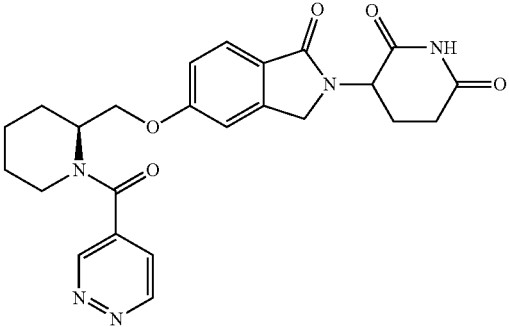 [SMILES: O=C1CCC(N2Cc3cc(OC[C@@H]4CCCCN4C(=O)c4ccnnc4)ccc3C2=O)C(=O)N1] | 464.3 | 0.47 |
| I-72kd | 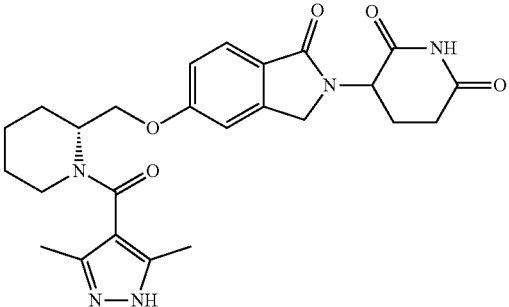 [SMILES: Cc1n[nH]c(C)c1C(=O)N1CCCC[C@@H]1COc1ccc2c(c1)CN(C1CCC(=O)NC1=O)C2=O] | 480.31 | 0.52 |

-continued

| Compound Number | Structure | LCMS [M + H] | LCMS Rt |
|---|---|---|---|
| I-72ke | 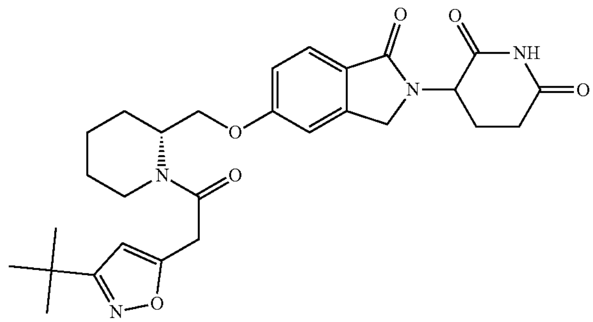 [SMILES: CC(C)(C)c1cc(CC(=O)N2CCCC[C@@H]2COc2ccc3c(c2)CN(C2CCC(=O)NC2=O)C3=O)on1] | 523.31 | 0.58 |
| I-72kf | 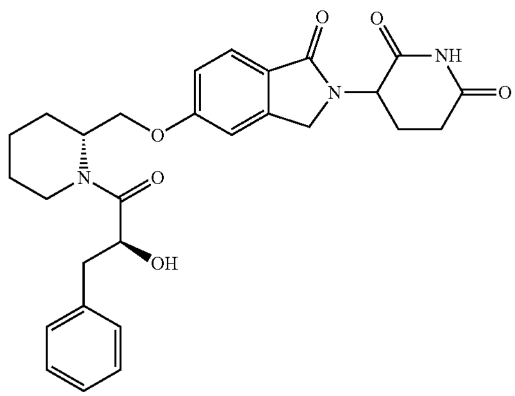 [SMILES: O=C1CCC(N2Cc3cc(OC[C@H]4CCCCN4C(=O)[C@@H](O)Cc4ccccc4)ccc3C2=O)C(=O)N1] | 506.32 | 0.58 |
| I-72kg | 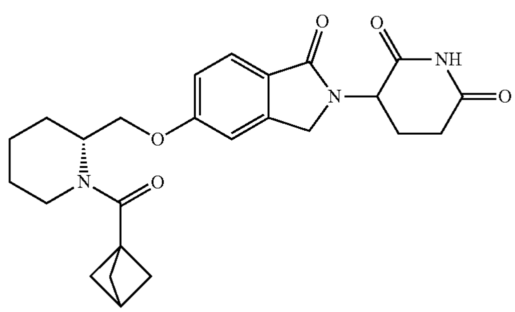 [SMILES: O=C1CCC(N2Cc3cc(OC[C@H]4CCCCN4C(=O)C45CC(C4)C5)ccc3C2=O)C(=O)N1] | 452.27 | 0.58 |
| I-72kh | 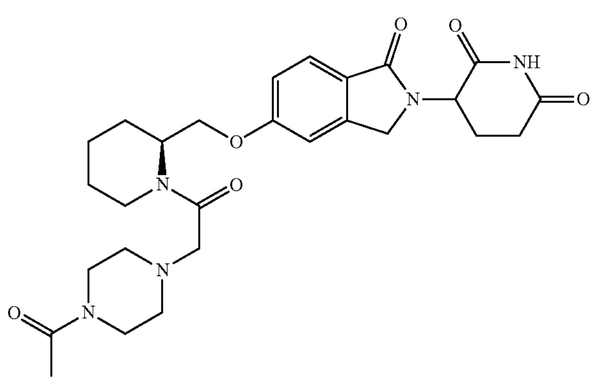 [SMILES: CC(=O)N1CCN(CC(=O)N2CCCC[C@H]2COc2ccc3c(c2)CN(C2CCC(=O)NC2=O)C3=O)CC1] | 526.29 | 0.4 |

-continued

| Compound Number | Structure | LCMS [M + H] | LCMS Rt |
|---|---|---|---|
| I-72ki | 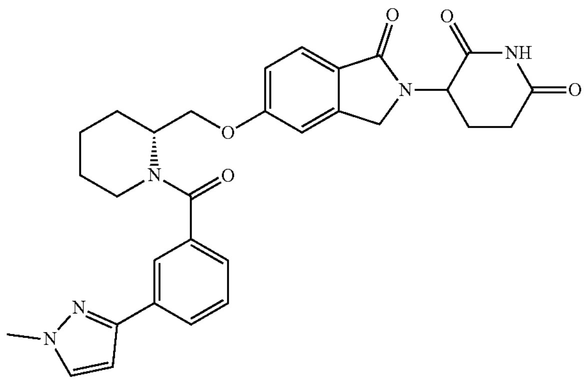 [SMILES: Cn1ccc(-c2cccc(C(=O)N3CCCC[C@@H]3COc3ccc4c(c3)CN(C3CCC(=O)NC3=O)C4=O)c2)n1] | 542.28 | 0.57 |
| I-72kj | 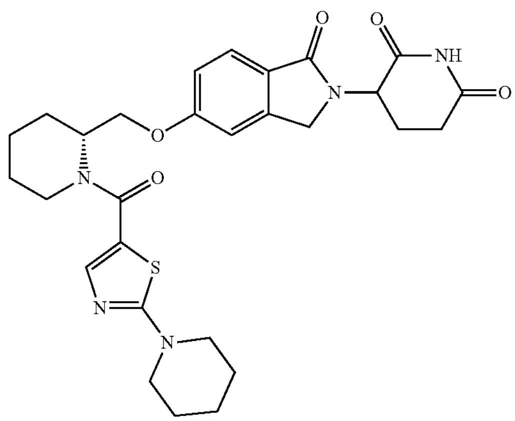 [SMILES: O=C1CCC(N2Cc3cc(OC[C@H]4CCCCN4C(=O)c4cnc(N5CCCCC5)s4)ccc3C2=O)C(=O)N1] | 552.28 | 0.6 |
| I-72kk | 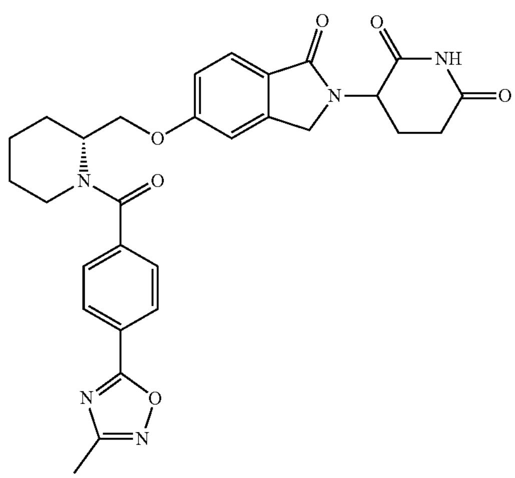 [SMILES: Cc1noc(-c2ccc(C(=O)N3CCCC[C@@H]3COc3ccc4c(c3)CN(C3CCC(=O)NC3=O)C4=O)cc2)n1] | 544.26 | 0.58 |
| I-72kl | 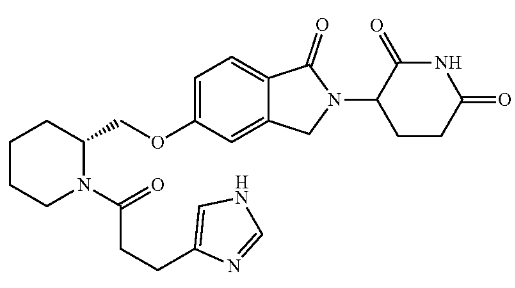 | 480.31 | 0.42 |

| Compound Number | Structure | LCMS [M + H] | LCMS Rt |
|---|---|---|---|
| I-72km | 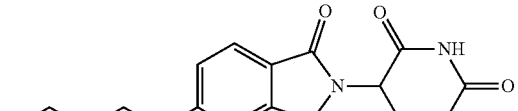 | 548.35 | 0.65 |
| I-72kn | 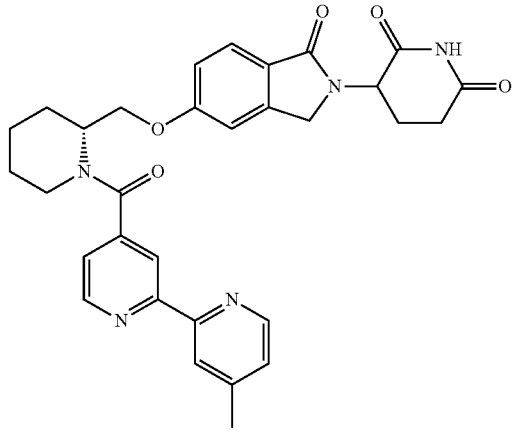 [SMILES: Cc1ccnc(-c2cc(C(=O)N3CCCC[C@@H]3COc3ccc4c(c3)CN(C3CCC(=O)NC3=O)C4=O)ccn2)c1] | 554.28 | 0.54 |
| I-72ko | 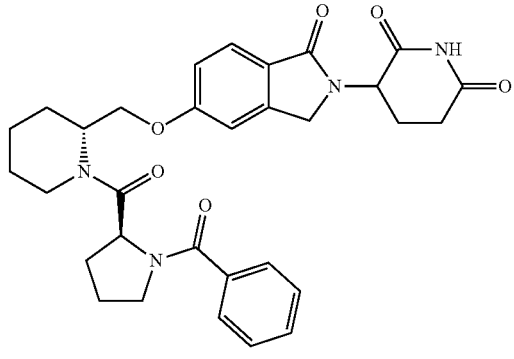 [SMILES: O=C1CCC(N2Cc3cc(OC[C@H]4CCCCN4C(=O)[C@@H]4CCCN4C(=O)c4ccccc4)ccc3C2=O)C(=O)N1] | 559.26 | 0.56 |
| I-72kp | 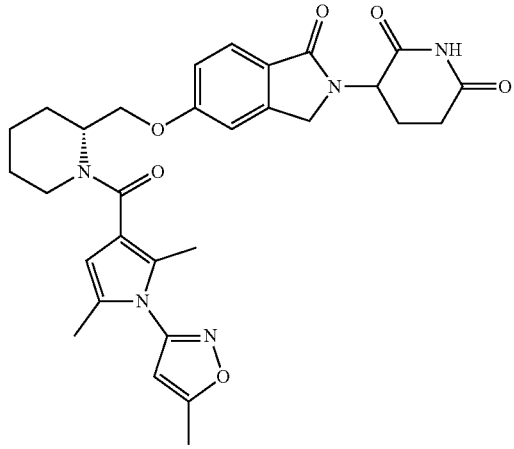 [SMILES: Cc1cc(-n2c(C)cc(C(=O)N3CCCC[C@@H]3COc3ccc4c(c3)CN(C3CCC(=O)NC3=O)C4=O)c2C)no1] | 560.33 | 0.59 |

-continued
| Compound Number | Structure | LCMS [M + H] | LCMS Rt |
|---|---|---|---|
| I-72kq | 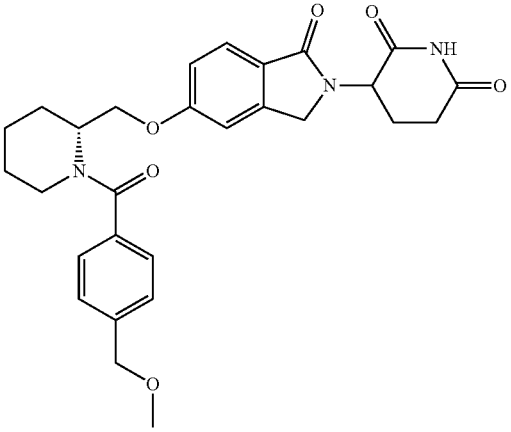 [SMILES: COCc1ccc(C(=O)N2CCCC[C@@H]2COc2ccc3c(c2)CN(C2CCC(=O)NC2=O)C3=O)cc1] | 506.27 | 0.57 |
| I-72kr | 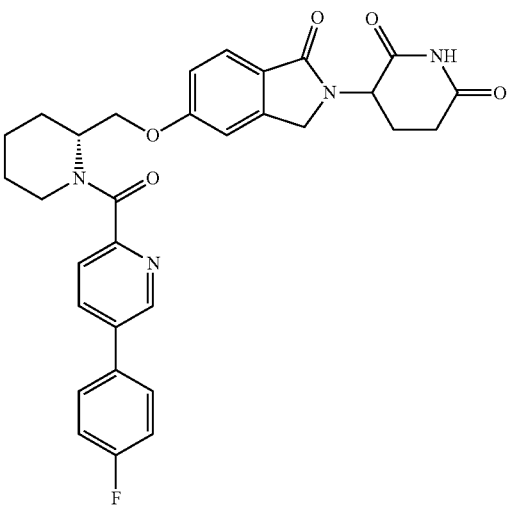 [SMILES: O=C1CCC(N2Cc3cc(OC[C@H]4CCCCN4C(=O)c4ccc(-c5ccc(F)cc5)cn4)ccc3C2=O)C(=O)N1] | 557.27 | 0.6 |
| I-72ks | 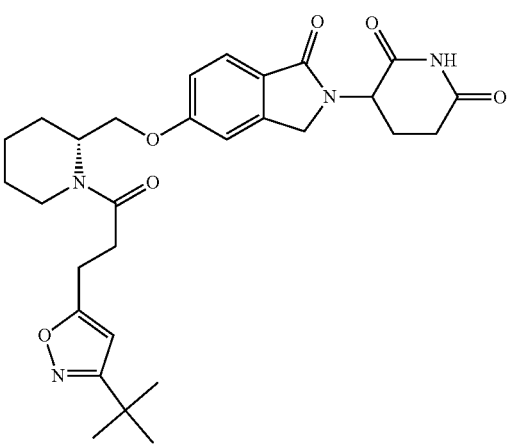 [SMILES: CC(C)(C)c1cc(CCC(=O)N2CCCC[C@@H]2COc2ccc3c(c2)CN(C2CCC(=O)NC2=O)C3=O)on1] | 537.32 | 0.6 |

Example 40: Tert-butyl 4-(4-(((2R)-2-(((2-(2,6-di-oxopiperidin-3-yl)-1-oxoisoindolin-5-yl)oxy)methyl)piperidin-1-yl)methyl)phenyl)piperazine-1-carboxylate (I-73)

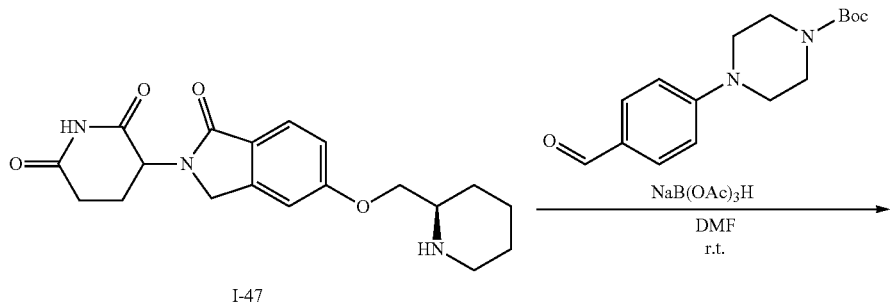

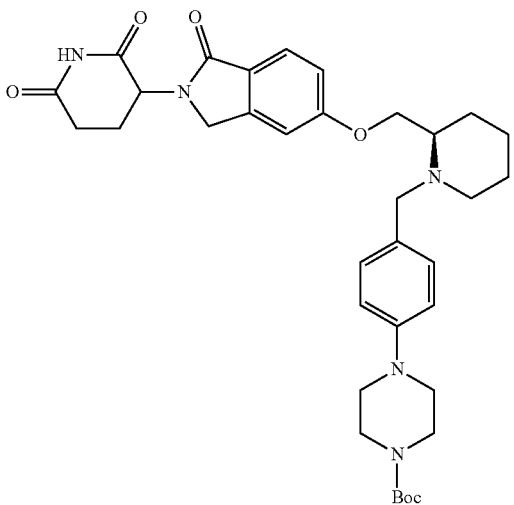

Compound I-73 was prepared according to General Method III starting from 3-(1-oxo-5-(((R)-piperidin-2-yl)methoxy)isoindolin-2-yl)piperidine-2,6-dione I-47 (0.45 g, 1.259 mmol) and 1-boc-4-(4-formylphenyl)piperazine (550 mg, 1.894 mmol). The crude material was purified by silica gel chromatography (eluting with 0-100% 3:1 ethyl acetate: ethanol with 1% TEA in heptane). Pure fractions were combined, concentrated, and lyophilized to afford tert-butyl 4-(4-(((2R)-2-(((2-(2,6-dioxopiperidin-3-yl)-1-oxoisoindolin-5-yl)oxy)methyl)piperidin-1-yl)methyl)phenyl)piperazine-1-carboxylate I-73 (599 mg, 0.948 mmol, 75% yield) as a white solid. LCMS [M+H]$^+$: 632.6. $^1$H NMR (400 MHz, Chloroform-d) δ 7.98 (d, J=14.3 Hz, 1H), 7.81 (d, J=8.4 Hz, 1H), 7.25 (d, J=8.2 Hz, 2H), 7.03 (dd, J=8.3, 2.2 Hz, 1H), 6.95 (s, 1H), 6.89 (d, J=8.4 Hz, 2H), 5.22 (dd, J=13.2, 5.2 Hz, 1H), 4.46 (d, J=15.8 Hz, 1H), 4.32-4.19 (m, 2H), 4.09 (dd, J=9.8, 4.8 Hz, 1H), 3.99 (d, J=13.6 Hz, 1H), 3.63-3.53 (m, 4H), 3.39 (d, J=13.6 Hz, 1H), 3.16-3.06 (m, 4H), 2.99-2.74 (m, 4H), 2.36 (qd, J=13.0, 5.0 Hz, 1H), 2.27-2.12 (m, 2H), 1.91-1.80 (m, 1H), 1.76-1.70 (m, 1H), 1.68-1.46 (m, 13H).

Example 41: 3-(1-oxo-5-(((R)-1-(4-(piperazin-1-yl)benzyl)piperidin-2-yl)methoxy)isoindolin-2-yl)piperidine-2,6-dione (INT-74)

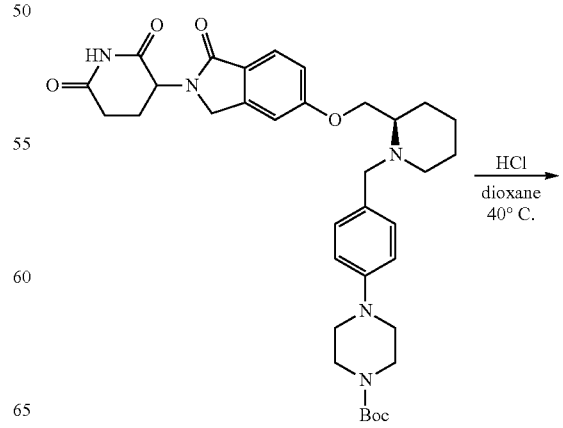

419

-continued

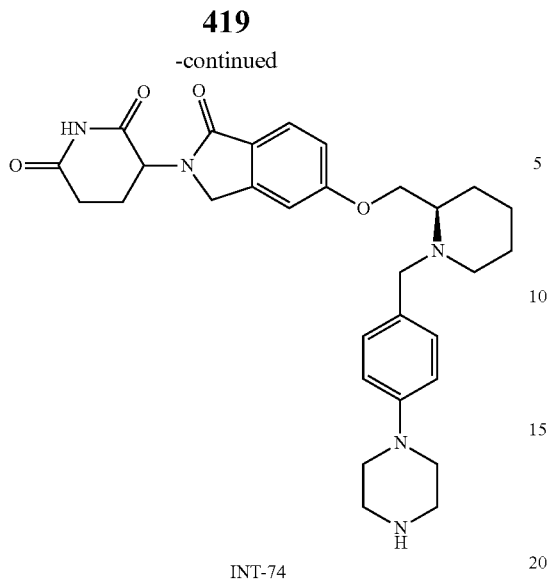

INT-74 tert-butyl 4-(4-(((2R)-2-(((2-(2,6-dioxopiperidin-3-yl)-1-oxoisoindolin-5-yl)oxy)methyl)piperidin-1-yl)methyl)phenyl)piperazine-1-carboxylate I-73 (0.599 g, 0.948 mmol) was suspended in dioxane (Volume: 4 mL, Ratio: 1.333) and dissolved in trifluoroethanol (Volume: 3 mL, Ratio: 1.000). 4M HCl in dioxane (1.422 mL, 5.69 mmol) was added and the resulting mixture was stirred at r.t. overnight. The reaction mixture was concentrated to afford slightly impure 3-(1-oxo-5-(((R)-1-(4-(piperazin-1-yl)benzyl)piperidin-2-yl)methoxy)isoindolin-2-yl)piperidine-2,6-dione INT-74 (700 mg, 1.317 mmol) as a pink solid. The crude material was used in the next step without purification. LCMS [M+H]$^+$: 532.5.

Example 42: 3-(5-(((R)-1-(4-(4-ethylpiperazin-1-yl)benzyl)piperidin-2-yl)methoxy)-1-oxoisoindolin-2-yl)piperidine-2,6-dione (I-75)

420

-continued

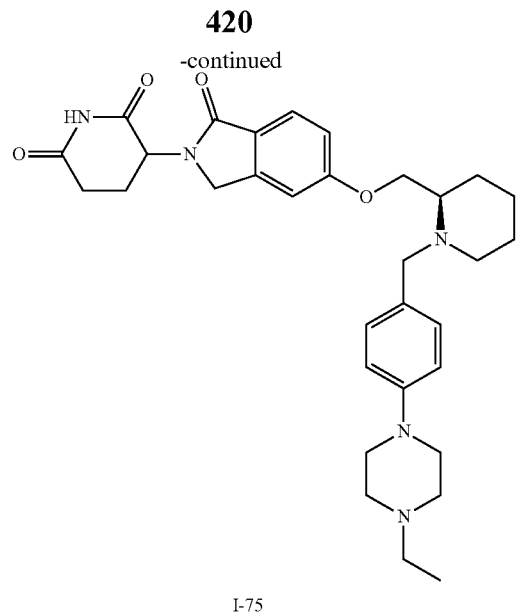

I-75

INT-74 was prepared according to General Method III starting from 3-(1-oxo-5-(((R)-1-(4-(piperazin-1-yl)benzyl)piperidin-2-yl)methoxy)isoindolin-2-yl)piperidine-2,6-dione INT-74 (0.1 g, 0.188 mmol) and acetaldehyde (50 mg, 1.129 mmol) The crude material was purified by silica gel chromatography (eluting with 0-100% 3:1 ethyl acetate:ethanol with 1% TEA in heptane). Pure fractions were combined, concentrated, and lyophilized to afford 3-(5-(((R)-1-(4-(4-ethylpiperazin-1-yl)benzyl)piperidin-2-yl)methoxy)-1-oxoisoindolin-2-yl)piperidine-2,6-dione I-75 (41.77 mg, 0.073 mmol, 38.9% yield) as a white solid. LCMS [M+H]$^+$: 560.3. $^1$H NMR (400 MHz, DMSO-d$_6$) δ 10.90 (s, 1H), 7.54 (d, J=8.4 Hz, 1H), 7.14-7.02 (m, 3H), 6.99 (dd, J=8.4, 2.3 Hz, 1H), 6.78 (d, J=8.4 Hz, 2H), 5.00 (dd, J=13.3, 5.2 Hz, 1H), 4.32-4.11 (m, 3H), 4.05 (dd, J=10.3, 5.5 Hz, 1H), 3.81 (d, J=13.5 Hz, 1H), 3.23-3.18 (m, 1H), 3.01 (t, J=5.0 Hz, 4H), 2.84 (ddd, J=17.2, 13.6, 5.4 Hz, 1H), 2.69-2.56 (m, 2H), 2.56-2.48 (m, 1H), 2.42-2.23 (m, 7H), 2.07-1.97 (m, 1H), 1.96-1.85 (m, 1H), 1.74-1.66 (m, 1H), 1.62-1.53 (m, 1H), 1.49-1.36 (m, 2H), 1.36-1.21 (m, 2H), 0.95 (t, J=7.1 Hz, 3H).

Example 43: 3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione (I-76)

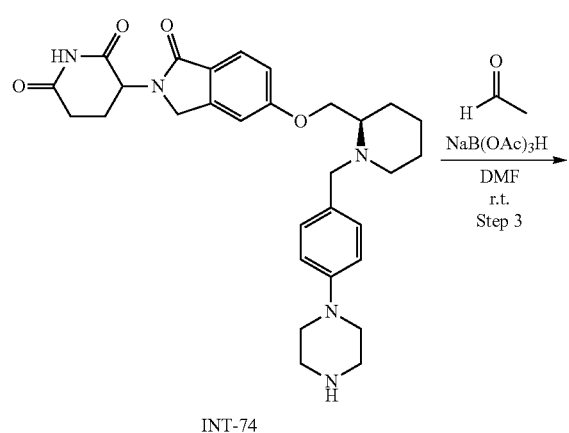

INT-74

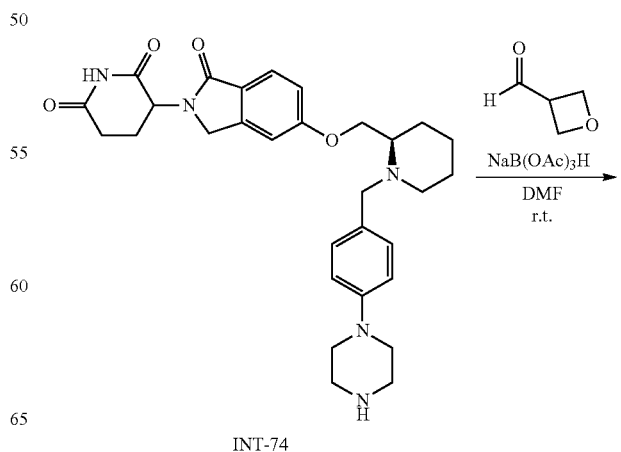

INT-74

421

-continued

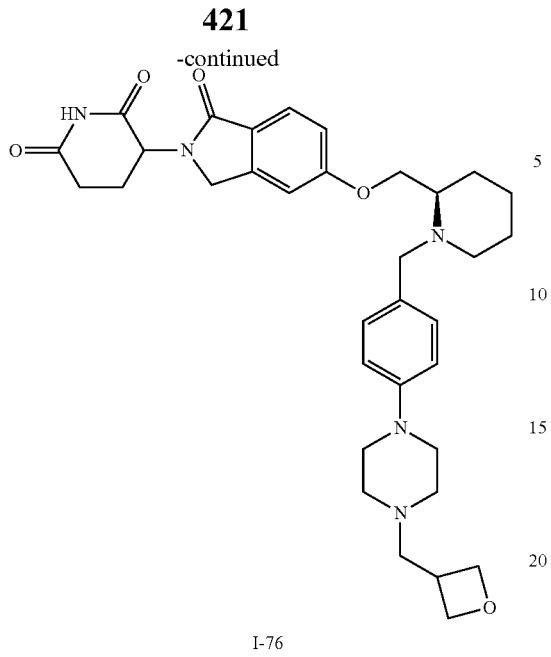

I-76

INT-74 was prepared according to General Method III starting from 3-(1-oxo-5-(((R)-1-(4-(piperazin-1-yl)benzyl)piperidin-2-yl)methoxy)isoindolin-2-yl)piperidine-2,6-dione INT-74 (0.15 g, 0.282 mmol) and oxetane-3-carbaldehyde (49 mg, 0.564 mmol). The crude material was purified by silica gel chromatography (eluting with 0-100% 3:1 ethyl acetate:ethanol with 1% TEA in heptane). Pure fractions were combined, concentrated, and lyophilized to afford 3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione I-76 (43.17 mg, 0.072 mmol, 25.4% yield) as a white solid. LCMS [M+H]$^+$: 602.3. $^1$H NMR (400 MHz, DMSO-d$_6$) δ 10.90 (s, 1H), 7.54 (d, J=8.4 Hz, 1H), 7.13-7.03 (m, 3H), 6.99 (dd, J=8.6, 2.2 Hz, 1H), 6.77 (d, J=8.4 Hz, 2H), 5.00 (dd, J=13.2, 5.0 Hz, 1H), 4.58 (dd, J=7.8, 5.8 Hz, 2H), 4.37-4.13 (m, 5H), 4.05 (dd, J=10.3, 5.5 Hz, 1H), 3.81 (d, J=13.2 Hz, 1H), 3.24-3.19 (m, 1H), 3.18-3.07 (m, 1H), 3.03-2.93 (m, 4H), 2.84 (ddd, J=17.3, 13.6, 5.4 Hz, 1H), 2.71-2.48 (m, 5H), 2.39-2.28 (m, 5H), 2.07-1.96 (m, 1H), 1.96-1.86 (m, 1H), 1.75-1.64 (m, 1H), 1.63-1.51 (m, 1H), 1.51-1.22 (m, 4H).

Example 44: 3-(5-(((R)-1-(4-(4-isobutylpiperazin-1-yl)benzyl)piperidin-2-yl)methoxy)-1-oxoisoindolin-2-yl)piperidine-2,6-dione (I-77)

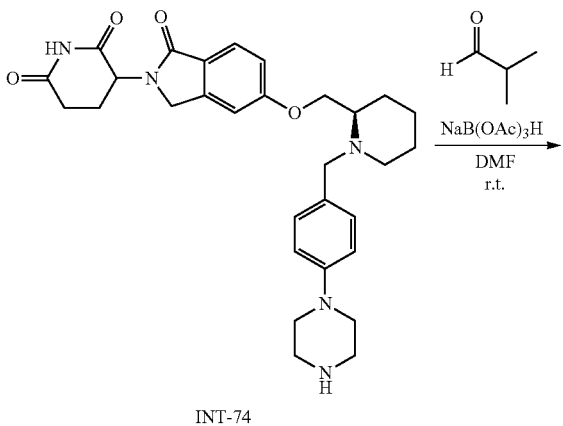

422

-continued

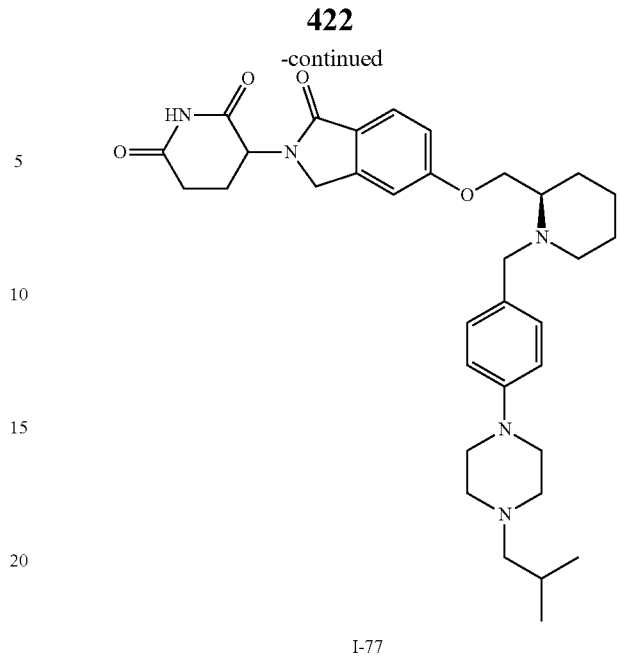

I-77

INT_70 was prepared according to General Method III starting from 3-(1-oxo-5-(((R)-1-(4-(piperazin-1-yl)benzyl)piperidin-2-yl)methoxy)isoindolin-2-yl)piperidine-2,6-dione INT-74 (0.1 g, 0.188 mmol) and isobutanal (0.034 mL, 0.376 mmol). The crude material was purified by silica gel chromatography (eluting with 0-100% 3:1 ethyl acetate:ethanol with 1% TEA in heptane). Pure fractions were combined, concentrated, and lyophilized to afford 3-(5-(((R)-1-(4-(4-isobutylpiperazin-1-yl)benzyl)piperidin-2-yl)methoxy)-1-oxoisoindolin-2-yl)piperidine-2,6-dione I-77 (39 mg, 0.063 mmol, 33.5% yield) as a white solid. LCMS [M+H]$^+$: 588.6. $^1$H NMR (400 MHz, DMSO-d$_6$) δ 10.89 (s, 1H), 7.54 (d, J=8.4 Hz, 1H), 7.13-7.01 (m, 3H), 6.99 (dd, J=8.4, 2.3 Hz, 1H), 6.78 (d, J=8.3 Hz, 2H), 5.00 (dd, J=13.2, 5.0 Hz, 1H), 4.36-4.10 (m, 3H), 4.05 (dd, J=10.2, 5.4 Hz, 1H), 3.81 (d, J=13.4 Hz, 1H), 3.24-3.17 (m, 1H), 3.01 (t, J=4.9 Hz, 4H), 2.84 (ddd, J=17.3, 13.7, 5.4 Hz, 1H), 2.68-2.57 (m, 2H), 2.56-2.47 (m, 1H), 2.41-2.24 (m, 5H), 2.06-1.97 (m, 3H), 1.95-1.86 (m, 1H), 1.77-1.65 (m, 2H), 1.63-1.53 (m, 1H), 1.49-1.21 (m, 4H), 0.80 (d, J=6.6 Hz, 6H).

Example 45: 3-(1-oxo-5-(((S)-pyrrolidin-2-yl)methoxy)isoindolin-2-yl)piperidine-2,6-dione (I-79)

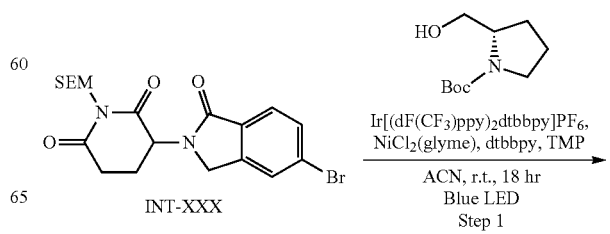

INT-XXX

Step 1

423

-continued

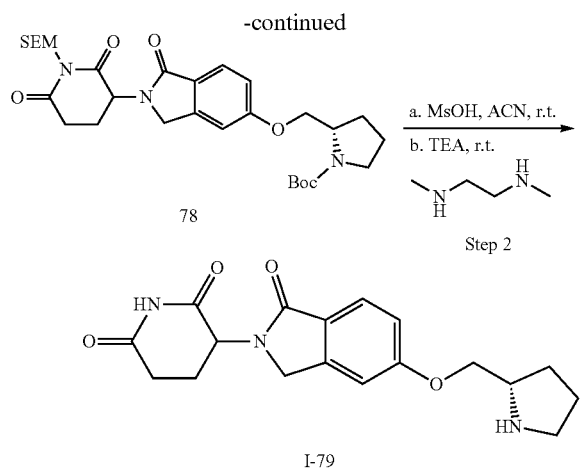

Step 1: tert-butyl (2S)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate (78)

Intermediate 78 was prepared according to General Method VI starting from 1-Boc-L-Prolinol (27 mg, 0.132 mmol) to afford tert-butyl (2S)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate 78. The crude material was carried on to the next step as a solution without workup or purification. LCMS [M+H−156.3 (TMSCH$_2$CH$_2$,tButyl)]$^+$: 418.2.

Step 2: 3-(1-oxo-5-(((S)-pyrrolidin-2-yl)methoxy)isoindolin-2-yl)piperidine-2,6-dione (I-79)

Compound I-79 was prepared according to General Method VII starting from tert-butyl (2S)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate 78 (63 mg, 0.110 mmol). The reaction mixture was concentrated. A PL-HCO3 MP SPE column (Polymer Lab (Varian), part #PL3540-C603, 500 mg pre-packed resin in 6 ml tube) was pre-washed with EtOH (5 mL). The crude material was dissolved in EtOH (3 mL) and filtered through column by applying a positive pressure. The column was washed with EtOH (5 mL) and the filtrate was concentrated and purified by basic mass triggered reverse phase HPLC (eluting with 10-30% ACN in water with 5 mM NH4OH as modifier). Each test-tube contained 3 drops of formic acid prior to sample collection. Pure fractions were combined, concentrated, and lyophilized to afford 3-(1-oxo-5-(((S)-pyrrolidin-2-yl)methoxy)isoindolin-2-yl)piperidine-2,6-dione I-79 (18.9 mg, 0.047 mmol, 42.3% yield) as a cream solid. LCMS [M+H]$^+$: 344.2. $^1$H NMR (400 MHz, DMSO-d$_6$) δ 10.96 (s, 1H), 8.27 (s, 1H), 7.63 (d, J=8.4 Hz, 1H), 7.18 (d, J=2.2 Hz, 1H), 7.06 (dd, J=8.4, 2.3 Hz, 1H), 5.07 (dd, J=13.4, 5.1 Hz, 1H), 4.39 (d, J=17.2 Hz, 1H), 4.26 (d, J=17.2 Hz, 1H), 4.06-3.93 (m, 2H), 3.55 (p, J=6.8 Hz, 1H), 2.96-2.85 (m, 3H), 2.59 (dd, J=16.8, 3.4 Hz, 1H), 2.44-2.32 (m, 1H), 2.03-1.87 (m, 2H), 1.83-1.66 (m, 2H), 1.59-1.47 (m, 1H).

424

Example 46: 3-(1-oxo-5-(((R)-pyrrolidin-2-yl)methoxy)isoindolin-2-yl)piperidine-2,6-dione (I-81)

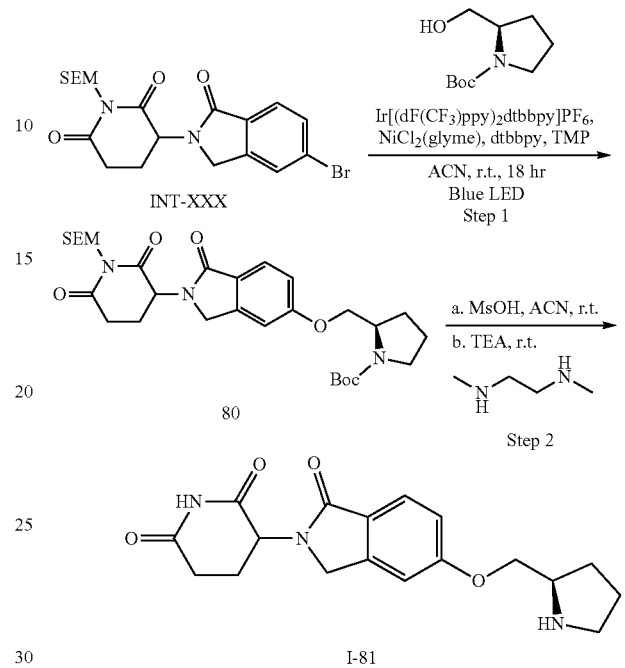

Step 1: tert-butyl (2R)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate (80)

Intermediate 80 was prepared according to General Method VI starting from N-Boc-D-prolinol (27 mg, 0.132 mmol) and 3-(5-bromo-1-oxoisoindolin-2-yl)-1-((2-(trimethylsilyl)ethoxy)methyl)piperidine-2,6-dione INT-XXX to afford tert-butyl (2R)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate 80. The crude material was carried on to the next step as a solution without workup or purification. LCMS [M+H−156.3 (TMSCH2CH2,tButyl)]$^+$: 418.6.

Step 2: 46: 3-(1-oxo-5-(((R)-pyrrolidin-2-yl)methoxy)isoindolin-2-yl)piperidine-2,6-dione (I-81)

Compound I-81 was prepared according to General Method VII starting from tert-butyl (2R)-2-(((2-(2,6-dioxo-1-((2-(trimethylsilyl)ethoxy)methyl)piperidin-3-yl)-1-oxoisoindolin-5-yl)oxy)methyl)pyrrolidine-1-carboxylate 80 (63 mg, 0.110 mmol). The crude material was concentrated and purified by basic mass triggered reverse phase HPLC (eluting with 10-30% ACN in water with 5 mM NH4OH as modifier). Each test-tube contained 3 drops of formic acid prior to sample collection. Pure fractions were combined, concentrated, and lyophilized to afford product as a triethylamine salt. A PL-HCO3 MP SPE column (Polymer Lab (Varian), part #PL3540-C603 (or equivalent); 500 mg pre-packed resin in 6 ml tube) was pre-washed with EtOH (5 mL). Product was dissolved in EtOH (3 mL) and filtered through column by applying a small pressure. The column was washed with EtOH (5 mL) and the filtrate was concentrated and lyophilized to afford 3-(1-oxo-5-(((R)-pyrrolidin-2-yl)methoxy)isoindolin-2-yl)piperidine-2,6-dione I-81 (7.3 mg, 0.021 mmol, 19.09% yield) as a white solid. LCMS [M+H]$^+$: 344.3. $^1$H NMR (400 MHz, DMSO-d$_6$) δ 10.93 (s, 1H), 7.63 (d, J=8.4 Hz, 1H), 7.17 (d, J=2.2 Hz, 1H), 7.05 (dd, J=8.3, 2.3 Hz, 1H), 5.07 (dd, J=13.3, 5.1 Hz, 1H), 4.39 (d, J=17.1 Hz, 1H), 4.26 (d, J=17.2 Hz, 1H), 4.05-3.92 (m, 2H), 3.54 (p, J=6.8 Hz, 1H), 2.97-2.83 (m, 3H), 2.59 (ddd, J=17.2, 4.6, 2.2 Hz, 1H), 2.45-2.30 (m, 1H), 2.03-1.86 (m, 2H), 1.86-1.62 (m, 2H), 1.59-1.44 (m, 2H).

Example 47: Benzyl (2S)-2-(((2-(2,6-dioxopiperidin-3-yl)-1-oxoisoindolin-5-yl)oxy)methyl)pyrrolidine-1-carboxylate (I-82)

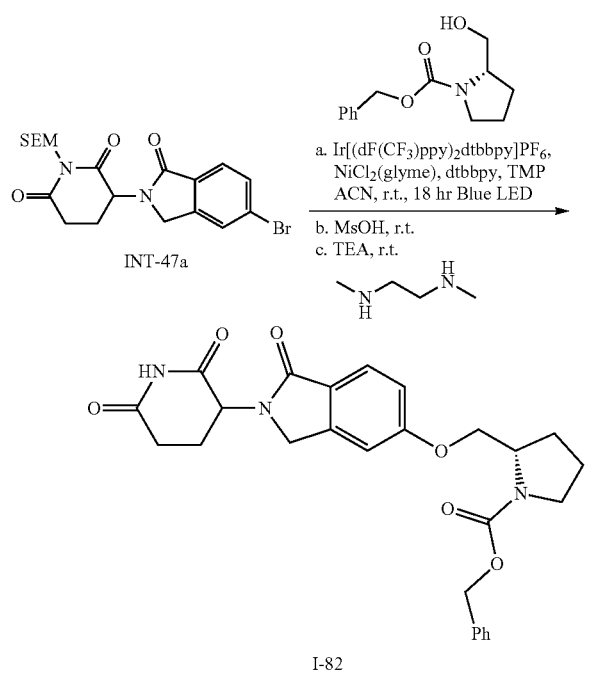

Compound I-82 was Prepared According to General Procedure X:

Preparation of 0.2 M INT-47a and 0.3 M TMP+0.004 M [Ir] catalyst stock solution in ACN: A 100 mL vial was charged with INT-47a (4.50 g, 9.92 mmol), TMP (2.6 mL, 14.8 mmol) and Ir[(dF(CF$_3$)ppy)$_2$dtbbpy]PF$_6$ (122 mg, 0.10 mmol) and was then diluted with ACN to a total volume of 50 mL. Preparation of 0.025 M [Ni] catalyst solution in ACN: To a 40 mL vial under nitrogen was added NiCl$_2$ (glyme) (113 mg, 0.50 mmol) and dtbbpy (138 mg, 0.50 mmol) and then diluted with ACN to a total volume of 20 mL. The obtained mixture was stirred vigorously until homogeneous. If precipitation of the catalyst occurred, the reaction mixture was heated at 70° C. for 15 min resulting in a homogeneous solution that remained homogeneous even at r.t.

A 1 dram vial was charged with benzyl (S)-2-(hydroxymethyl)pyrrolidine-1-carboxylate (35 mg, 0.15 mmoL). Next, 0.2 M solution of INT-47a+TMP+[Ir] stock solution in ACN (0.55 mL, 0.110 mmol) was added, followed by 0.025 M [Ni] catalyst solution in ACN (0.22 mL, 5.51 μmol). The reaction mixture was then stirred vigorously for 48 hrs under irradiation of Blue LED lights at r.t. in Rayonet LED reactor. Methanesulfonic acid (0.072 mL, 1.103 mmol) was then added and the reaction mixture stirred at r.t. overnight. TEA (0.22 mL, 1.544 mmol) and N1,N2-dimethylethane-1,2-diamine (0.014 mL, 0.132 mmol) were added simultaneously at 0° C., and the stirring was continued at r.t. overnight. The reaction mixture was concentrated to dryness and purified by reverse phase HPLC (eluting with 15-95% ACN in water with 0.1% formic acid as modifier) to afford Benzyl (2S)-2-(((2-(2,6-dioxopiperidin-3-yl)-1-oxoisoindolin-5-yl)oxy)methyl)pyrrolidine-1-carboxylate I-82 (2.5 mg, 4.97 μmol, 4.5% yield). LCMS [M+H]$^+$: 478.3, Rt 0.61 mins.

Example 48: 3-(5-(((R)-1-(2-methoxybenzoyl)pyrrolidin-2-yl)methoxy)-1-oxoisoindolin-2-yl)piperidine-2,6-dione (I-83)

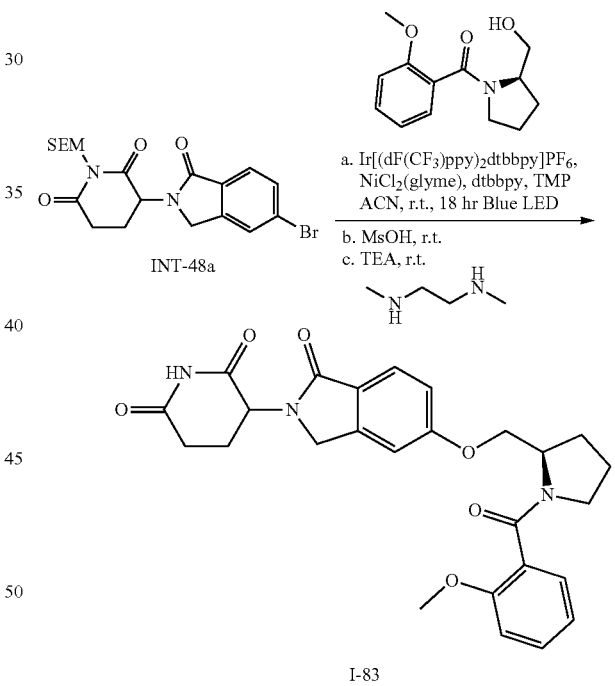

Compound I-83 was prepared according to General Procedure X starting from (R)-(2-(hydroxymethyl)pyrrolidin-1-yl)(2-methoxyphenyl)methanone (INT-48a, 35 mg, 0.15 mmol). The reaction mixture was concentrated to dryness and purified by reverse phase HPLC (eluting with 15-95% ACN in water with 0.1% formic acid as modifier) to afford 3-(5-(((R)-1-(2-methoxybenzoyl)pyrrolidin-2-yl)methoxy)-1-oxoisoindolin-2-yl)piperidine-2,6-dione I-83 (25.1 mg, 0.050 mmol, 45.3% yield). LCMS [M+H]$^+$: 478.3, Rt 0.56 mins.

Example 49: 3-(5-(((S)-4,4-difluoropyrrolidin-2-yl)methoxy)-1-oxoisoindolin-2-yl)piperidine-2,6-dione (I-84)

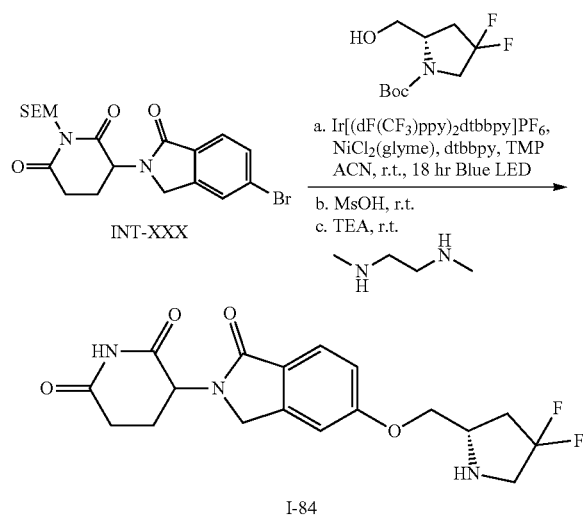

INT XXX was prepared according to General Procedure X starting from tert-butyl (S)-4,4-difluoro-2-(hydroxymethyl)pyrrolidine-1-carboxylate (35.3 mg, 0.15 mmol). The reaction mixture was concentrated to dryness and purified by reverse phase HPLC (eluting with 5-95% ACN in water with 0.1% formic acid as modifier) to afford 3-(5-(((S)-4,4-difluoropyrrolidin-2-yl)methoxy)-1-oxoisoindolin-2-yl)piperidine-2,6-dione I-84 (11.2 mg, 0.025 mmol, 22.7% yield). LCMS [M+H]$^+$: 380.2, Rt 0.35 mins.

Example 50: 3-(5-(((S)-1-benzylpyrrolidin-2-yl)methoxy)-1-oxoisoindolin-2-yl)piperidine-2,6-dione (I-90)

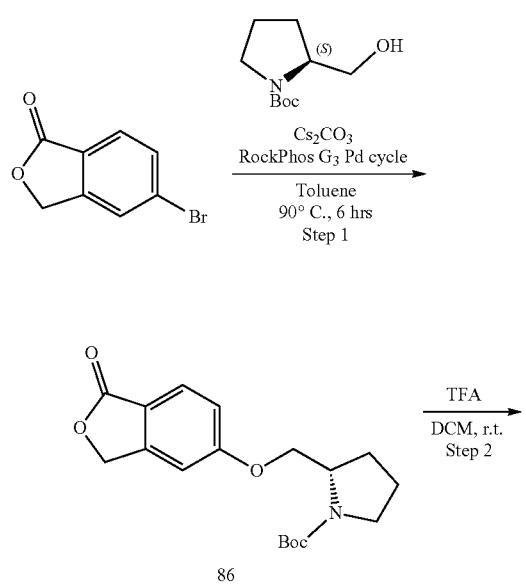

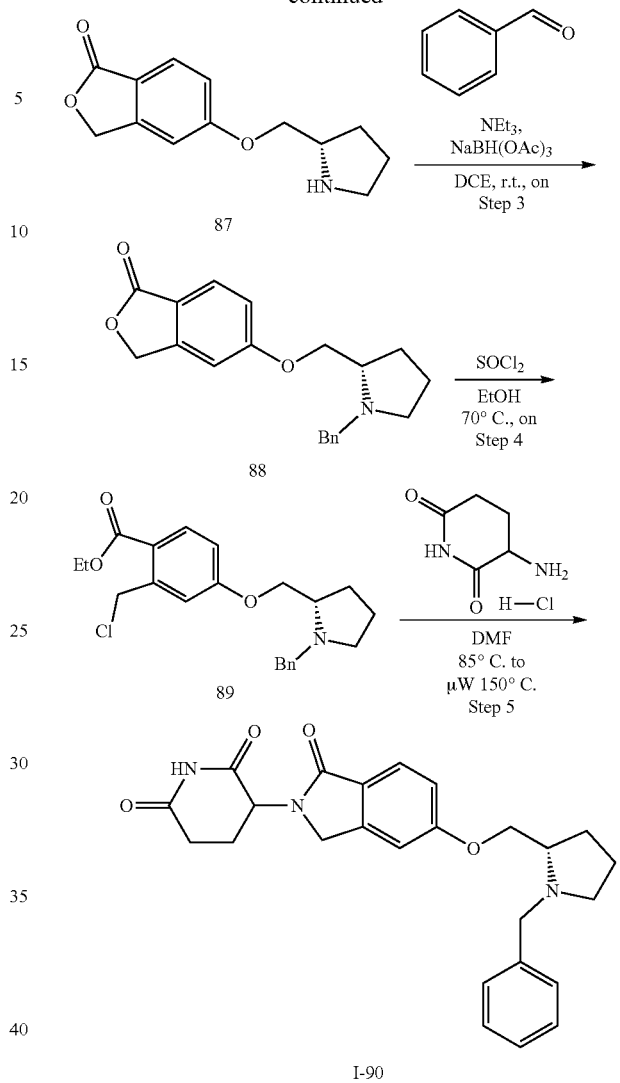

Step 1: (S)-tert-butyl 2-(((1-oxo-1,3-dihydroisobenzofuran-5-yl)oxy)methyl)pyrrolidine-1-carboxylate (86)

Reference: Angew. Chem. Int. Ed., 2011, 50, 9943. To a reaction vial was added 5-bromophthalide (98.4 mg, 0.462 mmol), Boc-L-prolinol (281.6 mg, 1.399 mmol), cesium carbonate (231.1 mg, 0.709 mmol), and RockPhos G3 Pd catalyst (27.6 mg, 0.033 mmol) and the vial was evacuated and backfilled with nitrogen three times. Toluene (2.0 mL) was added and the resulting mixture was stirred at 90° C. for 6 hours. The solution was diluted with ethyl acetate (80 mL) and washed with water (20 mL), saturated aqueous sodium bicarbonate solution (20 mL), and brine (20 mL). The organic phase was dried over magnesium sulfate, filtered, and concentrated. The crude product was diluted with dichloromethane and purified by silica gel chromatography (eluting with 0-100% EtOAc in heptane) to afford the product. The material was further purified by basic mass triggered reverse phase HPLC (eluting with 35-60% ACN in water with 10 mM NH$_4$OH as modifier). Fractions containing desired product were combined and concentrated to afford (S)-tert-butyl 2-(((1-oxo-1,3-dihydroisobenzofuran- 5-yl)oxy)methyl)pyrrolidine-1-carboxylate 86 (100.9 mg, 0.303 mmol, 65.5% yield).as a yellow solid. LCMS [M+H]$^+$: 334.4. $^1$H NMR (400 MHz, Methylene Chloride-d$_2$) δ 7.80 (d, J=8.5 Hz, 1H), 7.12 (dd, J=8.5, 2.2 Hz, 1H), 7.04 (s, 1H), 5.26 (s, 2H), 4.26 (s, 1H), 4.17 (d, J=4.4 Hz, 1H), 4.03 (s, 1H), 3.40 (d, J=7.6 Hz, 2H), 2.13-2.02 (m, 2H), 2.02-1.95 (m, 1H), 1.95-1.85 (m, 1H), 1.49 (s, 9H).

Step 2: (S)-5-(pyrrolidin-2-ylmethoxy)isobenzofuran-1(3H)-one (87) TFA Salt

To a reaction vial containing (S)-tert-butyl 2-(((1-oxo-1,3-dihydroisobenzofuran-5-yl)oxy)methyl)pyrrolidine-1-carboxylate 86 (100.9 mg, 0.303 mmol) dissolved in DCM (1 mL) was added Trifluoroacetic acid (0.1 mL, 1.298 mmol) and the resulting mixture was stirred at r.t. until complete consumption of starting material was observed. The reaction mixture was then concentrated to afford (S)-5-(pyrrolidin-2-ylmethoxy)isobenzofuran-1(3H)-one 87 TFA salt (150 mg, 0.643 mmol) as a clear gum. LCMS [M+H]$^+$: 234.3. $^1$H NMR (400 MHz, DMSO-d$_6$) δ 9.21 (s, 1H), 8.76 (s, 1H), 7.81 (d, J=8.5 Hz, 1H), 7.25 (t, J=1.4 Hz, 1H), 7.17 (dd, J=8.5, 2.3 Hz, 1H), 5.36 (s, 2H), 4.40 (dd, J=10.7, 3.5 Hz, 1H), 4.21 (dd, J=10.8, 8.4 Hz, 1H), 3.97 (dt, J=9.0, 3.4 Hz, 1H), 3.24 (dtd, J=11.7, 6.7, 5.8, 2.0 Hz, 2H), 2.15 (dtd, J=12.7, 7.8, 4.9 Hz, 1H), 2.06-1.84 (m, 2H), 1.75 (dq, J=12.8, 8.2 Hz, 1H).

Step 3: (S)-5-((1-benzylpyrrolidin-2-yl)methoxy)isobenzofuran-1(3H)-one (88)

References: Heterocycles, 2006, vol. 67, #2 p. 519-522; Bioorganic and Medicinal Chemistry, 2001, vol. 9, #2 p. 237-243.

To a reaction vial containing (S)-5-(pyrrolidin-2-ylmethoxy)isobenzofuran-1(3H)-one 87 (70.6 mg, 0.303 mmol) dissolved in DCE (1.5 mL) was added triethylamine (0.065 mL, 0.466 mmol) was added. The resulting mixture was stirred at r.t. for 5 minutes and then benzaldehyde (0.035 mL, 0.344 mmol) was added and stirring was continued at r.t. for 1 hour. Sodium triacetoxyborohydride (92.0 mg, 0.434 mmol) was added and the reaction mixture was stirred at r.t. overnight, and then diluted with EtOAc (40 mL) and washed with saturated aqueous sodium bicarbonate twice and brine. The organic phase was dried over magnesium sulfate, filtered, and concentrated. The crude material was diluted with dichloromethane and purified by silica gel chromatography (eluting with 0-80% EtOAc with 0.1% TEA in heptane) to afford (S)-5-((1-benzylpyrrolidin-2-yl)methoxy)isobenzofuran-1(3H)-one 88 (59.8 mg, 0.185 mmol, 61.1% yield). LCMS [M+H]$^+$: 324.4. $^1$H NMR (400 MHz, Methylene Chloride-d$_2$) δ 7.78 (d, J=8.5 Hz, 1H), 7.43-7.30 (m, 4H), 7.26 (t, J=7.1 Hz, 1H), 7.03 (dd, J=8.5, 2.2 Hz, 1H), 6.89 (s, 1H), 5.24 (s, 2H), 4.17-4.08 (m, 1H), 4.05 (dd, J=9.3, 5.2 Hz, 1H), 3.94 (dd, J=9.3, 6.4 Hz, 1H), 3.59 (d, J=13.2 Hz, 1H), 3.13-3.03 (m, 1H), 2.99 (dd, J=8.6, 5.2 Hz, 1H), 2.37 (q, J=8.4 Hz, 1H), 2.14-2.04 (m, 1H), 1.80 (q, J=6.8, 5.9 Hz, 3H).

Step 4: (S)-ethyl 4-((1-benzylpyrrolidin-2-yl)methoxy)-2-(chloromethyl)benzoate (89)

A 2-necked round bottomed flash containing (S)-5-((1-benzylpyrrolidin-2-yl)methoxy)isobenzofuran-1(3H)-one 88 (59.8 mg, 0.185 mmol) dissolved in Ethanol (2 mL) was fitted with a reflux condenser and heated to 70° C. The reflux condenser was fitted with a sodium bicarbonate scrubber. Thionyl chloride (0.08 mL, 1.096 mmol) was added to the reaction via the side neck and the resulting mixture was stirred at 70° C. for 4 hours. The solution was then diluted with water and neutralized with saturated aqueous sodium bicarbonate. The aqueous phase was extracted with ethyl acetate three times. The organic phases were combined, washed with 5% sodium bicarbonate solution, brine, dried over magnesium sulfate, filtered, and concentrated to afford (S)-ethyl 4-((1-benzylpyrrolidin-2-yl)methoxy)-2-(chloromethyl)benzoate 89 (59.7 mg, 0.139 mmol, 74.9% yield) as a brown gum. The material was taken on to the next step without purification. LCMS [M+H]$^+$: 388.3. $^1$H NMR (400 MHz, Methylene Chloride-d$_2$) δ 8.00 (d, J=8.7 Hz, 1H), 7.35 (dt, J=14.6, 7.5 Hz, 4H), 7.26 (t, J=7.0 Hz, 1H), 7.07 (d, J=2.6 Hz, 1H), 6.88 (dd, J=8.8, 2.6 Hz, 1H), 5.07 (s, 2H), 4.37 (q, J=7.1 Hz, 2H), 4.20-4.11 (m, 1H), 4.03 (d, J=7.6 Hz, 1H), 3.92 (dd, J=14.4, 6.0 Hz, 1H), 3.57 (d, J=13.1 Hz, 1H), 3.02 (d, J=29.4 Hz, 2H), 2.43-2.31 (m, 1H), 2.08 (dt, J=8.1, 4.9 Hz, 1H), 1.80 (s, 3H), 1.42 (t, J=7.1 Hz, 3H).

Step 5: 3-(5-(((S)-1-benzylpyrrolidin-2-yl)methoxy)-1-oxoisoindolin-2-yl)piperidine-2,6-dione (I-90)

To a reaction vial containing 3-aminopiperidine-2,6-dione hydrochloride (26.8 mg, 0.163 mmol) dissolved in DMF (0.5 mL) was added DIPEA (0.07 mL, 0.401 mmol) and the resulting mixture was stirred at r.t. for 15 minutes. (S)-ethyl 4-((1-benzylpyrrolidin-2-yl)methoxy)-2-(chloromethyl) benzoate 89 (59.7 mg, 0.154 mmol) in DMF (0.5 mL) was added and the reaction mixture was stirred at 85° C. overnight. The solution was cooled to r.t. and concentrated. The crude material was purified by acidic reversed phase column chromatography (eluting with 10-30% ACN in water with 0.1% Formic acid as modifier). Fractions containing desired product were combined and concentrated to afford 3-(5-(((S)-1-benzylpyrrolidin-2-yl)methoxy)-1-oxoisoindolin-2-yl)piperidine-2,6-dione I-90 (22.7 mg, 0.045 mmol, 29.2% yield) as a brown solid. LCMS [M+H]$^+$: 434.5. $^1$H NMR (400 MHz, DMSO-d$_6$) δ 10.96 (s, 1H), 8.14 (s, 1H), 7.60 (d, J=8.4 Hz, 1H), 7.37-7.27 (m, 4H), 7.23 (ddt, J=8.5, 5.1, 2.6 Hz, 1H), 7.12 (d, J=2.2 Hz, 1H), 7.02 (ddd, J=8.5, 2.2, 0.9 Hz, 1H), 5.07 (dd, J=13.3, 5.1 Hz, 1H), 4.44-4.19 (m, 2H), 4.18-4.04 (m, 2H), 3.94 (dd, J=9.7, 6.5 Hz, 1H), 3.48 (d, J=13.2 Hz, 1H), 2.98 (d, J=20.2 Hz, 1H), 2.90-2.79 (m, 2H), 2.64-2.55 (m, 1H), 2.38 (dd, J=13.2, 4.3 Hz, 1H), 2.26 (t, J=7.9 Hz, 1H), 1.99 (dt, J=7.2, 5.0 Hz, 2H), 1.69 (q, J=9.5, 8.9 Hz, 3H).

Example 51: 3-(5-(((R)-1-((6-fluoropyridin-3-yl)methyl)piperidin-2-yl)methoxy)-1-oxoisoindolin-2-yl)piperidine-2,6-dione (I-91)

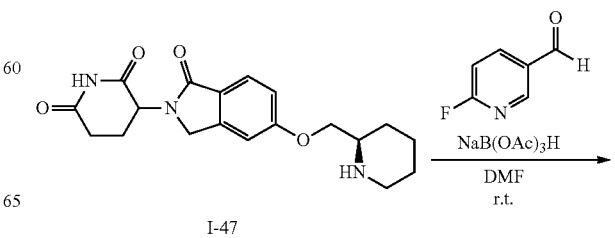

I-47

431

-continued

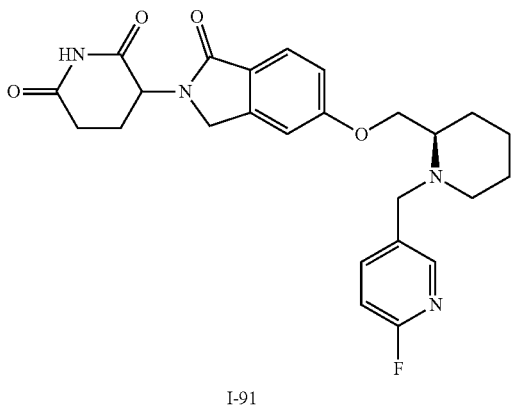

I-91

Compound I-47 was prepared according to General Method III starting from 3-(1-oxo-5-(((R)-piperidin-2-yl)methoxy)isoindolin-2-yl)piperidine-2,6-dione I-47 (0.15 g, 0.420 mmol) and 6-fluoropyridine-3-carboxaldehyde (0.079 g, 0.630 mmol). The reaction mixture was quenched with 50% saturated aqueous sodium bicarbonate in water and extracted 4 times with 4:1 dichloromethane:isopropanol. The organic phases were combined, passed through a phase separator and concentrated. The material was purified by silica gel chromatography (eluting with 0-100% 3:1 ethyl acetate:ethanol with 1% TEA in heptane). Pure fractions were combined, concentrated, and placed under high vacuumed overnight to afford 3-(5-(((R)-1-((6-fluoropyridin-3-yl)methyl)piperidin-2-yl)methoxy)-1-oxoisoindolin-2-yl)piperidine-2,6-dione I-91 (69.7 mg, 0.134 mmol, 32.0% yield) as a white solid. LCMS [M+H]$^+$: 467.2. $^1$H NMR (400 MHz, DMSO-d$_6$) δ 11.00 (s, 1H), 8.16 (d, J=2.4 Hz, 1H), 8.07-7.82 (m, 1H), 7.64 (d, J=8.4 Hz, 1H), 7.21 (d, J=2.2 Hz, 1H), 7.10 (ddd, J=13.4, 8.4, 2.5 Hz, 2H), 5.10 (dd, J=13.3, 5.1 Hz, 1H), 4.48-4.24 (m, 3H), 4.19-4.12 (m, 1H), 4.08-3.97 (m, 1H), 3.48 (d, J=14.1 Hz, 1H), 2.99-2.87 (m, 1H), 2.82-2.75 (m, 1H), 2.72-2.58 (m, 2H), 2.40 (qd, J=13.3, 4.5 Hz, 1H), 2.21-2.10 (m, 1H), 2.05-1.95 (m, 1H), 1.84-1.75 (m, 1H), 1.72-1.62 (m, 1H), 1.59-1.33 (m, 4H).

Example 52: 3-(5-(((R)-1-(4,4-difluorocyclohexyl)piperidin-2-yl)methoxy)-1-oxoisoindolin-2-yl)piperidine-2,6-dione (I-92)

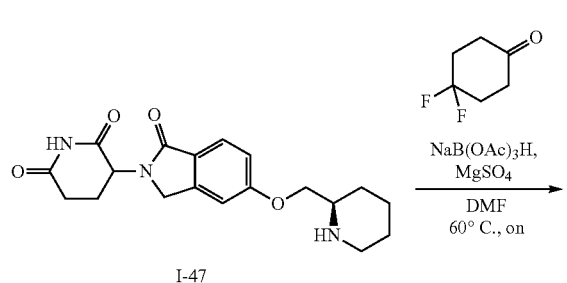

432

-continued

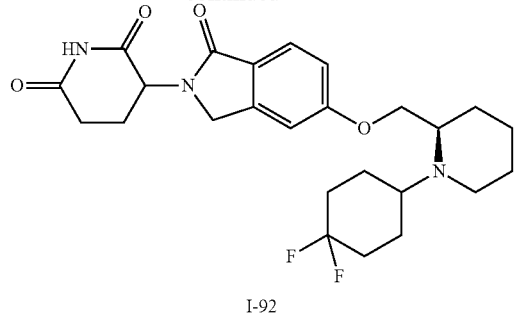

I-92

A 40 mL vial was charged with 3-(1-oxo-5-(((R)-piperidin-2-yl)methoxy)isoindolin-2-yl)piperidine-2,6-dione I-47 (0.2 g, 0.560 mmol), 4,4-difluorocyclohexan-1-one (1.50 g, 11.19 mmol), MgSO$_4$ (0.202 g, 1.679 mmol) and DMF (2 mL) and the resulting suspension was stirred at r.t. for 15 mins. NaBH(OAc)$_3$ (0.237 g, 1.119 mmol) was then added and stirring was continued overnight at 60° C. The reaction mixture was cooled to r.t. and quenched with 50% saturated aqueous sodium bicarbonate and extracted three times with 4:1 DCM:iPrOH. The organic phases were combined, passed through a phase separator and concentrated. The crude material was purified by silica gel chromatography (eluting with 0-100% 3:1 EtOAc:EtOH with 1% TEA in heptane) to afford 3-(5-(((R)-1-(4,4-difluorocyclohexyl)piperidin-2-yl)methoxy)-1-oxoisoindolin-2-yl)piperidine-2,6-dione I-92 (60.19 mg, 0.123 mmol, 21.94% yield) as a cream solid. LCMS [M+H]$^+$: 476.2. $^1$H NMR (400 MHz, DMSO-d$_6$) δ 10.99 (s, 1H), 7.65 (d, J=8.4 Hz, 1H), 7.20 (s, 1H), 7.07 (d, J=8.5 Hz, 1H), 5.09 (dd, J=13.3, 5.1 Hz, 1H), 4.40 (dd, J=17.2, 4.2 Hz, 1H), 4.34-4.11 (m, 2H), 4.11-3.96 (m, 1H), 2.97-2.87 (m, 3H), 2.83-2.76 (m, 1H), 2.65-2.56 (m, 1H), 2.40 (qd, J=12.9, 4.3 Hz, 1H), 2.26 (t, J=9.3 Hz, 1H), 2.09-1.95 (m, 3H), 1.90-1.52 (m, 8H), 1.48-1.24 (m, 4H).

Example 53:
(3-cyanobicyclo[1.1.1]pentan-1-yl)methyl methanesulfonate (INT-93)

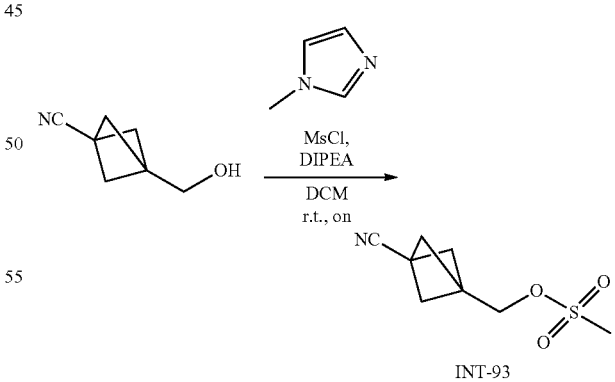

INT-93

To a solution of 3-(hydroxymethyl)bicyclo[1.1.1]pentane-1-carbonitrile (0.117 g, 0.950 mmol) in DCM (1.49 mL) was added DIPEA (0.33 mL, 1.900 mmol), 1-methyl-1H-imidazole (0.15 mL, 1.900 mmol), followed by methanesulfonyl chloride (0.11 mL, 1.425 mmol) dropwise. The resulting mixture was stirred at r.t. for 18 hrs. The reaction mixture was diluted with DCM (30 mL). The organic phase was washed with 1 M aqueous HCl three times and saturated aqueous sodium bicarbonate twice. The organic phase was passed through a phase separator and concentrated to afford (3-cyanobicyclo[1.1.1]pentan-1-yl)methyl methanesulfonate INT-93 (164 mg, 0.815 mmol, 86% yield) as beige solid. ¹H NMR (400 MHz, Chloroform-d) δ 4.12 (s, 2H), 2.95 (s, 3H), 2.23 (s, 6H).

Example 54: 3-(((2R)-2-(((2-(2,6-dioxopiperidin-3-yl)-1-oxoisoindolin-5-yl)oxy)methyl)piperidin-1-yl)methyl)bicyclo[1.1.1]pentane-1-carbonitrile (I-94)

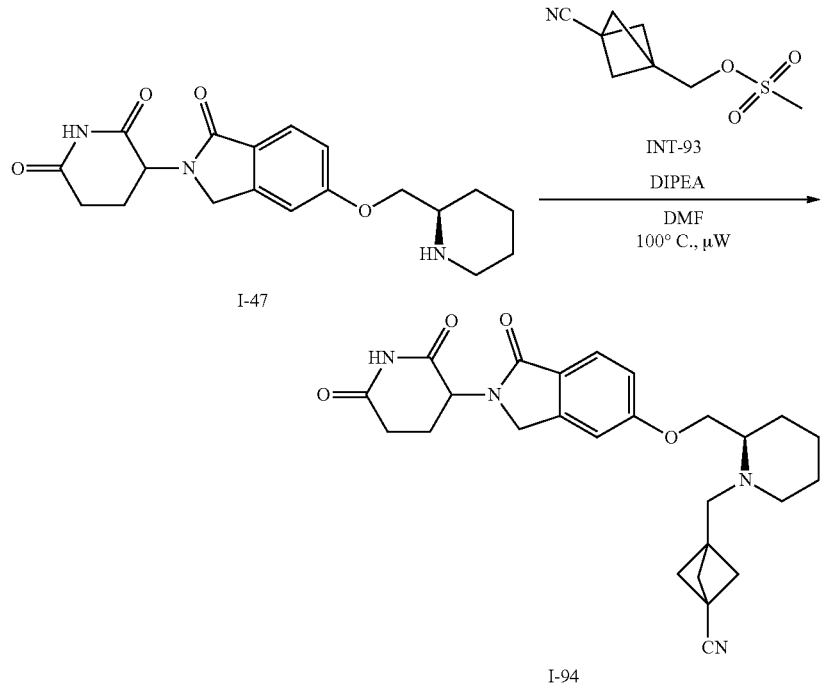

(3-cyanobicyclo[1.1.1]pentan-1-yl)methyl methanesulfonate INT-93 (81 mg, 0.403 mmol) was added to a 2 mL microwave vial and dissolved in DMF (1.68 mL). 3-(1-oxo-5-(((R)-piperidin-2-yl)methoxy)isoindolin-2-yl)piperidine-2,6-dione I-47 (0.12 g, 0.336 mmol) was added, followed by the addition of DIPEA (0.12 mL, 0.671 mmol). The resulting mixture was stirred at 100° C. for a total of 22 hrs under microwave radiation. The reaction mixture was quenched with 50% saturated aqueous sodium bicarbonate and extracted with 4:1 DCM: iPrOH three times. The organic phases were combined, passed through a phase separator and concentrated. The crude material was purified by silica gel chromatography (eluting with 0-100% 3:1 EtOAc:EtOH with 1% TEA in heptane) to afford 3-(((2R)-2-(((2-(2,6-dioxopiperidin-3-yl)-1-oxoisoindolin-5-yl)oxy)methyl)piperidin-1-yl)methyl)bicyclo[1.1.1]pentane-1-carbonitrile I-94 (18.3 mg, 0.036 mmol, 10.84% yield) as a white solid. LCMS [M+H]⁺: 463.2. ¹H NMR (400 MHz, DMSO-d₆) δ 10.90 (s, 1H), 7.56 (d, J=8.3 Hz, 1H), 7.11 (d, J=2.3 Hz, 1H), 6.99 (dd, J=8.3, 2.4 Hz, 1H), 5.00 (dd, J=13.3, 5.0 Hz, 1H), 4.32 (d, J=17.4 Hz, 1H), 4.20 (d, J=17.3 Hz, 1H), 4.08-4.00 (m, 1H), 3.96-3.82 (m, 1H), 2.90-2.78 (m, 1H), 2.75-2.63 (m, 3H), 2.56-2.49 (m, 1H), 2.35-2.22 (m, 3H), 2.11-2.04 (m, 6H), 1.96-1.87 (m, 1H), 1.68-1.52 (m, 2H), 1.47-1.19 (m, 4H).

Example 55: ((1r,3r)-3-methoxycyclobutyl)methyl methanesulfonate (INT-96)

Step 1: ((1r,3r)-3-methoxycyclobutyl)methanol (95)

Trans-3-methoxycyclobutane-1-carboxylic acid (0.1 g, 0.768 mmol) was dissolved in THF (2.56 mL) and cooled to 0° C. 1M borane THF complex in THF (2.3 mL, 2.31 mmol) was added dropwise. The reaction stirred at r.t. overnight. The reaction was cooled to 0° C. and quenched with methanol (1.87 mL, 46.1 mmol) and stirred at r.t. for 2 hrs. The reaction was concentrated to dryness then redissolved in methanol (5 mL). The reaction stirred at r.t. overnight. The reaction was concentrated to afford ((1r,3r)-3-methoxycyclobutyl)methanol 95 (89 mg, 0.768 mmol, 100% yield) as a clear oil. The material was taken on to the next step without purification assuming quantitative yield.

Step 2: ((1r,3r)-3-methoxycyclobutyl)methyl methanesulfonate (INT-96)

To a solution of ((1r,3r)-3-methoxycyclobutyl)methanol 95 (89 mg, 0.768 mmol) in DCM (1.5 mL) was added DIPEA (268 μL, 1.536 mmol), 1-methyl-1H-imidazole (122 μL, 1.536 mmol), then methanesulfonyl chloride (90 μL, 1.152 mmol) dropwise. The reaction stirred at r.t. for 18 hrs. The reaction was diluted with DCM (30 mL). The organic layer was washed with 1 M aqueous HCl three times and saturated aqueous sodium bicarbonate twice. The organic layer was passed through a phase separator and concentrated to afford ((1r,3r)-3-methoxycyclobutyl)methyl methanesulfonate INT-96 (176 mg, 0.906 mmol, 118% yield) as maroon oil. The material was taken on to the next step without purification and greater than quantitative yield due to impurities being present. ¹H NMR (400 MHz, CDCl₃) δ 4.16 (d, J=6.8 Hz, 2H), 3.94-3.82 (m, 1H), 3.16 (s, 3H), 2.96 (s, 3H), 2.63-2.51 (m, 1H), 2.09 (t, J=6.8 Hz, 4H).

Example 56: 3-(5-(((R)-1-(((1r,3R)-3-methoxycyclobutyl)methyl)piperidin-2-yl)methoxy)-1-oxoisoindolin-2-yl)piperidine-2,6-dione (I-97)

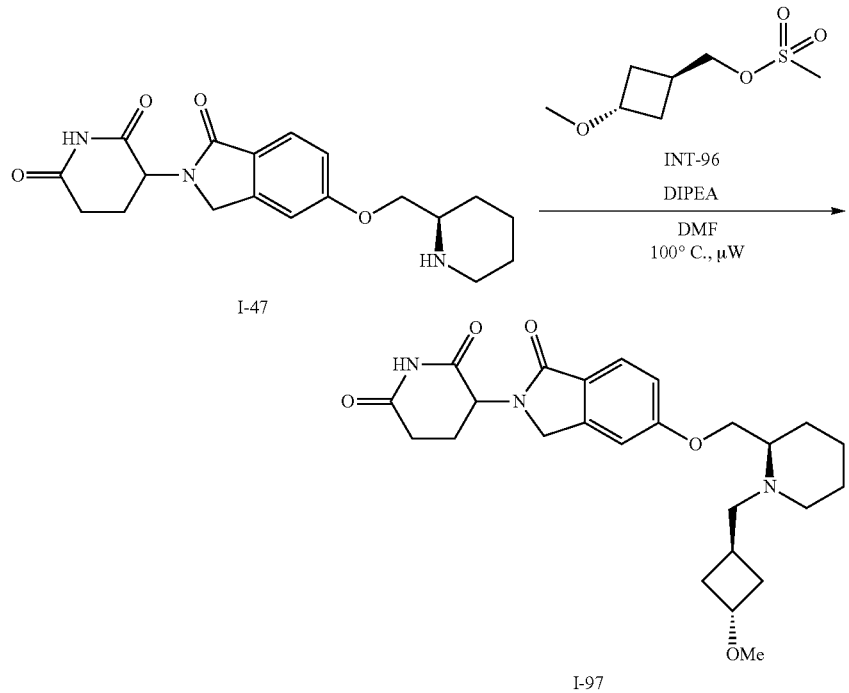

(((1r,3r)-3-methoxycyclobutyl)methyl methanesulfonate INT-96 (112 mg, 575 µmol) was added to a 2 mL microwave vial and dissolved in DMF (1.92 mL). 3-(1-oxo-5-(((R)-piperidin-2-yl)methoxy)isoindolin-2-yl)piperidine-2,6-dione I-47 (137 mg, 0.383 mmol) was added followed by the addition of DIPEA (0.13 mL, 0.767 mmol). The reaction was evacuated and backfilled with nitrogen three times. The reaction stirred at 100° C. for a total of 15 hrs under microwave radiation. Additional (((1r,3r)-3-methoxycyclobutyl)methyl methanesulfonate INT-96 (64 mg, 0.329 mmol) and DIPEA (0.13 mL, 0.767 mmol) were added and the reaction was evacuated and backfilled with nitrogen three times. The reaction stirred at 100° C. for an additional 12 hrs under microwave radiation. The reaction was quenched with saturated aqueous sodium bicarbonate and extracted with 4:1 DCM: iPrOH three times. The organic layers were combined, passed through a phase separator, and concentrated onto CELITE®. The crude material was purified by silica gel chromatography (0-100% 3:1 EtOAc:EtOH with 1% TEA in heptane) to afford impure product. The material was further purified by basic mass triggered reverse phase HPLC (25-50% ACN in water with 5 mM $NH_4OH$ as modifier). Test tubes contained 3 drops formic acid prior to sample collection. Pure fractions were combined and lyophilized to afford formate salt 3-(5-(((R)-1-(((1r,3R)-3-methoxycyclobutyl)methyl)piperidin-2-yl)methoxy)-1-oxoisoindolin-2-yl)piperidine-2,6-dione I-97 (44.6 mg, 0.089 mmol, 23.2% yield) as a white solid. LCMS $[M+H]^+$: 456.1. $^1$H NMR (400 MHz, DMSO-$d_6$) δ 10.84 (s, 1H), 8.24 (t, J=5.4 Hz, 1H), 7.56 (d, J=8.4 Hz, 1H), 7.13 (d, J=2.3 Hz, 1H), 6.99 (dd, J=8.4, 2.2 Hz, 1H), 5.00 (dd, J=13.3, 5.1 Hz, 1H), 4.32 (d, J=17.2 Hz, 1H), 4.20 (d, J=17.2 Hz, 1H), 4.15-4.04 (m, 1H), 4.03-3.91 (m, 1H), 3.73 (p, J=6.3 Hz, 1H), 2.97 (s, 3H), 2.84 (ddd, J=17.1, 13.6, 5.4 Hz, 1H), 2.77-2.64 (m, 2H), 2.63-2.48 (m, 2H), 2.35-2.24 (m, 3H), 2.13-2.04 (m, 1H), 1.98-1.72 (m, 5H), 1.68-1.52 (m, 2H), 1.46-1.20 (m, 4H).

Example 57: 3-fluorobicyclo[1.1.1]pentane-1-carbaldehyde (INT-99)

Step 1: (3-fluorobicyclo[1.1.1]pentan-1-yl)methanol (98)

Under a nitrogen atmosphere, 3-fluorobicyclo[1.1.1]pentane-1-carboxylic acid was dissolved in THF (mL) and cooled to 0° C. 1M borane THF complex in THF (mL, mmol) was added dropwise over 10 mins. The reaction was allowed to warm to r.t. and stirred at r.t. for 72 hrs. The reaction was cooled to 0° C. and MeOH (1 mL) was added dropwise. After gas evolution stopped, the solvent was concentrated to afford (3-fluorobicyclo[1.1.1]pentan-1-yl)methanol 98 (650 mg, 5.6 mmol, 143% yield). Material was used directly in the next step without purification with greater than quantitative yield due to impurities.

Step 2: 3-fluorobicyclo[1.1.1]pentane-1-carbaldehyde (INT-99)

A 40 mL vial was charged with (3-fluorobicyclo[1.1.1]pentan-1-yl)methanol 98 (454 mg, 3.91 mmol), $NaHCO_3$ (750 mg, 8.93 mmol) and DCM (6 mL). Dess-Martin periodinane (2.49 g, 5.87 mmol) was added and the reaction mixture stirred at r.t. for 3 hrs. Ether (18 mL) was added to the reaction and the reaction was filtered twice. The filtrate was concentrated, ether (20 mL) was added, and the solid was filtered. The filtrate was concentrated again to afford 3-fluorobicyclo[1.1.1]pentane-1-carbaldehyde INT-99 (449 mg, 3.93 mmol, 100% yield) as a yellow oil containing some white solid. A 1M solution in DMF was made and the material was used directly in the next step without purification assuming a quantitative yield.

Example 58: 3-(5-(((R)-1-((3-fluorobicyclo[1.1.1]pentan-1-yl)methyl)piperidin-2-yl)methoxy)-1-oxoisoindolin-2-yl)piperidine-2,6-dione (I-100)

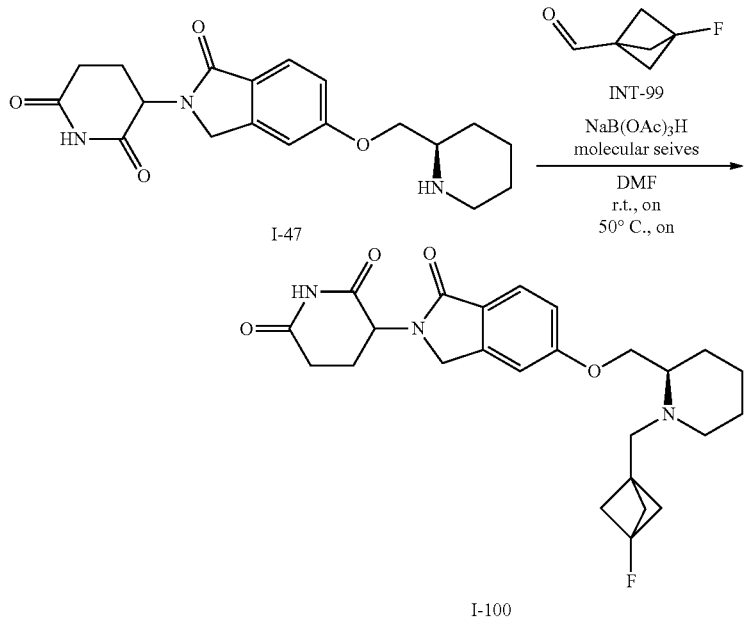

1M 3-fluorobicyclo[1.1.1]pentane-1-carbaldehyde INT-99 in DMF (0.8 mL, 0.80 mmol) was added to 3-(1-oxo-5-(((R)-piperidin-2-yl)methoxy)isoindolin-2-yl)piperidine-2,6-dione I-47 (150 mg, 0.420 mmol) in DMF (1.8 mL). The reaction mixture stirred at r.t. for 15 min. Sodium triacetoxyborohydride (205 mg, 0.965 mmol) was added and the reaction stirred at r.t. overnight.

A small amount of molecular sieves and additional 1M 3-fluorobicyclo[1.1.1]pentane-1-carbaldehyde INT-99 in DMF (0.8 mL, 0.80 mmol) were added. The reaction stirred at 50° C. for 1 hr. Additional sodium triacetoxyborohydride (205 mg, 0.965 mmol) was added and the reaction stirred at 50° C. overnight. The reaction was quenched with 50% saturated aqueous sodium bicarbonate and extracted three times with 4:1 DCM:iPrOH. The crude material was purified by silica gel chromatography (1-25% EtOH with 1% TEA in DCM with 0.1% TEA) to afford 3-(5-(((R)-1-((3-fluorobicyclo[1.1.1]pentan-1-yl)methyl)piperidin-2-yl)methoxy)-1-oxoisoindolin-2-yl)piperidine-2,6-dione I-100 (17 mg, 0.036 mmol, 8.5% yield). LCMS [M+H]⁺: 456.5. $^1$H NMR (400 MHz, DMSO-d$_6$) δ 10.96 (s, 1H), 7.62 (d, J=8.4 Hz, 1H), 7.18 (d, J=2.3 Hz, 1H), 7.06 (dd, J=8.6, 2.2 Hz, 1H), 5.07 (dd, J=13.3, 5.2 Hz, 1H), 4.39 (d, J=17.2 Hz, 1H), 4.27 (d, J=17.1 Hz, 1H), 4.18-3.90 (m, 2H), 3.30-3.28 (m, 1H), 3.03-2.85 (m, 2H), 2.84-2.71 (m, 3H), 2.63-2.55 (m, 1H), 2.44-2.35 (m, 2H), 2.03-1.90 (m, 7H), 1.75-1.59 (m, 2H), 1.51-1.31 (m, 3H).

The following compounds were made according to Example 26, starting from the final product of Example 24 (I-47).

| # | Structure/NMR data | LCMS [M + H] | LCMS Rt |
|---|---|---|---|
| I-101 | $^1$H NMR (400 MHz, DMSO-d6) δ 10.98 (s, 1H), 7.62 (d, J = 8.4 Hz, 1H), 7.49 (d, J = 7.5 Hz, 1H), 7.28-6.94 (m, 5H), 5.08 (dd, J = 13.2, 5.1 Hz, 1H), 4.44-4.21 (m, 3H), 4.17-4.06 (m, 1H), 3.96 (d, J = 13.9 Hz, 1H), 3.80-3.65 (m, 4H), 3.58 (d, J = 13.9 Hz, 1H), 2.97-2.66 (m, 7H), 2.64-2.56 (m, 1H), 2.46-2.33 (m, 1H), 2.28-2.18 (m, 1H), 2.03-1.95 (m, 1H), 1.83-1.73 (m, 1H), 1.69-1.37 (m, 5H). | 533.2 | 0.42 |

| # | Structure/NMR data | LCMS [M + H] | LCMS Rt |
|---|---|---|---|
| I-113 | 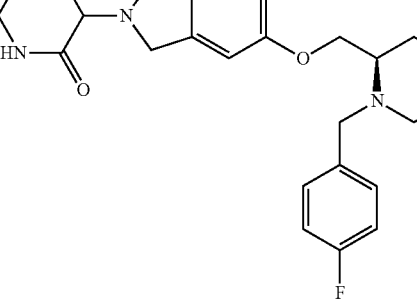<br>¹H NMR (400 MHz, DMSO-d6) δ 10.97 (s, 1H), 7.62 (d, J = 8.5 Hz, 1H), 7.36 (dd, J = 8.5, 5.7 Hz, 2H), 7.20 (d, J = 2.2 Hz, 1H), 7.16-7.01 (m, 3H), 5.08 (dd, J = 13.3, 5.1 Hz, 1H), 4.43-4.21 (m, 3H), 4.20-4.08 (m, 1H), 3.98 (d, J = 13.7 Hz, 1H), 3.39 (d, J = 13.8 Hz, 1H), 2.91 (ddd, J = 17.2, 13.6, 5.4 Hz, 1H), 2.82-2.74 (m, 1H), 2.72-2.64 (m, 1H), 2.63-2.57 (m, 1H), 2.45-2.33 (m, 1H), 2.17-2.07 (m, 1H), 2.02-1.93 (m, 1H), 1.85-1.75 (m, 1H), 1.70-1.61 (m, 1H), 1.59-1.30 (m, 4H). | 466.4 | 0.41 |
| I-114 | 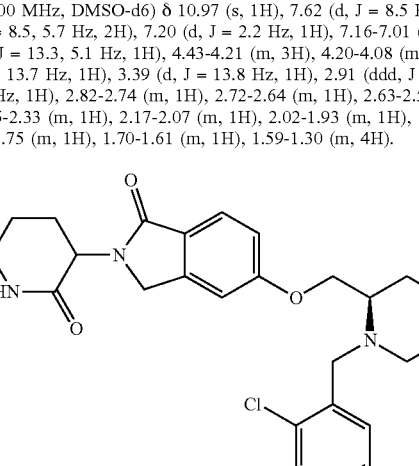<br>¹H NMR (400 MHz, DMSO-d6) δ 10.89 (s, 1H), 7.59-7.45 (m, 2H), 7.28 (dd, J = 8.9, 2.6 Hz, 1H), 7.17-7.06 (m, 2H), 6.98 (dd, J = 8.7, 2.3 Hz, 1H), 5.00 (dd, J = 13.3, 5.1 Hz, 1H), 4.34-4.12 (m, 3H), 4.11-4.02 (m, 1H), 3.96 (d, J = 14.7 Hz, 1H), 3.45 (d, J = 14.8 Hz, 1H), 2.90-2.74 (m, 2H), 2.67-2.57 (m, 1H), 2.56-2.48 (m, 1H), 2.37-2.25 (m, 1H), 2.20-2.10 (m, 1H), 1.95-1.87 (m, 1H), 1.77-1.69 (m, 1H), 1.65-1.55 (m, 1H), 1.54-1.28 (m, 4H). | 500.1 | 0.44 |
| I-115 | 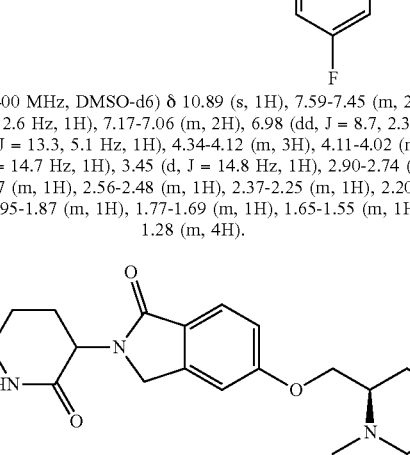<br>¹H NMR (400 MHz, DMSO-d6) δ 10.89 (s, 1H), 8.36 (d, J = 2.8 Hz, 1H), 7.65-7.40 (m, 3H), 7.10 (d, J = 2.2 Hz, 1H), 6.98 (dd, J = 8.4, 2.2 Hz, 1H), 5.00 (dd, J = 13.3, 5.2 Hz, 1H), 4.36-4.13 (m, 3H), 4.11-4.01 (m, 1H), 3.96 (d, J = 14.7 Hz, 1H), 3.57 (d, J = 14.6 Hz, 1H), 2.84 (ddd, J = 17.2, 13.7, 5.5 Hz, 1H), 2.75-2.64 (m, 2H), 2.55-2.48 (m, 1H), 2.36-2.26 (m, 1H), 2.21-2.12 (m, 1H), 1.95-1.87 (m, 1H), 1.76-1.67 (m, 1H), 1.64-1.55 (m, 1H), 1.51-1.22 (m, 4H). | 467.4 | 0.38 |

| # | Structure/NMR data | LCMS [M + H] | LCMS Rt |
|---|---|---|---|

I-119

¹H NMR (400 MHz, DMSO-d6) δ 10.97 (s, 1H), 7.61 (d, J = 8.3 Hz, 1H), 7.54-7.44 (m, 1H), 7.21-7.11 (m, 2H), 7.11-6.94 (m, 3H), 5.08 (dd, J = 13.3, 5.1 Hz, 1H), 4.43-4.19 (m, 3H), 4.13-4.04 (m, 1H), 3.92 (d, J = 14.1 Hz, 1H), 3.57 (d, J = 14.0 Hz, 1H), 2.97-2.66 (m, 7H), 2.64-2.56 (m, 1H), 2.45-2.33 (m, 1H), 2.29-2.19 (m, 1H), 2.03-1.94 (m, 1H), 1.84-1.75 (m, 1H), 1.70-1.37 (m, 11H).

531.5    0.48

I-158

¹H NMR (400 MHz, DMSO-d6) δ 10.97 (s, 1H), 7.62 (d, J = 8.4 Hz, 1H), 7.34-7.28 (m, 2H), 7.28-7.21 (m, 2H), 7.19 (d, J = 2.0 Hz, 1H), 7.07 (dd, J = 8.4, 2.2 Hz, 1H), 5.08 (dd, J = 13.3, 5.1 Hz, 1H), 4.47-4.21 (m, 3H), 4.13 (dd, J = 10.2, 5.3 Hz, 1H), 3.97 (d, J = 13.7 Hz, 1H), 3.37 (d, J = 13.7 Hz, 1H), 3.00-2.82 (m, 1H), 2.82-2.66 (m, 2H), 2.66-2.55 (m, 1H), 2.46-2.32 (m, 1H), 2.20-2.07 (m, 1H), 2.05-1.93 (m, 1H), 1.86-1.75 (m, 1H), 1.67 (d, J = 10.9 Hz, 1H), 1.60-1.32 (m, 4H), 1.26 (s, 9H).

504.7    0.51

I-184

¹H NMR (400 MHz, DMSO-d6) δ 10.97 (s, 1H), 7.61 (d, J = 8.4 Hz, 1H), 7.34 (d, J = 1.6 Hz, 1H), 7.28 (d, J = 8.2 Hz, 1H), 7.19-7.09 (m, 2H), 7.05 (dd, J = 8.4, 2.2 Hz, 1H), 5.08 (dd, J = 13.3, 5.1 Hz, 1H), 4.41-4.19 (m, 3H), 4.11 (dd, J = 10.3, 5.0 Hz, 1H), 3.98 (d, J = 14.1 Hz, 1H), 3.43 (d, J = 14.1 Hz, 1H), 2.98-2.86 (m, 1H), 2.81-2.65 (m, 2H), 2.64-2.55 (m, 1H), 2.38 (qd, J = 13.2, 4.5 Hz, 1H), 2.20-2.07 (m, 1H), 2.03-1.92 (m, 1H), 1.82-1.73 (m, 1H), 1.69-1.60 (m, 1H), 1.58-1.31 (m, 4H).

528.2    0.47

-continued
| # | Structure/NMR data | LCMS [M + H] | LCMS Rt |
|---|---|---|---|
| I-192 | 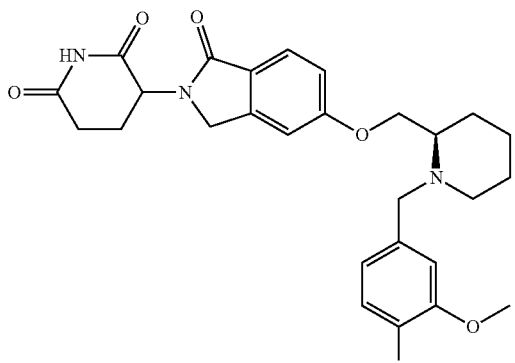<br>¹H NMR (400 MHz, DMSO-d6) δ 10.89 (s, 1H), 7.60-7.45 (m, 2H), 7.13-7.06 (m, 2H), 7.06-6.87 (m, 2H), 5.00 (dd, J = 13.3, 5.1 Hz, 1H), 4.30 (d, J = 17.1 Hz, 1H), 4.25-4.13 (m, 2H), 4.05 (dd, J = 10.3, 4.9 Hz, 1H), 3.98 (d, J = 14.8 Hz, 1H), 3.81 (s, 3H), 3.45 (d, J = 14.9 Hz, 1H), 2.90-2.78 (m, 1H), 2.78-2.70 (m, 1H), 2.68-2.57 (m, 1H), 2.56-2.48 (m, 1H), 2.38-2.24 (m, 1H), 2.17-2.08 (m, 1H), 1.96-1.85 (m, 1H), 1.77-1.68 (m, 1H), 1.67-1.55 (m, 1H), 1.55-1.27 (m, 4H). | 503.4 | 0.41 |
| I-193 | 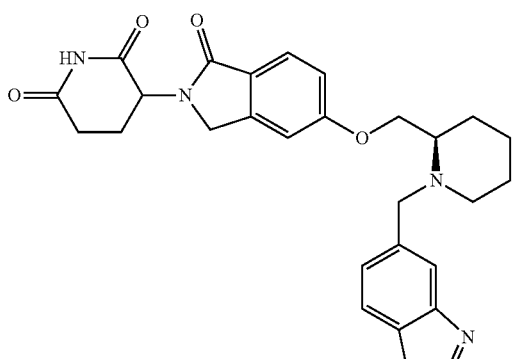<br>¹H NMR (400 MHz, DMSO-d6) δ 12.24 (d, J = 19.0 Hz, 1H), 10.89 (s, 1H), 8.07 (s, 1H), 7.56-7.31 (m, 3H), 7.17-7.05 (m, 2H), 7.01 (dd, J = 8.4, 2.3 Hz, 1H), 5.00 (dd, J = 13.3, 5.0 Hz, 1H), 4.37-4.23 (m, 2H), 4.23-3.99 (m, 3H), 3.42 (d, J = 13.4 Hz, 1H), 2.84 (ddd, J = 17.1, 13.6, 5.3 Hz, 1H), 2.75-2.62 (m, 2H), 2.56-2.48 (m, 1H), 2.37-2.25 (m, 1H), 2.12-2.03 (m, 1H), 1.94-1.86 (m, 1H), 1.79-1.69 (m, 1H), 1.63-1.56 (m, 1H), 1.51-1.26 (m, 4H). | 488.3 | 0.35 |
| I-202 | 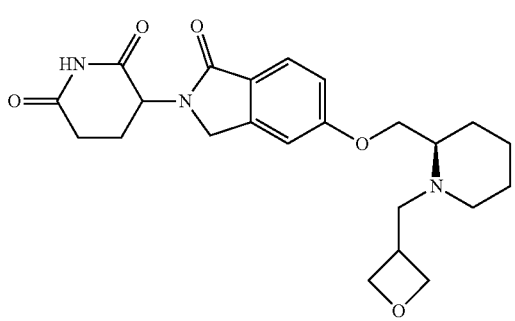<br>¹H NMR (400 MHz, DMSO-d6) δ 10.89 (s, 1H), 7.56 (d, J = 8.3 Hz, 1H), 7.13 (d, J = 2.2 Hz, 1H), 7.00 (dd, J = 8.4, 2.2 Hz, 1H), 5.00 (dd, J = 13.3, 5.1 Hz, 1H), 4.58-4.49 (m, 2H), 4.32 (d, J = 17.1 Hz, 1H), 4.24-4.07 (m, 4H), 4.02-3.93 (m, 1H), 3.15-3.05 (m, 1H), 3.04-2.96 (m, 1H), 2.91-2.78 (m, 1H), 2.70-2.61 (m, 1H), 2.61-2.48 (m, 3H), 2.38-2.26 (m, 1H), 2.08-1.98 (m, 1H), 1.97-1.85 (m, 1H), 1.68-1.52 (m, 2H), 1.47-1.22 (m, 4H). | 428.4 | 0.38 |

Example 60: 3-(5-(((R)-1-(4-(4-(cyclopropylmethyl)piperazin-1-yl)benzyl)piperidin-2-yl)methoxy)-1-oxoisoindolin-2-yl)piperidine-2,6-dione (I-102)

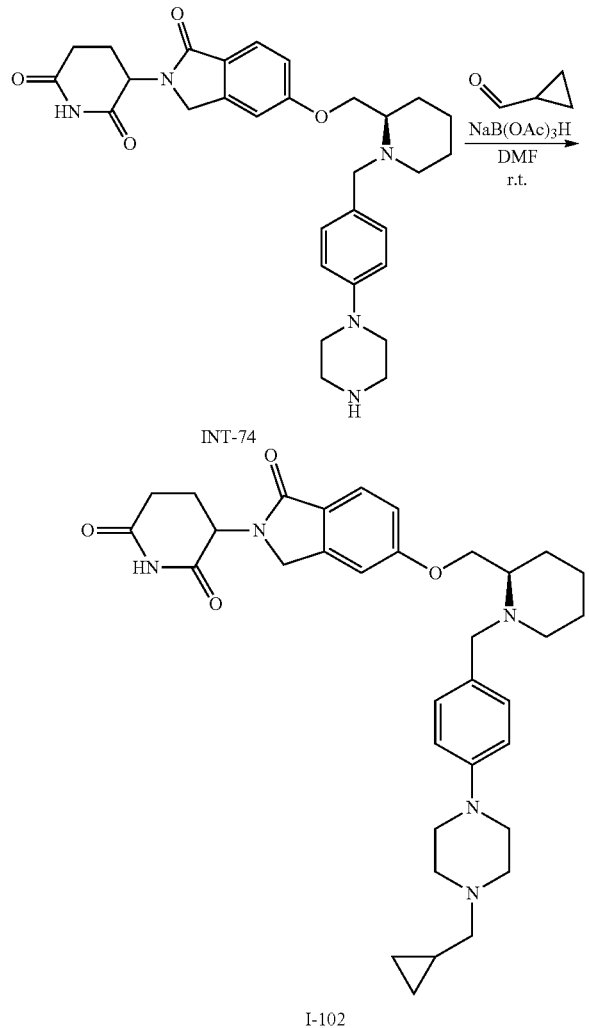

Compound I-102 was prepared according to General Method III starting from 3-(1-oxo-5-(((R)-1-(4-(piperazin-1-yl)benzyl)piperidin-2-yl)methoxy)isoindolin-2-yl)piperidine-2,6-dione INT-74 (100 mg, 0.188 mmol) and cyclopropanecarboxaldehyde (28 μL, 0.376 mmol). The reaction was quenched with 50% saturated aqueous sodium bicarbonate in water and extracted 4 times with 4:1 dichloromethane:isopropanol. The organic layers were combined, passed through a phase separator and concentrated. The material was purified by silica gel chromatography (0-100% 3:1 ethylaceate:ethanol with 1% TEA in heptane). Pure fractions were combined, concentrated, and lyophilized to afford 3-(5-(((R)-1-(4-(4-(cyclopropylmethyl)piperazin-1-yl)benzyl)piperidin-2-yl)methoxy)-1-oxoisoindolin-2-yl)piperidine-2,6-dione I-102 (65.9 mg, 0.111 mmol, 59.2% yield) as a white solid. LCMS [M+H]+: 586.6. $^1$H NMR (400 MHz, DMSO-$d_6$) δ 10.87 (s, 1H), 7.52 (d, J=8.4 Hz, 1H), 7.13-7.01 (m, 3H), 6.97 (dd, J=8.6, 2.2 Hz, 1H), 6.76 (d, J=8.3 Hz, 2H), 4.98 (dd, J=13.3, 5.1 Hz, 1H), 4.34-4.08 (m, 3H), 4.02 (dd, J=10.3, 5.6 Hz, 1H), 3.79 (d, J=13.5 Hz, 1H), 3.03-2.95 (m, 4H), 2.86-2.75 (m, 1H), 2.65-2.56 (m, 2H), 2.53-2.42 (m, 6H), 2.35-2.22 (m, 1H), 2.12 (d, J=6.6 Hz, 2H), 2.02-1.95 (m, 1H), 1.92-1.84 (m, 1H), 1.71-1.63 (m, 1H), 1.62-1.49 (m, 1H), 1.46-1.16 (m, 4H), 0.82-0.68 (m, 1H), 0.42-0.35 (m, 2H), 0.03--0.04 (m, 2H).

Example 61: (2-oxaspiro[3.3]heptan-6-yl)methyl methanesulfonate (INT-103)

To a solution of (2-oxaspiro[3.3]heptan-6-yl)methanol (0.1 g, 0.780 mmol) in DCM (1.5 mL) was added DIPEA (0.27 mL, 1.56 mmol), 1-methyl-1H-imidazole (0.12 mL, 1.56 mmol), then methanesulfonyl chloride (0.09 mL, 1.17 mmol) dropwise. The reaction stirred at r.t. for 18 hrs. The reaction was diluted with DCM (30 mL). The organic layer was washed with 1 M aqueous HCl three times and saturated aqueous sodium bicarbonate twice. The organic layer was passed through a phase separator and concentrated to afford (2-oxaspiro[3.3]heptan-6-yl)methyl methanesulfonate INT-103 (137.5 mg, 0.667 mmol, 85% yield) as a brown oil. $^1$H NMR (400 MHz, CDCl$_3$) δ 4.73 (s, 2H), 4.64 (s, 2H), 4.15 (d, J=6.2 Hz, 2H), 3.03 (s, 3H), 2.59-2.49 (m, 1H), 2.47-2.38 (m, 2H), 2.13-2.03 (m, 2H).

Example 62: 3-(5-(((R)-1-((2-oxaspiro[3.3]heptan-6-yl)methyl)piperidin-2-yl)methoxy)-1-oxoisoindolin-2-yl)piperidine-2,6-dione (I-104)

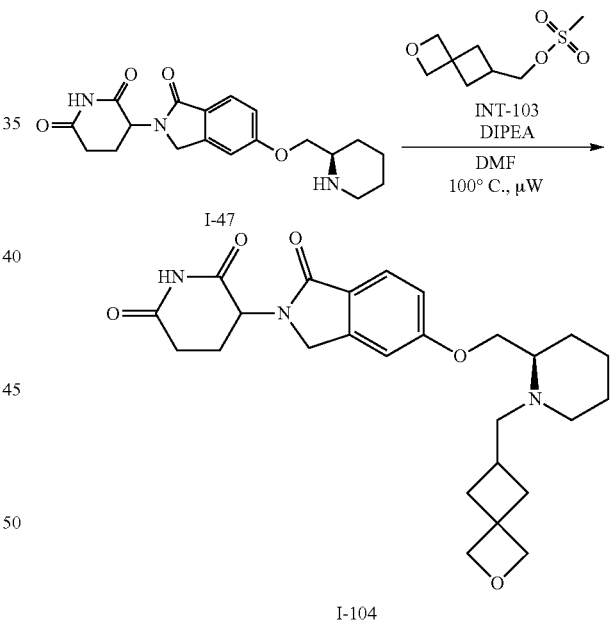

(2-oxaspiro[3.3]heptan-6-yl)methyl methanesulfonate INT-103 (95 mg, 0.462 mmol) was added to a 2 mL microwave vial and dissolved in DMF (1.5 mL). 3-(1-oxo-5-(((R)-piperidin-2-yl)methoxy)isoindolin-2-yl)piperidine-2,6-dione I-47 (0.11 g, 0.308 mmol) was added followed by the addition of DIPEA (0.11 mL, 0.616 mmol). The reaction was evacuated and backfilled with nitrogen three times. The reaction stirred at 100° C. for 12 hrs under microwave radiation. The reaction was quenched with 50% saturated aqueous sodium bicarbonate and extracted with 4:1 DCM:iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-((2-oxaspiro[3.3]heptan-6-yl)methyl)piperidin-2-yl)methoxy)-1-oxoisoindolin-2-yl)piperidine-2,6-dione INT-104 (46.1 mg, 0.094 mmol, 30.4% yield) as a white solid. LCMS [M+H]+: 468.5. 1H NMR (400 MHz, DMSO-d6) δ 10.97 (s, 1H), 7.63 (d, J=8.5 Hz, 1H), 7.19 (d, J=2.3 Hz, 1H), 7.06 (dd, J=8.4, 2.3 Hz, 1H), 5.08 (dd, J=13.3, 5.0 Hz, 1H), 4.54 (s, 2H), 4.43-4.33 (m, 3H), 4.27 (d, J=17.1 Hz, 1H), 4.16-4.10 (m, 1H), 4.06-3.98 (m, 1H), 2.91 (ddd, J=17.2, 13.5, 5.4 Hz, 1H), 2.81-2.71 (m, 1H), 2.65-2.56 (m, 3H), 2.43-2.31 (m, 2H), 2.29-2.20 (m, 3H), 2.18-2.10 (m, 1H), 2.02-1.95 (m, 1H), 1.84-1.60 (m, 4H), 1.54-1.25 (m, 4H).

Example 63: Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperazine-1-carboxylate (I-105)

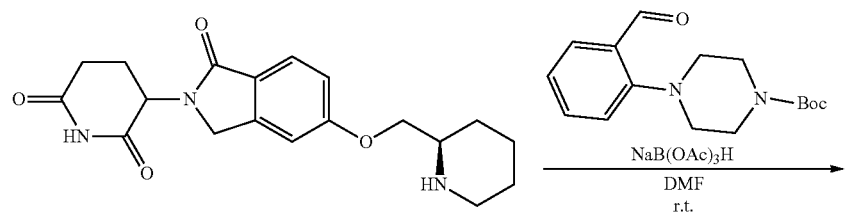

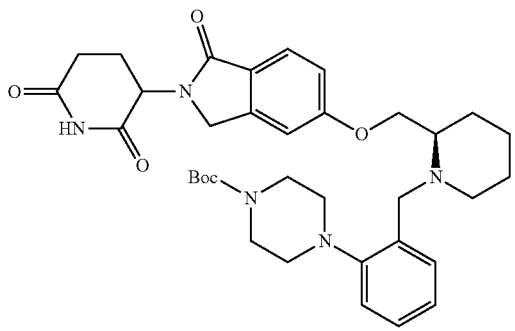 [SMILES: O=C1CCC(N2Cc3cc(OC[C@H]4CCCCN4Cc4ccccc4N4CCOCC4)ccc3C2=O)C(=O)N1]

Compound I-105 was prepared according to General Method III starting from 3-(1-oxo-5-(((R)-piperidin-2-yl)methoxy)isoindolin-2-yl)piperidine-2,6-dione I-47 (100 mg, 0.280 mmol) and tert-butyl 4-(2-formylphenyl)piperazine-1-carboxylate (122 mg, 0.420 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford tert-butyl 4-(2-(((2R)-2-(((2-(2,6-dioxopiperidin-3-yl)-1-oxoisoindolin-5-yl)oxy)methyl)piperidin-1-yl)methyl)phenyl)piperazine-1-carboxylate I-105 (170.6 mg, 0.268 mmol, 95.4% yield) as a white solid. LCMS [M+H]+: 632.6. 1H NMR (400 MHz, DMSO-d6) δ 10.97 (s, 1H), 7.61 (d, J=8.3 Hz, 1H), 7.51-7.42 (m, 1H), 7.22-7.12 (m, 2H), 7.10-6.99 (m, 3H), 5.08 (dd, J=13.2, 5.0 Hz, 1H), 4.42-4.19 (m, 3H), 4.16-4.04 (m, 1H), 3.95 (d, J=13.8 Hz, 1H), 3.58 (d, J=13.8 Hz, 1H), 3.49-3.36 (m, 4H), 2.97-2.70 (m, 7H), 2.63-2.55 (m, 1H), 2.44-2.32 (m, 1H), 2.28-2.18 (m, 1H), 2.02-1.93 (m, 1H), 1.83-1.72 (m, 1H), 1.69-1.54 (m, 2H), 1.50-1.37 (m, 12H).

Example 64: 3-(1-oxo-5-(((R)-1-(2-(piperazin-1-yl)benzyl)piperidin-2-yl)methoxy)isoindolin-2-yl)piperidine-2,6-dione (I-106)

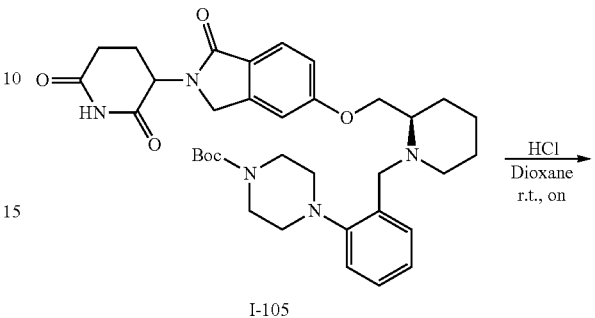

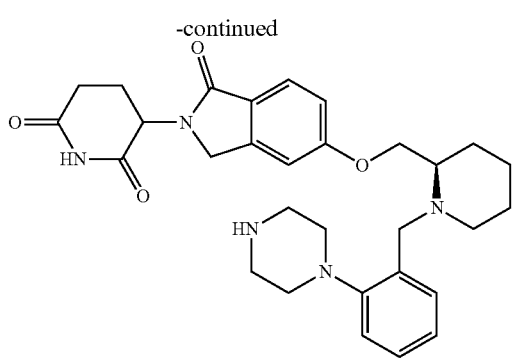

Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperazine-1-carboxylate I-105 (0.14 g, 0.222 mmol)

was suspended in Dioxane (0.89 mL) and dissolved in trifluoroethanol (0.59 mL). 4M HCl in dioxane (0.33 mL, 1.33 mmol) was added and the reaction stirred at r.t. overnight. The reaction was concentrated and then diluted with 4:1 DCM:iPrOH. The reaction was quenched with 50% saturated aqueous sodium bicarbonate. The aqueous layer was extracted 4 times with 4:1 DCM:iPrOH. The organic layers were combined, passed through a phase separator and concentrated. The crude material was purified by silica gel chromatography (0-100% EtOH with 1% TEA in DCM) to afford 3-(1-oxo-5-(((R)-1-(2-(piperazin-1-yl)benzyl)piperidin-2-yl)methoxy)isoindolin-2-yl)piperidine-2,6-dione I-106 (80.1 mg, 0.140 mmol, 63.2% yield) as a white solid. LCMS [M+H]⁺: 532.4. ¹H NMR (400 MHz, DMSO-d6) δ 10.97 (s, 1H), 7.61 (d, J=8.6 Hz, 1H), 7.53-7.44 (m, 1H), 7.22-7.10 (m, 2H), 7.08-6.97 (m, 3H), 5.08 (dd, J=13.3, 5.1 Hz, 1H), 4.44-4.19 (m, 3H), 4.14-4.04 (m, 1H), 3.93 (d, J=13.9 Hz, 1H), 3.58 (d, J=13.9 Hz, 1H), 2.97-2.66 (m, 11H), 2.64-2.56 (m, 1H), 2.45-2.33 (m, 1H), 2.28-2.19 (m, 1H), 2.03-1.94 (m, 1H), 1.82-1.74 (m, 1H), 1.70-1.62 (m, 1H), 1.60-1.36 (m, 4H).

Example 65: 3-(5-(((R)-1-(2-(4-isobutylpiperazin-1-yl)benzyl)piperidin-2-yl)methoxy)-1-oxoisoindolin-2-yl)piperidine-2,6-dione (I-107)

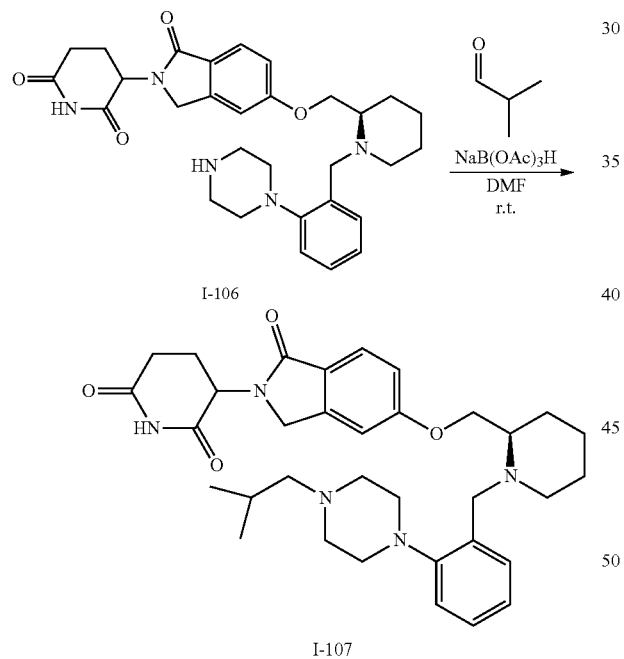

I-107

Compound I-107 was prepared according to General Method III starting from 3-(1-oxo-5-(((R)-1-(2-(piperazin-1-yl)benzyl)piperidin-2-yl)methoxy)isoindolin-2-yl)piperidine-2,6-dione I-106 (75 mg, 0.141 mmol) and isobutanal (0.02 mL, 0.212 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-(2-(4-isobutylpiperazin-1-yl)benzyl)piperidin-2-yl)methoxy)-1-oxoisoindolin-2-yl)piperidine-2,6-dione I-107 (53.8 mg, 0.090 mmol, 63.6% yield) as a white solid. LCMS [M+H]⁺: 588.2. ¹H NMR (400 MHz, DMSO-d6) δ 10.97 (s, 1H), 7.61 (d, J=8.3 Hz, 1H), 7.47 (dd, J=7.8, 1.8 Hz, 1H), 7.23-7.09 (m, 2H), 7.09-6.97 (m, 3H), 5.08 (dd, J=13.4, 5.1 Hz, 1H), 4.43-4.20 (m, 3H), 4.14-4.05 (m, 1H), 3.93 (d, J=13.8 Hz, 1H), 3.55 (d, J=13.8 Hz, 1H), 2.97-2.76 (m, 6H), 2.74-2.69 (m, 1H), 2.62-2.56 (m, 1H), 2.41 (ddd, J=22.3, 10.9, 4.5 Hz, 5H), 2.27-2.18 (m, 1H), 2.07-1.94 (m, 3H), 1.82-1.72 (m, 2H), 1.68-1.37 (m, 5H), 0.86 (d, J=6.4 Hz, 6H).

Example 66: 3-(1-oxo-5-(((R)-1-(2-(4-((tetrahydro-2H-pyran-4-yl)methyl)piperazin-1-yl)benzyl)piperidin-2-yl)methoxy)isoindolin-2-yl)piperidine-2,6-dione (I-108)

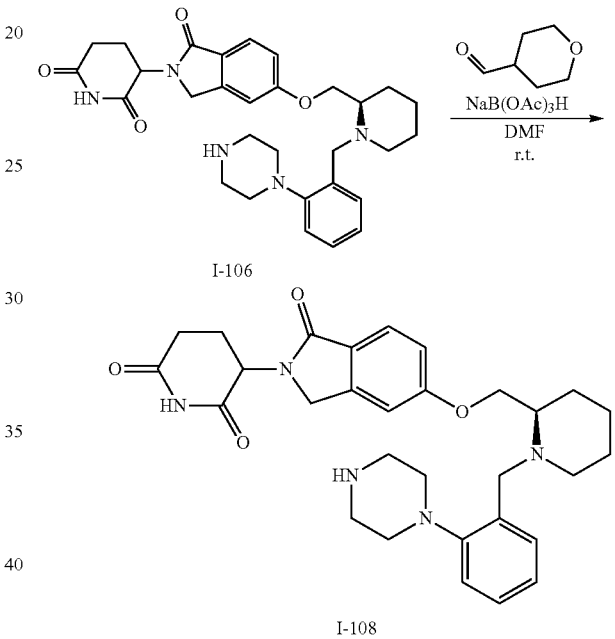

I-108

Compound I-108 was prepared according to General Method III starting from 3-(1-oxo-5-(((R)-1-(2-(piperazin-1-yl)benzyl)piperidin-2-yl)methoxy)isoindolin-2-yl)piperidine-2,6-dione I-106 (75 mg, 0.141 mmol) and tetrahydro-2H-pyran-4-carbaldehyde (22 µL, 0.212 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(1-oxo-5-(((R)-1-(2-(4-((tetrahydro-2H-pyran-4-yl)methyl)piperazin-1-yl)benzyl)piperidin-2-yl)methoxy)isoindolin-2-yl)piperidine-2,6-dione I-108 (61.5 mg, 0.095 mmol, 67.1% yield) as a white solid. LCMS [M+H]⁺: 630.6. ¹H NMR (400 MHz, DMSO-d6) δ 10.89 (s, 1H), 7.54 (d, J=8.4 Hz, 1H), 7.45-7.35 (m, 1H), 7.17-7.02 (m, 2H), 7.02-6.90 (m, 3H), 5.00 (dd, J=13.3, 5.2 Hz, 1H), 4.36-4.15 (m, 3H), 4.09-3.97 (m, 1H), 3.85 (d, J=13.8 Hz, 1H), 3.80-3.69 (m, 2H), 3.47 (d, J=13.9 Hz, 1H), 3.23-3.16 (m, 3H), 2.90-2.63 (m, 6H), 2.56-2.49 (m, 1H), 2.39-2.27 (m, 4H), 2.21-2.10 (m, 1H), 2.08-2.03 (m, 2H), 1.94-1.85 (m, 1H), 1.75-1.26 (m, 10H), 1.11-0.97 (m, 2H).

Example 67: 3-(1-oxo-5-(((R)-1-(4-(4-(tetrahydro-2H-pyran-4-yl)piperazin-1-yl)benzyl)piperidin-2-yl)methoxy)isoindolin-2-yl)piperidine-2,6-dione (I-109)

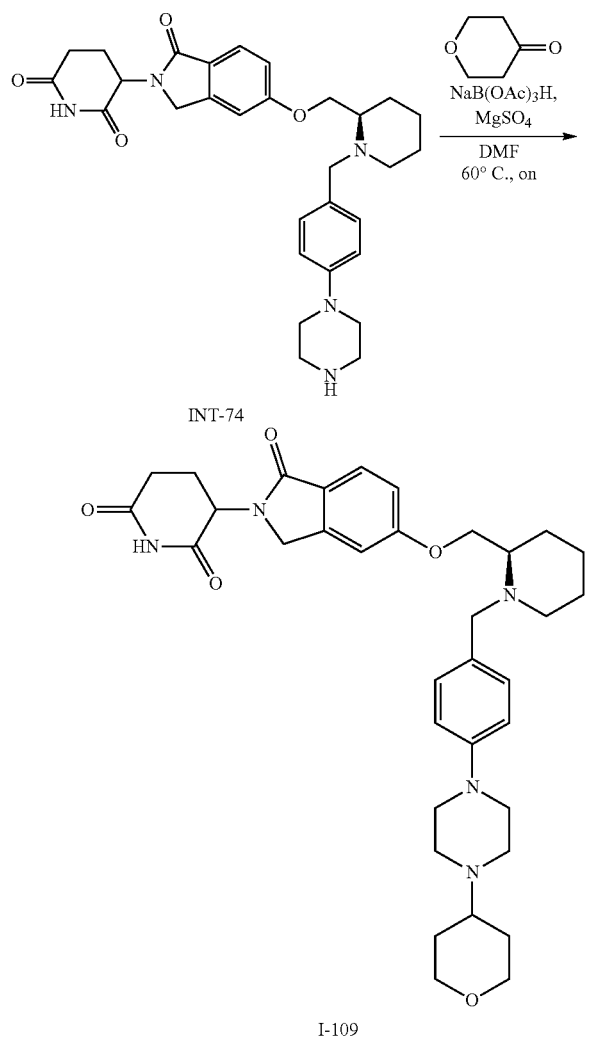

A 40 mL vial was charged with 3-(1-oxo-5-(((R)-1-(4-(piperazin-1-yl)benzyl)piperidin-2-yl)methoxy)isoindolin-2-yl)piperidine-2,6-dione INT-74 (0.1 g, 0.188 mmol), tetrahydro-4H-pyran-4-one (0.35 mL, 3.76 mmol), MgSO$_4$ (68 mg, 0.564 mmol) and DMF (1 mL). The suspension stirred at r.t. for 15 mins. NaB(OAc)$_3$H (80 mg, 0.376 mmol) was added and the reaction mixture stirred overnight at 60° C. The reaction was cooled to r.t. and quenched with 50% saturated aqueous sodium bicarbonate and extracted three times with 4:1 DCM:iPrOH. The organic layers were combined, passed through a phase separator and concentrated. The crude material was purified by silica gel chromatography (0-100% 3:1 EtOAc:EtOH with 1% TEA in heptanes). Fractions containing desired product were combined and concentrated. Product was further purified by basic reverse phase HPLC (25-50% ACN in water with 5 mM NH$_4$OH as modifier). Test tubes contained 3 drops formic acid prior to sample collection. Fractions containing pure product were combined and lyophilized to afford 3-(1-oxo-5-(((R)-1-(4-(4-(tetrahydro-2H-pyran-4-yl)piperazin-1-yl)benzyl)piperidin-2-yl)methoxy)isoindolin-2-yl)piperidine-2,6-dione I-109 (47.4 mg, 0.075 mmol, 39.7% yield) as a white solid. LCMS [M+H]$^+$: 616.6. $^1$H NMR (400 MHz, DMSO-d6) δ 10.90 (s, 1H), 7.55 (d, J=8.3 Hz, 1H), 7.15-7.04 (m, 3H), 7.00 (d, J=8.3 Hz, 1H), 6.79 (d, J=8.2 Hz, 2H), 5.00 (dd, J=13.4, 5.2 Hz, 1H), 4.36-4.12 (m, 3H), 4.11-3.99 (m, 1H), 3.83 (dd, J=10.7, 4.4 Hz, 3H), 3.23-3.18 (m, 4H), 3.06-2.96 (m, 4H), 2.91-2.77 (m, 1H), 2.68-2.62 (m, 1H), 2.57-2.51 (m, 3H), 2.39-2.28 (m, 4H), 2.06-1.97 (m, 1H), 1.95-1.87 (m, 1H), 1.76-1.62 (m, 3H), 1.62-1.54 (m, 1H), 1.51-1.24 (m, 6H).

Example 68: Tert-butyl 7-(((2R)-2-(((2-(2,6-dioxopiperidin-3-yl)-1-oxoisoindolin-5-yl)oxy)methyl)piperidin-1-yl)methyl)indoline-1-carboxylate (I-110)

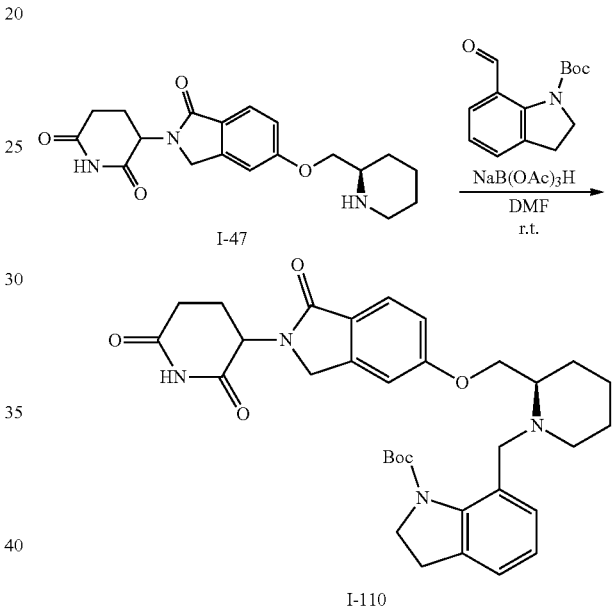

Compound I-10 was prepared according to General Method III starting from 1-(hydroxymethyl)-3-(1-oxo-5-(((R)-piperidin-2-yl)methoxy)isoindolin-2-yl)piperidine-2,6-dione I-47 (75 mg, 0.210 mmol) and tert-butyl 7-formylindoline-1-carboxylate (78 mg, 0.315 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford tert-butyl 7-(((2R)-2-(((2-(2,6-dioxopiperidin-3-yl)-1-oxoisoindolin-5-yl)oxy)methyl)piperidin-1-yl)methyl)indoline-1-carboxylate I-110 (87.3 mg, 0.148 mmol, 70.3% yield) as a white solid. LCMS [M+H]$^+$: 589.2. $^1$H NMR (400 MHz, DMSO-d6) δ 10.97 (s, 1H), 7.60 (d, J=8.5 Hz, 1H), 7.35 (d, J=7.7 Hz, 1H), 7.13-7.06 (m, 2H), 7.02 (t, J=7.6 Hz, 2H), 5.08 (dd, J=13.3, 5.0 Hz, 1H), 4.37 (d, J=17.2 Hz, 1H), 4.31-4.18 (m, 2H), 4.10-3.89 (m, 4H), 3.50 (d, J=15.1 Hz, 1H), 2.98-2.85 (m, 3H), 2.79-2.70 (m, 1H), 2.63-2.56 (m, 2H), 2.44-2.31 (m, 1H), 2.14-2.06 (m, 1H), 2.03-1.93 (m, 1H), 1.81-1.71 (m, 1H), 1.65-1.33 (m, 14H).

Example 69: 3-(5-(((R)-1-(indolin-7-ylmethyl)piperidin-2-yl)methoxy)-1-oxoisoindolin-2-yl)piperidine-2,6-dione (I-111)

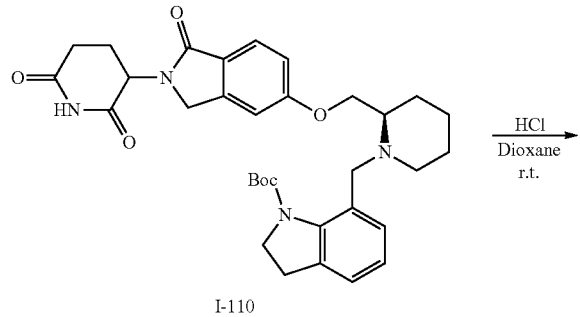

tert-butyl 7-(((2R)-2-(((2-(2,6-dioxopiperidin-3-yl)-1-oxoisoindolin-5-yl)oxy)methyl)piperidin-1-yl)methyl)indoline-1-carboxylate I-110 (78.6 mg, 0.134 mmol) was suspended in dioxane (0.45 mL) and dissolved in trifluoroethanol (0.45 mL). 4M HCl in dioxane (0.20 mL, 0.801 mmol) was added and the reaction stirred at r.t. for 72 hrs. The reaction was concentrated and then diluted with 4:1 DCM:iPrOH. The reaction was quenched with 50% saturated aqueous sodium bicarbonate. The aqueous layer was extracted 4 times with 4:1 DCM:iPrOH. The organic layers were combined, passed through a phase separator and concentrated to afford 3-(5-(((R)-1-(indolin-7-ylmethyl)piperidin-2-yl)methoxy)-1-oxoisoindolin-2-yl)piperidine-2,6-dione I-111 (32.7 mg, 67 µmol, 50% yield) as a white solid. This material was carried on to the next step without purification. The rest of the material was purified by basic reverse phase HPLC (35-60% ACN in H₂O with 5 mM NH₄OH as modifier). Test tubes contained 3 drops of formic acid prior to sample collection. Fractions containing product were combined and lyophilized to afford impure product. Material was further purified by achiral acidic reverse phase HPLC (5-95% ACN in H₂O with 0.1% acetic acid as modifier, Xbridge Prep C18, 19×50 mm, 5 µm OBD, flow rate 25 mL/min at 25° C.) to afford product which was dissolved in ACN and water, and lyophilized to afford 3-(5-(((R)-1-(indolin-7-ylmethyl)piperidin-2-yl)methoxy)-1-oxoisoindolin-2-yl)piperidine-2,6-dione I-111 (4 mg, 7.61 µmol, 5.70% yield) as a white solid. LCMS [M+H]⁺: 489.2.

¹H NMR (400 MHz, DMSO-d6) δ 10.91 (s, 1H), 7.62 (dd, J=13.5, 6.4 Hz, 1H), 7.22-6.91 (m, 4H), 6.57-6.36 (m, 1H), 5.02 (dd, J=13.4, 5.1 Hz, 1H), 4.60-4.33 (m, 3H), 4.23 (d, J=16.9 Hz, 1H), 4.10 (ddd, J=8.9, 5.8, 3.1 Hz, 1H), 3.74 (d, J=85.7 Hz, 1H), 3.46-3.37 (m, 2H), 2.99 (s, 1H), 2.92-2.82 (m, 2H), 2.57-2.50 (m, 1H), 2.34 (dt, J=12.8, 6.6 Hz, 1H), 1.94 (t, J=9.1 Hz, 1H), 1.74-1.67 (m, 2H), 1.52-1.39 (m, 1H), 1.13 (s, 2H), 1.11-1.07 (m, 3H), 1.04 (s, 1H), 0.98 (d, J=6.2 Hz, 1H).

Example 70: 3-(5-(((R)-1-((1-ethylindolin-7-yl)methyl)piperidin-2-yl)methoxy)-1-oxoisoindolin-2-yl)piperidine-2,6-dione (I-112)

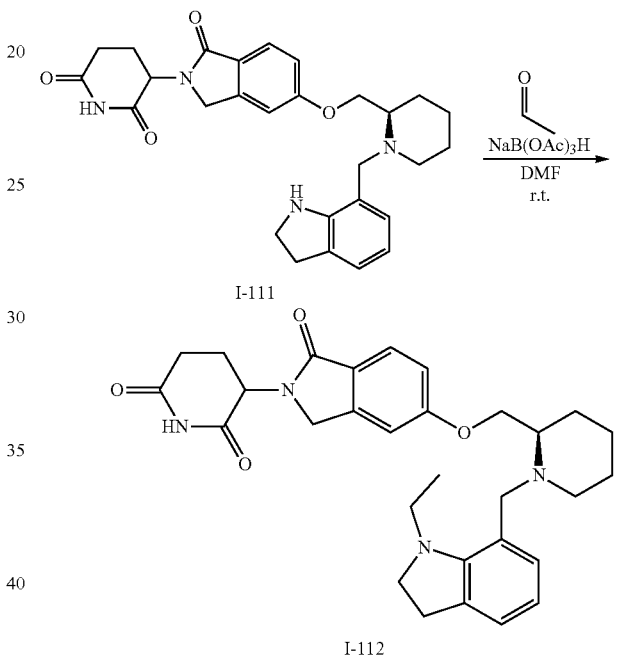

Compound I-112 was prepared according to General Method III starting from 3-(5-(((R)-1-(indolin-7-ylmethyl)piperidin-2-yl)methoxy)-1-oxoisoindolin-2-yl)piperidine-2,6-dione I-111 (32.7 mg, 67 µmol) and acetaldehyde (0.01 mL, 0.177 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-((1-ethylindolin-7-yl)methyl)piperidin-2-yl)methoxy)-1-oxoisoindolin-2-yl)piperidine-2,6-dione I-112 (25.5 mg, 0.047 mmol, 70.7% yield) as a white solid. LCMS [M−H]⁻: 515.4. ¹H NMR (400 MHz, DMSO-d6) δ 10.89 (s, 1H), 7.54 (d, J=8.4 Hz, 1H), 7.09 (d, J=2.4 Hz, 1H), 6.97 (dd, J=8.3, 2.3 Hz, 1H), 6.93-6.79 (m, 2H), 6.47 (t, J=7.3 Hz, 1H), 5.00 (dd, J=13.3, 5.1 Hz, 1H), 4.31 (d, J=17.6 Hz, 1H), 4.27-4.07 (m, 3H), 3.91 (d, J=13.2 Hz, 1H), 3.47-3.36 (m, 1H), 3.29 (d, J=10.8 Hz, 2H), 2.89-2.76 (m, 3H), 2.72-2.65 (m, 1H), 2.54 (tt, J=15.0, 3.0 Hz, 2H), 2.37-2.28 (m, 1H), 2.10-1.87 (m, 3H), 1.70-1.63 (m, 1H), 1.60-1.48 (m, 2H), 1.47-1.26 (m, 4H), 0.92 (t, J=7.0 Hz, 3H).

Example 74: ((1s,3s)-3-methoxycyclobutyl)methyl methanesulfonate (INT-117)

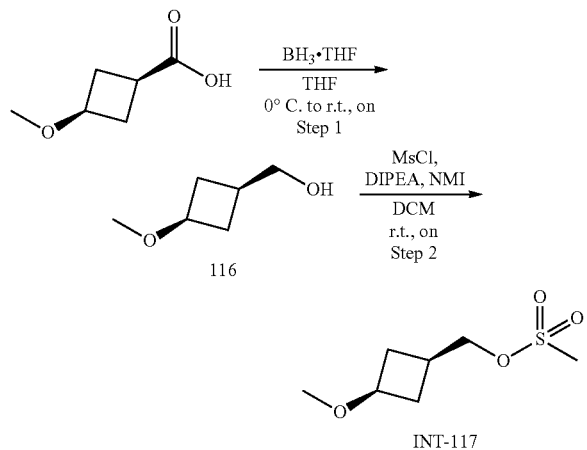

Step 1: ((1s,3s)-3-methoxycyclobutyl)methanol (116)

Cis-3-methoxycyclobutanecarboxylic acid (0.1 g, 0.768 mmol) was dissolved in THF (2.56 mL) and cooled to 0° C. 1M borane THF complex in THF (2.31 mL, 2.31 mmol) was added dropwise. The reaction stirred at r.t. overnight. The reaction was cooled to 0° C. and quenched with methanol (1.87 mL, 46.1 mmol) and stirred at r.t. for 2 hrs. The reaction was concentrated to dryness and redissolved in methanol (5 mL). The reaction stirred at r.t. overnight. The reaction was concentrated to afford ((1s,3s)-3-methoxycyclobutyl)methanol 116 (89 mg, 0.768 mmol, 100% yield) as a clear oil. Material was taken on crude to the next reaction without purification assuming quantitative yield $^1$H NMR (400 MHz, CDCl$_3$) δ 3.81 (p, J=7.2 Hz, 1H), 3.63 (d, J=6.2 Hz, 2H), 3.26 (s, 3H), 2.42-2.33 (m, 2H), 2.15-2.01 (m, 1H), 1.73-1.63 (m, 3H).

Step 2: ((1s,3s)-3-methoxycyclobutyl)methyl methanesulfonate (INT-117)

To a solution of ((1s,3s)-3-methoxycyclobutyl)methanol 116 (89 mg, 0.768 mmol) in DCM (1.5 mL) was added DIPEA (268 µL, 1.536 mmol), 1-methyl-1H-imidazole (122 µL, 1.536 mmol), then methanesulfonyl chloride (90 µL, 1.152 mmol) dropwise. The reaction stirred at r.t. for 18 hrs. The reaction was diluted with DCM (30 mL). The organic layer was washed with 1 M aqueous HCl three times and saturated aqueous sodium bicarbonate twice. The organic layer was passed through a phase separator and concentrated to afford ((1s,3s)-3-methoxycyclobutyl)methyl methanesulfonate INT-117 (121 mg, 0.623 mmol, 81% yield) as a brown oil. $^1$H NMR (400 MHz, CDCl$_3$) δ 4.22 (d, J=6.4 Hz, 2H), 3.82 (p, J=7.2 Hz, 1H), 3.25 (s, 3H), 3.03 (s, 3H), 2.50-2.39 (m, 2H), 2.34-2.21 (m, 1H), 1.81-1.68 (m, 2H).

Example 75: 3-(5-(((R)-1-(((1s,3S)-3-methoxycyclobutyl)methyl)piperidin-2-yl)methoxy)-1-oxoisoindolin-2-yl)piperidine-2,6-dione (I-118)

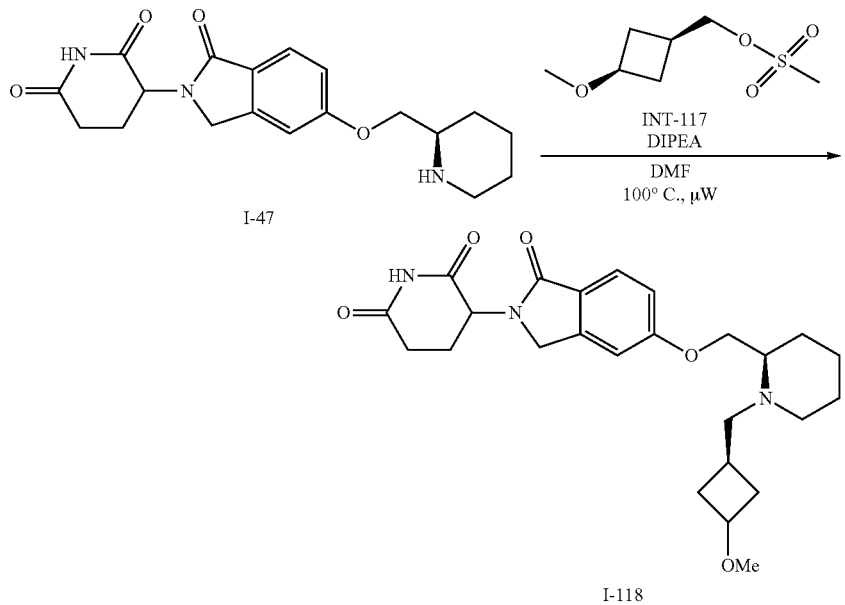

((1s,3s)-3-methoxycyclobutyl)methyl methanesulfonate INT-117 (121 mg, 0.623 mmol) was added to a 2 mL microwave vial and dissolved in DMF (1.92 mL). 3-(1-oxo-5-(((R)-piperidin-2-yl)methoxy)isoindolin-2-yl)piperidine-2,6-dione I-47 (137 mg, 0.383 mmol) was added followed by the addition of DIPEA (0.15 mL, 0.843 mmol). The reaction was evacuated and backfilled with nitrogen three times. The reaction stirred at 100° C. for 12 hrs under microwave radiation. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford slightly impure product. The material was further purified by basic mass triggered reverse phase HPLC (25-50% ACN in water with 5 mM NH₄OH as modifier). Test tubes contained 3 drops formic acid prior to sample collection. Pure fractions were combined and lyophilized to afford formate salt of 3-(5-(((R)-1-(((1s,3S)-3-methoxycyclobutyl)methyl)piperidin-2-yl)methoxy)-1-oxoisoindolin-2-yl)piperidine-2,6-dione I-118 (44.2 mg, 0.087 mmol, 22.76% yield) as a white solid. LCMS [M+H]⁺: 456.5. ¹H NMR (400 MHz, DMSO-d6) δ 10.89 (s, 1H), 8.16 (s, 1H), 7.55 (d, J=8.3 Hz, 1H), 7.12 (d, J=2.2 Hz, 1H), 6.98 (dd, J=8.4, 2.3 Hz, 1H), 5.00 (dd, J=13.3, 5.1 Hz, 1H), 4.32 (d, J=17.2 Hz, 1H), 4.20 (d, J=17.1 Hz, 1H), 4.13-4.02 (m, 1H), 3.96-3.88 (m, 1H), 3.57 (p, J=7.3 Hz, 2H), 2.99 (s, 3H), 2.89-2.78 (m, 1H), 2.76-2.68 (m, 1H), 2.67-2.48 (m, 3H), 2.40-2.35 (m, 1H), 2.31 (dd, J=13.2, 4.5 Hz, 1H), 2.27-2.16 (m, 2H), 2.16-2.07 (m, 1H), 1.97-1.84 (m, 2H), 1.70-1.50 (m, 2H), 1.49-1.15 (m, 5H).

Example 77: Tert-butyl 4-(2-formylphenyl)piperidine-1-carboxylate (INT-121)

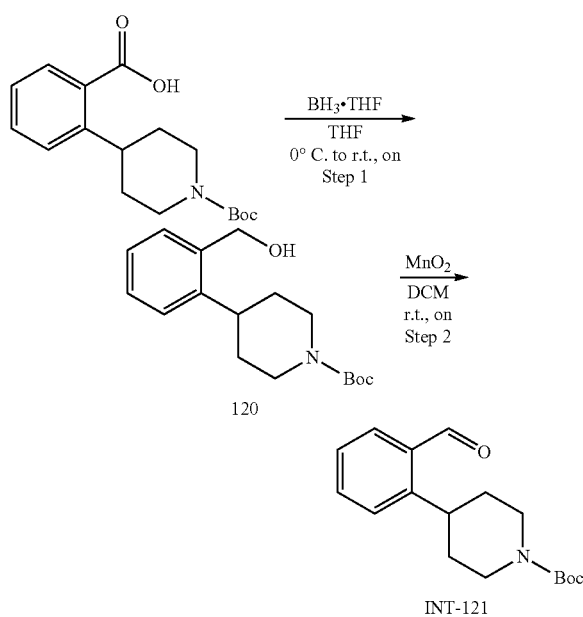

Step 1: Tert-butyl 4-(2-(hydroxymethyl)phenyl)piperidine-1-carboxylate, (2-(piperidin-4-yl)phenyl)methanol (120)

2-(1-(tert-butoxycarbonyl)piperidin-4-yl)benzoic acid (0.2 g, 0.655 mmol) was dissolved in THF (2.18 mL) and cooled to 0° C. 1M borane THF complex in THF (1.96 mL, 1.97 mmol) was added dropwise. The reaction stirred at r.t. overnight. The reaction was cooled to 0° C. and quenched with methanol (1.59 mL, 39.3 mmol) and stirred at r.t. for 2 hrs. The reaction was concentrated to dryness and redissolved in methanol (5 mL). The reaction stirred at r.t. overnight. The reaction was concentrated to afford tert-butyl 4-(2-(hydroxymethyl)phenyl)piperidine-1-carboxylate 120 (191 mg, 0.655 mmol, 100% yield) as a clear googey oil. Material was carried on crude to the next step assuming quantitative yield. LCMS [M+H−tert-butyl]⁺: 192.1. ¹H NMR (400 MHz, CD₃OD) δ 7.23 (d, J=7.5 Hz, 1H), 7.17-7.11 (m, 2H), 7.09-7.03 (m, 1H), 4.58 (s, 2H), 4.16-4.05 (m, 2H), 2.88-2.71 (m, 2H), 1.72-1.62 (m, 2H), 1.58-1.46 (m, 3H), 1.38 (s, 9H).

Step 2: Tert-butyl 4-(2-formylphenyl)piperidine-1-carboxylate (INT-121)

Tert-butyl 4-(2-(hydroxymethyl)phenyl)piperidine-1-carboxylate 120 (191 mg, 0.655 mmol) was dissolved in DCM (3.28 mL). MnO₂ (569 mg, 6.55 mmol) was added and the reaction mixture stirred for 3 hrs at r.t. Additional MnO₂ (569 mg, 6.55 mmol) was added and the reaction stirred at r.t. for 18 hrs. The reaction was diluted with DCM and passed through a layer of CELITE®. The filtrate was concentrated to afford tert-butyl 4-(2-formylphenyl)piperidine-1-carboxylate INT-121 (180 mg, 0.622 mmol, 95% yield) as a yellow oil. LCMS [M+H−tert-butyl]⁺: 190.2. ¹H NMR (400 MHz, CDCl₃) δ 10.19 (s, 1H), 7.74 (dd, J=7.9, 1.6 Hz, 1H), 7.49 (td, J=7.6, 1.5 Hz, 1H), 7.39-7.30 (m, 2H), 4.26-4.12 (m, 2H), 2.87-2.71 (m, 2H), 1.78-1.70 (m, 2H), 1.64-1.52 (m, 3H), 1.42 (s, 9H).

Example 78: Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperidine-1-carboxylate (I-122)

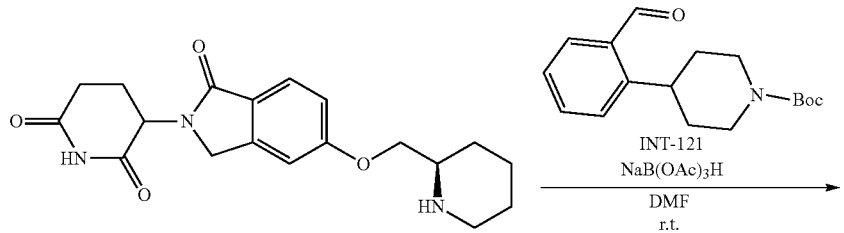

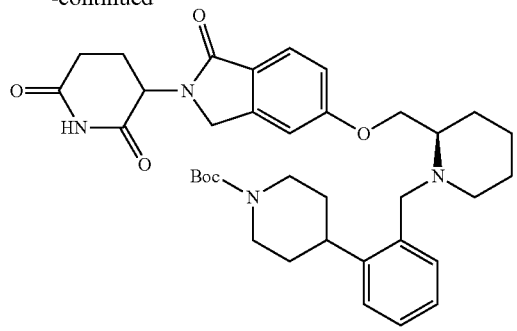

I-122

Compound I-122 was prepared according to General Method III starting from 3-(1-oxo-5-(((R)-piperidin-2-yl)methoxy)isoindolin-2-yl)piperidine-2,6-dione I-47 (150 mg, 0.420 mmol) and tert-butyl 4-(2-formylphenyl)piperidine-1-carboxylate INT-121 (182 mg, 0.630 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1 EtOAc:EtOH with 1% TEA in heptane) to afford tert-butyl 4-(2-(((2R)-2-(((2-(2,6-dioxopiperidin-3-yl)-1-oxoisoindolin-5-yl)oxy)methyl)piperidin-1-yl)methyl)phenyl)piperidine-1-carboxylate I-122 (208 mg, 0.330 mmol, 78.5% yield) as a white solid. LCMS [M+H]$^+$: 631.4. $^1$H NMR (400 MHz, DMSO-d6) δ 10.97 (s, 1H), 7.63 (d, J=8.4 Hz, 1H), 7.27-7.17 (m, 4H), 7.10 (td, J=8.6, 7.9, 2.1 Hz, 2H), 5.08 (dd, J=13.3, 5.1 Hz, 1H), 4.42-4.32 (m, 2H), 4.30-4.22 (m, 2H), 4.15-3.99 (m, 3H), 3.42-3.35 (m, 1H), 3.20-3.10 (m, 1H), 2.97-2.77 (m, 3H), 2.64-2.56 (m, 2H), 2.42-2.35 (m, 1H), 2.14-2.05 (m, 1H), 2.03-1.94 (m, 1H), 1.42 (s, 20H).

Example 79: 3-(5-(((R)-1-(2-(1-ethylpiperidin-4-yl)benzyl)piperidin-2-yl)methoxy)-1-oxoisoindolin-2-yl)piperidine-2,6-dione (I-124)

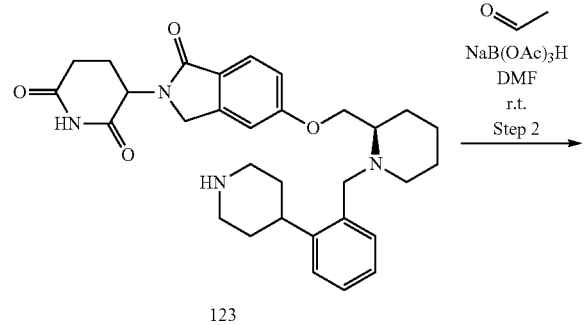

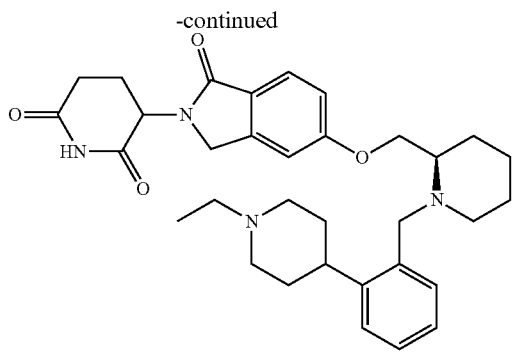

I-124

Step 1: 3-(1-oxo-5-(((R)-1-(2-(piperidin-4-yl)benzyl)piperidin-2-yl)methoxy)isoindolin-2-yl)piperidine-2,6-dione (123)

Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperidine-1-carboxylate I-122 (191 mg, 0.303 mmol) was suspended in dioxane (1.0 mL) and dissolved in trifluoroethanol (1.0 mL). 4M HCl in dioxane (0.45 mL, 1.817 mmol) was added and the reaction stirred at r.t. for 72 hrs. The reaction was concentrated and then diluted with 4:1 DCM:iPrOH. The reaction was quenched with 50% saturated aqueous sodium bicarbonate. The aqueous layer was extracted 4 times with 4:1 DCM:iPrOH. The organic layers were combined, passed through a phase separator and concentrated to afford 3-(1-oxo-5-(((R)-1-(2-(piperidin-4-yl)benzyl)piperidin-2-yl)methoxy)isoindolin-2-yl)piperidine-2,6-dione 123 (159 mg, 0.300 mmol, 99% yield) as a white sticky solid. LCMS [M+H]$^+$: 531.5.

Step 2: 3-(5-(((R)-1-(2-(1-ethylpiperidin-4-yl)benzyl)piperidin-2-yl)methoxy)-1-oxoisoindolin-2-yl)piperidine-2,6-dione (I-124)

Compound I-124 was prepared according to General Method III starting from 3-(1-oxo-5-(((R)-1-(2-(piperidin-4-yl)benzyl)piperidin-2-yl)methoxy)isoindolin-2-yl)piperidine-2,6-dione 123 (159 mg, 0.300 mmol) and acetaldehyde (0.03 mL, 0.531 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-(2-(1-ethylpiperidin-4-yl)benzyl)piperidin-2-yl)methoxy)-1-oxoisoindolin-2-yl)piperidine-2,6-dione I-124 (58 mg, 0.102 mmol, 34.0% yield) as a white solid. LCMS [M+H]−+: 559.6. $^1$H NMR (400 MHz, DMSO-d6) δ 10.89 (s, 1H), 7.56 (d, J=8.4 Hz, 1H), 7.21-7.11 (m, 4H), 7.03 (dd, J=8.1, 1.9 Hz, 2H), 5.01 (dd, J=13.4, 5.1 Hz, 1H), 4.35-4.26 (m, 2H), 4.23-4.12 (m, 2H), 4.03 (d, J=13.0 Hz, 1H), 3.32-3.26 (m, 1H), 2.95-2.77 (m, 4H), 2.77-2.69 (m, 1H), 2.57-2.47 (m, 2H), 2.35-2.22 (m, 3H), 2.05-1.96 (m, 1H), 1.95-1.86 (m, 2H), 1.80-1.72 (m, 1H), 1.70-1.45 (m, 7H), 1.41-1.24 (m, 3H), 0.94 (t, J=7.1 Hz, 3H).

Example 80: Tert-butyl 4-(4-formylphenyl)piperidine-1-carboxylate, 4-(4-formylphenyl)piperidine-1-carboxylic Acid, 4-(piperidin-4-yl)benzaldehyde (INT-126)

Step 1: Tert-butyl 4-(4-(hydroxymethyl)phenyl)piperidine-1-carboxylate, (4-(piperidin-4-yl)phenyl)methanol (125)

4-(1-(tert-butoxycarbonyl)piperidin-4-yl)benzoic acid (0.2 g, 0.655 mmol) was dissolved in THF (2.18 mL) and cooled to 0° C. 1M borane THF complex in THF (1.97 mL, 1.97 mmol) was added dropwise. The reaction stirred at r.t. overnight. The reaction was cooled to 0° C. and quenched with methanol (1.59 mL, 39.3 mmol) and stirred at r.t. for 2 hrs. The reaction was concentrated to dryness and redissolved in methanol (5 mL). The reaction stirred at r.t. overnight. The reaction was concentrated to afford tert-butyl 4-(4-(hydroxymethyl)phenyl)piperidine-1-carboxylate 125 (191 mg, 0.655 mmol, 100% yield) as a clear googey oil. Material was carried on crude to the next step assuming quantitative yield. LCMS [M+H−tert-butyl]$^+$: 192.3. $^1$H NMR (400 MHz, CD$_3$OD) δ 7.18 (d, J=8.0 Hz, 2H), 7.10 (d, J=8.1 Hz, 2H), 4.46 (s, 2H), 4.13-4.04 (m, 2H), 2.89-2.66 (m, 2H), 2.66-2.55 (m, 1H), 1.70 (d, J=12.4 Hz, 2H), 1.54-1.42 (m, 3H), 1.38 (s, 9H).

Step 2: Tert-butyl 4-(4-formylphenyl)piperidine-1-carboxylate, 4-(4-formylphenyl)piperidine-1-carboxylic acid, 4-(piperidin-4-yl)benzaldehyde (INT-126)

Tert-butyl 4-(4-(hydroxymethyl)phenyl)piperidine-1-carboxylate 125 (191 mg, 0.655 mmol) was dissolved in DCM (3.28 mL). MnO$_2$ (569 mg, 6.55 mmol) was added and the reaction mixture stirred for 3 hrs at r.t. Additional MnO$_2$ (569 mg, 6.55 mmol) was added and the reaction stirred at r.t. for 18 hrs. The reaction was diluted with DCM and passed through a layer of CELITE®. The filtrate was concentrated to afford tert-butyl 4-(4-formylphenyl)piperidine-1-carboxylate INT-126 (208 mg, 0.719 mmol, 110% yield) as a yellow oil. Material was carried on crude to the next step without purification and greater than 100% yield due to impurities being present. LCMS [M+H−tert-butyl]$^+$: 190.2. $^1$H NMR (400 MHz, CDCl$_3$) δ 9.91 (s, 1H), 7.82-7.70 (m, 2H), 7.34-7.27 (m, 2H), 4.33-4.12 (m, 2H), 2.82-2.63 (m, 2H), 1.83-1.73 (m, 2H), 1.66-1.54 (m, 3H), 1.42 (s, 9H).

Example 81: Tert-butyl 4-(4-(((2R)-2-(((2-(2,6-dioxopiperidin-3-yl)-1-oxoisoindolin-5-yl)oxy)methyl)piperidin-1-yl)methyl)phenyl)piperidine-1-carboxylate (I-127)

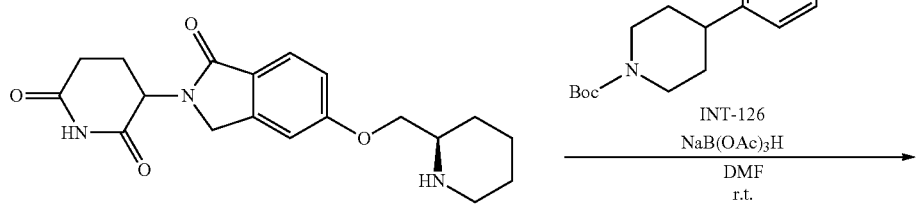

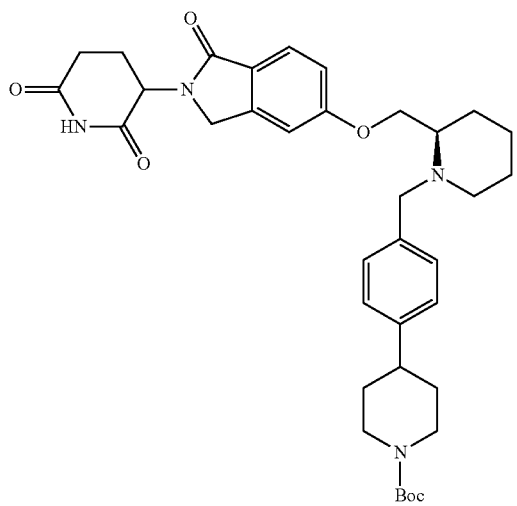

Compound I-127 was prepared according to General Method III starting from 3-(1-oxo-5-(((R)-piperidin-2-yl)methoxy)isoindolin-2-yl)piperidine-2,6-dione I-47 (150 mg, 0.420 mmol) and tert-butyl 4-(4-formylphenyl)piperidine-1-carboxylate INT-126 (182 mg, 0.630 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1 EtOAc:EtOH with 1% TEA in heptane) to afford tert-butyl 4-(4-(((2R)-2-(((2-(2,6-dioxopiperidin-3-yl)-1-oxoisoindolin-5-yl)oxy)methyl)piperidin-1-yl)methyl)phenyl)piperidine-1-carboxylate I-127 (241 mg, 0.381 mmol, 90.5% yield) as a white solid. LCMS [M+H]$^+$: 631.6. $^1$H NMR (400 MHz, DMSO-d6) δ 10.89 (s, 1H), 7.54 (d, J=8.4 Hz, 1H), 7.17 (d, J=7.9 Hz, 2H), 7.13-7.05 (m, 3H), 6.98 (dd, J=8.4, 2.3 Hz, 1H), 5.00 (dd, J=13.2, 5.0 Hz, 1H), 4.36-4.14 (m, 3H), 4.10-3.84 (m, 4H), 2.90-2.58 (m, 5H), 2.56-2.47 (m, 2H), 2.36-2.27 (m, 1H), 2.08-1.99 (m, 1H), 1.95-1.86 (m, 1H), 1.77-1.54 (m, 4H), 1.51-1.25 (m, 16H).

Example 82: 3-(1-oxo-5-(((R)-1-(4-(piperidin-4-yl)benzyl)piperidin-2-yl)methoxy)isoindolin-2-yl)piperidine-2,6-dione (INT-128)

Tert-butyl 4-(4-(((2R)-2-(((2-(2,6-dioxopiperidin-3-yl)-1-oxoisoindolin-5-yl)oxy)methyl)piperidin-1-yl)methyl)phenyl)piperidine-1-carboxylate I-127 (223 mg, 0.354 mmol) was suspended in dioxane (1.18 mL) and dissolved in trifluoroethanol (1.18 mL). 4M HCl in dioxane (0.53 mL, 2.121 mmol) was added and the reaction stirred at r.t. for 72 hrs. The reaction was concentrated and diluted with 4:1 DCM:iPrOH. The reaction was quenched with 50% saturated aqueous sodium bicarbonate. The aqueous layer was extracted 4 times with 4:1 DCM:iPrOH. The organic layers were combined, passed through a phase separator and concentrated to afford 3-(1-oxo-5-(((R)-1-(4-(piperidin-4-yl)benzyl)piperidin-2-yl)methoxy)isoindolin-2-yl)piperidine-2,6-dione INT-128 (250 mg, 0.471 mmol, 133% yield) as a clear oil. Material was taken on to the next step without purification and greater than quantitative yield due to impurities. LCMS [M+H]$^+$: 531.5.

Example 83: 3-(5-(((R)-1-(4-(1-ethylpiperidin-4-yl)benzyl)piperidin-2-yl)methoxy)-1-oxoisoindolin-2-yl)piperidine-2,6-dione (I-129)

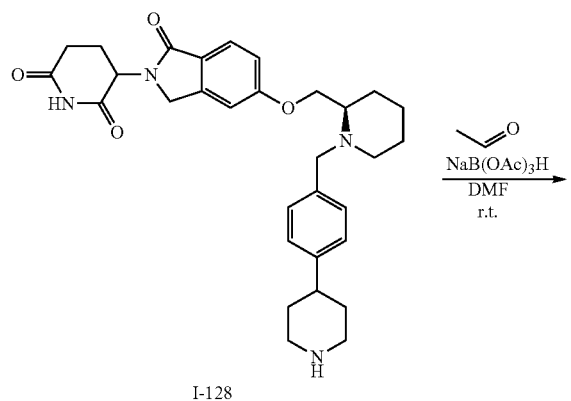

I-128

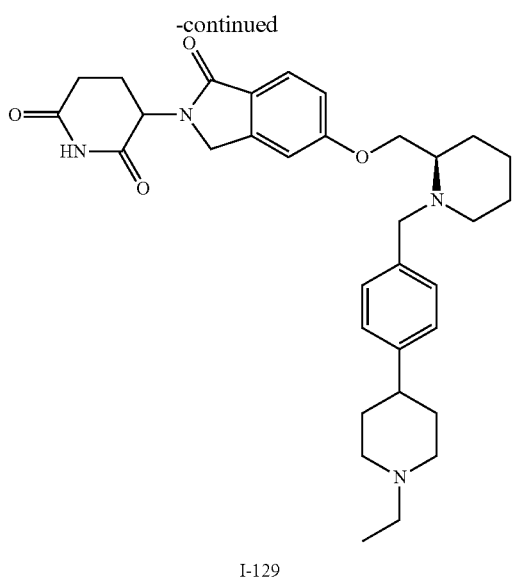

I-129

Compound I-129 was prepared according to General Method III starting from 3-(1-oxo-5-(((R)-1-(4-(piperidin-4-yl)benzyl)piperidin-2-yl)methoxy)isoindolin-2-yl)piperidine-2,6-dione INT-128 (250 mg, 0.471 mmol) and acetaldehyde (0.04 mL, 0.707 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-(4-(1-ethylpiperidin-4-yl)benzyl)piperidin-2-yl)methoxy)-1-oxoisoindolin-2-yl)piperidine-2,6-dione I-129 (77.7 mg, 0.135 mmol, 28.6% yield) as a white solid. LCMS [M+H]$^{-+}$: 559.5. $^1$H NMR (400 MHz, DMSO-d6) δ 10.89 (s, 1H), 7.53 (d, J=8.4 Hz, 1H), 7.16 (d, J=7.9 Hz, 2H), 7.13-7.06 (m, 3H), 6.98 (dd, J=8.4, 2.2 Hz, 1H), 5.00 (dd, J=13.3, 5.1 Hz, 1H), 4.36-4.13 (m, 3H), 4.05 (dd, J=10.3, 5.3 Hz, 1H), 3.88 (d, J=13.6 Hz, 1H), 3.30-3.26 (m, 1H), 2.95-2.78 (m, 3H), 2.71-2.58 (m, 2H), 2.56-2.47 (m, 1H), 2.40-2.24 (m, 4H), 2.08-1.99 (m, 1H), 1.97-1.83 (m, 3H), 1.75-1.69 (m, 1H), 1.68-1.24 (m, 9H), 0.95 (t, J=7.1 Hz, 3H).

Example 84: 2,4-dimethoxybenzaldehyde (INT-130)

(2,4-dimethoxyphenyl)methanol (0.1 g, 0.595 mmol) was dissolved in DCM (2.97 mL). MnO$_2$ (1.03 g, 11.89 mmol) was added and the reaction mixture stirred at r.t. for 24 hrs. the reaction was diluted with DCM and passed through a layer of CELITE®. The filtrate was concentrated to afford 2,4-dimethoxybenzaldehyde INT-130 (110 mg, 0.662 mmol, 111% yield) as a yellow solid. Material was taken on to the next step without purification and greater than quantitative yield due to slight impurity. LCMS [M+H]$^+$: 167.1. $^1$H NMR (400 MHz, Chloroform-d) δ 10.32 (s, 1H), 7.84 (d, J=8.7 Hz, 1H), 6.57 (dd, J=8.7, 2.2 Hz, 1H), 6.47 (d, J=2.3 Hz, 1H), 3.93 (s, 3H), 3.90 (s, 3H).

Example 85: 3-(5-(((R)-1-(2,4-dimethoxybenzyl)piperidin-2-yl)methoxy)-1-oxoisoindolin-2-yl)piperidine-2,6-dione (I-131)

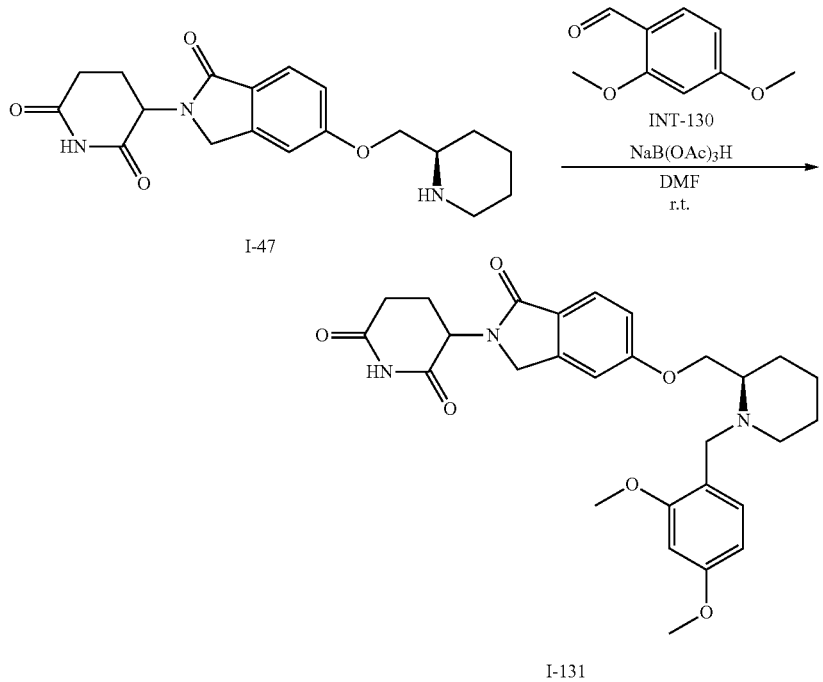

Compound I-131 was prepared according to General Method III starting from 3-(1-oxo-5-(((R)-piperidin-2-yl)methoxy)isoindolin-2-yl)piperidine-2,6-dione I-47 (150 mg, 0.420 mmol) and 2,4-dimethoxybenzaldehyde INT-130 (105 mg, 0.630 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1 EtOAc:EtOH with 1% TEA in heptane) to afford 3-(5-(((R)-1-(2,4-dimethoxybenzyl)piperidin-2-yl)methoxy)-1-oxoisoindolin-2-yl)piperidine-2,6-dione I-131 (80.5 mg, 0.152 mmol, 36.3% yield) as a white solid. LCMS [M+H]$^+$: 508.3. $^1$H NMR (400 MHz, DMSO-d6) δ 10.97 (s, 1H), 7.62 (d, J=8.3 Hz, 1H), 7.26-7.15 (m, 2H), 7.06 (dd, J=8.4, 2.2 Hz, 1H), 6.53-6.41 (m, 2H), 5.08 (dd, J=13.3, 5.1 Hz, 1H), 4.43-4.22 (m, 3H), 4.09 (dd, J=10.1, 5.4 Hz, 1H), 3.85 (d, J=13.9 Hz, 1H), 3.73 (s, 3H), 3.72 (s, 3H), 3.39-3.33 (m, 1H), 2.97-2.85 (m, 1H), 2.78-2.68 (m, 2H), 2.67-2.55 (m, 1H), 2.39 (qd, J=13.0, 4.3 Hz, 1H), 2.18-2.08 (m, 1H), 2.03-1.95 (m, 1H), 1.83-1.75 (m, 1H), 1.71-1.61 (m, 1H), 1.56-1.31 (m, 4H).

Example 86: 2-methoxybenzaldehyde (INT-132)

(2-methoxyphenyl)methanol (96 µL, 0.724 mmol) was dissolved in DCM (3.62 mL). MnO$_2$ (1.26 g, 14.5 mmol) was added and the reaction mixture stirred at r.t. for 24 hrs. The reaction was diluted with DCM and passed through a layer of CELITE®. The filtrate was concentrated to afford 2-methoxybenzaldehyde INT-132 (105 mg, 0.771 mmol, 107% yield) as a yellow oil. Material was taken on to the next step without purification and above quantitative yield due to slight impurity. LCMS [M+H]$^+$: 137.0. $^1$H NMR (400 MHz, CDCl$_3$) δ 10.50 (s, 1H), 7.86 (dd, J=7.7, 1.9 Hz, 1H), 7.65-7.50 (m, 1H), 7.09-6.97 (m, 2H), 3.96 (s, 3H).

Example 87: 3-(5-(((R)-1-(2-methoxybenzyl)piperidin-2-yl)methoxy)-1-oxoisoindolin-2-yl)piperidine-2,6-dione (I-133)

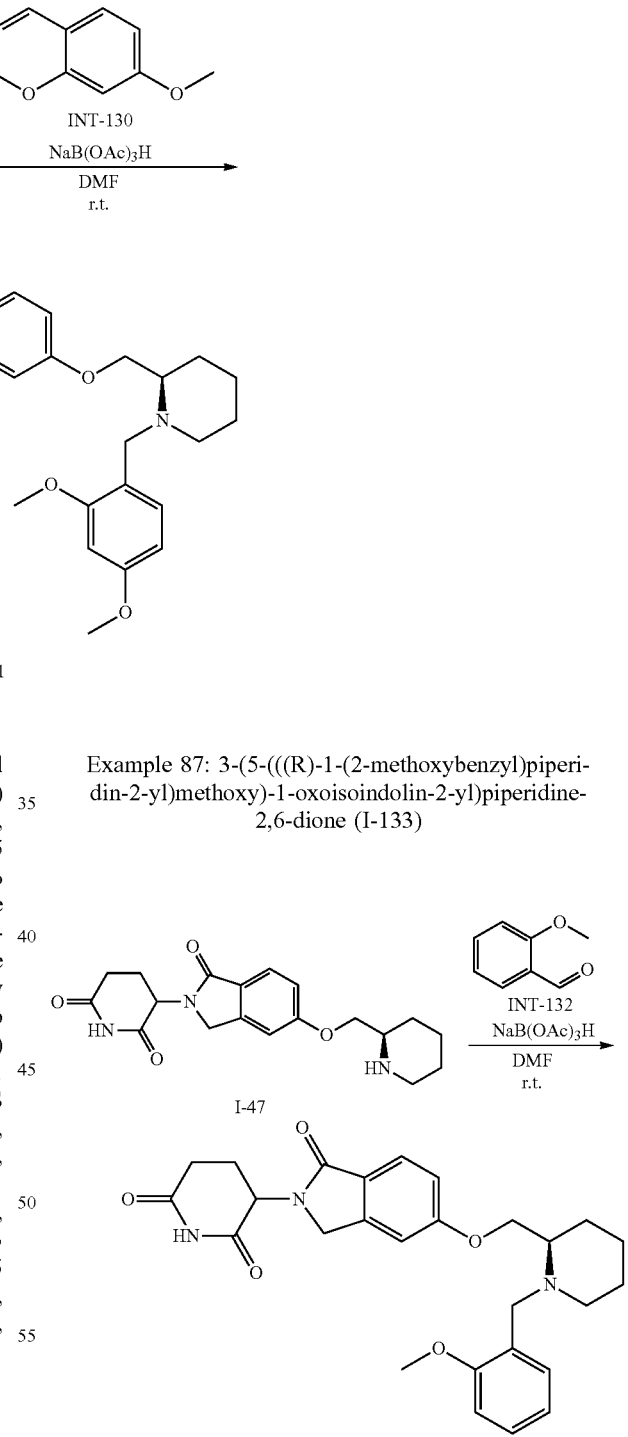

Compound I-133 was prepared according to General Method III starting from 3-(1-oxo-5-(((R)-piperidin-2-yl)methoxy)isoindolin-2-yl)piperidine-2,6-dione I-47 (150 mg, 0.420 mmol) and 2-methoxybenzaldehyde INT-132 (86 mg, 0.630 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1 EtOAc:EtOH with 1% TEA in heptane) to afford 3-(5-(((R)-1-(2-methoxybenzyl)piperidin-2-yl)methoxy)-1-oxoisoindolin-2-yl)piperidine-2,6-dione I-133 (75 mg, 0.151 mmol, 35.9% yield) as a white solid. LCMS [M+H]$^+$: 478.4. $^1$H NMR (400 MHz, DMSO-d6) δ 10.97 (s, 1H), 7.62 (d, J=8.4 Hz, 1H), 7.38 (dd, J=7.3, 1.8 Hz, 1H), 7.23-7.16 (m, 2H), 7.06 (dd, J=8.3, 2.3 Hz, 1H), 6.98-6.87 (m, 2H), 5.08 (dd, J=13.3, 5.1 Hz, 1H), 4.42-4.24 (m, 3H), 4.10 (dd, J=10.2, 5.4 Hz, 1H), 3.93 (d, J=14.6 Hz, 1H), 3.74 (s, 3H), 3.44 (d, J=14.5 Hz, 1H), 2.97-2.87 (m, 1H), 2.81-2.71 (m, 2H), 2.64-2.56 (m, 1H), 2.39 (qd, J=13.1, 4.3 Hz, 1H), 2.21-2.14 (m, 1H), 2.04-1.95 (m, 1H), 1.85-1.78 (m, 1H), 1.73-1.63 (m, 1H), 1.57-1.33 (m, 4H).

Example 88: 2,3-dihydrobenzo[b][1,4]dioxine-5-carbaldehyde (INT-134)

(2,3-dihydrobenzo[b][1,4]dioxin-5-yl)methanol (0.1 g, 0.602 mmol) was dissolved in DCM (3.01 mL). MnO$_2$ (1.05 g, 12.0 mmol) was added and the reaction mixture stirred for 3 hrs at r.t. Additional MnO$_2$ (1.05 g, 12.0 mmol) was added and the reaction stirred at r.t. for 18 hrs. the reaction was diluted with DCM and passed through a layer of CELITE®. The filtrate was concentrated to afford 2,3-dihydrobenzo[b][1,4]dioxine-5-carbaldehyde INT-134 (75 mg, 0.457 mmol, 76% yield) as a white solid. Material was taken on to the next step without purification. LCMS [M+H]$^+$: 165.2. $^1$H NMR (400 MHz, CDCl$_3$) δ 10.39 (s, 1H), 7.42 (dd, J=7.8, 1.6 Hz, 1H), 7.12 (dd, J=8.0, 1.6 Hz, 1H), 6.93 (t, J=7.9 Hz, 1H), 4.45-4.38 (m, 2H), 4.38-4.30 (m, 2H).

Example 89: 3-(5-(((R)-1-((2,3-dihydrobenzo[b][1,4]dioxin-5-yl)methyl)piperidin-2-yl)methoxy)-1-oxoisoindolin-2-yl)piperidine-2,6-dione (I-135)

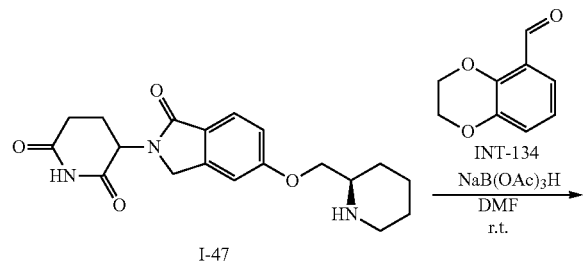

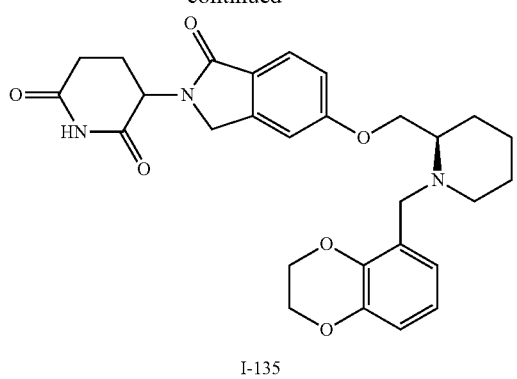

I-135

Compound I-135 was prepared according to General Method III starting from 3-(1-oxo-5-(((R)-piperidin-2-yl)methoxy)isoindolin-2-yl)piperidine-2,6-dione I-47 (110 mg, 0.308 mmol) and 2,3-dihydrobenzo[b][1,4]dioxine-5-carbaldehyde INT-134 (76 mg, 0.462 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1:0.01 EtOAc:EtOH:TEA in heptane) to afford 3-(5-(((R)-1-((2,3-dihydrobenzo[b][1,4]dioxin-5-yl)methyl)piperidin-2-yl)methoxy)-1-oxoisoindolin-2-yl)piperidine-2,6-dione I-135 (84.7 mg, 0.164 mmol, 53.3% yield) as a white solid. LCMS [M+H]$^+$: 506.5. $^1$H NMR (400 MHz, DMSO-d6) δ 10.97 (s, 1H), 7.62 (d, J=8.4 Hz, 1H), 7.18 (d, J=2.4 Hz, 1H), 7.06 (dd, J=8.4, 2.3 Hz, 1H), 6.94 (dd, J=7.4, 1.8 Hz, 1H), 6.77 (t, J=7.8 Hz, 1H), 6.73-6.67 (m, 1H), 5.08 (dd, J=13.3, 5.0 Hz, 1H), 4.45-4.24 (m, 3H), 4.19 (d, J=2.7 Hz, 4H), 4.10 (dd, J=10.2, 5.4 Hz, 1H), 3.90 (d, J=14.4 Hz, 1H), 3.43 (d, J=14.6 Hz, 1H), 2.97-2.86 (m, 1H), 2.81-2.74 (m, 2H), 2.64-2.56 (m, 1H), 2.39 (qd, J=13.1, 4.3 Hz, 1H), 2.21-2.14 (m, 1H), 2.03-1.95 (m, 1H), 1.85-1.76 (m, 1H), 1.71-1.63 (m, 1H), 1.56-1.33 (m, 4H).

Example 90: Benzo[d][1,3]dioxole-5-carbaldehyde (INT-136)

Piperonyl alcohol (0.1 g, 0.657 mmol) was dissolved in DCM (3.29 mL). MnO$_2$ (1.14 g, 13.2 mmol) was added and the reaction mixture stirred for 3 hrs at r.t. Additional MnO$_2$ (1.14 g, 13.2 mmol) was added and the reaction stirred at r.t. for 18 hrs. The reaction was diluted with DCM and passed through a layer of CELITE®. The filtrate was concentrated to afford benzo[d][1,3]dioxole-5-carbaldehyde INT-136 (87 mg, 0.579 mmol, 88% yield) as a clear oil. Material was taken on to the next step without purification. LCMS [M+H]$^+$: 151.1. $^1$H NMR (400 MHz, CDCl$_3$) δ 9.84 (s, 1H), 7.44 (dd, J=7.9, 1.6 Hz, 1H), 7.37 (d, J=1.6 Hz, 1H), 6.96 (d, J=7.9 Hz, 1H), 6.10 (s, 2H).

Example 91: 3-(5-(((R)-1-(benzo[d][1,3]dioxol-5-ylmethyl)piperidin-2-yl)methoxy)-1-oxoisoindolin-2-yl)piperidine-2,6-dione (I-137)

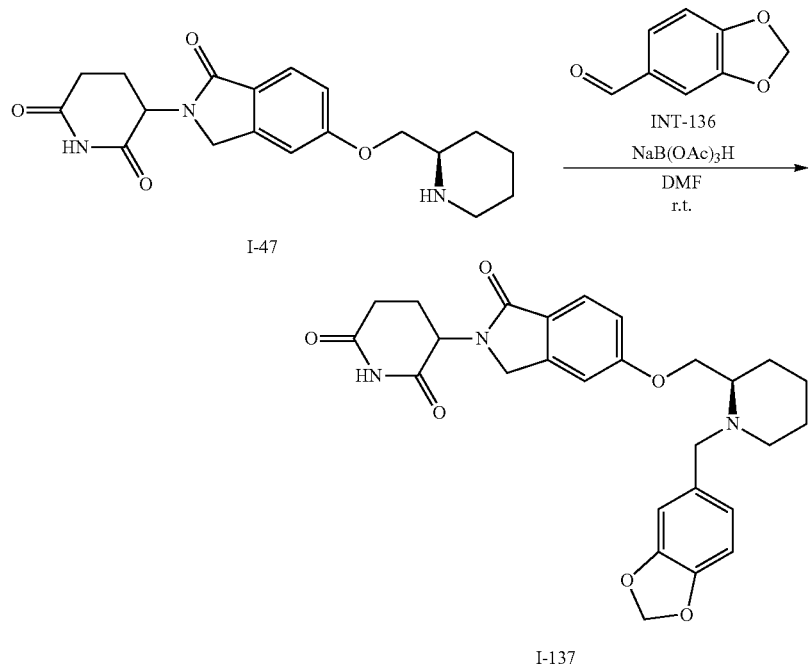

Compound I-137 was prepared according to General Method III starting from 3-(1-oxo-5-(((R)-piperidin-2-yl)methoxy)isoindolin-2-yl)piperidine-2,6-dione I-47 (130 mg, 0.364 mmol) and benzo[d][1,3]dioxole-5-carbaldehyde INT-136 (82 mg, 0.546 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1 EtOAc:EtOH with 1% TEA in heptane) to afford 3-(5-(((R)-1-(benzo[d][1,3]dioxol-5-ylmethyl)piperidin-2-yl)methoxy)-1-oxoisoindolin-2-yl)piperidine-2,6-dione I-137 (68 mg, 0.137 mmol, 37.7% yield) as a white solid. LCMS [M+H]$^+$: 492.2. $^1$H NMR (400 MHz, DMSO-d6) δ 10.89 (s, 1H), 7.54 (d, J=8.4 Hz, 1H), 7.16-7.04 (m, 1H), 6.99 (dd, J=8.4, 2.2 Hz, 1H), 6.81 (d, J=1.5 Hz, 1H), 6.76-6.66 (m, 2H), 5.89 (s, 2H), 5.00 (dd, J=13.3, 5.1 Hz, 1H), 4.37-4.11 (m, 3H), 4.05 (dd, J=11.2, 5.2 Hz, 1H), 3.82 (d, J=13.6 Hz, 1H), 3.24-3.21 (m, 1H), 2.89-2.76 (m, 1H), 2.71-2.58 (m, 2H), 2.56-2.47 (m, 1H), 2.37-2.24 (m, 1H), 2.07-1.99 (m, 1H), 1.95-1.86 (m, 1H), 1.74-1.66 (m, 1H), 1.63-1.55 (m, 1H), 1.49-1.22 (m, 4H).

Example 92: (1r,3r)-3-((tert-butyldiphenylsilyl)oxy)cyclobutane-1-carbaldehyde (INT-139)

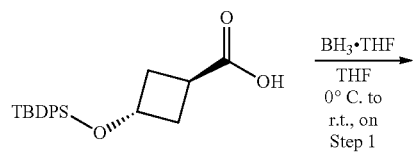

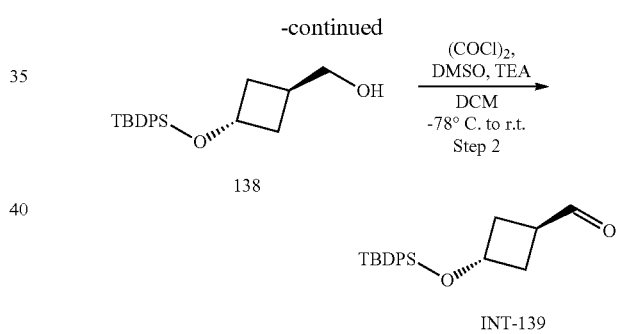

Step 1: ((1r,3r)-3-((tert-butyldiphenylsilyl)oxy)cyclobutyl)methanol (138)

(1r,3r)-3-((tert-butyldiphenylsilyl)oxy)cyclobutane-1-carboxylic acid (1.77 g, 4.99 mmol) was dissolved in THF (16.6 mL) and cooled to 0° C. 1M borane THF complex in THF (15 mL, 15 mmol) was added dropwise. The reaction stirred at r.t. overnight. The reaction was cooled to 0° C. and quenched with methanol (12.1 mL, 299 mmol) and stirred at r.t. for 2 hrs. The reaction was concentrated to dryness and redissolved in methanol (5 mL). The reaction was left to stir at r.t. overnight. The reaction was concentrated to afford slightly impure product. Material was purified by silica gel chromatography (0-100% EtOAc in heptane) to afford ((1r,3r)-3-((tert-butyldiphenylsilyl)oxy)cyclobutyl)methanol 138 (1.12 g, 3.29 mmol, 65.9% yield) as a clear oil. LCMS [M+H]$^+$: 341.4. $^1$H NMR (400 MHz, CDCl$_3$) δ 7.76-7.66 (m, 4H), 7.50-7.37 (m, 6H), 4.41 (p, J=6.9 Hz, 1H), 3.50 (d, J=7.1 Hz, 2H), 2.42-2.19 (m, 3H), 2.11-1.98 (m, 2H), 1.08 (s, 9H).

Step 2: (1r,3r)-3-((tert-butyldiphenylsilyl)oxy)cyclobutane-1-carbaldehyde (INT-139)

In 40 mL vial, DCM (0.73 mL) was added followed by oxalyl chloride (0.02 mL, 0.228 mmol) then cooled to −78° C. DMSO (0.03 mL, 0.423 mmol) in DCM (0.73 mL) was added dropwise and the reaction mixture continue to stir at −78° C. for 30 mins. ((1r,3r)-3-((tert-butyldiphenylsilyl)oxy)cyclobutyl)methanol 138 (50 mg, 0.147 mmol) in DCM (1.47 mL) was added dropwise and the reaction mixture continued to stir at −78° C. for 1 hr. Triethylamine (102 μL, 0.734 mmol) was added and the reaction was placed at r.t. for 1 hr. The reaction was quenched with saturated aqueous ammonium chloride and extracted with DCM three times. The organic layers were combined, passed through a phase separator, and concentrated in-vacuo to afford (1r,3r)-3-((tert-butyldiphenylsilyl)oxy)cyclobutane-1-carbaldehyde INT-139 (66 mg, 0.195 mmol, 133% yield) as a viscous cream solid. Material was carried on to the next step without purification. ¹H NMR (400 MHz, CDCl₃) δ 9.61 (d, J=1.9 Hz, 1H), 7.60-7.53 (m, 4H), 7.36-7.27 (m, 6H), 4.31-4.19 (m, 1H), 2.97-2.86 (m, 1H), 2.43-2.32 (m, 2H), 2.32-2.18 (m, 2H), 0.96 (s, 9H).

Example 93: 3-(5-(((R)-1-(((1r,3R)-3-hydroxycyclobutyl)methyl)piperidin-2-yl)methoxy)-1-oxoisoindolin-2-yl)piperidine-2,6-dione and 3-(5-(((R)-1-(((1s,3S)-3-hydroxycyclobutyl)methyl)piperidin-2-yl)methoxy)-1-oxoisoindolin-2-yl)piperidine-2,6-dione (I-141a and I-141b)

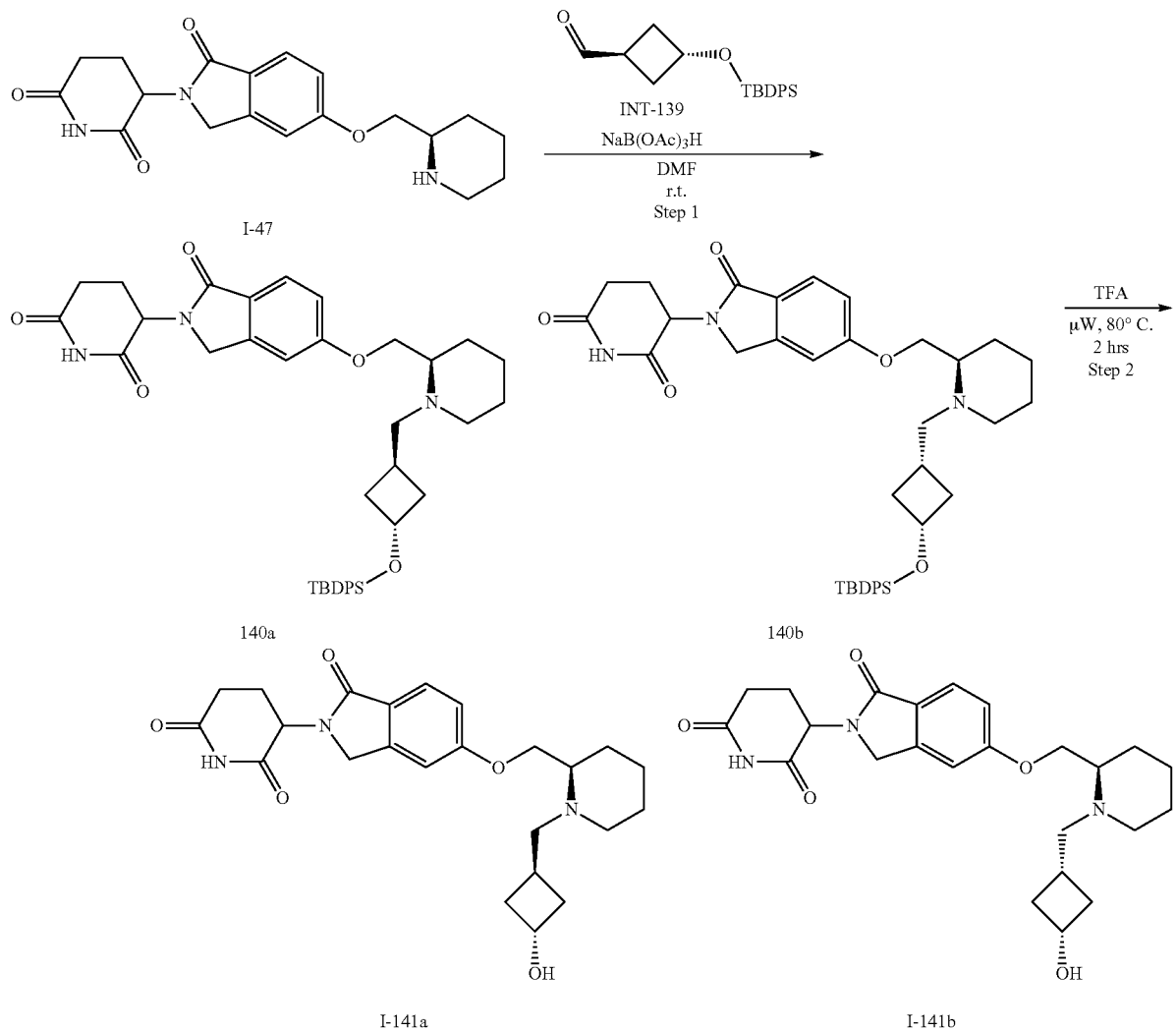

Step 1: 3-(5-(((R)-1-(((1r,3R)-3-((tert-butyldiphenylsilyl)oxy)cyclobutyl)methyl)piperidin-2-yl)methoxy)-1-oxoisoindolin-2-yl)piperidine-2,6-dione and 3-(5-(((R)-1-(((1s,3S)-3-((tert-butyldiphenylsilyl)oxy)cyclobutyl)methyl)piperidin-2-yl)methoxy)-1-oxoisoindolin-2-yl)piperidine-2,6-dione (140a and 140b)

Compound I-140a was prepared according to General Method III starting from 3-(1-oxo-5-(((R)-piperidin-2-yl)methoxy)isoindolin-2-yl)piperidine-2,6-dione I-47 (45 mg, 0.126 mmol) and (1r,3r)-3-((tert-butyldiphenylsilyl)oxy)cyclobutane-1-carbaldehyde INT-139 (50 mg, 0.148 mmol). The reaction was quenched with 50% saturated aqueous sodium bicarbonate and extracted three times with 4:1

DCM:iPrOH. The organic layers were combined, passed through phase separator and concentrated. The crude material was purified by silica gel chromatography (0-100% 3:1 EtOAc:EtOH with 1% TEA in heptane) to afford 3-(5-(((R)-1-(((1r,3R)-3-((tert-butyldiphenylsilyl)oxy)cyclobutyl)methyl)piperidin-2-yl)methoxy)-1-oxoisoindolin-2-yl)piperidine-2,6-dione 140a (45 mg, 0.066 mmol, 52.6% yield) and 3-(5-(((R)-1-(((1s,3S)-3-((tert-butyldiphenylsilyl)oxy)cyclobutyl)methyl)piperidin-2-yl)methoxy)-1-oxoisoindolin-2-yl)piperidine-2,6-dione 140b (27 mg, 0.040 mmol, 31.5% yield) both as clear oils. LCMS [M+H]+: 680.3.

Step 2: 3-(5-(((R)-1-(((1r,3R)-3-hydroxycyclobutyl)methyl)piperidin-2-yl)methoxy)-1-oxoisoindolin-2-yl)piperidine-2,6-dione and 3-(5-(((R)-1-(((1s,3S)-3-hydroxycyclobutyl)methyl)piperidin-2-yl)methoxy)-1-oxoisoindolin-2-yl)piperidine-2,6-dione (I-141a and I-141b)

3-(5-(((R)-1-(((1r,3R)-3-((tert-butyldiphenylsilyl)oxy)cyclobutyl)methyl)piperidin-2-yl)methoxy)-1-oxoisoindolin-2-yl)piperidine-2,6-dione 140a (45 mg, 0.066 mmol) was dissolved in TFA (1.32 mL) and transferred to a 2 mL microwave vial. The reaction stirred at 80° C. for 2 hrs under microwave radiation. The material was dissolved in 4:1 DCM:iPrOH and quenched with saturated aqueous sodium bicarbonate. The aqueous layer was extracted three times with 4:1 DCM:iPrOH. The organic layers were combined, passed through a phase separator and concentrated. The crude material was purified by basic mass triggered reverse phase HPLC (15-40% ACN in water with 5 mM NH4OH as modifier). Test tubes contained 3 drops formic acid prior to sample collection. Fractions containing desired product were combined and lyophilized to afford 6.7:1 trans:cis ratio of 3-(5-(((R)-1-(((1r,3R)-3-hydroxycyclobutyl)methyl)piperidin-2-yl)methoxy)-1-oxoisoindolin-2-yl)piperidine-2,6-dione and 3-(5-(((R)-1-(((1s,3S)-3-hydroxycyclobutyl)methyl)piperidin-2-yl)methoxy)-1-oxoisoindolin-2-yl)piperidine-2,6-dione I-141a and I-141b (17 mg, 0.039 mmol, 58.2% yield) as a white solid. LCMS [M+H]+: 442.4. 1H NMR (400 MHz, DMSO-d6) δ 10.90 (s, 1H), 7.56 (d, J=8.4 Hz, 1H), 7.12 (d, J=2.4 Hz, 1H), 6.99 (dd, J=8.5, 2.2 Hz, 1H), 5.01 (dd, J=13.3, 5.1 Hz, 1H), 4.77 (s, 1H), 4.33 (d, J=17.2 Hz, 1H), 4.20 (d, J=17.2 Hz, 1H), 4.14-3.92 (m, 3H), 2.89-2.79 (m, 1H), 2.77-2.65 (m, 2H), 2.58-2.48 (m, 2H), 2.38-2.16 (m, 3H), 2.11-2.03 (m, 1H), 1.95-1.85 (m, 2H), 1.84-1.73 (m, 3H), 1.68-1.52 (m, 2H), 1.46-1.23 (m, 4H).

Example 94: 3-(5-(((R)-1-(3-fluoro-4-methoxybenzyl)piperidin-2-yl)methoxy)-1-oxoisoindolin-2-yl)piperidine-2,6-dione (I-142)

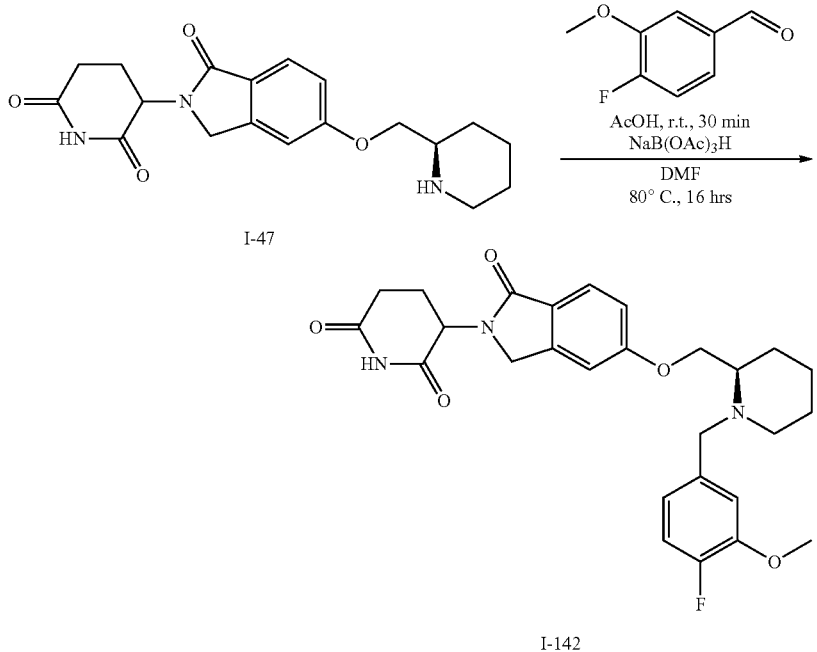

To a stirred solution of 3-(1-oxo-5-(((R)-piperidin-2-yl)methoxy)isoindolin-2-yl)piperidine-2,6-dione I-47 (100 mg, 0.27 mmol) in DMF (3 mL) was added 4-fluoro-3-methoxybenzaldehyde (84 mg, 0.55 mmol) and AcOH (0.01 mL). The reaction stirred at r.t. for 30 min. Sodium triacetoxyborohydride (116 mg, 0.55 mmol) was added and the reaction stirred at 80° C. for 16 hrs. The reaction was quenched with 50% saturated aqueous sodium hydrogen carbonate and extracted with 4:1 DCM:iPrOH. The organic layer was concentrated and the crude material was purified by silica gel chromatography (80% EtOAc in hexane) to afford 3-(5-(((R)-1-(3-fluoro-4-methoxybenzyl)piperidin-2-yl)methoxy)-1-oxoisoindolin-2-yl)piperidine-2,6-dione I-142 (15 mg, 0.03 mmol, 11.1% yield) as a light yellow sticky solid. LCMS [M+H]⁺: 496.15. ¹H NMR (300 MHz, DMSO-d6): δ 7.69 (d, J=8.7 Hz, 1H), 7.11-7.07 (m, 3H), 7.00-6.93 (m, 1H), 6.88-6.86 (m, 1H), 5.14-5.08 (m, 1H), 4.43-4.42 (m, 2H), 4.28-4.20 (m 2H), 4.02 (d, J=13.2 Hz, 1H), 3.81 (s, 3H), 3.39 (d, J=13.8 Hz, 1H), 2.90-2.74 (m, 4H), 2.55-2.45 (m 1H), 2.18-2.13 (m, 2H), 1.82 (m, 2H), 1.65-1.55 (m, 3H), 1.39 (m 1H).

The following compounds were made according to Example 94, starting from the final product of Example 24 (I-47).

| Cmpd # | Structure/NMR data | LCMS [M + H] | LCMS Rt |
|---|---|---|---|
| I-143 | ¹H NMR (300 MHz, CD₃OD): δ 7.67 (d, J = 8.4 Hz, 1H), 7.09-7.05 (m, 2H), 6.80-6.77 (m, 2H), 6.60 (m, 1H), 5.14-5.09 (m, 1H), 4.42-4.40 (m, 2H), 4.31-4.25 (m 2H), 4.20-4.15 (m, 1H), 3.70-3.60 (m, 1H), 2.99 (m, 1H), 2.83-2.78 (m, 4H), 2.50-2.30 (m, 2H), 2.15 (m 1H), 1.84-1.82 (m, 2H), 1.70-1.40 (m, 3H). | 482.20 | 0.4 |
| I-144 | ¹H NMR (400 MHz, CD₃OD): δ 7.70 (d, J = 8.4 Hz, 1H), 7.16-7.04 (m, 4H), 5.14-4.88 (m, 1H), 4.44-4.43 (m, 2H), 4.22-4.20 (m 1H), 4.15-4.13 (m, 1H), 4.01 (d, J = 14.4 Hz, 1H), 3.46 (d, J = 14.4 Hz, 1H), 2.91-2.80 (m, 4H), 2.50-2.45 (m, 1H), 2.24 (m, 1H), 2.18-2.17 (m 1H), 1.83-1.40 (m, 6H). | 502.2 | 0.45 |
| I-145 | ¹H NMR (300 MHz, CD₃OD): δ 8.30 (brs, 1H), 7.71 (d, J = 8.7 Hz, 1H), 7.15-7.10 (m, 2H), 5.13-5.07 (m, 1H), 4.44-4.43 (m, 2H), 4.28-4.23 (m, 3H), 3.86 (d, J = 14.4 Hz, 1H), 3.05-3.01 (m, 2H), 2.87-2.77 (m, 2H), 2.58 (s, 3H), 2.49-2.43 (m, 2H), 2.31-2.30 (m, 3H), 2.17-2.14 (m, 1H), 1.86-1.63 (m, 5H), 1.55-1.45 (m, 1H). | 483.2 | 0.39 |

| Cmpd # | Structure/NMR data | LCMS [M + H] | LCMS Rt |
|---|---|---|---|
| I-146 | 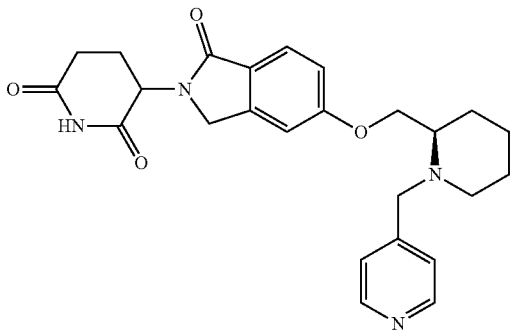 [SMILES: O=C1CCC(N2Cc3cc(OC[C@H]4CCCCN4Cc4ccncc4)ccc3C2=O)C(=O)N1]<br>¹H NMR (300 MHz, CD₃OD): δ 8.39 (d, J = 5.4 Hz, 2H), 7.68 (d, J = 7.8 Hz, 1H), 7.47-7.45 (m, 2H), 7.07-7.03 (m, 2H), 5.13-5.07 (m, 1H), 4.41-4.40 (m, 2H), 4.25-4.10 (m, 3H), 3.55 (d, J = 14.4 Hz, 1H), 2.90-2.78 (m, 4H), 2.48-2.43 (m, 1H), 2.27-2.11 (m, 2H), 1.84-1.46 (m, 6H). | 449.2 | 0.36 |
| I-147 | 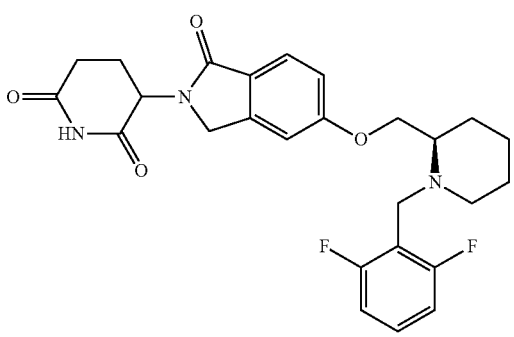 [SMILES: O=C1CCC(N2Cc3cc(OC[C@H]4CCCCN4Cc4c(F)cccc4F)ccc3C2=O)C(=O)N1]<br>¹H NMR (300 MHz, CD₃OD): δ 7.72 (d, J = 8.4 Hz, 1H), 7.32-7.30 (m, 1H), 7.16-7.10 (m, 2H), 6.97-6.92 (m, 2H), 5.15-5.08 (m, 1H), 4.45-4.35 (m, 4H), 4.25-4.16 (m, 2H), 3.53 (d, J = 12.3 Hz, 1H), 2.90-2.74 (m, 5H), 2.50-2.44 (m, 1H), 2.26-2.13 (m, 2H), 1.83-1.74 (m, 2H), 1.64-1.50 (m, 2H), ppm. | 484.2 | 0.41 |
| I-148 | 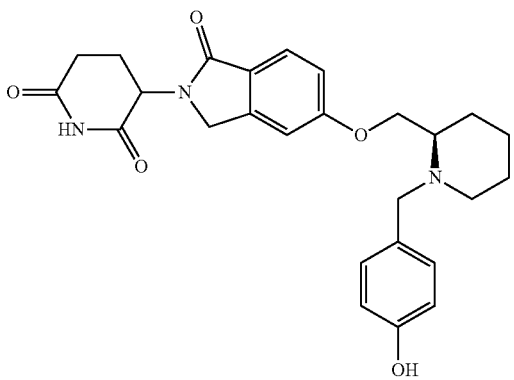 [SMILES: O=C1CCC(N2Cc3cc(OC[C@H]4CCCCN4Cc4ccc(O)cc4)ccc3C2=O)C(=O)N1]<br>¹H NMR (300 MHz, CD₃OD) δ 8.48 (s, 1H), 7.78 (d, J = 8.2 Hz, 1H), 7.31-7.19 (m, 4H), 6.83 (d, J = 8.1 Hz, 2H), 5.14 (dd, J = 13.2, 5.2 Hz, 1H), 4.67-4.54 (m, 1H), 4.52-4.35 (m, 4H), 4.03 (d, J = 13.2 Hz, 1H), 3.65-3.48 (m, 1H), 3.41-3.32 (m, 1H), 2.98-2.72 (m, 3H), 2.49 (qd, J = 13.1, 4.7 Hz, 1H), 2.22-2.11 (m, 1H), 2.05-1.76 (m, 5H), 1.70-1.57 (m, 1H). | 464.2 | 0.37 |

| Cmpd # | Structure/NMR data | LCMS [M + H] | LCMS Rt |
|---|---|---|---|
| I-149 | 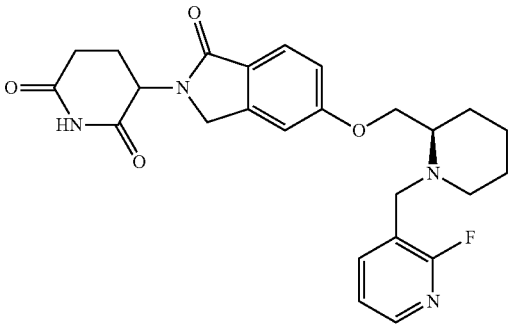 [SMILES: O=C1CCC(N2Cc3cc(OC[C@H]4CCCCN4Cc4cccnc4F)ccc3C2=O)C(=O)N1]　<br>¹H NMR (300 MHz, CD₃OD): δ 8.10-7.95 (m, 2H), 7.70 (d, J = 8.4 Hz, 1H), 7.25 (t, J = 6.3 Hz, 1H), 7.14-7.02 (m, 2H), 5.12 (dd, J = 13.2, 5.2 Hz, 1H), 4.51-4.35 (m, 2H), 4.32-4.08 (m, 3H), 3.55 (d, J = 14.7 Hz, 1H), 2.92-2.79 (m, 5H), 2.56-2.38 (m, 1H), 2.35-2.25 (m, 1H), 2.21-2.09 (m, 1H), 1.90-1.72 (m, 2H), 1.70-1.55 (m, 2H), 1.52-1.42 (m, 1H). | 467.20 | 0.36 |
| I-150 | 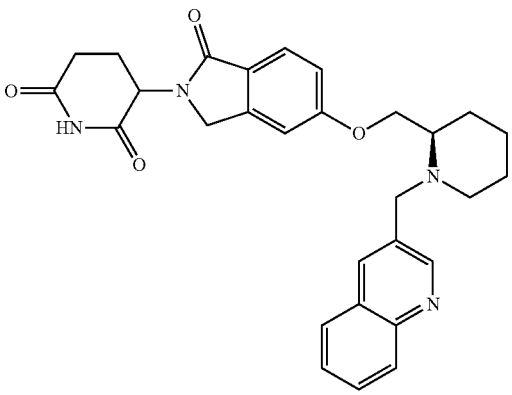 [SMILES: O=C1CCC(N2Cc3cc(OC[C@H]4CCCCN4Cc4cnc5ccccc5c4)ccc3C2=O)C(=O)N1]　<br>¹H NMR (300 MHz, CD₃OD): δ 8.87 (s, 1H), 8.22 (s, 1H), 7.91 (d, J = 6.6 Hz, 1H), 7.80 (d, J = 8.7 Hz, 1H), 7.67 (t, J = 7.2 Hz, 1H), 7.57-7.54 (m, 2H), 6.97-6.94 (m, 2H), 5.10-5.07 (m, 1H), 4.32-4.21 (m, 5H), 3.81 (d, J = 14.4 Hz, 1H), 2.98-278 (m, 4H), 2.46-2.43 (m, 2H), 2.20-2.10 (m, 1H), 1.83-1.80 (m, 3H), 1.64-1.60 (m, 2H), 1.50-1.40 (m, 1H), ppm. | 499.20 | 0.39 |
| I-151 | 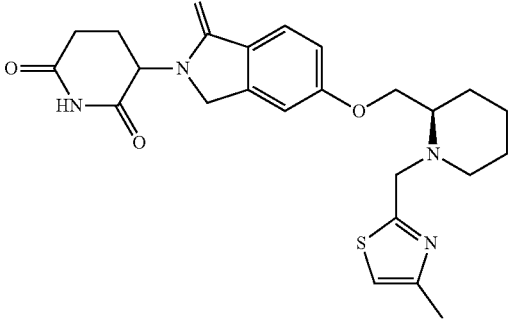　<br>¹H NMR (300 MHz, CD₃OD): δ 7.68 (d, J = 8.4 Hz, 1H), 7.09-7.03 (m, 2H), 6.97 (s, 1H), 5.13-5.07 (m, 1H), 4.41 (brs, 2H), 4.27-4.18 (m, 3H), 3.93 (d, J = 15.9 Hz, 1H), 3.34 (s, 1H), 2.93-2.78 (m, 4H), 2.47-2.42 (m, 2H), 2.32 (s, 3H), 1.80 (m, 2H), 1.64-1.60 (m, 3H), 1.50-1.40 (m, 1H). | 469.15 | 0.42 |

| Cmpd # | Structure/NMR data | LCMS [M + H] | LCMS Rt |
|---|---|---|---|
| I-152 | 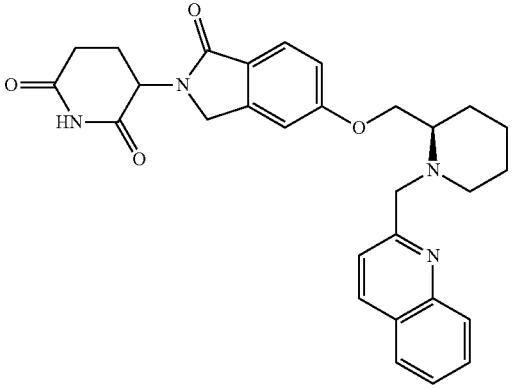 [SMILES: O=C1CCC(N2Cc3cc(OC[C@H]4CCCCN4Cc4ccc5ccccc5n4)ccc3C2=O)C(=O)N1]<br>¹H NMR (300 MHz, DMSO-d6): δ 8.15 (d, J = 8.4 Hz, 1H), 7.88 (d, J = 6.6 Hz, 1H), 7.74-7.68 (m, 3H), 7.50-7.46 (m, 2H), 6.87-6.79 (m, 2H), 5.10-5.08 (m, 1H), 4.23-4.16 (m, 5H), 4.05-3.95 (m 1H), 3.15-3.05 (m, 1H), 2.95-2.45 (m, 5H), 2.20-2.10 (m, 1H), 1.82 (m, 3H), 1.70 (m, 2H), 1.55-1.50 (m, 1H) ppm. | 499.2 | 0.42 |

Example 105: Tert-butyl 4-(2-ethyl-4-formylphenyl)piperidine-1-carboxylate (INT-154)

Tert-butyl 4-(2-ethyl-4-(hydroxymethyl)phenyl)piperidine-1-carboxylate 153 (147.6 mg, 0.462 mmol) and manganese dioxide (415.7 mg, 4.78 mmol) were suspended in DCM (2 mL). The reaction stirred at r.t. for 22 hrs. The reaction was filtered through CELITE® and washed with dichloromethane. The filtrate was concentrated and purified by silica gel chromatography (0-60% EtOAc in heptane) to afford tert-butyl 4-(2-ethyl-4-formylphenyl)piperidine-i-carboxylate INT-154 (157 mg, 0.485 mmol, 105% yield) as a clear liquid. LCMS [M+H–tert-butyl]⁺: 262.2. ¹H NMR (400 MHz, CD₂Cl₂) δ 9.94 (s, 1H), 7.72-7.64 (m, 2H), 7.37 (d, J=7.9 Hz, 1H), 4.25 (dp, J=13.5, 1.9 Hz, 2H), 2.98 (tt, J=11.6, 3.9 Hz, 1H), 2.90-2.72 (m, 4H), 1.80-1.55 (m, 4H), 1.47 (s, 9H), 1.32-1.25 (m, 3H).

Example 106: Tert-butyl 4-(4-(((2R)-2-(((2-(2,6-dioxopiperidin-3-yl)-1-oxoisoindolin-5-yl)oxy)methyl)piperidin-1-yl)methyl)-2-ethylphenyl)piperidine-1-carboxylate (I-155)

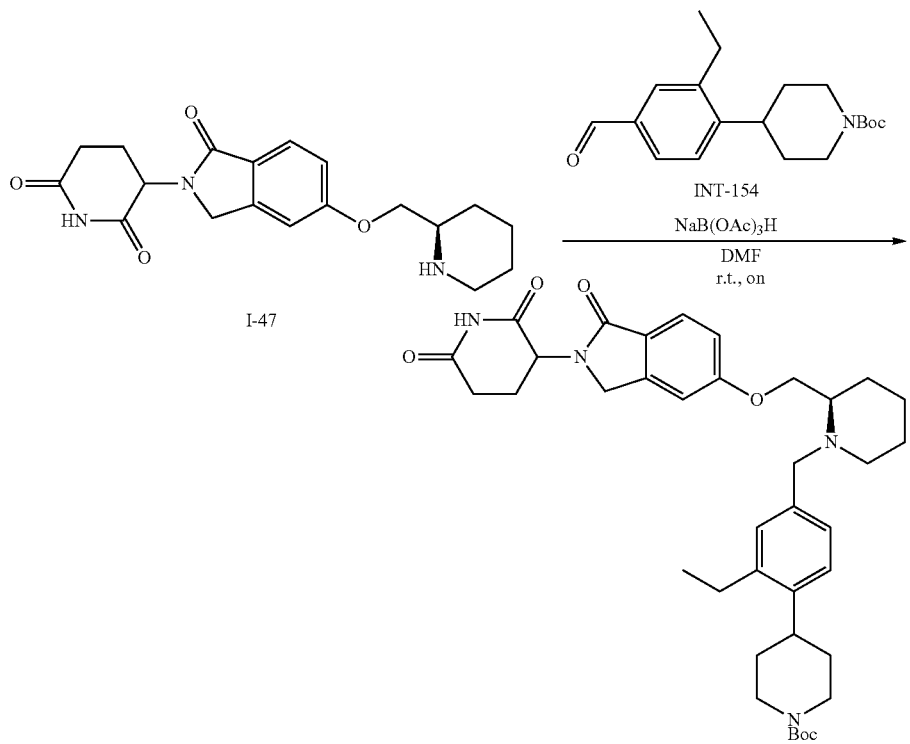

3-(1-oxo-5-(((R)-piperidin-2-yl)methoxy)isoindolin-2-yl)piperidine-2,6-dione I-47 (57.8 mg, 0.162 mmol) and tert-butyl 4-(2-ethyl-4-formylphenyl)piperidine-1-carboxylate INT-154 (72.3 mg, 0.228 mmol) were dissolved in DMF (1 mL). Sodium triacetoxyborohydride (78.6 mg, 0.371 mmol) was added and the reaction stirred at room temperature overnight. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-80% 3:1 EtOAc:EtOH with 1% TEA in DCM) to afford tert-butyl 4-(4-(((2R)-2-(((2-(2,6-dioxopiperidin-3-yl)-1-oxoisoindolin-5-yl)oxy)methyl)piperidin-1-yl)methyl)-2-ethylphenyl)piperidine-1-carboxylate I-155 (36.9 mg, 0.055 mmol, 34% yield) as a white solid. LCMS [M+H]$^+$: 659.6. $^1$H NMR (400 MHz, DMSO-d6) δ 10.95 (s, 1H), 7.60 (d, J=8.4 Hz, 1H), 7.17 (d, J=2.2 Hz, 1H), 7.14-7.00 (m, 4H), 5.07 (dd, J=13.3, 5.1 Hz, 1H), 4.43-4.18 (m, 3H), 4.16-3.98 (m, 3H), 3.92 (d, J=13.8 Hz, 1H), 2.98-2.65 (m, 8H), 2.65-2.55 (m, 3H), 2.44-2.33 (m, 1H), 2.11 (t, J=9.5 Hz, 1H), 2.03-1.93 (m, 1H), 1.86-1.72 (m, 1H), 1.71-1.29 (m, 17H), 1.16-1.07 (m, 3H).

Example 107: 3-(5-(((R)-1-(3-ethyl-4-(piperidin-4-yl)benzyl)piperidin-2-yl)methoxy)-1-oxoisoindolin-2-yl)piperidine-2,6-dione (I-156)

Tert-butyl 4-(4-(((2R)-2-(((2-(2,6-dioxopiperidin-3-yl)-1-oxoisoindolin-5-yl)oxy)methyl)piperidin-1-yl)methyl)-2-ethylphenyl)piperidine-1-carboxylate I-155 (30 mg, 0.046 mmol) was dissolved in 4M HCl in dioxane (1 mL, 4.00 mmol) and stirred at room temperature overnight. The reaction was concentrated, triturated with diethyl ether, filtered, and placed under high vacuum overnight to afford 3-(5-(((R)-1-(3-ethyl-4-(piperidin-4-yl)benzyl)piperidin-2-yl)methoxy)-1-oxoisoindolin-2-yl)piperidine-2,6-dione I-156 (25 mg, 0.038 mmol, 83% yield) as a white solid. LCMS [M+H]$^+$: 559.8. $^1$H NMR (400 MHz, DMSO-d6) δ 10.97 (s, 1H), 10.32-10.07 (m, 1H), 8.83-8.59 (m, 2H), 7.69 (d, J=8.4 Hz, 1H), 7.49-7.33 (m, 2H), 7.26 (s, 1H), 7.22-7.07 (m, 2H), 5.09 (dd, J=13.3, 5.1 Hz, 1H), 4.73-4.48 (m, 3H), 4.48-4.24 (m, 4H), 4.16 (dd, J=13.2, 7.0 Hz, 1H), 3.37-3.30 (m, 2H), 3.13-2.88 (m, 5H), 2.68-2.61 (m, 2H), 2.44-2.36 (m, 1H), 2.11-1.65 (m, 10H), 1.19-1.13 (m, 3H).

Example 108: 3-(5-(((R)-1-(3-ethyl-4-(1-ethylpiperidin-4-yl)benzyl)piperidin-2-yl)methoxy)-1-oxoisoindolin-2-yl)piperidine-2,6-dione (I-157)

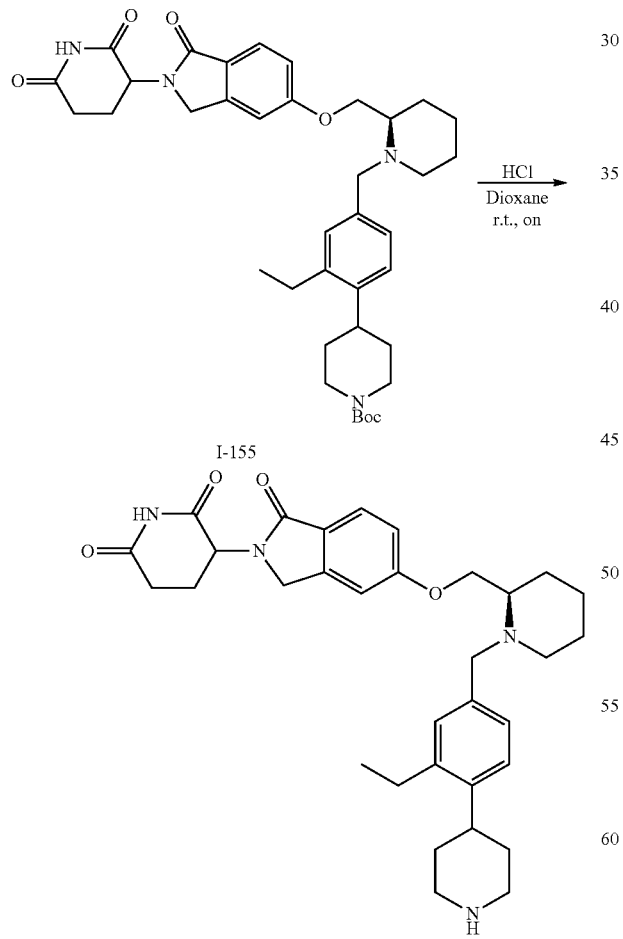

I-155

I-156

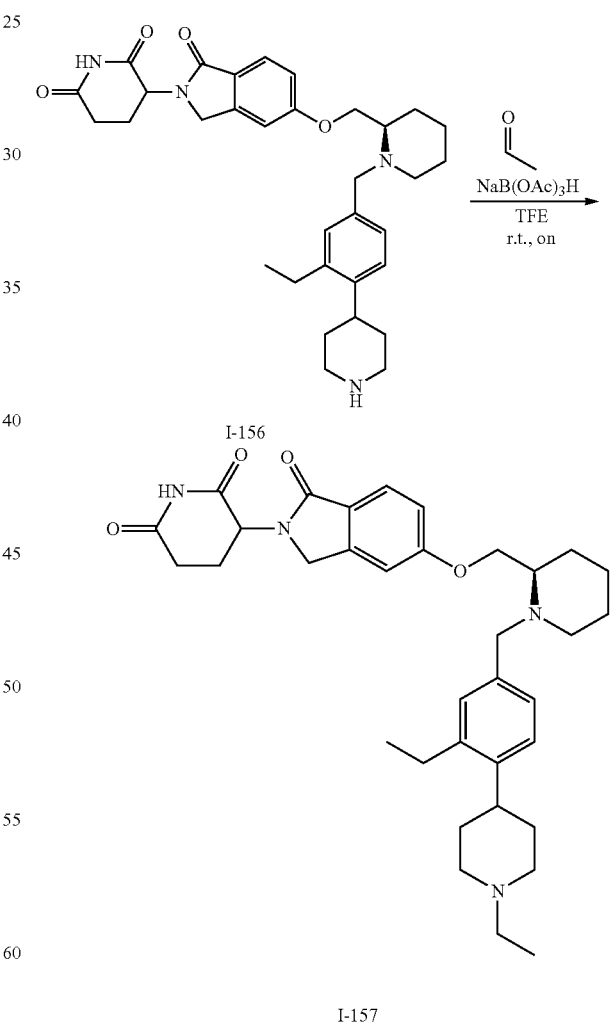

I-156

I-157

3-(5-(((R)-1-(3-ethyl-4-(piperidin-4-yl)benzyl)piperidin-2-yl)methoxy)-1-oxoisoindolin-2-yl)piperidine-2,6-dione I-156 (25 mg, 0.040 mmol) and acetaldehyde (3.11 μL, 0.055 mmol) were dissolved in 2,2,2-trifluoroethanol (0.5 mL) and stirred for 5 minutes. Sodium triacetoxyborohydride (16.78 mg, 0.079 mmol) was added and the reaction stirred at room temperature overnight. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-60% 3:1 EtOAc:EtOH with 1% TEA in DCM) to afford 3-(5-(((R)-1-(3-ethyl-4-(1-ethylpiperidin-4-yl)benzyl)piperidin-2-yl)methoxy)-1-oxoisoindolin-2-yl)piperidine-2,6-dione I-157 (11.8 mg, 0.020 mmol, 50% yield) as a white solid. LCMS [M+H]$^+$: 587.8. $^1$H NMR (400 MHz, DMSO-d6) δ 10.96 (s, 1H), 7.60 (d, J=8.4 Hz, 1H), 7.26-6.91 (m, 5H), 5.07 (dd, J=13.3, 5.1 Hz, 1H), 4.47-4.18 (m, 3H), 4.11 (dd, J=10.3, 5.3 Hz, 1H), 3.92 (d, J=13.8 Hz, 1H), 3.03-2.84 (m, 3H), 2.74 (dt, J=8.9, 4.7 Hz, 2H), 2.58 (q, J=7.3 Hz, 4H), 2.43-2.32 (m, 3H), 2.11 (ddd, J=11.5, 8.6, 3.1 Hz, 1H), 2.01-1.89 (m, 3H), 1.78 (d, J=11.3 Hz, 1H), 1.72-1.30 (m, 10H), 1.10 (t, J=7.5 Hz, 3H), 1.01 (t, J=7.1 Hz, 3H).

Example 110: 4-(piperidin-1-yl)benzaldehyde (INT-160)

Step 1: (4-(piperidin-1-yl)phenyl)methanol (159)

1M DIBAL-H in toluene (259 mg, 1.824 mmol) was added to a mixture of methyl 4-(piperidin-1-yl)benzoate (200 mg, 0.912 mmol) in THF (4.5 mL) at 0° C. The reaction was warmed slowly to room temperature over 17 hrs. Additional 1M DIBAL-H in toluene (259 mg, 1.824 mmol) was added and the solution stirred at room temperature for 2.5 hrs. The reaction was quenched with saturated aqueous Rochelle's salt, further diluted with water, and extracted with EtOAc. The organic layers were combined, washed with brine, dried over Na$_2$SO$_4$, filtered, and concentrated in-vacuo. The crude material was purified by silica gel chromatography (0-100% EtOAc in heptane) to afford (4-(piperidin-1-yl)phenyl)methanol 159 (90.5 mg, 0.473 mmol, 52% yield) as a clear oil. LCMS [M+H]$^+$: 192.3. $^1$H NMR (400 MHz, CDCl$_3$) δ 7.25 (d, J=8.3 Hz, 2H), 6.93 (d, J=8.2 Hz, 2H), 4.59 (d, J=4.9 Hz, 2H), 3.20-3.10 (m, 4H), 1.71 (p, J=5.7 Hz, 4H), 1.58 (p, J=5.7, 5.3 Hz, 2H), 1.46 (t, J=5.7 Hz, 1H).

Step 2: 4-(piperidin-1-yl)benzaldehyde (INT-160)

(4-(piperidin-1-yl)phenyl)methanol 159 (90.5 mg, 0.473 mmol) and manganese dioxide (411 mg, 4.73 mmol) were suspended in DCM (2 mL). The reaction stirred at room temperature overnight. The reaction was filtered through CELITE® and rinsed with dichloromethane. The filtrate was concentrated in-vacuo. The crude material was purified by silica gel chromatography (0-60% EtOAc in heptane) to afford 4-(piperidin-1-yl)benzaldehyde INT-160 (73.9 mg, 0.387 mmol, 82% yield) as a clear liquid that crystalized into a white solid. LCMS [M+H]$^+$: 190.0. $^1$H NMR (400 MHz, CD$_2$Cl$_2$) δ 9.74 (s, 1H), 7.81-7.66 (m, 2H), 7.01 (d, J=8.5 Hz, 2H), 3.47-3.33 (m, 4H), 1.80-1.61 (m, 6H).

Example 111: 3-(1-oxo-5-(((R)-1-(4-(piperidin-1-yl)benzyl)piperidin-2-yl)methoxy)isoindolin-2-yl)piperidine-2,6-dione (I-161)

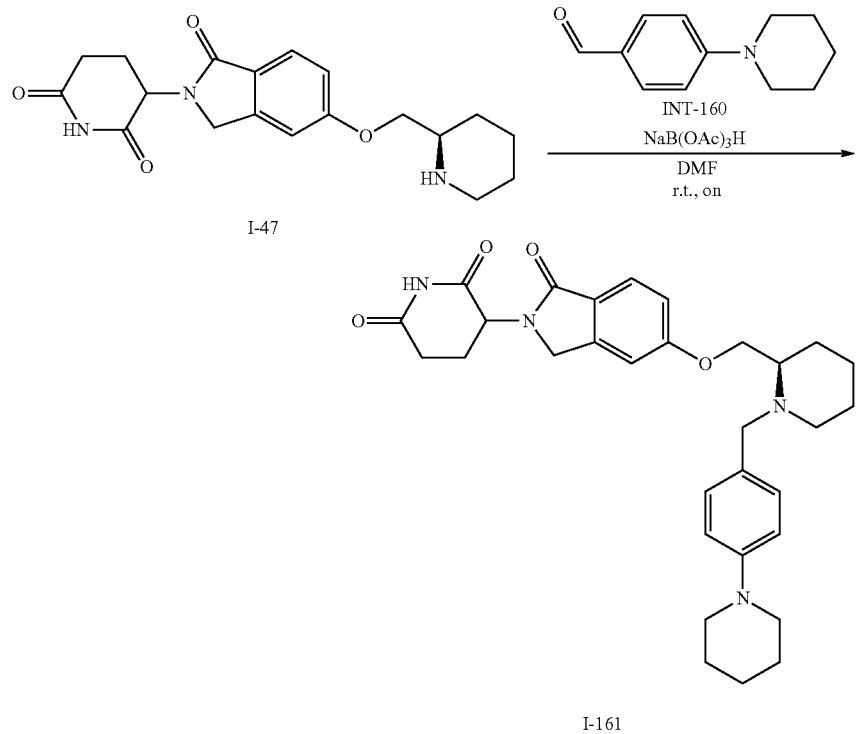

3-(1-oxo-5-(((R)-piperidin-2-yl)methoxy)isoindolin-2-yl)piperidine-2,6-dione I-47 (26.5 mg, 0.074 mmol) and 4-(piperidin-1-yl)benzaldehyde INT-160 (16.6 mg, 0.088 mmol) were dissolved in DMF (0.5 mL). Sodium triacetoxyborohydride (44 mg, 0.208 mmol) was added and the reaction stirred at room temperature overnight. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-100% 3:1 EtOAc:EtOH with 1% TEA in DCM) to afford 3-(1-oxo-5-(((R)-1-(4-(piperidin-1-yl)benzyl)piperidin-2-yl)methoxy)isoindolin-2-yl)piperidine-2,6-dione I-161 (15.9 mg, 0.029 mmol, 39% yield) as a white solid. LCMS [M+H]+: 531.4. $^1$H NMR (400 MHz, DMSO-d6) δ 10.96 (s, 1H), 7.61 (d, J=8.4 Hz, 1H), 7.17 (s, 1H), 7.12 (d, J=8.5 Hz, 2H), 7.06 (dd, J=8.4, 2.2 Hz, 1H), 6.90-6.79 (m, 2H), 5.07 (dd, J=13.3, 5.1 Hz, 1H), 4.46-4.18 (m, 3H), 4.17-4.08 (m, 1H), 3.87 (d, J=13.3 Hz, 1H), 3.06 (t, J=5.4 Hz, 4H), 2.91 (ddd, J=18.0, 13.6, 5.4 Hz, 1H), 2.77-2.66 (m, 2H), 2.59 (d, J=17.5 Hz, 1H), 2.38 (dd, J=13.2, 4.4 Hz, 1H), 2.08 (t, J=9.8 Hz, 1H), 1.97 (d, J=10.6 Hz, 1H), 1.76 (d, J=4.4 Hz, 1H), 1.70-1.43 (m, 10H), 1.35 (q, J=11.8 Hz, 2H).

Example 112: 3-methoxybicyclo[1.1.1]pentane-1-carbaldehyde (INT-162)

In 40 mL vial, DCM (1.5 mL) was added followed by oxalyl chloride (0.08 mL, 0.914 mmol) then cooled to −78° C. DMSO (0.15 mL, 2.11 mmol) in DCM (1.5 mL) was added dropwise and the reaction mixture continue to stir at −78° C. for 30 mins. (3-methoxybicyclo[1.1.1]pentan-1-yl)methanol (89.2 mg, 0.696 mmol) in DCM (3 mL) was added dropwise and the reaction mixture continued to stir at −78° C. for 1 hr. Triethylamine (500 µL, 3.59 mmol) was added and the reaction warmed to r.t. overnight The reaction was quenched with saturated aqueous ammonium chloride and extracted with DCM three times. The organic layers were combined, passed through a phase separated and concentrated in-vacuo. The crude material was purified by silica gel chromatography (0-100% EtOAc in heptane) to afford 3-methoxybicyclo[1.1.1]pentane-1-carbaldehyde INT-162 (27.6 mg, 0.208 mmol, 30% yield) as a clear liquid. $^1$H NMR (400 MHz, CD$_2$Cl$_2$) δ 9.71 (s, 1H), 3.28 (s, 3H), 2.13 (s, 6H).

Example 113: 3-(5-(((R)-1-((3-methoxybicyclo[1.1.1]pentan-1-yl)methyl)piperidin-2-yl)methoxy)-1-oxoisoindolin-2-yl)piperidine-2,6-dione (I-163)

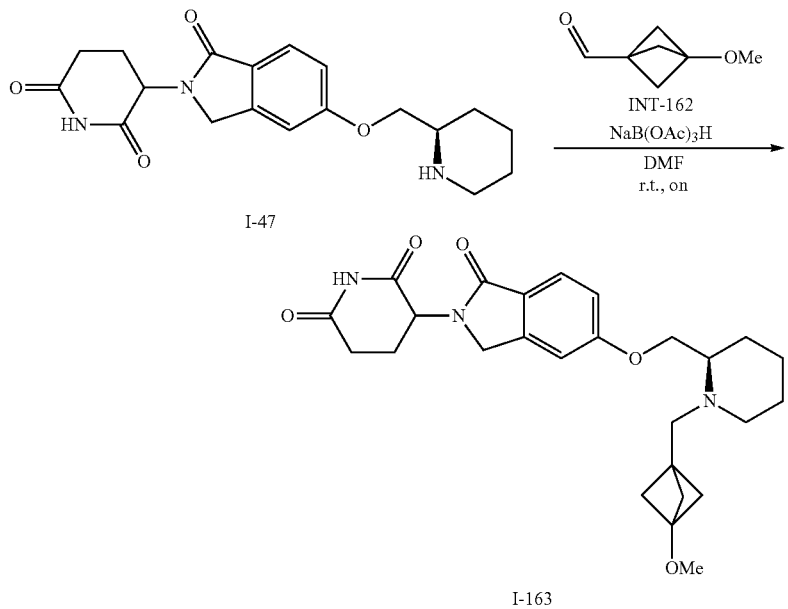

3-(1-oxo-5-(((R)-piperidin-2-yl)methoxy)isoindolin-2-yl)piperidine-2,6-dione I-47 (48.3 mg, 0.135 mmol) and 3-methoxybicyclo[1.1.1]pentane-1-carbaldehyde INT-162 (27.6 mg, 0.219 mmol) were dissolved in DMF (0.5 mL). Sodium triacetoxyborohydride (93 mg, 0.439 mmol) was added and the reaction stirred at room temperature overnight. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-80% 3:1 EtOAc:EtOH with 1% TEA in DCM) to afford 3-(5-(((R)-1-((3-methoxybicyclo[1.1.1]pentan-1-yl)methyl)piperidin-2-yl)methoxy)-1-oxoisoindolin-2-yl)piperidine-2,6-dione I-163 (33.6 mg, 0.070 mmol, 52.1% yield) as an off-white solid. LCMS [M+H]+: 468.5. $^1$H NMR (400 MHz, DMSO-d6) δ 10.96 (s, 1H), 7.62 (d, J=8.4 Hz, 1H), 7.18 (d, J=2.2 Hz, 1H), 7.05 (dd, J=8.4, 2.2 Hz, 1H), 5.07 (dd, J=13.3, 5.1 Hz, 1H), 4.44-4.22 (m, 2H), 4.14 (ddd, J=10.1, 4.7, 2.6 Hz, 1H), 3.99 (ddd, J=10.0, 5.4, 2.1 Hz, 1H), 3.14 (s, 3H), 2.97-2.84 (m, 2H), 2.85-2.74 (m, 2H), 2.70-2.64 (m, 1H), 2.63-2.54 (m, 1H), 2.45-2.35 (m, 2H), 2.04-1.93 (m, 1H), 1.78-1.68 (m, 7H), 1.68-1.58 (m, 1H), 1.57-1.25 (m, 4H).

Example 114: Tert-butyl 4-(4-fluoro-2-formylphenyl)piperazine-1-carboxylate (INT-166)

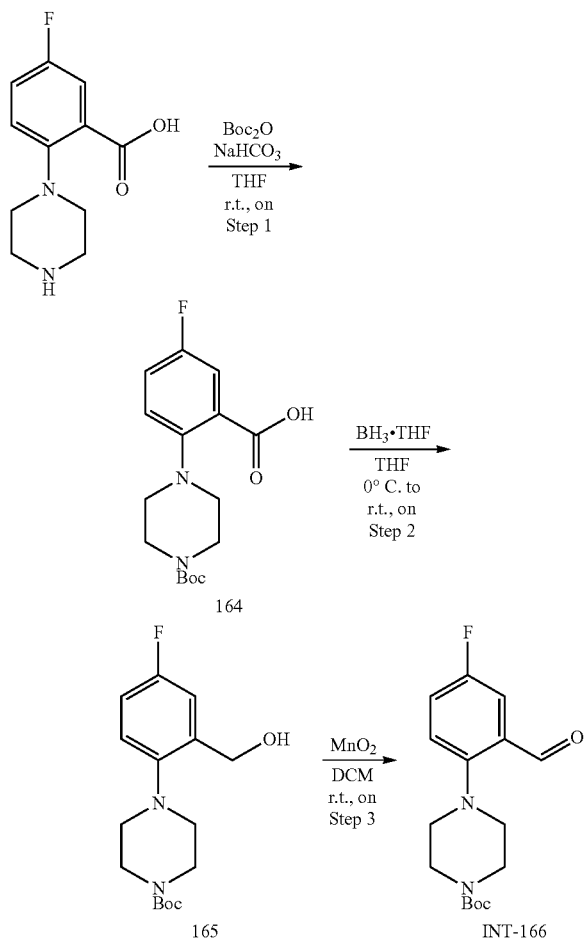

Step 1: 2-(4-(tert-butoxycarbonyl)piperazin-1-yl)-5-fluorobenzoic Acid (164)

5-fluoro-2-(piperazin-1-yl)benzoic acid (300.9 mg, 1.342 mmol), Boc-anhydride (352.4 mg, 1.615 mmol), and sodium bicarbonate (353.0 mg, 4.20 mmol) were suspended in THF (4.5 mL). The reaction stirred at room temperature overnight. The reaction was quenched with water and washed with DCM. The DCM layer was separated and discarded. The aqueous layer was acidified with 1 N HCl to pH 5 and extracted with DCM three times. The organic layers were combined, dired overed magnesium sulfate, filtered and concentrated in-vacuo to afford 2-(4-(tert-butoxycarbonyl)piperazin-1-yl)-5-fluorobenzoic acid 164 (46.0 mg, 0.140 mmol, 10.5% yield) as a white foam. LCMS [M+H]$^+$: 325.6. $^1$H NMR (400 MHz, DMSO-d6) δ 7.72 (dd, J=8.9, 4.9 Hz, 1H), 7.67 (dd, J=9.1, 3.1 Hz, 1H), 7.50 (ddd, J=8.9, 8.0, 3.2 Hz, 1H), 3.52 (t, J=5.0 Hz, 4H), 3.02 (t, J=5.0 Hz, 4H), 1.43 (s, 9H).

Step 2: Tert-butyl 4-(4-fluoro-2-(hydroxymethyl)phenyl)piperazine-1-carboxylate (165)

2-(4-(tert-butoxycarbonyl)piperazin-1-yl)-5-fluorobenzoic acid 164 (46 mg, 0.142 mmol) was dissolved in THF (0.5 mL) and cooled to 0° C. 1 M borane tetrahydrofuran complex in THF (0.5 mL, 0.500 mmol) was added and the reaction warmed to room temperature overnight. The reaction was cooled to 0° C. and quenched methanol (0.3 mL). The solution was then concentrated to dryness and reconstituted in MeOH (1.000 mL) and stirred at room temperature overnight. The reaction was concentrated in-vacuo and purified by silica gel chromatography (0-80% EtOAc in heptane) to afford tert-butyl 4-(4-fluoro-2-(hydroxymethyl)phenyl)piperazine-1-carboxylate 165 (41.7 mg, 0.134 mmol, 95% yield) as a clear, viscous liquid. LCMS [M+H]$^+$: 311.2. $^1$H NMR (400 MHz, CD$_2$Cl$_2$) δ 7.22-7.12 (m, 1H), 7.06-6.94 (m, 2H), 4.76 (s, 2H), 3.61 (t, J=5.0 Hz, 4H), 2.91 (t, J=5.0 Hz, 4H), 1.46 (s, 9H).

Step 3: Tert-butyl 4-(4-fluoro-2-formylphenyl)piperazine-1-carboxylate (INT-166)

Tert-butyl 4-(4-fluoro-2-(hydroxymethyl)phenyl)piperazine-1-carboxylate 165 (41.7 mg, 0.134 mmol) and manganese dioxide (122.4 mg, 1.408 mmol) were suspended in DCM (1 mL). The reaction stirred at room temperature for 4 days. The reaction was filtered with CELITE® and rinsed with DCM. The filtrated was concentrated in-vacuo and purified by silica gel chromatography (0-60% EtOAc in heptane) to afford tert-butyl 4-(4-fluoro-2-formylphenyl)piperazine-1-carboxylate INT-166 (26.3 mg, 0.085 mmol, 63.5% yield) as a yellow viscous gum. LCMS [M+H]$^+$: 309.5. $^1$H NMR (400 MHz, CD$_2$Cl$_2$) δ 10.37 (d, J=2.9 Hz, 1H), 7.53-7.46 (m, 1H), 7.28 (ddd, J=8.9, 7.7, 3.1 Hz, 1H), 7.25-7.19 (m, 1H), 3.65-3.58 (m, 4H), 3.04-2.96 (m, 4H), 1.46 (s, 9H).

Example 115: Tert-butyl 4-(2-(((2R)-2-(((2-(2,6-dioxopiperidin-3-yl)-1-oxoisoindolin-5-yl)oxy)methyl)piperidin-1-yl)methyl)-4-fluorophenyl)piperazine-1-carboxylate (I-167)

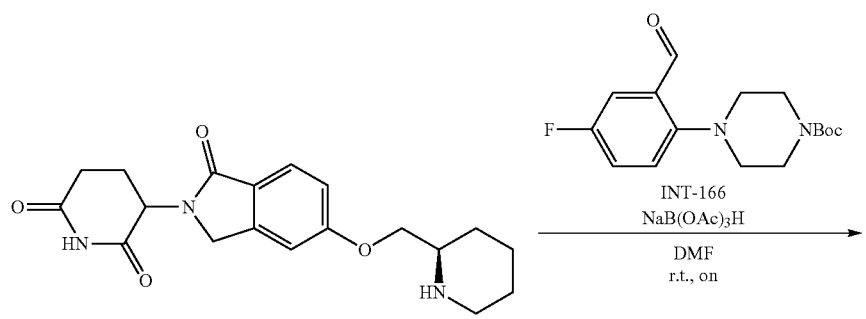

I-47

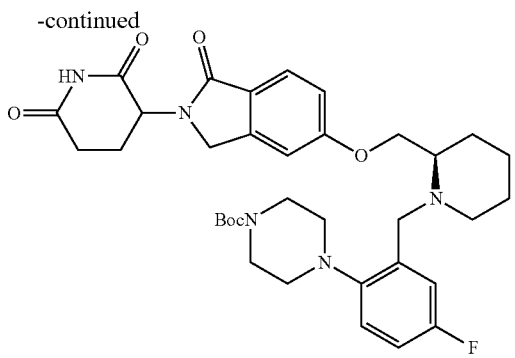

I-167

3-(1-oxo-5-(((R)-piperidin-2-yl)methoxy)isoindolin-2-yl)piperidine-2,6-dione I-47 (25.8 mg, 0.072 mmol) and tert-butyl 4-(4-fluoro-2-formylphenyl)piperazine-1-carboxylate INT-166 (26.3 mg, 0.085 mmol) were dissolved in DMF (0.5 mL). Sodium triacetoxyborohydride (50.6 mg, 0.239 mmol) was added and the reaction stirred at room temperature for 36 hrs. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-80% 3:1 EtOAc:EtOH with 1% TEA in DCM) to afford tert-butyl 4-(2-(((2R)-2-(((2-(2,6-dioxopiperidin-3-yl)-1-oxoisoindolin-5-yl)oxy)methyl)piperidin-1-yl)methyl)-4-fluorophenyl)piperazine-1-carboxylate I-167 (20.3 mg, 0.030 mmol, 42.0% yield) was isolated as a white solid. LCMS [M+H]⁺: 468.5. ¹H NMR (400 MHz, DMSO-d6) δ 10.96 (s, 1H), 7.62 (d, J=8.4 Hz, 1H), 7.18 (d, J=2.2 Hz, 1H), 7.05 (dd, J=8.4, 2.2 Hz, 1H), 5.07 (dd, J=13.3, 5.1 Hz, 1H), 4.44-4.22 (m, 2H), 4.14 (ddd, J=10.1, 4.7, 2.6 Hz, 1H), 3.99 (ddd, J=10.0, 5.4, 2.1 Hz, 1H), 3.14 (s, 3H), 2.97-2.84 (m, 2H), 2.85-2.74 (m, 2H), 2.70-2.64 (m, 1H), 2.63-2.54 (m, 1H), 2.45-2.35 (m, 2H), 2.04-1.93 (m, 1H), 1.78-1.68 (m, 7H), 1.68-1.58 (m, 1H), 1.57-1.25 (m, 4H).

Example 116: 3-(5-(((R)-1-(5-fluoro-2-(piperazin-1-yl)benzyl)piperidin-2-yl)methoxy)-1-oxoisoindolin-2-yl)piperidine-2,6-dione (I-168)

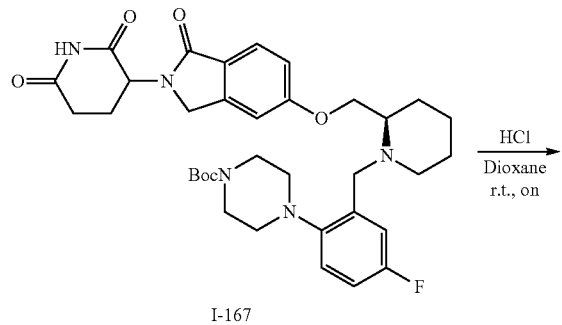

I-167

HCl
Dioxane
r.t., on

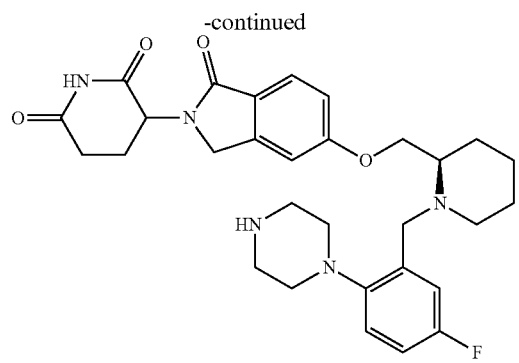

I-168

Tert-butyl 4-(2-(((2R)-2-(((2-(2,6-dioxopiperidin-3-yl)-1-oxoisoindolin-5-yl)oxy)methyl)piperidin-1-yl)methyl)-4-fluorophenyl)piperazine-1-carboxylate I-167 (18.0 mg, 0.028 mmol) was dissolved in 4M HCl in dioxane (0.8 mL, 3.20 mmol) and stirred at room temperature overnight. The reaction was concentrated and triturated with diethyl ether, filtered, and dried under high vacuum overnight to afford HCl salt of 3-(5-(((R)-1-(5-fluoro-2-(piperazin-1-yl)benzyl)piperidin-2-yl)methoxy)-1-oxoisoindolin-2-yl)piperidine-2,6-dione I-168 (14.8 mg, 0.024 mmol, 86% yield) as a white solid. LCMS [M+H]⁺: 550.5. ¹H NMR (400 MHz, DMSO-d6) δ 10.98 (s, 1H), 10.12-9.72 (m, 1H), 9.06 (s, 2H), 7.77-7.57 (m, 2H), 7.43-7.22 (m, 3H), 7.21-7.09 (m, 1H), 5.10 (ddd, J=13.2, 5.2, 2.2 Hz, 1H), 4.65 (t, J=11.5 Hz, 1H), 4.58-4.24 (m, 4H), 3.90 (d, J=33.5 Hz, 1H), 3.30-3.11 (m, 4H), 3.10-2.86 (m, 5H), 2.67-2.57 (m, 1H), 2.47-2.36 (m, 1H), 2.21-1.88 (m, 3H), 1.88-1.69 (m, 3H), 1.69-1.52 (m, 1H), 1.10 (t, J=7.0 Hz, 3H).

Example 117: 3-(5-(((R)-1-(2-(4-ethylpiperazin-1-yl)-5-fluorobenzyl)piperidin-2-yl)methoxy)-1-oxoisoindolin-2-yl)piperidine-2,6-dione (I-169)

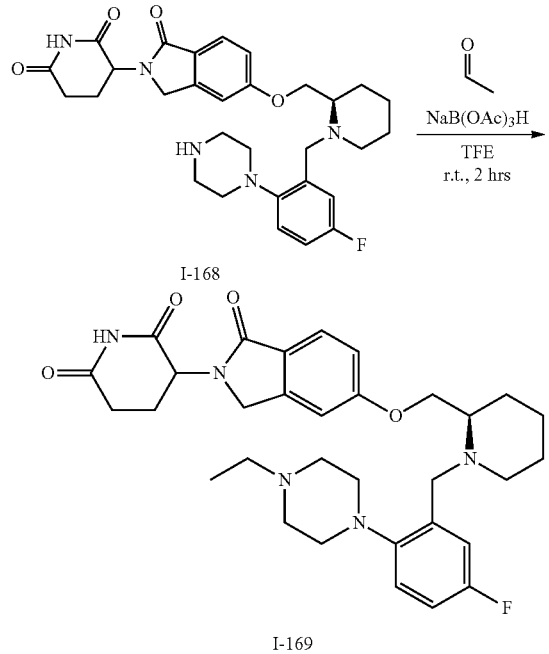

I-168

I-169

3-(5-(((R)-1-(5-fluoro-2-(piperazin-1-yl)benzyl)piperidin-2-yl)methoxy)-1-oxoisoindolin-2-yl)piperidine-2,6-dione I-168 (13.5 mg, 0.023 mmol) and acetaldehyde (1.81 μL, 0.032 mmol) were dissolved in 2,2,2-trifluoroethanol (0.5 mL) and stirred for 5 minutes. Sodium triacetoxyborohydride (9.76 mg, 0.046 mmol) was added in one portion and the stirred at room temperature for 2 hrs. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-60% 3:1 EtOAc:EtOH with 1% TEA in DCM) to afford 3-(5-(((R)-1-(2-(4-ethylpiperazin-1-yl)-5-fluorobenzyl)piperidin-2-yl)methoxy)-1-oxoisoindolin-2-yl)piperidine-2,6-dione I-169 (9.1 mg, 0.015 mmol, 67% yield) as a white solid. LCMS [M+H]+: 578.5. 1H NMR (400 MHz, DMSO-d6) δ 10.95 (s, 1H), 7.60 (d, J=8.4 Hz, 1H), 7.28 (dd, J=10.2, 3.2 Hz, 1H), 7.15-7.10 (m, 1H), 7.07 (dd, J=8.8, 5.3 Hz, 1H), 7.04-6.88 (m, 2H), 5.07 (dd, J=13.3, 5.1 Hz, 1H), 4.42-4.19 (m, 3H), 4.12-4.04 (m, 1H), 3.92 (d, J=14.7 Hz, 1H), 3.56 (d, J=14.7 Hz, 1H), 2.98-2.69 (m, 6H), 2.64-2.54 (m, 1H), 2.47-2.28 (m, 8H), 2.26-2.16 (m, 1H), 2.01-1.92 (m, 1H), 1.84-1.71 (m, 1H), 1.71-1.34 (m, 5H), 1.00 (t, J=7.1 Hz, 3H).

Example 118: 4-(1-(trifluoromethyl)cyclopropyl)benzaldehyde (INT-172)

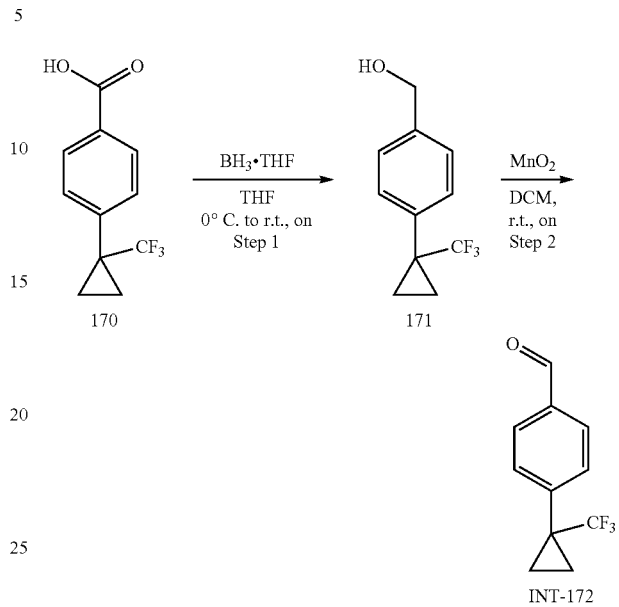

170 comes from ACS medicinal chemistry letters, 2013, Vol. 4(6), p. 514-516; DOI: 10.1021/ml400045j

Step 1: (4-(1-(trifluoromethyl)cyclopropyl)phenyl)methanol (171)

4-(1-(trifluoromethyl)cyclopropyl)benzoic acid 170 (257.4 mg, 1.118 mmol) was dissolved in THF (3.5 mL) and cooled to 0° C. 1M borane tetrahydrofuran complex in THF (3.1 mL, 3.10 mmol) was added and the reaction warmed to room temperature overnight. The reaction was cooled to 0° C. and quenched with methanol (2.2 mL). The reaction was concentrated to dryness, reconstituted in MeOH (7 mL) and stirred at room temperature overnight. The reaction was concentrated in-vacuo and purified by silica gel chromatography (0-80% EtOAc in heptane) to afford (4-(1-(trifluoromethyl)cyclopropyl)phenyl)methanol 171 (163.7 mg, 0.757 mmol, 67.7% yield) as a clear liquid. 1H NMR (400 MHz, CD2Cl2) δ 7.50 (d, J=8.1 Hz, 2H), 7.42-7.34 (m, 2H), 4.71 (s, 2H), 1.42-1.36 (m, 2H), 1.12-1.04 (m, 2H).

Step 2: 4-(1-(trifluoromethyl)cyclopropyl)benzaldehyde (INT-172)

(4-(1-(trifluoromethyl)cyclopropyl)phenyl)methanol 171 (163.7 mg, 0.757 mmol) and manganese dioxide (659.7 mg, 7.59 mmol) were suspended in DCM (5 mL). The stirred at room temperature for 36 hrs. The reaction was filtered through CELITE® and rinsed with DCM. The filtrate was concentrated in-vacuo and purified by silica gel chromatography (0-60% EtOAc in heptane) to afford 4-(1-(trifluoromethyl)cyclopropyl)benzaldehyde INT-172 (114.4 mg, 0.529 mmol, 69.8% yield) as a clear liquid. LCMS [M+H]+: 215.1. 1H NMR (400 MHz, CD2Cl2) δ 10.02 (s, 1H), 7.91-7.82 (m, 2H), 7.71-7.59 (m, 2H), 1.47-1.40 (m, 2H), 1.14-1.08 (m, 2H).

Example 119: 3-(1-oxo-5-(((R)-1-(4-(1-(trifluoromethyl)cyclopropyl)benzyl)piperidin-2-yl)methoxy)isoindolin-2-yl)piperidine-2,6-dione (I-173)

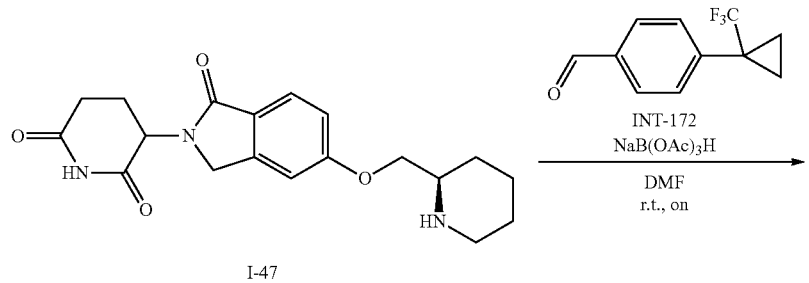

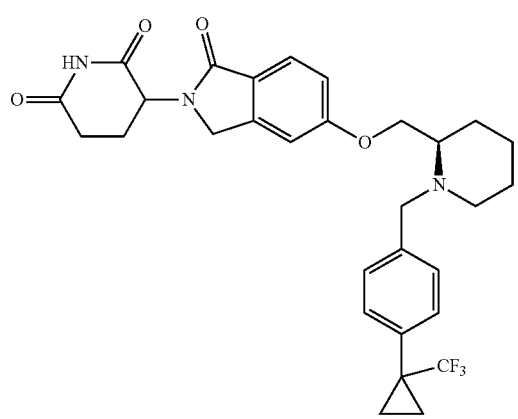

3-(1-oxo-5-(((R)-piperidin-2-yl)methoxy)isoindolin-2-yl)piperidine-2,6-dione I-47 (133.2 mg, 0.373 mmol) and 4-(1-(trifluoromethyl)cyclopropyl)benzaldehyde INT-172 (114.4 mg, 0.534 mmol) were dissolved in DMF (2 mL). Sodium triacetoxyborohydride (246 mg, 1.161 mmol) was added and the reaction stirred at room temperature overnight. The reaction was quenched with 50% saturated aqueous sodium bicarbonate. The reaction was extracted with 4:1 dichloromethane:isopropanol. The organic layers were combined, passed through a phase separator, and concentrated in-vacuo. The crude material was purified by silica gel chromatography (0-80% 3:1 EtOAc:EtOH with 1% TEA in DCM) to afford 3-(1-oxo-5-(((R)-1-(4-(1-(trifluoromethyl)cyclopropyl)benzyl)piperidin-2-yl)methoxy)isoindolin-2-yl)piperidine-2,6-dione I-173 (138.9 mg, 0.248 mmol, 66.4% yield) was isolated as a white solid. LCMS [M+H]$^+$: 556.2. $^1$H NMR (400 MHz, DMSO-d6) δ 10.95 (s, 1H), 7.60 (d, J=8.4 Hz, 1H), 7.41-7.28 (m, 4H), 7.20-7.13 (m, 1H), 7.04 (dd, J=8.4, 2.2 Hz, 1H), 5.07 (dd, J=13.3, 5.1 Hz, 1H), 4.44-4.20 (m, 3H), 4.16-4.06 (m, 1H), 4.00 (d, J=14.1 Hz, 1H), 3.41 (d, J=14.1 Hz, 1H), 2.90 (ddd, J=17.2, 13.4, 5.4 Hz, 1H), 2.81-2.64 (m, 2H), 2.64-2.54 (m, 1H), 2.44-2.32 (m, 1H), 2.19-2.08 (m, 1H), 2.03-1.90 (m, 1H), 1.86-1.74 (m, 1H), 1.72-1.61 (m, 1H), 1.60-1.32 (m, 4H), 1.32-1.26 (m, 2H), 1.09-1.01 (m, 2H).

Example 120: 3,4-dihydro-2H-benzo[b][1,4]oxazine-5-carbaldehyde (INT-176) and 3-oxo-3,4-dihydro-2H-benzo[b][1,4]oxazine-5-carbaldehyde (INT-177)

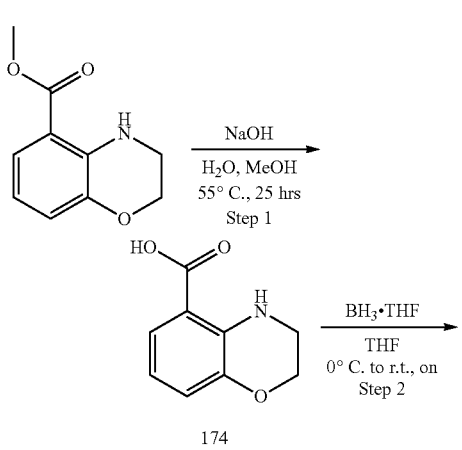

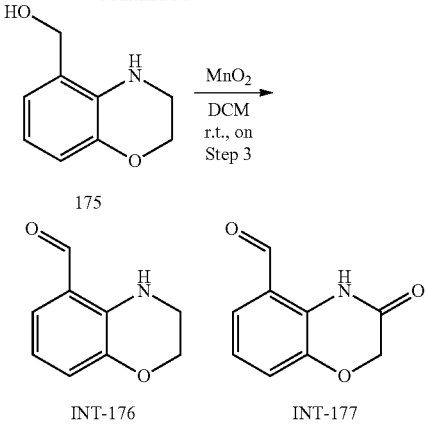

Step 1: 3,4-dihydro-2H-benzo[b][1,4]oxazine-5-carboxylic Acid (174)

Methyl 3,4-dihydro-2H-benzo[b][1,4]oxazine-5-carboxylate (207.6 mg, 1.08 mmol) was dissolved in MeOH (1.5 mL) and water (1 mL). 1 M aqueous sodium hydroxide (2.2 mL, 2.200 mmol) was added and the reaction stirred at 55° C. for 25 hrs. The reaction was partially concentrated to remove methanol and then acidified with 1 M HCl solution to pH ~2. The precipitate was collected by filtration and washed with diethyl ether to afford 3,4-dihydro-2H-benzo[b][1,4]oxazine-5-carboxylic acid 174 (61.9 mg, 0.339 mmol, 31.5% yield) as a white solid. The material was taken on to the next step without purification. LCMS [M+H]⁺= 180.1. ¹H NMR (400 MHz, DMSO-d6) δ 12.54 (s, 1H), 8.51-7.37 (m, 1H), 7.34 (dd, J=8.1, 1.5 Hz, 1H), 6.83 (dd, J=7.7, 1.5 Hz, 1H), 6.43 (t, J=7.9 Hz, 1H), 4.18-4.02 (m, 2H), 3.51-3.40 (m, 2H).

Step 2: (3,4-dihydro-2H-benzo[b][1,4]oxazin-5-yl)methanol (175)

3,4-dihydro-2H-benzo[b][1,4]oxazine-5-carboxylic acid 174 (61.9 mg, 0.345 mmol) was dissolved in THF (1 mL) and cooled to 0° C. 1 M borane tetrahydrofuran complex in THF (1 mL, 1.00 mmol) was added to the reaction. The reaction warmed to r.t. overnight. The reaction was cooled to 0° C. and quenched with methanol (0.7 mL). The reaction was concentrated to dryness, reconstituted in MeOH (2 mL) and stirred at r.t. overnight. The reaction was concentrated and purified by silica gel chromatography (0-100% EtOAc in heptane) to afford (3,4-dihydro-2H-benzo[b][1,4]oxazin-5-yl)methanol 175 (62.5 mg, 0.341 mmol, 99% yield) as an opaque, viscous liquid. LCMS [M+H]⁺=166.2. ¹H NMR (400 MHz, CD₂Cl₂) −δ 6.73 (dd, J=7.9, 1.6 Hz, 1H), 6.71-6.67 (m, 1H), 6.64-6.56 (m, 1H), 4.63 (s, 2H), 4.25-4.17 (m, 2H), 3.51-3.42 (m, 2H).

Step 3: 3,4-dihydro-2H-benzo[b][1,4]oxazine-5-carbaldehyde (INT-176) and 3-oxo-3,4-dihydro-2H-benzo[b][1,4]oxazine-5-carbaldehyde (INT-177)

(3,4-dihydro-2H-benzo[b][1,4]oxazin-5-yl)methanol 175 (57.1 mg, 0.346 mmol) and manganese dioxide (306.5 mg, 3.53 mmol) were suspended in DCM (2 mL). The reaction stirred at r.t. overnight. The reaction was filtered through CELITE® and washed with DCM. The filtrated was concentrated and purified by silica gel chromatography (0-60% EtOAc in heptane) to afford 3,4-dihydro-2H-benzo[b][1,4]oxazine-5-carbaldehyde INT-176 (11.5 mg, 0.070 mmol, 20.2% yield) as a yellow liquid and 3-oxo-3,4-dihydro-2H-benzo[b][1,4]oxazine-5-carbaldehyde INT-177 (12.2 mg, 0.067 mmol, 19.3% yield) as an orange solid.

3,4-dihydro-2H-benzo[b][1,4]oxazine-5-carbaldehyde INT-176: LCMS [M+H]⁺=164.2. ¹H NMR (400 MHz, CD₂Cl₂) δ 9.86 (s, 1H), 8.57-7.27 (m, 1H), 7.16 (dd, J=7.8, 1.5 Hz, 1H), 6.95 (dd, J=7.7, 1.5 Hz, 1H), 6.64 (t, J=7.8 Hz, 1H), 4.29-4.21 (m, 2H), 3.63-3.53 (m, 2H).

3-oxo-3,4-dihydro-2H-benzo[b][1,4]oxazine-5-carbaldehyde INT-177: LCMS [M+H]⁺=178.2. ¹H NMR (400 MHz, CD₂Cl₂) δ 10.37 (s, 1H), 9.96 (s, 1H), 7.40 (dd, J=7.6, 1.4 Hz, 1H), 7.23 (ddd, J=8.1, 1.4, 0.7 Hz, 1H), 7.17-7.09 (m, 1H), 4.66 (s, 2H).

Example 121: 3-(5-(((R)-1-((3,4-dihydro-2H-benzo[b][1,4]oxazin-5-yl)methyl)piperidin-2-yl)methoxy)-1-oxoisoindolin-2-yl)piperidine-2,6-dione (I-178)

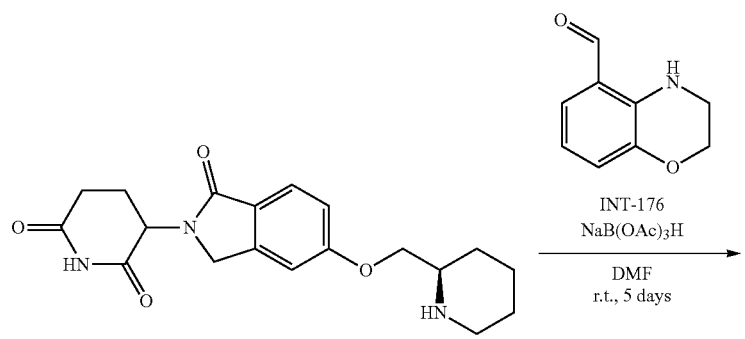

I-47

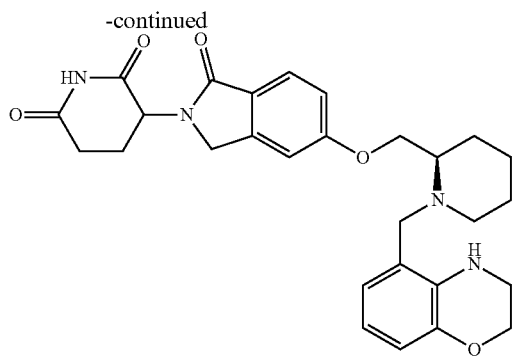

I-178

3-(1-oxo-5-(((R)-piperidin-2-yl)methoxy)isoindolin-2-yl)piperidine-2,6-dione I-47 (18.3 mg, 0.051 mmol) and 3,4-dihydro-2H-benzo[b][1,4]oxazine-5-carbaldehyde INT-176 (11.5 mg, 0.070 mmol) were dissolved in DMF (0.5 mL). Sodium triacetoxyborohydride (34.5 mg, 0.163 mmol) was added and the reaction stirred at r.t. for 5 days. The reaction was quenched with 50% saturated aqueous sodium bicarbonate. The reaction was extracted with 4:1 dichloromethane:isopropanol three times. The organic layers were combined, passed through a phase separator, and concentrated in-vacuo. The crude material was purified by silica gel chromatography (0-80% 3:1 EtOAc:EtOH with 1% TEA in DCM) to afford 3-(5-(((R)-1-((3,4-dihydro-2H-benzo[b][1,4]oxazin-5-yl)methyl)piperidin-2-yl)methoxy)-1-oxoisoindolin-2-yl)piperidine-2,6-dione I-178 (7.9 mg, 0.015 mmol, 29.0% yield) as a white solid. LCMS [M+H]$^+$: 468.5. $^1$H NMR (400 MHz, DMSO-d6) δ 10.96 (s, 1H), 7.63 (d, J=8.4 Hz, 1H), 7.19 (d, J=2.2 Hz, 1H), 7.08 (dd, J=8.4, 2.2 Hz, 1H), 6.58 (ddd, J=12.3, 7.7, 1.5 Hz, 2H), 6.42 (dd, J=8.0, 7.3 Hz, 1H), 5.92 (s, 1H), 5.07 (dd, J=13.3, 5.1 Hz, 1H), 4.49-4.18 (m, 4H), 4.15-3.93 (m, 3H), 3.45-3.36 (m, 1H), 3.23 (dd, J=12.8, 3.3 Hz, 1H), 2.97-2.84 (m, 1H), 2.73-2.70 (m, 1H), 2.70-2.64 (m, 2H), 2.63-2.54 (m, 1H), 2.38 (dd, J=13.2, 4.5 Hz, 1H), 2.11-1.94 (m, 2H), 1.70 (dd, J=21.6, 11.9 Hz, 3H), 1.59-1.45 (m, 1H), 1.45-1.32 (m, 2H).

Example 122: 3-(5-(((R)-1-((4-ethyl-3,4-dihydro-2H-benzo[b][1,4]oxazin-5-yl)methyl)piperidin-2-yl)methoxy)-1-oxoisoindolin-2-yl)piperidine-2,6-dione (I-179)

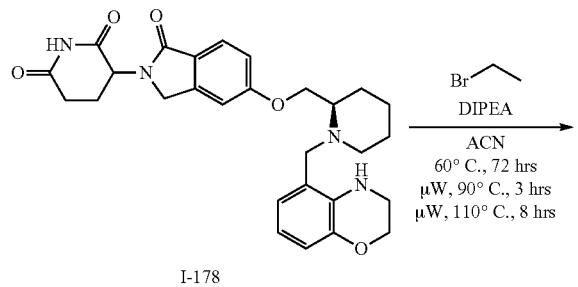

I-178

Br⁀ / DIPEA / ACN / 60° C., 72 hrs / μW, 90° C., 3 hrs / μW, 110° C., 8 hrs →

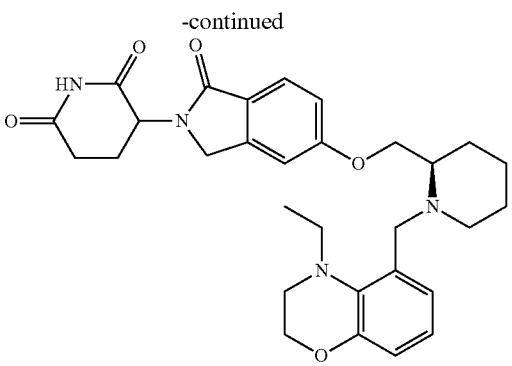

I-179

3-(5-(((R)-1-((3,4-dihydro-2H-benzo[b][1,4]oxazin-5-yl)methyl)piperidin-2-yl)methoxy)-1-oxoisoindolin-2-yl)piperidine-2,6-dione I-178 (9.5 mg, 0.019 mmol) and bromoethane (2.46 mg, 0.023 mmol) were dissolved in acetonitrile (0.5 mL). DIPEA (0.01 mL, 0.057 mmol) was added and the reaction stirred at 60° C. for 72 hrs. The solution was transferred to a microwave vial and additional bromoethane (2.46 mg, 0.023 mmol) was added. The reaction stirred at 90° C. under microwave radiation for 3 hrs. Additional bromoethane (2.46 mg, 0.023 mmol) and DIPEA (0.01 mL, 0.057 mmol) were added. The reaction stirred at 110° C. under microwave radiation for 8 hrs. The reaction was quenched with 50% saturated aqueous sodium bicarbonate. The reaction was extracted with 4:1 dichloromethane:isopropanol three times. The organic layers were combined, passed through a phase separator, and concentrated in-vacuo. The crude material was purified by silica gel chromatography (0-50% 3:1 EtOAc:EtOH with 1% TEA in DCM) to afford 3-(5-(((R)-1-((4-ethyl-3,4-dihydro-2H-benzo[b][1,4]oxazin-5-yl)methyl)piperidin-2-yl)methoxy)-1-oxoisoindolin-2-yl)piperidine-2,6-dione I-179 (2.7 mg, 4.56 μmol, 24.23% yield) as a white solid. LCMS [M+H]$^+$: 533.8. $^1$H NMR (400 MHz, DMSO-d$_6$) δ 10.95 (s, 1H), 7.60 (d, J=8.4 Hz, 1H), 7.14-7.11 (m, 1H), 7.08 (dd, J=7.6, 1.6 Hz, 1H), 7.02 (dd, J=8.4, 2.2 Hz, 1H), 6.85 (t, J=7.8 Hz, 1H), 6.66-6.61 (m, 1H), 5.06 (dd, J=13.3, 5.1 Hz, 1H), 4.42-4.21 (m, 3H), 4.12-3.97 (m, 4H), 3.87 (d, J=14.5 Hz, 1H), 3.50 (d, J=14.5 Hz, 1H), 3.04-2.88 (m, 2H), 2.88-2.69 (m, 3H), 2.64-2.54 (m, 1H), 2.46-2.35 (m, 3H), 2.28-2.17 (m, 1H), 2.04-1.93 (m, 1H), 1.85-1.74 (m, 1H), 1.70-1.60 (m, 1H), 1.59-1.33 (m, 3H), 1.21-1.13 (m, 3H).

Example 123: 3-(1-oxo-5-(((R)-1-((3-oxo-3,4-dihydro-2H-benzo[b][1,4]oxazin-5-yl)methyl)piperidin-2-yl)methoxy)isoindolin-2-yl)piperidine-2,6-dione (I-180)

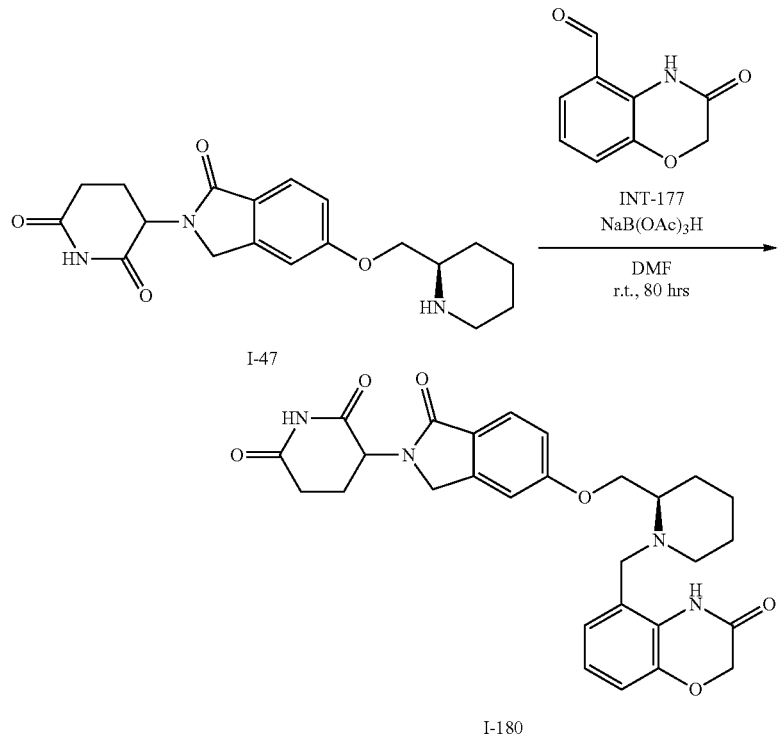

3-(1-oxo-5-(((R)-piperidin-2-yl)methoxy)isoindolin-2-yl)piperidine-2,6-dione I-47 (26.8 mg, 0.075 mmol) and 3-oxo-3,4-dihydro-2H-benzo[b][1,4]oxazine-5-carbaldehyde INT-177 (12.2 mg, 0.069 mmol) were dissolved in DMF (0.5 mL). Sodium triacetoxyborohydride (44.7 mg, 0.211 mmol) was added and the reaction stirred at room temperature for 80 hrs. The reaction was quenched with 50% saturated aqueous sodium bicarbonate. The reaction was extracted with 4:1 dichloromethane:isopropanol three times. The organic layers were combined, passed through a phase separator, and concentrated in-vacuo. The crude material was purified by silica gel chromatography (0-80% 3:1 EtOAc:EtOH with 1% TEA in DCM) to afford 3-(1-oxo-5-(((R)-1-((3-oxo-3,4-dihydro-2H-benzo[b][1,4]oxazin-5-yl)methyl)piperidin-2-yl)methoxy)isoindolin-2-yl)piperidine-2,6-dione 1-180 (3.1 mg, 5.80 μmol, 7.73% yield) as a white solid. LCMS [M+H]$^+$: 519.3. $^1$H NMR (400 MHz, CDCl$_3$) δ 10.62 (s, 1H), 7.94 (d, J=6.2 Hz, 1H), 7.79 (d, J=8.5 Hz, 1H), 7.24-7.14 (m, 1H), 7.10 (dt, J=8.5, 1.9 Hz, 1H), 6.92-6.77 (m, 2H), 6.77-6.68 (m, 1H), 5.18 (ddd, J=13.3, 5.3, 1.5 Hz, 1H), 4.67-4.19 (m, 6H), 4.03 (ddd, J=10.2, 4.8, 3.2 Hz, 1H), 3.31 (d, J=13.3 Hz, 1H), 2.98-2.75 (m, 3H), 2.71-2.58 (m, 1H), 2.33 (qd, J=13.1, 5.0 Hz, 1H), 2.25-2.14 (m, 1H), 2.13-2.06 (m, 1H), 2.00-1.88 (m, 1H), 1.86-1.78 (m, 1H), 1.78-1.67 (m, 1H), 1.50-1.37 (m, 2H).

Example 124: 2-(benzyloxy)acetaldehyde (INT-182)

Step 1: 2-(benzyloxy)ethan-1-ol (181)

2-(benzyloxy)acetic acid (319.6 mg, 1.923 mmol) was dissolved in THF (4 mL) and cooled to 0° C. 1 M borane tetrahydrofuran complex in THF (5.3 mL, 5.30 mmol) was added and the reaction warmed to room temperature overnight. The reaction was cooled to 0° C. and quenched with methanol (4 mL). The reaction was concentrated to dryness and reconstituted in MeOH (8.00 mL) and stirred at room temperature overnight. The reaction was concentrated and purified by silica gel chromatography (0-100% EtOAc in heptane) to afford 2-(benzyloxy)ethan-1-ol 181 as a clear liquid. $^1$H NMR (400 MHz, CD$_2$Cl$_2$) δ 7.39-7.25 (m, 5H), 4.55 (s, 2H), 3.74-3.67 (m, 2H), 3.62-3.53 (m, 2H).

Step 2: 2-(benzyloxy)acetaldehyde

In 40 mL vial, DCM (3.0 mL) was added followed by oxalyl chloride (0.2 mL, 2.29 mmol) then cooled to −78° C. DMSO (0.4 mL, 5.64 mmol) in DCM (3.0 mL) was added dropwise and the reaction mixture continue to stir at −78° C. for 30 mins. 2-(benzyloxy)ethan-1-ol 181 (293 mg, 1.925 mmol) in DCM (6 mL) was added dropwise and the reaction mixture continued to stir at −78° C. for 1 hr. Triethylamine (1.3 mL, 9.33 mmol) was added and the reaction warmed to r.t. overnight. The reaction was quenched with saturated aqueous ammonium chloride and extracted with DCM three times. The organic layers were combined, passed through a phase separated and concentrated in-vacuo. The crude material was purified by silica gel chromatography (0-100% EtOAc in heptane) to afford 2-(benzyloxy)acetaldehyde INT-182 (57.0 mg, 0.380 mmol, 19.7% yield) as a yellow liquid. $^1$H NMR (400 MHz, CD$_2$Cl$_2$) δ 9.71 (s, 1H), 3.28 (s, 3H), 2.13 (s, 6H).

Example 125: 3-(5-(((R)-1-(2-(benzyloxy)ethyl)piperidin-2-yl)methoxy)-1-oxoisoindolin-2-yl)piperidine-2,6-dione (I-183)

hydride (83.9 mg, 0.396 mmol) was added and the reaction stirred at room temperature overnight. The reaction was quenched with 50% saturated aqueous sodium bicarbonate. The reaction was extracted with 4:1 dichloromethane:isopropanol three times. The organic layers were combined, passed through a phase separator, and concentrated in-vacuo. The crude material was purified by silica gel chromatography (0-80% 3:1 EtOAc:EtOH with 1% TEA in DCM) to afford 3-(5-(((R)-1-(2-(benzyloxy)ethyl)piperidin-2-yl)methoxy)-1-oxoisoindolin-2-yl)piperidine-2,6-dione I-183 (33.3 mg, 0.065 mmol, 54.7% yield) as a white solid. LCMS [M+H]$^+$: 492.7. $^1$H NMR (400 MHz, DMSO-d6) δ 10.96 (s, 1H), 7.60 (d, J=8.4 Hz, 1H), 7.36-7.21 (m, 5H), 7.14 (d, J=2.2 Hz, 1H), 7.03 (dd, J=8.4, 2.2 Hz, 1H), 5.07 (dd, J=13.3, 5.1 Hz, 1H), 4.45 (s, 2H), 4.42-4.15 (m, 3H), 4.05-3.98 (m, 1H), 3.60-3.46 (m, 2H), 2.98-2.80 (m, 3H), 2.78-2.55 (m, 3H), 2.41-2.29 (m, 2H), 2.04-1.93 (m, 1H), 1.79-1.69 (m, 1H), 1.69-1.58 (m, 1H), 1.58-1.36 (m, 3H), 1.36-1.22 (m, 1H).

Example 127: 6-morpholinonicotinaldehyde (INT-185)

(6-morpholinopyridin-3-yl)methanol (150 mg, 0.772 mmol) was dissolved in DCM (3.9 mL). MnO$_2$ (1.34 g, 15.45 mmol) was added and the reaction mixture stirred at r.t. for 36 hrs. The reaction was diluted with DCM and passed through a layer of CELITE®. The filtrate was concentrated in-vacuo to afford 6-morpholinonicotinaldehyde

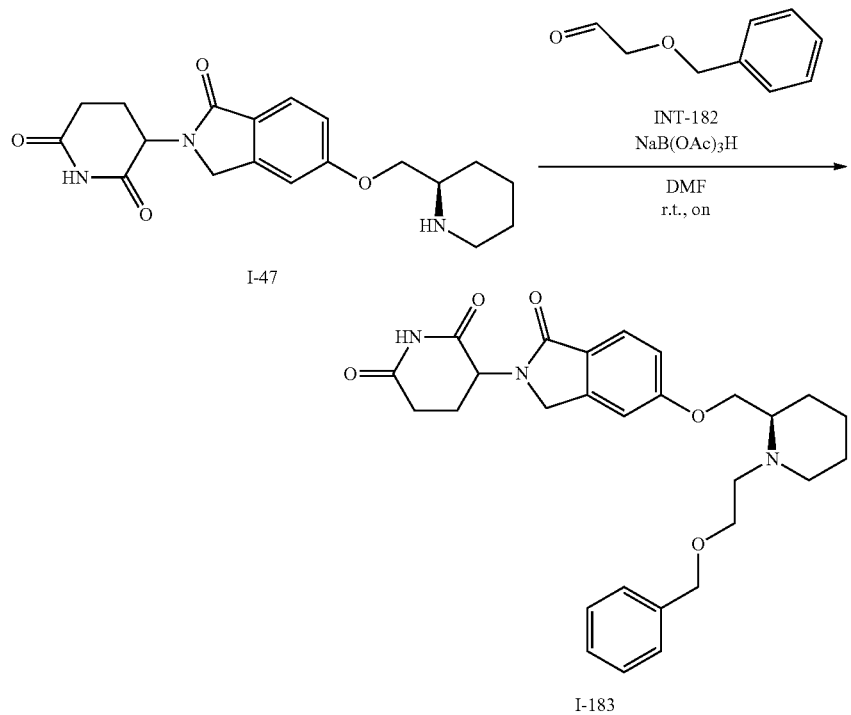

3-(1-oxo-5-(((R)-piperidin-2-yl)methoxy)isoindolin-2-yl)piperidine-2,6-dione I-47 (42.5 mg, 0.119 mmol) and 2-(benzyloxy)acetaldehyde INT-182 (57.0 mg, 0.380 mmol) were dissolved in DMF (0.8 mL). Sodium triacetoxyboro- INT-185 (121.5 mg, 0.632 mmol, 82% yield) as a light yellow solid. LCMS [M+H]$^+$: 193.2. $^1$H NMR (400 MHz, DMSO-d6) δ 9.76 (s, 1H), 8.61 (d, J=2.3 Hz, 1H), 7.91 (dd, J=9.1, 2.4 Hz, 1H), 6.96 (d, J=9.0 Hz, 1H), 3.69 (s, 8H).

Example 128: 3-(5-(((R)-1-((6-morpholinopyridin-3-yl)methyl)piperidin-2-yl)methoxy)-1-oxoisoindolin-2-yl)piperidine-2,6-dione (I-186)

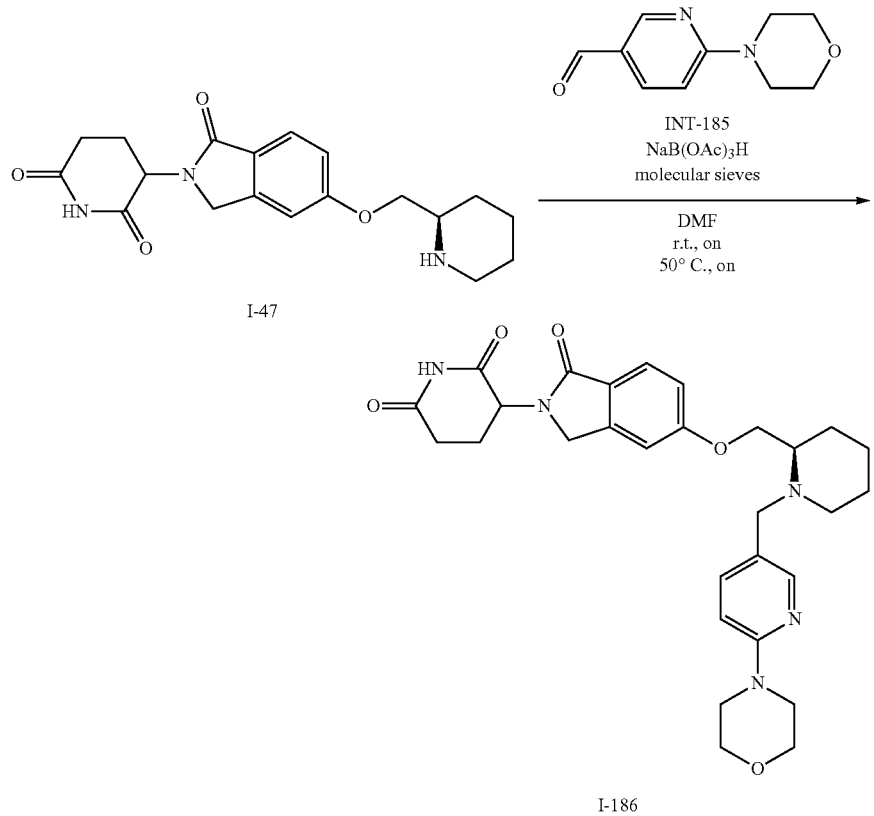

Compound I-186 was prepared according to General Method III starting from 3-(1-oxo-5-(((R)-piperidin-2-yl)methoxy)isoindolin-2-yl)piperidine-2,6-dione I-47 (0.1 g, 0.280 mmol) and 6-morpholinonicotinaldehyde INT-185 (81 mg, 0.420 mmol). The reaction was quenched with 50% saturated aqueous sodium bicarbonate and extracted three times with 4:1 DCM:iPrOH. The organic layers were combined, passed through phase separator and concentrated. The crude material was purified by silica gel chromatography (0-100% 3:1:0.01 EtOAc:EtOH:TEA in heptane). Fractions containing desired product were concentrated and lyophilized to afford 3-(5-(((R)-1-((6-morpholinopyridin-3-yl)methyl)piperidin-2-yl)methoxy)-1-oxoisoindolin-2-yl)piperidine-2,6-dione I-186 (73.6 mg, 0.138 mmol, 49.3% yield) as a white solid. LCMS [M+H]$^+$: 534.5. $^1$H NMR (400 MHz, DMSO-d6) δ 10.89 (s, 1H), 7.96 (d, J=2.3 Hz, 1H), 7.55 (d, J=8.4 Hz, 1H), 7.43 (dd, J=8.7, 2.3 Hz, 1H), 7.13 (s, 1H), 7.00 (dd, J=8.4, 2.3 Hz, 1H), 6.70 (d, J=8.7 Hz, 1H), 5.00 (dd, J=13.2, 5.0 Hz, 1H), 4.35-4.16 (m, 3H), 4.12-4.00 (m, 1H), 3.78 (d, J=13.5 Hz, 1H), 3.61 (dd, J=5.7, 3.9 Hz, 4H), 3.31 (t, J=4.9 Hz, 4H), 3.24-3.20 (m, 1H), 2.84 (ddd, J=17.2, 13.7, 5.4 Hz, 1H), 2.68-2.58 (m, 2H), 2.56-2.49 (m, 1H), 2.37-2.27 (m, 1H), 2.10-1.98 (m, 1H), 1.95-1.86 (m, 1H), 1.74-1.64 (m, 1H), 1.63-1.52 (m, 1H), 1.51-1.37 (m, 2H), 1.35-1.22 (m, 2H).

Example 129: 4-(3,6-dihydro-2H-pyran-4-yl)benzaldehyde (INT-187)

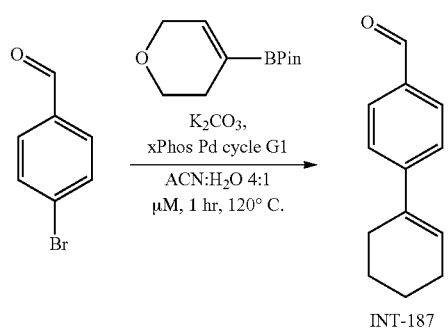

To a 5 mL microwave vial, 4-bromobenzaldehyde (0.3 g, 1.62 mmol), 2-(3,6-dihydro-2H-pyran-4-yl)-4,4,5,5-tetramethyl-1,3,2-dioxaborolane (0.511 g, 2.43 mmol), K$_2$CO$_3$ (0.672 g, 4.86 mmol), and XPhos Pd cycle G1 (0.120 g, 0.162 mmol) were added and suspended in acetonitrile (13 mL) and water (3.24 mL). The reaction was evacuated and backfilled with nitrogen three times. The reaction stirred at 100° C. for 1 hr under microwave radiation. The reaction was diluted with saturated ammonium chloride and extracted three times with dichloromethane. The organic layers were combined, passed through a phase separator and concentrated onto CELITE®. The crude material was purified by silica gel chromatography (0-50% ethyl acetate in heptane) to afford 4-(3,6-dihydro-2H-pyran-4-yl)benzaldehyde INT-187 (290 mg, 1.541 mmol, 95% yield) as a black oil. LCMS [M+H]+: 189.1. $^1$H NMR (400 MHz, CDCl$_3$) δ 10.02 (s, 1H), 7.91-7.82 (m, 2H), 7.60-7.54 (m, 2H), 6.34 (tt, J=3.1, 1.6 Hz, 1H), 4.39 (q, J=2.8 Hz, 2H), 3.98 (t, J=5.4 Hz, 2H), 2.62-2.52 (m, 2H).

Example 130: 3-(5-(((R)-1-(4-(3,6-dihydro-2H-pyran-4-yl)benzyl)piperidin-2-yl)methoxy)-1-oxoisoindolin-2-yl)piperidine-2,6-dione (I-188)

and extracted three times with 4:1 DCM:iPrOH. The organic layers were combined, passed through phase separator and concentrated in-vacuo. The crude material was purified by silica gel chromatography (0-100% 3:1:0.01 EtOAc:EtOH:TEA in heptane) to afford 3-(5-(((R)-1-(4-(3,6-dihydro-2H-pyran-4-yl)benzyl)piperidin-2-yl)methoxy)-1-oxoisoindolin-2-yl)piperidine-2,6-dione I-188 (159 mg, 0.300 mmol, 42.9% yield) as a white solid. LCMS [M+H]+: 530.1. $^1$H NMR (400 MHz, DMSO-d6) δ 10.89 (s, 1H), 7.54 (d, J=8.4 Hz, 1H), 7.30 (d, J=8.2 Hz, 2H), 7.23 (d, J=8.0 Hz, 2H), 7.10 (d, J=2.4 Hz, 1H), 6.99 (dd, J=8.4, 2.3 Hz, 1H), 6.16-6.09 (m, 1H), 5.00 (dd, J=13.3, 5.0 Hz, 1H), 4.33-4.09 (m, 5H),

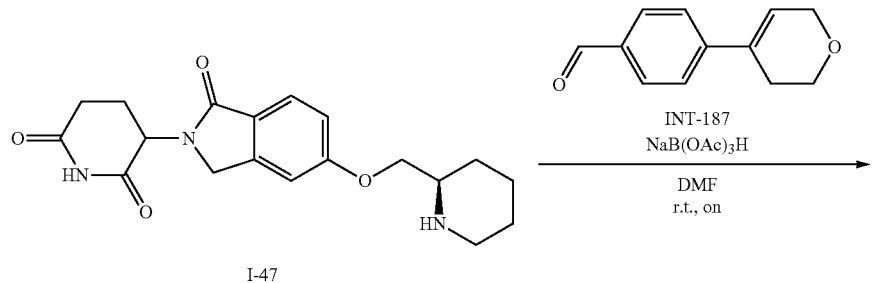

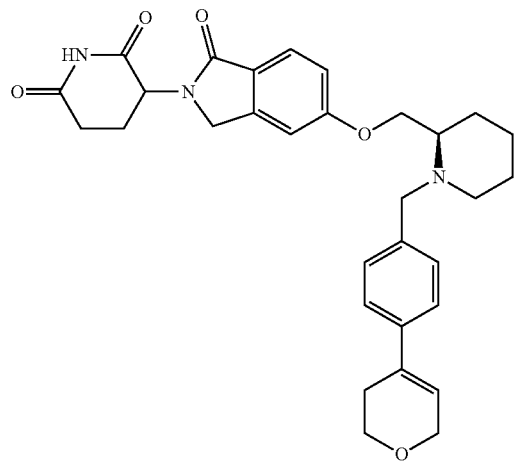

I-188

Compound I-188 was prepared according to General Method III starting from 3-(1-oxo-5-(((R)-piperidin-2-yl)methoxy)isoindolin-2-yl)piperidine-2,6-dione I-47 (0.25 g, 0.699 mmol) and 4-(3,6-dihydro-2H-pyran-4-yl)benzaldehyde INT-187 (0.197 g, 1.049 mmol). The reaction was quenched with 50% saturated aqueous sodium bicarbonate 4.06 (dd, J=10.3, 5.4 Hz, 1H), 3.91 (d, J=13.9 Hz, 1H), 3.74 (t, J=5.4 Hz, 2H), 3.33 (d, J=13.8 Hz, 1H), 2.84 (ddd, J=17.2, 13.6, 5.4 Hz, 1H), 2.72-2.57 (m, 2H), 2.57-2.48 (m, 1H), 2.38-2.28 (m, 3H), 2.11-2.01 (m, 1H), 1.96-1.86 (m, 1H), 1.75-1.68 (m, 1H), 1.64-1.52 (m, 1H), 1.51-1.25 (m, 4H).

Example 131: Tert-butyl 4-(5-(((2R)-2-(((2-(2,6-dioxopiperidin-3-yl)-1-oxoisoindolin-5-yl)oxy)methyl)piperidin-1-yl)methyl)pyridin-2-yl)piperazine-1-carboxylate (I-189)

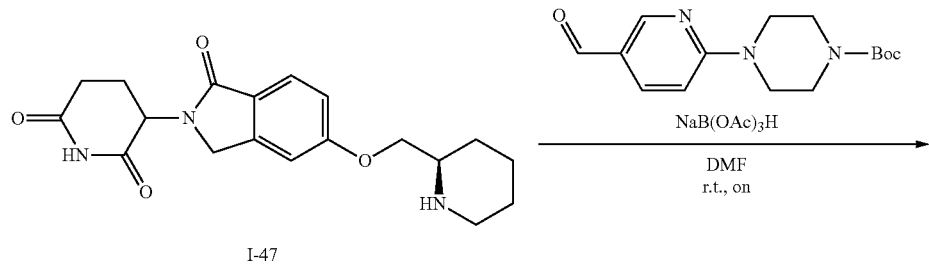

I-47

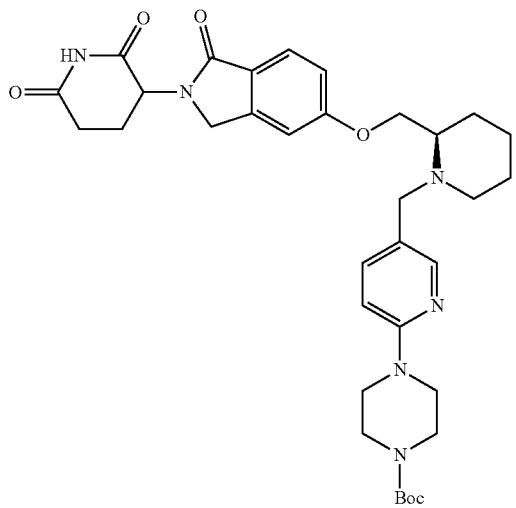

I-189

Compound I-189 was prepared according to General Method III starting from 3-(1-oxo-5-(((R)-piperidin-2-yl)methoxy)isoindolin-2-yl)piperidine-2,6-dione I-47 (0.121 g, 0.339 mmol) and 4-(5-formylpyridin-2-yl)piperazine, N1-boc protected (0.148 g, 0.508 mmol). The reaction was quenched with 50% saturated aqueous sodium bicarbonate and extracted three times with 4:1 DCM:iPrOH. The organic layers were combined, passed through phase separator and concentrated in-vacuo. The crude material was purified by silica gel chromatography (0-100% 3:1:0.01 EtOAc:EtOH:TEA in heptane) to afford tert-butyl 4-(5-(((2R)-2-(((2-(2,6-dioxopiperidin-3-yl)-1-oxoisoindolin-5-yl)oxy)methyl)piperidin-1-yl)methyl)pyridin-2-yl)piperazine-1-carboxylate I-189 (104 mg, 0.164 mmol, 48.5% yield) as a white solid. LCMS [M+H]$^+$: 633.6. $^1$H NMR (400 MHz, DMSO-d6) δ 10.97 (s, 1H), 8.03 (d, J=2.4 Hz, 1H), 7.62 (d, J=8.5 Hz, 1H), 7.50 (dd, J=8.7, 2.3 Hz, 1H), 7.21 (d, J=2.2 Hz, 1H), 7.08 (dd, J=8.4, 2.2 Hz, 1H), 6.80 (d, J=8.7 Hz, 1H), 5.08 (dd, J=13.3, 5.1 Hz, 1H), 4.43-4.23 (m, 4H), 4.14 (dd, J=10.3, 5.3 Hz, 1H), 3.85 (d, J=13.6 Hz, 1H), 2.96-2.78 (m, 3H), 2.76-2.69 (m, 2H), 2.63-2.56 (m, 1H), 2.43-2.37 (m, 1H), 2.15-2.04 (m, 1H), 2.02-1.94 (m, 1H), 1.82-1.73 (m, 2H), 1.69-1.59 (m, 2H), 1.53-1.46 (m, 4H), 1.45-1.40 (m, 11H), 1.38-1.32 (m, 2H).

Example 132: 3-(5-(((R)-1-((6-(4-ethylpiperazin-1-yl)pyridin-3-yl)methyl)piperidin-2-yl)methoxy)-1-oxoisoindolin-2-yl)piperidine-2,6-dione (I-191)

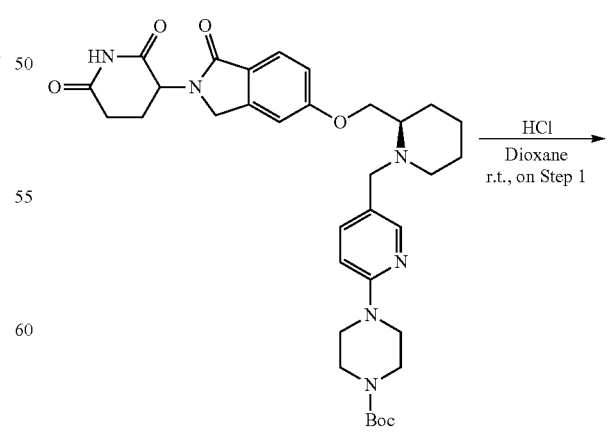

I-189

-continued

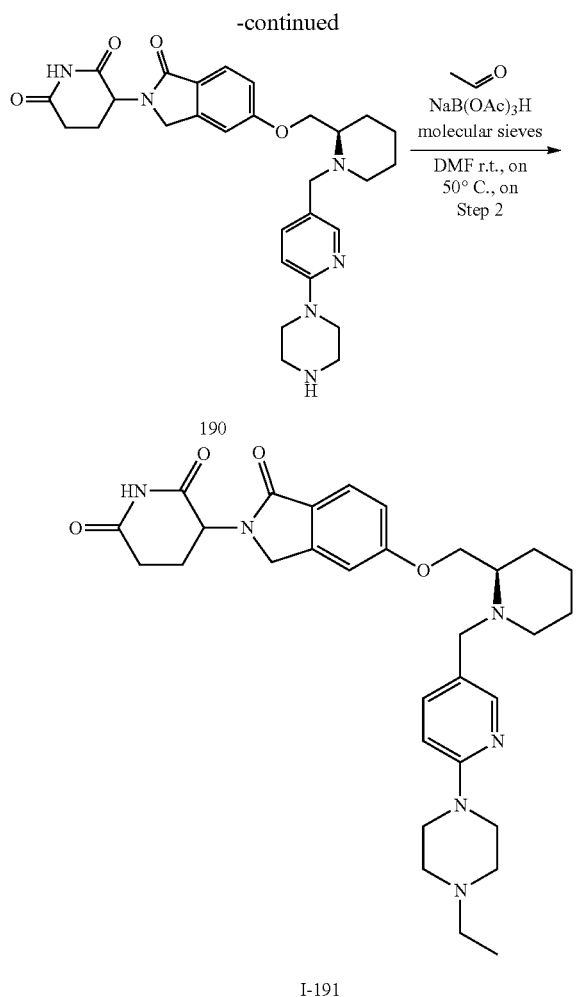

Step 1: 3-(1-oxo-5-(((R)-1-((6-(piperazin-1-yl)pyridin-3-yl)methyl)piperidin-2-yl)methoxy)isoindolin-2-yl)piperidine-2,6-dione (190)

Tert-butyl 4-(5-(((2R)-2-(((2-(2,6-dioxopiperidin-3-yl)-1-oxoisoindolin-5-yl)oxy)methyl)piperidin-1-yl)methyl)pyridin-2-yl)piperazine-1-carboxylate I-189 (0.104 g, 0.164 mmol) was suspended in dioxane (0.55 mL) and dissolved in trifluoroethanol (0.55 mL). 4M HCl in dioxane (0.25 mL, 0.986 mmol) was added and the reaction stirred at r.t. for 96 hrs. Reaction was concentrated then diluted with 4:1 DCM: iPrOH. The reaction was quenched with 50% saturated aqueous sodium bicarbonate. The aqueous layer was extracted 4 times with 4:1 DCM:iPrOH. The organic layers were combined, passed through a phase separator and concentrated to afford 3-(1-oxo-5-(((R)-1-((6-(piperazin-1-yl)pyridin-3-yl)methyl)piperidin-2-yl)methoxy)isoindolin-2-yl)piperidine-2,6-dione 190 as a cream solid. The material was taken on to the next step without purification. LCMS [M+H]+: 533.5.

Step 2: 3-(5-(((R)-1-((6-(4-ethylpiperazin-1-yl)pyridin-3-yl)methyl)piperidin-2-yl)methoxy)-1-oxoisoindolin-2-yl)piperidine-2,6-dione (I-191)

To a solution of 3-(1-oxo-5-(((R)-1-((6-(piperazin-1-yl)pyridin-3-yl)methyl)piperidin-2-yl)methoxy)isoindolin-2-yl)piperidine-2,6-dione 190 (93.6 mg, 0.176 mmol) in DMF (1 mL), sodium triacetoxyborohydride (74 mg, 0.351 mmol) was added. Then acetaldehyde (0.015 mL, 0.264 mmol) was added. The reaction stirred at r.t. for 36 hrs. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-((6-(4-ethylpiperazin-1-yl)pyridin-3-yl)methyl)piperidin-2-yl)methoxy)-1-oxoisoindolin-2-yl)piperidine-2,6-dione I-191 (61.4 mg, 0.108 mmol, 61.7% yield) as a white solid. LCMS [M+H]+: 561.6. 1H NMR (400 MHz, DMSO-d6) δ 10.89 (s, 1H), 7.93 (d, J=2.3 Hz, 1H), 7.55 (d, J=8.4 Hz, 1H), 7.40 (dd, J=8.3, 2.3 Hz, 1H), 7.18-7.09 (m, 1H), 7.00 (dd, J=8.3, 2.3 Hz, 1H), 6.70 (d, J=8.6 Hz, 1H), 5.00 (dd, J=13.2, 5.0 Hz, 1H), 4.36-4.14 (m, 3H), 4.06 (dd, J=10.3, 5.4 Hz, 1H), 3.76 (d, J=13.5 Hz, 1H), 3.40-3.30 (m, 4H), 3.23-3.19 (m, 1H), 2.84 (ddd, J=17.2, 13.6, 5.5 Hz, 1H), 2.64 (dt, J=9.0, 4.5 Hz, 2H), 2.56-2.48 (m, 1H), 2.38-2.25 (m, 7H), 2.06-1.98 (m, 1H), 1.95-1.86 (m, 1H), 1.74-1.66 (m, 1H), 1.61-1.52 (m, 1H), 1.48-1.37 (m, 2H), 1.35-1.21 (m, 2H), 0.96 (t, J=7.2 Hz, 3H).

Example 135: 5-formyl-2-methoxybenzonitrile (INT-195)

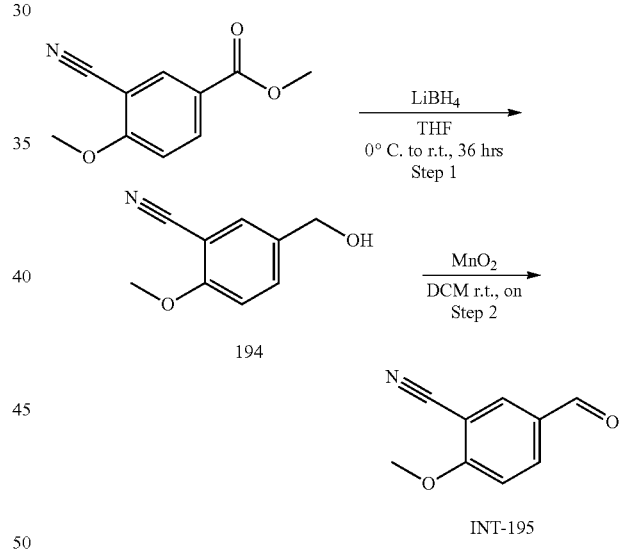

Step 1: 5-(hydroxymethyl)-2-methoxybenzonitrile, (3-(aminomethyl)-4-methoxyphenyl)methanol (194)

Methyl 3-cyano-4-methoxybenzoate (0.15 g, 0.785 mmol) was dissolved in THF (3.92 mL) and cooled to 0° C. 2M LiBH4 in THF (1.57 mL, 3.14 mmol) was added dropwise and the reaction stirred at r.t. for 36 hrs. The reaction was cooled to 0° C. and quenched with MeOH (10 mL). The reaction stirred at r.t. for 2 hrs. The reaction was concentrated, diluted with EtOAc and washed with saturated aqueous ammonium chloride. The aqueous layer was extracted three times with EtOAc. The organic layers were combined, passed through a phase separator and concentrated to afford 5-(hydroxymethyl)-2-methoxybenzonitrile 194 as a clear light yellow oil. The material was taken on to the next step without purification. ¹H NMR (400 MHz, CD₃OD) δ 7.53-7.42 (m, 2H), 7.02 (d, J=8.6 Hz, 1H), 4.44 (s, 2H), 3.82 (s, 3H).

Step 2: 5-formyl-2-methoxybenzonitrile (INT-195)

5-(hydroxymethyl)-2-methoxybenzonitrile 194 (0.137 g, 0.840 mmol) was dissolved in DCM (4.2 mL). MnO₂ (1.46 g, 16.79 mmol) was added and the reaction mixture stirred at r.t. for 18 hrs. The reaction was diluted with DCM and passed through a layer of CELITE®. The filtrate was concentrated to afford 5-formyl-2-methoxybenzonitrile INT-195 (101 mg, 0.627 mmol, 74.6% yield) as a light cream solid. The material was taken on to the next step without purification. ¹H NMR (400 MHz, CDCl₃) δ 9.83 (s, 1H), 8.06-7.98 (m, 2H), 7.06 (d, J=8.5 Hz, 1H), 3.98 (s, 3H).

Example 136: 5-(((2R)-2-(((2-(2,6-dioxopiperidin-3-yl)-1-oxoisoindolin-5-yl)oxy)methyl)piperidin-1-yl)methyl)-2-methoxybenzonitrile (I-196)

0.476 mmol) and 5-formyl-2-methoxybenzonitrile INT-195 (0.101 g, 0.627 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 5-(((2R)-2-(((2-(2,6-dioxopiperidin-3-yl)-1-oxoisoindolin-5-yl)oxy)methyl)piperidin-1-yl)methyl)-2-methoxybenzonitrile I-196 (60.8 mg, 0.121 mmol, 25.4% yield) as a white solid. LCMS [M+H]⁺: 503.2. ¹H NMR (400 MHz, DMSO-d6) δ 10.89 (s, 1H), 7.61-7.45 (m, 3H), 7.12-7.02 (m, 2H), 6.97 (dt, J=8.3, 2.4 Hz, 1H), 5.00 (dd, J=13.3, 5.0 Hz, 1H), 4.31 (d, J=17.1 Hz, 1H), 4.26-4.13 (m, 2H), 4.10-4.00 (m, 1H), 3.85 (d, J=14.0 Hz, 1H), 3.79 (d, J=1.5 Hz, 3H), 3.33 (d, J=13.9 Hz, 1H), 2.84 (ddd, J=17.2, 13.5, 5.4 Hz, 1H), 2.70-2.60 (m, 2H), 2.56-

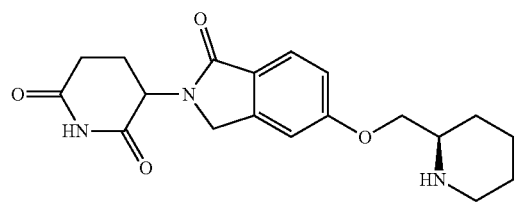

I-47

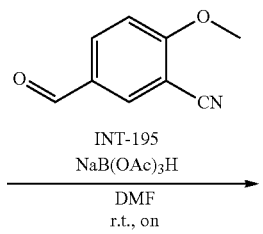

INT-195
NaB(OAc)₃H
────────→
DMF
r.t., on

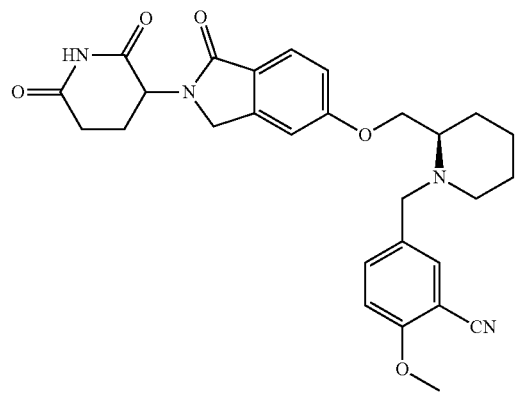

I-196

Compound I-196 was prepared according to General Method III starting from 3-(1-oxo-5-(((R)-piperidin-2-yl)methoxy)isoindolin-2-yl)piperidine-2,6-dione I-47 (0.17 g, 2.49 (m, 1H), 2.38-2.24 (m, 1H), 2.11-2.03 (m, 1H), 1.95-1.87 (m, 1H), 1.74-1.67 (m, 1H), 1.64-1.54 (m, 1H), 1.51-1.25 (m, 4H).

Example 137: 3-(1-oxo-5-(((R)-1-(4-(1-((tetrahydro-2H-pyran-4-yl)methyl)piperidin-4-yl)benzyl)piperidin-2-yl)methoxy)isoindolin-2-yl)piperidine-2,6-dione (I-197)

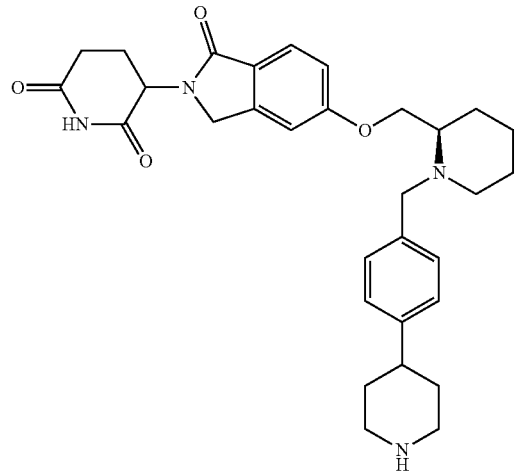

INT-128

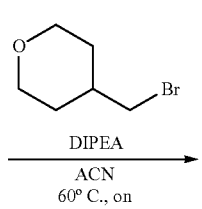

DIPEA
ACN
60° C., on

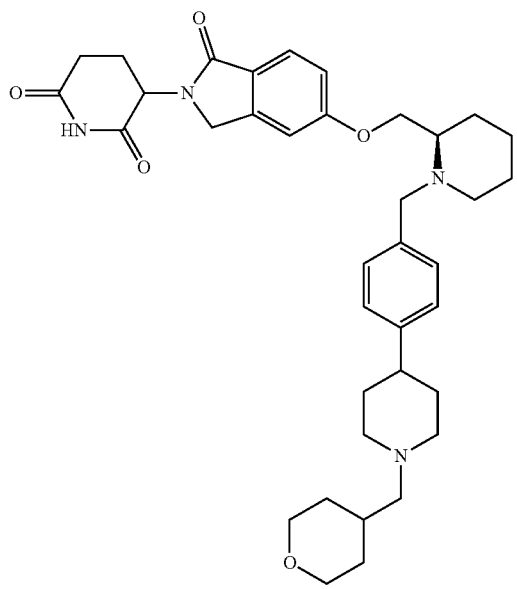

I-197

To a suspension of 3-(1-oxo-5-(((R)-1-(4-(piperidin-4-yl)benzyl)piperidin-2-yl)methoxy)isoindolin-2-yl)piperidine-2,6-dione INT-128 (75 mg, 0.141 mmol) in ACN (1 mL) was added 4-(bromomethyl)tetrahydro-2H-pyran (0.028 mL, 0.212 mmol). DIPEA (0.074 mL, 0.424 mmol) was added and the reaction stirred at 60° C. overnight. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(1-oxo-5-(((R)-1-(4-(1-((tetrahydro-2H-pyran-4-yl)methyl)piperidin-4-yl)benzyl)piperidin-2-yl)methoxy)isoindolin-2-yl)piperidine-2,6-dione I-197 (22.6 mg, 0.033 mmol, 23.40% yield) as a white solid. LCMS [M+H]–: 629.6. $^1$H NMR (400 MHz, DMSO-d6) δ 10.89 (s, 1H), 7.53 (d, J=8.4 Hz, 1H), 7.16 (d, J=7.9 Hz, 2H), 7.13-7.05 (m, 3H), 6.98 (dd, J=8.4, 2.2 Hz, 1H), 5.00 (dd, J=13.3, 5.1 Hz, 1H), 4.34-4.10 (m, 3H), 4.05 (dd, J=10.3, 5.3 Hz, 1H), 3.88 (d, J=13.7 Hz, 1H), 3.81-3.70 (m, 2H), 3.23-3.21 (m, 2H), 2.90-2.77 (m, 3H), 2.71-2.62 (m, 2H), 2.56-2.48 (m, 1H), 2.36-2.28 (m, 2H), 2.09-1.99 (m, 3H), 1.96-1.81 (m, 3H), 1.77-1.24 (m, 14H), 1.06 (dd, J=12.7, 8.5 Hz, 2H).

Example 138: 3-(5-(((R)-1-(4-(1-(2-fluoroethyl)piperidin-4-yl)benzyl)piperidin-2-yl)methoxy)-1-oxoisoindolin-2-yl)piperidine-2,6-dione (I-198)

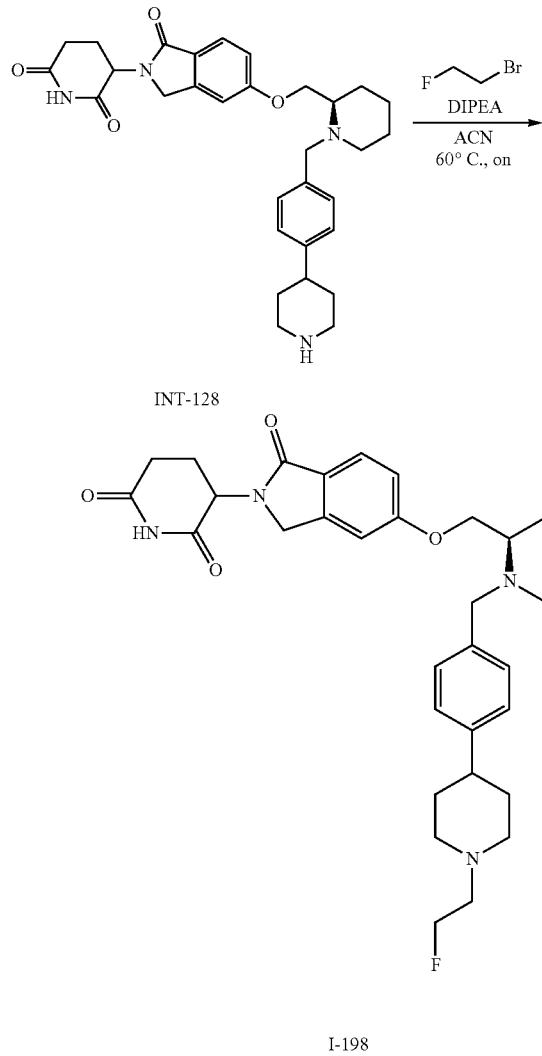

To a suspension of 3-(1-oxo-5-(((R)-1-(4-(piperidin-4-yl)benzyl)piperidin-2-yl)methoxy)isoindolin-2-yl)piperidine-2,6-dione INT-128 (75 mg, 0.141 mmol) in ACN (1 mL), 1-bromo-2-fluoroethane (0.016 mL, 0.212 mmol) was added. Then DIPEA (0.074 mL, 0.424 mmol) was added. The reaction stirred at 60° C. overnight. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-(4-(1-(2-fluoroethyl)piperidin-4-yl)benzyl)piperidin-2-yl)methoxy)-1-oxoisoindolin-2-yl)piperidine-2,6-dione I-198 (48.9 mg, 0.083 mmol, 58.8% yield) as a white solid. LCMS [M+H]⁻⁺: 577.6. ¹H NMR (400 MHz, DMSO-d6) δ 10.89 (s, 1H), 7.54 (d, J=8.4 Hz, 1H), 7.16 (d, J=8.1 Hz, 2H), 7.12-7.05 (m, 3H), 6.98 (dd, J=8.7, 2.3 Hz, 1H), 5.00 (dd, J=13.3, 5.1 Hz, 1H), 4.53 (t, J=4.9 Hz, 1H), 4.41 (t, J=4.9 Hz, 1H), 4.36-4.14 (m, 3H), 4.05 (dd, J=10.3, 5.3 Hz, 1H), 3.89 (d, J=13.8 Hz, 1H), 2.95-2.78 (m, 3H), 2.72-2.57 (m, 3H), 2.56-2.48 (m, 2H), 2.38-2.27 (m, 2H), 2.10-1.97 (m, 3H), 1.95-1.86 (m, 1H), 1.76-1.23 (m, 11H).

Example 139: Benzo[d]oxazole-5-carbaldehyde (INT-200)

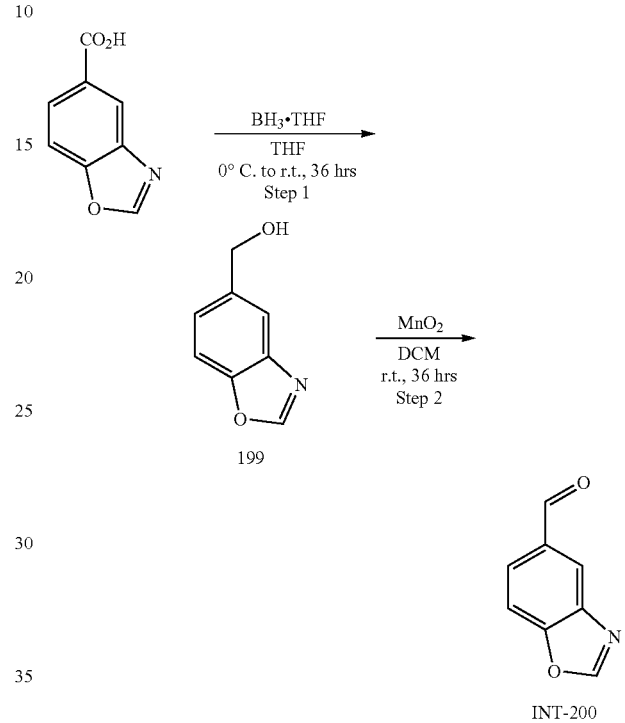

Step 1: Benzo[d]oxazol-5-ylmethanol (199)

Benzo[d]oxazole-5-carboxylic acid (0.1 g, 0.613 mmol) was dissolved in THF (2.04 mL) and cooled to 0° C. 1 M borane tetrahydrofuran complex in THF (1.84 mL, 1.84 mmol) was added dropwise. The reaction stirred at r.t. for 36 hrs. The reaction was cooled to 0° C. and quenched with methanol (1.5 mL) and stirred at r.t. for 2 hrs. The reaction was concentrated to dryness then redissolved in methanol (5 mL). The reaction was left to stir at r.t. for 96 hrs. The reaction was concentrated to afford benzo[d]oxazol-5-ylmethanol 199 as a brown oil. Material was taken on to the next step without purification assuming quantitative yield. LCMS [M+H]⁺: 150.1.

Step 2: Benzo[d]oxazole-5-carbaldehyde (INT-200)

Benzo[d]oxazol-5-ylmethanol 199 (91 mg, 0.613 mmol) was dissolved in DCM (3.9 mL). MnO₂ (1.07 g, 12.3 mmol) was added and the reaction mixture stirred at r.t. for 36 hrs. The reaction was diluted with DCM and passed through a layer of CELITE®. The filtrate was concentrated to afford benzo[d]oxazole-5-carbaldehyde INT-200 (46.5 mg, 0.316 mmol, 51.6% yield) as a red-brown solid. LCMS [M+H]⁺: 148.1. ¹H NMR (400 MHz, CDCl₃) δ 10.05 (s, 1H), 8.26 (d, J=1.6 Hz, 1H), 8.15 (s, 1H), 7.94 (dd, J=8.4, 1.6 Hz, 1H), 7.67 (d, J=8.5 Hz, 1H).

Example 140: 3-(5-(((R)-1-(benzo[d]oxazol-5-ylmethyl)piperidin-2-yl)methoxy)-1-oxoisoindolin-2-yl)piperidine-2,6-dione (I-201)

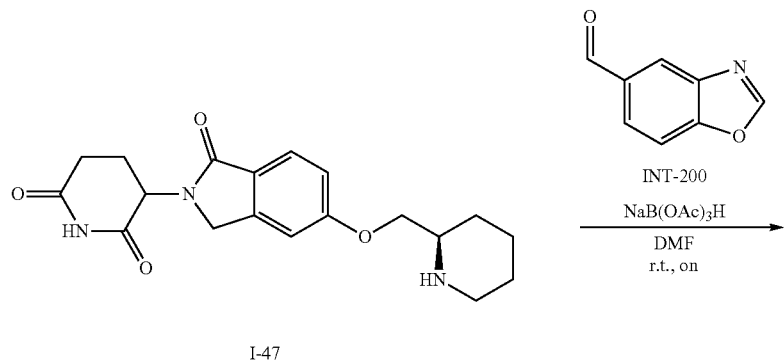

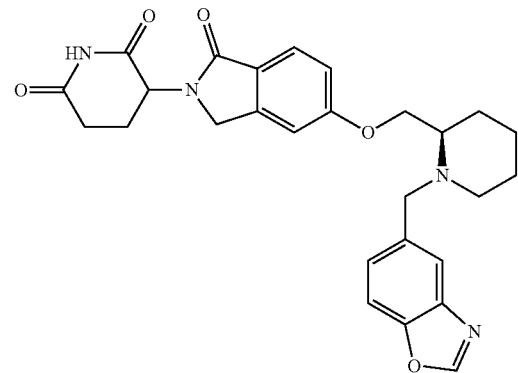

I-201

Compound I-201 was prepared according to General Method III starting from 3-(1-oxo-5-(((R)-piperidin-2-yl)methoxy)isoindolin-2-yl)piperidine-2,6-dione I-47 (0.08 g, 0.224 mmol) and benzo[d]oxazole-5-carbaldehyde INT-200 (46.5 mg, 0.316 mmol). The reaction was quenched with 50% saturated aqueous sodium bicarbonate and extracted three times with 4:1 DCM:iPrOH. The organic layers were combined, passed through phase separator and concentrated in-vacuo. The crude material was purified by silica gel chromatography (0-100% 3:1:0.01 EtOAc:EtOH:TEA in heptane). Product was further purified by reverse phase HPLC (25-50% ACN in H$_2$O with 5 mM NH$_4$OH as modifier). Fractions contained 3 drops formic acid prior to sample collection. Fractions containing pure product were combined and lyophilized to afford formate salt of 3-(5-(((R)-1-(benzo[d]oxazol-5-ylmethyl)piperidin-2-yl)methoxy)-1-oxoisoindolin-2-yl)piperidine-2,6-dione I-201 (3.17 mg, 5.63 µmol, 2.52% yield) as a light beige solid. LCMS [M+H]$^+$: 489.4. $^1$H NMR (400 MHz, DMSO-d6) δ 10.89 (s, 1H), 8.61 (d, J=1.4 Hz, 1H), 8.20 (s, 1H), 7.66 (d, J=1.5 Hz, 1H), 7.60 (d, J=8.3 Hz, 1H), 7.53 (d, J=8.4 Hz, 1H), 7.35 (dd, J=8.5, 1.5 Hz, 1H), 7.11 (t, J=2.7 Hz, 1H), 7.05-6.96 (m, 1H), 5.00 (dd, J=13.3, 5.1 Hz, 1H), 4.35-4.24 (m, 2H), 4.24-3.98 (m, 3H), 3.47 (d, J=13.7 Hz, 1H), 2.89-2.79 (m, 1H), 2.76-2.69 (m, 1H), 2.69-2.63 (m, 1H), 2.56-2.49 (m, 1H), 2.37-2.27 (m, 1H), 2.15-2.06 (m, 1H), 1.95-1.89 (m, 1H), 1.79-1.70 (m, 1H), 1.64-1.56 (m, 1H), 1.51-1.27 (m, 4H).

Example 142: 3-(5-(((R)-1-(4-(1-(oxetan-3-ylmethyl)piperidin-4-yl)benzyl)piperidin-2-yl)methoxy)-1-oxoisoindolin-2-yl)piperidine-2,6-dione (I-203)

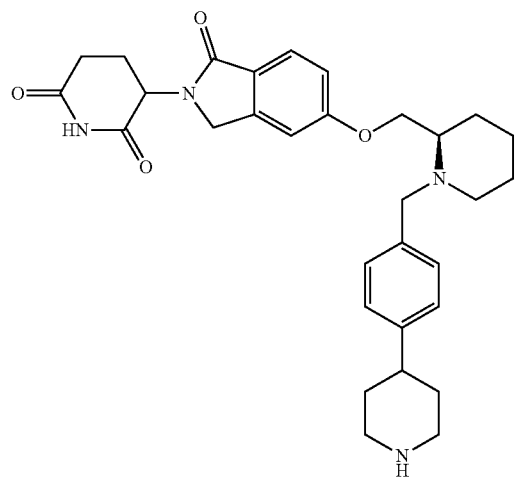

INT-128

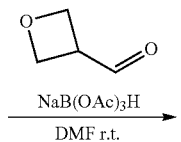

NaB(OAc)₃H
DMF r.t.

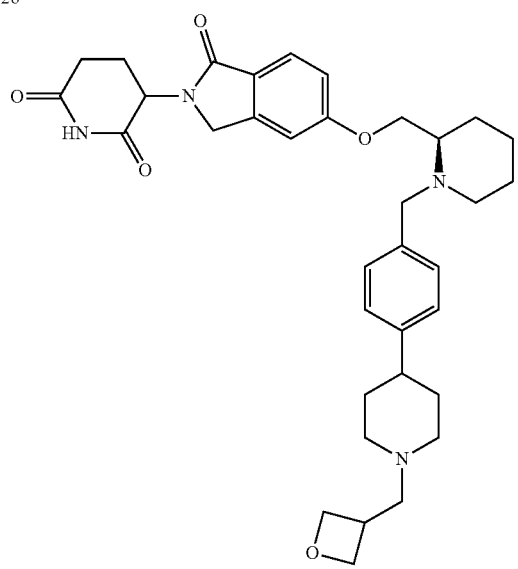

I-203

Compound I-203 was prepared according to General Method III starting from 3-(1-oxo-5-(((R)-1-(4-(piperidin-4-yl)benzyl)piperidin-2-yl)methoxy)isoindolin-2-yl)piperidine-2,6-dione INT-128 (0.078 g, 0.147 mmol) and oxetane-3-carbaldehyde (0.015 ml, 0.220 mmol). The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% 3:1 EtOAc:EtOH with 1% TEA in heptane) to afford 3-(5-(((R)-1-(4-(1-(oxetan-3-ylmethyl)piperidin-4-yl)benzyl)piperidin-2-yl)methoxy)-1-oxoisoindolin-2-yl)piperidine-2,6-dione I-203 (40.2 mg, 0.066 mmol, 45.1% yield) as a white solid. LCMS [M+H]⁻⁺: 601.3. ¹H NMR (400 MHz, DMSO-d6) δ 10.97 (s, 1H), 7.61 (d, J=8.4 Hz, 1H), 7.23 (d, J=7.8 Hz, 2H), 7.21-7.10 (m, 3H), 7.06 (dd, J=8.4, 2.2 Hz, 1H), 5.08 (dd, J=13.4, 5.1 Hz, 1H), 4.65 (dd, J=7.8, 5.8 Hz, 2H), 4.42-4.21 (m, 5H), 4.12 (dd, J=10.2, 5.3 Hz, 1H), 3.96 (d, J=13.8 Hz, 1H), 3.24-3.14 (m, 1H), 2.96-2.80 (m, 3H), 2.78-2.70 (m, 2H), 2.66-2.56 (m, 3H), 2.45-2.36 (m, 2H), 2.16-2.06 (m, 1H), 2.03-1.93 (m, 3H), 1.84-1.74 (m, 1H), 1.72-1.30 (m, 10H).

Example 143: Tetrahydrofuran-3-carbaldehyde (INT-205)

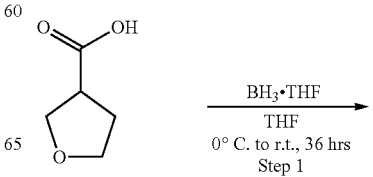

BH₃•THF
THF
0° C. to r.t., 36 hrs
Step 1

Step 1: (tetrahydrofuran-3-yl)methanol (204)

Tetrahydrofuran-3-carboxylic acid (304 mg, 2.62 mmol) was dissolved in THF (4 mL) and cooled to 0° C. 1M borane tetrahydrofuran complex in THF (7.9 mL, 7.90 mmol) was added and the reaction warmed to r.t. overnight. The reaction was then cooled to 0° C. and quenched with methanol (5 mL). The reaction was concentrated to dryness, reconstituted in MeOH (8.00 mL) and stirred at r.t. overnight. The reaction was concentrated and purified by silica gel chromatography (0-80% 3:1:0.01 EtOAc:EtOH:TEA in dichloromethane) to afford (tetrahydrofuran-3-yl)methanol 204 (162.2 mg, 1.59 mmol, 60.6% yield) as a clear liquid. $^1$H NMR (400 MHz, CDCl$_3$) δ 3.91-3.80 (m, 2H), 3.74 (ddd, J=8.5, 7.6, 6.9 Hz, 1H), 3.68-3.54 (m, 3H), 2.55-2.37 (m, 1H), 2.10-1.96 (m, 1H), 1.64 (dddd, J=12.5, 8.0, 7.0, 5.6 Hz, 1H).

Step 2: Tetrahydrofuran-3-carbaldehyde (INT-205)

In 40 mL vial, DCM (2.0 mL) was added followed by oxalyl chloride (0.18 mL, 2.056 mmol) then cooled to −78° C. DMSO (0.35 mL, 4.93 mmol) in DCM (2.0 mL) was added dropwise and the reaction mixture continue to stir at −78° C. for 30 mins. (tetrahydrofuran-3-yl)methanol 204 (162.2 mg, 1.59 mmol) in DCM (3 mL) was added dropwise and the reaction mixture continued to stir at −78° C. for 1 hr. Triethylamine (1.1 mL, 7.89 mmol) was added and the reaction warmed to r.t. overnight. The reaction was quenched with saturated aqueous ammonium chloride and extracted with DCM three times. The organic layers were combined, passed through a phase separated and concentrated to afford tetrahydrofuran-3-carbaldehyde INT-205 as a yellow liquid with a white precipitate. The material was taken on to the next step without purification.

Example 144: Diastereomers 5-(((2R)-1-((tetrahydrofuran-3-yl)methyl)piperidin-2-yl)methoxy)isobenzofuran-1(3H)-one (INT-209)

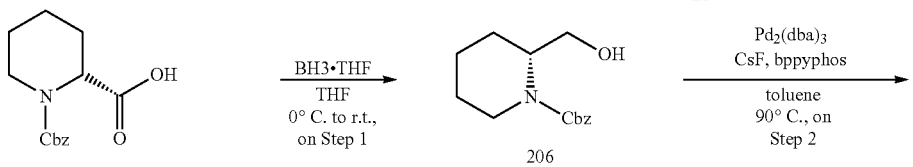

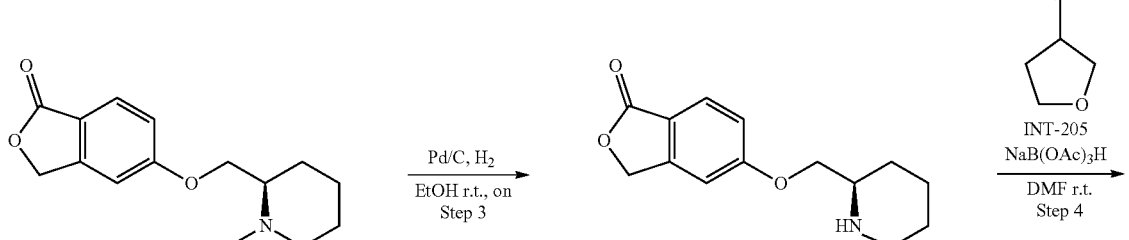

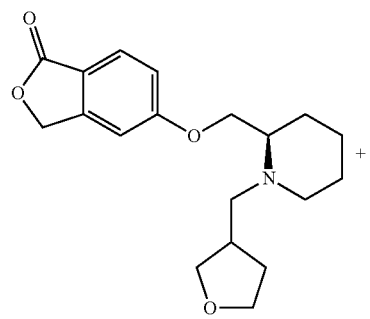

INT-209
peak 1

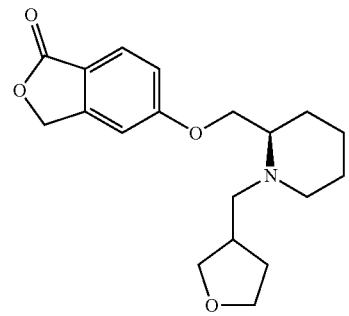

INT-209
peak 2

Step 1: Benzyl (R)-2-(hydroxymethyl)piperidine-1-carboxylate (206)

To a solution of (R)-1-((benzyloxy)carbonyl)piperidine-2-carboxylic acid (5 g, 19 mmol) in THF (76 mL) at 0-5° C. was added 1M borane-tetrahydrofuran complex in THF (3.1 g, 36.1 mmol) dropwise keeping the internal temperature below 5° C. The reaction warmed to r.t. and stirred at r.t. overnight. Ice was slowly added to the reaction and the reaction was allowed to come to r.t. The reaction was extracted twice with EtOAc. The organic layers were combined, washed with brine, dried over anhydrous $Na_2SO_4$, filtered and concentrated in-vacuo. The crude material was purified by silica gel chromatography (0-100% EtOAc in heptane) to afford benzyl (R)-2-(hydroxymethyl)piperidine-1-carboxylate 206 (4.15 g, 16.7 mmol, 88% yield) as an oil. LCMS $[M+H]^{-+}$: 250.2.

Step 2: Benzyl (R)-2-(((1-oxo-1,3-dihydroisobenzofuran-5-yl)oxy)methyl)piperidine-1-carboxylate (207)

CsF (1.23 g, 8.06 mmol), bppyphos (68 mg, 0.134 mmol), $Pd_2dba_3$ (62 mg, 0.067 mmol) and 5-bromoisobenzofuran-1(3H)-one (687 mg, 3.22 mmol) were suspended in toluene (13.4 mL) and purged with Nitrogen. The reaction mixture stirred at 90° C. and until a color change was visible. Benzyl (R)-2-(hydroxymethyl)piperidine-1-carboxylate 206 (670 mg, 2.69 mmol) was added and the reaction stirred at 90° C. overnight. The reaction mixture was cooled to r.t. and filtered through a pad of CELITE®. The mixture was washed with saturated aqueous $NaHCO_3$, brine, dried over $Na_2SO_4$, filtered and concentrated in-vacuo. The crude material was purified by silica gel chromatography (10-60% EtOAc in heptane) to afford benzyl (R)-2-(((1-oxo-1,3-dihydroisobenzofuran-5-yl)oxy)methyl)piperidine-1-carboxylate 207 (880 mg, 2.31 mmol, 86% yield). LCMS $[M+H]^{-+}$: 382.4.

Step 3: (R)-5-(piperidin-2-ylmethoxy)isobenzofuran-1(3H)-one (208)

Benzyl (R)-2-(((1-oxo-1,3-dihydroisobenzofuran-5-yl)oxy)methyl)piperidine-1-carboxylate 207 (0.880 g, 2.307 mmol) was dissolved in EtOH (23.1 mL). The reaction was purged with nitrogen for 5 minutes. Then 10% wet Pd on carbon (0.246 g, 0.231 mmol) was added. The reaction was purged with a hydrogen balloon for 10 minutes. The reaction stirred at r.t. for 24 hrs with a hydrogen balloon on top. The reaction was purged with nitrogen for 5 minutes then passed through a plug of CELITE® rinsing with DCM. The filtrate was concentrated to afford (R)-5-(piperidin-2-ylmethoxy)isobenzofuran-1(3H)-one 208 (556.7 mg, 2.251 mmol, 98% yield) as a cream solid. Material was taken on to the next step without purification. LCMS $[M+H]^+$: 248.3.

Step 4: Diastereomers 5-(((2R)-1-((tetrahydrofuran-3-yl)methyl)piperidin-2-yl)methoxy)isobenzofuran-1(3H)-one (INT-209)

(R)-5-(piperidin-2-ylmethoxy)isobenzofuran-1(3H)-one 208 (112.6 mg, 0.455 mmol) and tetrahydrofuran-3-carbaldehyde INT-205 (325.8 mg, 1.627 mmol) were dissolved in DMF (1.5 mL). Sodium triacetoxyborohydride (280 mg, 1.321 mmol) was added and the reaction stirred at r.t. 48 hrs. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-80% 3:1 EtOAc:EtOH with 1% TEA in heptane) to afford a mixture of Diastereomers 5-(((2R)-1-((tetrahydrofuran-3-yl)methyl)piperidin-2-yl)methoxy)isobenzofuran-1(3H)-one INT-209 (187.1 mg, 0.565 mmol) as a yellow liquid. LCMS [M+H]$^+$: 332.2. The mixture of diastereomers was separated via chiral SFC [Column Chiralcel OJ-H 21×250 mm 5 uM, CO$_2$ Co-solvent 10-30% MeOH with 10 mM NH$_3$; at 80 g/min at 125 bar] to afford diastereomers: Peak 1: diastereomer 1 of 5-(((2R)-1-((tetrahydrofuran-3-yl)methyl)piperidin-2-yl)methoxy)isobenzofuran-1(3H)-one (30.5 mg, 0.092 mmol). Chiral SFC Rt 1.35 mins. $^1$H NMR (400 MHz, CD$_2$Cl$_2$) δ 7.86-7.71 (m, 1H), 7.16-6.89 (m, 2H), 5.27-5.19 (m, 2H), 4.24-4.09 (m, 1H), 4.07-3.92 (m, 1H), 3.87-3.61 (m, 3H), 3.61-3.09 (m, 2H), 3.00-2.81 (m, 1H), 2.79-2.59 (m, 2H), 2.52-2.15 (m, 3H), 2.10-1.82 (m, 2H), 1.81-1.34 (m, 5H). Peak 2: diastereomer 2 of 5-(((2R)-1-((tetrahydrofuran-3-yl)methyl)piperidin-2-yl)methoxy)isobenzofuran-1(3H)-one (28.6 mg, 0.086 mmol). Chiral SFC Rt 1.43 mins. $^1$H NMR (400 MHz, CD$_2$Cl$_2$) δ 7.77 (d, J=8.5 Hz, 1H), 7.13-6.87 (m, 2H), 5.23 (s, 2H), 4.22-4.09 (m, 1H), 4.09-3.96 (m, 1H), 3.83-3.61 (m, 3H), 3.49-3.36 (m, 1H), 2.95-2.83 (m, 1H), 2.83-2.63 (m, 2H), 2.49-2.22 (m, 3H), 2.02-1.87 (m, 1H), 1.84-1.72 (m, 1H), 1.71-1.52 (m, 5H), 1.47-1.34 (m, 1H).

Example 145: Diastereomer 3-(1-oxo-5-(((2R)-1-((tetrahydrofuran-3-yl)methyl)piperidin-2-yl)methoxy)isoindolin-2-yl)piperidine-2,6-dione (I-211)

Step 1: Single Diastereomer Ethyl 2-(chloromethyl)-4-(((2R)-1-((tetrahydrofuran-3-yl)methyl)piperidin-2-yl)methoxy)benzoate (210)

Compound 210 was prepared according to General Method IV starting from 5-(((2R)-1-((tetrahydrofuran-3-yl)methyl)piperidin-2-yl)methoxy)isobenzofuran-1(3H)-one INT-209 peak 1 (30.5 mg, 0.092 mmol). The reaction was cooled to r.t., diluted with water, and quenched with saturated sodium bicarbonate. The reaction was extracted with ethyl acetate 3 times. The organic layers were combined, passed through a phase separator and concentrated to afford single diastereomer ethyl 2-(chloromethyl)-4-(((2R)-1-((tetrahydrofuran-3-yl)methyl)piperidin-2-yl)methoxy)benzoate (36.4 mg, 0.092 mmol, 100% yield) 210 as a brown oil. Material was taken on to the next step without purification assuming quantitative yield. LCMS [M+H]$^+$: 396.3.

Step 2: Diastereomer 3-(1-oxo-5-(((2R)-1-((tetrahydrofuran-3-yl)methyl)piperidin-2-yl)methoxy)isoindolin-2-yl)piperidine-2,6-dione (I-211)

Compound I-211 was prepared according to General Method V starting from single diastereomer ethyl 2-(chloromethyl)-4-(((2R)-1-((tetrahydrofuran-3-yl)methyl)piperidin-2-yl)methoxy)benzoate 210 (36.4 mg, 0.092 mmol). The reaction was concentrated and purified by silica gel chromatography (0-100% 3:1 EtOAc:EtOH with 1% TEA in heptane) to afford diastereomer 3-(1-oxo-5-(((2R)-1-((tetrahydrofuran-3-yl)methyl)piperidin-2-yl)methoxy)isoindolin-2-yl)piperidine-2,6-dione I-211 (18.2 mg, 0.039 mmol, 42.6% yield) as a cream solid. LCMS [M+H]$^+$: 442.3. 1H NMR (400 MHz, DMSO-d6) δ 10.89 (s, 1H), 7.55 (d, J=8.3

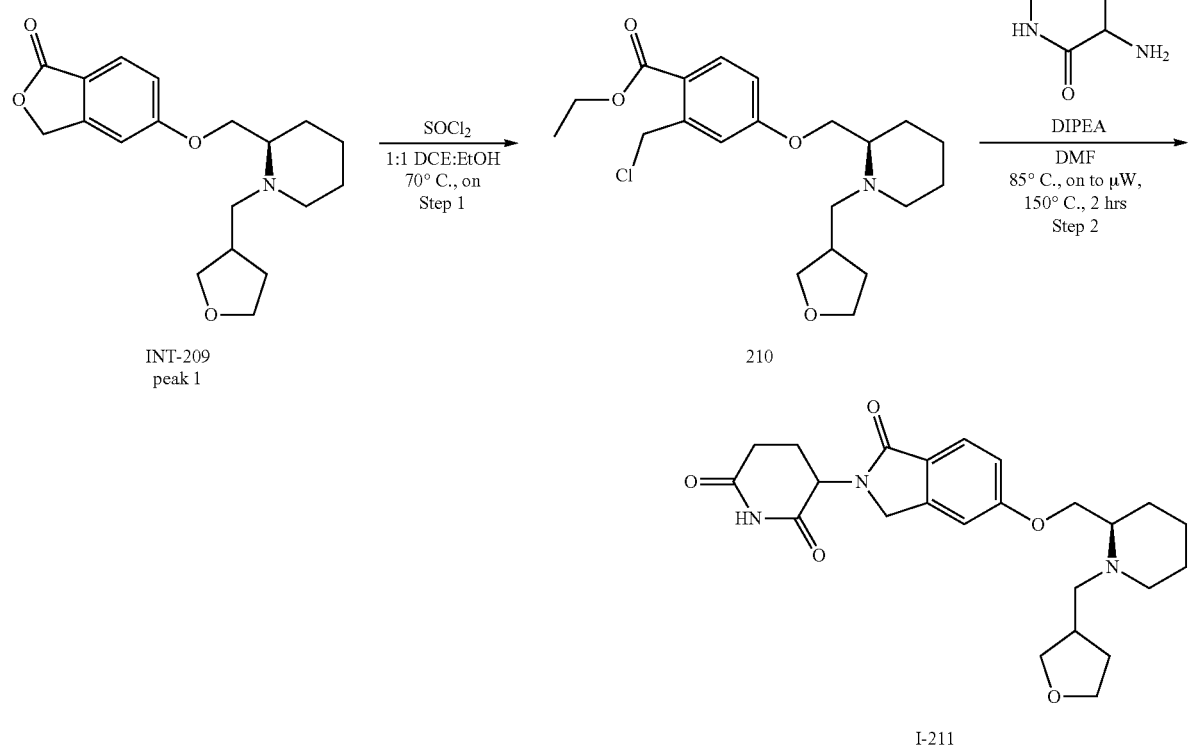

Hz, 1H), 7.12 (d, J=2.2 Hz, 1H), 6.98 (dd, J=8.4, 2.1 Hz, 1H), 5.00 (dd, J=13.3, 5.2 Hz, 1H), 4.32 (d, J=17.2 Hz, 1H), 4.19 (d, J=17.2 Hz, 1H), 4.14-4.04 (m, 1H), 4.02-3.92 (m, 1H), 3.66-3.53 (m, 2H), 3.49 (q, J=7.6 Hz, 1H), 3.31 (dd, J=8.3, 5.8 Hz, 1H), 2.85-2.78 (m, 1H), 2.61-2.49 (m, 3H), 2.36-2.25 (m, 3H), 2.14-2.05 (m, 1H), 1.95-1.79 (m, 3H), 1.68-1.53 (m, 2H), 1.49-1.23 (m, 5H).

Example 146: Diastereomer 3-(1-oxo-5-(((2R)-1-((tetrahydrofuran-3-yl)methyl)piperidin-2-yl)methoxy)isoindolin-2-yl)piperidine-2,6-dione (I-213)

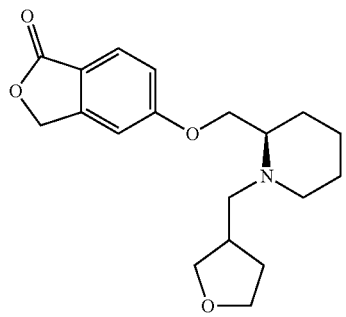

INT-209
peak 2

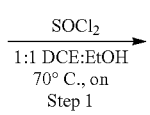

SOCl₂
1:1 DCE:EtOH
70° C., on
Step 1

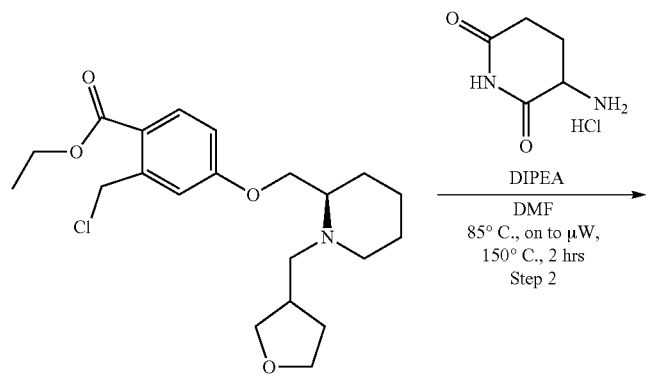

210

(34 mg, 0.086 mmol, 100% yield) as a brown oil. Material was taken on to the next step without purification assuming quantitative yield. LCMS [M+H]⁺: 396.5.

Step 2: Diastereomer 3-(1-oxo-5-(((2R)-1-((tetrahydrofuran-3-yl)methyl)piperidin-2-yl)methoxy)isoindolin-2-yl)piperidine-2,6-dione (I-213)

Compound I-213 was prepared according to General Method V starting from single diastereomer ethyl 2-(chloromethyl)-4-(((2R)-1-((tetrahydrofuran-3-yl)methyl)piperidin-2-yl)methoxy)benzoate 212 (34.0 mg, 0.086 mmol). The

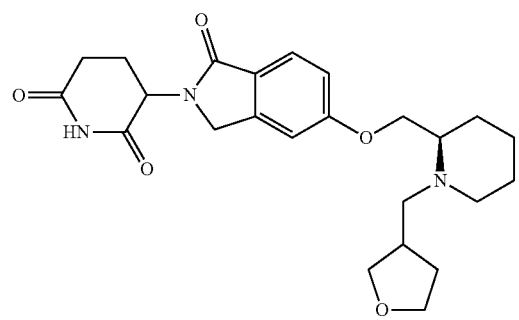

I-213

Step 1: Single Diastereomer Ethyl 2-(chloromethyl)-4-(((2R)-1-((tetrahydrofuran-3-yl)methyl)piperidin-2-yl)methoxy)benzoate (212)

Compound 212 was prepared according to General Method IV starting from 5-(((2R)-1-((tetrahydrofuran-3-yl)methyl)piperidin-2-yl)methoxy)isobenzofuran-1(3H)-one INT-209 peak 2 (28.6 mg, 0.086 mmol). The reaction cooled to r.t., diluted with water, and quenched with saturated sodium bicarbonate. The reaction was extracted with ethyl acetate 3 times. The organic layers were combined, passed through a phase separator and concentrated to afford single diastereomer ethyl 2-(chloromethyl)-4-(((2R)-1-((tetrahydrofuran-3-yl)methyl)piperidin-2-yl)methoxy)benzoate 212 reaction was concentrated and purified by silica gel chromatography (0-100% 3:1 EtOAc:EtOH with 1% TEA in heptane) to afford diastereomer 3-(1-oxo-5-(((2R)-1-((tetrahydrofuran-3-yl)methyl)piperidin-2-yl)methoxy)isoindolin-2-yl)piperidine-2,6-dione I-213 (17.6 mg, 0.038 mmol, 44.0% yield) as a cream solid. LCMS [M+H]⁺: 442.4. ¹H NMR (400 MHz, DMSO-d6) δ 10.97 (s, 1H), 7.63 (d, J=8.4 Hz, 1H), 7.20 (d, J=2.2 Hz, 1H), 7.06 (dd, J=8.8, 2.0 Hz, 1H), 5.08 (dd, J=13.3, 5.2 Hz, 1H), 4.40 (d, J=17.1 Hz, 1H), 4.27 (d, J=17.1 Hz, 1H), 4.21-4.12 (m, 1H), 4.12-4.02 (m, 1H), 3.75-3.52 (m, 3H), 2.98-2.82 (m, 2H), 2.77-2.65 (m, 2H), 2.65-2.55 (m, 1H), 2.43-2.36 (m, 2H), 2.31-2.21 (m, 2H), 2.02-1.83 (m, 3H), 1.76-1.45 (m, 6H), 1.40-1.31 (m, 1H).

Example 147: 3-(5-(((R)-1-(cyclopropylmethyl)piperidin-2-yl)methoxy)-1-oxoisoindolin-2-yl)piperidine-2,6-dione (I-214)

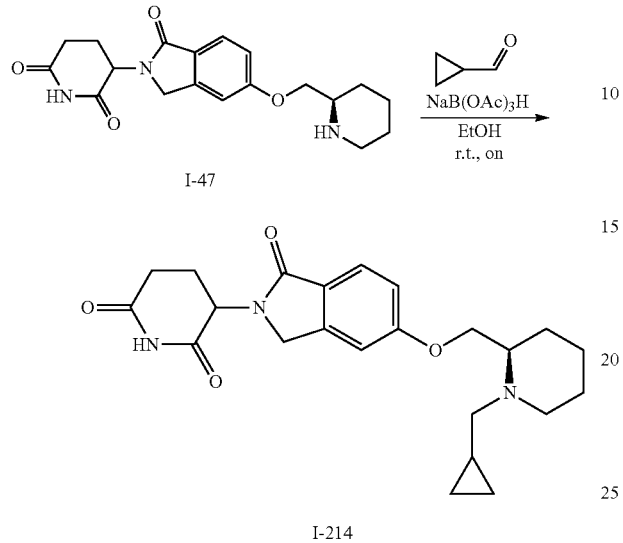

Example 148: 5-(1-(1-(((1r,4r)-4-methoxycyclohexyl)methyl)piperidin-2-yl)ethoxy)isobenzofuran-1(3H)-one (INT-215)

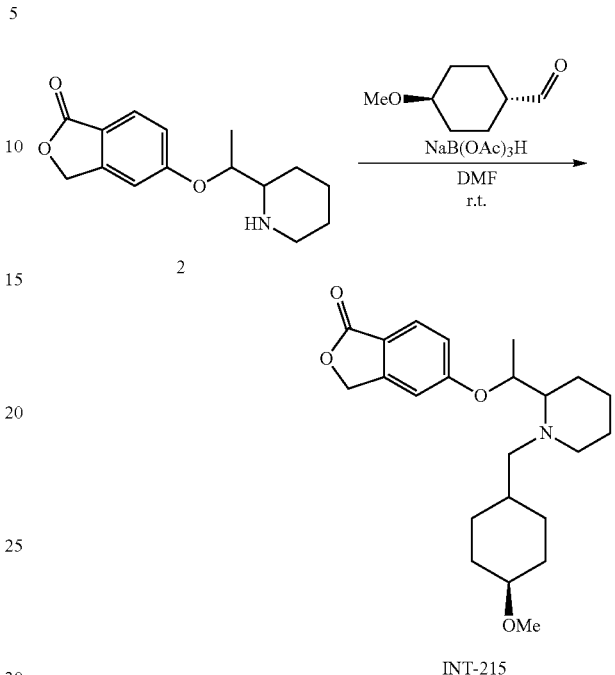

To a solution of 3-(1-oxo-5-(((R)-piperidin-2-yl)methoxy)isoindolin-2-yl)piperidine-2,6-dione I-47 (100 mg, 0.280 mmol) in EtOH (1.5 mL), sodium triacetoxyborohydride (119 mg, 0.560 mmol) then cyclopropanecarbaldehyde (29 mg, 0.420 mmol) were added. The reaction stirred at r.t. and after 1 hr additional cyclopropanecarbaldehyde (14 mg, 0.167 mmol) was added and the reaction stirred at r.t. overnight. Additional EtOH (1 mL) was added followed by sodium triacetoxyborohydride (80 mg, 0.377 mmol) and cyclopropanecarbaldehyde (14 mg, 0.167 mmol). The reaction stirred at r.t. for an additional 1 hr. The reaction was concentrated onto Isolute and purified by silica gel chromatography (0-100% 3:1 EtOAc:EtOH with 1% TEA in DCM). Product was concentrated, diluted with 1:1 water:acetonitrile, and lyophilized to afford 3-(5-(((R)-1-(cyclopropylmethyl)piperidin-2-yl)methoxy)-1-oxoisoindolin-2-yl)piperidine-2,6-dione I-214 (67 mg, 0.155 mmol, 55.3% yield). LCMS [M+H]$^+$=412.7. $^1$H NMR (400 MHz, DMSO-d6) δ 10.96 (s, 1H), 7.61 (d, J=8.4 Hz, 1H), 7.19 (d, J=2.2 Hz, 1H), 7.05 (dd, J=8.4, 2.3 Hz, 1H), 5.07 (dd, J=13.3, 5.0 Hz, 1H), 4.44-4.21 (m, 2H), 4.17 (ddd, J=10.3, 4.8, 2.2 Hz, 1H), 4.02 (dd, J=10.2, 5.3 Hz, 1H), 3.05-2.83 (m, 2H), 2.75-2.64 (m, 1H), 2.64-2.52 (m, 2H), 2.43-2.25 (m, 3H), 2.05-1.91 (m, 1H), 1.82-1.70 (m, 1H), 1.65 (dt, J=8.8, 4.3 Hz, 1H), 1.55 (dt, J=8.3, 4.1 Hz, 1H), 1.50-1.37 (m, 2H), 1.37-1.25 (m, 1H), 0.91-0.77 (m, 1H), 0.43 (dt, J=7.7, 3.5 Hz, 2H), 0.05 (q, J=4.0 Hz, 2H).

Compound INT-215 was prepared according to General Method III starting from 5-(1-(piperidin-2-yl)ethoxy)isobenzofuran-1(3H)-one 2 (0.62 g, 1.19 mmol) and (1r,4r)-4-methoxycyclohexane-1-carbaldehyde (0.227 g, 1.596 mmol). The crude material was purified by silica gel chromatography (0-100% ethyl acetate in heptane) to afford a mixture of diastereomers 5-(1-(1-((4-methoxycyclohexyl)methyl)piperidin-2-yl)ethoxy)isobenzofuran-1(3H)-one from a major peak INT-215 (227 mg, 0.586 mmol, 49.4% yield) as an orange oil and a mixture of diastereomers 5-(1-(1-((4-methoxycyclohexyl)methyl)piperidin-2-yl)ethoxy)isobenzofuran-1(3H)-one from a minor peak (32.5 mg, 0.084 mmol, 7.07% yield) as an orange oil. LCMS [M+H]$^+$: 388.6.

The mixture of diastereomers from the major peak was first separated via chiral SFC [Column Chiralpak IB 5 um 21×250 mm, CO$_2$ Co-solvent 15% MeOH with 10 mM NH$_3$; at 80 g/min at 125 bar] to afford two peaks. Peak 1 was further separated via chiral SFC [Column ChiralPak IA 21×250 mm, CO$_2$ Co-solvent 10% 1:1 MeOH:IPA with 10 mM NH$_3$; at 80 g/min at 125 bar] to afford diastereomers: Fraction 10: diastereomer 1 of 5-(1-(1-((4-methoxycyclohexyl)methyl)piperidin-2-yl)ethoxy)isobenzofuran-1(3H)-one (32.5 mg, 0.084 mmol). Chiral SFC Rt 1.72 mins. Fraction 12: diastereomer 2 of 5-(1-(1-((4-methoxycyclohexyl)methyl)piperidin-2-yl)ethoxy)isobenzofuran-1(3H)-one (29.6 mg, 0.076 mmol). Chiral SFC Rt 1.79 mins. Peak 2 was further separated vai chiral SFC [Column ChiralPak IG 21×250 mm, CO$_2$ Co-solvent 15% 1 MeOH with 10 mM NH$_4$OH; at 80 g/min at 125 bar] to afford diastereomers: Fraction 5: diastereomer 3 of 5-(1-(1-((4-methoxycyclohexyl)methyl)piperidin-2-yl)ethoxy)isobenzofuran-1 (3H)-one (11.1 mg, 0.029 mmol). Chiral SFC Rt 2.44 mins. Fraction 7: diastereomer 4 of 5-(1-(1-((4-methoxycyclohexyl)methyl)piperidin-2-yl)ethoxy)isobenzofuran-1(3H)-one (11.3 mg, 0.029 mmol). Chiral SFC Rt 2.55 mins.

Example 149: Diastereomers 3-(5-(1-(1-((4-methoxycyclohexyl)methyl)piperidin-2-yl)ethoxy)-1-oxoisoindolin-2-yl)piperidine-2,6-dione (I-217)

Step 2: Diastereomers 3-(5-(1-(1-((4-methoxycyclohexyl)methyl)piperidin-2-yl)ethoxy)-1-oxoisoindolin-2-yl)piperidine-2,6-dione (I-217)

Compound I-217 was prepared according to General Method V starting from ethyl 2-(chloromethyl)-4-(1-(1-((4-

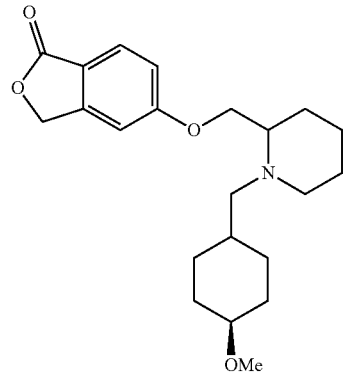

INT-215
Fraction 10

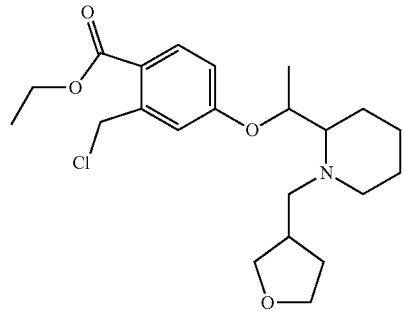

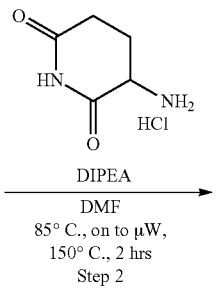

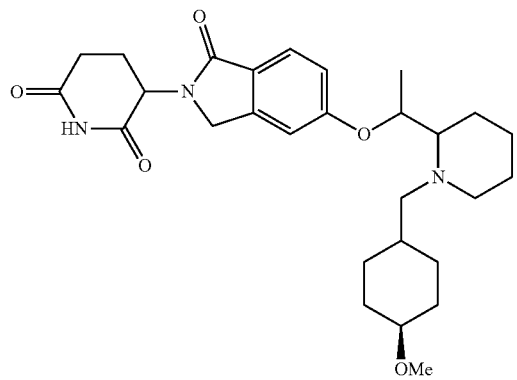

I-217

Step 1: Single Diastereomer Ethyl 2-(chloromethyl)-4-(1-(1-((4-methoxycyclohexyl)methyl)piperidin-2-yl)ethoxy)benzoate (216)

Compound 216 was prepared according to General Method IV starting from 5-(1-(1-(((1r,4r)-4-methoxycyclohexyl)methyl)piperidin-2-yl)ethoxy)isobenzofuran-1(3H)-one INT-215 Fraction 10 (32.5 g, 0.084 mmol). The reaction cooled to r.t., diluted with water, and quenched with saturated sodium bicarbonate. The reaction was extracted with ethyl acetate 3 times. The organic layers were combined, passed through a phase separator and concentrated to afford single diastereomer ethyl 2-(chloromethyl)-4-(1-(1-((4-methoxycyclohexyl)methyl)piperidin-2-yl)ethoxy) 216 (38 mg, 0.084 mmol) as a brown oil. Material was taken through to the next step without purification assuming quantitative yield. LCMS [M+H]$^+$: 452.2.

methoxycyclohexyl)methyl)piperidin-2-yl)ethoxy)benzoate 216 (38.0 mg, 0.084 mmol). The reaction was concentrated and purified by silica gel chromatography (0-100% 3:1 ethyl acetate:ethanol with 1% triethylamine in heptane) to afford impure product. Material was further purified by basic mass triggered reverse phase HPLC (35-60% ACN in water with 5 mM NH$_4$OH as modifier). Test tubes contained 3 drops formic acid prior to sample collection. Fractions containing pure product were combined and lyophilized to afford formate salt of diastereomers 3-(5-(1-(1-((4-methoxycyclohexyl)methyl)piperidin-2-yl)ethoxy)-1-oxoisoindolin-2-yl) piperidine-2,6-dione I-217 (8.07 mg, 0.015 mmol, 17.38% yield) as a white solid. LCMS [M+H]$^+$: 498.2. 1H NMR (400 MHz, DMSO-d6) δ 10.89 (s, 1H), 8.18 (s, 1H), 7.54 (d, J=8.4 Hz, 1H), 7.12 (d, J=2.3 Hz, 1H), 6.96 (dd, J=8.5, 2.1 Hz, 1H), 5.00 (dd, J=13.3, 5.0 Hz, 1H), 4.70 (p, J=6.0 Hz, 1H), 4.31 (dd, J=17.1, 4.9 Hz, 1H), 4.19 (dd, J=17.3, 3.3 Hz, 1H), 2.99-2.75 (m, 3H), 2.61-2.48 (m, 3H), 2.37-2.24 (m, 4H), 2.14-1.98 (m, 2H), 1.94-1.81 (m, 3H), 1.79-1.52 (m, 4H), 1.46-1.37 (m, 2H), 1.32-1.17 (m, 6H), 1.01-0.86 (m, 2H), 0.85-0.63 (m, 2H).

Example 150: Diastereomers 3-(5-(1-(1-((4-methoxycyclohexyl)methyl)piperidin-2-yl)ethoxy)-1-oxoisoindolin-2-yl)piperidine-2,6-dione (I-219)

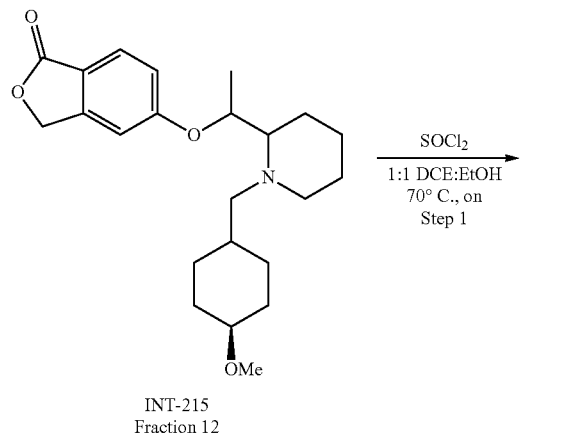

INT-215
Fraction 12

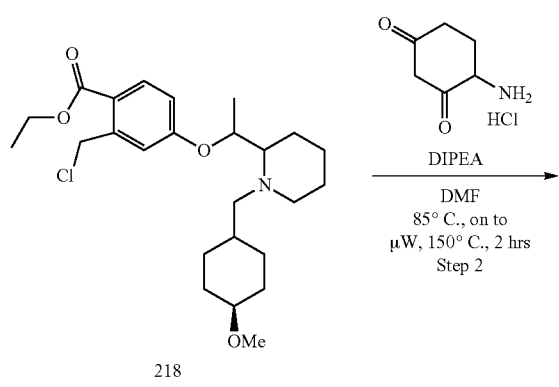

218

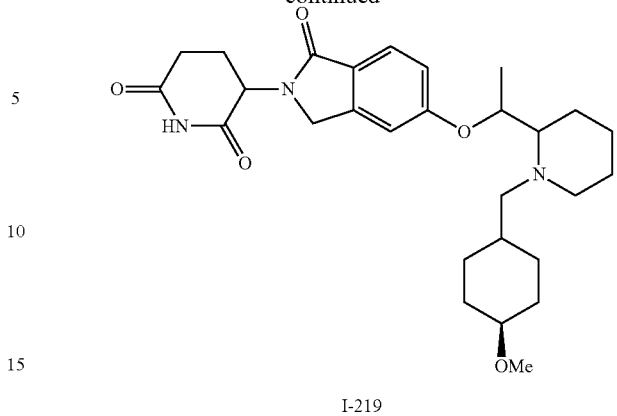

I-219

Compound I-219 was prepared in the same manner as Example 149 starting from INT-215 Fraction 12. The reaction of Step 2 was concentrated and purified by silica gel chromatography (0-100% 3:1 ethyl acetate:ethanol with 1% triethylamine as modifier in heptane). Fractions containing desired product were combined, concentrated, and lyophilized to afford 3-(5-(1-(1-((4-methoxycyclohexyl)methyl)piperidin-2-yl)ethoxy)-1-oxoisoindolin-2-yl)piperidine-2,6-dione I-219 (15.8 mg, 0.030 mmol, 39.7% yield) as a grey solid. LCMS [M+H]$^+$: 498.2. $^1$H NMR (400 MHz, DMSO-d6) δ 10.89 (s, 1H), 7.54 (d, J=8.3 Hz, 1H), 7.12 (d, J=2.3 Hz, 1H), 6.96 (dd, J=8.4, 2.2 Hz, 1H), 5.00 (dd, J=13.3, 5.1 Hz, 1H), 4.70 (p, J=6.1 Hz, 1H), 4.31 (dd, J=17.1, 4.9 Hz, 1H), 4.19 (dd, J=17.4, 3.4 Hz, 1H), 2.99-2.78 (m, 3H), 2.71-2.48 (m, 4H), 2.39-2.27 (m, 3H), 2.14-1.97 (m, 2H), 1.96-1.81 (m, 3H), 1.78-1.53 (m, 4H), 1.46-1.36 (m, 2H), 1.32-1.17 (m, 6H), 1.01-0.87 (m, 2H), 0.83-0.64 (m, 2H).

Example 151: 3-(5-(((1R,3S,4S)-2-ethyl-2-azabicyclo[2.2.1]heptan-3-yl)methoxy)-1-oxoisoindolin-2-yl)piperidine-2,6-dione (I-223)

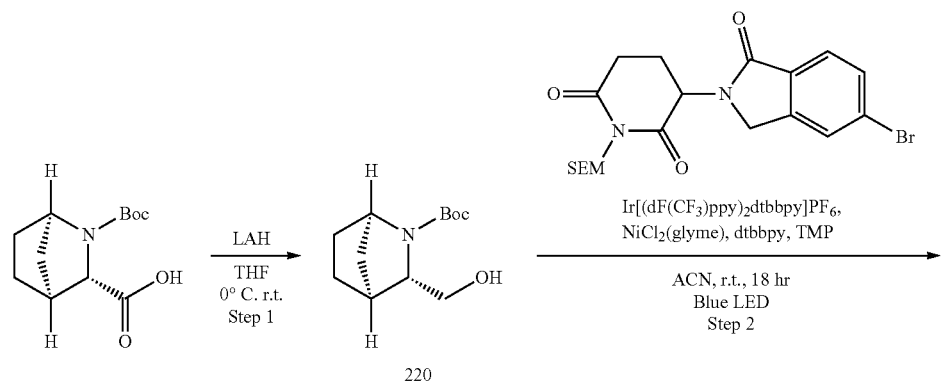

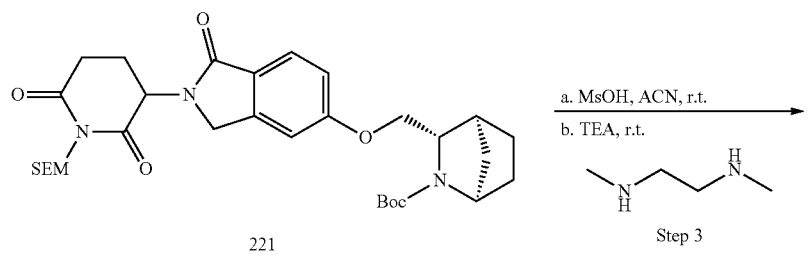

221

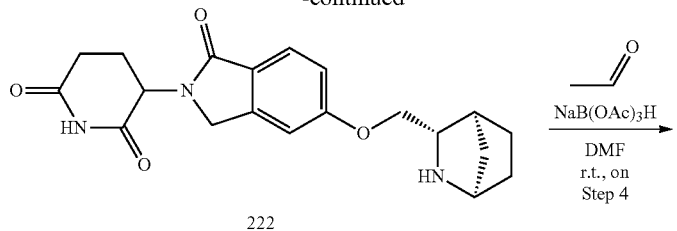

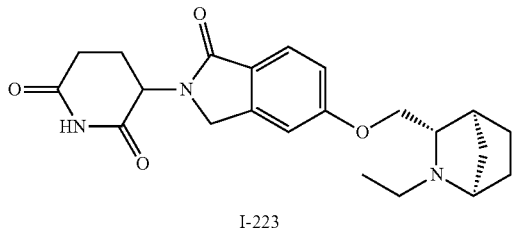

I-223

Step 1: Tert-butyl (1R,3S,4S)-3-(hydroxymethyl)-2-azabicyclo[2.2.1]heptane-2-carboxylate (220)

(1R,3S,4S)-2-(tert-butoxycarbonyl)-2-azabicyclo[2.2.1]heptane-3-carboxylic acid (0.113 g, 0.468 mmol) was dissolved in THF (1.56 mL) and cooled to 0° C. 2M lithium aluminum hydride in THF (0.35 mL, 0.702 mmol) was added dropwise and the reaction stirred at r.t. for 2 hrs. The reaction was quenched with saturated Rochelle salts and stirred at r.t. for 1 hr. Reaction was extracted 3 times with DCM and 2 times with EtOAc. The organic layers were combined and concentrated to afford tert-butyl (1R,3S,4S)-3-(hydroxymethyl)-2-azabicyclo[2.2.1]heptane-2-carboxylate 220 (98 mg, 0.431 mmol, 92% yield) as a clear oil.

Step 2: Tert-butyl (1R,3S,4S)-3-(((2-(2,6-dioxo-1-((2-(trimethylsilyl)ethoxy)methyl)piperidin-3-yl)-1-oxoisoindolin-5-yl)oxy)methyl)-2-azabicyclo[2.2.1]heptane-2-carboxylate (221)

Compound 221 was prepared according to General Method VI starting from 3-(5-bromo-1-oxoisoindolin-2-yl)-1-((2-(trimethylsilyl)ethoxy)methyl)piperidine-2,6-dione (0.12 g, 0.265 mmol) and tert-butyl (1R,3S,4S)-3-(hydroxymethyl)-2-azabicyclo[2.2.1]heptane-2-carboxylate 220 (98 mg, 0.431 mmol). The reaction was concentrated and purified by silica gel chromatography (0-100% EtOAc in heptane) to afford tert-butyl (1R,3S,4S)-3-(((2-(2,6-dioxo-1-((2-(trimethylsilyl)ethoxy)methyl)piperidin-3-yl)-1-oxoisoindolin-5-yl)oxy)methyl)-2-azabicyclo[2.2.1]heptane-2-carboxylate 221 (134 mg, 0.223 mmol, 84% yield) as a yellow oil. LCMS [M+H– 156.3 (TMSCH$_2$CH$_2$,tButyl)]$^+$: 444.4.

Step 3: 3-(5-(((1R,3S,4S)-2-azabicyclo[2.2.1]heptan-3-yl)methoxy)-1-oxoisoindolin-2-yl)piperidine-2,6-dione (222)

Compound 222 was prepared according to General Method VII starting from tert-butyl (1R,3S,4S)-3-(((2-(2,6-dioxo-1-((2-(trimethylsilyl)ethoxy)methyl)piperidin-3-yl)-1-oxoisoindolin-5-yl)oxy)methyl)-2-azabicyclo[2.2.1]heptane-2-carboxylate 221 (134 mg, 0.223 mmol). The reaction was quenched with 50% saturated aqueous sodium hydrogen carbonate and extracted with 4:1 DCM:iPrOH four times. The organic layers were combined, passed through a phase separator and concentrated to afford 3-(5-(((1R,3S,4S)-2-azabicyclo[2.2.1]heptan-3-yl)methoxy)-1-oxoisoindolin-2-yl)piperidine-2,6-dione 222 (105 mg, 0.284 mmol, 127% yield) as a yellow solid. LCMS [M+H]$^+$: 370.4.

Step 4: 3-(5-(((1R,3S,4S)-2-ethyl-2-azabicyclo[2.2.1]heptan-3-yl)methoxy)-1-oxoisoindolin-2-yl)piperidine-2,6-dione (I-223)

Compound I-223 was prepared according to General Method III starting from 3-(5-(((1R,3S,4S)-2-azabicyclo[2.2.1]heptan-3-yl)methoxy)-1-oxoisoindolin-2-yl)-1-(hydroxymethyl)piperidine-2,6-dione 222 (105 mg, 0.284 mmol) and acetaldehyde (0.08 mL, 1.42 mmol). The reaction was quenched with 50% saturated aqueous sodium bicarbonate in water and extracted 4 times with 4:1 dichloromethane:isopropanol. The organic layers were combined, passed through a phase separator and concentrated. The crude material was purified by silica gel chromatography (0-100% 3:1 ethylaceate:ethanol with 1% TEA in heptane).

Fractions were combined, concentrated, and high vacuumed overnight to afford slightly impure product. Material was further purified by basic reverse phase HPLC (25-50% ACN in water with 5 mM NH$_4$OH as modifier). Test tubes contained 3 drops formic acid prior to sample collection.

Fractions were combined and lyophilized to afford formate salt of 3-(5-(((1R,3S,4S)-2-ethyl-2-azabicyclo[2.2.1]heptan-3-yl)methoxy)-1-oxoisoindolin-2-yl)piperidine-2,6-dione I-223 (4.95 mg, 10.60 μmol, 3.73% yield) as a white solid. LCMS [M+H]$^+$: 398.3. $^1$H NMR (400 MHz, DMSO-d6) δ 10.89 (s, 1H), 8.18 (s, 1H), 7.53 (d, J=8.4 Hz, 1H), 7.09 (d, J=2.2 Hz, 1H), 6.97 (dd, J=8.6, 2.2 Hz, 1H), 5.00 (dd, J=13.3, 5.1 Hz, 1H), 4.31 (d, J=17.3 Hz, 1H), 4.18 (d, J=17.1 Hz, 1H), 3.77-3.69 (m, 1H), 3.69-3.61 (m, 1H), 2.84 (ddd, J=17.1, 13.5, 5.4 Hz, 1H), 2.64-2.47 (m, 2H), 2.39-2.25 (m, 2H), 2.22-2.15 (m, 2H), 1.95-1.85 (m, 1H), 1.81-1.70 (m, 1H), 1.60 (d, J=9.6 Hz, 1H), 1.57-1.46 (m, 1H), 1.26-1.10 (m, 4H), 0.92 (t, J=7.2 Hz, 3H).

Example 152: 1-(4-(chloromethyl)phenyl)-4-isopropylpiperazine (INT-226)

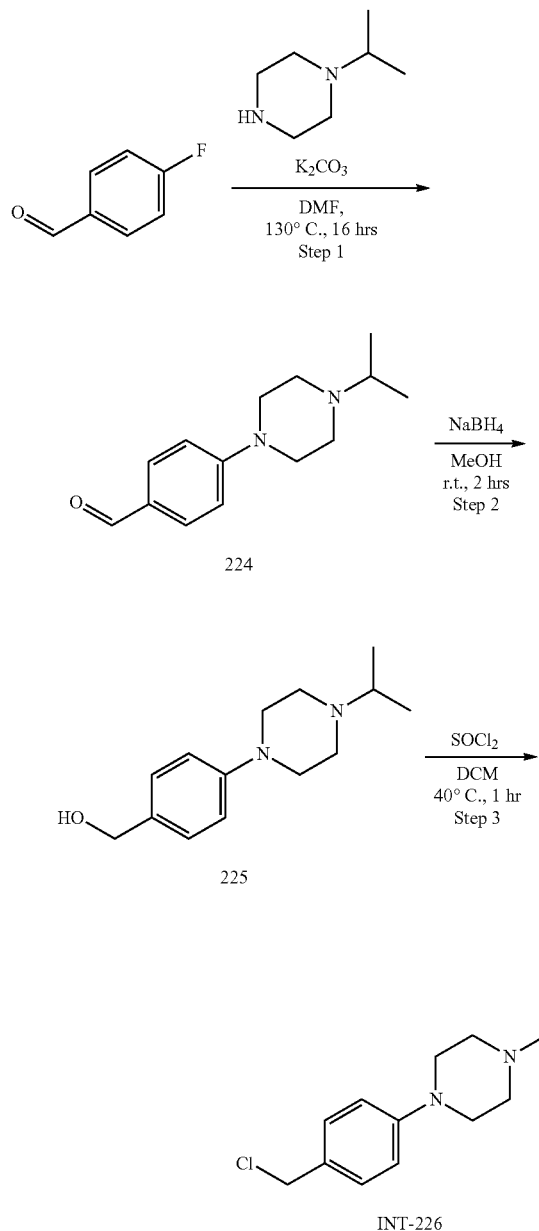

Step 1: 4-(4-isopropylpiperazin-1-yl)benzaldehyde (224)

To a solution of 4-fluorobenzaldehyde (1.00 g, 8.06 mmol) in DMF (10 mL) was added 1-isopropylpiperazine (1.24 g, 9.67 mmol), K$_2$CO$_3$ (1.67 g, 12.09 mmol). The reaction mixture stirred at 130° C. for 16 hrs. The reaction was quenched with H$_2$O (40 mL) and extracted three times with ethyl acetate. The organic layers were combined, washed with saturated aqueous sodium chloride, dried over Na$_2$SO$_4$, filtered, and concentrated in-vacuo to afford 4-(4-isopropylpiperazin-1-yl)benzaldehyde 224 as a yellow solid. Material was taken through to the next step without purification. $^1$H NMR (400 MHz, DMSO-d6) δ=9.71 (s, 1H), 7.76-7.60 (m, 2H), 7.02 (d, J=8.8 Hz, 2H), 3.37-3.34 (m, 4H), 2.70-2.63 (m, 1H), 2.57-2.51 (m, 4H), 0.99 (d, J=6.4 Hz, 6H).

Step 2: (4-(4-isopropylpiperazin-1-yl)phenyl)methanol (225)

To a solution of 4-(4-isopropylpiperazin-1-yl)benzaldehyde 224 (500 mg, 2.15 mmol) in MeOH (5 mL) was slowly added NaBH$_4$ (122.1 mg, 3.23 mmol) at 0° C. under N$_2$ atmosphere.

The reaction was placed at r.t. and stirred for 2 hrs. The reaction was filtered to remove insoluble material and concentrated in-vacuo to afford (4-(4-isopropylpiperazin-1-yl)phenyl)methanol 225 (0.5 g, 2.13 mmol, 99% yield) as a white solid. The crude product was used in the next step directly. LCMS [M+H]$^+$: 235.2.

Step 3: 1-(4-(chloromethyl)phenyl)-4-isopropylpiperazine (INT-226)

To a solution of (4-(4-isopropylpiperazin-1-yl)phenyl)methanol 225 (500 mg, 2.13 mmol) in DCM (5 mL) was added SOCl$_2$ (0.76 mL, 10.67 mmol) at 25° C. The reaction stirred at 40° C. for 2 hrs. The reaction was concentrated under reduced pressure to afford 1-(4-(chloromethyl)phenyl)-4-isopropylpiperazine INT-226 (0.5 g, 1.98 mmol, 93% yield) as a yellow solid. The crude product was used in the next step directly.

Example 153: 3-(5-(((R)-1-(4-(4-isopropylpiperazin-1-yl)benzyl)piperidin-2-yl)methoxy)-1-oxoisoindolin-2-yl)piperidine-2,6-dione (I-227)

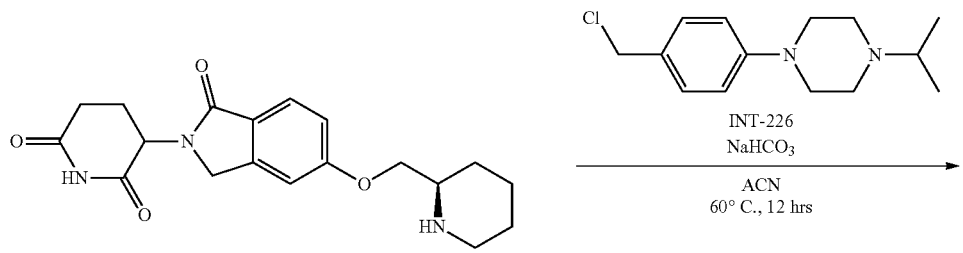

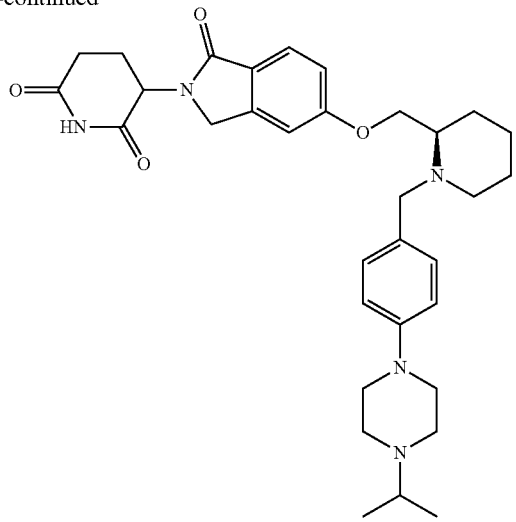

I-227

To a solution of 3-(1-oxo-5-(((R)-piperidin-2-yl)methoxy)isoindolin-2-yl)piperidine-2,6-dione I-47 (200 mg, 0.7 mmol) and 1-(4-(chloromethyl)phenyl)-4-isopropylpiperazine INT-226 (283 mg, 1.12 mmol) in CH$_3$CN (2 mL) was added NaHCO$_3$ (199 mg, 2.3 mmol) at 25° C. The reaction was stirred at 60° C. for 12 hrs. The reaction was filtered to remove insoluble material. The filtrate was concentrated in-vacuo. The crude material was purified by reverse phase HPLC (Column: Waters Xbridge 150*25 mm*5 um; Mobile phase: A for H$_2$O (10 mM NH$_4$HCO$_3$) and B for Acetonitrile; Gradient: B 35%-65% in 10 min linearly; Flow rate: 25 ml/min; Column temperature: R.T. Wavelength: 220 nm/254 nm) to afford formate salt of 3-(5-(((R)-1-(4-(4-isopropylpiperazin-1-yl)benzyl)piperidin-2-yl)methoxy)-1-oxoisoindolin-2-yl)piperidine-2,6-dione I-227 (42.31 mg, 0.08 mmol, 27% yield, 100% purity). LCMS [M+H]$^+$: 574.2. $^1$H NMR (400 MHz, DMSO-d$_6$) δ=10.97 (s, 1H), 8.20 (s, 1H), 7.62 (d, J=8.4 Hz, 1H), 7.22-7.11 (m, 3H), 7.10-7.05 (m, 1H), 6.86 (m, 2H), 5.08 (m, 1H), 4.35-4.27 (m, 2H), 4.13 (m, 2H), 3.89 (m, 2H), 3.32 (m, 2H), 3.09 (m, 4H), 2.77-2.69 (m, 4H), 2.61 (m, 2H), 2.43-2.32 (m, 2H), 2.15-2.08 (m, 1H), 2.03-1.95 (m, 1H), 1.82-1.75 (m, 1H), 1.65 (m, 1H), 1.56-1.46 (m, 2H), 1.42-1.31 (m, 2H), 1.02 (d, J=6.4 Hz, 6H).

Example 154: 4-(4-(tert-butyl)piperazin-1-yl)benzaldehyde (INT-228)

To a solution of 4-fluorobenzaldehyde (1.00 g, 8.06 mmol) in DMF (10 mL) was added 1-(tert-butyl)piperazine (1.65 g, 12.0 mmol), K$_2$CO$_3$ (1.67 g, 12.09 mmol). The reaction mixture stirred at 130° C. for 16 hrs. The reaction was quenched with H$_2$O (40 mL) and extracted three times with ethyl acetate. The organic layers were combined, washed with saturated aqueous sodium chloride, dried over Na$_2$SO$_4$, filtered, and concentrated in-vacuo to afford 4-(4-(tert-butyl)piperazin-1-yl)benzaldehyde INT-228 (1.5 g, 6.09 mmol, 76.1% yield) as a yellow solid. Material was taken through to the next step without purification. $^1$HNMR (400 MHz, DMSO-d$_6$) δ=9.70 (s, 1H), 7.70 (d, J=8.8 Hz, 2H), 7.02 (d, J=8.8 Hz, 2H), 3.36 (br s, 4H), 2.64-2.57 (m, 4H), 1.04 (s, 9H).

Example 155: 3-(5-(((R)-1-(4-(4-(tert-butyl)piperazin-1-yl)benzyl)piperidin-2-yl)methoxy)-1-oxoisoindolin-2-yl)piperidine-2,6-dione (I-229)

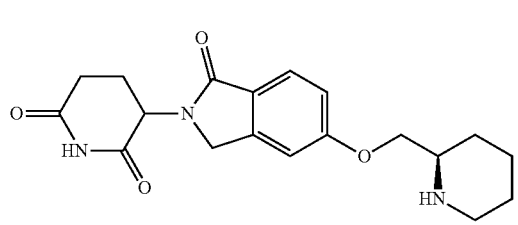

I-47

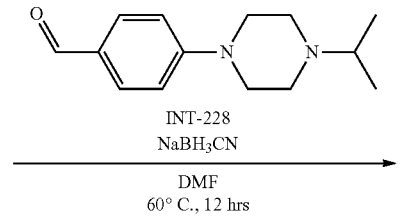

INT-228

NaBH$_3$CN
——————→
DMF
60° C., 12 hrs

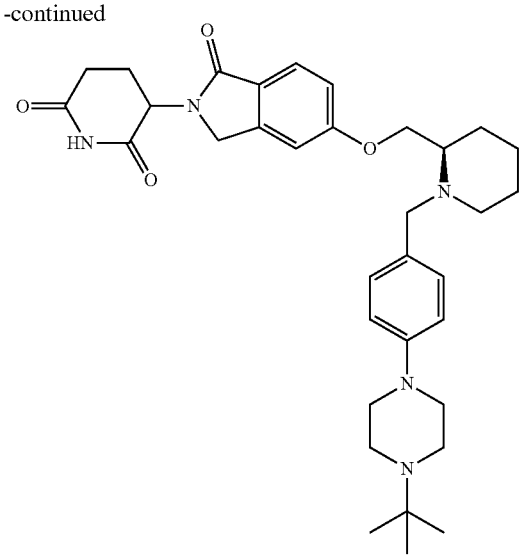

I-229

To a solution of 3-(1-oxo-5-(((R)-piperidin-2-yl)methoxy)isoindolin-2-yl)piperidine-2,6-dione I-47 (200 mg, 0.55 mmol, formic acid salt) and 4-(4-(tert-butyl)piperazin-1-yl)benzaldehyde INT-228 (275 mg, 1.12 mmol) in DMF (2 mL) was added NaBH$_3$CN (70 mg, 1.12 mmol) at r.t. The reaction stirred at 60° C. for 12 hrs. The reaction was diluted with water (2 mL) and extracted three times with ethyl acetate. The organic layers were combined, washed with saturated aqueous sodium chloride, dried over Na$_2$SO$_4$, filtered, and concentrated in-vacuo. The crude material was purified by reverse phase HPLC (Instrument: ACS-WH-GX-F; Column: Phenomenex luna C18 150*25 mm*10 um; Mobile phase: A for H$_2$O (0.225% FA) and B for Acetonitrile; Gradient: B 6%-36% in 10 min linearly; Flow rate: 25 ml/min; Column temperature: R.T. Wavelength: 220 nm/254 nm) to afford the 3-(5-(((R)-1-(4-(4-(tert-butyl)piperazin-1-yl)benzyl)piperidin-2-yl)methoxy)-1-oxoisoindolin-2-yl)piperidine-2,6-dione I-229 SO-EE-STCJ (59.33 mg, 0.10 mmol, 18% yield) as yellow oil. LCMS [M+H]$^+$: 588.7. $^1$H NMR (400 MHz, DMSO-d6) δ 8.37-8.24 (m, 1H), 7.61 (d, J=8.4 Hz, 1H), 7.22-7.11 (m, 3H), 7.08-7.04 (m, 1H), 6.84 (d, J=8.4 Hz, 2H), 5.10-5.04 (m, 1H), 4.41-4.21 (m, 4H), 4.14-4.09 (m, 1H), 3.90-3.86 (m, 1H), 3.31-3.27 (m, 1H), 3.12-2.99 (m, 4H), 2.96-2.84 (m, 1H), 2.76-2.58 (m, 6H), 2.40-2.35 (m, 1H), 2.12-2.04 (m, 1H), 2.02-1.93 (m, 1H), 1.82-1.72 (m, 1H), 1.70-1.57 (m, 1H), 1.55-1.28 (m, 4H), 1.04 (s, 9H).

Example 156: 1-(4-(chloromethyl)phenyl)-4-cyclopropylpiperazine (INT-232)

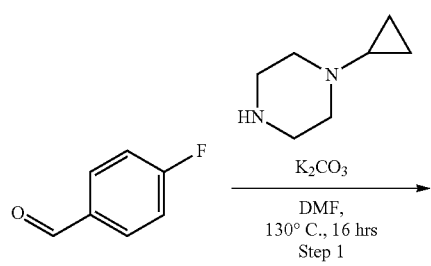

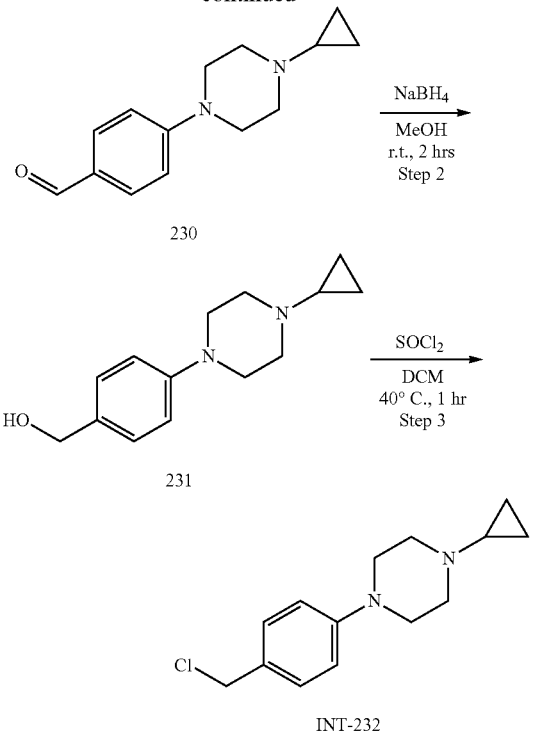

Step 1: 4-(4-cyclopropylpiperazin-1-yl)benzaldehyde (230)

To a solution of 4-fluorobenzaldehyde (1.00 g, 8.06 mmol) in DMF (10 mL) was added 1-cyclopropylpiperazine (1.22 g, 9.67 mmol), K$_2$CO$_3$ (1.67 g, 12.09 mmol). The reaction mixture stirred at 130° C. for 16 hrs. The reaction was quenched with H$_2$O (40 mL) and extracted three times with ethyl acetate. The organic layers were combined, washed with saturated aqueous sodium chloride, dried over Na$_2$SO$_4$, filtered, and concentrated in-vacuo. The crude material was triturated with petroleum ether (10 ml), filtered and the filter cake was washed with additional petroleum ether. The filter cake was collected to afford 4-(4-cyclopropylpiperazin-1-yl)benzaldehyde 230 (1.1 g, 4.73 mmol, 58.7% yield) as a yellow solid. $^1$HNMR (400 MHz, CDCl$_3$) δ=9.69 (s, 1H), 7.70-7.61 (m, 2H), 6.84 (d, J=8.8 Hz, 2H), 3.35-3.26 (m, 4H), 2.71-2.62 (m, 4H), 1.62-1.54 (m, 1H), 0.44-0.37 (m, 4H).

Step 2: (4-(4-cyclopropylpiperazin-1-yl)phenyl)methanol (231)

To a solution of 4-(4-cyclopropylpiperazin-1-yl)benzaldehyde 230 (500 mg, 2.17 mmol) in MeOH (5 mL) was slowly added NaBH$_4$ (164 mg, 4.34 mmol) at 0° C. under N$_2$ atmosphere. The reaction was placed at r.t. and stirred for 2 hrs. The reaction was filtered to remove insoluble material and concentrated in-vacuo to afford (4-(4-cyclopropylpiperazin-1-yl)phenyl)methanol 231 (0.5 g, 2.15 mmol, 99% yield) as a white solid. The crude product was used directly in the next step. LCMS [M+H]$^+$: 233.2.

Step 3: 1-(4-(chloromethyl)phenyl)-4-cyclopropylpiperazine (INT-232)

To a solution of (4-(4-cyclopropylpiperazin-1-yl)phenyl)methanol 231 (400 mg, 1.72 mmol) in DCM (4 mL) was added SOCl$_2$ (1.02 mL, 8.61 mmol) at 25° C. The reaction stirred at 40° C. for 2 hrs. The reaction was concentrated under reduced pressure to afford 1-(4-(chloromethyl)phenyl)-4-cyclopropylpiperazine INT-232 (0.4 g, 1.60 mmol, 93% yield) as a yellow solid. The crude product was used directly in the next step.

Example 157: 3-(5-(((R)-1-(4-(4-cyclopropylpiperazin-1-yl)benzyl)piperidin-2-yl)methoxy)-1-oxoisoindolin-2-yl)piperidine-2,6-dione (I-233)

To a solution of 3-(1-oxo-5-(((R)-piperidin-2-yl)methoxy)isoindolin-2-yl)piperidine-2,6-dione I-47 (200 mg, 0.55 mmol) and 1-(4-(chloromethyl)phenyl)-4-cyclopropylpiperazine INT-232 (280 mg, 1.12 mmol) in ACN (2 mL) was added NaHCO$_3$ (188 mg, 2.24 mmol) at r.t. The reaction stirred at 40° C. for 12 hrs. The reaction concentrated in-vacuo. The crude material was purified by reverse phase HPLC (column: Waters Xbridge 150*25 mm*5 um; mobile phase: [water (10 mM NH$_4$HCO$_3$)-ACN]; B %: 38%-68%, 10 min) and further purified by reverse phase HPLC (column: Waters Xbridge 150*25 mm*5 um; mobile phase: [water (10 mM NH$_4$HCO$_3$)-ACN]; B %: 45%-75%, 10 min) to afford the 3-(5-(((R)-1-(4-(4-cyclopropylpiperazin-1-yl)benzyl)piperidin-2-yl)methoxy)-1-oxoisoindolin-2-yl)piperidine-2,6-dione I-233 SO-EE-STEN (21.3 mg, 0.037 mmol, 6.65% yield) as an off white solid. LCMS [M+H]$^+$: 572.4. $^1$H NMR (400 MHz, DMSO-d6) δ=8.28 (s, 1H), 7.61 (d, J=8.0 Hz, 1H), 7.21-7.12 (m, 3H), 7.07 (m, 1H), 6.85 (d, J=8.0 Hz, 2H), 5.08 (m, 1H), 4.41-4.26 (m, 4H), 4.12 (m, 2H), 3.90 (m, 2H), 3.29 (m, 2H), 3.07-3.02 (m, 4H), 2.91 (m, 1H), 2.66 (m, 4H), 2.12-2.07 (m, 1H), 2.02-1.96 (m, 1H), 1.83-1.76 (m, 1H), 1.67-1.62 (m, 2H), 1.54-1.45 (m, 2H), 1.42-1.32 (m, 2H), 0.47-0.41 (m, 2H), 0.34 (m, 2H).

Example 158: Methyl (2R,4R)-4-fluoro-1-((R)-1-phenylethyl)piperidine-2-carboxylate (INT-238) and Methyl (2S,4S)-4-fluoro-1-((R)-1-phenylethyl)piperidine-2-carboxylate (INT-239)

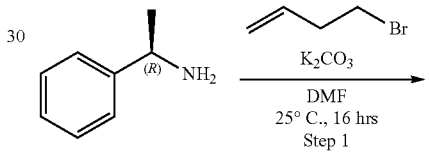

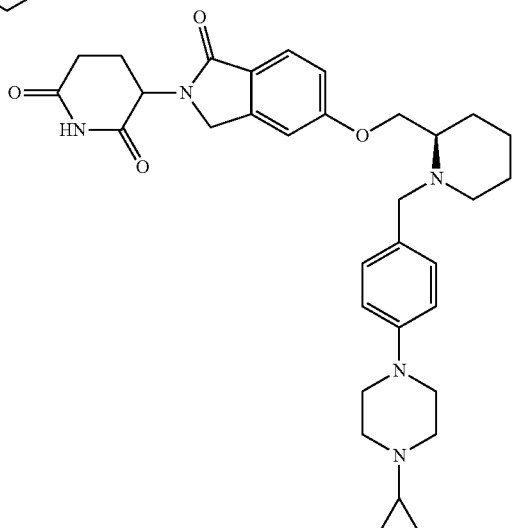

I-47

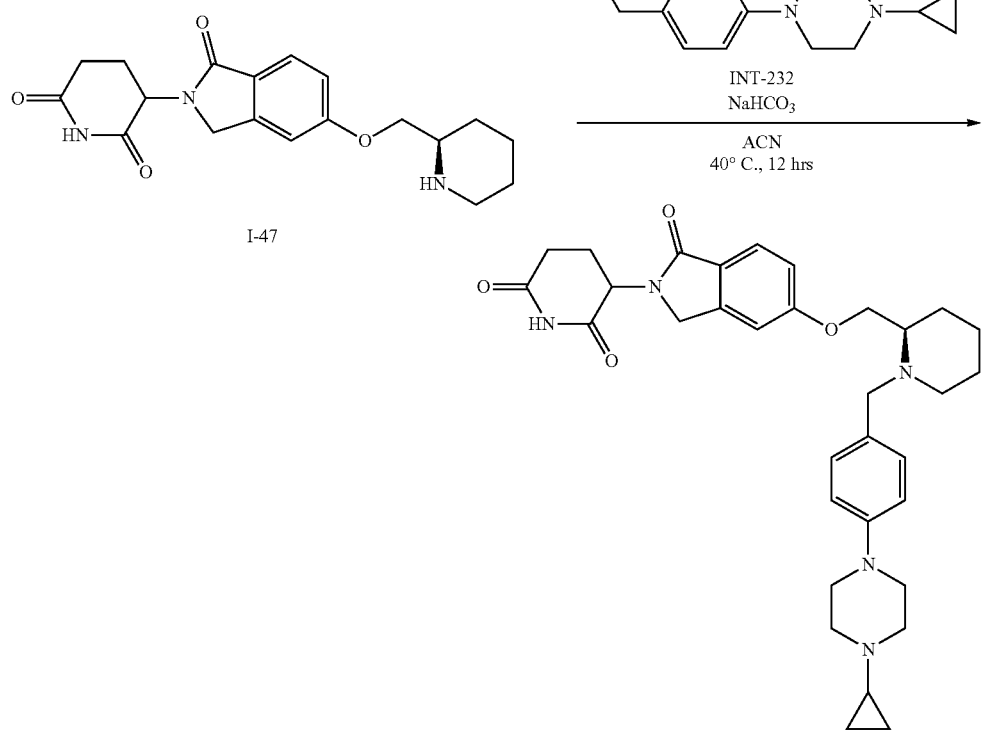

I-233

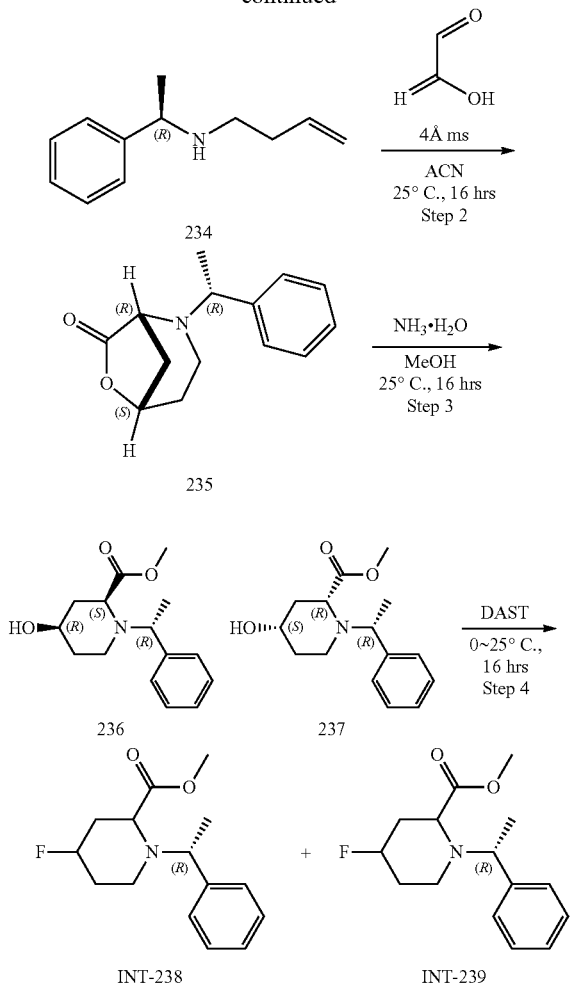

Step 1: (R)—N-(1-phenylethyl)but-3-en-1-amine (234)

To a solution of (R)-1-phenylethan-1-amine (15 g, 123.8 mmol) in DMF (123 mL) was added 4-bromobut-1-ene (16.7 g, 45.4 mmol) and $K_2CO_3$ (17.1 g, 123.8 mmol). The mixture was stirred at r.t. for 16 hrs under $N_2$ atmosphere. The reaction mixture was diluted with water (200 mL), and extracted three times with ethyl acetate. The organic layers were combined, washed with saturated aqueous sodium chloride three times, dried over $Na_2SO_4$, filtered and concentrated in-vacuo. The crude material was purified by silica gel chromatography (0-40% ethyl acetate in petroleum ether) to afford (R)—N-(1-phenylethyl)but-3-en-1-amine 234 (14.4 g, 80.5 mmol, 65% yield) as yellow oil. LCMS [M+H]$^+$: 176.1. $^1$H NMR (400 MHz, DMSO-$d_6$) δ=7.34-7.26 (m, 4H), 7.23-7.15 (m, 1H), 5.82-5.72 (m, 1H), 5.03-4.91 (m, 2H), 3.70-3.65 (m, 1H), 2.46-2.27 (m, 2H), 2.17-2.09 (m, 2H), 1.92-1.81 (m, 1H), 1.23 (d, J=6.4 Hz, 3H).

Step 2: (1R,5S)-2-((R)-1-phenylethyl)-6-oxa-2-azabicyclo[3.2.1]octan-7-one (235)

To a solution of (R)—N-(1-phenylethyl)but-3-en-1-amine 234 (18.8 g, 107.3 mmol) in ACN (188 mL) was added 2-oxoacetic acid (25.4 g, 171.6 mmol) and 4 Å molecular sieves (10 g). The reaction mixture stirred at r.t. for 16 hrs under $N_2$. The reaction mixture was filtered, diluted with water (200 mL), and extracted three times with ethyl acetate. The organic layers were combined, dried over $Na_2SO_4$, filtered and concentrated in-vacuo. The crude material was purified by silica gel chromatography (0-100% ethyl acetate in petroleum ether) to afford (1R,5S)-2-((R)-1-phenylethyl)-6-oxa-2-azabicyclo[3.2.1]octan-7-one 235 (18.50 g, 72.0 mmol 67.1% yield) as yellow oil. LCMS [M+H]$^+$: 232.3.

Step 3: Methyl (2R,4S)-4-hydroxy-1-((R)-1-phenylethyl)piperidine-2-carboxylate (236) and methyl (2S,4R)-4-hydroxy-1-((R)-1-phenylethyl)piperidine-2-carboxylate (237)

To a solution of (1R,5S)-2-((R)-1-phenylethyl)-6-oxa-2-azabicyclo[3.2.1]octan-7-one 235 (18.5 g, 80.0 mmol) in MeOH (185 mL) was added $NH_3.H_2O$ (4.62 mL, 120 mmol). The mixture stirred at r.t. for 16 hrs. The reaction mixture was concentrated in-vacuo and purified by silica gel chromatography (0-100% ethyl acetate in petroleum ether) to afford methyl (2R,4S)-4-hydroxy-1-((R)-1-phenylethyl) piperidine-2-carboxylate 236 (8.20 g, 30.1 mmol, 37.7% yield) as yellow oil and methyl (2S,4R)-4-hydroxy-1-((R)-1-phenylethyl)piperidine-2-carboxylate 237 (9.90 g, 37.6 mmol, 46.2% yield) as yellow oil.

Methyl (2R,4S)-4-hydroxy-1-((R)-1-phenylethyl)piperidine-2-carboxylate (236): LCMS [M+H]$^+$: 264.3, Rt 1.073 mins. $^1$H NMR (400 MHz, CDCl$_3$) δ=7.44-7.40 (m, 2H), 7.35-7.30 (m, 2H), 7.27-7.22 (m, 1H), 4.01-3.94 (m, 1H), 3.89-3.84 (m, 1H), 3.77 (s, 3H), 3.75-3.72 (m, 1H), 2.91-2.84 (m, 1H), 2.35-2.29 (m, 1H), 2.16-2.08 (m, 2H), 1.80-1.70 (m, 1H), 1.56-1.48 (m, 1H), 1.31-1.28 (m, 3H). Optical Rotation: Specific Rotation=+87.207°, C=1 g/100 mL CHCl$_3$ at 25° C.

Methyl (2S,4R)-4-hydroxy-1-((R)-1-phenylethyl)piperidine-2-carboxylate (237): reference for assigning stereochemistry: *Bioorganic & Medicinal Chemistry Letters*, Vol. 6, No. 8, pp. 963-966, 1996. LCMS [M+H]$^+$: 264.3, Rt 1.009 mins. $^1$H NMR (400 MHz, CDCl$_3$) δ=7.36-7.31 (m, 2H), 7.30-7.26 (m, 1H), 7.25-7.20 (m, 2H), 3.98-3.93 (m, 1H), 3.77 (s, 3H), 3.70-3.64 (m, 1H), 3.23-3.13 (m, 2H), 2.33-2.27 (m, 1H), 2.03-1.98 (m, 1H), 1.93-1.81 (m, 2H), 1.75-1.65 (m, 1H), 1.46 (d, J=6.8 Hz, 3H). Optical Rotation: Specific Rotation=+13.951°, C=1 g/100 mL CHCl$_3$ at 25° C.

Step 4: Single Diastereomer Methyl 4-fluoro-1-((R)-1-phenylethyl)piperidine-2-carboxylate (INT-238) and Single Diastereomer Methyl 4-fluoro-1-((R)-1-phenylethyl)piperidine-2-carboxylate (INT-239)

To a solution of methyl (2S,4R)-4-hydroxy-1-((R)-1-phenylethyl)piperidine-2-carboxylate 237 (5.0 g, 19.0 mmol) in DCM (50 mL) was added DAST (6.98 mL, 57.0 mmol) at 0° C. The mixture stirred at r.t. for 16 hrs under $N_2$. The reaction mixture was diluted with water, and extracted three times with ethyl acetate. The organic layers were combined, dried over $Na_2SO_4$, filtered and concentrated in-vacuo. The crude material was purified by reverse phase HPLC (column: Waters Xbridge BEH C18 250*50 mm*10 um); mobile phase: [water (0.05% ammonia hydroxide v/v)-ACN]; B %: 45%-75%, 20 min). Fractions containing desired products were concentrated to remove organic solvents then lyophilized to afford single diastereomer methyl (2S,4S)-4-fluoro-1-((R)-1-phenylethyl)piperidine-2-carboxylate INT-239 (1.2 g, 4.50 mmol, 23.7% yield) as yellow oil and single diastereomer methyl (2R,4R)-4-fluoro-1-((R)-1-phenylethyl)piperidine-2-carboxylate INT-238 (0.62 g, 2.34 mmol, 12.3% yield) as yellow oil.

Single Diastereomer Methyl 4-fluoro-1-((R)-1-phenylethyl)piperidine-2-carboxylate (INT-239): LCMS [M+H]$^+$: 266.3, Rt 1.287 mins. $^1$H NMR (400 MHz, DMSO-d$_6$) δ=7.36-7.27 (m, 3H), 7.25-7.21 (m, 2H), 4.83-4.65 (m, 1H), 3.89-3.81 (m, 1H), 3.66 (s, 3H), 2.94-2.88 (m, 1H), 2.59-2.52 (m, 1H), 2.48-2.21 (m, 1H), 1.95-1.85 (m, 1H), 1.84-1.63 (m, 2H), 1.33 (d, J=6.8 Hz, 3H), 1.30-1.21 (m, 1H).

Single Diastereomer Methyl 4-fluoro-1-((R)-1-phenylethyl)piperidine-2-carboxylate (INT-238): LCMS [M+H]$^+$: 266.3, Rt 1.191 mins. $^1$H NMR (400 MHz, DMSO-d$_6$) δ=7.39-7.28 (m, 4H), 7.26-7.19 (m, 1H), 4.83-4.65 (m, 1H), 3.94-3.92 (m, 1H), 3.89-3.94 (m, 1H), 3.68 (s, 3H), 2.57-2.52 (m, 1H), 2.47 (s, 1H), 2.27-2.12 (m, 1H), 1.98-1.86 (m, 1H), 1.84-1.69 (m, 1H), 1.63-1.47 (m, 1H), 1.24 (d, J=6.8 Hz, 3H).

Example 159: 3-(5-(((2R,4R)-1-ethyl-4-fluoropiperidin-2-yl)methoxy)-1-oxoisoindolin-2-yl)piperidine-2,6-dione (I-244)

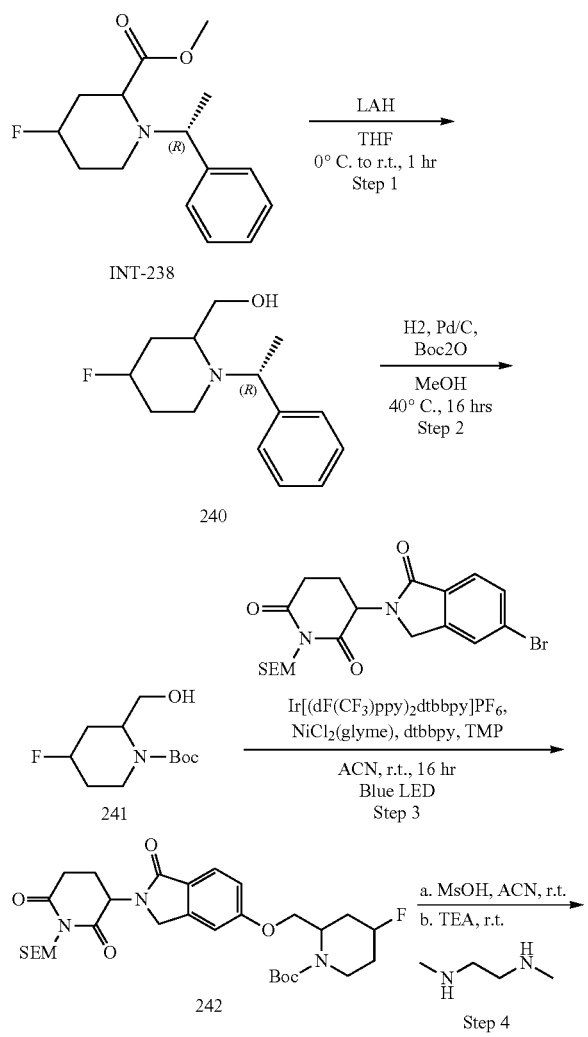

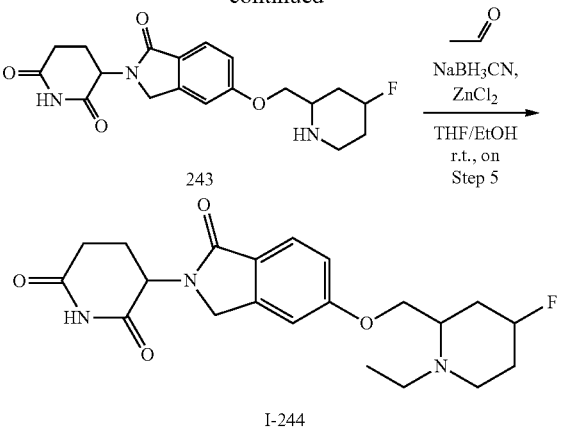

Step 1: (4-fluoro-1-((R)-1-phenylethyl)piperidin-2-yl)methanol (240)

To a solution of methyl 4-fluoro-1-((R)-1-phenylethyl) piperidine-2-carboxylate INT-238 (620 mg, 2.34 mmol) in THF (12 mL) was added LAH (133 mg, 3.51 mmol) in portions at 0° C. The mixture stirred at r.t. for 1 hr. The reaction mixture was quenched with aqueous saturated NH$_4$Cl (10 mL) and extracted twice with ethyl acetate. The organic layers were combined, dried over Na$_2$SO$_4$, filtered and concentrated in-vacuo to afford (4-fluoro-1-((R)-1-phenylethyl)piperidin-2-yl)methanol 240 as a colorless oil. The material was used directly in the next step without purification. LCMS [M+H]$^+$: 238.2.

Step 2: tert-butyl 4-fluoro-2-(hydroxymethyl)piperidine-1-carboxylate (241)

To a solution of (4-fluoro-1-((R)-1-phenylethyl)piperidin-2-yl)methanol 240 (620 mg, 2.61 mmol) in MeOH (6 mL) was added Boc$_2$O (627 mg, 2.87 mmol) and 10% Pd/C (150 mg, 0.141 mmol). The reaction stirred at 40° C. for 16 hrs under H$_2$ (15 psi). The suspension was filtered through a pad of CELITE® and washed three times with ethyl acetate. The combined filtrates were concentrated in-vacuo to afford tert-butyl 4-fluoro-2-(hydroxymethyl)piperidine-1-carboxylate 241 (550 mg, 2.35 mmol, 90% yield) as a colorless oil. The material was used directly in the next step without any other purification. $^1$H NMR (400 MHz, CDCl$_3$) δ 4.98-4.66 (m, 1H), 4.48-4.31 (m, 1H), 4.04-4.01 (m, 1H), 3.78-3.61 (m, 2H), 3.08-3.01 (m, 1H), 2.19-1.97 (m, 2H), 1.84-1.59 (m, 2H), 1.47 (s, 9H).

Step 3: tert-butyl 2-(((2-(2,6-dioxo-1-((2-(trimethylsilyl)ethoxy)methyl)piperidin-3-yl)-1-oxoisoindolin-5-yl)oxy)methyl)-4-fluoropiperidine-1-carboxylate (242)

A mixture of tert-butyl 4-fluoro-2-(hydroxymethyl)piperidine-1-carboxylate 241 (550 mg, 2.36 mmol), 3-(5-bromo-1-oxoisoindolin-2-yl)-1-((2-(trimethylsilyl)ethoxy)methyl)piperidine-2,6-dione (356 mg, 0.79 mmol), Ir[dF(CF$_3$)ppy]$_2$(dtbpy)(PF$_6$) (9 mg, 0.008 mmol) and NiCl$_2$.dtbbpy (15 mg, 0.039 mmol), quinuclidine (9 mg, 0.079 mmol), TMP (217 mg, 1.58 mmol) in MeCN (10 mL) was degassed three times under N$_2$. The reaction vial was then sealed with parafilm, placed 2 cm away from one blue LED light, and irradiated at 25° C. for 16 hrs. The reaction mixture was filtered and the filter cake was washed three times with ACN. the combined filtrates were concentrated and purified by silica gel chromatography (0-100% Ethyl acetate in petroleum ether). Fractions containing desired product were combined and concentrated to afford tert-butyl 2-(((2-(2,6-dioxo-1-((2-(trimethylsilyl)ethoxy)methyl)piperidin-3-yl)-1-oxoisoindolin-5-yl)oxy)methyl)-4-fluoropiperidine-1-carboxylate 242 (320 mg, 0.528 mmol, 67.2% yield) as bright yellow oil. $^1$H NMR (400 MHz, DMSO-$d_6$) δ 7.64 (d, J=8.4 Hz, 1H), 7.20 (s, 1H), 7.10-7.04 (m, 1H), 5.24-5.14 (m, 1H), 5.11-4.88 (m, 3H), 4.73-4.59 (m, 1H), 4.46-4.36 (m, 1H), 4.29-4.13 (m, 3H), 3.60-3.45 (m, 2H), 3.13-2.91 (m, 2H), 2.86-2.71 (m, 1H), 2.46-2.30 (m, 2H), 2.26-2.16 (m, 1H), 2.10-2.00 (m, 2H), 1.73-1.62 (m, 1H), 1.52-1.42 (m, 1H), 1.36 (s, 9H), 0.89-0.77 (m, 2H), −0.02 (s, 9H).

Step 4: 3-(5-((4-fluoropiperidin-2-yl)methoxy)-1-oxoisoindolin-2-yl)piperidine-2,6-dione (243)

To a solution of tert-butyl 2-(((2-(2,6-dioxo-1-((2-(trimethylsilyl)ethoxy)methyl)piperidin-3-yl)-1-oxoisoindolin-5-yl)oxy)methyl)-4-fluoropiperidine-1-carboxylate 242 (320 mg, 0.53 mmol) in ACN (2 mL) was added MsOH (0.34 mL, 5.28 mmol). The reaction stirred at 40° C. for 3 hrs. Triethylamine (0.94 mL, 6.87 mmol) and DMEDA (0.23 mL, 2.11 mmol) were added at 0° C. The reaction mixture stirred at r.t. for 16 hrs. The reaction was concentrated to give crude material. The crude product was dissolved with H$_2$O (2 mL) and purified by reverse-phase HPLC (column: 26.8*125 mm, 40 g of XB-C18, 20-40 μm, 120 Å; Mobile phase: A for H$_2$O (0.1% FA v/v) and B for Acetonitrile; Gradient: B 0%-40% in 15 min; Flow rate: 25-40 ml/min; Column temperature: R.T. Wavelength: 220 nm/254 nm). The eluent was concentrated to remove ACN and lyophilized to afford 3-(5-((4-fluoropiperidin-2-yl)methoxy)-1-oxoisoindolin-2-yl)piperidine-2,6-dione 243 (120 mg, 0.32 mmol, 60.5% yield) as a yellow solid. LCMS [M+H]$^+$: 376.2.

Step 5: 3-(5-((1-ethyl-4-fluoropiperidin-2-yl)methoxy)-1-oxoisoindolin-2-yl)piperidine-2,6-dione (I-244)

To a solution of 3-(5-((4-fluoropiperidin-2-yl)methoxy)-1-oxoisoindolin-2-yl)piperidine-2,6-dione 243 (120 mg, 0.32 mmol) and acetaldehyde (176 mg, 1.6 mmol) in THF (0.6 mL) and EtOH (0.6 mL) was added 2M ZnCl$_2$ in THF (218 mg, 0.8 mL, 1.6 mmol). The reaction mixture stirred at r.t. for 1 hour, then NaBH$_3$CN (58 mg, 0.96 mmol) was added. The reaction mixture stirred at r.t. for 15 hrs. The reaction mixture was filtered, concentrated, purified by Prep-HPLC (column: Waters Xbridge 150*25 mm*5 um; mobile phase: [water (10 mM NH$_4$HCO$_3$)-ACN]; B %: 15%-45%, 9 min). Fractions containing desired product were combined, concentrated to remove organic solvents and the residual aqueous solution was lyophilized to afford formate salt of 3-(5-((1-ethyl-4-fluoropiperidin-2-yl)methoxy)-1-oxoisoindolin-2-yl)piperidine-2,6-dione I-244 (42.1 mg, 0.104 mmol, 32.6% yield) as an off-white solid. LCMS [M+H]$^+$: 404.4. $^1$H NMR (400 MHz, DMSO-$d_6$) δ=10.96 (br s, 1H), 8.22 (s, 1H), 7.62 (d, J=8.4 Hz, 1H), 7.24-7.02 (m, 2H), 5.11-5.03 (m, 1H), 5.03-4.84 (m, 1H), 4.43-4.22 (m, 2H), 4.17-4.04 (m, 2H), 2.99-2.85 (m, 2H), 2.78-2.66 (m, 2H), 2.63-2.52 (m, 3H), 2.44-2.33 (m, 1H), 2.06-1.90 (m, 2H), 1.88-1.66 (m, 3H), 0.98 (t, J=7.2 Hz, 3H), Example 160: 3-(5-(((2S,4S)-1-ethyl-4-fluoropiperidin-2-yl)methoxy)-1-oxoisoindolin-2-yl)piperidine-2,6-dione (I-249)

Example 160 was prepared analogously to Example 159 except that single diastereomer INT-239 was used instead of INT-238.

3-(5-((1-ethyl-4-fluoropiperidin-2-yl)methoxy)-1-oxoisoindolin-2-yl)piperidine-2,6-dione I-249, obtained in Step 5, was purified by reverse phase HPLC (column: Waters Xbridge 150*25 mm*5 um; mobile phase: [water (10 mM NH$_4$HCO$_3$)-ACN]; B %: 15%-45%, 9 min). Fractions containing desired product were combined, concentrated to remove organic solvents, and the residual aqueous solution was lyophilized to afford the formate salt of 3-(5-((1-ethyl-4-fluoropiperidin-2-yl)methoxy)-1-oxoisoindolin-2-yl)piperidine-2,6-dione I-249 (80.9 mg, 0.20 mmol, 62.7% yield) as an off-white solid. LCMS [M+H]$^+$: 404.3. $^1$H NMR (400 MHz, DMSO-$d_6$) δ 10.95 (br s, 1H), 8.22 (s, 1H), 7.62 (d, J=8.4 Hz, 1H), 7.22-7.02 (m, 2H), 5.11-5.03 (m, 1H), 5.02-4.85 (m, 1H), 4.41-4.24 (m, 2H), 4.16-4.07 (m, 2H), 3.01-2.84 (m, 2H), 2.80-2.66 (m, 2H), 2.62-2.52 (m, 3H), 2.43-2.32 (m, 1H), 2.03-1.91 (m, 2H), 1.87-1.69 (m, 3H), 0.98 (t, J=7.2 Hz, 3H).

Example 161: 3-(5-((4,4-difluoropiperidin-2-yl)methoxy)-1-oxoisoindolin-2-yl)piperidine-2,6-dione (I-251)

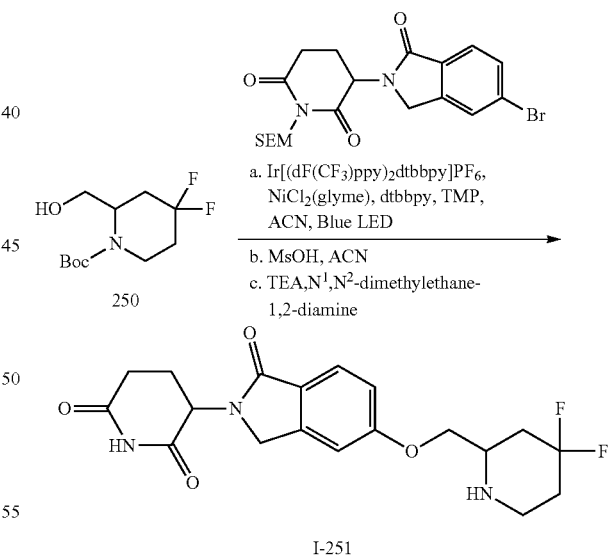

Photoredox catalysis between 3-(5-bromo-1-oxoisoindolin-2-yl)-1-((2-(trimethylsilyl)ethoxy)methyl)piperidine-2,6-dione (907 mg, 2.00 mmol) and tert-butyl 4,4-difluoro-2-(hydroxymethyl)piperidine-1-carboxylate 250 (prepared as described in WO2013/127913 A1) (553 mg, 2.19 mmol) using General Method VI, followed by global deprotection (General Method VII) and purification by silica gel chromatography (15-100% EtOH in DCM, with 1% TEA as modifier) afforded 3-(5-((4,4-difluoropiperidin-2-yl)

methoxy)-1-oxoisoindolin-2-yl)piperidine-2,6-dione I-251 (556 mg, 1.41 mmol, 70% yield) as a white solid. LCMS [M+H]+: 394.4. 1H NMR (400 MHz, CD2Cl2) δ 7.96 (s, 1H), 7.64 (d, J=8.4 Hz, 1H), 6.95 (dd, J=8.4, 2.2 Hz, 1H), 6.91 (d, J=2.2 Hz, 1H), 5.04 (dd, J=13.4, 5.2 Hz, 1H), 4.29 (d, J=16.1 Hz, 1H), 4.22 (d, J=16.1 Hz, 1H), 4.01 (dd, J=9.2, 3.7 Hz, 1H), 3.91 (dd, J=9.1, 7.0 Hz, 1H), 3.20 (td, J=7.7, 7.2, 3.6 Hz, 1H), 3.10 (ddt, J=12.7, 5.4, 2.7 Hz, 1H), 2.86-2.66 (m, 3H), 2.26 (qd, J=12.8, 5.6 Hz, 1H), 2.18-1.93 (m, 3H), 1.93-1.61 (m, 2H).

Example 162: Diastereomers 3-(5-((1-ethyl-4,4-difluoropiperidin-2-yl)methoxy)-1-oxoisoindolin-2-yl)piperidine-2,6-dione (I-252)

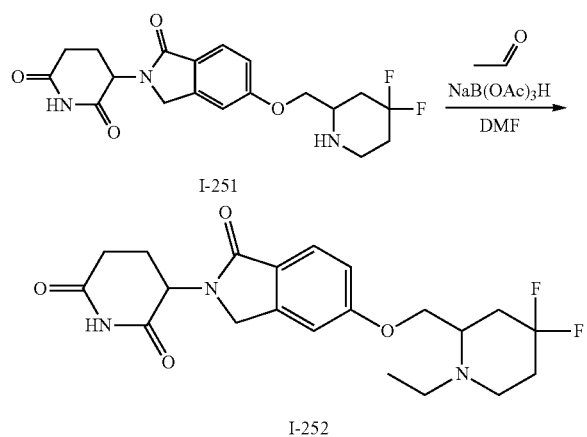

3-(5-((4,4-difluoropiperidin-2-yl)methoxy)-1-oxoisoindolin-2-yl)piperidine-2,6-dione I-251 (200 mg, 0.51 mmol) and acetaldehyde (0.09 ml, 1.53 mmol) were subjected to a reductive amination using General Method III. The crude material was purified by silica gel chromatography (silica gel saturated with Et3N, 15-80% 3:1 EtOAc:EtOH in heptane) to afford a mixture of isomers 3-(5-((1-ethyl-4,4-difluoropiperidin-2-yl)methoxy)-1-oxoisoindolin-2-yl)piperidine-2,6-dione I-252 (130 mg, 0.31 mmol, 60% yield) as a white solid. LCMS [M+H]+: 422.4. The mixture of isomers was separated via chiral SFC [Column Chiralpak IC 21×250 mm, CO2 Co-solvent 50% 3:1 ACN:EtOH; at 70 g/min at 100 bar] to afford two peaks. Peak 1 was further purified via chiral SFC [Column Chiralpak AD-H 21×250 mm, CO2 Co-solvent 45% 1:1 ACN:EtOH; at 70 g/min at 100 bar] to afford two isomers. Isomer 1 of 3-(5-((1-ethyl-4,4-difluoropiperidin-2-yl)methoxy)-1-oxoisoindolin-2-yl)piperidine-2,6-dione (6.4 mg, 0.02 mmol) as a white solid; Chiral SFC Rt 1.8 min [Column Chiralpak AD-H 4.6×100 mm, CO2 Co-solvent 40% 1:1 ACN:EtOH; at 4 mL/min at 125 bar]; 1H NMR (400 MHz, CD2Cl2) δ 7.97 (s, 1H), 7.75 (d, J=8.8 Hz, 1H), 7.04 (d, J=6.6 Hz, 2H), 5.17-5.07 (m, 1H), 4.39 (d, J=16.1 Hz, 1H), 4.32 (d, J=16.1 Hz, 1H), 4.15 (s, 2H), 3.24-2.95 (m, 1H), 2.94-2.72 (m, 4H), 2.75-2.56 (m, 1H), 2.35 (qd, J=12.9, 5.6 Hz, 1H), 2.20 (dtd, J=13.0, 5.0, 2.8 Hz, 2H), 2.13-1.90 (m, 2H), 1.74-1.42 (m, 2H), 1.43-1.01 (m, 3H). Isomer 2 of 3-(5-((1-ethyl-4,4-difluoropiperidin-2-yl)methoxy)-1-oxoisoindolin-2-yl)piperidine-2,6-dione (6.0 mg, 0.01 mmol) as a white solid; Chiral SFC Rt 2.3 min [Column Chiralpak AD-H 4.6×100 mm, CO2 Co-solvent 40% 1:1 ACN:EtOH; at 4 mL/min at 125 bar]; 1H NMR (400 MHz, CD2Cl2) δ 7.94 (s, 1H), 7.76 (d, J=8.8 Hz, 1H), 7.05 (d, J=9.0 Hz, 2H), 5.16-5.03 (m, 1H), 4.40 (d, J=16.1 Hz, 1H), 4.32 (d, J=16.1 Hz, 1H), 4.28-3.99 (m, 2H), 3.05-2.92 (m, 1H), 2.92-2.73 (m, 4H), 2.71-2.56 (m, 1H), 2.35 (qd, J=12.9, 5.5 Hz, 2H), 2.20 (dtd, J=13.0, 5.1, 2.7 Hz, 2H), 1.99 (d, J=29.1 Hz, 1H), 1.64-1.38 (m, 2H), 1.31-0.98 (m, 3H). Peak 2 was further purified via chiral SFC [Column ChiralpakAD-H 21×250 mm, CO2 Co-solvent 35% isopropanol; at 70 g/min at 100 bar] to afford two isomers. Isomer 3 of 3-(5-((1-ethyl-4,4-difluoropiperidin-2-yl)methoxy)-1-oxoisoindolin-2-yl)piperidine-2,6-dione (7.0 mg, 0.02 mmol) as a white solid; Chiral SFC Rt 2.1 min [Column Chiralpak AD-H 4.6×100 mm, CO2 Co-solvent 35% isopropanol; at 4 mL/min at 125 bar]; 1H NMR (400 MHz, CD2Cl2) δ 7.97 (s, 1H), 7.74 (d, J=8.3 Hz, 1H), 7.21-6.81 (m, 2H), 5.13 (dd, J=13.3, 5.2 Hz, 1H), 4.39 (d, J=16.1 Hz, 1H), 4.31 (d, J=16.1 Hz, 1H), 4.11 (s, 2H), 2.99 (s, 1H), 2.94-2.74 (m, 4H), 2.66 (s, 1H), 2.35 (qd, J=12.9, 5.6 Hz, 1H), 2.20 (dtd, J=13.2, 5.2, 2.9 Hz, 2H), 2.06 (s, 2H), 1.53 (s, 2H), 1.09 (s, 3H). Isomer 4 of 3-(5-((1-ethyl-4,4-difluoropiperidin-2-yl)methoxy)-1-oxoisoindolin-2-yl)piperidine-2,6-dione (6.0 mg, 0.01 mmol) as a white solid; Chiral SFC Rt 3.1 min [Column Chiralpak AD-H 4.6×100 mm, CO2 Co-solvent 35% isopropanol; at 4 mL/min at 125 bar]; 1H NMR (400 MHz, CD2Cl2) δ 7.99 (s, 1H), 7.74 (d, J=8.4 Hz, 1H), 7.16-6.89 (m, 2H), 5.13 (dd, J=13.3, 5.1 Hz, 1H), 4.39 (d, J=16.1 Hz, 1H), 4.31 (d, J=16.1 Hz, 1H), 4.21-4.00 (m, 2H), 3.11-2.93 (m, 1H), 2.94-2.75 (m, 3H), 2.75-2.50 (m, 2H), 2.35 (qd, J=12.8, 5.5 Hz, 1H), 2.20 (dtd, J=13.0, 5.1, 2.8 Hz, 2H), 2.04 (s, 2H), 1.73-1.42 (m, 2H), 1.08 (s, 3H).

Example 163: Diastereomers 3-(5-((endo-2-ethyl-2-azabicyclo[2.2.1]heptan-3-yl)methoxy)-1-oxoisoindolin-2-yl)piperidine-2,6-dione (I-255)

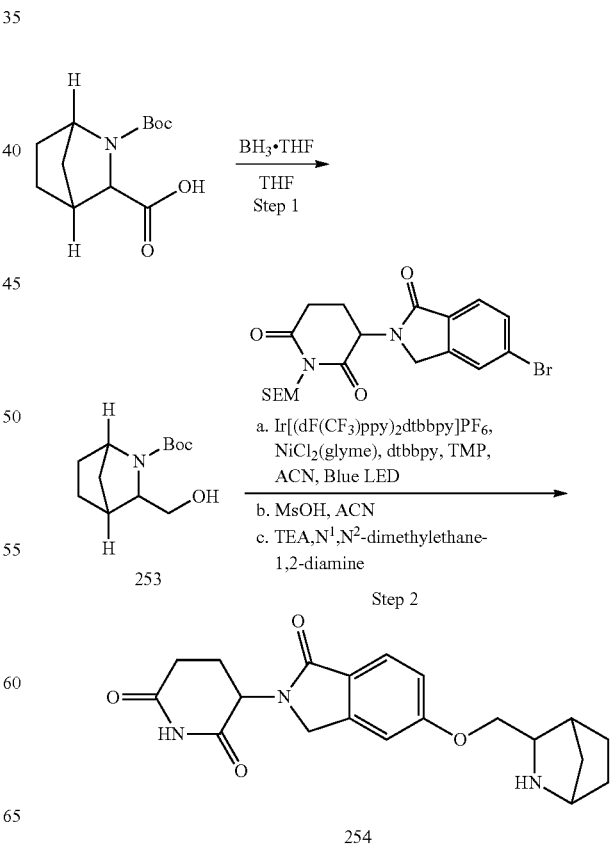

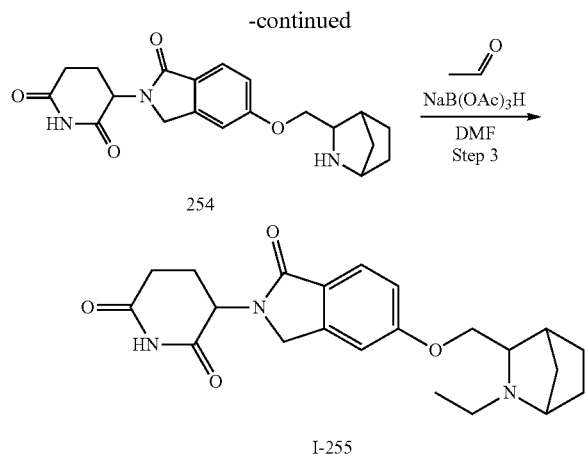

Step 1: tert-butyl (endo)-3-(hydroxymethyl)-2-azabicyclo[2.2.1]heptane-2-carboxylate (253)

The racemate of endo-2-(tert-butoxycarbonyl)-2-azabicyclo[2.2.1]heptane-3-carboxylic acid (0.30 g, 1.24 mmol) was dissolved in THF (6 mL) and cooled to 0° C. 1 M borane THF complex in THF (2.6 mL, 2.60 mmol) was added dropwise. The reaction stirred at r.t. overnight. The reaction was cooled to 0° C. and quenched with methanol (1.0 mL, 24.7 mmol) and stirred at r.t. for 2 hrs. The reaction was concentrated to dryness then redissolved in methanol (5 mL). The reaction was stirred at r.t. overnight. The reaction was concentrated to afford a racemic mixture of tert-butyl (endo)-3-(hydroxymethyl)-2-azabicyclo[2.2.1]heptane-2-carboxylate 253 (256 mg, 1.13 mmol, 91% yield) as a clear oil. The material was taken on to the next step without purification.

Step 2: 3-(5-((endo-2-azabicyclo[2.2.1]heptan-3-yl)methoxy)-1-oxoisoindolin-2-yl)piperidine-2,6-dione (254)

Photoredox catalysis between racemate tert-butyl endo-3-(hydroxymethyl)-2-azabicyclo[2.2.1]heptane-2-carboxylate 253 (1.65 g, 7.28 mmol) and 3-(5-bromo-1-oxoisoindolin-2-yl)-1-((2-(trimethylsilyl)ethoxy)methyl)piperidine-2,6-dione (3.00 g, 6.62 mmol) using General Method VI, followed by global deprotection (General Method VII) and purification by silica gel chromatography (15-100% EtOH in DCM, 1% TEA as modifier) afforded 3-(5-((endo-2-azabicyclo[2.2.1]heptan-3-yl)methoxy)-1-oxoisoindolin-2-yl)piperidine-2,6-dione 254 (1.07 g, 2.90 mmol, 44% yield) as a white solid. LCMS [M+H]$^+$: 370.4.

Step 3: Diastereomers 3-(5-((endo-2-ethyl-2-azabicyclo[2.2.1]heptan-3-yl)methoxy)-1-oxoisoindolin-2-yl)piperidine-2,6-dione (I-255)

3-(5-((endo-2-azabicyclo[2.2.1]heptan-3-yl)methoxy)-1-oxoisoindolin-2-yl)piperidine-2,6-dione 254 (200 mg, 0.54 mmol) and acetaldehyde (0.09 ml, 1.62 mmol) were subjected to a reductive amination using General Method III. The crude material was purified by silica gel chromatography (silica gel saturated with TEA, 15-80% 3:1 EtOAc:EtOH in heptane) to afford an isomeric mixture of 3-(5-((endo-2-ethyl-2-azabicyclo[2.2.1]heptan-3-yl)methoxy)-1-oxoisoindolin-2-yl)piperidine-2,6-dione I-255 (103 mg, 0.26 mmol, 48% yield) as a white solid. LCMS [M+H]$^+$: 398.3. The mixture of isomers was separated via chiral SFC [Column Chiralpak IC 21×250 mm, CO$_2$ Co-solvent 50% 3:1 ACN:EtOH with 0.25% TEA; at 80 g/min at 100 bar] to afford two peaks. Peak 1 was further purified via chiral HPLC [Column Chiralpak ID 30×250 mm, 3:1 TBME:EtOH with 0.05% TEA, at 20 mL/min] to afford two isomers. Isomer 3 of 3-(5-((endo-2-ethyl-2-azabicyclo[2.2.1]heptan-3-yl)methoxy)-1-oxoisoindolin-2-yl)piperidine-2,6-dione (5.5 mg, 0.01 mmol) as a white solid; Chiral SFC Rt 3.9 min [Column Chiralpak IA-3 3×100 mm, CO$_2$ Co-solvent 30% MeOH with 0.1% NH$_4$OH; at 2.5 mL/min at 1800 PSI]; $^1$H NMR (400 MHz, CD$_2$Cl$_2$) δ 7.95 (s, 1H), 7.74 (d, J=8.4 Hz, 1H), 7.12 (d, J=2.3 Hz, 1H), 7.07 (dd, J=8.4, 2.3 Hz, 1H), 5.12 (dd, J=13.3, 5.0 Hz, 1H), 4.79 (s, 1H), 4.40 (d, J=16.1 Hz, 1H), 4.33 (d, J=16.1 Hz, 1H), 3.89 (s, 1H), 3.45 (s, 1H), 3.11 (s, 2H), 2.94-2.72 (m, 3H), 2.36 (qd, J=12.9, 5.6 Hz, 1H), 2.19 (dtd, J=13.1, 5.3, 2.9 Hz, 1H), 2.05-1.93 (m, 1H), 1.84-1.40 (m, 9H). Isomer 4 of 3-(5-((endo-2-ethyl-2-azabicyclo[2.2.1]heptan-3-yl)methoxy)-1-oxoisoindolin-2-yl)piperidine-2,6-dione (5.6 mg, 0.01 mmol) as a white solid; Chiral SFC Rt 4.5 min [Column Chiralpak IA-3 3×100 mm, CO$_2$ Co-solvent 30% MeOH with 0.1% NH$_4$OH; at 2.5 mL/min at 1800 PSI]; $^1$H NMR (400 MHz, CD$_2$Cl$_2$) δ 7.95 (s, 1H), 7.72 (d, J=8.9 Hz, 1H), 7.08-7.01 (m, 2H), 5.21-5.02 (m, 1H), 4.38 (d, J=16.0 Hz, 1H), 4.31 (d, J=16.1 Hz, 1H), 4.21-3.79 (m, 1H), 3.19 (s, 1H), 3.04-2.74 (m, 3H), 2.74-2.45 (m, 2H), 2.35 (qd, J=12.9, 5.8 Hz, 1H), 2.19 (dtd, J=13.1, 5.1, 2.8 Hz, 1H), 1.85-0.92 (m, 11H). Peak 2 was further separated via chiral SFC [Column Chiralpak AD-H 21×250 mm, CO$_2$ Co-solvent 35% isopropanol with 0.25% TEA; at 70 g/min at 100 bar] to afford two isomers. Isomer 1 of 3-(5-((endo-2-ethyl-2-azabicyclo[2.2.1]heptan-3-yl)methoxy)-1-oxoisoindolin-2-yl)piperidine-2,6-dione (13 mg, 0.03 mmol) as a white solid; Chiral SFC Rt 3.4 min [Column Chiralpak IA-3 3×100 mm, CO$_2$ Co-solvent 30% MeOH with 0.1% NH$_4$OH; at 2.5 mL/min at 1800 PSI]; $^1$H NMR (400 MHz, CD$_2$Cl$_2$) δ 7.95 (s, 1H), 7.74 (d, J=8.4 Hz, 1H), 7.27-6.90 (m, 2H), 5.19-5.02 (m, 1H), 4.82 (s, 1H), 4.40 (d, J=16.3 Hz, 1H), 4.33 (d, J=16.1 Hz, 1H), 3.92 (s, 1H), 3.47 (s, 1H), 3.13 (s, 2H), 2.97-2.72 (m, 3H), 2.36 (qd, J=12.9, 5.5 Hz, 1H), 2.26-2.12 (m, 1H), 2.09-1.92 (m, 1H), 1.87-1.36 (m, 9H). Isomer 2 of 3-(5-((endo-2-ethyl-2-azabicyclo[2.2.1]heptan-3-yl)methoxy)-1-oxoisoindolin-2-yl)piperidine-2,6-dione (3.0 mg, 0.01 mmol) as a white solid; Chiral SFC Rt 3.8 min [Column Chiralpak IA-3 3×100 mm, CO$_2$ Co-solvent 30% MeOH with 0.1% NH$_4$OH; at 2.5 mL/min at 1800 PSI]; $^1$H NMR (400 MHz, CD$_2$Cl$_2$) δ 7.94 (s, 1H), 7.73 (d, J=8.4 Hz, 1H), 7.05 (d, J=9.2 Hz, 2H), 5.18-5.02 (m, 1H), 4.39 (d, J=16.0 Hz, 1H), 4.32 (d, J=16.3 Hz, 1H), 3.92 (s, 1H), 3.11 (s, 1H), 2.97-2.72 (m, 3H), 2.63 (s, 2H), 2.35 (qd, J=12.9, 5.6 Hz, 1H), 2.28-2.11 (m, 1H), 1.90-0.97 (m, 11H).

Biological Data

Abbreviations

| | |
|---|---|
| AMO | anti-miRNA oligonucleotide |
| BSA | bovine serum albumin |
| Cas9 | CRISPR associated protein 9 |
| CRISPR | Clustered regularly interspaced short palindromic repeats |
| crRNA | CRISPR RNA |
| DMEM | Dulbecco's modified eagle media |
| DMSO | Dimethyl sulfoxide |
| DTT | Dithiothreitol |

-continued

| Abbreviations | |
|---|---|
| EDTA | ethylenediaminetetraacetic acid |
| eGFP | enhanced green fluorescent protein |
| FACS | fluorescence-activated cell sorting |
| FBS | fetal bovine serum |
| FITC | fluorescein |
| Flt3L | Fms-related tyrosine kinase 3 ligand, Flt3L |
| HbF | Fetal hemoglobin |
| HEPES | (4-(2-hydroxyethyl)-1-piperazineethanesulfonic acid) |
| IMDM | Iscove's modified Dulbecco's medium |
| KCl | potassium chloride |
| mPB | mobilized peripheral blood |
| PBS | phosphate buffered saline |
| rhEPO | recombinant human erythropoietin |
| rhIL-3 | recombinant human interleukin-3 |
| rhIL-6 | recombinant human interleukin-6 |
| rhSCF | recombinant human stem cell factor |
| rhTPO | recominant human thrombopoietin |
| RNP | ribonucleoprotein |
| shRNA | short hairpin RNA |
| tracrRNA | trans-activating crRNA |
| WIZ | Widely-Interspaced Zinc Finger Containing Protein |

Materials and Methods

Example 164: Quantification of WIZ Protein Levels in HiBit Tag Fusion Protein Assay The Hibit system from Promega was used to develop high-throughput and quantitative assays to measure changes in WIZ protein levels in response to compounds. The HiBit tag was derived from a split Nanoluciferase and has the following protein sequence: VSGWRLFKKIS (SEQ ID No: 1). The complementary fragment of Nanoluciferase (known as LgBit, from Promega), was added to the HiBit tag to form an active Nanoluciferase enzyme whose activity can be precisely measured. In this way, the levels of a fusion protein with the HiBit tag can be quantified in cell lysates.

Lentiviral vectors, based on the INVITROGEN™ pLenti6.2/V5 DEST backbone were constructed that places the HiBit tag upstream of WIZ and expressed the fusion protein from an HSVTK promotor.

To ensure moderate and consistent expression of the HiBit-WIZ fusion protein across all cells in the population, stable cell lines were constructed from cells harboring a single copy of the construct. Lentivirus packaged with the constructs were made using the VIRAPOWER™ kit from INVITROGEN™. 293T cells from ATCC (Catalog number: CRL-3216), were infected with the virus at low multiplicity of infection and selected by 5 μg/mL blasticidin in culture media for 2 weeks.

The levels of HiBit-WIZ tagged fusion proteins in compound-treated cell lines were measured as follows:

On day 1, cells were diluted to $1.0 \times 10^6$ cells/ml in normal growth medium. 20 μL of cell suspension were plated in each well of a solid white 384-well plate. Plates were incubated overnight in a 37° C. and 5% $CO_2$ humidified tissue culture incubator.

On day 2, serial dilutions of compounds were made in 384-well plates. Compound plates were set up with DMSO in columns 1, 2, 23, 24, and 10-point compound dilution series in column 3-12 and column 13-22. 10 mM stock solution of compound were placed into column 3 or 13 and a 1:5 serial dilution was carried out until there was a 10-point dilution series per compound. 50 nL of diluted compounds were transferred into the plated cells by ECHO® (Labcyte) acoustic transfer. The highest concentration of compound was 25 μM. Plates were incubated overnight (about 18 hours) in a 37° C. and 5% $CO_2$ humidified tissue culture incubator.

On day 3, plates were removed from the incubator and allowed to equilibrate at room temperature for 60 minutes. HiBit substrate (NANO-GLO® HiBit Lytic Detection System, Promega Catalogue number: N3050) was added as described by the manufacturers protocols. Plates were incubated at room temperature for 30 minutes and luminescence was read using an ENVISION® reader (PERKINELMER®). Data was analyzed and visualized using the SPOTFIRE® software package.

WIZ Degradation Activity of Compounds (Table 1)

Table 1 shows WIZ degradation activity of compounds of the disclosure in the WIZ HiBit assay in 293T cells. WIZ Amax reflects the DMSO-normalized, curve-fitted percentage of WIZ-HiBit remaining at 25 uM. It was calculated by normalizing DMSO controls to 100%, parametric curve fitting of the dose response data (10-point, 5-fold), followed by calculation of response at 25 uM using the fitted equation (nd=not determined).

TABLE 1

| Cmpd No | WIZ $AC_{50}$ (μM) | WIZ Amax | % degradation of WIZ (100-Amax) |
|---|---|---|---|
| I-5 | 0.029 | 2.1 | 97.9 |
| I-17 | >25 | 73.6 | 26.4 |
| I-19 | >25 | 65.3 | 34.7 |
| I-25 | >25 | 53.4 | 46.6 |
| I-27 | >25 | 84.4 | 15.6 |
| I-44 | >25 | 89.7 | 10.3 |
| I-45 | >25 | 78.7 | 21.3 |
| I-50 | 0.277 | 9.9 | 90.1 |
| I-50a | >25 | 47.8 | 52.2 |
| I-50aa | 0.412 | 4.9 | 95.1 |
| I-50ab | >25 | 49.2 | 50.8 |
| I-50ac | 0.578 | 7.7 | 92.3 |
| I-50ae | >25 | 46.9 | 53.1 |
| I-50af | 21.067 | 42.8 | 57.2 |
| I-50ag | 15.218 | 37.2 | 62.8 |
| I-50ah | >25 | 55.6 | 44.4 |
| I-50ai | 0.591 | 22.2 | 77.8 |
| I-50aj | 0.016 | 1.0 | 99.0 |
| I-50ak | 0.347 | 18.7 | 81.3 |
| I-50al | >25 | 45.9 | 54.1 |
| I-50am | >25 | 60.0 | 40.0 |
| I-50an | 1.713 | 17.8 | 82.2 |
| I-50ao | 0.089 | 3.2 | 96.8 |
| I-50ap | >25 | 69.9 | 30.1 |
| I-50aq | >25 | 84.6 | 15.4 |
| I-50ar | 1.144 | 21.8 | 78.2 |
| I-50as | 0.327 | 15.7 | 84.3 |
| I-50at | >25 | 90.2 | 9.8 |
| I-50au | >25 | 75.8 | 24.2 |
| I-50av | 0.784 | 25.5 | 74.5 |
| I-50aw | >25 | 75.5 | 24.5 |
| I-50ax | 0.149 | 7.5 | 92.5 |
| I-50ay | >25 | 74.3 | 25.7 |
| I-50b | 1.483 | 17.0 | 83.0 |
| I-50bb | 18.323 | 43.2 | 56.8 |
| I-50bc | 0.058 | 6.6 | 93.4 |
| I-50bd | >25 | 58.9 | 41.1 |
| I-50be | >25 | 58.1 | 41.9 |
| I-50bf | >25 | 49.1 | 50.9 |
| I-50bg | 0.031 | 2.0 | 98.0 |
| I-50bh | 0.005 | 0.1 | 99.9 |
| I-50bi | 0.848 | 28.0 | 72.0 |
| I-50bj | >25 | 74.2 | 25.8 |
| I-50bl | >25 | 82.4 | 17.6 |
| I-50bm | >25 | 64.0 | 36.0 |
| I-50bn | 0.897 | 23.8 | 76.2 |
| I-50bo | 20.761 | 42.6 | 57.4 |
| I-50bp | 6.999 | 34.1 | 65.9 |
| I-50bq | 1.195 | 27.9 | 72.1 |

TABLE 1-continued

| Cmpd No | WIZ AC$_{50}$ (μM) | WIZ Amax | % degradation of WIZ (100-Amax) |
|---|---|---|---|
| I-50br | 0.044 | 5.9 | 94.1 |
| I-50bs | 0.018 | 5.5 | 94.5 |
| I-50bt | 4.268 | 33.9 | 66.1 |
| I-50bv | 0.001 | 0.1 | 99.9 |
| I-50bw | 0.150 | 4.0 | 96.0 |
| I-50bx | 21.031 | 43.6 | 56.4 |
| I-50by | >25 | 74.3 | 25.7 |
| I-50bz | 0.172 | 14.8 | 85.2 |
| I-50c | >25 | 61.9 | 38.1 |
| I-50ca | 0.239 | 23.7 | 76.3 |
| I-50cb | 5.800 | 25.5 | 74.5 |
| I-50cc | 5.972 | 28.3 | 71.7 |
| I-50cd | 3.743 | 30.3 | 69.7 |
| I-50ce | >25 | 56.1 | 43.9 |
| I-50cf | >25 | 61.9 | 38.1 |
| I-50cg | 0.043 | 7.3 | 92.7 |
| I-50ch | 9.241 | 40.9 | 59.1 |
| I-50ci | 0.306 | 16.8 | 83.2 |
| I-50cj | 0.757 | 28.2 | 71.8 |
| I-50ck | 0.766 | 16.8 | 83.2 |
| I-50cl | 0.644 | 22.3 | 77.7 |
| I-50cm | 1.768 | 32.8 | 67.2 |
| I-50cn | >25 | 75.7 | 24.3 |
| I-50co | 0.081 | 7.7 | 92.3 |
| I-50cp | 3.532 | 34.8 | 65.2 |
| I-50cq | >25 | 92.7 | 7.3 |
| I-50cr | >25 | 47.1 | 52.9 |
| I-50cs | 4.412 | 28.9 | 71.1 |
| I-50ct | 0.133 | 19.8 | 80.2 |
| I-50cv | >25 | 57.4 | 42.6 |
| I-50cw | >25 | 61.0 | 39.0 |
| I-50cx | 0.143 | 7.4 | 92.6 |
| I-50cy | 0.922 | 11.0 | 89.0 |
| I-50cz | >25 | 50.2 | 49.8 |
| I-50d | 0.784 | 21.7 | 78.3 |
| I-50da | 5.126 | 34.9 | 65.1 |
| I-50dc | >25 | 60.2 | 39.8 |
| I-50dd | >25 | 60.4 | 39.6 |
| I-50de | 18.436 | 41.5 | 58.5 |
| I-50df | 11.129 | 44.1 | 55.9 |
| I-50dg | >25 | 83.9 | 16.1 |
| I-50dh | 6.534 | 33.1 | 66.9 |
| I-50di | 1.176 | 21.0 | 79.0 |
| I-50dj | 2.450 | 0.3 | 99.7 |
| I-50dk | 0.147 | 13.0 | 87.0 |
| I-50dl | >25 | 56.0 | 44.0 |
| I-50dm | 0.007 | 0.0 | 100.0 |
| I-50dn | >25 | 78.8 | 21.2 |
| I-50do | 0.002 | 0.1 | 99.9 |
| I-50dp | 6.841 | 34.5 | 65.5 |
| I-50dq | 0.770 | 28.8 | 71.2 |
| I-50dr | 0.097 | 14.5 | 85.5 |
| I-50ds | 3.041 | 29.2 | 70.8 |
| I-50dt | 2.735 | 33.0 | 67.0 |
| I-50du | 4.264 | 21.6 | 78.4 |
| I-50dv | 2.987 | 35.0 | 65.0 |
| I-50dw | 0.008 | 1.0 | 99.0 |
| I-50dx | 0.002 | 2.0 | 98.0 |
| I-50dy | 0.019 | 3.4 | 96.6 |
| I-50dz | 3.271 | 37.2 | 62.8 |
| I-50e | >25 | 58.9 | 41.1 |
| I-50ea | 0.651 | 19.0 | 81.0 |
| I-50eb | 0.002 | 1.5 | 98.5 |
| I-50ec | 0.017 | 0.0 | 100.0 |
| I-50ed | 0.100 | 7.7 | 92.3 |
| I-50ee | 0.287 | 7.6 | 92.4 |
| I-50ef | 1.457 | 14.8 | 85.2 |
| I-50eg | 0.004 | 0.4 | 99.6 |
| I-50eh | 0.013 | 2.8 | 97.2 |
| I-50ei | >25 | 68.6 | 31.4 |
| I-50ej | >25 | 82.8 | 17.2 |
| I-50ek | 0.004 | 0.9 | 99.1 |
| I-50el | >25 | 69.7 | 30.3 |
| I-50em | 19.395 | 48.1 | 51.9 |
| I-50en | 0.004 | 0.2 | 99.8 |
| I-50eo | 0.074 | 6.0 | 94.0 |
| I-50ep | >25 | 87.6 | 12.4 |
| I-50eq | 0.272 | 11.6 | 88.4 |
| I-50er | 0.920 | 10.2 | 89.8 |
| I-50es | 0.003 | 0.5 | 99.5 |
| I-50et | >25 | 50.9 | 49.1 |
| I-50eu | 0.003 | 0.7 | 99.3 |
| I-50ev | 0.051 | 2.0 | 98.0 |
| I-50ew | 0.026 | 0.7 | 99.3 |
| I-50f | 0.816 | 17.4 | 82.6 |
| I-50g | 0.097 | 11.1 | 88.9 |
| I-50h | 13.621 | 40.6 | 59.4 |
| I-50i | >25 | 71.2 | 28.8 |
| I-50j | 3.490 | 34.6 | 65.4 |
| I-50k | >25 | 65.3 | 34.7 |
| I-50l | 1.882 | 28.9 | 71.1 |
| I-50m | >25 | 53.4 | 46.6 |
| I-50n | 0.022 | 1.7 | 98.3 |
| I-50o | 12.511 | 41.6 | 58.4 |
| I-50p | 0.047 | 6.8 | 93.2 |
| I-50q | >25 | 95.5 | 4.5 |
| I-50r | >25 | 65.6 | 34.4 |
| I-50s | 3.797 | 15.7 | 84.3 |
| I-50t | 0.269 | 14.8 | 85.2 |
| I-50u | 2.635 | 29.9 | 70.1 |
| I-50v | 0.345 | 17.4 | 82.6 |
| I-50w | >25 | 74.1 | 25.9 |
| I-50x | >25 | 78.0 | 22.0 |
| I-50y | 0.179 | 14.8 | 85.2 |
| I-50z | 3.204 | 20.8 | 79.2 |
| I-52 | 2.125 | 30.4 | 69.6 |
| I-53 | 1.085 | 20.4 | 79.6 |
| I-58 | >25 | 73.9 | 26.1 |
| I-60 | 2.036 | 32.7 | 67.3 |
| I-64 | >25 | 78.5 | 21.5 |
| I-72a | >25 | 88.8 | 11.2 |
| I-72ad | 17.426 | 47.2 | 52.8 |
| I-72ae | >25 | 85.3 | 14.7 |
| I-72af | >25 | 92.3 | 7.7 |
| I-72ag | >25 | 94.6 | 5.4 |
| I-72ah | >25 | 77.1 | 22.9 |
| I-72ai | >25 | 58.4 | 41.6 |
| I-72ak | 0.686 | 21.1 | 78.9 |
| I-72an | 13.803 | 46.2 | 53.8 |
| I-72ao | >25 | 91.7 | 8.3 |
| I-72ar | 2.567 | 28.2 | 71.8 |
| I-72au | >25 | 60.1 | 39.9 |
| I-72av | >25 | 75.7 | 24.3 |
| I-72aw | 8.518 | 39.6 | 60.4 |
| I-72ay | >25 | 82.4 | 17.6 |
| I-72bc | >25 | 97.0 | 3.0 |
| I-72be | >25 | 88.2 | 11.8 |
| I-72bi | >25 | 96.1 | 3.9 |
| I-72bm | >25 | 87.0 | 13.0 |
| I-72by | 19.758 | 48.0 | 52.0 |
| I-72bz | >25 | 53.3 | 46.7 |
| I-72c | >25 | 79.4 | 20.6 |
| I-72ca | >25 | 89.8 | 10.2 |
| I-72cf | >25 | 65.0 | 35.0 |
| I-72cg | >25 | 97.8 | 2.2 |
| I-72cp | >25 | 87.9 | 12.1 |
| I-72cq | >25 | 68.9 | 31.1 |
| I-72cy | >25 | 84.8 | 15.2 |
| I-72d | 1.896 | 28.4 | 71.6 |
| I-72dd | >25 | 80.5 | 19.5 |
| I-72dg | >25 | 78.9 | 21.1 |
| I-72dm | >25 | 88.5 | 11.5 |
| I-72do | >25 | 76.7 | 23.3 |
| I-72dp | >25 | 69.5 | 30.5 |
| I-72dt | >25 | 52.8 | 47.2 |
| I-72du | >25 | 76.4 | 23.6 |
| I-72dv | >25 | 86.7 | 13.3 |
| I-72e | >25 | 82.9 | 17.1 |
| I-72ed | >25 | 95.4 | 4.6 |
| I-72eg | 2.250 | 27.9 | 72.1 |

TABLE 1-continued

| Cmpd No | WIZ AC$_{50}$ (µM) | WIZ Amax | % degradation of WIZ (100-Amax) |
|---|---|---|---|
| I-72ek | >25 | 79.0 | 21.0 |
| I-72eo | >25 | 95.2 | 4.8 |
| I-72ep | 1.346 | 22.2 | 77.8 |
| I-72ew | 14.609 | 45.1 | 54.9 |
| I-72ez | >25 | 100.0 | 0.0 |
| I-72f | >25 | 99.1 | 0.9 |
| I-72fa | >25 | 94.9 | 5.1 |
| I-72fe | >25 | 81.5 | 18.5 |
| I-72fi | 2.047 | 29.8 | 70.2 |
| I-72fj | 3.913 | 36.3 | 63.7 |
| I-72fn | >25 | 97.4 | 2.6 |
| I-72fp | >25 | 90.5 | 9.5 |
| I-72fq | >25 | 99.7 | 0.3 |
| I-72fv | >25 | 98.9 | 1.1 |
| I-72fz | >25 | 90.9 | 9.1 |
| I-72gb | >25 | 76.1 | 23.9 |
| I-72gc | 10.088 | 41.7 | 58.3 |
| I-72gd | 0.919 | 19.9 | 80.1 |
| I-72gg | >25 | 76.0 | 24.0 |
| I-72gh | >25 | 89.1 | 10.9 |
| I-72gi | >25 | 85.1 | 14.9 |
| I-72gj | >25 | 97.7 | 2.3 |
| I-72gk | >25 | 93.5 | 6.5 |
| I-72gm | >25 | 93.2 | 6.8 |
| I-72gn | >25 | 73.6 | 26.4 |
| I-72gp | >25 | 85.6 | 14.4 |
| I-72gs | 7.391 | 42.1 | 57.9 |
| I-72gu | >25 | 99.8 | 0.2 |
| I-72gw | >25 | 80.9 | 19.1 |
| I-72gy | >25 | 55.9 | 44.1 |
| I-72gz | >25 | 86.3 | 13.7 |
| I-72hf | >25 | 93.2 | 6.8 |
| I-72hi | >25 | 86.2 | 13.8 |
| I-72hj | >25 | 99.3 | 0.7 |
| I-72hk | >25 | 90.8 | 9.2 |
| I-72hq | >25 | 86.7 | 13.3 |
| I-72hx | >25 | 94.9 | 5.1 |
| I-72id | >25 | 89.0 | 11.0 |
| I-72ij | 2.765 | 31.3 | 68.7 |
| I-72ir | >25 | 64.3 | 35.7 |
| I-72is | >25 | 99.1 | 0.9 |
| I-72it | >25 | 94.1 | 5.9 |
| I-72iu | 2.000 | 28.3 | 71.7 |
| I-72iv | >25 | 97.8 | 2.2 |
| I-72ix | >25 | 87.0 | 13.0 |
| I-72j | >25 | 78.5 | 21.5 |
| I-72jb | >25 | 99.7 | 0.3 |
| I-72jf | >25 | 65.8 | 34.2 |
| I-72jk | >25 | 92.8 | 7.2 |
| I-72jq | >25 | 88.3 | 11.7 |
| I-72ju | >25 | 85.5 | 14.5 |
| I-72jx | >25 | 93.9 | 6.1 |
| I-72jy | >25 | 88.7 | 11.3 |
| I-72kc | >25 | 90.6 | 9.4 |
| I-72m | >25 | 91.6 | 8.4 |
| I-72n | >25 | 76.6 | 23.4 |
| I-72s | 0.962 | 21.8 | 78.2 |
| I-72t | 1.474 | 30.1 | 69.9 |
| I-72x | >25 | 100.0 | 0.0 |
| I-72y | >25 | 97.1 | 2.9 |
| I-73 | 0.014 | 2.2 | 97.8 |
| I-81 | >25 | 58.9 | 41.1 |
| I-83 | >25 | 83.2 | 16.8 |
| I-84 | >25 | 78.8 | 21.2 |
| I-97 | 0.14 | 8.17 | 91.83 |
| I-100 | 0.41 | 17.77 | 82.23 |
| I-101 | 0.072 | 3.95 | 96.05 |
| I-102 | 0.24 | 17.27 | 82.73 |
| I-104 | 0.54 | 12.90 | 87.1 |
| I-105 | 0.055 | 5.23 | 94.77 |
| I-106 | 2.56 | 19.92 | 80.08 |
| I-107 | 0.016 | 0.21 | 99.79 |
| I-108 | 0.025 | 1.93 | 98.07 |
| I-109 | 1.50 | 29.86 | 70.14 |
| I-110 | 0.0086 | 0.48 | 99.52 |
| I-111 | 0.011 | 9.30 | 90.7 |
| I-112 | 0.059 | 3.13 | 96.87 |
| I-113 | 0.0038 | 0.64 | 99.36 |
| I-114 | 0.018 | 5.54 | 94.46 |
| I-115 | 0.17 | 10.49 | 89.51 |
| I-118 | 0.38 | 14.57 | 85.43 |
| I-119 | 0.01 | 2.56 | 97.44 |
| I-122 | 0.051 | 12.43 | 87.57 |
| I-124 | 0.040 | 5.61 | 94.39 |
| I-127 | 0.0019 | 6.64 | 93.36 |
| I-129 | 0.046 | 32.26 | 67.74 |
| I-131 | 0.00052 | 11.06 | 88.94 |
| I-133 | 0.0088 | 16.7 | 83.3 |
| I-135 | 0.034 | 18.22 | 81.78 |
| I-137 | 0.0015 | 10.02 | 89.98 |
| I-141a, I-141b | 2.46 | 27.64 | 72.36 |
| I-142 | 0.081 | 0.90 | 99.1 |
| I-143 | 137.28 | 62.57 | 37.43 |
| I-144 | 0.076 | 6.3 | 93.7 |
| I-145 | 0.019 | 2.68 | 97.32 |
| I-146 | 2.20 | 31.34 | 68.66 |
| I-147 | 1.08 | 28.36 | 71.64 |
| I-148 | 0.02 | 5.51 | 94.49 |
| I-149 | 11.38 | 43.12 | 56.88 |
| I-150 | 0.017 | 1.39 | 98.61 |
| I-151 | 3.43 | 34.89 | 65.11 |
| I-152 | 0.048 | 2.52 | 97.48 |
| I-155 | 0.02 | 24.85 | 75.15 |
| I-156 | na | na | na |
| I-157 | 0.16 | 37.01 | 62.99 |
| I-158 | 0.000083 | 5.93 | 94.07 |
| I-161 | 0.00037 | 8.45 | 91.55 |
| I-163 | 0.029 | 29.5 | 70.5 |
| I-167 | na | na | na |
| I-168 | na | na | na |
| I-169 | 0.034 | 15.43 | 84.57 |
| I-173 | 0.00022 | 5.71 | 94.29 |
| I-178 | 0.02 | 21.27 | 78.73 |
| I-179 | 0.0057 | 26.10 | 73.9 |
| I-180 | 0.02 | 84.72 | 15.28 |
| I-183 | 0.004 | 13.90 | 86.1 |
| I-184 | 0.00047 | 7.28 | 92.72 |
| I-186 | 0.0043 | 19.15 | 80.85 |
| I-188 | 0.00035 | 13.44 | 86.56 |
| I-189 | 0.0043 | 26.77 | 73.23 |
| I-191 | 0.15 | 32.85 | 67.15 |
| I-192 | 0.025 | 37.78 | 62.22 |
| I-193 | 0.49 | 44.32 | 55.68 |
| I-196 | 0.0042 | 21.18 | 78.82 |
| I-197 | 0.056 | 48.25 | 51.75 |
| I-198 | 0.013 | 32.02 | 67.98 |
| I-201 | 0.019 | 19.49 | 80.51 |
| I-202 | 0.083 | 41.27 | 58.73 |
| I-203 | 0.00092 | 32.48 | 67.52 |
| I-211 | 0.15 | 46.10 | 53.9 |
| I-213 | 0.12 | 44.32 | 55.68 |
| I-214 | 0.032 | 17.15 | 82.85 |
| I-217 | 0.0 | 99.6 | 0.4 |
| I-219 | 1.40 | 26.07 | 73.93 |
| I-223 | 0.072 | 17.15 | 82.85 |
| I-227 | 0.058 | 35.84 | 64.16 |
| I-229 | 0.002 | 26.55 | 73.45 |
| I-233 | 0.00073 | 18.86 | 81.14 |
| I-244 | na | na | na |
| I-249 | na | na | na |
| I-251 | 0.50 | 21.7 | 78.3 |
| I-252 (Isomer 1) | 0.05 | 41.9 | 58.1 |
| I-252 (Isomer 2) | 0.011 | 22.9 | 77.1 |

TABLE 1-continued

| Cmpd No | WIZ AC$_{50}$ (μM) | WIZ Amax | % degradation of WIZ (100-Amax) |
|---|---|---|---|
| I-252 (Isomer 3) | 0.045 | 44.9 | 55.1 |
| I-255 (Isomer 1) | 0.012 | 26.8 | 73.2 |
| I-255 (Isomer 2) | 0.098 | 71.2 | 28.8 |
| I-255 (Isomer 3) | 0.36 | 73.5 | 26.5 |
| I-255 (Isomer 4) | 0.034 | 27.0 | 73.0 | na = not measured

Example 165: Small Molecule HbF Induction Assay

Cryopreserved primary human CD34$^+$ hematopoietic stem and progenitor cells were obtained from AllCells, LLC. The CD34$^+$ cells were isolated from the peripheral blood of healthy donors after mobilization by administration of granulocyte colony-stimulating factor. Cells were differentiated ex vivo toward the erythroid lineage using a 2-phase culture method. In the first phase, cells were cultured in STEMSPAN™ Serum-Free Expansion Media (SFEM) (STEMCELL Technologies Inc.) supplemented with rhSCF (50 ng/mL, PEPROTECH®, Inc.), rhIL-6 (50 ng/mL, PEPROTECH®, Inc.), rhIL-3 (50 ng/mL, PEPROTECH®, Inc.), and rhFlt3L (50 ng/mL, PEPROTECH®, Inc.), and 1× antibiotic-antimycotic (Life Technologies, Thermo Fisher Scientific) for 6 days at 37° C. with 5% CO$_2$. During the second phase, cells were cultured in erythroid differentiation media at 5,000 cells/mL in the presence of compound for 7 days at 37° C. with 5% CO$_2$. Erythroid Differentiation Media is comprised of IMDM (Life Technologies) supplemented with insulin (10 μg/mL, Sigma Aldrich), heparin (2 U/mL Sigma Aldrich), holo-transferrin (330 μg/mL, Sigma Aldrich), human serum AB (5%, Sigma Aldrich), hydrocortisone (1 μM, STEMCELL Technologies), rhSCF (100 ng/mL, PEPROTECH®, Inc.), rhIL-3 (5 ng/mL, PEPROTECH®, Inc.), rhEPO (3 U/mL, PEPROTECH®, Inc.), and 1× antibiotic-antimycotic. All compounds were dissolved and diluted into dimethylsulfoxide (DMSO) and were added to culture media for a final concentration of 0.3% DMSO for testing in a 7-point, 1:3 dilution series starting at 30 uM.

Staining and Flow Cytometry

For viability analysis, samples were washed and resuspended in phosphate-buffered saline (PBS) and stained with LIVE/DEAD™ Fixable Violet Dead Cell Stain Kit (Life Technologies, L34963) for 20 minutes. Cells were then washed again with PBS and resuspended in PBS supplemented with 2% fetal bovine serum (FBS), and 2 mM EDTA to prepare for cell surface marker analysis. Cells were labeled with allophycocyanin-conjugated CD235a (1:100, BD Biosciences, 551336) and Brilliant Violet-conjugated CD71 (1:100, BD Biosciences, 563767) antibodies for 20 minutes. For analysis of cytoplasmic Fetal Hemoglobin (HbF), cells were fixed and permeabilized using the Fixation (BIOLEGEND®, 420801) and Permeabilization Wash (BIOLEGEND®, 421002) Buffers according to the manufacturer's protocol. During the permeabilization step, cells were stained with phycoerythrin-conjugated or FITC-conjugated HbF-specific antibody (1:10-1:25, INVITROGEN™, MHFH04-4) for 30 minutes. Stained cells were washed with phosphate-buffered saline before analysis on the FACSCANTO™ II flow cytometer or LSRFORTESSA™ (BD Biosciences). Data analysis was performed with FLOWJO™ Software (BD Biosciences).

HbF Induction Activity of Compounds (Table 2)

mPB CD34+ cells were expanded for 6 days, then erythroid differentiated in the presence of compound for 7 days. Cells were fixed, stained and analyzed by flow cytometry. Table 2 shows HbF induction activity of the compounds. HbF Amax=the highest percentage of cells staining positive for HbF (% HbF+ cells) in the fitted dose-response curve. The baseline % HbF+ cells for DMSO-treated cells is approximately 30-40%.

TABLE 2

| Cmpd no. | HbF AC50 (μM) | HbF Amax |
|---|---|---|
| I-5 | 0.080 | 78.3 |
| I-47 | 4.163 | 77.1 |
| I-49 | 0.542 | 69.3 |
| I-50 | 9.436 | 68.2 |
| I-50bi | >30 | 48.1 |
| I-50bt | >30 | 39.3 |
| I-50cn | >30 | 33.9 |
| I-50co | >30 | 66.8 |
| I-50dl | 0.730 | 82.6 |
| I-50ee | >30 | 56.0 |
| I-50em | 0.045 | 90.5 |
| I-52 | >30 | 45.5 |
| I-53 | 0.122 | 78.1 |
| I-58 | >30 | 39.2 |
| I-60 | 0.864 | 80.6 |
| I-81 | >30 | 54.3 |

Example 166: Cell Culture for shRNA and CRISPR Assays

HEK293T cells were maintained in DMEM high glucose complete media with sodium pyruvate, non-essential amino acids, 10% FBS, 2 mM L-glutamine, 100 U/mL pen/strep, 25 mM HEPES. Unless stated otherwise, all reagents for culturing HEK293T cells were obtained from INVITROGEN™.

Mobilized peripheral blood (mPB) CD34+ cells (AllCells, LLC) were maintained in STEMSPAN™ serum-free expansion media (SFEM) (STEMCELL Technologies Inc.) supplemented with 50 ng/mL each of rhTPO, rhIL-6, rhFLT3L, rhSCF for 2-3 days prior to shRNA transduction or targeted ribonucleoprotein (RNP) electroporation targeting WIZ. All cytokines were obtained from PEPROTECH®, Inc. Cell cultures were maintained at 37° C. and 5% CO$_2$ in a humidified tissue culture incubator.

Generation of shRNA Lentiviral Clones Targeting WIZ 5-phosphorylated sense and anti-sense complementary single-stranded DNA oligos of the respective shRNA against WIZ were synthesized by Integrated DNA Technologies, Inc. (IDT). Each DNA oligonucleotide was designed with PmeI/AscI restriction overhangs on 5'- and 3'-ends, respectively, for subsequent compatible ligation into the lentiviral vector backbone. Equimolar of each of the complementary oligonucleotides were annealed in NEB Buffer 2 (NEW ENGLAND BIOLABS® Inc.) by heating on a heating block at 98° C. for 5 minutes followed by cooling to room temperature on the bench top. Annealed double-stranded DNA oligonucleotides were ligated into pHAGE lentiviral backbone digested with PmeI/AscI using T4 DNA ligase kit (NEW ENGLAND BIOLABS®). Ligation reactions were transformed into chemically competent Stbl3 cells (INVITROGEN™) according to the manufacturer's protocol. Positive clones were verified using the sequencing primer (5'-ctacattttacatgatagg-3'; SEQ ID NO: 14) and plasmids were purified by Alta Biotech LLC.

Lentivirus particles for the respective shRNA constructs were generated by co-transfection of HEK293T cells with pCMV-dR8.91 and pCMV-VSV-G expressing envelope plasmid using Lipofectamine 3000 reagent in 150 mm tissue culture dish format as per manufacturer's instructions (INVITROGEN™). Lentivirus supernatant was harvested 48 hours after co-transfection, filtered through a 0.45 μm filter (Millipore) and concentrated using Amicon Ultra 15 with Ultracel-100 membrane (Millipore). Infectious units of each of the lentivirus particle was determined by flow cytometry using eGFP expression as marker of transduction after serial dilution and infection of HEK293T cells.

The shRNA sequences are as follows:

```
                                        (SEQ ID NO: 2)
shWIZ_#1  5'-AGCCCACAATGCCACGGAAAT-3';

(SEQ ID NO: 3)
shWIZ_#2  5'-GCAACATCTACACCCTCAAAT-3';

(SEQ ID NO: 4)
shWIZ_#4  5'-TGACCGAGTGGTACGTCAATG-3';

(SEQ ID NO: 5)
shWIZ_#5  5'-AGCGGCAGAACATCAACAAAT-3'.
```

Lentiviral shRNA Transduction and FACS of mPB CD34+ Cells mPB CD34+ transduction was performed on retronectin coated non-tissue culture treated 96 well-flat bottom plates (Corning, Inc.). Briefly, plates were coated with 100 μL of RETRONECTIN® (1 μg/mL) (TAKARABIO, Inc.), sealed and incubated at 4° C. overnight. RETRONECTIN® was then removed and plates were incubated with BSA (bovine serum albumin) (1%) in PBS for 30 minutes at room temperature. Subsequently, BSA (bovine serum albumin) was aspirated and replaced with 100 μL of lentiviral concentrate and centrifuged at 2000×g for 2 hours at room temperature. Next, residual supernatant was gently pipetted out and ready for transductions of mPB CD34+ cells. Ten thousand cells were plated in 150 μL of STEMSPAN™ Serum-free Expansion Medium (SFEM) supplemented with 50 ng/mL each of rhTPO, rhIL-6, rhFLT3L, rhSCF to initiate transduction. Cells were cultured for 72 hours prior to assessing transduction efficiencies using eGFP expression as a marker.

eGFP-positive cells were sorted on an FACSARIA™ III (BD Biosciences). Briefly, the transduced mPB CD34+ cell population was washed and re-suspended with FACS buffer containing 1× Hank's buffered saline solution, EDTA (1 mM) and FBS (2%). Sorted eGFP-positive cells were used for the erythroid differentiation assay.

Targeting CRISPR knockout of WIZ

Alt-R CRISPR-Cas9 crRNA and tracrRNA (5'-AGCAUAGCAAGUUAAAAUAAGGCUAGUCCGUUAUCAACUUGAAAAAGUGGCACCGAGUC GGUGCUUU-3'; SEQ ID NO: 6) were purchased from Integrated DNA Technologies, Inc.

Equimolar tracrRNA was annealed with WIZ targeting crRNA (Table 3) in Tris buffer (10 mM, pH 7.5) by heating at 95° C. for 5 minutes using a polymerase chain reaction (PCR) machine (Bio-Rad) followed by cooling to room temperature on the benchtop. Subsequently, a ribonucleoprotein (RNP) complex was generated by mixing annealed tracrRNA:crRNA with 6 ug of Cas9 at 37° C. for 5 minutes in 1× buffer containing HEPES (100 mM), KCl (50 mM), $MgCl_2$ (2.5 mM), glycerol (0.03%), DTT (1 mM) and Tris pH 7.5 (2 mM).

Electroporation of the RNP complex was performed on a 4D-NUCLEOFECTOR™ (Lonza) as per manufacturer's recommendation. Briefly, 50,000 mPB CD34+ cells resuspended in Primary Cell P3 Buffer with supplement (Lonza) were pre-mixed with 5 μL of RNP complex per well in nucleocuvettes and incubated for 5 minutes at room temperature. Subsequently, the mixture was electroporated using the CM-137 program. Cells were cultured for 72 hours post-RNP electroporation before initiating erythroid differentiation. The crRNA sequences are shown in Table 3 below.

TABLE 3

| Name | Sequence (5' to 3') | Target genomic region | Strand | SEQ ID NO |
|---|---|---|---|---|
| rg_0111 | ACGGAGGCTAAGCGTCGCAA | random guide, non-targeting | | 7 |
| WIZ_6 | AACATCTTTCGGGCCGTAGG | chr19: 15427143-15427163 | (+) | 8 |
| WIZ_9 | GACATCCGCTGCGAGTTCTG | chr19: 15427488-15427510 | (−) | 9 |
| WIZ_12 | TGCAGCGTCCCGGGCAGAGC | chr19: 15425751-15425773 | (−) | 10 |
| WIZ_14 | CAAGCCGTGCCTCATCAAGA | chr19: 15425571-15425593 | (−) | 11 |
| WIZ_15 | CGGGCACACCTGCGGCAGTT | chr19: 15424942-15424964 | (−) | 12 |
| WIZ_18 | AGTGGGTGCGGCACTTACAG | chr19: 15423169-15423191 | (−) | 13 |

Erythroid Differentiation of shRNA Transduced or RNP Electroporated mPB CD34+ Cells Erythroid differentiation was initiated by plating 8,000 RNP-electroporated or FACS sorted eGFP+ mPB CD34+ cells per well in 96-well tissue culture plate. Base differentiation media consists of IMDM (Iscove's Modified Dulbecco's Medium), human AB serum (5%), transferrin (330 μg/mL), Insulin (10 μg/mL) and Heparin (2 IU/mL). Differentiation media was supplemented with rhSCF (100 ng/mL), rhIL-3 (10 ng/mL), rhEPO (2.5 U/mL) and hydrocortisone (1 μM). After 4 days of differentiation, the cells were split (1:4) in fresh media to maintain optimal growth density. Cells were cultured for additional 3 days and utilized for assessment of fetal hemoglobin (HbF) expression.

Analysis of HbF Gene Expression by RNA-Seq

Two independent, targeted CRISPR/Cas9 knockout (KO) of WIZ was done using WIZ_6 and WIZ_18 gRNAs or a non-targeting scrambled gRNA negative control in mPB CD34+ HSCs. Cells from KO and negative control were then cultured for 7 days for erythroid differentiation and used for total RNA isolation (Zymo Research, catalogue #R1053). The quality of isolated RNA was determined before sequencing using Agilent RNA 6000 Pico Kit (Agilent, catalogue #5067-1513). RNA sequencing libraries were prepared using the Illumina TruSeq Stranded mRNA Sample Prep protocol and sequenced using the Illumina NovaSeq6000 platform (Illumina). Samples were sequenced to a length of 2×76 base-pairs. For each sample, salmon version 0.8.2 (Patro et al. 2017; doi: 10.1038/nmeth.4197) was used to map sequenced fragments to annotated transcripts in the human reference genome hg38 provided by the ENSEMBL database. Per-gene expression levels were obtained by summing the counts of transcript-level counts using tximport (Soneson et al. 2015; doi: 10.12688/f1000research.7563.1). DESeq2 was used to normalize for library size and transcript length differences, and to test for differential expression between samples treated with the gRNAs targeting WIZ and the samples treated with the scrambled gRNA controls (Love et al. 2014; doi: 10.1186/s13059-014-0550-8). Data were visualized using ggplot2 (Wickham H (2016). ggplot2: Elegant Graphics for Data Analysis. Springer-Verlag New York. ISBN 978-3-319-24277-4; ggplot2.tidyverse.org).

HbF Intracellular Staining

One hundred thousand cells were aliquoted into U-bottom 96-well plate and stained for 20 min in the dark with diluted LIVE/DEAD™ fixable violet viability dye as per manufacturer's recommendation (INVITROGEN™). Cells were washed with FACS staining buffer and subsequently stained with anti-CD71-BV711 (BD Biosciences) and anti-CD235a-APC (BD Biosciences) for 20 mins in the dark. After two rounds of washes with three volumes of 1×PBS, cells were fixed and permeabilized with 1×BD Cytofix/Cytoperm (BD Biosciences) for 30 minutes at room temperature in the dark. Subsequently, cells were washed twice with three volumes of 1× Perm/wash buffer (BD Biosciences). Anti-HbF-FITC (ThermoScientific) was diluted (1:25) in 1× perm/wash buffer, added to permeablized cells and incubated for 30 minutes at room temperature in the dark. Next, cells were washed twice with three volumes of 1× perm/wash buffer and analyzed by flow cytometry using LSRFORTESSA™ (BD Biosciences). Data was analyzed with FLOWJO™ software.

Results

WIZ KO Upregulates HBG1/2 Expression Upon Erythroid Differentiation

Targeted KO of WIZ using two independent gRNAs (WIZ_6 and WIZ_18) demonstrated upregulation of fetal hemoglobin genes (HBG1/2), as presented in FIG. 1A.

Figure 1B:
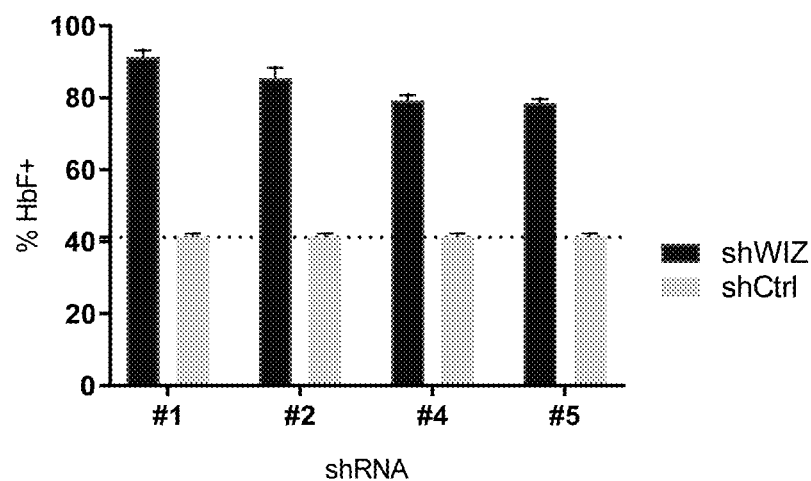
FIG. 1B depicts a bar graph showing the frequency of HbF+ cells due to shRNA- mediated loss of WIZ in human mobilized peripheral blood CD34+ derived erythroid cells.
Figure 1C:
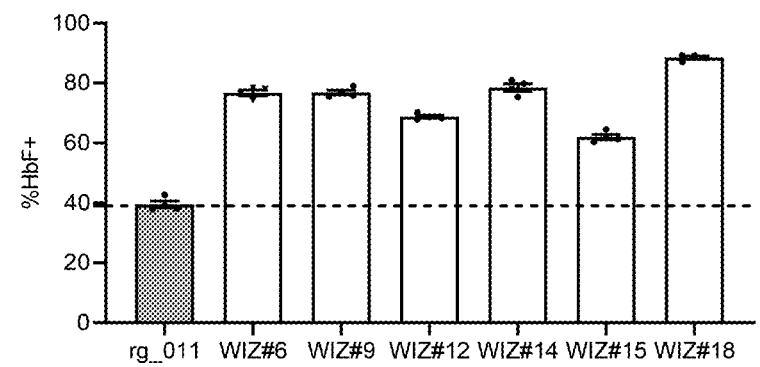
FIG. 1C depicts a bar graph showing the frequency of HbF+ cells due to CRISPR/Cas9-mediated loss of WIZ in human mobilized peripheral blood CD34+ derived erythroid cells.

Loss of WIZ Induces Fetal Hemoglobin Expression in mPB CD34+ Derived Erythroid Cells In order to validate whether WIZ is a negative regulator of HbF expression, shRNA and CRISPR-Cas9-mediated knockdown and knockout functional genetics approaches were employed. mPB CD34+ cells were treated with shRNA or CRISPR-Cas9 reagents and erythroid differentiated for 7 days prior to flow cytometry analysis. Targeted knockdown of WIZ transcript results in 78-91% HbF+ cells compared to 40% for the negative control scrambled shRNA. Error bars represent standard error of two biological replicates with three technical replicates each (FIG. 1B). CRISPR/Cas9-mediated targeted loss of WIZ results in 62-88% HbF+ cells compared to 39% for random guide crRNA. Error bars represent standard error of one biological sample with four technical replicates (FIG. 1C). To summarize, the results indicate that loss of WIZ induces HbF in human primary erythroid cells. As such, the zinc finger transcription factor Widely Interspaced Zinc Finger Motifs (WIZ) was identified as a novel target for HbF induction. These data provide genetic evidence that WIZ is a regulator of fetal hemoglobin expression and represents a novel target for the treatment of sickle cell disease and beta-thalassemia.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula (I') or a pharmaceutically acceptable salt thereof

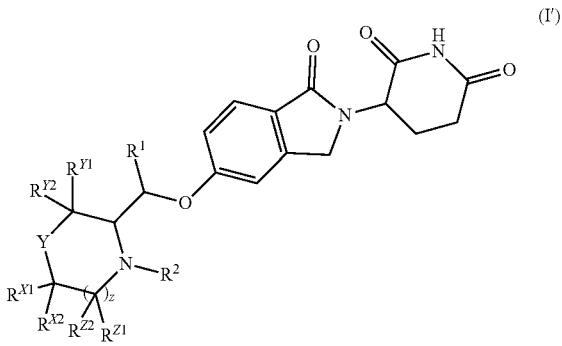

(I')

wherein:

Y is selected from O, $CH_2$, $CF_2$, and CHF;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

$R^{Z1}$ and $R^{Z2}$ are both hydrogen, or 1 of $R^{Z1}$ and $R^{Z2}$ and 1 of $R^{Y1}$ and $R^{Y2}$ together form a $C_1$-$C_2$alkylene bridging group and the other of $R^{Z1}$ and $R^{Z2}$ and $R^{Y1}$ and $R^{Y2}$ are both hydrogen;

$R^1$ is selected from hydrogen and $C_1$-$C_6$alkyl;

$R^2$ is selected from hydrogen, —C(=O)—$R^3$, $C_3$-$C_8$cycloalkyl, $C_1$-$C_6$haloalkyl, and $C_1$-$C_{10}$alkyl, wherein the alkyl is substituted with 0-1 substituent independently selected from $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, $C_3$-$C_8$cycloalkyl and —O—($R^{2a}$), wherein the aryl, heteroaryl, heterocyclyl, and cycloalkyl are each independently substituted with 0-5 $R^4$;

$R^{2a}$ is $C_1$-$C_6$alkyl wherein the alkyl is substituted with 0-1 substituent independently selected from $C_6$-$C_{10}$aryl;

$R^3$ is selected from —CH=$CR^{3a}R^{3b}$, $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, $C_3$-$C_8$cycloalkyl, and $C_1$-$C_6$alkyl, wherein the alkyl is substituted with 0-3 $R^{3c}$, and wherein the aryl, heteroaryl, heterocyclyl, and cycloalkyl are each independently substituted with 0-5 $R^4$;

$R^{3a}$ and $R^{3b}$ together with the carbon atom to which they are attached form a $C_3$-$C_8$cycloalkyl ring;

each $R^{3c}$ is at each occurrence independently selected from —C(=O)—$R^{3d}$, $NR^{3e}R^{3f}$, $C_1$-$C_6$alkoxyl, —O—$R^{3d}$, hydroxyl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), $C_6$-$C_{10}$aryl, 5- to 10-membered heteroaryl comprising 1-4 heteroatoms independently selected from N, O, and S, 4- to 6-membered heterocyclyl comprising 1-2 heteroatoms independently selected from N, O, and S, and $C_3$-$C_8$cycloalkyl, wherein the —O-aryl, arylalkyl-O—, and —O-heteroaryl are each independently substituted with 0-3 $R^{4a}$, and wherein the aryl, heteroaryl, heterocyclyl, and cycloalkyl are each independently substituted with 0-5 $R^4$;

$R^{3d}$ is a 4- to 6-membered heterocyclyl comprising 1-2 heteroatoms independently selected from N, O, and S;

$R^{3e}$ and $R^{3f}$ are each independently selected from hydrogen and $C_1$-$C_6$alkyl;

each $R^4$ is at each occurrence independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, $C_1$-$C_{10}$alkyl, $C_1$-$C_6$alkoxyl, $C_1$-$C_6$haloalkyl, —$SO_2R^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—($R^5$), —C(=O)—($R^5$), —C(=O)—$NR^{6a}R^{6b}$, $NR^{6a}R^{6b}$, —NH—C(=O)—O—($C_1$-$C_6$alkyl), and $C_3$-$C_8$cycloalkyl, wherein the aryl, —O-aryl, arylalkyl-O—, —O-heteroaryl, heteroaryl, and heterocyclyl are each independently substituted with 0-3 $R^4$, wherein the alkyl and alkoxyl are each independently substituted with 0-1 $R^{4b}$, and wherein the cycloalkyl is substituted with 0-3 substituents each independently selected from —CN, $C_1$-$C_6$alkyl, $C_1$-$C_6$alkoxyl, hydroxyl and $C_1$-$C_6$haloalkyl;

$R^{4a}$ is at each occurrence independently selected from —CN, $C_1$-$C_6$alkoxyl, $C_1$-$C_6$haloalkyl, halogen, hydroxyl, —C(═O)—O—(R⁵), 5- to 10-membered heteroaryl comprising 1-4 heteroatoms independently selected from N, O, and S, di(C₁-C₆alkyl)aminoC₁-C₆alkyl, C₁-C₆alkyl, 4- to 6-membered heterocyclyl comprising 1-2 heteroatoms independently selected from N, O, and S and C₃-C₆cycloalkyl, wherein the alkyl is substituted with 0-1 R⁴ᵇ, and wherein the heteroaryl is substituted with 0-3 R⁴ᵃ⁻¹;

R⁴ᵃ⁻¹ is at each occurrence independently selected from C₁-C₆alkyl, di(C₁-C₆alkyl)aminoC₁-C₆alkyl, —CN, C₁-C₆alkoxyl, and C₁-C₆haloalkyl;

R⁴ᵇ is at each occurrence independently selected from —CN, halogen, —C(═O)NR⁶ᵃR⁶ᵇ, NR⁶ᵃR⁶ᵇ, 5- to 10-membered heteroaryl comprising 1-4 heteroatoms independently selected from N, O, and S, —C(═O)—OH, C₁-C₆alkoxyl, 4- to 6-membered heterocyclyl comprising 1 or 2 heteroatoms independently selected from N, O, and S, C₃-C₈cycloalkyl, C₂-C₄alkynyl, and C₆-C₁₀aryl, wherein the aryl is substituted with 0-1 substituent each independently selected from —CN, C₁-C₆haloalkyl, and C₁-C₆alkyl;

R⁴ᶜ is selected from C₆-C₁₀aryl, hydroxyl, NH₂, and halogen;

R⁵ is selected from C₁-C₆alkyl, C₆-C₁₀aryl, and C₆-C₁₀arylC₁-C₆alkyl;

R⁶ᵃ and R⁶ᵇ are each independently selected from hydrogen and C₁-C₆alkyl;

or R⁶ᵃ and R⁶ᵇ together with the nitrogen atom to which they are attached form a 5- or 6-membered heterocyclyl comprising 0-1 additional heteroatoms selected from N, O, and S, wherein the heterocyclyl is substituted with 0-2 R⁶ᶜ;

R⁶ᶜ is at each occurrence independently selected from C₆-C₁₀arylC₁-C₆alkyl, —C(═O)—O—(C₁-C₆alkyl), —C(═O)—(C₁-C₆alkyl), oxo, and C₁-C₆alkyl, wherein the alkyl is substituted with 0-1 substituent independently selected from —CN and 4- to 6-membered heterocyclyl comprising 1-2 heteroatoms independently selected from N, O, and S.

2. The compound of claim 1 or a pharmaceutically acceptable salt thereof, of Formula

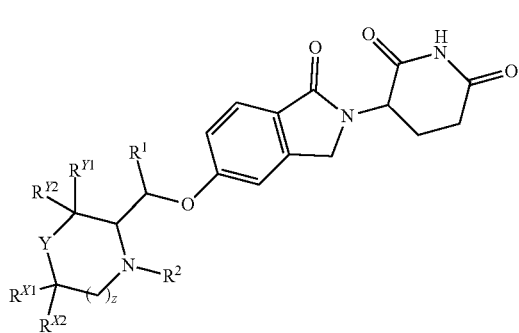

(I)

wherein:
Y is selected from O, CH₂, and CF₂;
z is an integer from 0 to 2;
$R^{X1}$ and $R^{X2}$ are each independently selected from hydrogen and C₁-C₆alkyl;
$R^{Y1}$ and $R^{Y2}$ are each independently selected from hydrogen and C₁-C₆alkyl;
R¹ is selected from hydrogen and C₁-C₆alkyl;
R² is selected from hydrogen, —C(═O)—R³, C₃-C₈cycloalkyl, C₁-C₆haloalkyl, and C₁-C₁₀alkyl, wherein the alkyl is substituted with 0-1 substituent independently selected from C₆-C₁₀aryl, 5- to 10-membered heteroaryl comprising 1-4 heteroatoms independently selected from N, O, and S, 4- to 6-membered heterocyclyl comprising 1-2 heteroatoms independently selected from N, O, and S, and C₃-C₈cycloalkyl, wherein the aryl, heteroaryl, heterocyclyl, and cycloalkyl are each independently substituted with 0-5 R⁴;

R³ is selected from —CH═CR³ᵃR³ᵇ, C₆-C₁₀aryl, 5- to 10-membered heteroaryl comprising 1-4 heteroatoms independently selected from N, O, and S, 4- to 6-membered heterocyclyl comprising 1-2 heteroatoms independently selected from N, O, and S, C₃-C₈cycloalkyl, and C₁-C₆alkyl, wherein the alkyl is substituted with 0-3 R³ᶜ, and wherein the aryl, heteroaryl, heterocyclyl, and cycloalkyl are each independently substituted with 0-5 R⁴;

R³ᵃ and R³ᵇ together with the carbon atom to which they are attached form a C₃-C₈cycloalkyl ring;

each R³ᶜ is at each occurrence independently selected from —C(═O)—R³ᵈ, NR³ᵉR³ᶠ, C₁-C₆alkoxyl, —O—R³ᵈ, hydroxyl, —O—C₆-C₁₀aryl, C₁-C₆arylC₆-C₁₀alkyl-O—, —O-(5- to 10-membered heteroaryl comprising 1-4 heteroatoms independently selected from N, O, and S), C₆-C₁₀aryl, 5- to 10-membered heteroaryl comprising 1-4 heteroatoms independently selected from N, O, and S, 4- to 6-membered heterocyclyl comprising 1-2 heteroatoms independently selected from N, O, and S, and C₃-C₈cycloalkyl, wherein the —O-aryl, arylalkyl-O—, and —O-heteroaryl are each independently substituted with 0-3 R⁴ᵃ, and wherein the aryl, heteroaryl, heterocyclyl, and cycloalkyl are each independently substituted with 0-5 R⁴;

R³ᵈ is a 4- to 6-membered heterocyclyl comprising 1-2 heteroatoms independently selected from N, O, and S;

R³ᵉ and R³ᶠ are each independently selected from hydrogen and C₁-C₆alkyl;

each R⁴ is at each occurrence independently selected from C₆-C₁₀aryl, —O—C₆-C₁₀aryl, C₁-C₆arylC₆-C₁₀alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N, O, and S, C₁-C₁₀alkyl, C₁-C₆alkoxyl, C₁-C₆haloalkyl, —SO₂R⁴ᶜ, halogen, hydroxyl, —CN, —O-4- to 6-membered heterocyclyl comprising 1-2 heteroatoms independently selected from N, O, and S, oxo, C₁-C₆haloalkoxyl, —C(═O)—O—(R⁵), —C(═O)—(R⁵), —C(═O)—NR⁶ᵃR⁶ᵇ, NR⁶ᵃR⁶ᵇ, —NH—C(═O)—O—(C₁-C₆alkyl), and C₃-C₈cycloalkyl, wherein the aryl, —O-aryl, arylalkyl-O—, —O-heteroaryl, heteroaryl, and heterocyclyl are each independently substituted with 0-3 R⁴, wherein the alkyl and alkoxyl are each independently substituted with 0-1 R⁴ᵇ, and wherein the cycloalkyl is substituted with 0-3 substituents each independently selected from —CN, C₁-C₆alkyl, C₁-C₆alkoxyl, and hydroxyl;

R⁴ᵃ is at each occurrence independently selected from —CN, C₁-C₆alkoxyl, C₁-C₆haloalkyl, halogen, hydroxyl, —C(═O)—O—(R⁵), 5- to 10-membered heteroaryl comprising 1-4 heteroatoms independently selected from N, O, and S, di(C₁-C₆alkyl)aminoC₁-

$C_6$alkyl, and $C_1$-$C_6$alkyl, wherein the alkyl is substituted with 0-1 $R^{4b}$, and wherein the heteroaryl is substituted with 0-3 $R^{4a-1}$;

$R^{4a-1}$ is at each occurrence independently selected from $C_1$-$C_6$alkyl, di($C_1$-$C_6$alkyl)amino$C_1$-$C_6$alkyl, —CN, $C_1$-$C_6$alkoxyl, and $C_1$-$C_6$haloalkyl;

$R^{4b}$ is at each occurrence independently selected from —CN, —C(=O)NR$^{6a}$R$^{6b}$, NR$^{6a}$R$^{6b}$, 5- to 10-membered heteroaryl comprising 1-4 heteroatoms independently selected from N, O, and S, —C(=O)—OH, $C_1$-$C_6$alkoxyl, 4- to 6-membered heterocyclyl comprising 1 or 2 heteroatoms independently selected from N, O, and S, $C_3$-$C_8$cycloalkyl, $C_2$-$C_4$alkynyl, and $C_6$-$C_{10}$aryl, wherein the aryl is substituted with 0-1 substituent each independently selected from —CN, $C_1$-$C_6$haloalkyl, and $C_1$-$C_6$alkyl;

$R^{4c}$ is selected from $C_6$-$C_{10}$aryl, hydroxyl, NH$_2$, and halogen;

$R^5$ is selected from $C_1$-$C_6$alkyl, $C_6$-$C_{10}$aryl, and $C_6$-$C_{10}$aryl$C_1$-$C_6$alkyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N, O, and S, wherein the heterocyclyl is substituted with 0-2 $R^{6c}$;

$R^{6c}$ is at each occurrence independently selected from $C_6$-$C_{10}$aryl$C_1$-$C_6$alkyl, —C(=O)—O—($C_1$-$C_6$alkyl), —C(=O)—($C_1$-$C_6$alkyl), oxo, and $C_1$-$C_6$alkyl, wherein the alkyl is substituted with 0-1 substituent independently selected from —CN and 4- to 6-membered heterocyclyl comprising 1-2 heteroatoms independently selected from N, O, and S.

3. The compound of claim 1 or a pharmaceutically acceptable salt thereof, wherein:

Y is selected from O, and CH$_2$;

z is an integer from 0 to 2;

$R^{X1}$ and $R^{X2}$ are each independently selected from hydrogen and $C_1$-$C_6$alkyl;

$R^{Y1}$ and $R^{Y2}$ are each independently selected from hydrogen and $C_1$-$C_6$alkyl;

wherein when $R^{X1}$ and $R^{X2}$ are both $C_1$-$C_6$alkyl, then $R^{Y1}$ and $R^{Y2}$ are both hydrogen, and wherein $R^{X1}$ and $R^{X2}$ are both hydrogen, then $R^{Y1}$ and $R^{Y2}$ are both $C_1$-$C_6$alkyl;

$R^1$ is selected from hydrogen and $C_1$-$C_6$alkyl;

$R^2$ is selected from $C_1$-$C_6$alkyl, —(CH$_2$)-phenyl, —(CH$_2$)-5- to 10-membered heteroaryl comprising 1-4 heteroatoms independently selected from N, O, and S, —(CH$_2$)-6-membered heterocyclyl comprising 1 heteroatom independently selected from N and O, and —(CH$_2$)—$C_3$-$C_8$cycloalkyl, and wherein the phenyl, heteroaryl, heterocyclyl, and cycloalkyl are each independently substituted with 0-3 $R^4$;

$R^4$ is at each occurrence independently selected from phenyl, —O-phenyl, —O-(5- to 10-membered heteroaryl comprising 1-4 heteroatoms independently selected from N, O, and S), 5- to 10-membered heteroaryl comprising 1-4 heteroatoms independently selected from N, O, and S, 6-membered heterocyclyl comprising 1-2 heteroatoms independently selected from N and O, $C_1$-$C_{10}$alkyl, $C_1$-$C_6$alkoxyl, $C_1$-$C_6$fluoroalkyl, —SO$_2$R$^{4c}$, halogen, hydroxyl, —CN, oxo, $C_1$-$C_6$fluoroalkoxyl, —C(=O)—O—(R$^5$), —C(=O)—NR$^{6a}$R$^{6b}$, NR$^{6a}$R$^{6b}$, —NH—C(=O)—O—($C_1$-$C_6$alkyl), and $C_3$-$C_8$cycloalkyl, wherein the phenyl, —O-phenyl, —O-heteroaryl, heteroaryl, and heterocyclyl are each independently substituted with 0-3 $R^{4a}$, wherein the alkyl and alkoxyl are each independently substituted with 0-1 $R^{4b}$, and wherein the cycloalkyl is substituted with 0-1 substituent independently selected from —CN;

$R^{4a}$ is at each occurrence independently selected from $C_1$-$C_6$fluoroalkyl, fluoro, —C(=O)—O—(R$^5$), 5- to 10-membered heteroaryl comprising 1-4 heteroatoms independently selected from N, O, and S, and $C_1$-$C_6$alkyl, wherein the alkyl is substituted with 0-1 $R^{4b}$, and wherein the heteroaryl is substituted with 0-2 $R^{4a-1}$;

$R^{4a-1}$ is at each occurrence independently selected from $C_1$-$C_6$alkyl, and di($C_1$-$C_6$alkyl)amino$C_1$-$C_6$alkyl;

$R^{4b}$ is at each occurrence independently selected from —C(=O)NR$^{6a}$R$^{6b}$, 5- to 10-membered heteroaryl comprising 1-4 heteroatoms independently selected from N, O, and S, —C(=O)—OH, 4- to 6-membered heterocyclyl comprising 1 or 2 heteroatoms independently selected from N and O, and phenyl, wherein the phenyl is substituted with 0-1 substituent each independently selected from —CN;

$R^{4c}$ is selected from phenyl, and NH$_2$;

$R^5$ is selected from $C_1$-$C_6$alkyl, and benzyl;

$R^{6a}$ and $R^{6b}$ are each independently selected from hydrogen and $C_1$-$C_6$alkyl;

or $R^{6a}$ and $R^{6b}$ together with the nitrogen atom to which they are attached form a 5- or 6-membered heterocyclyl comprising 0-1 additional heteroatoms selected from N and O, wherein the heterocyclyl is substituted with 0-1 $R^{6c}$;

$R^{6c}$ is at each occurrence independently selected from benzyl, —C(=O)—O—($C_1$-$C_6$alkyl), oxo, and $C_1$-$C_6$alkyl, wherein the alkyl is substituted with 0-1 substituent independently selected from 4-membered heterocyclyl comprising 1 O heteroatom.

4. The compound of claim 1 or a pharmaceutically acceptable salt thereof, wherein $R^3$ is selected from phenyl, 5- to 10-membered heteroaryl comprising 1-4 heteroatoms independently selected from N, O, and S, 4- to 6-membered heterocyclyl comprising 1-2 heteroatoms independently selected from N and O, $C_3$-$C_6$cycloalkyl, and $C_1$-$C_6$alkyl, wherein the alkyl is substituted with 0-3 $R^{3c}$, and wherein the phenyl, heteroaryl, heterocyclyl, and cycloalkyl are each independently substituted with 0-4 $R^4$.

5. The compound of claim 1 or a pharmaceutically acceptable salt thereof, wherein each $R^4$ is, at each occurrence, independently selected from $C_6$-$C_{10}$aryl, —O—$C_6$-$C_{10}$aryl, $C_1$-$C_6$aryl$C_6$-$C_{10}$alkyl-O—, —O-(5- to 10-membered heteroaryl comprising 1-4 heteroatoms independently selected from N, O, and S), 5- to 10-membered heteroaryl comprising 1-4 heteroatoms independently selected from N, O, and S, 4- to 6-membered heterocyclyl comprising 1-2 heteroatoms independently selected from N and O, $C_1$-$C_{10}$alkyl, $C_1$-$C_6$alkoxyl, $C_1$-$C_6$haloalkyl, —SO$_2$R$^{4c}$, halogen, hydroxyl, —CN, —O-4- to 6-membered heterocyclyl comprising 1-2 heteroatoms independently selected from N, O, and S, oxo, $C_1$-$C_6$haloalkoxyl, —C(=O)—O—(R$^5$), —C(=O)—(R$^5$), —C(=O)—NR$^{6a}$R$^{6b}$, NR$^{6a}$R$^{6b}$, —NH—C(=O)—O—($C_1$-$C_6$alkyl), and $C_3$-$C_8$cycloalkyl, wherein the aryl, heteroaryl, and heterocyclyl are each independently substituted with 0-2 $R^{4a}$, wherein the —O-aryl, arylalkyl-O—, and —O-heteroaryl, are each independently substituted with 0-3 $R^4$, wherein the alkyl and alkoxyl are each independently substituted with 0-1 $R^{4b}$, and wherein the cycloalkyl is substituted with 0-2 substituents each independently selected from —CN, $C_1$-$C_6$alkyl, methoxy and ethoxy.

6. The compound of claim 1 or a pharmaceutically acceptable salt thereof, wherein $R^2$ is unsubstituted $C_1$-$C_6$ alkyl or $C_1$-$C_{10}$ alkyl substituted with 5- to 10-membered heteroaryl comprising 1-4 heteroatoms independently selected from N, O, and S, or —C(=O)—$R^3$, wherein $R^3$ is 5- to 10-membered heteroaryl comprising 1-4 heteroatoms independently selected from N, O, and S, or $C_1$-$C_6$alkyl substituted with 5- to 10-membered heteroaryl comprising 1-4 heteroatoms independently selected from N, O, and S, wherein the heteroaryl is, at each occurrence, independently selected from:

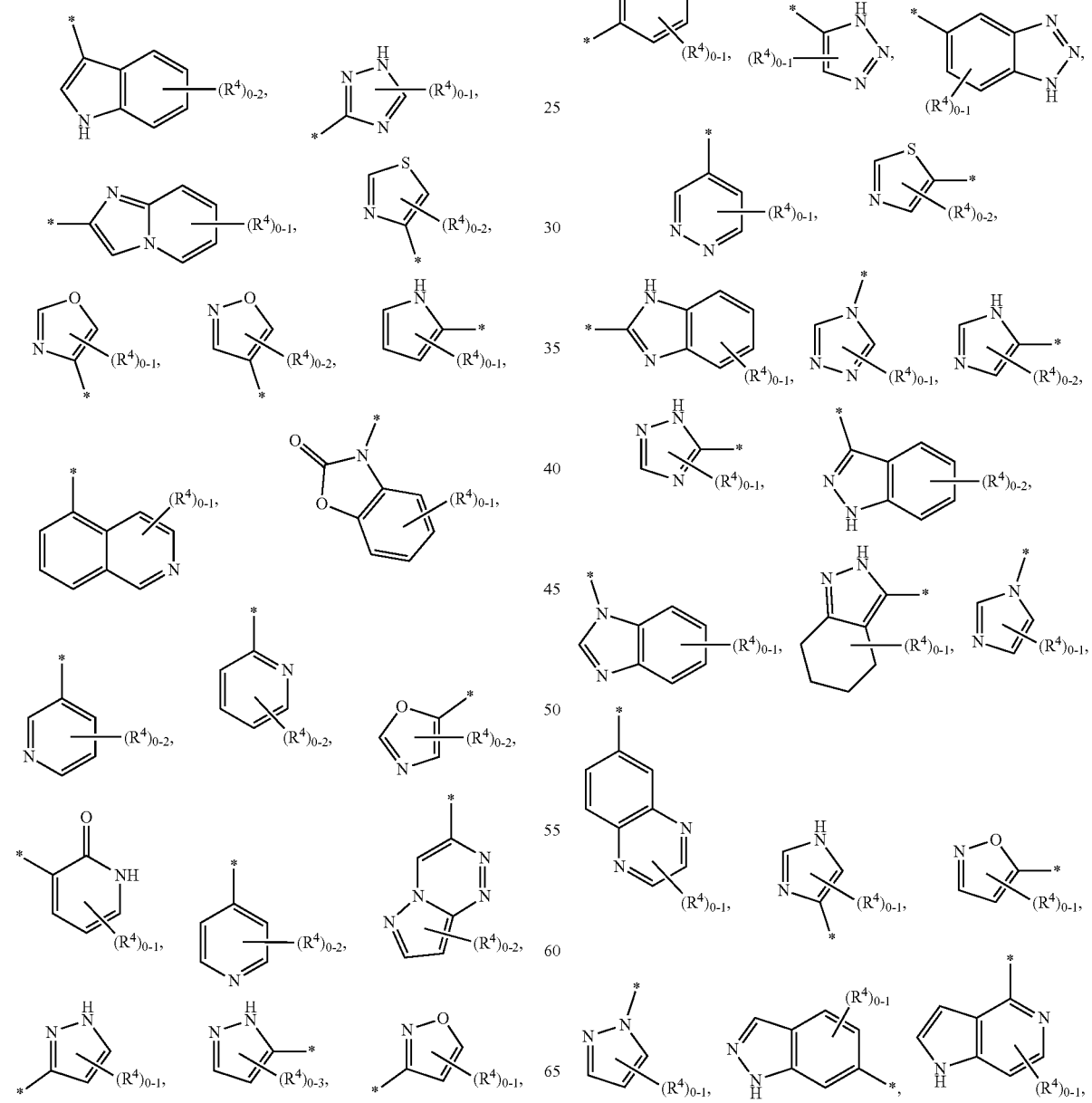

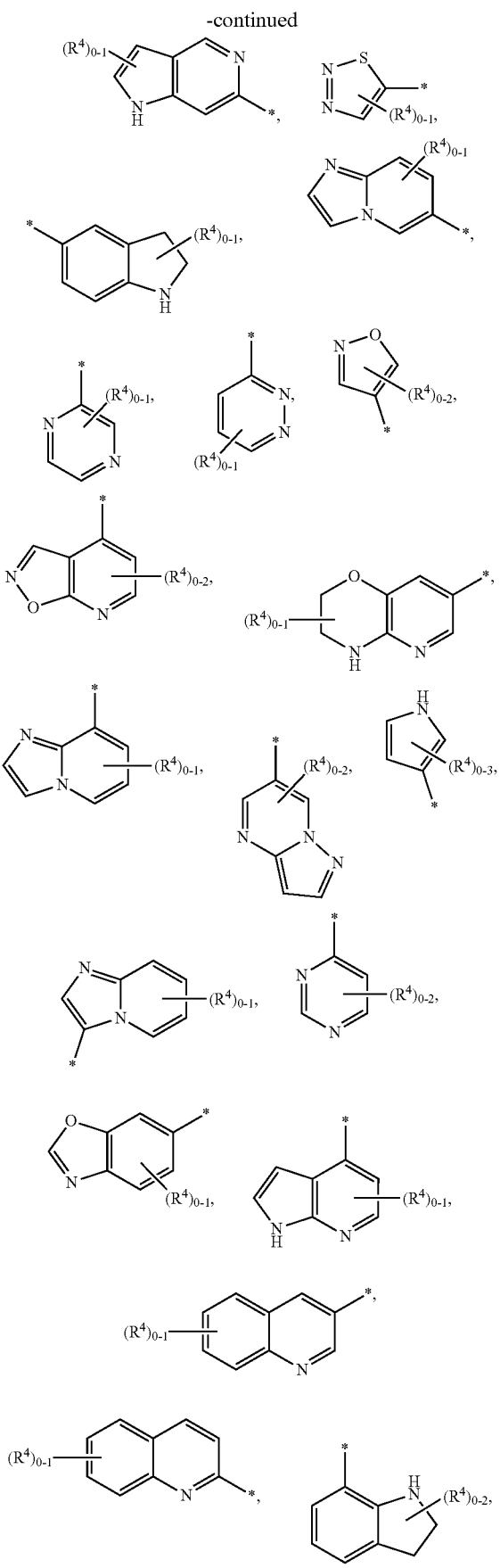
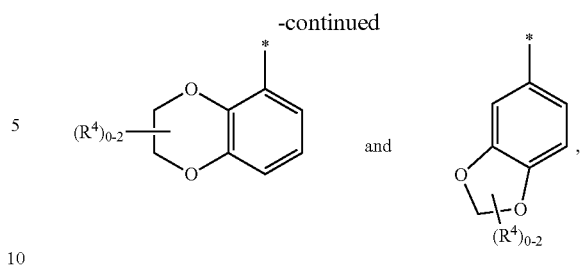
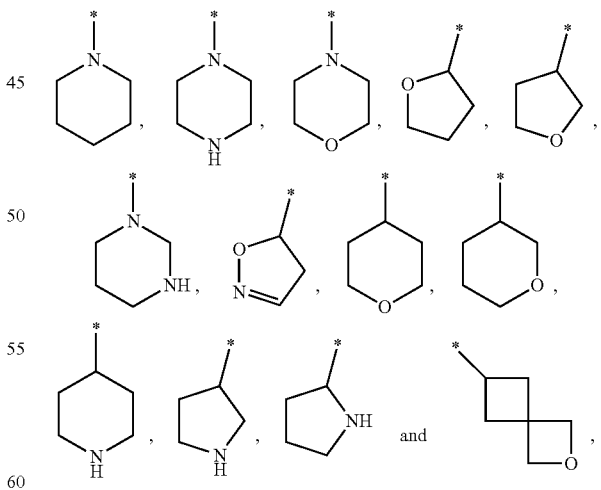

wherein R⁴ is as defined in claim 1.

7. The compound of claim 1 or a pharmaceutically acceptable salt thereof, wherein $R^2$ is unsubstituted $C_1$-$C_6$ alkyl or $C_1$-$C_{10}$ alkyl substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from piperidinyl, piperazinyl, morpholinyl, tetrahydrofuran, dihydroisoxazolyl, tetrahydropyran, pyrrolidinyl and 2-oxaspiro[3.3]heptanyl, and wherein said heterocyclyl is, at each occurrence, independently substituted with 0-4 $R^4$, wherein $R^4$ is as defined in claim 1.

8. The compound of claim 1 or a pharmaceutically acceptable salt thereof, wherein $R^2$ is unsubstituted $C_1$-$C_6$ alkyl or $C_1$-$C_{10}$ alkyl substituted with 4- to 6-membered heterocyclyl comprising 1-2 heteroatoms independently selected from N, O, and S, or —C(=O)—$R^3$, wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S, wherein the heterocyclyl is, at each occurrence, independently selected from:

and wherein said heterocyclyl is, at each occurrence, independently substituted with 0-3 $R^4$, wherein $R^4$ is as defined in claim 1.

9. The compound of claim 1 or a pharmaceutically acceptable salt thereof, wherein $R^2$ is unsubstituted $C_1$-$C_6$ alkyl or $C_1$-$C_{10}$ alkyl substituted with 4- to 6-membered heterocyclyl comprising 1-2 heteroatoms independently selected from N, O, and S, or —C(=O)—$R^3$,
wherein $R^3$ is 4- to 6-membered heterocyclyl comprising 1-2 heteroatoms independently selected from N, O, and S, or $C_1$-$C_6$alkyl substituted with 4- to 6-membered heterocyclyl comprising 1-2 heteroatoms independently selected from N, O, and S,
wherein the heterocyclyl is, at each occurrence, independently selected from

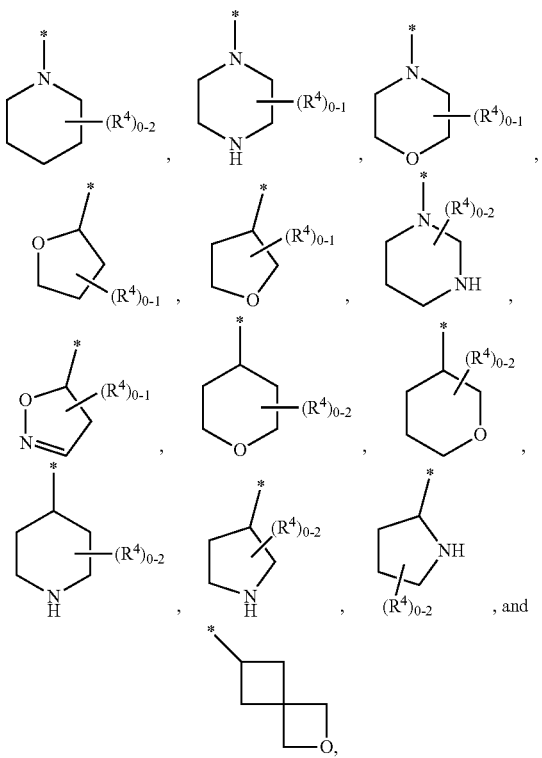

wherein $R^4$ is as defined in claim 1.

10. The compound of claim 1 or a pharmaceutically acceptable salt thereof, wherein $R^2$ is selected from $C_1$-$C_6$ alkyl,

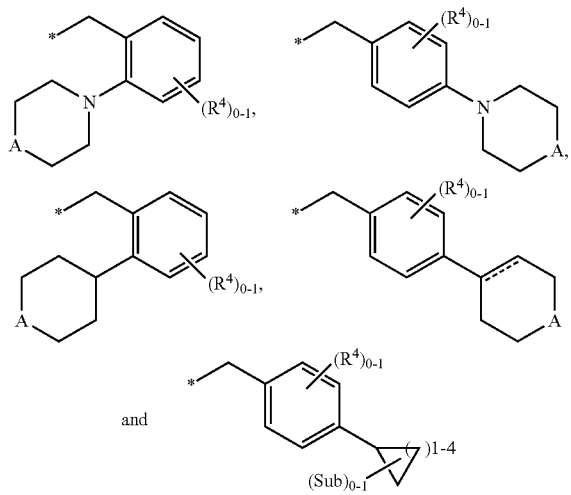

wherein
- - - represents an optional C=C double bond, which when present, A is O;
A is selected from N—$R^{4d}$, O and $CH_2$;
$R^4$ is selected from $C_1$-$C_6$alkyl, $C_1$-$C_6$alkoxyl, $C_1$-$C_6$haloalkyl, fluoro, chloro, iodo, hydroxyl and —CN;
$R^{4d}$ is selected from hydrogen, —C(=O)—O—($C_1$-$C_6$alkyl), 4- to 6-membered heterocyclyl comprising 1 heteroatom selected from N and O, $C_3$-$C_6$cycloalkyl, $C_1$-$C_6$haloalkyl and $C_1$-$C_6$alkyl, wherein the alkyl is substituted with 0-1 substituent selected from $C_3$-$C_6$cycloalkyl, 4- to 6-membered heterocyclyl comprising 1-2 heteroatoms independently selected from N and O; and
Sub is selected from $C_1$-$C_6$alkyl, halogen and $C_1$-$C_6$haloalkyl.

11. The compound of claim 1 or a pharmaceutically acceptable salt thereof, wherein $R^2$ is unsubstituted $C_1$-$C_6$ alkyl or $C_1$-$C_6$ alkyl substituted with one $C_3$-$C_8$cycloalkyl selected from:

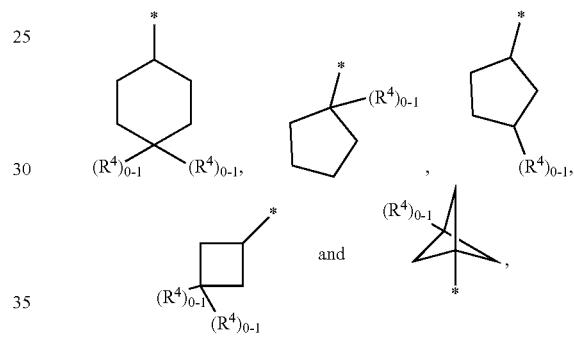

wherein $R^4$ is as defined in claim 1.

12. The compound of claim 1 or a pharmaceutically acceptable salt thereof, wherein $R^2$ is unsubstituted $C_1$-$C_6$ alkyl or $C_1$-$C_6$ alkyl substituted with one $C_3$-$C_8$cycloalkyl selected from

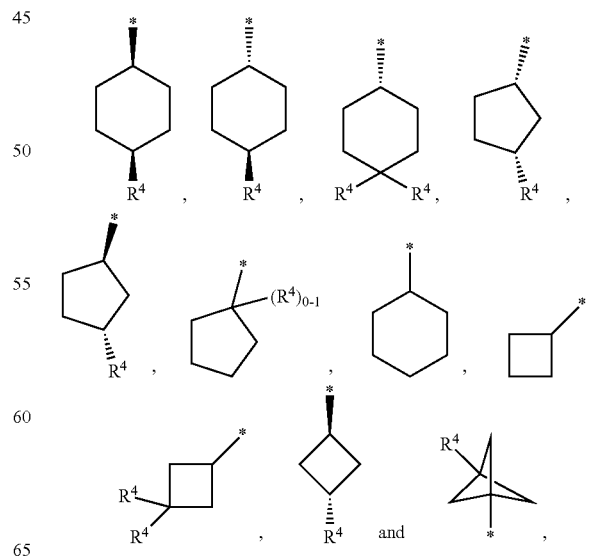

wherein $R^4$ is as defined in claim 1.

13. The compound of claim 1 or a pharmaceutically acceptable salt thereof, wherein each $R^4$ is, at each occurrence, independently selected from $C_1$-$C_6$alkoxyl, —NH—C(=O)—O—($C_1$-$C_6$alkyl), —C(=O)—O—($C_1$-$C_6$alkyl), halogen, and —CN.

14. The compound of claim 1 or a pharmaceutically acceptable salt thereof, of formula (Ia)

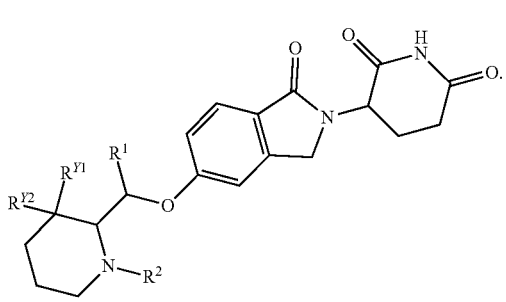

(Ia)

15. The compound of claim 1 or a pharmaceutically acceptable salt thereof, selected from:

3-(5-(((R)-1-((1-cyclohexyl-1H-pyrazol-4-yl)methyl)piperidin-2-yl)methoxy)-1-oxoisoindolin-2-yl)piperidine-2,6-dione;

3-(5-(((R)-1-((1-methyl-5-phenyl-1H-pyrazol-3-yl)methyl)piperidin-2-yl)methoxy)-1-oxoisoindolin-2-yl)piperidine-2,6-dione;

methyl 4-(4-(((2R)-2-(((2-(2,6-dioxopiperidin-3-yl)-1-oxoisoindolin-5-yl)oxy)methyl)piperidin-1-yl)methyl)phenoxy)benzoate;

3-(5-(((R)-1-((1-benzyl-1H-pyrazol-4-yl)methyl)piperidin-2-yl)methoxy)-1-oxoisoindolin-2-yl)piperidine-2,6-dione;

3-(1-oxo-5-(((R)-1-(3-(pyrrolidin-1-yl)benzyl)piperidin-2-yl)methoxy)isoindolin-2-yl)piperidine-2,6-dione;

3-(5-(((R)-1-(3-((1H-pyrazol-1-yl)methyl)benzyl)piperidin-2-yl)methoxy)-1-oxoisoindolin-2-yl)piperidine-2,6-dione;

3-(1-oxo-5-(((R)-1-((3-(m-tolyl)-1H-pyrazol-4-yl)methyl) piperidin-2-yl)methoxy)isoindolin-2-yl)piperidine-2,6-dione;

3-(5-(((R)-1-(4-(2H-1,2,3-triazol-2-yl)benzyl)piperidin-2-yl)methoxy)-1-oxoisoindolin-2-yl)piperidine-2,6-dione;

3-(1-oxo-5-(((R)-1-((6-(pyrrolidin-1-yl)pyridin-3-yl)methyl) piperidin-2-yl)methoxy)isoindolin-2-yl)piperidine-2,6-dione;

3-(5-(((R)-1-(3-methoxy-4-methylbenzyl)piperidin-2-yl)methoxy)-1-oxoisoindolin-2-yl)piperidine-2,6-dione;

3-(5-(((R)-1-(4-(2-methyl-1H-imidazol-1-yl)benzyl)piperidin-2-yl)methoxy)-1-oxoisoindolin-2-yl)piperidine-2,6-dione;

3-(5-(((R)-1-(4-((1H-imidazol-1-yl)methyl)benzyl)piperidin-2-yl)methoxy)-1-oxoisoindolin-2-yl)piperidine-2,6-dione;

3-(5-(((R)-1-((1-isobutyl-1H-pyrazol-4-yl)methyl)piperidin-2-yl)methoxy)-1-oxoisoindolin-2-yl)piperidine-2,6-dione;

3-(5-(((2S)-1-((1-(cyclohex-3-en-1-ylmethyl)piperidin-4-yl)methyl)piperidin-2-yl)methoxy)-1-oxoisoindolin-2-yl)piperidine-2,6-dione;

3-(5-(((R)-1-((6-(diethylamino)pyridin-3-yl)methyl)piperidin-2-yl)methoxy)-1-oxoisoindolin-2-yl)piperidine-2,6-dione;

3-(5-(((S)-1-(2-chloro-6-fluorobenzyl)piperidin-2-yl)methoxy)-1-oxoisoindolin-2-yl)piperidine-2,6-dione;

3-(5-(((R)-1-((5-(benzyloxy)-6-methoxy-1H-indazol-3-yl)methyl)piperidin-2-yl)methoxy)-1-oxoisoindolin-2-yl)piperidine-2,6-dione;

3-(5-(((R)-1-((1-benzylpiperidin-4-yl)methyl)piperidin-2-yl)methoxy)-1-oxoisoindolin-2-yl)piperidine-2,6-dione;

3-(5-(((R)-1-(4-morpholinobenzyl)piperidin-2-yl)methoxy)-1-oxoisoindolin-2-yl)piperidine-2,6-dione;

3-(5-((R)-1-((R)-1-ethylpiperidin-2-yl)ethoxy)-1-oxoisoindolin-2-yl)piperidine-2,6-dione;

tert-butyl 4-(4-(((2R)-2-(((2-(2,6-dioxopiperidin-3-yl)-1-oxoisoindolin-5-yl)oxy)methyl)piperidin-1-yl)methyl)phenyl)piperazine-1-carboxylate;

3-(5-(((R)-1-(3-((1H-imidazol-1-yl)methyl)benzyl)piperidin-2-yl)methoxy)-1-oxoisoindolin-2-yl)piperidine-2,6-dione;

3-(5-(((S)-1-((3,5-dimethylisoxazol-4-yl)methyl)piperidin-2-yl)methoxy)-1-oxoisoindolin-2-yl)piperidine-2,6-dione;

3-(5-(((R)-1-((1-methyl-1H-indol-4-yl)methyl)piperidin-2-yl)methoxy)-1-oxoisoindolin-2-yl)piperidine-2,6-dione;

3-(5-(((R)-1-(2-(4-methylpiperazin-1-yl)benzyl)piperidin-2-yl)methoxy)-1-oxoisoindolin-2-yl)piperidine-2,6-dione;

3-(1-oxo-5-(((S)-1-(3-(pyrrolidin-1-yl)benzyl)piperidin-2-yl)methoxy)isoindolin-2-yl)piperidine-2,6-dione;

3-(1-oxo-5-(((R)-1-(4-(pyrrolidine-1-carbonyl)benzyl)piperidin-2-yl)methoxy)isoindolin-2-yl)piperidine-2,6-dione;

3-(5-(((R)-1-(4-(4-benzylpiperazin-1-yl)benzyl)piperidin-2-yl)methoxy)-1-oxoisoindolin-2-yl)piperidine-2,6-dione;

3-(5-(((R)-1-((1-ethyl-1H-pyrazol-4-yl)methyl)piperidin-2-yl)methoxy)-1-oxoisoindolin-2-yl)piperidine-2,6-dione;

3-(5-(((S)-1-((5-(cyclohexa-1,5-dien-1-yl)-1-methyl-1H-pyrazol-3-yl)methyl)piperidin-2-yl)methoxy)-1-oxoisoindolin-2-yl)piperidine-2,6-dione;

3-(5-(((S)-1-((1-cyclohexyl-1H-pyrazol-4-yl)methyl)piperidin-2-yl)methoxy)-1-oxoisoindolin-2-yl)piperidine-2,6-dione;

3-(5-(((R)-1-(4-(2-morpholinoethoxy)benzyl)piperidin-2-yl)methoxy)-1-oxoisoindolin-2-yl)piperidine-2,6-dione;

3-(5-(((S)-1-((1H-pyrrolo[2,3-b]pyridin-4-yl)methyl)piperidin-2-yl)methoxy)-1-oxoisoindolin-2-yl)piperidine-2,6-dione;

3-(5-(((R)-1-((1-benzyl-1H-imidazol-2-yl)methyl)piperidin-2-yl)methoxy)-1-oxoisoindolin-2-yl)piperidine-2,6-dione;

3-(5-(((S)-1-ethylpiperidin-2-yl)methoxy)-1-oxoisoindolin-2-yl)piperidine-2,6-dione;

3-(5-(((R)-1-(4-(4-methylpiperazin-1-yl)benzyl) piperidin-2-yl)methoxy)-1-oxoisoindolin-2-yl)piperidine-2,6-dione;

3-(5-(((S)-1-((4-methyl-1H-imidazol-5-yl)methyl)piperidin-2-yl)methoxy)-1-oxoisoindolin-2-yl)piperidine-2,6-dione;

3-(5-(((R)-1-(2-(2-morpholinoethoxy)benzyl)piperidin-2-yl)methoxy)-1-oxoisoindolin-2-yl)piperidine-2,6-dione;

3-(5-(((R)-1-ethylpiperidin-2-yl)methoxy)-1-oxoisoindolin-2-yl)piperidine-2,6-dione;

(R)-3-(5-(((R)-1-ethylpiperidin-2-yl)methoxy)-1-oxoisoindolin-2-yl)piperidine-2,6-dione;
(S)-3-(5-(((R)-1-ethylpiperidin-2-yl)methoxy)-1-oxoisoindolin-2-yl)piperidine-2,6-dione;
ethyl 3-(((2R)-2-(((2-(2,6-dioxopiperidin-3-yl)-1-oxoisoindolin-5-yl)oxy)methyl)piperidin-1-yl)methyl)-1H-indazole-4-carboxylate;
3-(5-(((S)-1-((2-ethyl-4-methyl-1H-imidazol-5-yl)methyl)piperidin-2-yl)methoxy)-1-oxoisoindolin-2-yl)piperidine-2,6-dione;
methyl 4-(4-(((2S)-2-(((2-(2,6-dioxopiperidin-3-yl)-1-oxo-2,3,3a,7a-tetrahydro-1H-isoindol-5-yl)oxy)methyl)piperidin-1-yl)methyl)phenoxy)benzoate;
3-(5-(((R)-1-((5-methylisoxazol-3-yl)methyl)piperidin-2-yl)methoxy)-1-oxoisoindolin-2-yl)piperidine-2,6-dione;
3-(5-(((R)-1-((1H-pyrrolo[2,3-b]pyridin-4-yl)methyl)piperidin-2-yl)methoxy)-1-oxoisoindolin-2-yl)piperidine-2,6-dione;
3-(5-(((R)-1-((2-morpholinopyridin-4-yl)methyl)piperidin-2-yl)methoxy)-1-oxoisoindolin-2-yl)piperidine-2,6-dione;
3-(5-(((R)-1-((1-methyl-1H-benzo[d][1,2,3]triazol-5-yl)methyl)piperidin-2-yl)methoxy)-1-oxoisoindolin-2-yl)piperidine-2,6-dione;
3-(5-(((S)-1-((1-methyl-1H-indol-4-yl)methyl)piperidin-2-yl)methoxy)-1-oxoisoindolin-2-yl)piperidine-2,6-dione;
4-(((2R)-2-(((2-(2,6-dioxopiperidin-3-yl)-1-oxoisoindolin-5-yl)oxy)methyl)piperidin-1-yl)methyl)benzenesulfonamide;
3-(5-(((S)-1-(3-((1H-pyrazol-1-yl)methyl)benzyl)piperidin-2-yl)methoxy)-1-oxoisoindolin-2-yl)piperidine-2,6-dione;
3-(5-(((S)-1-((6-(diethylamino)pyridin-3-yl)methyl)piperidin-2-yl)methoxy)-1-oxoisoindolin-2-yl)piperidine-2,6-dione;
3-(5-(((S)-1-(3-methoxy-4-methylbenzyl)piperidin-2-yl)methoxy)-1-oxoisoindolin-2-yl)piperidine-2,6-dione;
3-(5-(((S)-1-((1-isobutyl-1H-pyrazol-4-yl)methyl)piperidin-2-yl)methoxy)-1-oxoisoindolin-2-yl)piperidine-2,6-dione;
3-(5-(((S)-1-((1-benzyl-1H-pyrazol-4-yl)methyl)piperidin-2-yl)methoxy)-1-oxoisoindolin-2-yl)piperidine-2,6-dione;
3-(5-(((S)-1-(3-chloro-4-hydroxybenzyl)piperidin-2-yl)methoxy)-1-oxoisoindolin-2-yl)piperidine-2,6-dione;
3-(1-oxo-5-(((S)-1-((1-(phenylsulfonyl)-1H-pyrrol-2-yl)methyl)piperidin-2-yl)methoxy)isoindolin-2-yl)piperidine-2,6-dione;
3-(5-(((S)-1-(2-(4-methylpiperazin-1-yl)benzyl)piperidin-2-yl)methoxy)-1-oxoisoindolin-2-yl)piperidine-2,6-dione;
3-(5-(((R)-1-((1H-pyrazol-4-yl)methyl)piperidin-2-yl)methoxy)-1-oxoisoindolin-2-yl)piperidine-2,6-dione;
3-(1-oxo-5-(((S)-1-((6-(pyrrolidin-1-yl)pyridin-3-yl)methyl)piperidin-2-yl)methoxy)isoindolin-2-yl)piperidine-2,6-dione;
3-(5-(((R)-1-((1-isopropylpiperidin-4-yl)methyl)piperidin-2-yl)methoxy)-1-oxoisoindolin-2-yl)piperidine-2,6-dione;
3-(1-oxo-5-(((R)-1-((1-(pyrazin-2-yl)-1H-pyrazol-4-yl)methyl)piperidin-2-yl)methoxy)isoindolin-2-yl)piperidine-2,6-dione;
3-(5-(((S)-1-(3-isopropyl-1-methyl-1H-pyrazole-5-carbonyl)piperidin-2-yl)methoxy)-1-oxoisoindolin-2-yl)piperidine-2,6-dione;
3-(5-(((R)-1-isopropylpiperidin-2-yl)methoxy)-1-oxoisoindolin-2-yl)piperidine-2,6-dione;
3-(5-(((S)-1-((5-chloro-3-(4-(2-((dimethylamino)methyl)-1-methyl-1H-imidazol-5-yl)phenoxy)pyridin-2-yl)methyl)piperidin-2-yl)methoxy)-1-oxoisoindolin-2-yl)piperidine-2,6-dione;
3-(5-(((R)-1-((5-chloro-3-(4-(2-((dimethylamino)methyl)-1-methyl-1H-imidazol-5-yl)phenoxy)pyridin-2-yl)methyl)piperidin-2-yl)methoxy)-1-oxoisoindolin-2-yl)piperidine-2,6-dione;
3-(5-(((S)-1-(5-(4-bromophenyl)isoxazole-3-carbonyl)piperidin-2-yl)methoxy)-1-oxoisoindolin-2-yl)piperidine-2,6-dione;
3-(5-(((R)-1-(3-(5-methyl-1,2,4-oxadiazol-3-yl)benzyl)piperidin-2-yl)methoxy)-1-oxoisoindolin-2-yl)piperidine-2,6-dione;
3-(5-(((S)-1-(2-methoxybenzyl)piperidin-2-yl)methoxy)-1-oxoisoindolin-2-yl)piperidine-2,6-dione;
3-(5-(((R)-1-((2-(dimethylamino)pyrimidin-5-yl)methyl)piperidin-2-yl)methoxy)-1-oxoisoindolin-2-yl)piperidine-2,6-dione;
3-(5-(((S)-1-(3,5-diethylisoxazole-4-carbonyl)piperidin-2-yl)methoxy)-1-oxoisoindolin-2-yl)piperidine-2,6-dione;
3-(5-(((S)-1-(4-(2H-1,2,3-triazol-2-yl)benzyl)piperidin-2-yl)methoxy)-1-oxoisoindolin-2-yl)piperidine-2,6-dione;
3-(5-(((S)-1-(3',5-dimethyl-[3,5'-biisoxazole]-4'-carbonyl)piperidin-2-yl)methoxy)-1-oxoisoindolin-2-yl)piperidine-2,6-dione;
benzyl 4-(((2R)-2-(((2-(2,6-dioxopiperidin-3-yl)-1-oxoisoindolin-5-yl)oxy)methyl)piperidin-1-yl)methyl)piperidine-1-carboxylate;
3-(5-(((R)-1-(imidazo[1,2-a]pyridin-8-ylmethyl)piperidin-2-yl)methoxy)-1-oxoisoindolin-2-yl)piperidine-2,6-dione;
3-(5-(((S)-1-((2-morpholinopyridin-4-yl)methyl)piperidin-2-yl)methoxy)-1-oxoisoindolin-2-yl)piperidine-2,6-dione;
3-(5-(((S)-1-(3,4-dimethoxybenzyl)piperidin-2-yl)methoxy)-1-oxoisoindolin-2-yl)piperidine-2,6-dione;
3-(5-(((S)-1-(4-(4-methylpiperazin-1-yl)benzyl)piperidin-2-yl)methoxy)-1-oxoisoindolin-2-yl)piperidine-2,6-dione;
3-(5-(((S)-1-((1-isopropylpiperidin-4-yl)methyl)piperidin-2-yl)methoxy)-1-oxoisoindolin-2-yl)piperidine-2,6-dione;
3-(5-(((S)-1-(3,5-difluoro-4-methoxybenzoyl)piperidin-2-yl)methoxy)-1-oxoisoindolin-2-yl)piperidine-2,6-dione;
methyl (1R,3S)-3-(((2R)-2-(((2-(2,6-dioxopiperidin-3-yl)-1-oxoisoindolin-5-yl)oxy)methyl)piperidin-1-yl)methyl)cyclopentane-1-carboxylate;
3-(5-(((R)-1-(((1r,4R)-4-methoxycyclohexyl)methyl)piperidin-2-yl)methoxy)-1-oxoisoindolin-2-yl)piperidine-2,6-dione;
3-(5-(((R)-1-((2-(methylamino)pyridin-3-yl)methyl)piperidin-2-yl)methoxy)-1-oxoisoindolin-2-yl)piperidine-2,6-dione;
3-(5-(((S)-1-(4-(3-methyl-1,2,4-oxadiazol-5-yl)benzoyl)piperidin-2-yl)methoxy)-1-oxoisoindolin-2-yl)piperidine-2,6-dione;
3-(5-(((S)-1-(2,5-dimethyl-1-(5-methylisoxazol-3-yl)-1H-pyrrole-3-carbonyl)piperidin-2-yl)methoxy)-1-oxoisoindolin-2-yl)piperidine-2,6-dione;
3-(5-(((S)-1-((1H-pyrazol-4-yl)methyl)piperidin-2-yl)methoxy)-1-oxoisoindolin-2-yl)piperidine-2,6-dione;

3-(5-(((S)-1-(3-(benzyloxy)-4-methoxybenzoyl)piperidin-2-yl)methoxy)-1-oxoisoindolin-2-yl)piperidine-2,6-dione;
3-(1-oxo-5-(((R)-1-(2-(2-oxo-2-(piperidin-1-yl)ethoxy)benzyl)piperidin-2-yl)methoxy)isoindolin-2-yl)piperidine-2,6-dione;
3-(5-(((R)-1-(((1s,4S)-4-methoxycyclohexyl)methyl)piperidin-2-yl)methoxy)-1-oxoisoindolin-2-yl)piperidine-2,6-dione;
3-(5-(((R)-1-((4-methyl-1H-imidazol-5-yl)methyl)piperidin-2-yl)methoxy)-1-oxoisoindolin-2-yl)piperidine-2,6-dione;
3-(5-(((R)-1-((1H-imidazol-4-yl)methyl)piperidin-2-yl)methoxy)-1-oxoisoindolin-2-yl)piperidine-2,6-dione;
3-(1-oxo-5-(((S)-1-(2-(piperidin-1-yl)thiazole-5-carbonyl)piperidin-2-yl)methoxy)isoindolin-2-yl)piperidine-2,6-dione;
3-(5-(((S)-1-(4-(2-methyl-1H-imidazol-1-yl)benzyl)piperidin-2-yl)methoxy)-1-oxoisoindolin-2-yl)piperidine-2,6-dione;
3-(1-oxo-5-(((S)-1-(4-pentylbenzoyl)piperidin-2-yl)methoxy)isoindolin-2-yl)piperidine-2,6-dione;
3-(5-(((R)-1-((2-methylimidazo[1,2-a]pyridin-3-yl)methyl)piperidin-2-yl)methoxy)-1-oxoisoindolin-2-yl)piperidine-2,6-dione;
3-(5-(((R)-1-((3,3-difluorocyclobutyl)methyl)piperidin-2-yl)methoxy)-1-oxoisoindolin-2-yl)piperidine-2,6-dione;
3-(5-(((S)-1-(4-methyl-3,4-dihydro-2H-pyrido[3,2-b][1,4]oxazine-7-carbonyl)piperidin-2-yl)methoxy)-1-oxoisoindolin-2-yl)piperidine-2,6-dione;
3-(5-(((S)-4-ethyl-6,6-dimethylmorpholin-3-yl)methoxy)-1-oxoisoindolin-2-yl)piperidine-2,6-dione;
4-(((2R)-2-(((2-(2,6-dioxopiperidin-3-yl)-1-oxoisoindolin-5-yl)oxy)methyl)piperidin-1-yl)methyl)-3-methoxybenzonitrile;
2-(((2R)-2-(((2-(2,6-dioxopiperidin-3-yl)-1-oxoisoindolin-5-yl)oxy)methyl)piperidin-1-yl)methyl)imidazo[1,2-a]pyridine-7-carbonitrile;
3-(5-(((R)-1-((2-ethyl-4-methyl-1H-imidazol-5-yl)methyl)piperidin-2-yl)methoxy)-1-oxoisoindolin-2-yl)piperidine-2,6-dione;
3-(5-(((R)-1-(cyclohexylmethyl)piperidin-2-yl)methoxy)-1-oxoisoindolin-2-yl)piperidine-2,6-dione;
3-(5-(((R)-1-((2-methyl-1H-imidazol-5-yl)methyl)piperidin-2-yl)methoxy)-1-oxoisoindolin-2-yl)piperidine-2,6-dione;
3-(1-oxo-5-(((R)-1-((2-oxo-1,2-dihydropyridin-3-yl)methyl)piperidin-2-yl)methoxy)isoindolin-2-yl)piperidine-2,6-dione;
3-(1-oxo-5-(((S)-1-(4-(pyrrolidine-1-carbonyl)benzyl)piperidin-2-yl)methoxy)isoindolin-2-yl)piperidine-2,6-dione;
3-((3-(((2R)-2-(((2-(2,6-dioxopiperidin-3-yl)-1-oxoisoindolin-5-yl)oxy)methyl)piperidin-1-yl)methyl)-2-oxopyridin-1(2H)-yl)methyl)benzonitrile;
2-(4-(((2R)-2-(((2-(2,6-dioxopiperidin-3-yl)-1-oxoisoindolin-5-yl)oxy)methyl)piperidin-1-yl)methyl)-1H-imidazol-1-yl)acetic acid;
3-(5-(((R)-1-(4-(5-methyl-1,3,4-oxadiazol-2-yl)benzyl)piperidin-2-yl)methoxy)-1-oxoisoindolin-2-yl)piperidine-2,6-dione;
3-(5-(((S)-1-(5-(4-fluorophenyl)picolinoyl)piperidin-2-yl)methoxy)-1-oxoisoindolin-2-yl)piperidine-2,6-dione;
3-(5-(((S)-1-((1-methyl-1H-imidazol-5-yl)methyl)piperidin-2-yl)methoxy)-1-oxoisoindolin-2-yl)piperidine-2,6-dione;
2-(((2R)-2-(((2-(2,6-dioxopiperidin-3-yl)-1-oxoisoindolin-5-yl)oxy)methyl)piperidin-1-yl)methyl)benzonitrile;
3-(5-(((S)-1-(5-butyl-4-methoxypyrimidine-2-carbonyl)piperidin-2-yl)methoxy)-1-oxoisoindolin-2-yl)piperidine-2,6-dione;
2-(((2S)-2-(((2-(2,6-dioxopiperidin-3-yl)-1-oxoisoindolin-5-yl)oxy)methyl)piperidin-1-yl)methyl)benzonitrile;
ethyl 4-(((2R)-2-(((2-(2,6-dioxopiperidin-3-yl)-1-oxoisoindolin-5-yl)oxy)methyl)piperidin-1-yl)methyl)-1H-pyrazole-3-carboxylate;
4-(((2S)-2-(((2-(2,6-dioxopiperidin-3-yl)-1-oxoisoindolin-5-yl)oxy)methyl)piperidin-1-yl)methyl)benzenesulfonamide;
3-(1-oxo-5-(((S)-1-(4-(2-oxopyrrolidin-1-yl)benzyl)piperidin-2-yl)methoxy)isoindolin-2-yl)piperidine-2,6-dione;
3-(5-(((S)-1-(4-(3-methyloxetan-3-yl)benzoyl)piperidin-2-yl)methoxy)-1-oxoisoindolin-2-yl)piperidine-2,6-dione;
3-(5-(((S)-1-(3,5-dimethyl-1-phenyl-1H-pyrazole-4-carbonyl)piperidin-2-yl)methoxy)-1-oxoisoindolin-2-yl)piperidine-2,6-dione;
3-(5-(((S)-1-((6-morpholinopyridin-2-yl)methyl)piperidin-2-yl)methoxy)-1-oxoisoindolin-2-yl)piperidine-2,6-dione;
3-(1-oxo-5-(((S)-1-((5-(pyridin-3-yloxy)-1H-indazol-3-yl)methyl) piperidin-2-yl)methoxy)isoindolin-2-yl)piperidine-2,6-dione;
3-(5-(((S)-1-(3-(5-methyl-1,2,4-oxadiazol-3-yl)benzyl)piperidin-2-yl)methoxy)-1-oxoisoindolin-2-yl)piperidine-2,6-dione;
3-(5-(((S)-1-(2,3-dihydroxybenzyl)piperidin-2-yl)methoxy)-1-oxoisoindolin-2-yl)piperidine-2,6-dione;
3-(5-(((R)-1-((1-methyl-1H-imidazol-5-yl)methyl)piperidin-2-yl)methoxy)-1-oxoisoindolin-2-yl)piperidine-2,6-dione;
3-(1-oxo-5-(((S)-1-(4-(pent-3-yn-1-yloxy)benzoyl)piperidin-2-yl)methoxy)isoindolin-2-yl)piperidine-2,6-dione;
3-(5-(((S)-1-((1H-imidazol-4-yl)methyl)piperidin-2-yl)methoxy)-1-oxoisoindolin-2-yl)piperidine-2,6-dione;
3-(5-(((S)-1-(4-morpholinobenzoyl)piperidin-2-yl)methoxy)-1-oxoisoindolin-2-yl)piperidine-2,6-dione;
3-(5-(((S)-1-((5-(benzyloxy)-6-methoxy-1H-indazol-3-yl)methyl)piperidin-2-yl)methoxy)-1-oxoisoindolin-2-yl)piperidine-2,6-dione;
benzyl 4-(((2S)-2-(((2-(2,6-dioxopiperidin-3-yl)-1-oxoisoindolin-5-yl)oxy)methyl)piperidin-1-yl)methyl)piperidine-1-carboxylate;
3-(5-(((S)-1-(4-chloro-3-iodobenzoyl)piperidin-2-yl)methoxy)-1-oxoisoindolin-2-yl)piperidine-2,6-dione;
3-(5-(((S)-1-(3-fluoro-4-methoxybenzyl)piperidin-2-yl)methoxy)-1-oxoisoindolin-2-yl)piperidine-2,6-dione;
3-(5-(((S)-1-(4-methyl-3-phenyl-1H-pyrazole-5-carbonyl)piperidin-2-yl)methoxy)-1-oxoisoindolin-2-yl)piperidine-2,6-dione;
3-(1-oxo-5-(((R)-1-((tetrahydro-2H-pyran-4-yl)methyl)piperidin-2-yl)methoxy)isoindolin-2-yl)piperidine-2,6-dione;
3-(5-(((S)-1-((6-methoxypyridin-3-yl)methyl)piperidin-2-yl)methoxy)-1-oxoisoindolin-2-yl)piperidine-2,6-dione;

3-(5-(((S)-1-(2-(2-morpholinoethoxy)benzyl)piperidin-2-yl)methoxy)-1-oxoisoindolin-2-yl)piperidine-2,6-dione;

methyl (1R,3S)-3-(((2S)-2-(((2-(2,6-dioxopiperidin-3-yl)-1-oxoisoindolin-5-yl)oxy)methyl)piperidin-1-yl)methyl)cyclopentane-1-carboxylate;

3-(5-(((R)-1-((1H-imidazol-2-yl)methyl)piperidin-2-yl)methoxy)-1-oxoisoindolin-2-yl)piperidine-2,6-dione;

3-(1-oxo-5-(((S)-1-(1-phenyl-1H-1,2,4-triazole-3-carbonyl)piperidin-2-yl)methoxy)isoindolin-2-yl)piperidine-2,6-dione;

3-(5-(((S)-1-(5-neopentylisoxazole-3-carbonyl)piperidin-2-yl)methoxy)-1-oxoisoindolin-2-yl)piperidine-2,6-dione;

3-(5-(1-((S)-1-ethylpyrrolidin-2-yl)ethoxy)-1-oxoisoindolin-2-yl)piperidine-2,6-dione;

3-(5-((R)-1-((S)-1-ethylpyrrolidin-2-yl)ethoxy)-1-oxoisoindolin-2-yl)piperidine-2,6-dione;

3-(5-(((S)-1-((2-(dimethylamino)pyrimidin-5-yl)methyl)piperidin-2-yl)methoxy)-1-oxoisoindolin-2-yl)piperidine-2,6-dione;

3-(5-(((S)-1-((1-methyl-1H-benzo[d][1,2,3]triazol-5-yl)methyl)piperidin-2-yl)methoxy)-1-oxoisoindolin-2-yl)piperidine-2,6-dione;

3-(5-(((S)-1-(4-(5-methyl-1,3,4-oxadiazol-2-yl)benzoyl)piperidin-2-yl)methoxy)-1-oxoisoindolin-2-yl)piperidine-2,6-dione;

3-(5-(((R)-1-isobutylpiperidin-2-yl)methoxy)-1-oxoisoindolin-2-yl)piperidine-2,6-dione;

3-(1-oxo-5-(((R)-1-(pyrimidin-5-ylmethyl)piperidin-2-yl)methoxy)isoindolin-2-yl)piperidine-2,6-dione;

3-(5-(((S)-1-((2-hydroxypyridin-4-yl)methyl)piperidin-2-yl)methoxy)-1-oxoisoindolin-2-yl)piperidine-2,6-dione;

3-(5-(((S)-1-((2-aminopyrimidin-5-yl)methyl)piperidin-2-yl)methoxy)-1-oxoisoindolin-2-yl)piperidine-2,6-dione;

3-(5-(((S)-1-(3-(4-methoxyphenyl)-1H-pyrazole-5-carbonyl)piperidin-2-yl)methoxy)-1-oxoisoindolin-2-yl)piperidine-2,6-dione;

2-chloro-5-(((2S)-2-(((2-(2,6-dioxopiperidin-3-yl)-1-oxoisoindolin-5-yl)oxy)methyl)piperidin-1-yl)methyl)benzenesulfonamide;

3-(5-(((S)-1-(oxazol-4-ylmethyl)piperidin-2-yl)methoxy)-1-oxoisoindolin-2-yl)piperidine-2,6-dione;

3-(1-oxo-5-(((S)-1-(2-(2-oxo-2-(piperidin-1-yl)ethoxy)benzyl)piperidin-2-yl)methoxy)isoindolin-2-yl)piperidine-2,6-dione;

3-(1-oxo-5-(((S)-1-(5-propylisoxazole-3-carbonyl)piperidin-2-yl)methoxy)isoindolin-2-yl)piperidine-2,6-dione;

methyl 4-(((2R)-2-(((2-(2,6-dioxopiperidin-3-yl)-1-oxoisoindolin-5-yl)oxy)methyl)piperidin-1-yl)methyl)-1-(3-(trifluoromethyl) phenyl)-1H-pyrazole-3-carboxylate;

3-(5-(((R)-1-(2-((1H-1,2,4-triazol-1-yl)methyl)benzyl)piperidin-2-yl)methoxy)-1-oxoisoindolin-2-yl)piperidine-2,6-dione;

3-(5-(((R)-1-((1-methyl-1H-benzo[d]imidazol-2-yl)methyl)piperidin-2-yl)methoxy)-1-oxoisoindolin-2-yl) piperidine-2,6-dione;

2-(((2S)-2-(((2-(2,6-dioxopiperidin-3-yl)-1-oxoisoindolin-5-yl)oxy)methyl)piperidin-1-yl)methyl)imidazo[1,2-a]pyridine-7-carbonitrile;

tert-butyl (1-(((2R)-2-(((2-(2,6-dioxopiperidin-3-yl)-1-oxoisoindolin-5-yl)oxy)methyl)piperidin-1-yl)methyl)cyclopentyl)carbamate;

3-(((2S)-2-(((2-(2,6-dioxopiperidin-3-yl)-1-oxoisoindolin-5-yl)oxy)methyl)piperidin-1-yl)methyl)benzonitrile;

3-(5-(((S)-1-(1-methyl-5-phenyl-1H-pyrazole-3-carbonyl)piperidin-2-yl)methoxy)-1-oxoisoindolin-2-yl)piperidine-2,6-dione;

3-(5-(((S)-1-(5-isopropylisoxazole-3-carbonyl)piperidin-2-yl)methoxy)-1-oxoisoindolin-2-yl)piperidine-2,6-dione;

3-(1-oxo-5-(((S)-1-((2-oxo-1,2-dihydropyridin-3-yl)methyl)piperidin-2-yl)methoxy)isoindolin-2-yl)piperidine-2,6-dione;

3-(5-((1-ethyl-3,3-dimethylpiperidin-2-yl)methoxy)-1-oxoisoindolin-2-yl)piperidine-2,6-dione;

3-(5-(((S)-1-ethyl-3,3-dimethylpiperidin-2-yl)methoxy)-1-oxoisoindolin-2-yl)piperidine-2,6-dione;

4-(((2S)-2-(((2-(2,6-dioxopiperidin-3-yl)-1-oxoisoindolin-5-yl)oxy)methyl)piperidin-1-yl)methyl)-3-methoxybenzonitrile;

3-(5-(((S)-1-(2-ethylthiazole-5-carbonyl)piperidin-2-yl)methoxy)-1-oxoisoindolin-2-yl)piperidine-2,6-dione;

3-(5-(((S)-1-((2-(methylamino)pyridin-3-yl)methyl)piperidin-2-yl)methoxy)-1-oxoisoindolin-2-yl)piperidine-2,6-dione;

3-(5-(((R)-1-(2-hydroxy-5-(5-(trifluoromethyl)-1H-tetrazol-1-yl) benzyl)piperidin-2-yl)methoxy)-1-oxo-1,3,3a,4,7,7a-hexahydro-2H-isoindol-2-yl)piperidine-2,6-dione;

3-(5-(((S)-1-(7-methoxy-1H-indole-3-carbonyl)piperidin-2-yl)methoxy)-1-oxoisoindolin-2-yl)piperidine-2,6-dione;

3-(5-(((S)-1-(3-isopropylisoxazole-5-carbonyl)piperidin-2-yl)methoxy)-1-oxoisoindolin-2-yl)piperidine-2,6-dione;

3-(5-(((R)-1-((3,5-dimethylisoxazol-4-yl)methyl)piperidin-2-yl)methoxy)-1-oxoisoindolin-2-yl)piperidine-2,6-dione;

3-(5-(((S)-1-((1-methyl-1H-benzo[d]imidazol-2-yl)methyl)piperidin-2-yl)methoxy)-1-oxoisoindolin-2-yl)piperidine-2,6-dione;

3-(5-(1-((S)-1-ethylpyrrolidin-2-yl)ethoxy)-1-oxoisoindolin-2-yl)piperidine-2,6-dione;

3-(5-((S)-1-((S)-1-ethylpyrrolidin-2-yl)ethoxy)-1-oxoisoindolin-2-yl)piperidine-2,6-dione;

3-(5-((4-ethyl-6,6-dimethylmorpholin-3-yl)methoxy)-1-oxoisoindolin-2-yl)piperidine-2,6-dione;

3-(5-(((R)-4-ethyl-6,6-dimethylmorpholin-3-yl)methoxy)-1-oxoisoindolin-2-yl)piperidine-2,6-dione;

3-(5-(((R)-1-((4-methyltetrahydro-2H-pyran-4-yl)methyl)piperidin-2-yl)methoxy)-1-oxoisoindolin-2-yl) piperidine-2,6-dione;

3-(5-(((S)-4-ethylmorpholin-3-yl)methoxy)-1-oxoisoindolin-2-yl)piperidine-2,6-dione;

3-(1-oxo-5-(((S)-1-(pyrimidin-5-ylmethyl)piperidin-2-yl)methoxy)isoindolin-2-yl)piperidine-2,6-dione;

3-(5-(((S)-1-((5-methylisoxazol-3-yl)methyl)piperidin-2-yl)methoxy)-1-oxoisoindolin-2-yl)piperidine-2,6-dione;

4-(((2S)-2-(((2-(2,6-dioxopiperidin-3-yl)-1-oxoisoindolin-5-yl)oxy)methyl)piperidin-1-yl)methyl)picolinonitrile;

3-(1-oxo-5-(((S)-1-(quinoxaline-6-carbonyl)piperidin-2-yl)methoxy)isoindolin-2-yl)piperidine-2,6-dione;

3-(5-(((S)-1-(3-(difluoromethoxy)benzoyl)piperidin-2-yl)methoxy)-1-oxoisoindolin-2-yl)piperidine-2,6-dione;

3-(5-(((S)-1-(3-(1-methyl-1H-pyrazol-3-yl)benzoyl)piperidin-2-yl)methoxy)-1-oxoisoindolin-2-yl)piperidine-2,6-dione;

3-(5-(((S)-1-(2-morpholinothiazole-4-carbonyl)piperidin-2-yl)methoxy)-1-oxoisoindolin-2-yl)piperidine-2,6-dione;

3-(5-(((S)-1-(3-fluorobicyclo[1.1.1]pentane-1-carbonyl)piperidin-2-yl)methoxy)-1-oxoisoindolin-2-yl)piperidine-2,6-dione;

3-(5-(((1-ethyl-3,3-dimethylpiperidin-2-yl)methoxy)-1-oxoisoindolin-2-yl)piperidine-2,6-dione;

3-(5-(((R)-1-ethyl-3,3-dimethylpiperidin-2-yl)methoxy)-1-oxoisoindolin-2-yl)piperidine-2,6-dione;

3-(5-(((R)-1-((6-fluoropyridin-3-yl)methyl)piperidin-2-yl)methoxy)-1-oxoisoindolin-2-yl)piperidine-2,6-dione;

3-(5-(((R)-1-(4,4-difluorocyclohexyl)piperidin-2-yl)methoxy)-1-oxoisoindolin-2-yl)piperidine-2,6-dione;

3-(5-(((R)-1-(4-(4-ethylpiperazin-1-yl)benzyl) piperidin-2-yl)methoxy)-1-oxoisoindolin-2-yl)piperidine-2,6-dione;

3-(1-oxo-5-(((R)-1-(4-(trifluoromethoxy)benzyl)piperidin-2-yl)methoxy)isoindolin-2-yl)piperidine-2,6-dione;

3-(5-((S)-1-((R)-1-ethylpiperidin-2-yl)ethoxy)-1-oxoisoindolin-2-yl)piperidine-2,6-dione;

3-(5-((S)-1-((S)-1-ethylpiperidin-2-yl)ethoxy)-1-oxoisoindolin-2-yl)piperidine-2,6-dione;

3-(5-(((R)-1-isobutyrylpiperidin-2-yl)methoxy)-1-oxoisoindolin-2-yl)piperidine-2,6-dione;

3-(5-(((R)-1-(2,4-difluorobenzyl)piperidin-2-yl)methoxy)-1-oxoisoindolin-2-yl)piperidine-2,6-dione;

3-(((2R)-2-(((2-(2,6-dioxopiperidin-3-yl)-1-oxoisoindolin-5-yl)oxy)methyl)piperidin-1-yl)methyl)bicyclo[1.1.1]pentane-1-carbonitrile;

3-(5-(((R)-1-(4-(4-(oxetan-3-ylmethyl)piperazin-1-yl)benzyl)piperidin-2-yl)methoxy)-1-oxoisoindolin-2-yl)piperidine-2,6-dione;

3-(5-(((R)-1-(3,4-difluorobenzyl)piperidin-2-yl)methoxy)-1-oxoisoindolin-2-yl)piperidine-2,6-dione;

3-(5-((R)-1-((S)-1-ethylpiperidin-2-yl)ethoxy)-1-oxoisoindolin-2-yl)piperidine-2,6-dione;

3-(5-(((R)-1-(4-(4-isobutylpiperazin-1-yl)benzyl)piperidin-2-yl)methoxy)-1-oxoisoindolin-2-yl)piperidine-2,6-dione;

3-(5-(((R)-1-benzoylpiperidin-2-yl)methoxy)-1-oxoisoindolin-2-yl)piperidine-2,6-dione;

3-(5-((1-ethylazepan-2-yl)methoxy)-1-oxoisoindolin-2-yl)piperidine-2,6-dione;

3-(5-(((R)-1-(oxazole-5-carbonyl)piperidin-2-yl)methoxy)-1-oxoisoindolin-2-yl)piperidine-2,6-dione;

3-(5-(((R)-1-(((1r,3R)-3-methoxycyclobutyl)methyl)piperidin-2-yl)methoxy)-1-oxoisoindolin-2-yl)piperidine-2,6-dione;

3-(5-(((R)-1-((3-fluorobicyclo[1.1.1]pentan-1-yl)methyl)piperidin-2-yl)methoxy)-1-oxoisoindolin-2-yl)piperidine-2,6-dione;

3-(5-(((R)-1-(2-morpholinobenzyl)piperidin-2-yl)methoxy)-1-oxoisoindolin-2-yl)piperidine-2,6-dione;

3-(5-(((R)-1-(4-(4-(cyclopropylmethyl)piperazin-1-yl)benzyl)piperidin-2-yl)methoxy)-1-oxoisoindolin-2-yl)piperidine-2,6-dione;

3-(5-(((R)-1-((2-oxaspiro[3.3]heptan-6-yl)methyl)piperidin-2-yl)methoxy)-1-oxoisoindolin-2-yl)piperidine-2,6-dione;

Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperazine-1-carboxylate;

3-(1-oxo-5-(((R)-1-(2-(piperazin-1-yl)benzyl)piperidin-2-yl)methoxy)isoindolin-2-yl)piperidine-2,6-dione;

3-(5-(((R)-1-(2-(4-isobutylpiperazin-1-yl)benzyl)piperidin-2-yl)methoxy)-1-oxoisoindolin-2-yl)piperidine-2,6-dione;

3-(1-oxo-5-(((R)-1-(2-(4-((tetrahydro-2H-pyran-4-yl)methyl)piperazin-1-yl)benzyl)piperidin-2-yl)methoxy)isoindolin-2-yl)piperidine-2,6-dione;

3-(1-oxo-5-(((R)-1-(4-(4-(tetrahydro-2H-pyran-4-yl) piperazin-1-yl) benzyl) piperidin-2-yl)methoxy)isoindolin-2-yl)piperidine-2,6-dione;

Tert-butyl 7-(((2R)-2-(((2-(2,6-dioxopiperidin-3-yl)-1-oxoisoindolin-5-yl)oxy)methyl)piperidin-1-yl)methyl)indoline-1-carboxylate;

3-(5-(((R)-1-(indolin-7-ylmethyl)piperidin-2-yl)methoxy)-1-oxoisoindolin-2-yl)piperidine-2,6-dione;

3-(5-(((R)-1-((1-ethylindolin-7-yl)methyl)piperidin-2-yl)methoxy)-1-oxoisoindolin-2-yl)piperidine-2,6-dione;

3-(5-(((R)-1-(4-fluorobenzyl)piperidin-2-yl)methoxy)-1-oxoisoindolin-2-yl)piperidine-2,6-dione;

3-(5-(((R)-1-(2-chloro-4-fluorobenzyl)piperidin-2-yl)methoxy)-1-oxoisoindolin-2-yl)piperidine-2,6-dione;

3-(5-(((R)-1-((5-fluoropyridin-2-yl)methyl)piperidin-2-yl)methoxy)-1-oxoisoindolin-2-yl)piperidine-2,6-dione;

3-(5-(((R)-1-(((1s,3S)-3-methoxycyclobutyl)methyl)piperidin-2-yl)methoxy)-1-oxoisoindolin-2-yl)piperidine-2,6-dione;

3-(1-oxo-5-(((R)-1-(2-(piperidin-1-yl)benzyl)piperidin-2-yl)methoxy)isoindolin-2-yl)piperidine-2,6-dione;

Tert-butyl 4-(2-(((2R)-2-(((2-(2,6-dioxopiperidin-3-yl)-1-oxoisoindolin-5-yl)oxy)methyl)piperidin-1-yl)methyl)phenyl)piperidine-1-carboxylate;

3-(5-(((R)-1-(2-(1-ethylpiperidin-4-yl) benzyl)piperidin-2-yl)methoxy)-1-oxoisoindolin-2-yl)piperidine-2,6-dione;

Tert-butyl 4-(4-(((2R)-2-(((2-(2,6-dioxopiperidin-3-yl)-1-oxoisoindolin-5-yl)oxy)methyl)piperidin-1-yl)methyl)phenyl)piperidine-1-carboxylate;

3-(5-(((R)-1-(4-(1-ethylpiperidin-4-yl) benzyl)piperidin-2-yl)methoxy)-1-oxoisoindolin-2-yl)piperidine-2,6-dione;

3-(5-(((R)-1-(2,4-dimethoxybenzyl)piperidin-2-yl)methoxy)-1-oxoisoindolin-2-yl)piperidine-2,6-dione;

3-(5-(((R)-1-(2-methoxybenzyl)piperidin-2-yl)methoxy)-1-oxoisoindolin-2-yl)piperidine-2,6-dione;

3-(5-(((R)-1-((2,3-dihydrobenzo[b][1,4]dioxin-5-yl)methyl)piperidin-2-yl)methoxy)-1-oxoisoindolin-2-yl)piperidine-2,6-dione;

3-(5-(((R)-1-(benzo[d][1,3]dioxol-5-ylmethyl)piperidin-2-yl)methoxy)-1-oxoisoindolin-2-yl)piperidine-2,6-dione;

3-(5-(((R)-1-(((1r,3R)-3-hydroxycyclobutyl)methyl)piperidin-2-yl)methoxy)-1-oxoisoindolin-2-yl)piperidine-2,6-dione;

3-(5-(((R)-1-(((1s,3S)-3-hydroxycyclobutyl)methyl)piperidin-2-yl)methoxy)-1-oxoisoindolin-2-yl)piperidine-2,6-dione;

3-(5-(((R)-1-(3-fluoro-4-methoxybenzyl) piperidin-2-yl)methoxy)-1-oxoisoindolin-2-yl)piperidine-2,6-dione;

3-(5-(((R)-1-(3-fluoro-2-hydroxybenzyl)piperidin-2-yl)methoxy)-1-oxoisoindolin-2-yl)piperidine-2,6-dione;

3-(1-oxo-5-(((R)-1-(3,4,5-trifluorobenzyl)piperidin-2-yl)methoxy)isoindolin-2-yl)piperidine-2,6-dione;

(5-(((R)-1-((2,4-dimethylthiazol-5-yl)methyl) piperidin-2-yl)methoxy)-1-oxoisoindolin-2-yl)piperidine-2,6-dione;
3-(5-(((R)-1-((2,4-dimethylthiazol-5-yl)methyl)piperidin-2-yl)methoxy)-1-oxoisoindolin-2-yl)piperidine-2,6-dione;
3-(1-oxo-5-(((R)-1-(pyridin-4-ylmethyl)piperidin-2-yl)methoxy)isoindolin-2-yl)piperidine-2,6-dione;
3-(5-(((R)-1-(2,6-difluorobenzyl)piperidin-2-yl)methoxy)-1-oxoisoindolin-2-yl)piperidine-2,6-dione;
3-(5-(((R)-1-(4-hydroxybenzyl)piperidin-2-yl)methoxy)-1-oxoisoindolin-2-yl)piperidine-2,6-dione;
3-(5-(((R)-1-((2-fluoropyridin-3-yl)methyl)piperidin-2-yl)methoxy)-1-oxoisoindolin-2-yl)piperidine-2,6-dione;
3-(1-oxo-5-(((R)-1-(quinolin-3-ylmethyl)piperidin-2-yl)methoxy)isoindolin-2-yl)piperidine-2,6-dione;
3-(5-(((R)-1-((4-methylthiazol-2-yl)methyl)piperidin-2-yl)methoxy)-1-oxoisoindolin-2-yl)piperidine-2,6-dione;
3-(1-oxo-5-(((R)-1-(quinolin-2-ylmethyl)piperidin-2-yl)methoxy)isoindolin-2-yl)piperidine-2,6-dione;
Tert-butyl 4-(4-(((2R)-2-(((2-(2,6-dioxopiperidin-3-yl)-1-oxoisoindolin-5-yl)oxy)methyl)piperidin-1-yl)methyl)-2-ethylphenyl)piperidine-1-carboxylate;
3-(5-(((R)-1-(3-ethyl-4-(piperidin-4-yl)benzyl)piperidin-2-yl)methoxy)-1-oxoisoindolin-2-yl)piperidine-2,6-dione;
3-(5-(((R)-1-(3-ethyl-4-(1-ethylpiperidin-4-yl)benzyl)piperidin-2-yl)methoxy)-1-oxoisoindolin-2-yl)piperidine-2,6-dione;
3-(5-(((R)-1-(4-(tert-butyl)benzyl)piperidin-2-yl)methoxy)-1-oxoisoindolin-2-yl)piperidine-2,6-dione;
3-(1-oxo-5-(((R)-1-(4-(piperidin-1-yl)benzyl)piperidin-2-yl)methoxy)isoindolin-2-yl)piperidine-2,6-dione;
3-(5-(((R)-1-((3-methoxybicyclo[1.1.1]pentan-1-yl)methyl)piperidin-2-yl)methoxy)-1-oxoisoindolin-2-yl)piperidine-2,6-dione;
Tert-butyl 4-(2-(((2R)-2-(((2-(2,6-dioxopiperidin-3-yl)-1-oxoisoindolin-5-yl)oxy)methyl)piperidin-1-yl)methyl)-4-fluorophenyl)piperazine-1-carboxylate;
3-(5-(((R)-1-(5-fluoro-2-(piperazin-1-yl)benzyl)piperidin-2-yl)methoxy)-1-oxoisoindolin-2-yl)piperidine-2,6-dione;
3-(5-(((R)-1-(2-(4-ethylpiperazin-1-yl)-5-fluorobenzyl)piperidin-2-yl)methoxy)-1-oxoisoindolin-2-yl)piperidine-2,6-dione;
3-(1-oxo-5-(((R)-1-(4-(1-(trifluoromethyl)cyclopropyl)benzyl)piperidin-2-yl)methoxy)isoindolin-2-yl)piperidine-2,6-dione;
3-(5-(((R)-1-((3,4-dihydro-2H-benzo[b][1,4]oxazin-5-yl)methyl)piperidin-2-yl)methoxy)-1-oxoisoindolin-2-yl)piperidine-2,6-dione;
3-(5-(((R)-1-((4-ethyl-3,4-dihydro-2H-benzo[b][1,4]oxazin-5-yl)methyl)piperidin-2-yl)methoxy)-1-oxoisoindolin-2-yl)piperidine-2,6-dione;
3-(1-oxo-5-(((R)-1-((3-oxo-3,4-dihydro-2H-benzo[b][1,4]oxazin-5-yl)methyl)piperidin-2-yl)methoxy)isoindolin-2-yl)piperidine-2,6-dione;
3-(5-(((R)-1-(2-(benzyloxy)ethyl)piperidin-2-yl)methoxy)-1-oxoisoindolin-2-yl)piperidine-2,6-dione;
3-(5-(((R)-1-((2,2-difluorobenzo[d][1,3]dioxol-5-yl)methyl)piperidin-2-yl)methoxy)-1-oxoisoindolin-2-yl)piperidine-2,6-dione;
3-(5-(((R)-1-((6-morpholinopyridin-3-yl)methyl)piperidin-2-yl)methoxy)-1-oxoisoindolin-2-yl)piperidine-2,6-dione;
3-(5-(((R)-1-(4-(3,6-dihydro-2H-pyran-4-yl)benzyl)piperidin-2-yl)methoxy)-1-oxoisoindolin-2-yl)piperidine-2,6-dione;
Tert-butyl 4-(5-(((2R)-2-(((2-(2,6-dioxopiperidin-3-yl)-1-oxoisoindolin-5-yl)oxy)methyl)piperidin-1-yl)methyl)pyridin-2-yl)piperazine-1-carboxylate;
3-(5-(((R)-1-((6-(4-ethylpiperazin-1-yl)pyridin-3-yl)methyl)piperidin-2-yl)methoxy)-1-oxoisoindolin-2-yl)piperidine-2,6-dione;
4-(((2R)-2-(((2-(2,6-dioxopiperidin-3-yl)-1-oxoisoindolin-5-yl)oxy)methyl)piperidin-1-yl)methyl)-2-methoxybenzonitrile;
3-(5-(((R)-1-((1H-benzo[d]imidazol-5-yl)methyl)piperidin-2-yl)methoxy)-1-oxoisoindolin-2-yl)piperidine-2,6-dione;
5-(((2R)-2-(((2-(2,6-dioxopiperidin-3-yl)-1-oxoisoindolin-5-yl)oxy)methyl)piperidin-1-yl)methyl)-2-methoxybenzonitrile;
3-(1-oxo-5-(((R)-1-(4-(1-((tetrahydro-2H-pyran-4-yl)methyl)piperidin-4-yl) benzyl) piperidin-2-yl)methoxy)isoindolin-2-yl)piperidine-2,6-dione;
3-(5-(((R)-1-(4-(1-(2-fluoroethyl)piperidin-4-yl)benzyl)piperidin-2-yl)methoxy)-1-oxoisoindolin-2-yl)piperidine-2,6-dione;
3-(5-(((R)-1-(benzo[d]oxazol-5-ylmethyl)piperidin-2-yl)methoxy)-1-oxoisoindolin-2-yl)piperidine-2,6-dione;
3-(5-(((R)-1-(oxetan-3-ylmethyl)piperidin-2-yl)methoxy)-1-oxoisoindolin-2-yl)piperidine-2,6-dione;
3-(5-(((R)-1-(4-(1-(oxetan-3-ylmethyl)piperidin-4-yl)benzyl)piperidin-2-yl)methoxy)-1-oxoisoindolin-2-yl)piperidine-2,6-dione;
3-(1-oxo-5-(((R)-1-(((R)-tetrahydrofuran-3-yl)methyl)piperidin-2-yl)methoxy)isoindolin-2-yl)piperidine-2,6-dione;
3-(1-oxo-5-(((R)-1-(((S)-tetrahydrofuran-3-yl)methyl)piperidin-2-yl)methoxy)isoindolin-2-yl)piperidine-2,6-dione;
3-(5-(((R)-1-(cyclopropylmethyl)piperidin-2-yl)methoxy)-1-oxoisoindolin-2-yl)piperidine-2,6-dione;
3-(5-(((1S)-1-(1-(((1r,4S)-4-methoxycyclohexyl)methyl)piperidin-2-yl)ethoxy)-1-oxoisoindolin-2-yl)piperidine-2,6-dione;
3-(5-(((1R)-1-(1-(((1r,4R)-4-methoxycyclohexyl)methyl)piperidin-2-yl)ethoxy)-1-oxoisoindolin-2-yl)piperidine-2,6-dione;
3-(5-(((1R,3S,4S)-2-ethyl-2-azabicyclo[2.2.1]heptan-3-yl)methoxy)-1-oxoisoindolin-2-yl)piperidine-2,6-dione;
3-(5-(((R)-1-(4-(4-isopropylpiperazin-1-yl)benzyl)piperidin-2-yl)methoxy)-1-oxoisoindolin-2-yl)piperidine-2,6-dione;
3-(5-(((R)-1-(4-(4-(tert-butyl)piperazin-1-yl)benzyl)piperidin-2-yl)methoxy)-1-oxoisoindolin-2-yl)piperidine-2,6-dione;
3-(5-(((R)-1-(4-(4-cyclopropylpiperazin-1-yl)benzyl)piperidin-2-yl)methoxy)-1-oxoisoindolin-2-yl)piperidine-2,6-dione;
3-(5-((1-ethyl-4-fluoropiperidin-2-yl)methoxy)-1-oxoisoindolin-2-yl)piperidine-2,6-dione;
3-(5-((4,4-difluoropiperidin-2-yl)methoxy)-1-oxoisoindolin-2-yl)piperidine-2,6-dione;
(S)-3-(5-(((S)-1-ethyl-4,4-difluoropiperidin-2-yl)methoxy)-1-oxoisoindolin-2-yl)piperidine-2,6-dione;
(R)-3-(5-(((S)-1-ethyl-4,4-difluoropiperidin-2-yl)methoxy)-1-oxoisoindolin-2-yl)piperidine-2,6-dione;
(R)-3-(5-(((R)-1-ethyl-4,4-difluoropiperidin-2-yl)methoxy)-1-oxoisoindolin-2-yl)piperidine-2,6-dione;

(S)-3-(5-(((R)-1-ethyl-4,4-difluoropiperidin-2-yl)methoxy)-1-oxoisoindolin-2-yl)piperidine-2,6-dione;

(R)-3-(5-(((1S,3S,4R)-2-ethyl-2-azabicyclo[2.2.1]heptan-3-yl)methoxy)-1-oxoisoindolin-2-yl)piperidine-2,6-dione;

(S)-3-(5-(((1S,3S,4R)-2-ethyl-2-azabicyclo[2.2.1]heptan-3-yl)methoxy)-1-oxoisoindolin-2-yl)piperidine-2,6-dione;

(R)-3-(5-(((1R,3R,4S)-2-ethyl-2-azabicyclo[2.2.1]heptan-3-yl)methoxy)-1-oxoisoindolin-2-yl)piperidine-2,6-dione and (S)-3-(5-(((1R,3R,4S)-2-ethyl-2-azabicyclo[2.2.1]heptan-3-yl)methoxy)-1-oxoisoindolin-2-yl)piperidine-2,6-dione.

16. A pharmaceutical composition comprising a therapeutically effective amount of a compound of claim 1 or a pharmaceutically acceptable salt thereof, and a pharmaceutically acceptable carrier or excipient.

17. A pharmaceutical combination comprising a compound of claim 1 or a pharmaceutically acceptable salt thereof, and one or more additional therapeutic agent(s).

18. A method of degrading WIZ protein in a subject in need thereof, the method comprising administering to the subject a therapeutically effective amount of a compound of claim 1 or a pharmaceutically acceptable salt thereof.

19. A method of treating a sickle cell disease in a subject in need thereof, the method comprising administering to the subject a therapeutically effective amount of a compound of claim 1 or a pharmaceutically acceptable salt thereof.

20. A method of treating beta-thalassemia in a subject in need thereof, the method comprising administering to the subject a therapeutically effective amount of a compound of claim 1 or a pharmaceutically acceptable salt thereof.

* * * * *